United States Patent
Dakin et al.

(10) Patent No.: US 12,281,102 B2
(45) Date of Patent: *Apr. 22, 2025

(54) INHIBITORS OF APOL1 AND METHODS OF USING SAME

(71) Applicant: Vertex Pharmaceuticals Incorporated, Boston, MA (US)

(72) Inventors: Leslie A. Dakin, Framingham, MA (US); Timothy J. Senter, Arlington, MA (US); Jingrong Cao, Newton, MA (US); Jon H. Come, Cambridge, MA (US); Francois Denis, St-Lazare (CA); Warren A. Dorsch, Waltham, MA (US); Anne Fortier, Jamaica Plain, MA (US); Martine Hamel, Laval (CA); Elaine B. Krueger, Milton, MA (US); Brian Ledford, Norton, MA (US); Francois Maltais, Stoneham, MA (US); Suganthini S. Nanthakumar, Newton, MA (US); Olivier Nicolas, Montreal (CA); Camil E. Sayegh, Belmont, MA (US); Tiansheng Wang, Concord, MA (US); Stephanie Dorich, Pointe-Claire (CA); Lee Fader, Hawkesbury (CA); Claudio Sturino, Ile Bizard (CA); Janek Szychowski, Montreal (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,268

(22) Filed: Jun. 11, 2021

(65) Prior Publication Data
US 2023/0011118 A1 Jan. 12, 2023

Related U.S. Application Data

(60) Provisional application No. 63/040,183, filed on Jun. 17, 2020, provisional application No. 63/038,275, filed on Jun. 12, 2020.

(51) Int. Cl.
*C07D 209/14* (2006.01)
*C07D 401/12* (2006.01)
*C07D 403/08* (2006.01)
*C07D 403/12* (2006.01)
*C07D 405/12* (2006.01)
*C07D 409/12* (2006.01)
*C07D 413/12* (2006.01)
*C07D 417/12* (2006.01)
*C07D 471/04* (2006.01)

(52) U.S. Cl.
CPC ........ *C07D 403/12* (2013.01); *C07D 209/14* (2013.01); *C07D 401/12* (2013.01); *C07D 403/08* (2013.01); *C07D 405/12* (2013.01); *C07D 409/12* (2013.01); *C07D 413/12* (2013.01); *C07D 417/12* (2013.01); *C07D 471/04* (2013.01); *C07B 2200/05* (2013.01)

(58) Field of Classification Search
CPC .................................................... C07D 209/14
See application file for complete search history.

(56) References Cited

U.S. PATENT DOCUMENTS

| | | |
|---|---|---|
| 6,518,273 B1 | 2/2003 | Chapman et al. |
| 6,605,633 B1 | 8/2003 | Paquet et al. |
| 11,618,746 B2 | 4/2023 | Cao et al. |
| 11,801,234 B2 | 10/2023 | Mallalieu et al. |
| 11,866,446 B2 | 1/2024 | Ahn et al. |
| 2001/0039286 A1 | 11/2001 | Dinnell et al. |
| 2004/0006237 A1 | 1/2004 | Dolitzky et al. |
| 2004/0138287 A1 | 7/2004 | Barth et al. |

(Continued)

FOREIGN PATENT DOCUMENTS

| | | |
|---|---|---|
| EP | 0924209 A1 | 6/1999 |
| WO | WO 2001/017965 A2 | 3/2001 |

(Continued)

OTHER PUBLICATIONS

Horner, et al. DE 1266763 (abstract) retrieved from STN Accession No. 1968:506703, Caplus; Apr. 25, 1968.*

(Continued)

*Primary Examiner* — Shawquia Jackson
(74) *Attorney, Agent, or Firm* — Finnegan, Henderson, Farabow, Garrett & Dunner, LLP

(57) ABSTRACT

The disclosure provides at least one compound, deuterated derivative, or pharmaceutically acceptable salt chosen from compounds of formula (I), deuterated derivatives thereof, and pharmaceutically acceptable salts of any of the foregoing, compositions comprising the same, and methods of making and using the same, including use in treating APOL1 mediated kidney disease.

38 Claims, 1 Drawing Sheet

(56) References Cited

U.S. PATENT DOCUMENTS

| | | |
|---|---|---|
| 2005/0100902 A1 | 5/2005 | Barth et al. |
| 2013/0237532 A1 | 9/2013 | Kim et al. |
| 2018/0118681 A1 | 5/2018 | Ross et al. |
| 2020/0377479 A1 | 12/2020 | Cao et al. |
| 2021/0246121 A1 | 8/2021 | Lai et al. |
| 2021/0275496 A1 | 9/2021 | Mallalieu et al. |
| 2022/0106327 A1 | 10/2022 | Ahn et al. |
| 2022/0340523 A1 | 10/2022 | Dakin et al. |
| 2023/0011118 A1 | 1/2023 | Dakin et al. |
| 2023/0014907 A1 | 1/2023 | Dakin et al. |
| 2023/0119114 A1 | 4/2023 | Daniel et al. |
| 2023/0201201 A1 | 6/2023 | Skorecki et al. |
| 2023/0203000 A1 | 6/2023 | Dakin et al. |
| 2023/0250087 A1 | 8/2023 | Gagnon et al. |

FOREIGN PATENT DOCUMENTS

| | | |
|---|---|---|
| WO | WO 2001/038305 A2 | 5/2001 |
| WO | WO 2002/028831 A1 | 4/2002 |
| WO | WO 2002/092568 A1 | 11/2002 |
| WO | WO 2003/104180 A1 | 12/2003 |
| WO | WO 2004/058717 A1 | 7/2004 |
| WO | WO 2005/021505 A1 | 3/2005 |
| WO | WO 2005/092854 A1 | 10/2005 |
| WO | WO 2007/061763 A2 | 5/2007 |
| WO | WO 2008/092231 A1 | 8/2008 |
| WO | WO 2010/137351 A1 | 12/2010 |
| WO | WO 2012/025155 A1 | 3/2012 |
| WO | WO 2014/085154 A1 | 6/2014 |
| WO | WO 2015/048301 A1 | 4/2015 |
| WO | WO 2015/147639 A1 | 10/2015 |
| WO | WO 2016/055517 A1 | 4/2016 |
| WO | WO 2017/033093 A1 | 3/2017 |
| WO | WO 2019/213148 A1 | 11/2019 |
| WO | WO 2019/226611 A1 | 11/2019 |
| WO | WO 2020/131807 A1 | 6/2020 |
| WO | WO 2021/154997 A1 | 8/2021 |
| WO | WO 2021/158666 A1 | 8/2021 |
| WO | WO 2021/178768 A1 | 9/2021 |
| WO | WO 2021/224927 A1 | 9/2021 |
| WO | WO 2021/252849 A1 | 12/2021 |
| WO | WO2021/252859 A1 | 12/2021 |
| WO | WO 2021/252863 A1 | 12/2021 |
| WO | WO 2022/047031 A1 | 3/2022 |
| WO | WO 2023/028237 A1 | 3/2023 |
| WO | WO 2023/101981 A1 | 6/2023 |
| WO | WO 2023/154309 A1 | 8/2023 |
| WO | WO 2023/154310 A1 | 8/2023 |
| WO | WO 2023/154314 A1 | 8/2023 |
| WO | WO 2023/154344 A1 | 8/2023 |

OTHER PUBLICATIONS

Turnu, et al. Organic Letters (2019), 21 (18), 7329-7332 (abstract) retrieved from STN Accession No. 2019:1709376, Caplus; entered in STN on Sep. 6, 2019.*
Johansson, et al. RSC Advances, 2013, 3, 945.*
Naik, et al. ACS Medicinal Chemistry Letters (abstract), 2014, 5(9), 1005-1009; retrieved from STN; Accession No. 2014:1142884; entered in STN on Jul. 15, 2014.*
Dummer, P.D. et al. (2015), "APOL1 kidney disease risk variants—an evolving landscape," *Semin Nephrol.* 35(3): 22-236. HHS Public Access Author Manuscript; available in PMC May 1, 2016 (25 pages).
International Search Report and Written Opinion for International Application No. PCT/US2021/036954, mailed Sep. 23, 2021 (10 pages).
Lin, J. et al. (2021), "Oncogene APOL1 promotes proliferation and inhibits apoptosis via activating NOTCH1 signaling pathway in pancreatic cancer," *Cell Death and Disease* 12:760 (11 pages).
Turnu, F. et al. (2019) "Catalytic Tandem Friedel-Crafts Alkylation/C4-C3 Ring-Contraction Reaction: An Efficient Route for the Synthesis of Indolyl Cyclopropanecarbaldehydes and Ketones," *Org. Lett.* 21:7329-7332, (4 pages).
Vajgel, G. et al. (2020), "A single *APOL1* nephropathy variant increases risk of advanced lupus nephritis in Brazilians," *J Rheumatol.* 47(8): 1209-1217. HHS Public Access Author Manuscript; available in PMC Aug. 1, 2021 (18 pages).
Takasawa, R. et al. (2011), "Discovery of a new type inhibitor of human glyoxalase I by myricetin-based 4-point pharmacophore," *Bioorganic Med. Chem. Lett.* 21:4337-4342.
*Vertex Announces Positive Results From Phase 2 Study of VX-147 in APOL1-Mediated Focal Segmental Glomerulosclerosis*, Vertex (Dec. 1, 2021), https://news.vrtx.com/press-release/vertex-announces-positive-results-phase-2-study-vx-147-apol1-mediated-focal-segmental (6 pages).
U.S. Appl. No. 17/161,474, filed Jan. 28, 2021, by Dakin et al.
U.S. Appl. No. 17/345,256, filed Jun. 11, 2021, by Dakin et al.
U.S. Appl. No. 17/345,268, filed Jun. 11, 2021, by Dakin et al.
U.S. Appl. No. 17/446,135, filed Aug. 26, 2021, by Ahn et al.
Balasubramanian, M. et al. (1970) "Studies on Conformation: Part X-Addition of Grignard Reagents to 4-Piperidones." *Indian J. Chem.*, vol. 8, May 1, 1970, pp. 420-422.
Bartolucci, S. et al. (2015), "Iridium-Catalyzed Direct Synthesis of Tryptamine Derivatives from Indoles: Exploiting N-Protected Amino Alcohols as Alkylating Agents," *J. Org. Chem*, 2015, 80, 3217-3222.
Casy, A.F. et al. (1976), "Reversed ester analogues of pethidine: isomeric 4-acetoxy-1,2,6-trimethyl-4-phenyrpiperidines." *JPP*, vol. 28, No. 2, pp. 106-110.
Database Registry (2002), Chembridge Corporation: 4-Piperidinol, 4-(2-methoxyphenyl)-1-methyl-2,6-diphenyl-II XP093022694, Database accession No. 471293-86-4 compound with Registry No. 471293-86-4.
Database Registry (2016), Aurora Fine Chemicals: "Piperidine,4-[(1,3-diethyl-IH-pyrazol-5-yl)methyl]-2, 6-dimethyl," XP093022702, Database accession No. 1993174-76-7 compounds with Registry Nos. 1993174- 76-7, 1993166-16-7 and 1993166-02-1.
Database Registry (2018), Aurora Fine Chemicals: "4-Piperidinol, 1,2,6-trimethyl-4-(2-methylphenyl)-", XP093022693, Database accession No. 2182802-01-1 compound with Registry No. 2182802-01-1.
Database Registry (2021), "2'-Cyclopropyl-7,8-dihydro-6'-methylspiro [1,6-naphthyridine-5(6H),4'-piperidine]," XP093024331, retrieved from STN Database accession No. 2645191-67-7 abstract.
Database Registry (2021), "2'-Cyclopropyl-6,7-dihydro-6,6'-dimethylspiro[1,7-naphthyridine-8(5H),4'-piperidine]," XP093024335, retrieved from STN Database accession No. 2644543-73-5 abstract.
Database Registry (2021), Anonymous: "Name not yet assigned", XP093024338, retrieved from STN Database accession No. 2642534-36-7 abstract.
Database Registry (2021), Anonymous: "2'-Cyclopropyl-3,4-dihydro-6'-methylspiro [isoquinoline-1(2H),4'-piperidin]-7-ol," XP093024340, retrieved from STN Database accession No. 2631256-91-0 abstract.
Database Registry (2021), Anonymous: "2-Cyclopropyl-7', 8'-dihydro-2', 6-dimethyl spiro[piperidine-4,5' (3'H)-pyrido[4,3-d]py rimidin]-4' (6 'H) -one", XP093024343, retrieved from STN Database accession No. 2631119-41-8 abstract.
Database Registry (2021), Anonymous: "Name not yet assigned", XP093024344, retrieved from STN Database accession No. 2630494-88-9 abstract.
Database Registry (2021), Anonymous: "2'-Cyclopropyl-6,7-dihydro-6'-methylspiro [1,7-naphthyridine-8(5H), 4' piperidine]-6-methanol," XP093024346, retrieved from STN Database accession No. 2626788-69-8 abstract.
Database Registry (2021), Anonymous: "rel-(2'R,6'R)-3,4-Dihydro-7-methoxy-2',6'-dimethylspiro[2,6- naphthyridine 1(2H), 4'-p iperidine]," "XP093024348, retrieved from STN Database accession No. 2625380-27-8 abstract.
Database Registry (2021), Anonymous: "2'-Cyclopropyl-3,4-dihydro-3,6'-dimethyls piro[2,6-naphthyridine-1(2H), 4'piperidine]," XP093024352, retrieved from STN Database accession No. 2620609-98-3 abstract.

(56) References Cited

OTHER PUBLICATIONS

Database Registry (2021), Anonymous: "2'-Cyclopropyl-6,7-dihydro-6'-methylspiro [I,7-naphthyridine-8(5H), 4' piperidine]-5-methanol," XP093024350, retrieved from STN Database accession No. 2617381-98-1 abstract.
Harish, B. et al. (2017) "N-Heterocyclic carbene (NHC)-catalysed atom economical construction of 2,40- disubstituted indoles," Chem. Commun, 2017, 53, 3338-3341.
Harper N.J. et al. (1960) "Some isomeric hydroxypiperidines." J. Am. Chem. Soc., Jan. 1, 1960, pp. 2704-2711.
Jones, A.J. et al. (1973), "Carbon-13 Magnetic Resonance: the Stereochemistry of 1,2- and 1,3-Dimethyl-4-phenylpiperidine Derivatives." Can. J. Chem., vol. 41, No. 11, pp. 1782-1789.
Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.
Kozikowski, A.P. et al. (1993), "Chemistry, binding affinities, and behavioral properties of a new class of "antineophobic" mitochondrial DBI receptor complex (mDRC) ligands," J. Med. Chem. 36(20):2908-2920.
Manimekalai, A. et al. (2007), "Benzyl group conformation in 4-benzyl-4-hydroxypiperidines," J. Struct. Chem., vol. 48, No. 6, pp. 1036-1045.
Meyers, A.L. et al. (1985), ".alpha.-Amino carbanions. Preparation, metalation, and alkylation of enamidines. Synthesis of piperidine and pyrrolidine natural products and homologation of carbonyl compounds," J. Org. Chem., vol. 50, No. 7, pp. 1019-1026.
Notice of Allowance and Fee(s) Due for U.S. Appl. No. 16/717,099, mailed Nov. 7, 2022.
Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.
Trotter, B.W. et al. (2001) "2-Arylindole-3-acetamides: FPP-Competitive Inhibitors of Farnesyl Protein Transferase," Bioorg. Med. Chem. Lett. 11(2001) 865-869.
U.S. Appl. No. 17/895,582, filed Aug. 25, 2022, by Daniel et al.
U.S. Appl. No. 17/923,508, filed Nov. 11, 2022 by Skorecki, et al.
U.S. Appl. No. 18/001,371, filed Dec. 9, 2022 by Gagnon, et al.
U.S. Appl. No. 18/071,153, filed Nov. 29, 2022, by Dakin et al.
Valles, D.A. et al. (2021), "[alpha], [alpha]'-C—H Bond Difunctionalization of Unprotected Alicyclic Amines," Org. Lett., vol. 23, No. 16, pp. 6367-6371.
Winters, M.P. et al. (2008), "Carboxylic acid bioisosteres acylsulfonamides, acylsulfamides, and sulfonylureas as novel antagonists of the CXCR2 receptor," Bioorganic Med. Chem. Lett. 18:1926-1930.
CAplus Registry No. RN 847480-40-4.
Brittain H. G. et al., (2001) "X-Ray Diffraction III: Pharmaceutical Applications of X-ray Powder Diffraction," Spectroscopy, 16(7), pp. 14-18.
Database Registry (2007), Chemical Abstracts Service, Columbus, Ohio, Accession No. RN 930014-44- 1, Entered STN: Apr. 13, 2007.
Database Registry (2007), Chemical Abstracts Service, Columbus, Ohio, Accession No. RN 1391756-29-8, Entered STN: Aug. 16, 2012.
Database Registry (2007), Chemical Abstracts Service, Columbus, Ohio, Accession No. RN 1391756-83- 4, Entered STN: Aug. 16, 2012.
Joshi, K.C. et al. (1978), "Synthesis and CNS Activity of Some Fluorine Containing 3-Indolylglyoxamides and Tryptamines" Agric. Biol. Chem., 42(9), pp. 1723-1726.
Kang H. et al. (2018), "Potent aromatase inhibitors and molecular mechanism of inhibitory action," European Journal of Medicinal Chemistry, 143, 426-437.
Notice of Allowance and Fee(s) Due for U.S. Appl. No. 17/161,474, mailed Mar. 5, 2024.
Notice of Allowance and Fee(s) Due for U.S. Appl. No. 18/106,569, mailed Mar. 18, 2024.
Shaw D. et al. (2001), "2-Aryl Indole NK1 Antagonists: Optimisation of the Amide Substituent," Bioorg. Med. Chem. Lett., 11, 3031-3034.
The United States Pharmacopeia, Jan. 1, 1995, 23rd Revision, USP 23/NF 18, General Chapter on X-ray diffraction, pp. 1843-1844.
U.S. Appl. No. 18/476,131, filed Sep. 27, 2023.
U.S. Appl. No. 18/504,559, filed Nov. 8, 2023.
Zhang, G.-N. et al. (2019), "An Efficient Synthesis of N-Aryl-2-(Indol-3-yl)-Acetamides via Multi-Component Reactions, " Heterocycles, 98(4), 535-543.

* cited by examiner

 = control
 = control
 = control

INHIBITORS OF APOL1 AND METHODS OF USING SAME

This application claims the benefit of priority of U.S. Provisional Application No. 63/038,275, filed Jun. 12, 2020, and U.S. Provisional Application No. 63/040,183, filed Jun. 17, 2020, the contents of each of which are incorporated by reference herein in their entireties.

This disclosure provides compounds that inhibit apolipoprotein L1 (APOL1) and methods of using those compounds to treat APOL1 mediated kidney disease, including focal segmental glomerulosclerosis (FSGS) and/or non-diabetic kidney disease (NDKD). In some embodiments, the FSGS and/or NDKD is associated with common APOL1 genetic variants (G1: S342G:I384M and G2: N388del:Y389del).

FSGS is a disease of the podocyte (glomerular visceral epithelial cells) responsible for proteinuria and progressive decline in kidney function. NDKD is a disease characterized by hypertension and progressive decline in kidney function. Human genetics support a causal role for the G1 and G2 APOL1 variants in inducing kidney disease. Individuals with two APOL1 risk alleles are at increased risk of developing end-stage kidney disease (ESKD), including FSGS, human immunodeficiency virus (HIV)-associated nephropathy, NDKD, arterionephrosclerosis, lupus nephritis, microalbuminuria, and chronic kidney disease. See P. Dummer et al., Semin Nephrol. 35(3): 222-236 (2015).

APOL1 is a 44 kDa protein that is only expressed in humans, gorillas, and baboons. APOL1 is produced mainly by the liver and contains a signal peptide that allows for secretion into the bloodstream, where it circulates bound to a subset of high density lipoproteins. APOL1 is responsible for protection against the invasive parasite, Trypanosoma brucei brucei (T. b. brucei). APOL1 G1 and G2 variants confer additional protection against trypanosoma species that cause sleeping sickness. Although normal plasma concentrations of APOL1 are relatively high and can vary at least 20-fold in humans, circulating APOL1 is not causally associated with kidney disease.

However, APOL1 in the kidney is thought to be responsible for the development of kidney diseases, including FSGS and NDKD. Under certain circumstances, APOL1 protein synthesis can be increased by approximately 200-fold by pro-inflammatory cytokines such as interferons or tumor necrosis factor-α. In addition, several studies have shown that APOL1 protein can form pH-gated $Na^+/K^+$ pores in the cell membrane, resulting in a net efflux of intracellular $K^+$, ultimately resulting in activation of local and systemic inflammatory responses, cell swelling, and death.

The risk of ESKD is substantially higher in people of recent sub-Saharan African ancestry as compared to those of European ancestry. In the United States, ESKD is responsible for nearly as many lost years of life in women as from breast cancer and more lost years of life in men than from colorectal cancer. Currently, FSGS and NDKD are managed with symptomatic treatment, including blood pressure control using blockers of the renin angiotensin system, and patients with FSGS and heavy proteinuria may be offered high dose steroids. Corticosteroids induce remission in a minority of patients and are associated with numerous and, at times, severe side effects, and are often poorly tolerated. These patients, and particularly individuals of recent sub-Saharan African ancestry with two APOL1 risk alleles, experience faster disease progression leading to ESKD.

Thus, there is an unmet medical need for treatment for APOL1 mediated kidney diseases, including FSGS, NDKD, and ESKD. In view of evidence that APOL1 plays a causative role in inducing and accelerating the progression of kidney disease, inhibition of APOL1 should have a positive impact on patients with APOL1 mediated kidney disease, particularly those who carry two APOL1 risk alleles (i.e., are homozygous or compound heterozygous for the G1 or G2 alleles).

One aspect of the disclosure provides at least one compound, deuterated derivative, or pharmaceutically acceptable salt chosen from compounds of Formula I:

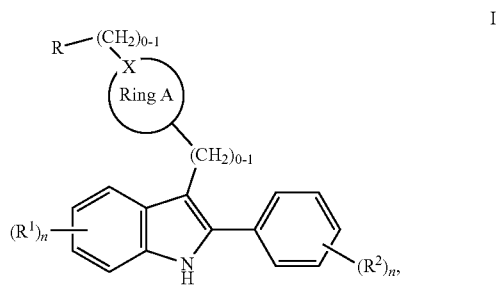

deuterated derivatives thereof, and pharmaceutically acceptable salts of any of the foregoing, wherein:

(i) R is selected from hydrogen, $-NR^3R^4$, $-C(O)R^3$, $-OR^3$, $-NR^5C(O)R^3$, $-NR^5C(O)OR^3$, $-NR^5SO_2R^3$, and $-NR^5SO_2NR^3R^4$;

(ii) X is selected from N and $CR^X$;

(iii) $R^X$ is absent or is selected from hydrogen, hydroxy, halogen, and $C_1$-$C_3$ linear and branched alkyl groups (e.g., $C_1$-$C_3$ linear and $C_3$ branched alkyl groups), wherein, when $R^X$ is absent, X is a bridgehead atom;

(iv) Ring A is a 3- to 7-membered ring, wherein the ring is a cyclic alkyl or a heterocycle;

(v) each n is independently selected from 0, 1, 2, and 3;

(vi) each $R^1$ is independently selected from:
  hydrogen,
  halogen,
  hydroxy,
  amino,
  $C_1$-$C_6$ linear and branched alkyl groups (e.g., $C_1$-$C_6$ linear and $C_3$-$C_6$ branched alkyl groups),
  $C_1$-$C_6$ linear, branched, and cyclic alkoxy groups (e.g., $C_1$-$C_6$ linear, $C_2$-$C_6$ branched, and $C_2$-$C_6$ cyclic alkoxy groups), and
  $C_1$-$C_6$ linear and branched haloalkyl groups (e.g., $C_1$-$C_6$ linear and $C_3$-$C_6$ branched haloalkyl groups);

(vii) each $R^2$ is independently selected from:
  hydrogen,
  halogen,
  hydroxy,
  amino,
  cyano,
  $C_1$-$C_4$ linear, branched, and cyclic alkyl groups (e.g., $C_1$-$C_4$ linear, $C_3$-$C_4$ branched, and $C_3$-$C_4$ cyclic alkyl groups),
  $C_1$-$C_4$ linear, branched, and cyclic hydroxyalkyl groups (e.g., $C_1$-$C_4$ linear, $C_3$-$C_4$ branched, and $C_3$-$C_4$ cyclic hydroxyalkyl groups),
  $C_1$-$C_4$ linear, branched, and cyclic alkoxy groups (e.g., $C_1$-$C_4$ linear, $C_2$-$C_4$ branched, and $C_1$-$C_4$ cyclic alkoxy groups),
  $C_1$-$C_4$ linear, branched, and cyclic haloalkyl groups (e.g., $C_1$-$C_4$ linear, $C_3$-$C_4$ branched, and $C_3$-$C_4$ cyclic haloalkyl groups), and $C_1$-$C_4$ linear, branched, and cyclic haloalkoxy groups (e.g., $C_1$-$C_4$ linear, $C_2$-$C_4$ branched, and $C_1$-$C_4$ cyclic haloalkoxy groups);

(viii) $R^3$ and $R^4$ are independently selected from:
hydrogen,
$C_1$-$C_6$ linear and branched alkylsulfonyl groups (e.g., $C_1$-$C_6$ linear and $C_2$-$C_6$ branched alkylsulfonyl groups) optionally substituted with amino (e.g., optionally substituted with one amino group),
$C_1$-$C_6$ linear and branched alkoxy groups (e.g., $C_1$-$C_6$ linear and $C_2$-$C_6$ branched alkoxy groups) optionally substituted with 1-4 groups independently selected from hydroxy, amino, halogen, and oxo,
$C_1$-$C_3$ linear and branched aminoalkyl groups optionally substituted with 1-2 groups independently selected from amido,
$C_3$-$C_6$ cyclic alkyl optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with a $C_1$-$C_6$ linear or branched alkyl group, and
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups,
3- to 6-membered heterocyclyl optionally substituted with 1-3 groups independently selected from:
halogen,
oxo,
hydroxy,
amido optionally substituted with $C_1$-$C_3$ alkyl,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups,
$C_1$-$C_3$ hydroxyalkyl and $C_1$-$C_3$ haloalkyl, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
3- to 10-membered heteroaryl optionally substituted with 1-2 groups independently selected from amino, hydroxy, oxo, and $C_1$-$C_6$ linear alkyl groups optionally substituted with 1-3 groups independently selected from halogen and amino,
$C_1$-$C_6$ linear and branched alkyl groups optionally substituted with 1-4 groups independently selected from:
$C_1$-$C_4$ alkyl groups,
amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
hydroxy,
oxo,
cyano,
carboxylic acid,
carbamate optionally substituted with 1-2 groups independently selected from $C_1$-$C_6$ linear, branched, and $C_3$-$C_6$ cyclic alkyl groups,
halogen,
amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
$C_3$-$C_6$ cyclic alkyl groups optionally substituted with 1-2 groups independently selected from halogen, $C_1$-$C_6$ linear and branched alkoxy groups, and hydroxy,
$C_1$-$C_6$ linear and branched alkoxy groups optionally substituted with hydroxy,
$C_1$-$C_6$ linear and branched alkylsulfonyl groups,
aryl optionally substituted with 1-2 groups independently selected from halogen, hydroxy, amido optionally substituted with $C_1$-$C_3$ alkyl, and $C_1$-$C_6$ linear and branched alkyl groups optionally substituted with 1-2 groups independently selected from hydroxy and $C_1$-$C_6$ linear and branched alkoxy groups,
4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and
4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl groups,
or $R^3$ and $R^4$, together with the nitrogen atom to which they are attached, form a 3- to 10-membered heterocyclyl or heteroaryl optionally substituted with 1-3 groups independently selected from:
amino optionally substituted with 1-2 groups independently selected from $C_1$-$C_6$ linear, branched, and $C_3$-$C_6$ cyclic alkyl groups, which are optionally substituted with oxo,
halogen,
hydroxy,
oxo,
$C_1$-$C_6$ linear, branched, and $C_3$-$C_6$ cyclic alkyl groups optionally substituted with 1-2 groups independently selected from hydroxy, amino, and C$_1$-C$_6$ linear and branched alkoxy groups, C$_1$-C$_3$ linear or branched hydroxyalkyl, and amide optionally substituted with 1-2 groups independently selected from C$_1$-C$_6$ linear, branched, and C$_3$-C$_6$ cyclic alkyl groups; and (ix) R$^5$ is selected from hydrogen, hydroxy, halogen, and C$_1$-C$_3$ linear and branched alkyl groups.

In some embodiments, when R is —C(O)R$^3$, X is N or R$^3$ is not bonded to the rest of the molecule through a nitrogen atom. In some embodiments, when R is —C(O)R$^3$, X is N. In some embodiments, when R is —C(O)R$^3$, R$^3$ is not bonded to the rest of the molecule through a nitrogen atom. In some embodiments, when R is —C(O)R$^3$, X is N and R$^3$ is not bonded to the rest of the molecule through a nitrogen atom.

In some embodiments, R$^3$ and R$^4$ are independently selected from:

hydrogen,

C$_1$-C$_6$ linear and branched alkylsulfonyl groups optionally substituted with amino (e.g., optionally substituted with one amino group), C$_1$-C$_6$ linear and branched alkoxy groups optionally substituted with 1-4 groups independently selected from hydroxy, amino, halogen, and oxo, C$_1$-C$_3$ linear and branched aminoalkyl groups optionally substituted with 1-2 groups independently selected from amido, C$_3$-C$_6$ cyclic alkyl optionally substituted with 1-2 groups independently selected from:
  halogen,
  hydroxy,
  oxo,
  amido,
  amino substituted with 1-2 groups independently selected from C$_1$-C$_6$ linear, branched, and C$_3$-C$_6$ cyclic alkyl groups,
  aryl optionally substituted with 1-2 groups independently selected from halogen,
  C$_1$-C$_6$ linear and branched alkoxy groups,
  carbamate optionally substituted with a C$_1$-C$_6$ linear or branched alkyl group, and
  C$_1$-C$_6$ linear, branched, and C$_3$-C$_6$ cyclic alkyl groups optionally substituted with 1-3 groups independently selected from hydroxy, oxo, halogen, C$_1$-C$_6$ linear and branched alkoxy groups, and carbamate optionally substituted with 1-3 groups independently selected from C$_1$-C$_6$ linear and branched alkyl groups, 3- to 6-membered heterocyclyl optionally substituted with 2-3 groups independently selected from:
  halogen,
  oxo,
  hydroxy,
  C$_1$-C$_6$ linear and branched alkoxy groups optionally substituted with oxo,
  C$_1$-C$_6$ linear, branched, and C$_3$-C$_6$ cyclic alkyl groups optionally substituted with 1-2 groups independently selected from hydroxy, oxo, and C$_1$-C$_6$ linear and branched alkoxy groups, and
  carbamate optionally substituted with 1-2 groups independently selected from C$_1$-C$_6$ linear, branched, and C$_3$-C$_6$ cyclic alkyl groups,
  aryl optionally substituted with 1-4 groups independently selected from halogen, hydroxy, and C$_1$-C$_6$ linear and branched alkyl groups optionally substituted with 1-2 groups independently selected from hydroxy and C$_1$-C$_6$ linear and branched alkoxy groups, 3- to 6-membered heteroaryl optionally selected from amino, hydroxy, oxo, and C$_1$-C$_6$ linear alkyl groups optionally substituted with 1-3 groups independently selected from halogen and amino, C$_1$-C$_6$ linear and branched alkyl groups optionally substituted with 1-4 groups independently selected from:
  amino optionally substituted with 1-2 groups independently selected from C$_1$-C$_6$ linear and branched alkylsulfonyl groups and C$_1$-C$_6$ linear, branched, and C$_3$-C$_6$ cyclic alkyl groups (optionally substituted with 1-2 groups independently selected from oxo, hydroxy, amido, and C$_1$-C$_6$ linear and branched alkylsulfonyl groups),
  hydroxy,
  oxo,
  cyano,
  carboxylic acid,
  carbamate optionally substituted with 1-2 groups independently selected from C$_1$-C$_6$ linear, branched, and C$_3$-C$_6$ cyclic alkyl groups,
  halogen,
  amido optionally substituted with 1-2 groups independently selected from C$_1$-C$_6$ linear, branched, and cyclic alkyl groups (e.g., C$_1$-C$_6$ linear, C$_3$-C$_6$ branched, and C$_3$-C$_6$ cyclic alkyl groups) and C$_1$-C$_6$ linear, branched, and cyclic hydroxyalkyl groups (e.g., C$_1$-C$_6$ linear, C$_3$-C$_6$ branched, and C$_3$-C$_6$ cyclic hydroxyalkyl groups),
  C$_3$-C$_6$ cyclic alkyl groups optionally substituted with 1-2 groups independently selected from halogen, C$_1$-C$_6$ linear and branched alkoxy groups, and hydroxy,
  C$_1$-C$_6$ linear and branched alkoxy groups optionally substituted with hydroxy,
  C$_1$-C$_6$ linear and branched alkylsulfonyl groups,
  aryl optionally substituted with 1-2 groups independently selected from halogen, hydroxy, and C$_1$-C$_6$ linear and branched alkyl groups optionally substituted with 1-2 groups independently selected from hydroxy and C$_1$-C$_6$ linear and branched alkoxy groups,
  4- to 10-membered heterocyclyl optionally substituted with 1-2 groups independently selected from halogen groups, oxo, hydroxy, and C$_1$-C$_6$ linear and branched alkyl groups optionally substituted with 1-2 groups independently selected from hydroxy and C$_1$-C$_6$ linear and branched alkoxy groups, and
  4- to 10-membered heteroaryl optionally substituted with 1-3 groups independently selected from halogen groups, oxo, hydroxy, C$_1$-C$_6$ linear, branched, and C$_3$-C$_6$ cyclic alkyl groups optionally substituted with 1-3 groups independently selected from halogen, hydroxy, and C$_1$-C$_6$ linear and branched alkoxy groups, and amido groups optionally substituted with 1-2 groups independently selected from C$_1$-C$_6$ linear, branched, and C$_3$-C$_6$ cyclic alkyl groups, or R$^3$ and R$^4$, together with the nitrogen atom to which they are attached, form a 4- to 10-membered heterocyclyl or heteroaryl optionally substituted with 1-3 groups independently selected from:
  amino optionally substituted with 1-2 groups independently selected from C$_1$-C$_6$ linear, branched, and C$_3$-C$_6$ cyclic alkyl groups, which are optionally substituted with oxo, halogen,
hydroxy,
oxo,
$C_1$-$C_6$ linear, branched, and $C_3$-$C_6$ cyclic alkyl groups optionally substituted with 1-2 groups independently selected from hydroxy, amino, and $C_1$-$C_6$ linear and branched alkoxy groups, and
amide optionally substituted with 1-2 groups independently selected from $C_1$-$C_6$ linear, branched, and $C_3$-$C_6$ cyclic alkyl groups.

In some embodiments, $R^5$ is selected from hydrogen and $C_1$-$C_3$ linear and branched alkyl groups.

In some embodiments, $R^3$ and $R^4$ are independently selected from:
hydrogen,
$C_1$-$C_6$ linear and branched alkylsulfonyl groups optionally substituted with amino (e.g., optionally substituted with one amino group),
$C_1$-$C_6$ linear and branched alkoxy groups optionally substituted with 1-4 groups independently selected from hydroxy, amino, halogen, and oxo,
$C_1$-$C_3$ linear and branched aminoalkyl groups optionally substituted with 1-2 groups independently selected from amido,
$C_3$-$C_6$ cyclic alkyl optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with a $C_1$-$C_6$ linear or branched alkyl group, and
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups,
3- to 6-membered heterocyclyl optionally substituted with 2-3 groups independently selected from:
halogen,
oxo,
hydroxy,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
3- to 6-membered heteroaryl optionally substituted with 1-2 groups independently selected from amino, hydroxy, oxo, and $C_1$-$C_6$ linear alkyl groups optionally substituted with 1-3 groups independently selected from halogen and amino,
$C_1$-$C_6$ linear and branched alkyl groups optionally substituted with 1-4 groups independently selected from:
amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
hydroxy,
oxo,
cyano,
carboxylic acid,
carbamate optionally substituted with 1-2 groups independently selected from $C_1$-$C_6$ linear, branched, and $C_3$-$C_6$ cyclic alkyl groups,
halogen,
amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
$C_3$-$C_6$ cyclic alkyl groups optionally substituted with 1-2 groups independently selected from halogen, $C_1$-$C_6$ linear and branched alkoxy groups, and hydroxy,
$C_1$-$C_6$ linear and branched alkoxy groups optionally substituted with hydroxy,
$C_1$-$C_6$ linear and branched alkylsulfonyl groups,
aryl optionally substituted with 1-2 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and
4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl groups,
or $R^3$ and $R^4$, together with the nitrogen atom to which they are attached, form a 4- to 10-membered heterocyclyl or heteroaryl optionally substituted with 1-3 groups independently selected from:
amino optionally substituted with 1-2 groups independently selected from $C_1$-$C_6$ linear, branched, and $C_3$-$C_6$ cyclic alkyl groups, which are optionally substituted with oxo,
halogen,
hydroxy,
oxo, $C_1$-$C_6$ linear, branched, and $C_3$-$C_6$ cyclic alkyl groups optionally substituted with 1-2 groups independently selected from hydroxy, amino, and $C_1$-$C_6$ linear and branched alkoxy groups, and amide optionally substituted with 1-2 groups independently selected from $C_1$-$C_6$ linear, branched, and $C_3$-$C_6$ cyclic alkyl groups; and $R^5$ is selected from hydrogen and $C_1$-$C_3$ linear and branched alkyl groups.

In one aspect of the disclosure, the at least one compound, deuterated derivative, or pharmaceutically acceptable salt is chosen from compounds of Formulae I-A, I-B, I-C, I-D, I-E, and I-F, deuterated derivatives of those compounds, and pharmaceutically acceptable salts of any of the foregoing. In one aspect of the disclosure, the at least one compound, reiterated derivative, or pharmaceutically acceptable salt is chosen from Compounds 1 to 456, deuterated derivatives of those compounds, and pharmaceutically acceptable salts of any of the foregoing.

In some embodiments, the disclosure provides pharmaceutical compositions comprising at least one compound, deuterated derivative, or pharmaceutically acceptable salt chosen from compounds of Formulae I, I-A, I-B, I-C, I-D, I-E, and I-F, deuterated derivatives of those compounds, and pharmaceutically acceptable salts of any of the foregoing. In some embodiments, the pharmaceutical compositions may comprise at least one compound, deuterated derivative, or pharmaceutically acceptable salt chosen from Compounds 1 to 456, deuterated derivatives of those compounds, and pharmaceutically acceptable salts of any of the foregoing. These compositions may further include at least one additional active pharmaceutical ingredient and/or at least one carrier.

Another aspect of the disclosure provides methods of treating FSGS and/or NDKD comprising administering to a subject in need thereof, at least one compound, deuterated derivative, or pharmaceutically acceptable salt chosen from compounds of Formulae I, I-A, I-B, I-C, I-D, I-E, and I-F, deuterated derivatives of those compounds, and pharmaceutically acceptable salts of any of the foregoing or a pharmaceutical composition comprising the at least one compound, deuterated derivative, or pharmaceutically acceptable salt. In some embodiments, the methods comprise administering at least one compound, deuterated derivative, or pharmaceutically acceptable salt chosen from Compounds 1 to 456, deuterated derivatives of those compounds, and pharmaceutically acceptable salts of any of the foregoing or a pharmaceutical composition comprising the at least one compound, deuterated derivative, or pharmaceutically acceptable salt.

In some embodiments, the methods of treatment include administration of at least one additional active agent to the subject in need thereof, either in the same pharmaceutical composition as the at least one compound, deuterated derivative, or pharmaceutically acceptable salt chosen from compounds of Formulae I, I-A, I-B, I-C, I-D, I-E, and I-F, deuterated derivatives of those compounds, and pharmaceutically acceptable salts of any of the foregoing. Alternatively, the additional active agent and the at least one compound, deuterated derivative, or pharmaceutically acceptable salt may be administered as separate pharmaceutical compositions. In some embodiments, the methods comprise administering at least one compound, deuterated derivative, or pharmaceutically acceptable salt chosen from Compounds 1 to 456, deuterated derivatives of those compounds, and pharmaceutically acceptable salts of any of the foregoing with at least one additional active agent either in the same pharmaceutical composition or in separate pharmaceutical compositions.

Also provided are methods of inhibiting APOL1, comprising administering to a subject in need thereof, at least one compound, deuterated derivative, or pharmaceutically acceptable salt chosen from compounds of Formulae I, I-A, I-B, I-C, I-D, I-E, and I-F, deuterated derivatives thereof, and pharmaceutically acceptable salts of any of the foregoing or a pharmaceutical composition comprising the at least one compound, deuterated derivative, or pharmaceutically acceptable salt. In some embodiments, the methods of inhibiting APOL1 comprise administering at least one compound, deuterated derivative, or pharmaceutically acceptable salt chosen from Compounds 1 to 456, deuterated derivatives thereof, and pharmaceutically acceptable salts of any of the foregoing or a pharmaceutical composition comprising the at least one compound, deuterated derivative, or pharmaceutically acceptable salt.

BRIEF DESCRIPTION OF THE DRAWINGS

FIG. 1 shows the plate map for assay ready plates for dose response (10 point dose response, 100 µM highest final assay, concentration in 20 µL, 2.5-fold serial dilution with total DMSO volume of 200 nL).

DEFINITIONS

The term "APOL1," as used herein, means apolipoprotein L1 protein, and the term "APOL1" means apolipoprotein L1 gene.

As used herein, the term "APOL1 mediated kidney disease" refers to a disease or condition that impairs kidney function and can be attributed to APOL1. In some embodiments, APOL1 mediated kidney disease is associated with patients having two APOL1 risk alleles, e.g., patients who are homozygous or compound heterozygous for the G1 or G2 alleles. In some embodiments, the APOL1 mediated kidney disease is chosen from ESKD, NDKD, FSGS, HIV-associated nephropathy, arterionephrosclerosis, lupus nephritis, microalbuminuria, and chronic kidney disease.

The term "FSGS," as used herein, means focal segmental glomerulosclerosis, which is a disease of the podocyte (glomerular visceral epithelial cells) responsible for proteinuria and progressive decline in kidney function. In some embodiments, FSGS is associated with two APOL1 risk alleles.

The term "NDKD," as used herein, means non-diabetic kidney disease, which is characterized by severe hypertension and progressive decline in kidney function. In some embodiments, NDKD is associated with two APOL1 risk alleles.

The terms "ESKD" and "ESRD" are used interchangeably herein to refer to end stage kidney disease or end stage renal disease. ESKD/ESRD is the last stage of kidney disease, i.e., kidney failure, and means that the kidneys have stopped working well enough for the patient to survive without dialysis or a kidney transplant. In some embodiments, ESKD/ESRD is associated with two APOL1 risk alleles.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted," whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer," as used herein, refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), or at least 6600 (99% deuterium incorporation).

The term "isotopic enrichment factor," as used herein, means the ratio between the isotopic abundance and the natural abundance of a specified isotope.

The term "alkyl" or "aliphatic," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic that has a single point of attachment to the rest of the molecule. Unless otherwise specified, alkyl groups contain 1 to 20 alkyl carbon atoms. In some embodiments, alkyl groups contain 1 to 10 aliphatic carbon atoms. In some embodiments, alkyl groups contain 1 to 8 aliphatic carbon atoms. In some embodiments, alkyl groups contain 1 to 6 alkyl carbon atoms, and in some embodiments, alkyl groups contain 1 to 4 alkyl carbon atoms, and in yet other embodiments, alkyl groups contain 1 to 3 alkyl carbon atoms. Non-limiting examples of alkyl groups include, but are not limited to, linear or branched, and substituted or unsubstituted alkyl. In some embodiments, alkyl groups are substituted. In some embodiments, alkyl groups are unsubstituted. In some embodiments, alkyl groups are straight-chain. In some embodiments, alkyl groups are branched.

The terms "cycloalkyl," "carbocycle," or "cyclic alkyl" refer to a fused, spirocyclic, or monocyclic $C_{3-8}$ hydrocarbon or a spirocyclic, bicyclic, bridged bicyclic, tricyclic, or bridged tricyclic $C_{4-14}$ hydrocarbon that is completely saturated or that contains one or more units of unsaturation, but which is not aromatic, wherein any individual ring in said bicyclic ring system has 3 to 7 members. Suitable cycloalkyl groups include, but are not limited to, cycloalkyl, bicyclic cycloalkyl (e.g., decalin), bridged bicycloalkyl such as norbornyl, [1.1.1]bicyclo-pentyl, or [2.2.2]bicyclo-octyl, or bridged tricyclic such as adamantyl. In some embodiments, cyclogroups are substituted. In some embodiments, cyclogroups are unsubstituted.

The term "heteroalkyl," as used herein, means aliphatic groups wherein one, two, or three carbon atoms are independently replaced by one or more of oxygen, sulfur, and/or nitrogen. In some embodiments, one or two carbon atoms may be replaced by phosphorus and/or silicon. Heteroalkyl groups may be substituted or unsubstituted, branched or unbranched, cyclic or acyclic, and include "heterocycle," "heterocyclyl," or "heterocyclic" groups. In some embodiments, the heteroalkyl is an aminoalkyl. In some embodiments, the heteroalkyl is a thioalkyl. In some embodiments, the heteroalkyl is an alkoxy. In some embodiments, the heteroalkyl has a combination of two or more heteroatoms independently selected from oxygen, nitrogen, phosphorus, and sulfur.

The term "alkenyl," as used herein, means a straight-chain (i.e., unbranched), branched, substituted, or unsubstituted hydrocarbon chain that contains one or more units of saturation, or a monocyclic hydrocarbon or bicyclic hydrocarbon that contains one or more units of unsaturation, but which is not aromatic (referred to herein as, "cyclic alkenyl"). In some embodiments, alkenyl groups are substituted. In some embodiments, alkenyl groups are unsubstituted. In some embodiments, alkenyl groups are straight-chain. In some embodiments, alkenyl groups are branched.

The term "heterocycle," "heterocyclyl," or "heterocyclic," as used herein, means non-aromatic, monocyclic, bicyclic, or tricyclic ring systems in which one or more ring members is an independently chosen heteroatom. In some embodiments, the "heterocycle," "heterocyclyl," or "heterocyclic" group has 3 to 14 ring members in which one or more ring members is a heteroatom independently chosen from oxygen, sulfur, nitrogen, phosphorus, silicon, and boron. In some embodiments, each ring in a bicyclic or tricyclic ring system contains 3 to 7 ring members. In some embodiments, the heterocycle has at least one unsaturated carbon-carbon bond. In some embodiments, the heterocycle has at least one unsaturated carbon-nitrogen bond. In some embodiments, the heterocycle has one to three heteroatoms independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has one heteroatom that is a sulfur atom. In some embodiments, the heterocycle has two heteroatoms that are each independently selected from nitrogen, sulfur, and oxygen. In some embodiments, the heterocycle has three heteroatoms that are each independently selected from nitrogen and oxygen. In some embodiments, heterocycles are substituted. In some embodiments, heterocycles are unsubstituted.

The term "heteroatom" means one or more of oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring, for example N (as in 3,4-dihydro-2H-pyrrolyl), NH (as in pyrrolidinyl), or NR$^+$ (as in N-substituted pyrrolidinyl)).

The term "unsaturated," as used herein, means that a moiety has one or more units or degrees of unsaturation. Unsaturation is the state in which not all of the available valance bonds in a compound are satisfied by substituents and thus the compound contains double or triple bonds.

The term "alkoxy" or "thioalkyl," as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. In some embodiments, one of the two carbon atoms that the oxygen or sulfur atom is linked between is not part of the alkoxy or thioalkyl groups, such as, e.g., when an "alkoxy" group is methoxy, ethoxy, or the like. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl. In some embodiments, "alkoxy" and/or "thioalkyl" groups are substituted. In some embodiments, "alkoxy" and/or "thioalkyl" groups are unsubstituted.

The terms "haloalkyl" and "haloalkoxy," as used herein, means a linear or branched alkyl or alkoxy, as the case may be, which is substituted with one or more halogen atoms. Non-limiting examples of haloalkyl groups include —CHF$_2$, —CH$_2$F, —CF$_3$, —CF$_2$—, and perhaloalkyls, such as —CF$_2$CF$_3$. Non-limiting examples of haloalkoxy groups include —OCHF$_2$, —OCH$_2$F, —OCF$_3$, and —OCF$_2$—.

The term "hydroxyalkyl" means an alkyl group which is substituted with one or more hydroxy groups.

The term "halogen" includes F, Cl, Br, and I, i.e., fluoro, chloro, bromo, and iodo, respectively.

The term "aminoalkyl" means an alkyl group which is substituted with or contains an amino group. An aminoalkyl group may be linear or branched.

As used herein, the term "alkylsulfonyl" refers to an alkyl group, as previously defined, wherein one carbon atom of the alkyl group, and the carbon atom's substituents, are replaced by a sulfur atom, and wherein the sulfur atom is further substituted with two oxo groups. An alkylsulfonyl group may be linear or branched. In some embodiments, alkylsulfonyl groups are substituted at the alkyl portion of the alkylsulfonyl group. In some embodiments, alkylsulfonyl groups are unsubstituted at the alkyl portion of the alkylsulfonyl group.

As used herein, an "amino" refers to a group which is a primary, secondary, or tertiary amine.

As used herein, a "carbonyl" group refers to C=O.

As used herein, a "cyano" or "nitrile" group refer to —CN.

As used herein, a "hydroxy" group refers to —OH.

As used herein, a "thiol" group refers to —SH.

As used herein, "tert" and "t-" each refer to tertiary.

As used herein, "Me" refers to methyl.

As used herein, an "amido" group refers to a carbonyl group, as previously defined, wherein the carbon of the carbonyl is bonded to an amino group, as previously defined. When a chemical group is said to be substituted by an amido group, that chemical group may be bonded to the carbonyl carbon or to the amino nitrogen of the amido group.

As used herein, a "carbamate" group refers to a carbonyl group, as previously defined, wherein the carbon of the carbonyl group is bonded to an amino group, as previously defined, and a divalent oxygen. When a chemical group is said to be substituted by a carbamate group, that chemical group may be bonded to the divalent oxygen or to the amino nitrogen of the carbamate group.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Non-limiting examples of aromatic groups include aryl and heteroaryl groups.

The term "aryl," used alone or as part of a larger moiety as in "arylalkyl," "arylalkoxy," or "aryloxyalkyl," refers to monocyclic, bicyclic, and tricyclic ring systems having a total of five to fourteen ring members, wherein at least one ring in the system is aromatic and wherein each ring in a bicyclic or tricyclic ring system contains 3 to 7 ring members. The term "aryl" also refers to heteroaryl ring systems as defined herein below. Non-limiting examples of aryl groups include phenyl rings. In some embodiments, aryl groups are substituted. In some embodiments, aryl groups are unsubstituted.

The term "heteroaryl," used alone or as part of a larger moiety as in "heteroarylalkyl" or "heteroarylalkoxy," refers to monocyclic, bicyclic, and tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. In some embodiments, heteroaryl groups are substituted. In some embodiments, heteroaryl groups have one or more heteroatoms chosen from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted.

Non-limiting examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis*, 3rd Edition (John Wiley & Sons, New York, 1999) and 4$^{th}$ Edition (John Wiley & Sons, New Jersey, 2014).

Non-limiting examples of suitable solvents that may be used in this disclosure include, but are not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include, but are not limited to, 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2$EtN; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences*, 1977, 66, 1 to 19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

The terms "patient" and "subject" are used interchangeably and refer to an animal, including a human.

The terms "effective dose" and "effective amount" are used interchangeably herein and refer to that amount of compound that produces the desired effect for which it is administered (e.g., improvement in symptoms of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates as used herein, include, but are not limited to the following: complete or partial remission, lower risk of kidney failure (e.g., ESRD), and disease-related complications (e.g., edema, susceptibility to infections, or thromboembolic events). Improvements in or lessening the severity of any of these symptoms can be readily assessed according to methods and techniques known in the art or subsequently developed. In some embodiments, the terms "treat," "treating," and "treatment" refer to the lessening of severity of one or more symptoms of FSGS and/or NDKD.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. In some embodiments, the term "about" refers to a value±10%, ±8%, ±6%, ±5%, ±4%, ±2%, or ±1% of a referenced value.

As used herein, the term "ambient conditions" means room temperature, open air, and uncontrolled humidity conditions.

The terms "selected from" and "chosen from" are used interchangeably herein.

The compound of Formulae I, I-A, I-B, I-C, I-D, I-E, and I-F, a deuterated derivative thereof, or a pharmaceutically acceptable salt of any of the foregoing may be administered once daily, twice daily, or three times daily, for example, for the treatment of FSGS. In some embodiments, the compound of Formulae I, I-A, I-B, I-C, I-D, I-E, and I-F, deuterated derivative thereof, and pharmaceutically acceptable salt of any of the foregoing is chosen from Compounds 1 to 456, deuterated derivatives thereof, and pharmaceutically acceptable salts of any of the foregoing. In some embodiments, at least one compound, deuterated derivative, or pharmaceutically acceptable salt chosen from compounds of Formulae I, I-A, I-B, I-C, I-D, I-E, and I-F, deuterated derivatives thereof, and pharmaceutically acceptable salts of any of the foregoing is administered once daily. In some embodiments, at least one compound, deuterated derivative, or pharmaceutically acceptable salt chosen from Compounds 1 to 456, deuterated derivatives thereof, and pharmaceutically acceptable salts of any of the foregoing is administered once daily. In some embodiments, at least one compound, deuterated derivative, or pharmaceutically acceptable salt chosen from compounds of Formulae I, I-A, I-B, I-C, I-D, I-E, and I-F, deuterated derivatives thereof, and pharmaceutically acceptable salts of any of the foregoing is administered twice daily. In some embodiments, at least one compound, deuterated derivative, or pharmaceutically acceptable salt chosen from Compounds 1 to 456, deuterated derivatives thereof, and pharmaceutically acceptable salts of any of the foregoing is administered twice daily. In some embodiments, at least one compound, deuterated derivative, or pharmaceutically acceptable salt chosen from compounds of Formulae I, I-A, I-B, I-C, I-D, I-E, and I-F, deuterated derivatives thereof, and pharmaceutically acceptable salts of any of the foregoing is administered three times daily. In some embodiments, at least one compound, deuterated derivative, or pharmaceutically acceptable salt chosen from Compounds 1 to 456, deuterated derivatives thereof, and pharmaceutically acceptable salts of any of the foregoing is administered three times daily.

In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of the at least one compound, deuterated derivative, or pharmaceutically acceptable salt chosen from compounds of Formulae I, I-A, I-B, I-C, I-D, I-E, and I-F, deuterated derivatives thereof, and pharmaceutically acceptable salts of any of the foregoing is administered once daily, twice daily, or three times daily. In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of the at least one compound, deuterated derivative, or pharmaceutically acceptable salt chosen from Compounds 1 to 456, deuterated derivatives thereof, and pharmaceutically acceptable salts of any of the foregoing is administered once daily, twice daily, or three times daily.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "10 mg of at least one compound chosen from compounds of Formula I, . . . and pharmaceutically acceptable salts thereof" includes 10 mg of a compound of Formula I, and a concentration of a pharmaceutically acceptable salt of that compound of Formula I that is equivalent to 10 mg of that compound of Formula I.

Compounds and Compositions

In some embodiments of the disclosure, the compound, deuterated derivative, or pharmaceutically acceptable salt for treating APOL1 mediated diseases, such as FSGS and/or NDKD, is selected from compounds of Formula I:

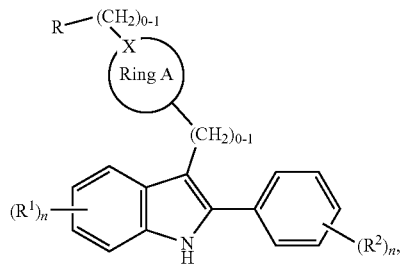

deuterated derivatives thereof, and pharmaceutically acceptable salts of any of the foregoing, wherein:

(i) R is selected from hydrogen, $-NR^3R^4$, $-C(O)R^3$, $-OR^3$, $-NR^5C(O)R^3$, $-NR^5C(O)OR^3$, $-NR^5SO_2R^3$, and $-NR^5SO_2NR^3R^4$;

(ii) X is selected from N and $CR^X$;

(iii) $R^X$ is absent or is selected from hydrogen, hydroxy, halogen, and $C_1$-$C_3$ linear and branched alkyl groups, wherein, when $R^X$ is absent, X is a bridgehead atom;

(iv) Ring A is a 3- to 7-membered ring, wherein the ring is a cyclic alkyl or a heterocycle;

(v) each n is independently selected from 0, 1, 2, and 3;

(vi) each $R^1$ is independently selected from:
hydrogen,
halogen,
hydroxy,
amino,
$C_1$-$C_6$ linear and branched alkyl groups,
$C_1$-$C_6$ linear, branched, and cyclic alkoxy groups, and
$C_1$-$C_6$ linear and branched haloalkyl groups;

(vii) each $R^2$ is independently selected from:
hydrogen,
halogen,
hydroxy,
amino,
cyano,
$C_1$-$C_4$ linear, branched, and cyclic alkyl groups (e.g., $C_1$-$C_4$ linear, $C_3$-$C_4$ branched, and $C_3$-$C_4$ cyclic alkyl groups), $C_1$-$C_4$ linear, branched, and cyclic hydroxyalkyl groups (e.g., $C_1$-$C_4$ linear, $C_3$-$C_4$ branched, and $C_3$-$C_4$ cyclic hydroxyalkyl groups), $C_1$-$C_4$ linear, branched, and cyclic alkoxy groups (e.g., $C_1$-$C_4$ linear, $C_2$-$C_4$ branched, and $C_1$-$C_4$ cyclic alkoxy groups), $C_1$-$C_4$ linear, branched, and cyclic haloalkyl groups (e.g., $C_1$-$C_4$ linear, $C_3$-$C_4$ branched, and $C_3$-$C_4$ cyclic haloalkyl groups), and $C_1$-$C_4$ linear, branched, and cyclic haloalkoxy groups (e.g., $C_1$-$C_4$ linear, $C_2$-$C_4$ branched, and $C_1$-$C_4$ cyclic haloalkoxy groups);

(viii) $R^3$ and $R^4$ are independently selected from:
hydrogen, $C_1$-$C_6$ linear and branched alkylsulfonyl groups optionally substituted with amino (e.g., optionally substituted with one amino group), $C_1$-$C_6$ linear and branched alkoxy groups optionally substituted with 1-4 groups independently selected from hydroxy, amino, halogen, and oxo, $C_1$-$C_3$ linear and branched aminoalkyl groups optionally substituted with 1-2 groups independently selected from amido, $C_3$-$C_6$ cyclic alkyl optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with a $C_1$-$C_6$ linear or branched alkyl group, and
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups, 3- to 6-membered heterocyclyl optionally substituted with 1-3 groups independently selected from:
halogen,
oxo,
hydroxy,
amido optionally substituted with $C_1$-$C_3$ alkyl,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups,
$C_1$-$C_3$ hydroxyalkyl and $C_1$-$C_3$ haloalkyl, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups, 3- to 10-membered heteroaryl optionally substituted with 1-2 groups independently selected from amino, hydroxy, oxo, and $C_1$-$C_6$ linear alkyl groups optionally substituted with 1-3 groups independently selected from halogen and amino, $C_1$-$C_6$ linear and branched alkyl groups optionally substituted with 1-4 groups independently selected from:
$C_1$-$C_4$ alkyl groups,
amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
hydroxy,
oxo,
cyano,
carboxylic acid,
carbamate optionally substituted with 1-2 groups independently selected from $C_1$-$C_6$ linear, branched, and $C_3$-$C_6$ cyclic alkyl groups,
halogen,
amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
$C_3$-$C_6$ cyclic alkyl groups optionally substituted with 1-2 groups independently selected from halogen, $C_1$-$C_6$ linear and branched alkoxy groups, and hydroxy,
$C_1$-$C_6$ linear and branched alkoxy groups optionally substituted with hydroxy,
$C_1$-$C_6$ linear and branched alkylsulfonyl groups,
aryl optionally substituted with 1-2 groups independently selected from halogen, hydroxy, amido optionally substituted with $C_1$-$C_3$ alkyl, and $C_1$-$C_6$ linear and branched alkyl groups optionally substituted with 1-2 groups independently selected from hydroxy and $C_1$-$C_6$ linear and branched alkoxy groups, 4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and 4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl groups, or $R^3$ and $R^4$, together with the nitrogen atom to which they are attached, form a 3- to 10-membered heterocyclyl or heteroaryl optionally substituted with 1-3 groups independently selected from:

amino optionally substituted with 1-2 groups independently selected from $C_1$-$C_6$ linear, branched, and $C_3$-$C_6$ cyclic alkyl groups, which are optionally substituted with oxo,
halogen,
hydroxy,
oxo,
$C_1$-$C_6$ linear, branched, and $C_3$-$C_6$ cyclic alkyl groups optionally substituted with 1-2 groups independently selected from hydroxy, amino, and $C_1$-$C_6$ linear and branched alkoxy groups,
$C_1$-$C_3$ linear or branched hydroxyalkyl, and
amide optionally substituted with 1-2 groups independently selected from $C_1$-$C_6$ linear, branched, and $C_3$-$C_6$ cyclic alkyl groups; and (ix) $R^5$ is selected from hydrogen, hydroxy, halogen, and $C_1$-$C_3$ linear and branched alkyl groups.

In some embodiments, when R is —C(O)$R^3$, X is N or $R^3$ is not bonded to the rest of the molecule through a nitrogen atom. In some embodiments, when R is —C(O)$R^3$, X is N. In some embodiments, when R is —C(O)$R^3$, $R^3$ is not bonded to the rest of the molecule through a nitrogen atom. In some embodiments, when R is —C(O)$R^3$, X is N and $R^3$ is not bonded to the rest of the molecule through a nitrogen atom.

In some embodiments, $R^3$ and $R^4$ are independently selected from:
hydrogen,
$C_1$-$C_6$ linear and branched alkylsulfonyl groups optionally substituted with amino (e.g., optionally substituted with one amino group),
$C_1$-$C_6$ linear and branched alkoxy groups optionally substituted with 1-4 groups independently selected from hydroxy, amino, halogen, and oxo,
$C_1$-$C_3$ linear and branched aminoalkyl groups optionally substituted with 1-2 groups independently selected from amido,
$C_3$-$C_6$ cyclic alkyl optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with a $C_1$-$C_6$ linear or branched alkyl group, and
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups,
3- to 6-membered heterocyclyl optionally substituted with 2-3 groups independently selected from:
halogen,
oxo,
hydroxy,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
3- to 6-membered heteroaryl optionally substituted with 1-2 groups independently selected from amino, hydroxy, oxo, and $C_1$-$C_6$ linear alkyl groups optionally substituted with 1-3 groups independently selected from halogen and amino,
$C_1$-$C_6$ linear and branched alkyl groups optionally substituted with 1-4 groups independently selected from:
amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
hydroxy,
oxo,
cyano,
carboxylic acid,
carbamate optionally substituted with 1-2 groups independently selected from $C_1$-$C_6$ linear, branched, and $C_3$-$C_6$ cyclic alkyl groups,
halogen,
amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
$C_3$-$C_6$ cyclic alkyl groups optionally substituted with 1-2 groups independently selected from halogen, $C_1$-$C_6$ linear and branched alkoxy groups, and hydroxy,
$C_1$-$C_6$ linear and branched alkoxy groups optionally substituted with hydroxy,
$C_1$-$C_6$ linear and branched alkylsulfonyl groups,
aryl optionally substituted with 1-2 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and
4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl groups, or $R^3$ and $R^4$, together with the nitrogen atom to which they are attached, form a 4- to 10-membered heterocyclyl or heteroaryl optionally substituted with 1-3 groups independently selected from:
  amino optionally substituted with 1-2 groups independently selected from $C_1$-$C_6$ linear, branched, and $C_3$-$C_6$ cyclic alkyl groups, which are optionally substituted with oxo,
  halogen,
  hydroxy,
  oxo,
  $C_1$-$C_6$ linear, branched, and $C_3$-$C_6$ cyclic alkyl groups optionally substituted with 1-2 groups independently selected from hydroxy, amino, and $C_1$-$C_6$ linear and branched alkoxy groups, and
  amide optionally substituted with 1-2 groups independently selected from $C_1$-$C_6$ linear, branched, and $C_3$-$C_6$ cyclic alkyl groups.

In some embodiments, $R^5$ is selected from hydrogen and $C_1$-$C_3$ linear and branched alkyl groups.

In some embodiments, $R^3$ and $R^4$ are independently selected from:
  hydrogen,
  $C_1$-$C_6$ linear and branched alkylsulfonyl groups optionally substituted with amino (e.g., optionally substituted with one amino group),
  $C_1$-$C_6$ linear and branched alkoxy groups optionally substituted with 1-4 groups independently selected from hydroxy, amino, halogen, and oxo,
  $C_1$-$C_3$ linear and branched aminoalkyl groups optionally substituted with 1-2 groups independently selected from amido,
  $C_3$-$C_6$ cyclic alkyl optionally substituted with 1-2 groups independently selected from:
    halogen,
    hydroxy,
    oxo,
    amido,
    amino substituted with 1-2 groups independently selected from $C_1$-$C_6$ linear, branched, and $C_3$-$C_6$ cyclic alkyl groups,
    aryl optionally substituted with 1-2 groups independently selected from halogen,
    $C_1$-$C_6$ linear and branched alkoxy groups,
    carbamate optionally substituted with a $C_1$-$C_6$ linear or branched alkyl group, and
    $C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups,
  3- to 6-membered heterocyclyl optionally substituted with 2-3 groups independently selected from:
    halogen,
    oxo,
    hydroxy,
    $C_1$-$C_6$ linear and branched alkoxy groups optionally substituted with oxo,
    $C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups, and
    carbamate optionally substituted with 1-2 groups independently selected from $C_1$-$C_6$ linear, branched, and $C_3$-$C_6$ cyclic alkyl groups,
    aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
  3- to 6-membered heteroaryl optionally substituted with 1-2 groups independently selected from amino, hydroxy, oxo, and $C_1$-$C_6$ linear alkyl groups optionally substituted with 1-3 groups independently selected from halogen and amino,
  $C_1$-$C_6$ linear and branched alkyl groups optionally substituted with 1-4 groups independently selected from:
    amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
    hydroxy,
    oxo,
    cyano,
    carboxylic acid,
    carbamate optionally substituted with 1-2 groups independently selected from $C_1$-$C_6$ linear, branched, and $C_3$-$C_6$ cyclic alkyl groups,
    halogen,
    amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
    $C_3$-$C_6$ cyclic alkyl groups optionally substituted with 1-2 groups independently selected from halogen, $C_1$-$C_6$ linear and branched alkoxy groups, and hydroxy,
    $C_1$-$C_6$ linear and branched alkoxy groups optionally substituted with hydroxy,
    $C_1$-$C_6$ linear and branched alkylsulfonyl groups,
    aryl optionally substituted with 1-2 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
    4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and
    4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl groups,
or $R^3$ and $R^4$, together with the nitrogen atom to which they are attached, form a 4- to 10-membered heterocyclyl or heteroaryl optionally substituted with 1-3 groups independently selected from:

amino optionally substituted with 1-2 groups independently selected from $C_1$-$C_6$ linear, branched, and $C_3$-$C_6$ cyclic alkyl groups, which are optionally substituted with oxo, halogen, hydroxy, oxo, $C_1$-$C_6$ linear, branched, and $C_3$-$C_6$ cyclic alkyl groups optionally substituted with 1-2 groups independently selected from hydroxy, amino, and $C_1$-$C_6$ linear and branched alkoxy groups, and amide optionally substituted with 1-2 groups independently selected from $C_1$-$C_6$ linear, branched, and $C_3$-$C_6$ cyclic alkyl groups; and $R^5$ is selected from hydrogen and $C_1$-$C_3$ linear and branched alkyl groups.

In some embodiments, Ring A is selected from:

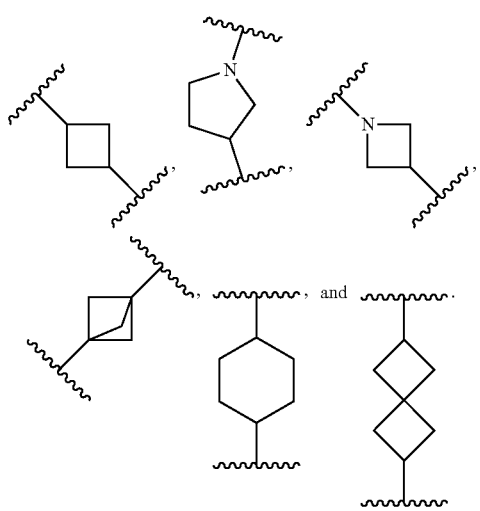

In some embodiments, the compound, deuterated derivative, or pharmaceutically acceptable salt is selected from compounds of Formulae:

I-A

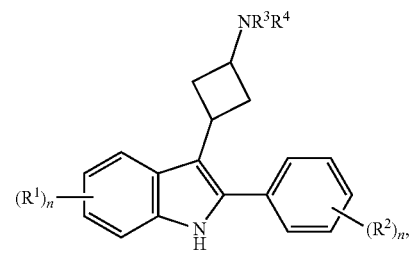

I-B

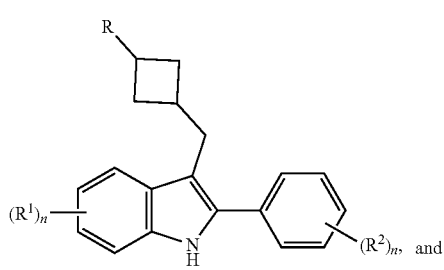

I-C

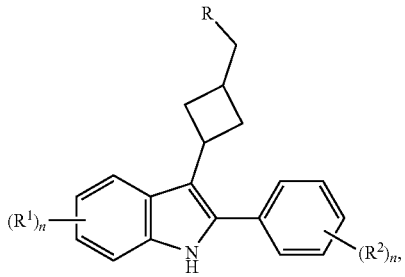

deuterated derivatives thereof, and pharmaceutically acceptable salts of any of the foregoing, wherein R, $R^1$, $R^2$, $R^3$, $R^4$, and n are as above for Formula I.

In some embodiments, each instance of the variable n in Formulae I, I-A, I-B, and I-C is 1 or 2.

In some embodiments, the compound, deuterated derivative, or pharmaceutically acceptable salt is selected from compounds of Formulae:

I-D

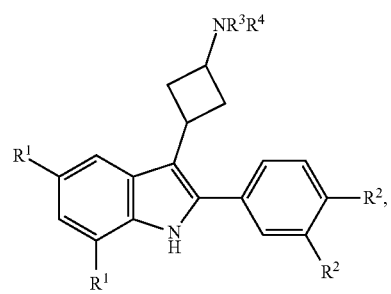

I-E

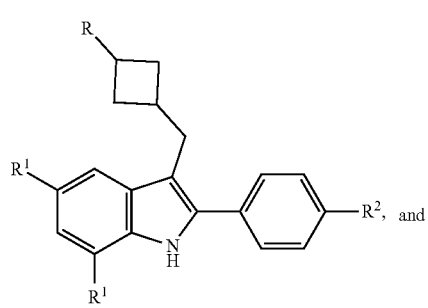

I-F

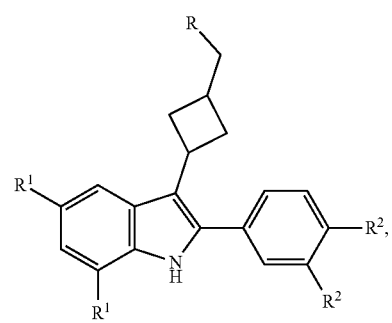

deuterated derivatives thereof, and pharmaceutically acceptable salts of any of the foregoing, wherein R, $R^1$, $R^2$, $R^3$, and $R^4$ are as above for Formula I.

In some embodiments, the compound of Formulae I, I-A, I-B, I-C, I-D, I-E, or I-F, deuterated derivative thereof, or pharmaceutically acceptable salt of any of the foregoing is selected from Compounds 1 to 456 depicted in Table 1, deuterated derivatives thereof, and pharmaceutically acceptable salts of any of the foregoing. A wavy line in a compound in Table 1 (i.e., ⌇ ) depicts a bond between two atoms and indicates a position of mixed stereochemistry for a collection of molecules, such as a racemic mixture, cis/trans isomers, or (E)/(Z) isomers.

TABLE 1

Compounds 1 to 456

TABLE 1-continued

Compounds 1 to 456

TABLE 1-continued
Compounds 1 to 456
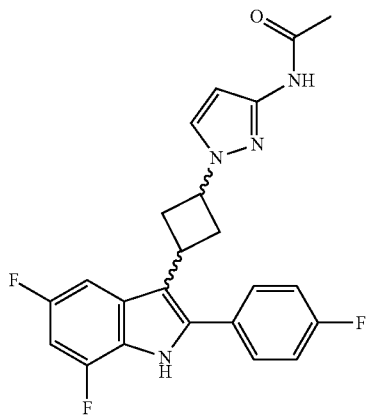 [SMILES: CC(=O)Nc1ccn(C2CC(c3c(-c4ccc(F)cc4)[nH]c4c(F)cc(F)cc34)C2)n1]
19
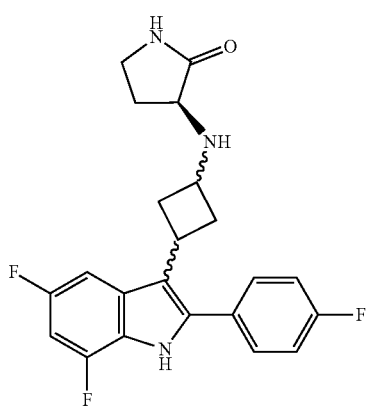 [SMILES: O=C1NCC[C@@H]1NC1CC(c2c(-c3ccc(F)cc3)[nH]c3c(F)cc(F)cc23)C1]
20
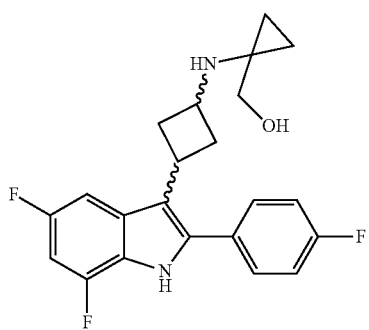 [SMILES: OCC1(NC2CC(c3c(-c4ccc(F)cc4)[nH]c4c(F)cc(F)cc34)C2)CC1]
21
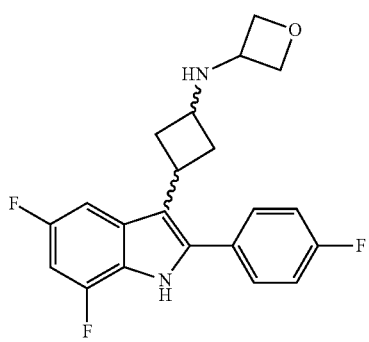 [SMILES: Fc1ccc(-c2[nH]c3c(F)cc(F)cc3c2C2CC(NC3COC3)C2)cc1]
22
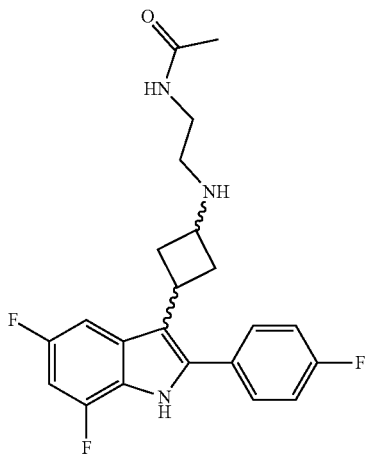 [SMILES: CC(=O)NCCNC1CC(c2c(-c3ccc(F)cc3)[nH]c3c(F)cc(F)cc23)C1]
23
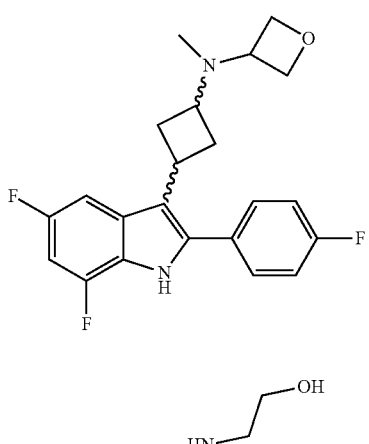
24
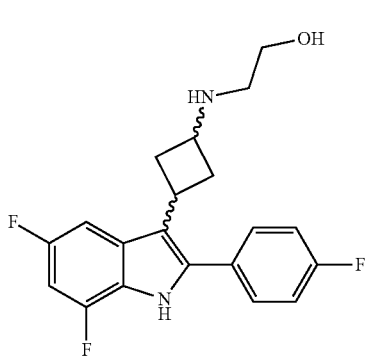 [SMILES: OCCNC1CC(c2c(-c3ccc(F)cc3)[nH]c3c(F)cc(F)cc23)C1]
25
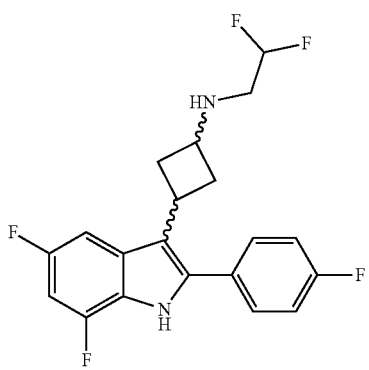 [SMILES: Fc1ccc(-c2[nH]c3c(F)cc(F)cc3c2C2CC(NCC(F)F)C2)cc1]
26

TABLE 1-continued
Compounds 1 to 456
27
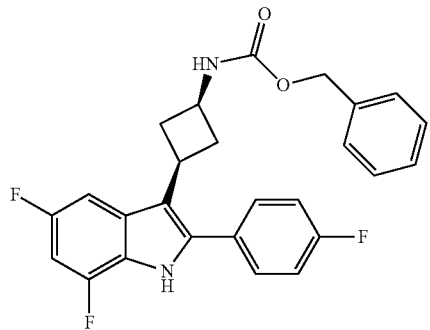 [SMILES: O=C(N[C@H]1C[C@@H](c2c(-c3ccc(F)cc3)[nH]c3c(F)cc(F)cc32)C1)OCc1ccccc1]
28
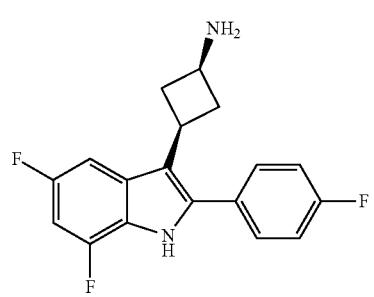 [SMILES: N[C@H]1C[C@@H](c2c(-c3ccc(F)cc3)[nH]c3c(F)cc(F)cc32)C1]
29
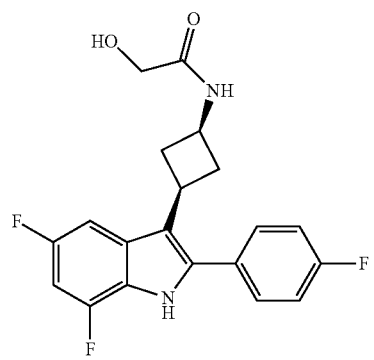 [SMILES: O=C(CO)N[C@H]1C[C@@H](c2c(-c3ccc(F)cc3)[nH]c3c(F)cc(F)cc32)C1]
30
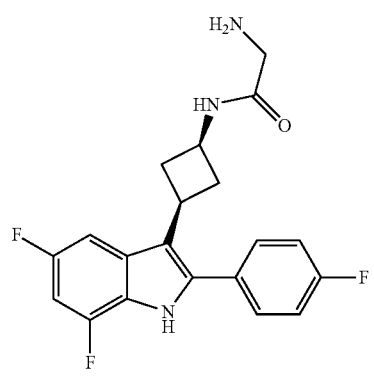 [SMILES: NCC(=O)N[C@H]1C[C@@H](c2c(-c3ccc(F)cc3)[nH]c3c(F)cc(F)cc32)C1]
31
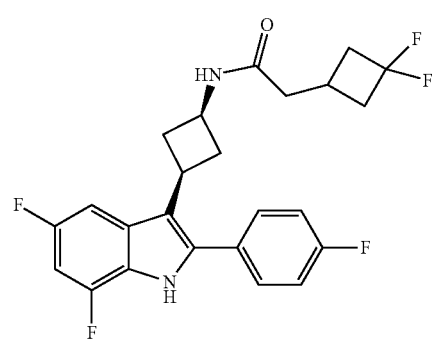 [SMILES: O=C(CC1CC(F)(F)C1)N[C@H]1C[C@@H](c2c(-c3ccc(F)cc3)[nH]c3c(F)cc(F)cc32)C1]
32
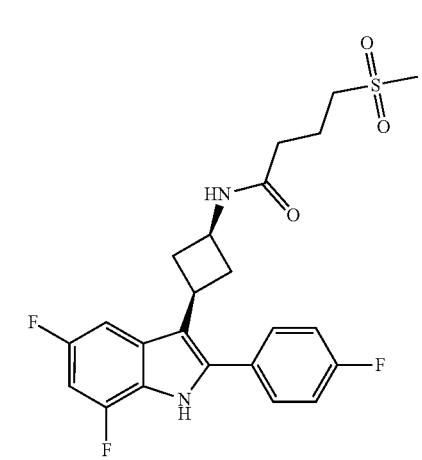 [SMILES: CS(=O)(=O)CCCC(=O)N[C@H]1C[C@@H](c2c(-c3ccc(F)cc3)[nH]c3c(F)cc(F)cc32)C1]
33
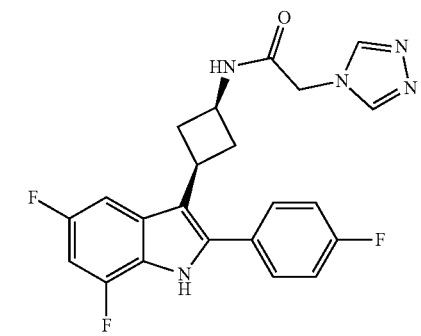 [SMILES: O=C(Cn1cnnc1)N[C@H]1C[C@@H](c2c(-c3ccc(F)cc3)[nH]c3c(F)cc(F)cc32)C1]
34
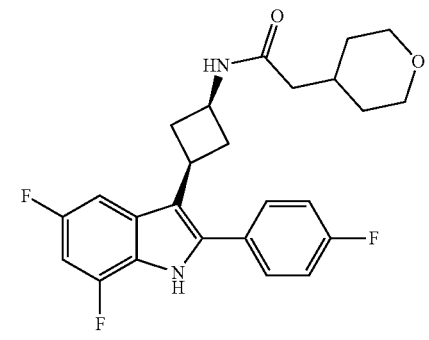

TABLE 1-continued
Compounds 1 to 456
35 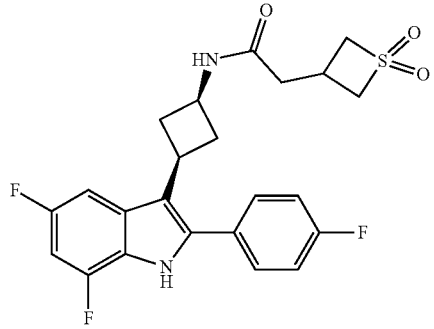 [SMILES: O=C(CC1CS(=O)(=O)C1)N[C@H]1C[C@@H](c2c(-c3ccc(F)cc3)[nH]c3c(F)cc(F)cc32)C1]
36 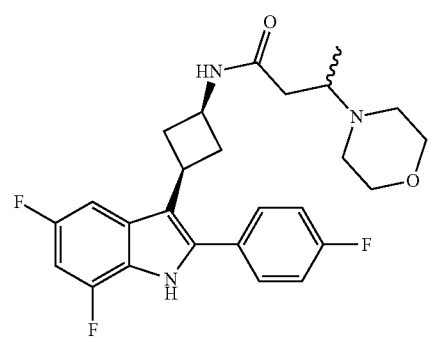 [SMILES: CC(CC(=O)N[C@H]1C[C@@H](c2c(-c3ccc(F)cc3)[nH]c3c(F)cc(F)cc32)C1)N1CCOCC1]
37 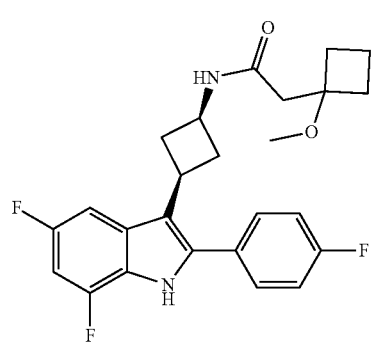 [SMILES: COC1(CC(=O)N[C@H]2C[C@@H](c3c(-c4ccc(F)cc4)[nH]c4c(F)cc(F)cc43)C2)CCC1]
38 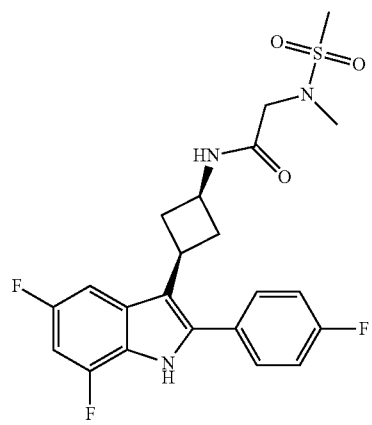 [SMILES: CN(CC(=O)N[C@H]1C[C@@H](c2c(-c3ccc(F)cc3)[nH]c3c(F)cc(F)cc32)C1)S(C)(=O)=O]
39 
40 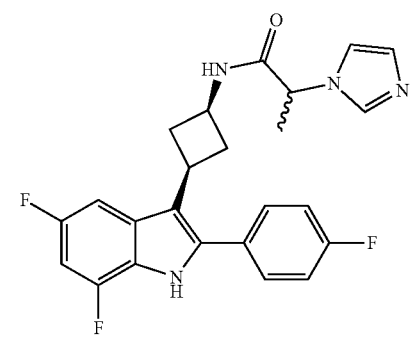 [SMILES: CC(C(=O)N[C@H]1C[C@@H](c2c(-c3ccc(F)cc3)[nH]c3c(F)cc(F)cc32)C1)n1ccnc1]
41 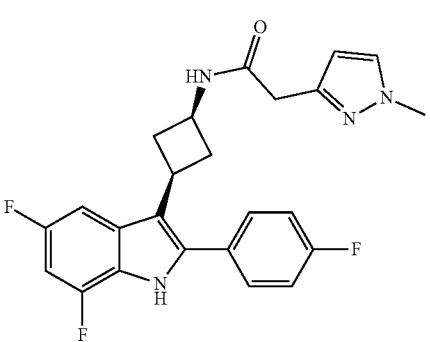 [SMILES: Cn1ccc(CC(=O)N[C@H]2C[C@@H](c3c(-c4ccc(F)cc4)[nH]c4c(F)cc(F)cc43)C2)n1]
42 

TABLE 1-continued
Compounds 1 to 456
43
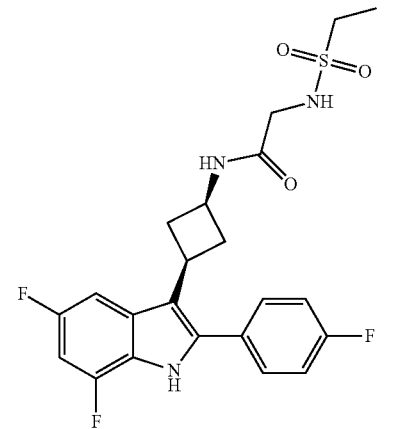 [SMILES: CCS(=O)(=O)NCC(=O)N[C@H]1C[C@@H](c2c(-c3ccc(F)cc3)[nH]c3c(F)cc(F)cc32)C1]
44
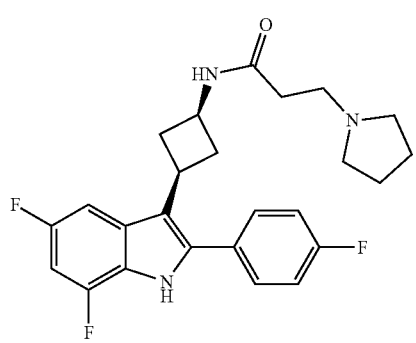 [SMILES: O=C(CCN1CCCC1)N[C@H]1C[C@@H](c2c(-c3ccc(F)cc3)[nH]c3c(F)cc(F)cc32)C1]
45
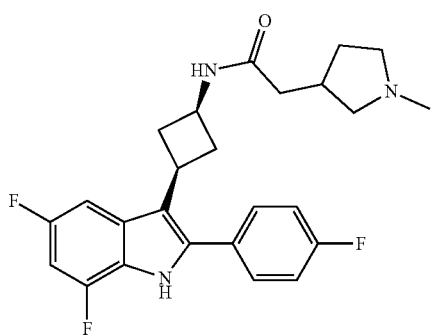
46
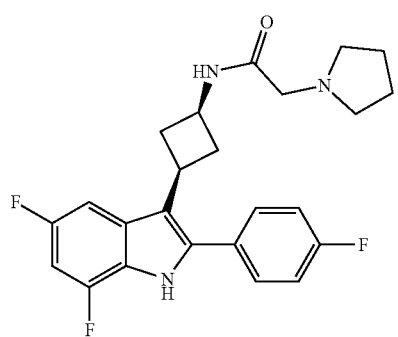 [SMILES: O=C(CN1CCCC1)N[C@H]1C[C@@H](c2c(-c3ccc(F)cc3)[nH]c3c(F)cc(F)cc32)C1]
TABLE 1-continued
Compounds 1 to 456
47
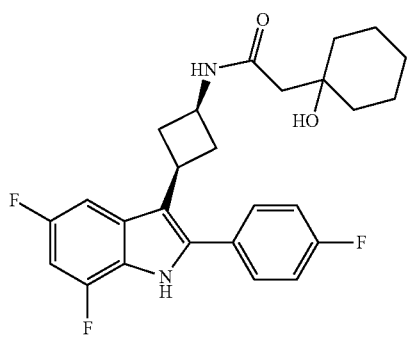 [SMILES: O=C(CC1(O)CCCCC1)N[C@H]1C[C@@H](c2c(-c3ccc(F)cc3)[nH]c3c(F)cc(F)cc32)C1]
48
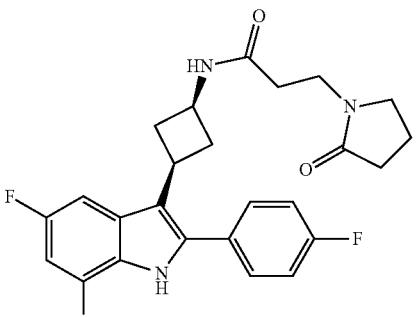
49
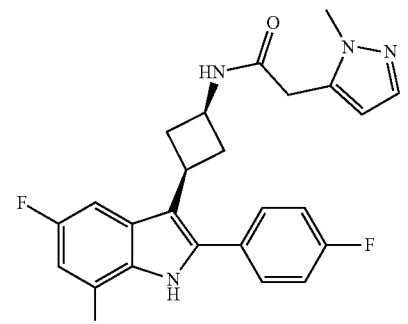
50
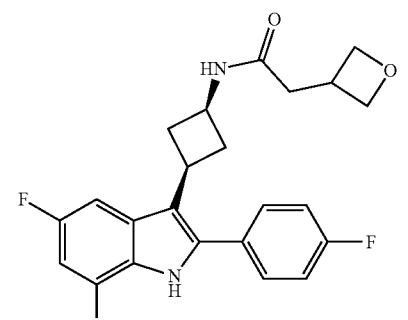

TABLE 1-continued
Compounds 1 to 456
51 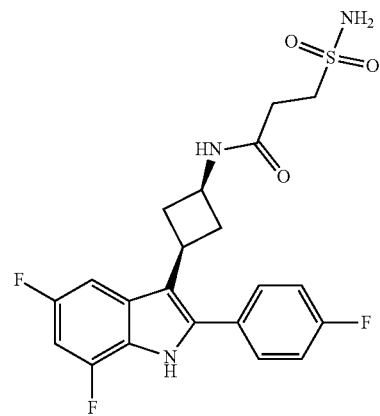 [SMILES: NS(=O)(=O)CCC(=O)N[C@H]1C[C@@H](c2c(-c3ccc(F)cc3)[nH]c3c(F)cc(F)cc32)C1]
52 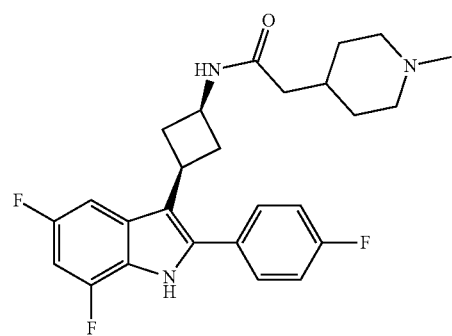 [SMILES: CN1CCC(CC(=O)N[C@H]2C[C@@H](c3c(-c4ccc(F)cc4)[nH]c4c(F)cc(F)cc43)C2)CC1]
53 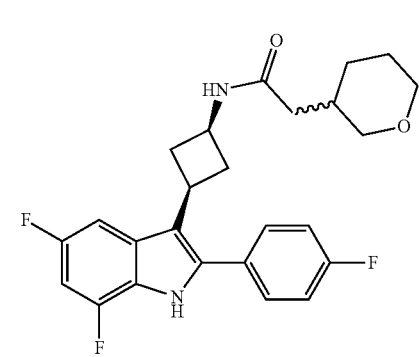 [SMILES: O=C(CC1CCCOC1)N[C@H]1C[C@@H](c2c(-c3ccc(F)cc3)[nH]c3c(F)cc(F)cc32)C1]
54 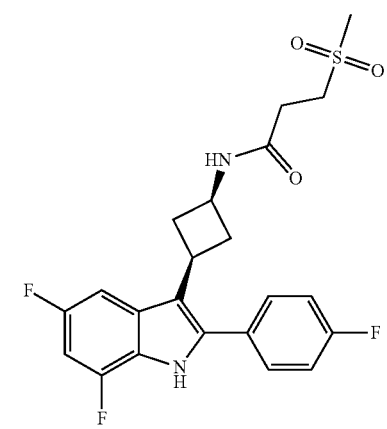 [SMILES: CS(=O)(=O)CCC(=O)N[C@H]1C[C@@H](c2c(-c3ccc(F)cc3)[nH]c3c(F)cc(F)cc32)C1]
55 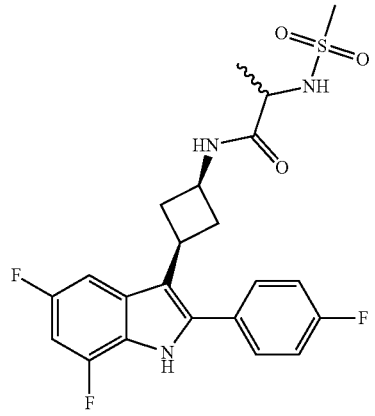
56 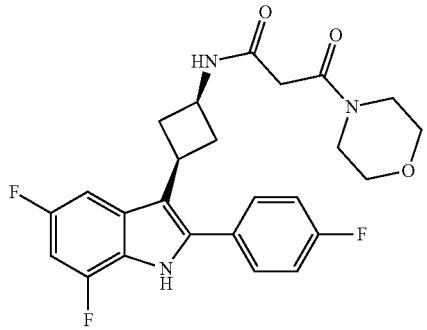 [SMILES: O=C(CC(=O)N1CCOCC1)N[C@H]1C[C@@H](c2c(-c3ccc(F)cc3)[nH]c3c(F)cc(F)cc32)C1]
57 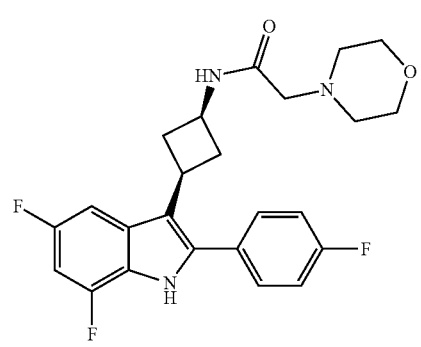 [SMILES: O=C(CN1CCOCC1)N[C@H]1C[C@@H](c2c(-c3ccc(F)cc3)[nH]c3c(F)cc(F)cc32)C1]
58 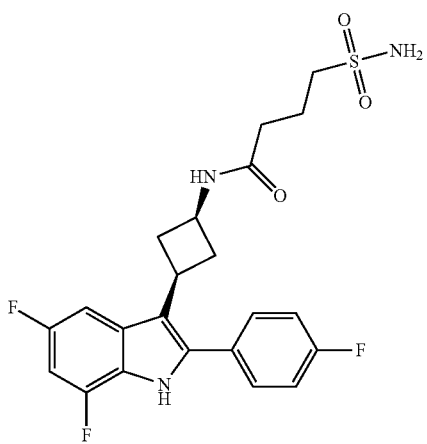 [SMILES: NS(=O)(=O)CCCC(=O)N[C@H]1C[C@@H](c2c(-c3ccc(F)cc3)[nH]c3c(F)cc(F)cc32)C1]

TABLE 1-continued
Compounds 1 to 456
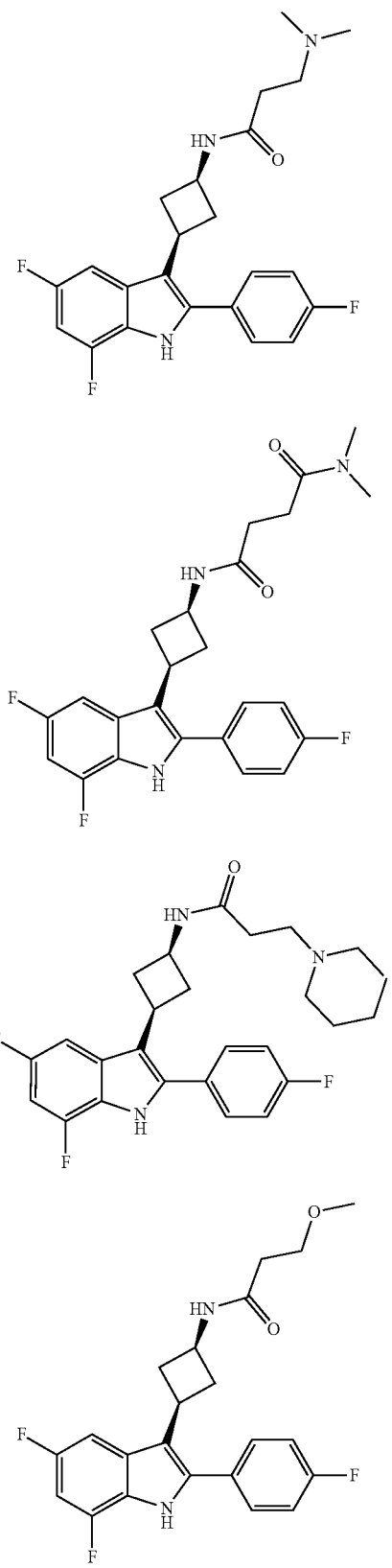
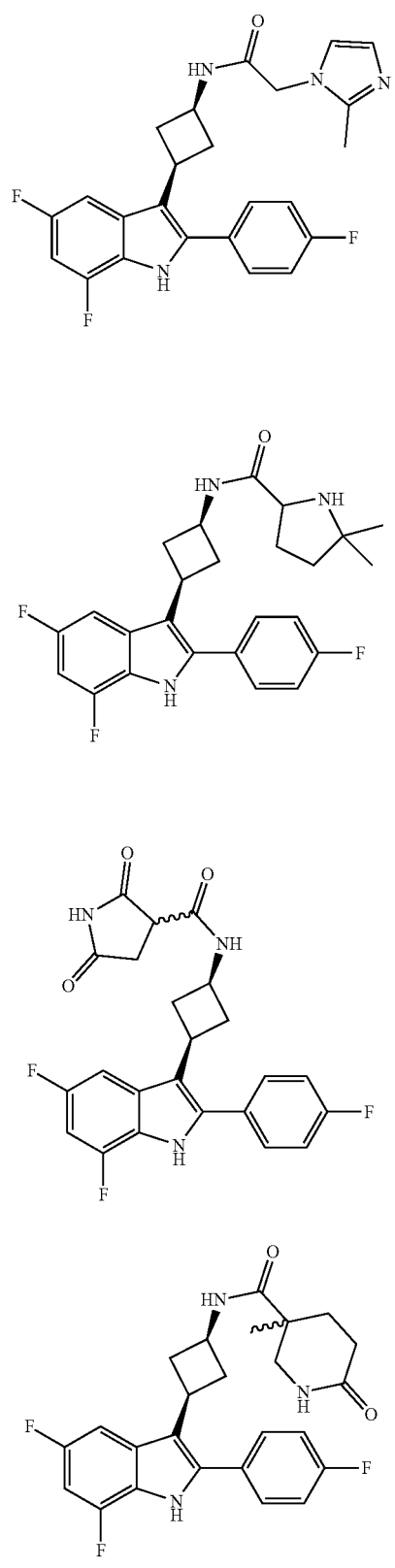

TABLE 1-continued
Compounds 1 to 456
67
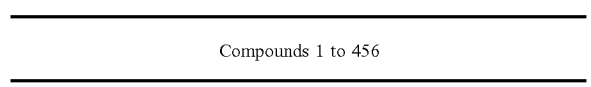
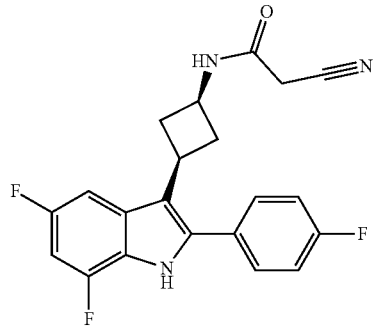 [SMILES: N#CCC(=O)N[C@H]1C[C@@H](c2c(-c3ccc(F)cc3)[nH]c3c(F)cc(F)cc32)C1]
68
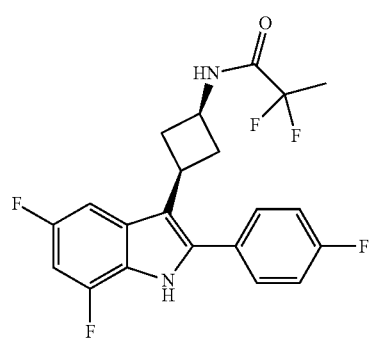 [SMILES: CC(F)(F)C(=O)N[C@H]1C[C@@H](c2c(-c3ccc(F)cc3)[nH]c3c(F)cc(F)cc32)C1]
69
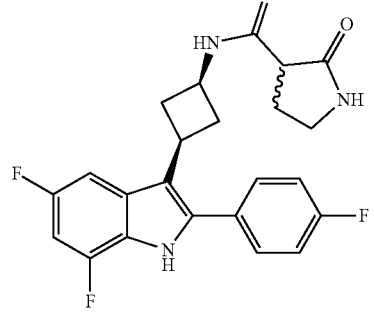
70
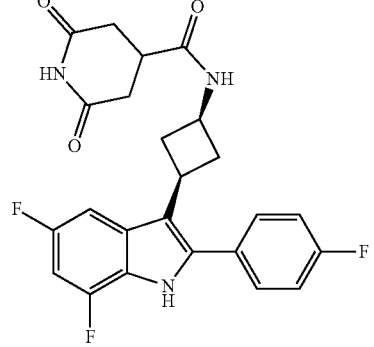
TABLE 1-continued
Compounds 1 to 456
71
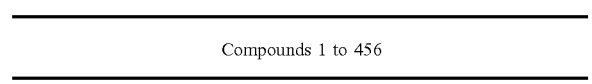
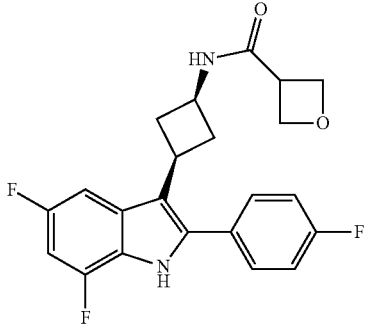 [SMILES: O=C(N[C@H]1C[C@@H](c2c(-c3ccc(F)cc3)[nH]c3c(F)cc(F)cc32)C1)C1COC1]
72
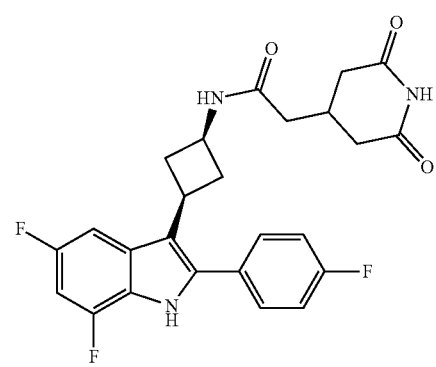 [SMILES: O=C1CC(CC(=O)N[C@H]2C[C@@H](c3c(-c4ccc(F)cc4)[nH]c4c(F)cc(F)cc43)C2)CC(=O)N1]
73
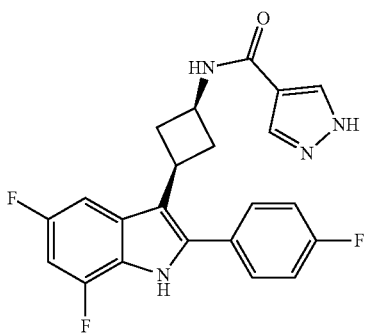 [SMILES: O=C(N[C@H]1C[C@@H](c2c(-c3ccc(F)cc3)[nH]c3c(F)cc(F)cc32)C1)c1cn[nH]c1]
74
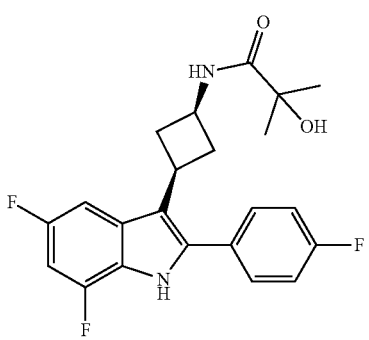 [SMILES: CC(C)(O)C(=O)N[C@H]1C[C@@H](c2c(-c3ccc(F)cc3)[nH]c3c(F)cc(F)cc32)C1]

TABLE 1-continued
Compounds 1 to 456
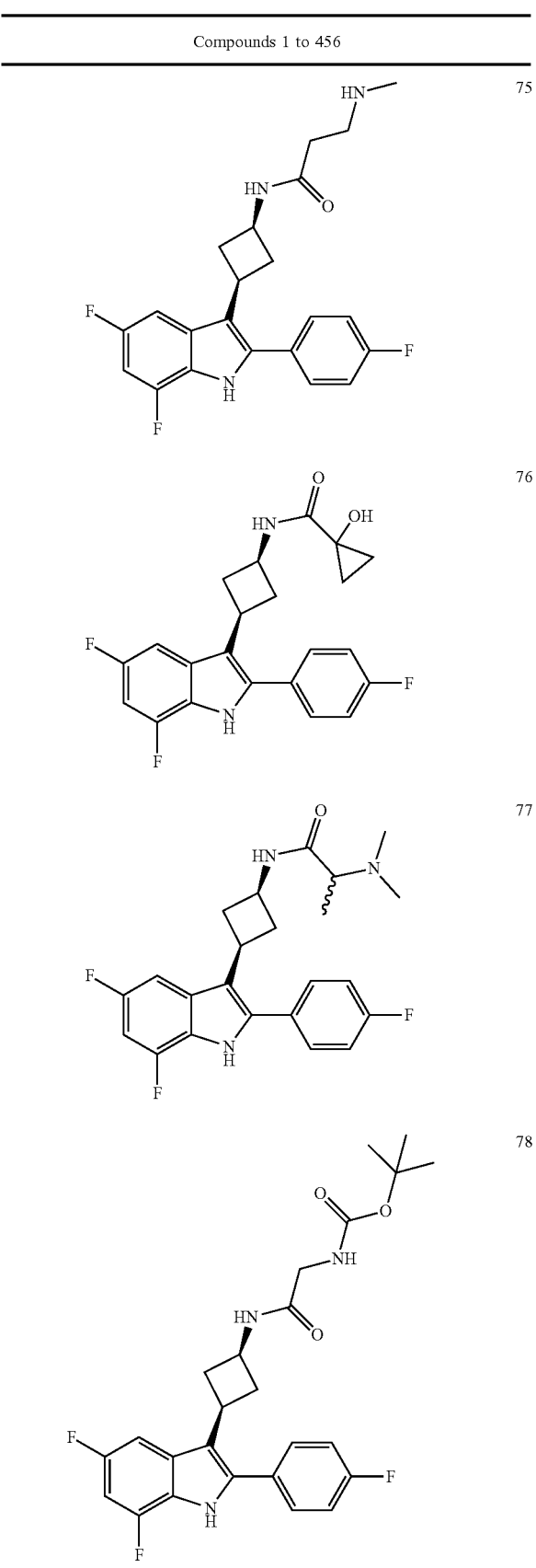
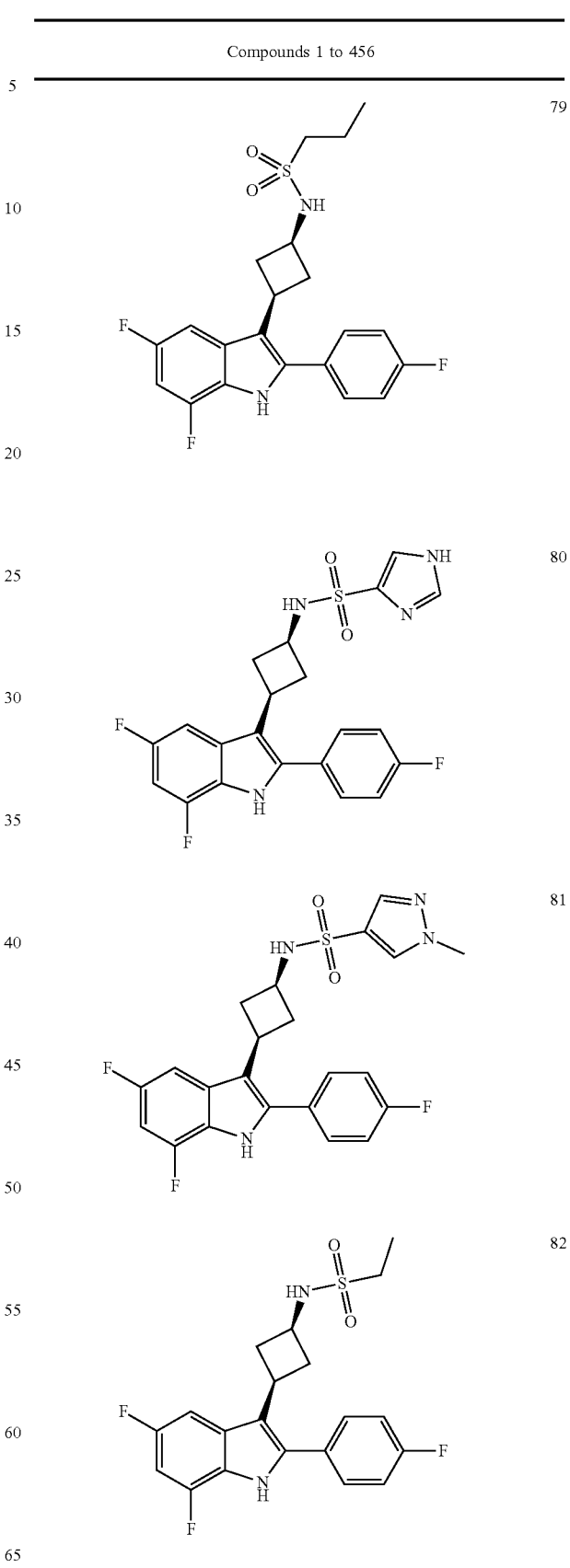

TABLE 1-continued
Compounds 1 to 456
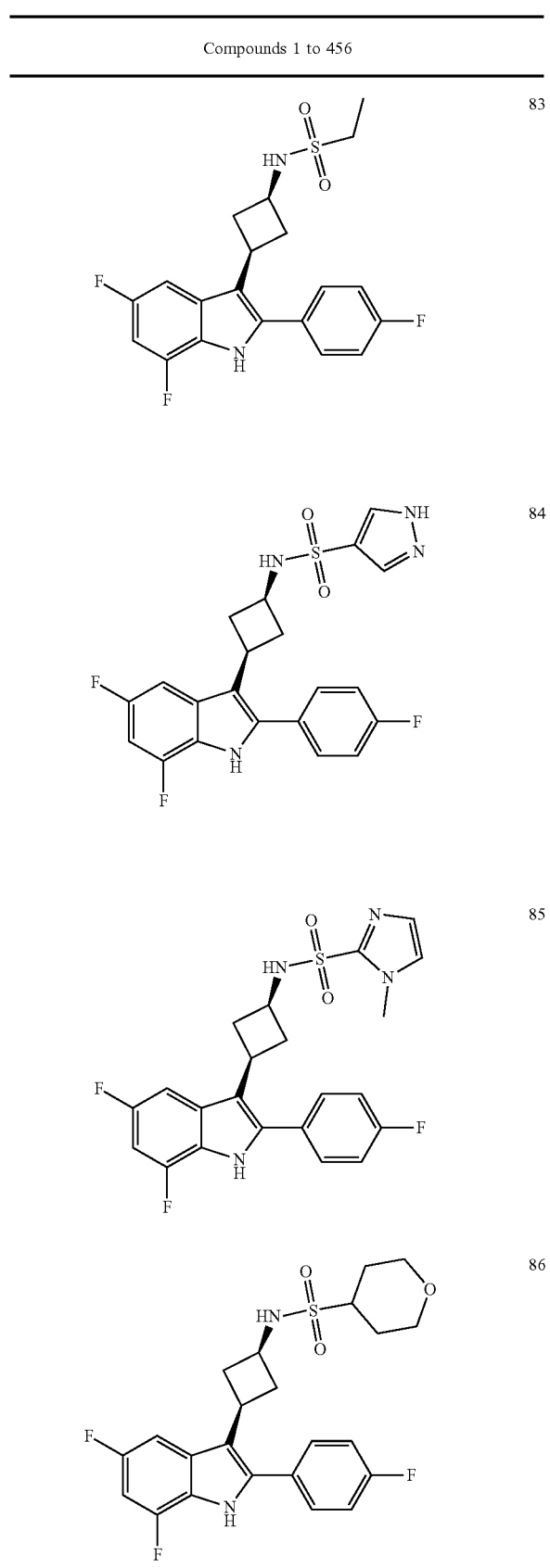
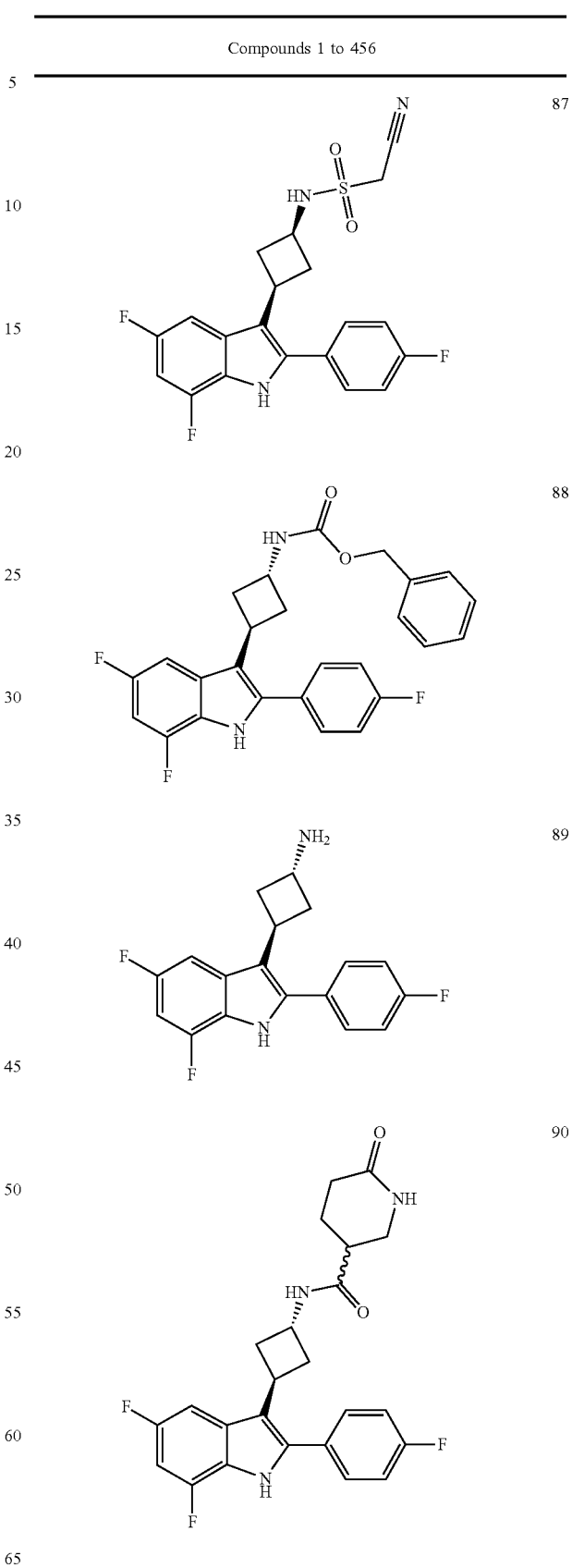

TABLE 1-continued
Compounds 1 to 456
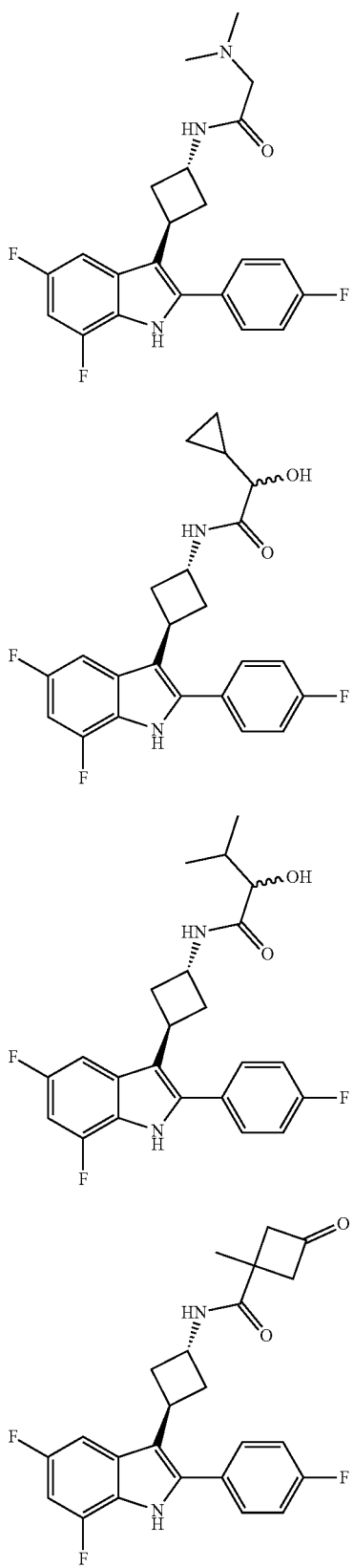
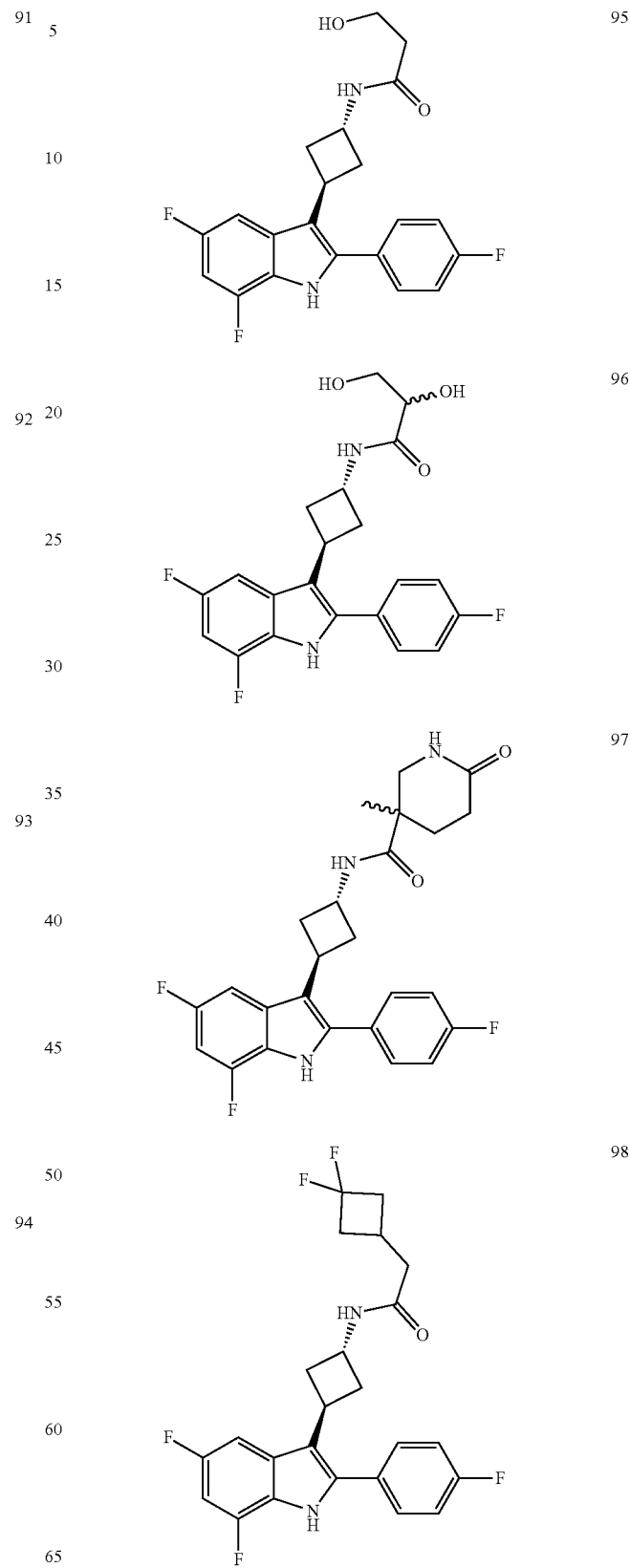

TABLE 1-continued
Compounds 1 to 456
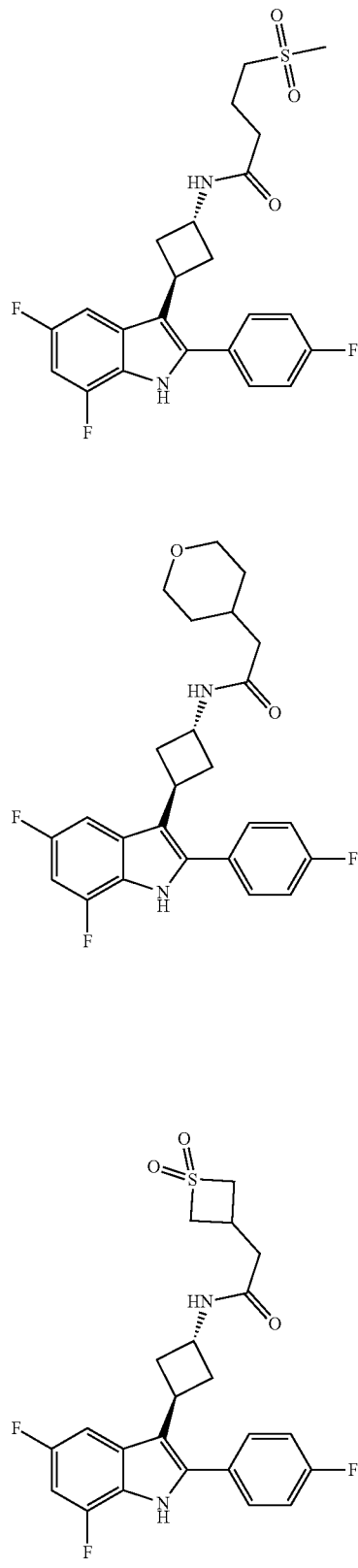
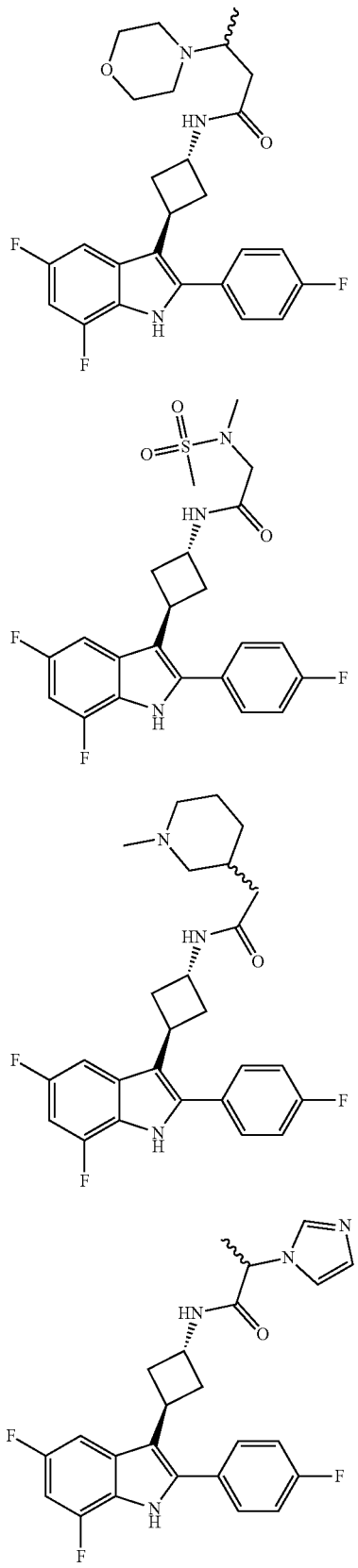

TABLE 1-continued
Compounds 1 to 456
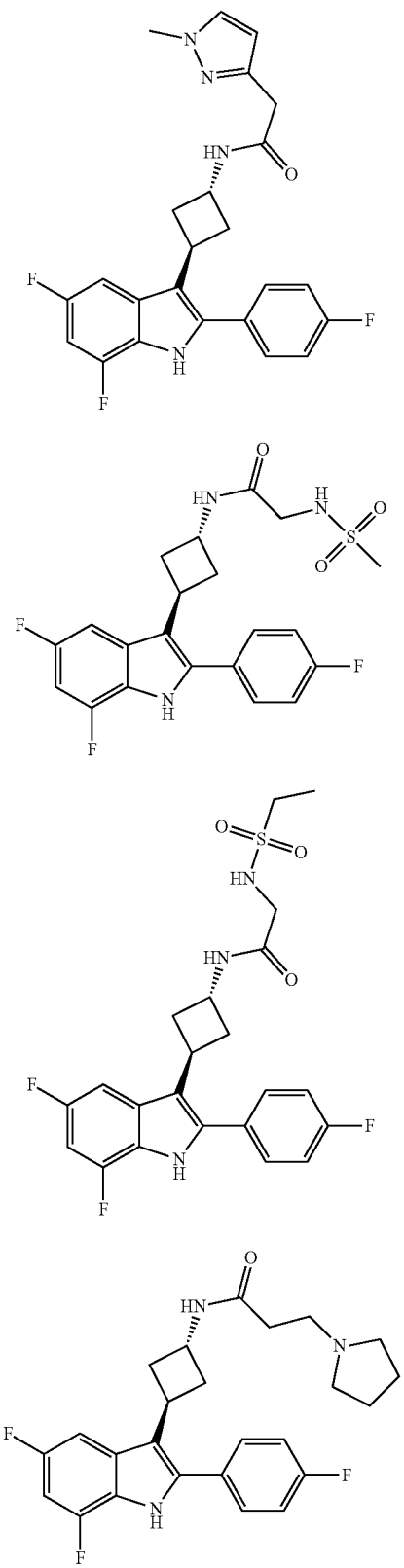
106
107
108
109
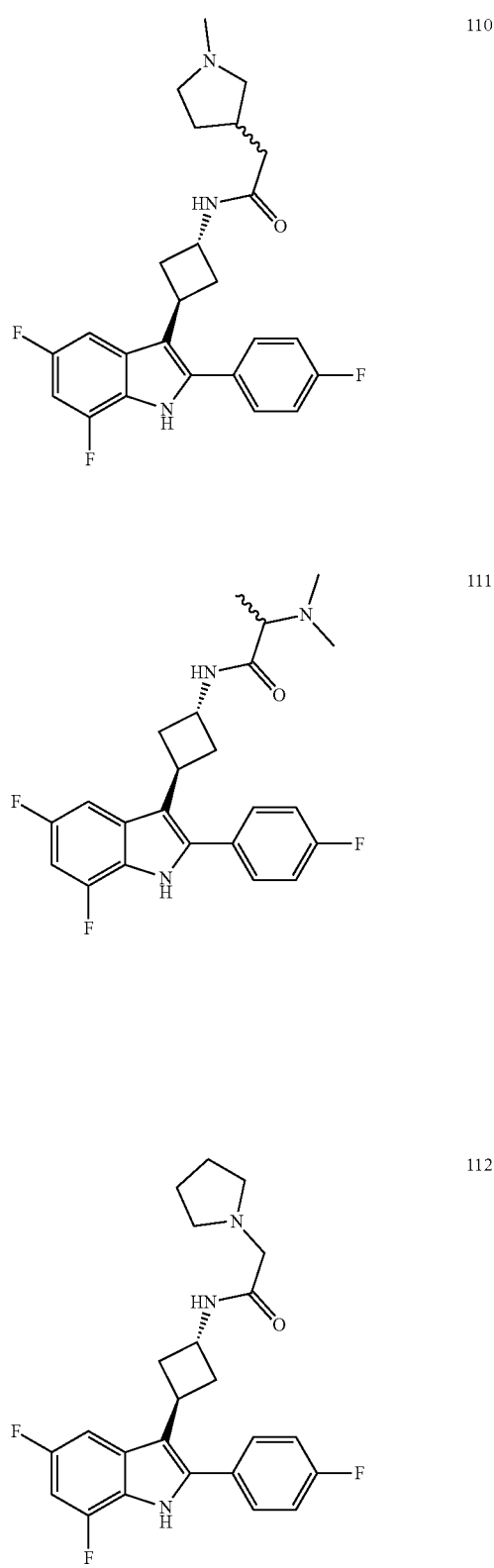
110
111
112

TABLE 1-continued
Compounds 1 to 456
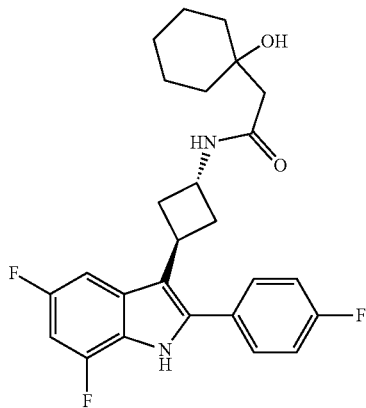 [SMILES: O=C(CC1(O)CCCCC1)N[C@H]1C[C@H](c2c(-c3ccc(F)cc3)[nH]c3c(F)cc(F)cc32)C1] 113
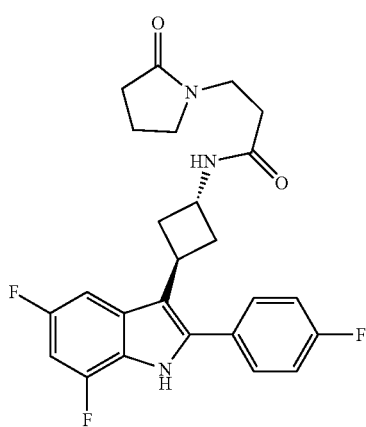 [SMILES: O=C(CCN1CCCC1=O)N[C@H]1C[C@H](c2c(-c3ccc(F)cc3)[nH]c3c(F)cc(F)cc32)C1] 114
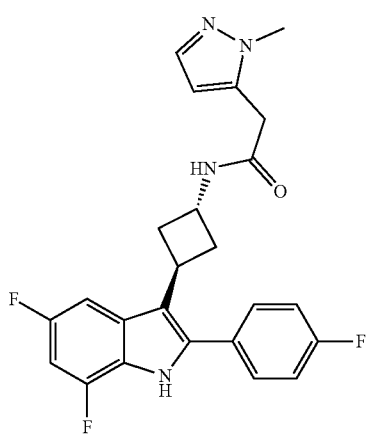 [SMILES: Cn1nccc1CC(=O)N[C@H]1C[C@H](c2c(-c3ccc(F)cc3)[nH]c3c(F)cc(F)cc32)C1] 115
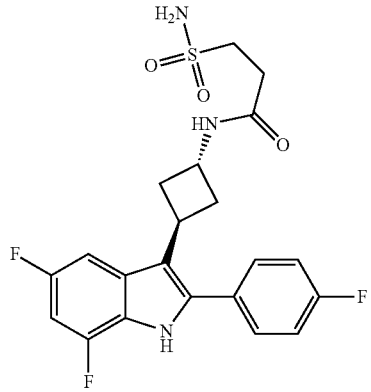 [SMILES: NS(=O)(=O)CCC(=O)N[C@H]1C[C@H](c2c(-c3ccc(F)cc3)[nH]c3c(F)cc(F)cc32)C1] 116
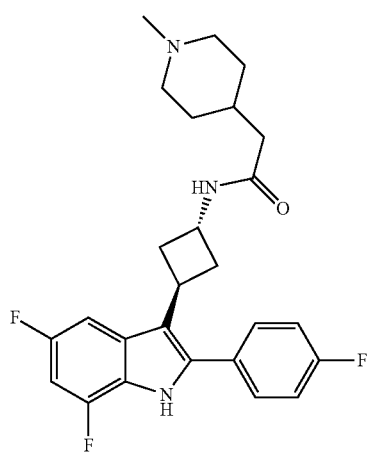 [SMILES: CN1CCC(CC(=O)N[C@H]2C[C@H](c3c(-c4ccc(F)cc4)[nH]c4c(F)cc(F)cc43)C2)CC1] 117
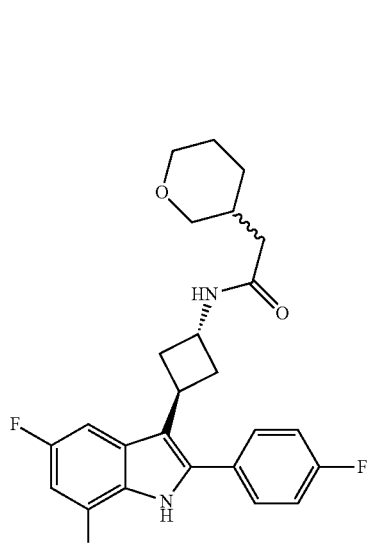 118

TABLE 1-continued
Compounds 1 to 456
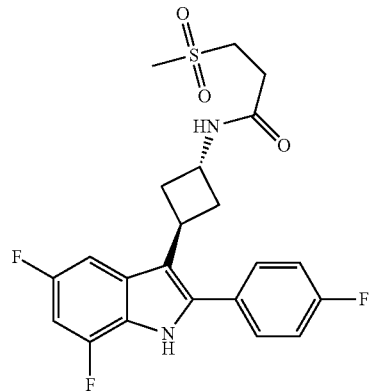 [SMILES: CS(=O)(=O)CCC(=O)N[C@H]1C[C@H](c2c(-c3ccc(F)cc3)[nH]c3c(F)cc(F)cc32)C1] 119
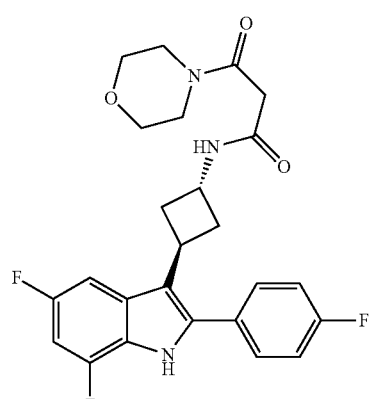 120
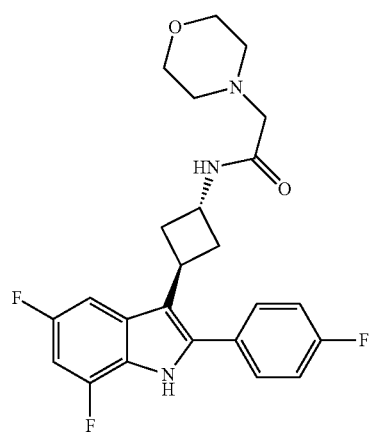 [SMILES: O=C(CN1CCOCC1)N[C@H]1C[C@H](c2c(-c3ccc(F)cc3)[nH]c3c(F)cc(F)cc32)C1] 121
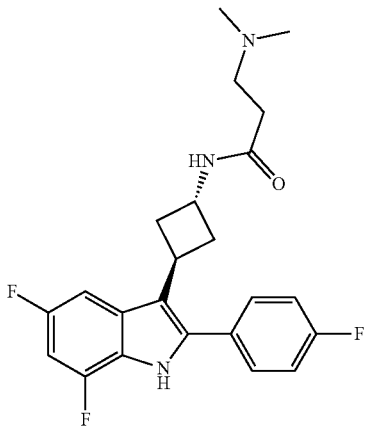 [SMILES: CN(C)CCC(=O)N[C@H]1C[C@H](c2c(-c3ccc(F)cc3)[nH]c3c(F)cc(F)cc32)C1] 122
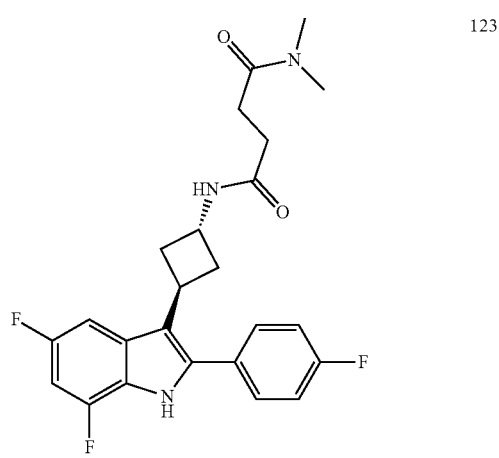 123
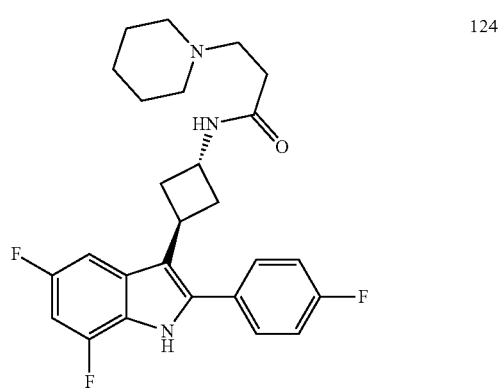 124

TABLE 1-continued
Compounds 1 to 456
125 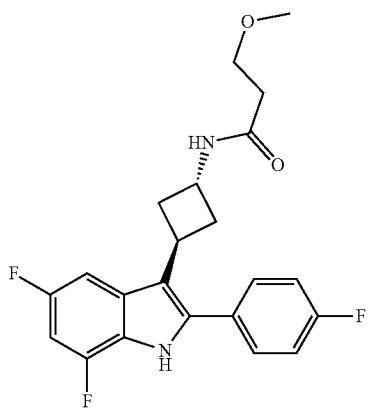 [SMILES: COCCC(=O)N[C@H]1C[C@H](c2c(-c3ccc(F)cc3)[nH]c3c(F)cc(F)cc32)C1]
126 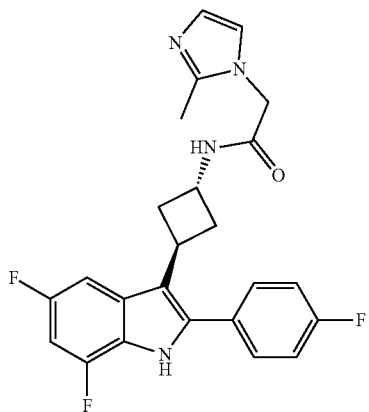 [SMILES: Cc1nccn1CC(=O)N[C@H]1C[C@H](c2c(-c3ccc(F)cc3)[nH]c3c(F)cc(F)cc32)C1]
127 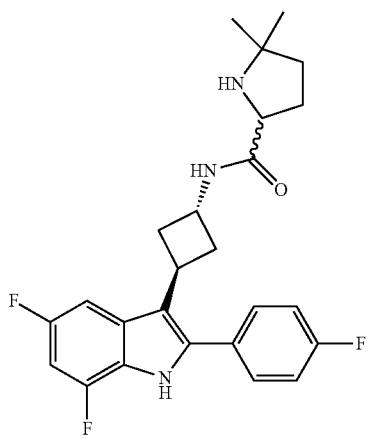 [SMILES: CC1(C)CCC(C(=O)N[C@H]2C[C@H](c3c(-c4ccc(F)cc4)[nH]c4c(F)cc(F)cc43)C2)N1]
TABLE 1-continued
Compounds 1 to 456
128 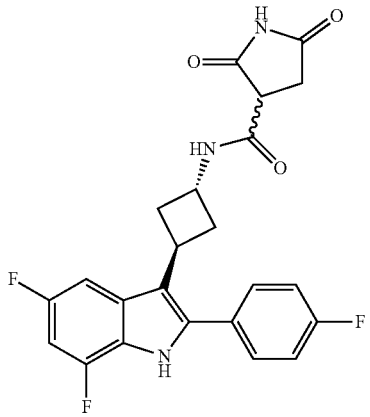 [SMILES: O=C1CC(C(=O)N[C@H]2C[C@H](c3c(-c4ccc(F)cc4)[nH]c4c(F)cc(F)cc43)C2)C(=O)N1]
129 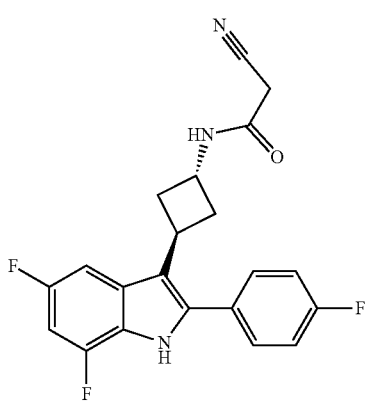 [SMILES: N#CCC(=O)N[C@H]1C[C@H](c2c(-c3ccc(F)cc3)[nH]c3c(F)cc(F)cc32)C1]
130 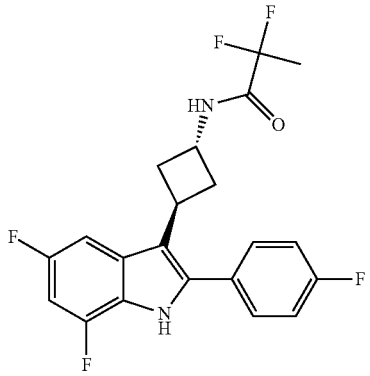 [SMILES: CC(F)(F)C(=O)N[C@H]1C[C@H](c2c(-c3ccc(F)cc3)[nH]c3c(F)cc(F)cc32)C1]
131 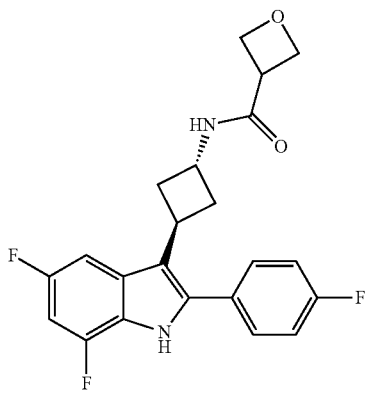 [SMILES: O=C(N[C@H]1C[C@H](c2c(-c3ccc(F)cc3)[nH]c3c(F)cc(F)cc32)C1)C1COC1]

TABLE 1-continued
Compounds 1 to 456
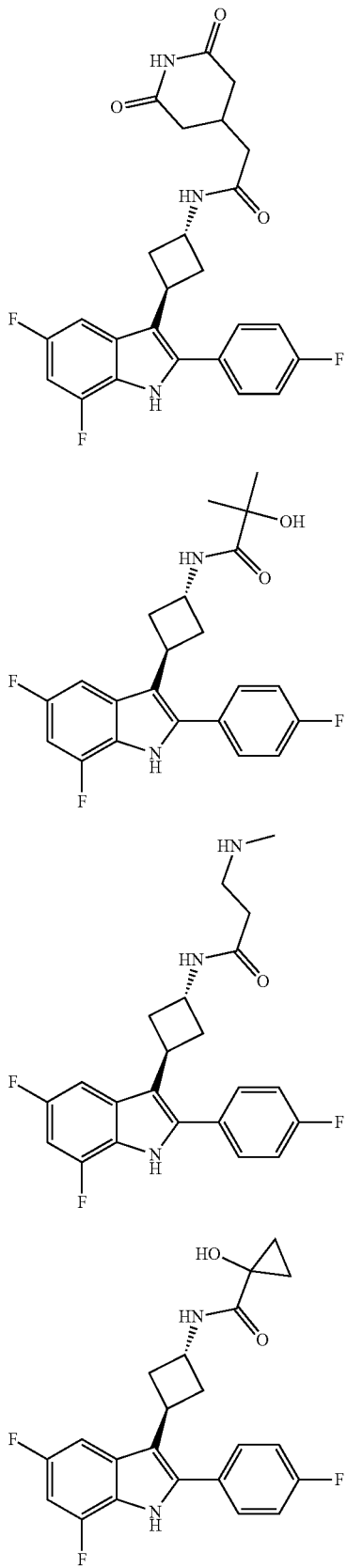
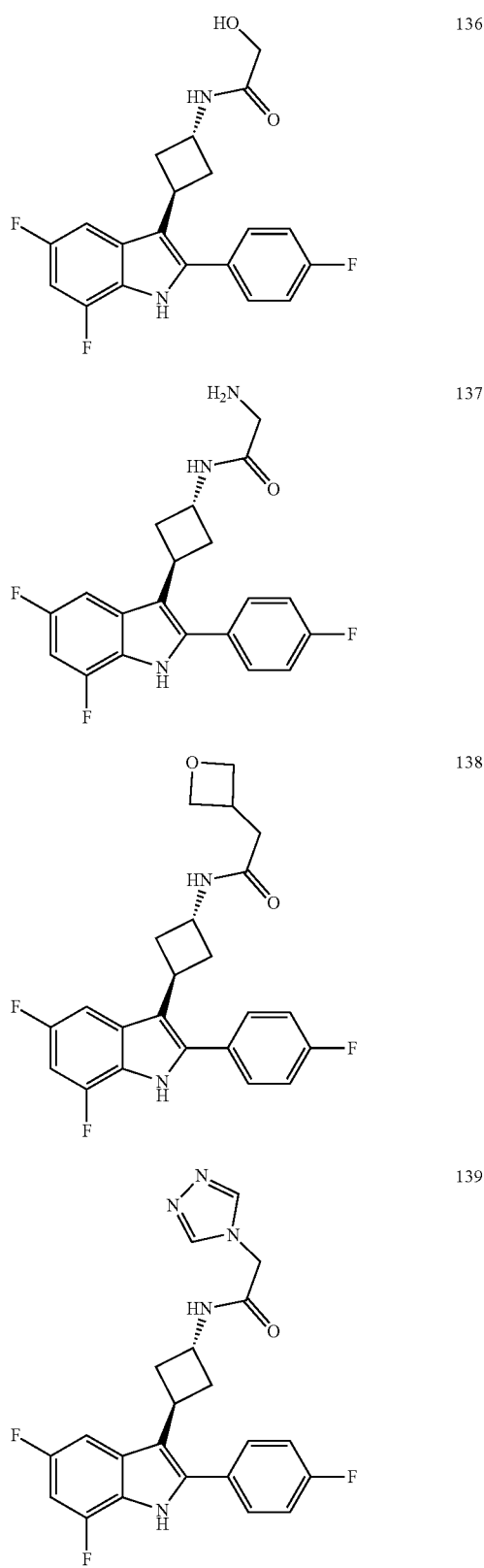

TABLE 1-continued
Compounds 1 to 456
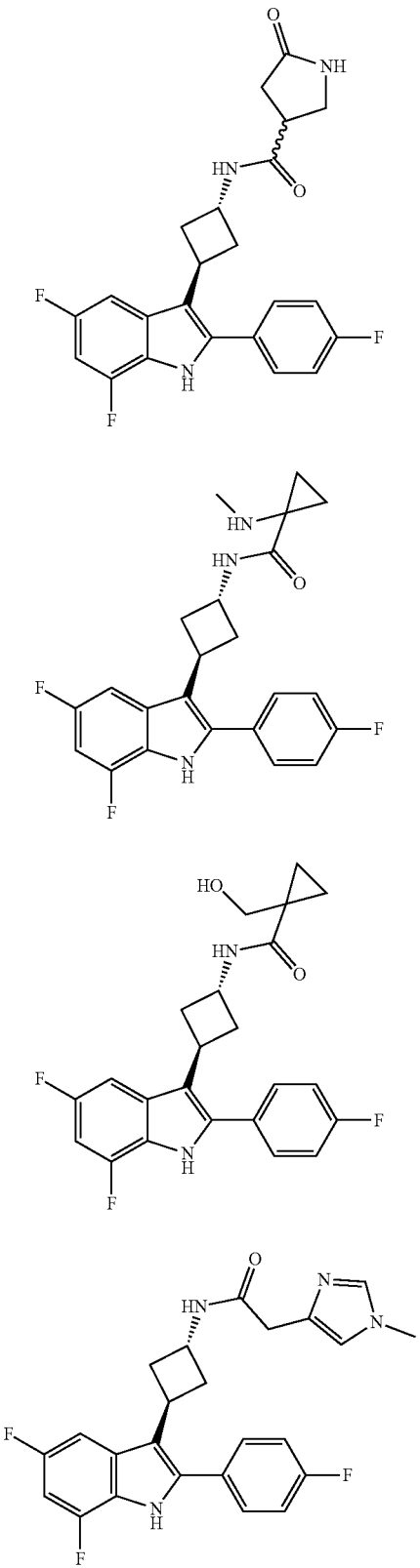
140
141
142
143
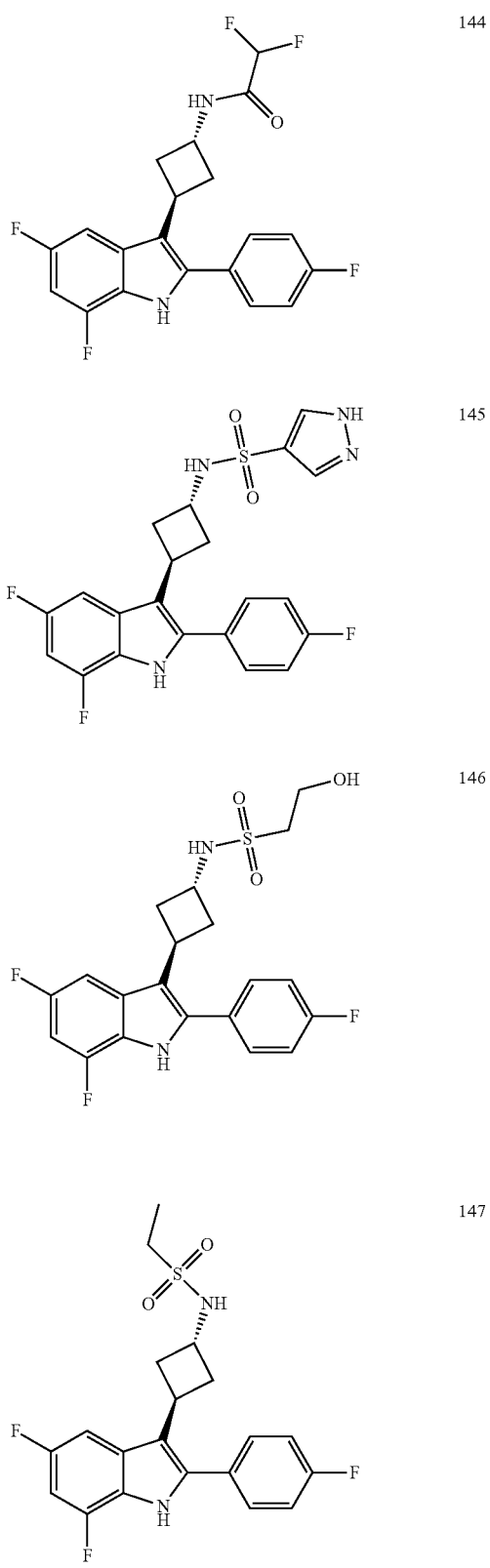
144
145
146
147

TABLE 1-continued
Compounds 1 to 456
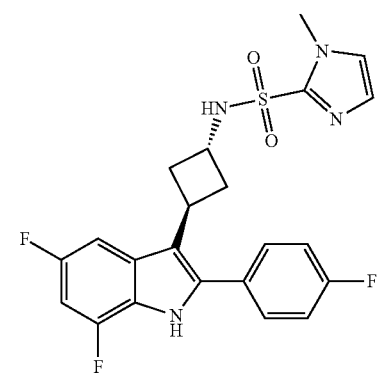 [SMILES: Cn1ccnc1S(=O)(=O)N[C@H]1C[C@H](c2c(-c3ccc(F)cc3)[nH]c3c(F)cc(F)cc32)C1]
148
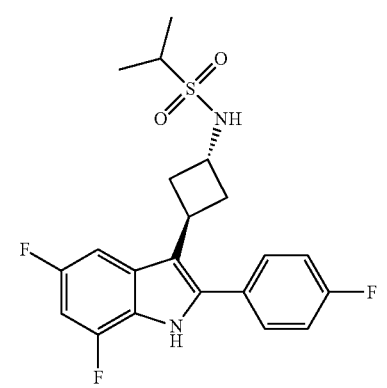 [SMILES: CC(C)S(=O)(=O)N[C@H]1C[C@H](c2c(-c3ccc(F)cc3)[nH]c3c(F)cc(F)cc32)C1]
149
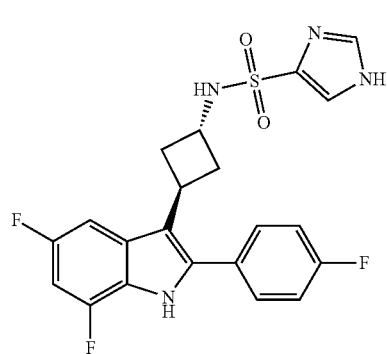 [SMILES: O=S(=O)(N[C@H]1C[C@H](c2c(-c3ccc(F)cc3)[nH]c3c(F)cc(F)cc32)C1)c1c[nH]cn1]
150
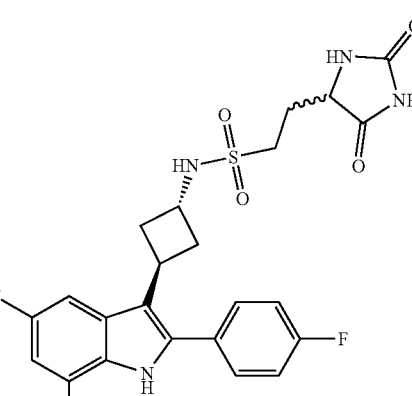
151
TABLE 1-continued
Compounds 1 to 456
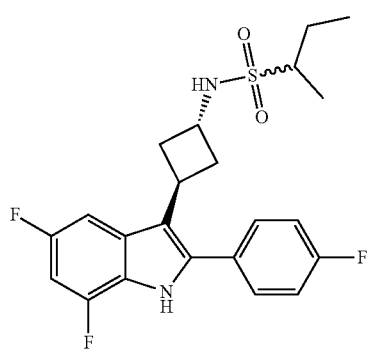
152
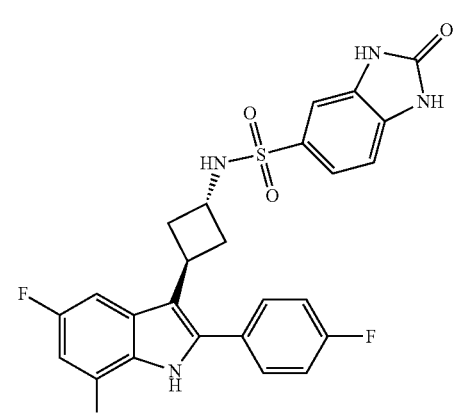
153
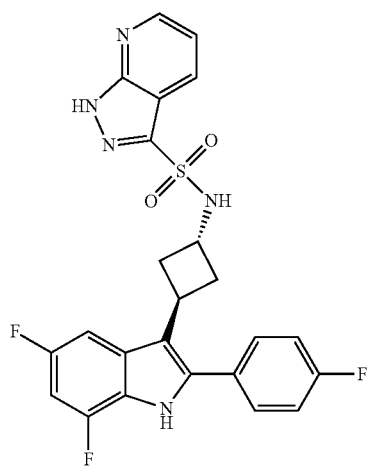 [SMILES: O=S(=O)(N[C@H]1C[C@H](c2c(-c3ccc(F)cc3)[nH]c3c(F)cc(F)cc32)C1)c1n[nH]c2ncccc12]
154

TABLE 1-continued

Compounds 1 to 456

TABLE 1-continued
Compounds 1 to 456
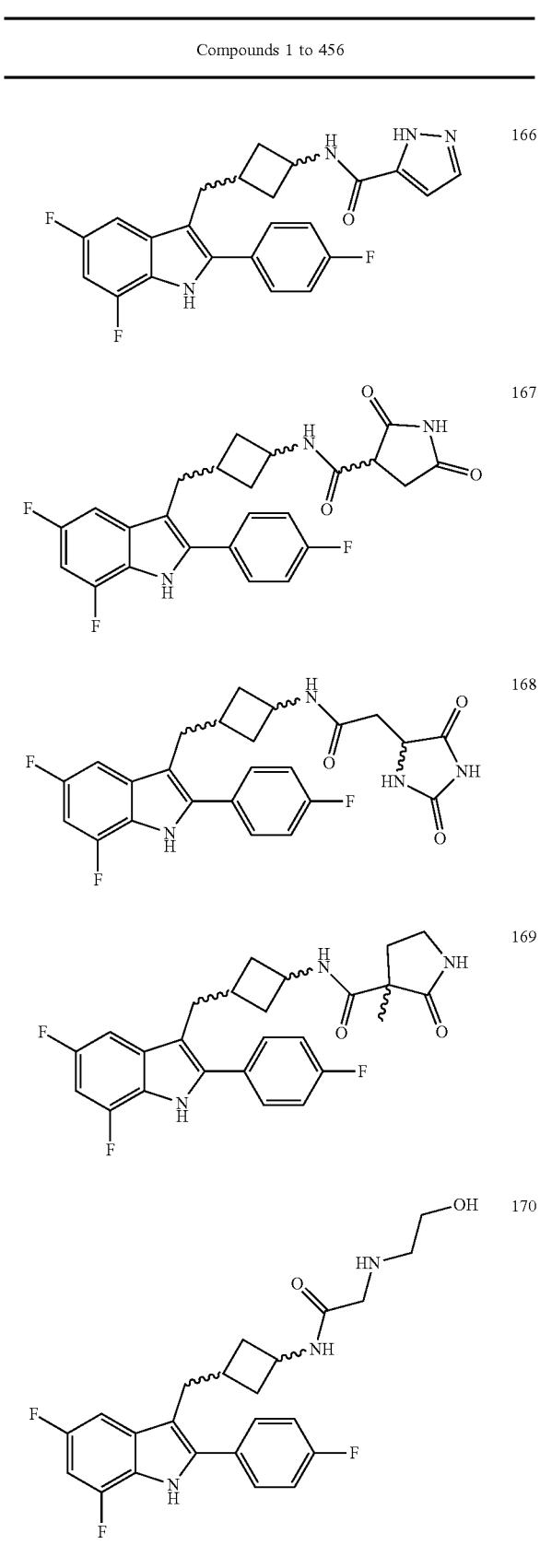
166
167
168
169
170
171
172
173
174
175

TABLE 1-continued

Compounds 1 to 456

| 176 | 5-fluoro-7-fluoro-2-(4-chlorophenyl)-3-(aminomethyl-cyclobutyl)-1H-indole |
| 177 | 5-fluoro-2-(4-cyclopropylphenyl)-3-(aminomethyl-cyclobutyl)-1H-indole |
| 178 | 5-trifluoromethyl-7-fluoro-2-(4-fluorophenyl)-3-(aminomethyl-cyclobutyl)-1H-indole |
| 179 | 5-fluoro-7-fluoro-2-(3-methyl-4-fluorophenyl)-3-(aminomethyl-cyclobutyl)-1H-indole |
| 180 | 5-fluoro-7-fluoro-2-(4-trifluoromethoxyphenyl)-3-(aminomethyl-cyclobutyl)-1H-indole |
| 181 | 5-fluoro-7-fluoro-2-(3-methylphenyl)-3-(aminomethyl-cyclobutyl)-1H-indole |
| 182 | 5-fluoro-7-fluoro-2-(4-difluoromethoxyphenyl)-3-(aminomethyl-cyclobutyl)-1H-indole |
| 183 | 5-fluoro-7-fluoro-2-(4-methoxyphenyl)-3-(aminomethyl-cyclobutyl)-1H-indole |
| 184 | 5-fluoro-7-fluoro-2-(4-methylphenyl)-3-(aminomethyl-cyclobutyl)-1H-indole |
| 185 | 5-fluoro-7-fluoro-2-(4-cyanophenyl)-3-(aminomethyl-cyclobutyl)-1H-indole |

TABLE 1-continued
Compounds 1 to 456
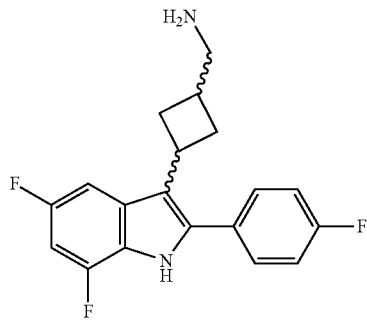 [SMILES: NCC1CC(c2c(-c3ccc(F)cc3)[nH]c3c(F)cc(F)cc23)C1] 186
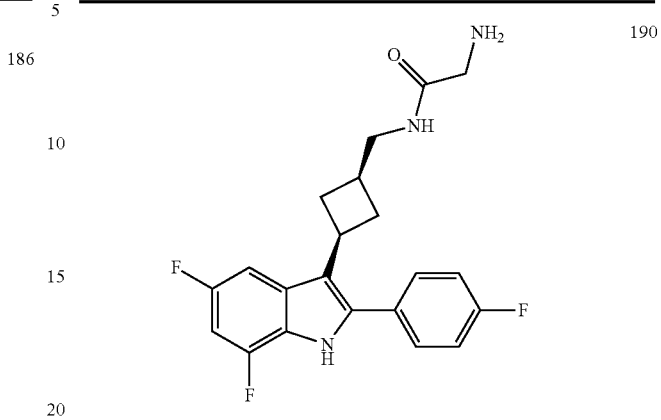
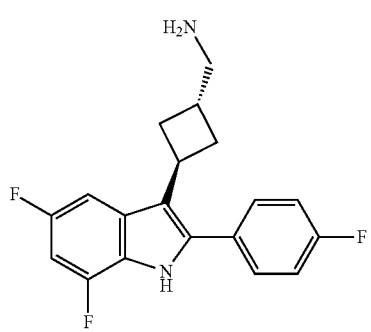 [SMILES: NC[C@H]1C[C@H](c2c(-c3ccc(F)cc3)[nH]c3c(F)cc(F)cc32)C1] 187
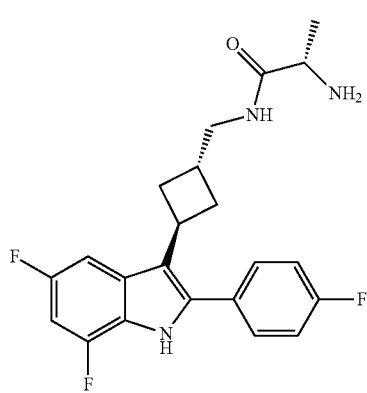 [SMILES: C[C@H](N)C(=O)NC[C@H]1C[C@H](c2c(-c3ccc(F)cc3)[nH]c3c(F)cc(F)cc32)C1] 188

TABLE 1-continued
Compounds 1 to 456
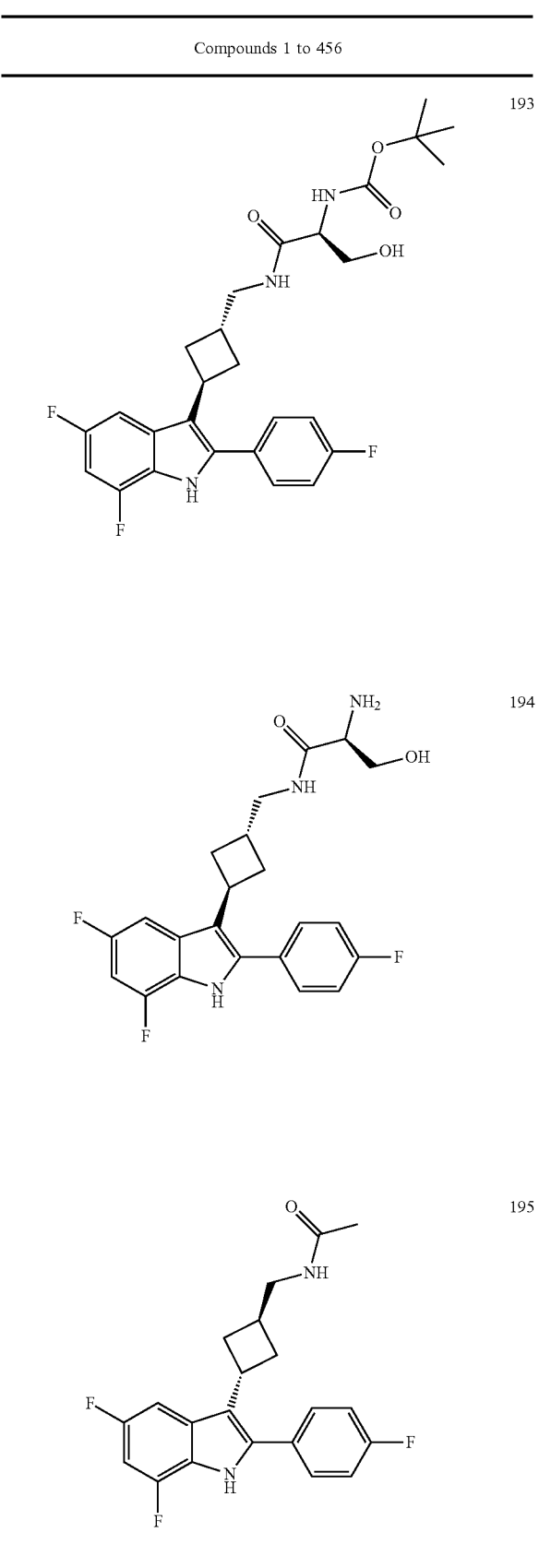
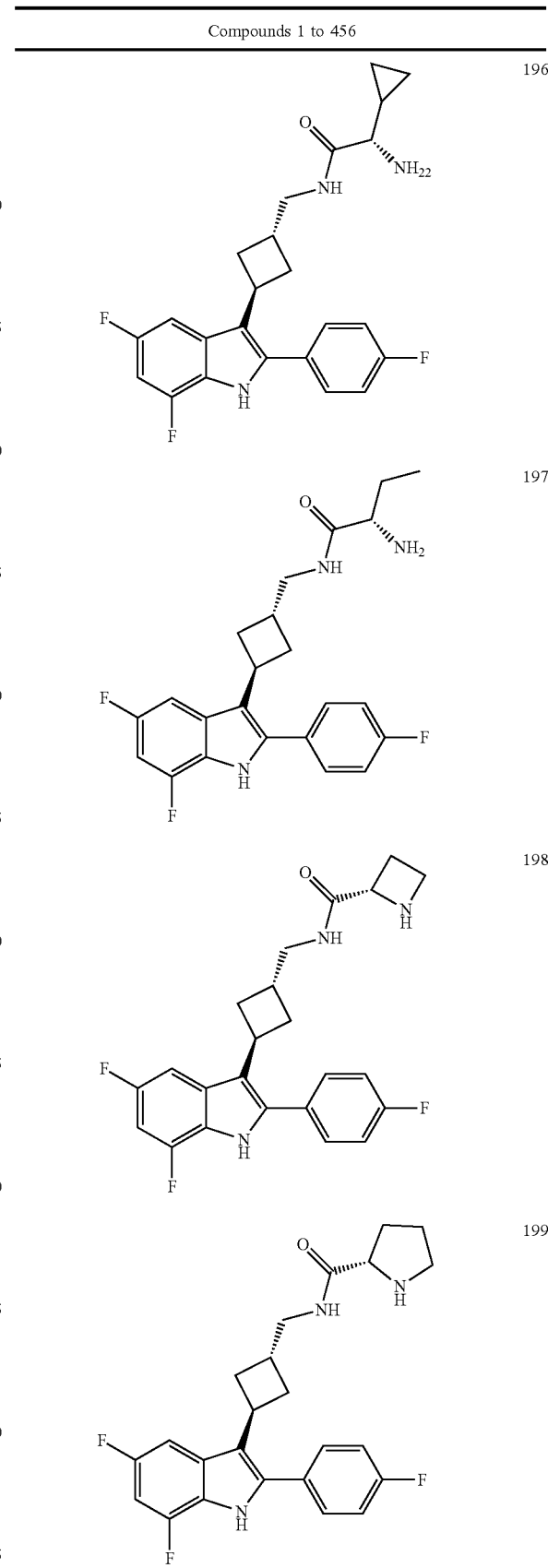

TABLE 1-continued
Compounds 1 to 456
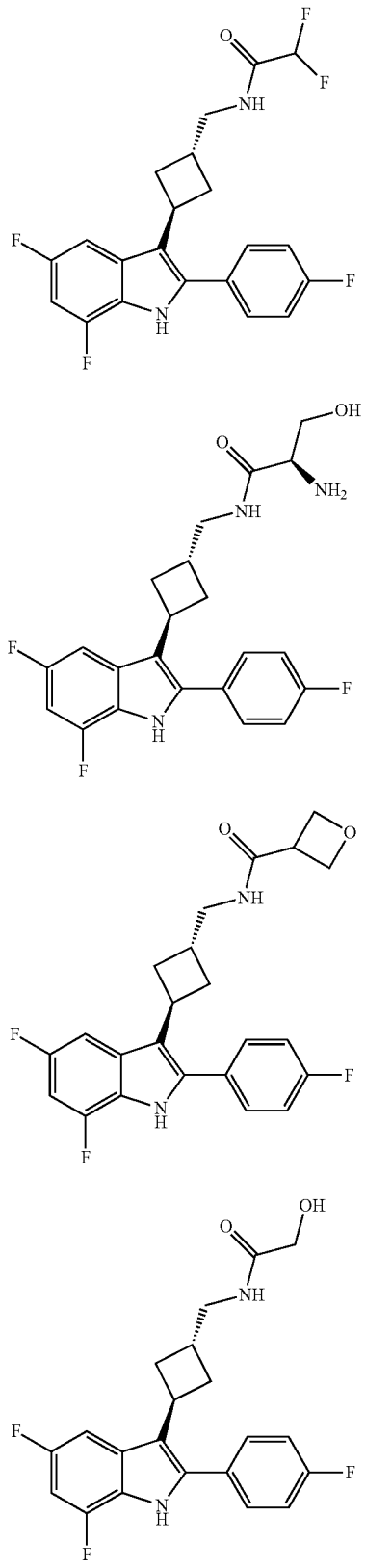
200
201
202
203
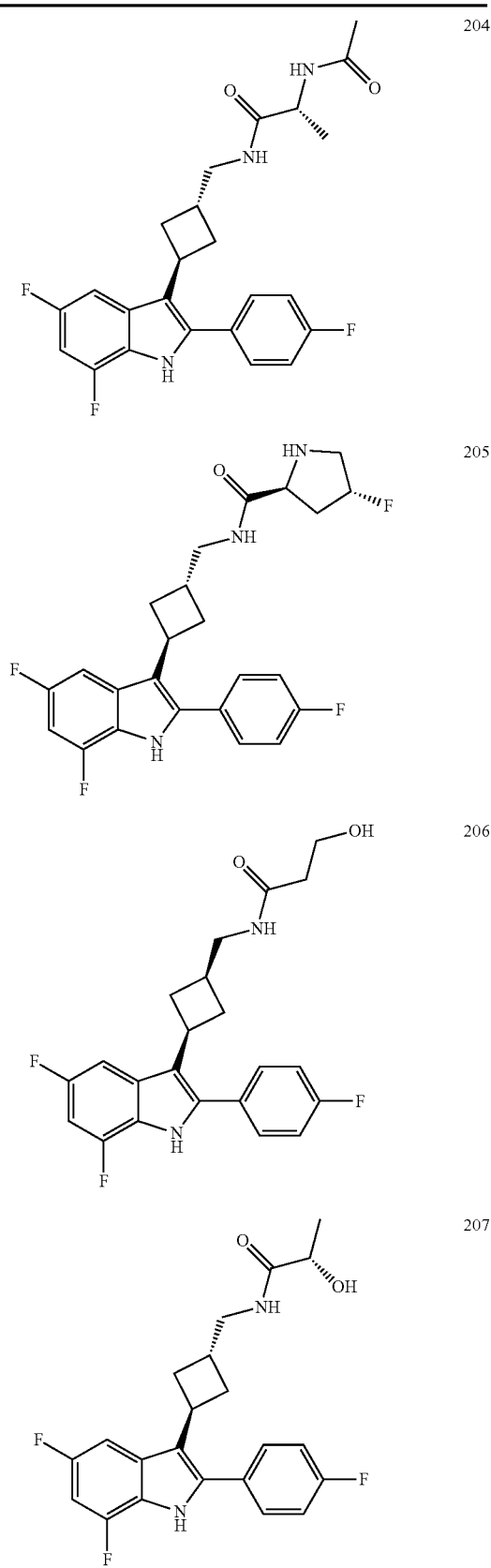
204
205
206
207

TABLE 1-continued
Compounds 1 to 456
208
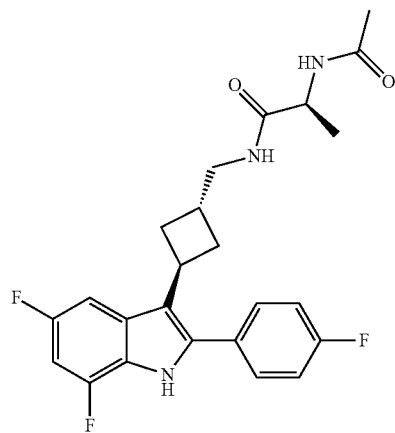
209
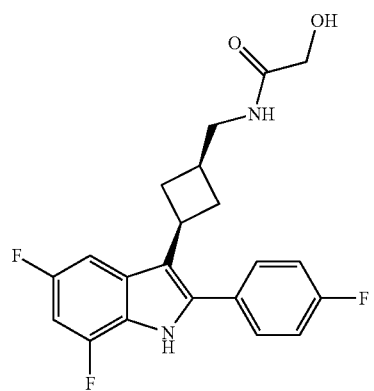 [SMILES: NCC(=O)NC[C@H]1C[C@@H](c2c(-c3ccc(F)cc3)[nH]c3c(F)cc(F)cc32)C1]
210
211
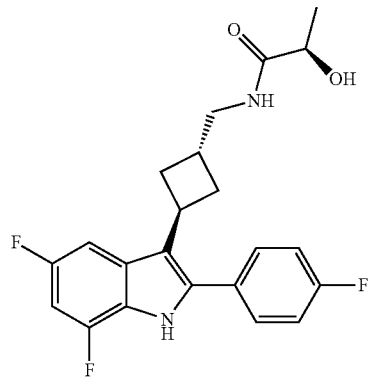 [SMILES: C[C@@H](O)C(=O)NC[C@H]1C[C@H](c2c(-c3ccc(F)cc3)[nH]c3c(F)cc(F)cc32)C1]
212
213

TABLE 1-continued
Compounds 1 to 456
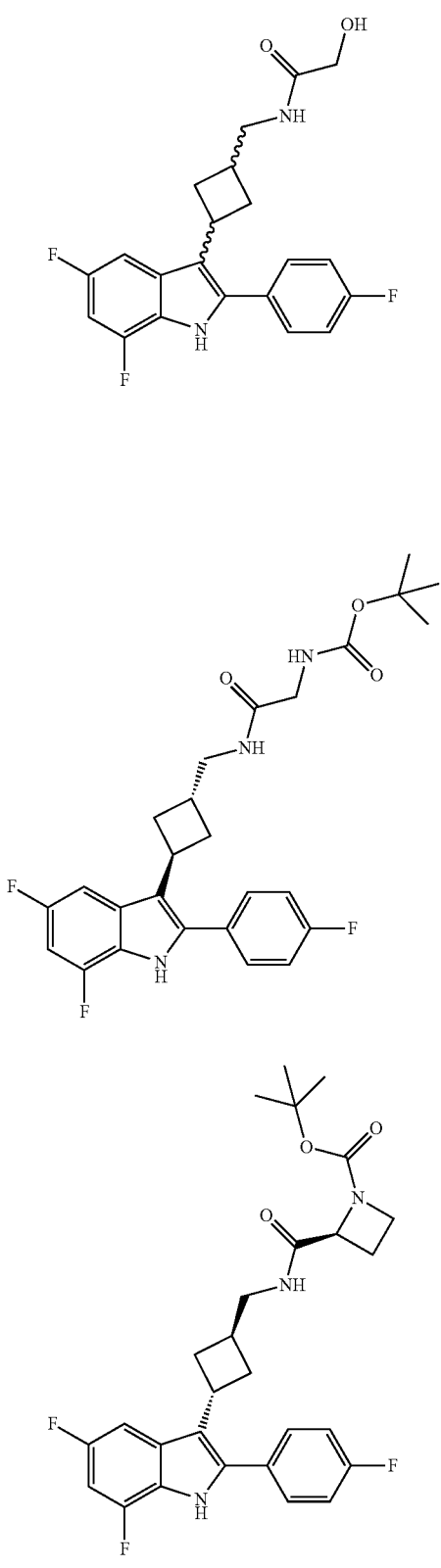
214
215
216
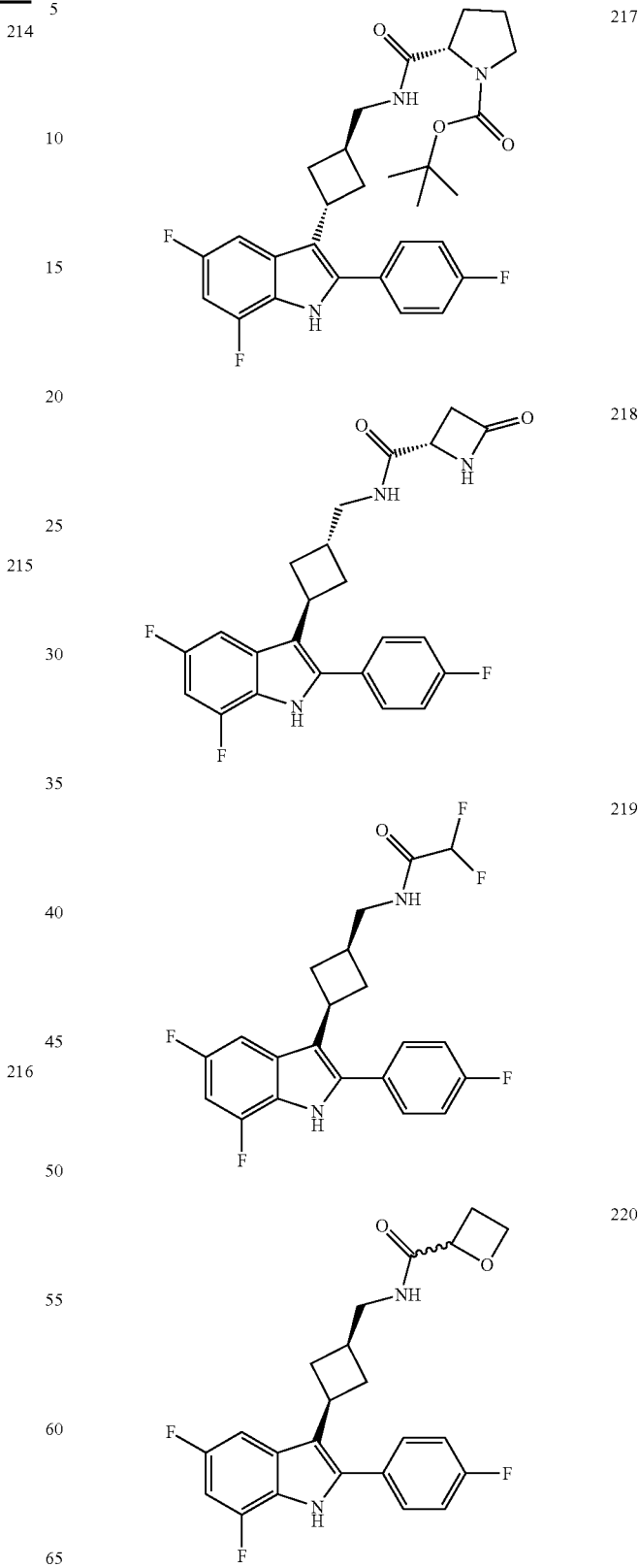
217
218
219
220

TABLE 1-continued
Compounds 1 to 456
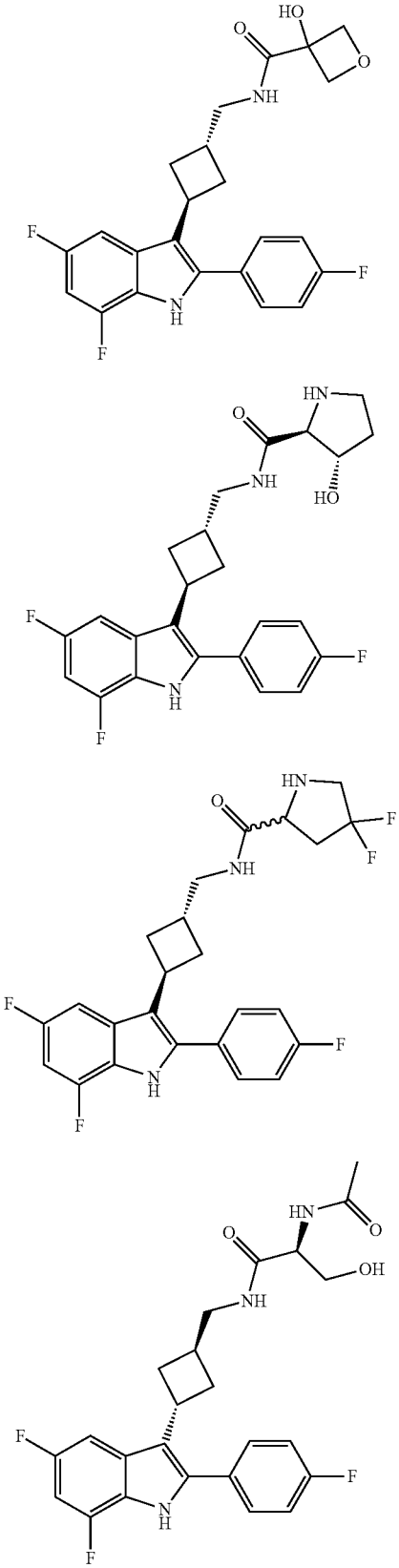
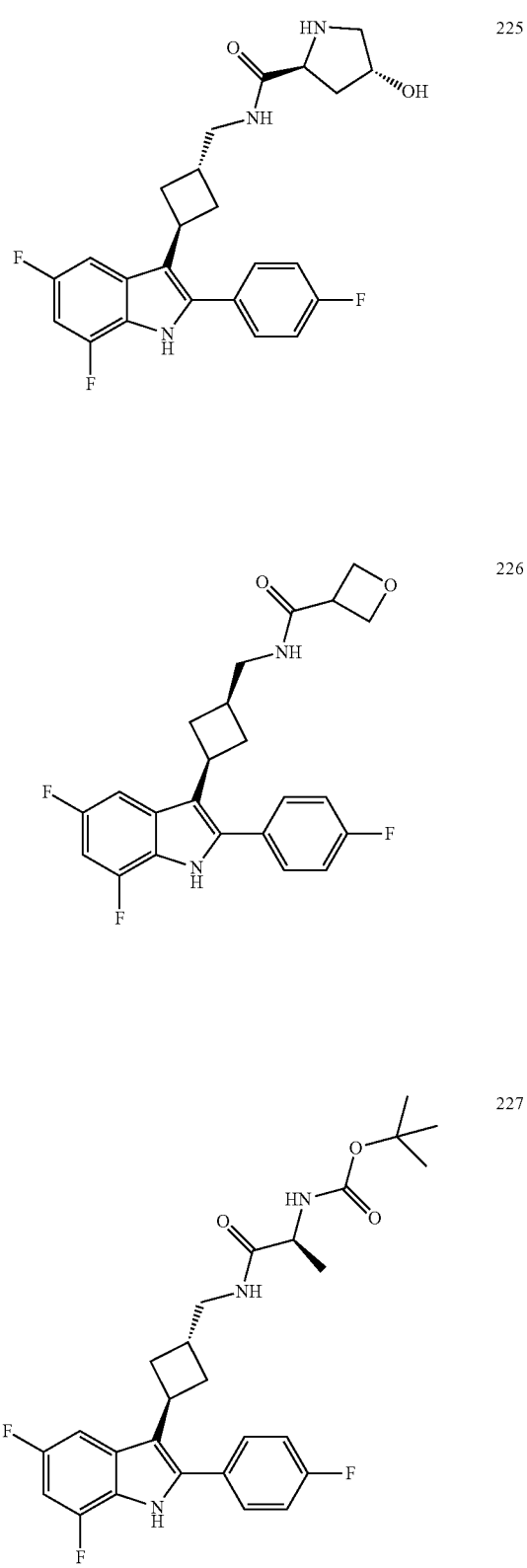

TABLE 1-continued
Compounds 1 to 456
228 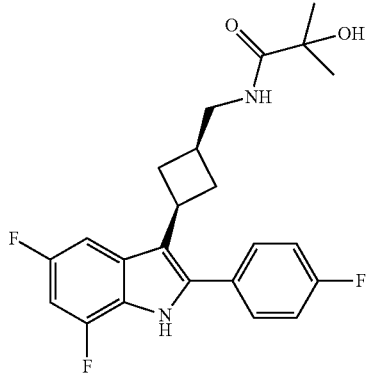 [SMILES: CC(C)(O)C(=O)NC[C@H]1C[C@@H](c2c(-c3ccc(F)cc3)[nH]c3c(F)cc(F)cc32)C1]
229 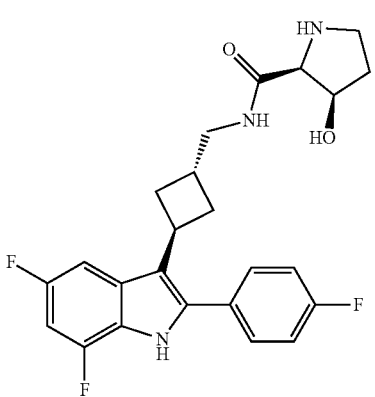 [SMILES: O=C(NC[C@H]1C[C@H](c2c(-c3ccc(F)cc3)[nH]c3c(F)cc(F)cc32)C1)[C@H]1NCC[C@H]1O]
230 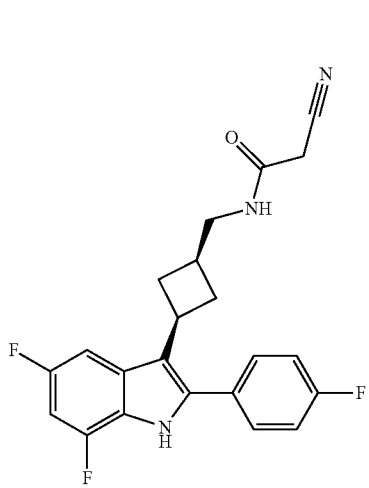 [SMILES: N#CCC(=O)NC[C@H]1C[C@@H](c2c(-c3ccc(F)cc3)[nH]c3c(F)cc(F)cc32)C1]
231 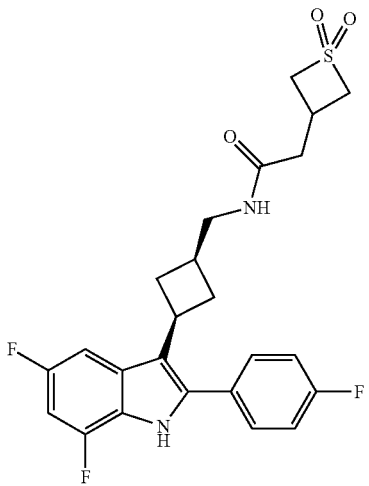 [SMILES: O=C(CC1CS(=O)(=O)C1)NC[C@H]1C[C@@H](c2c(-c3ccc(F)cc3)[nH]c3c(F)cc(F)cc32)C1]
232 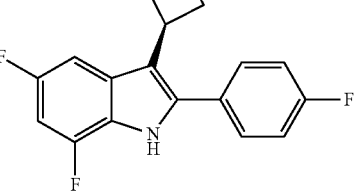
233 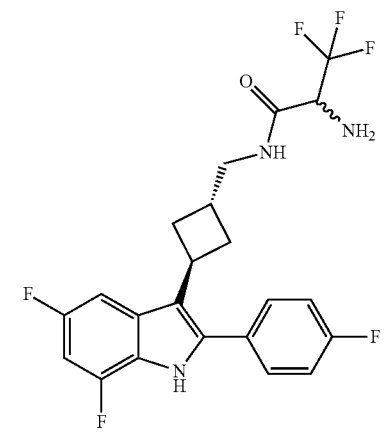 [SMILES: NC(C(=O)NC[C@H]1C[C@H](c2c(-c3ccc(F)cc3)[nH]c3c(F)cc(F)cc32)C1)C(F)(F)F]

TABLE 1-continued
Compounds 1 to 456
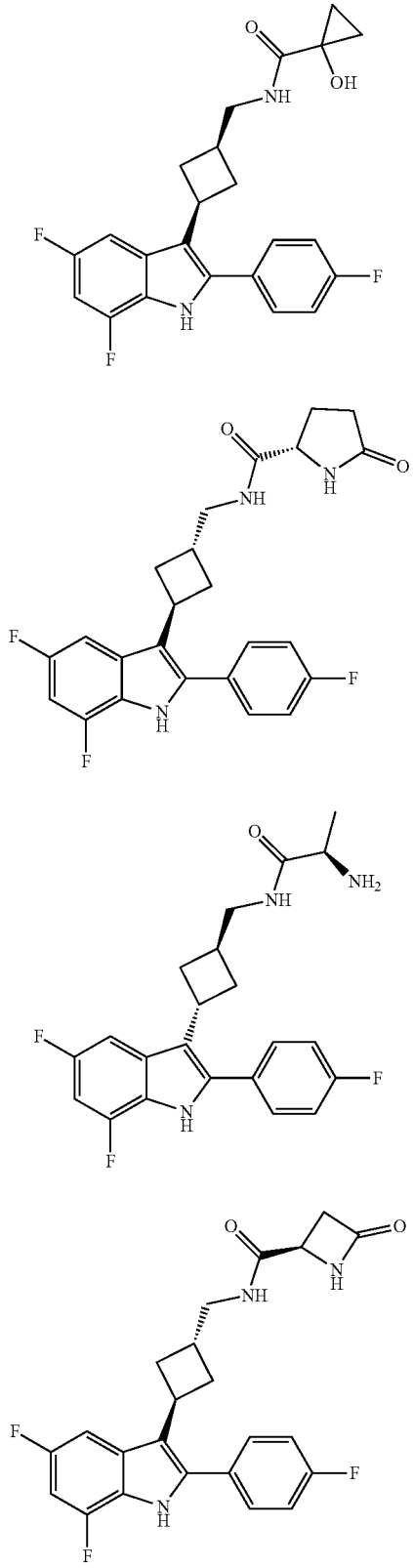
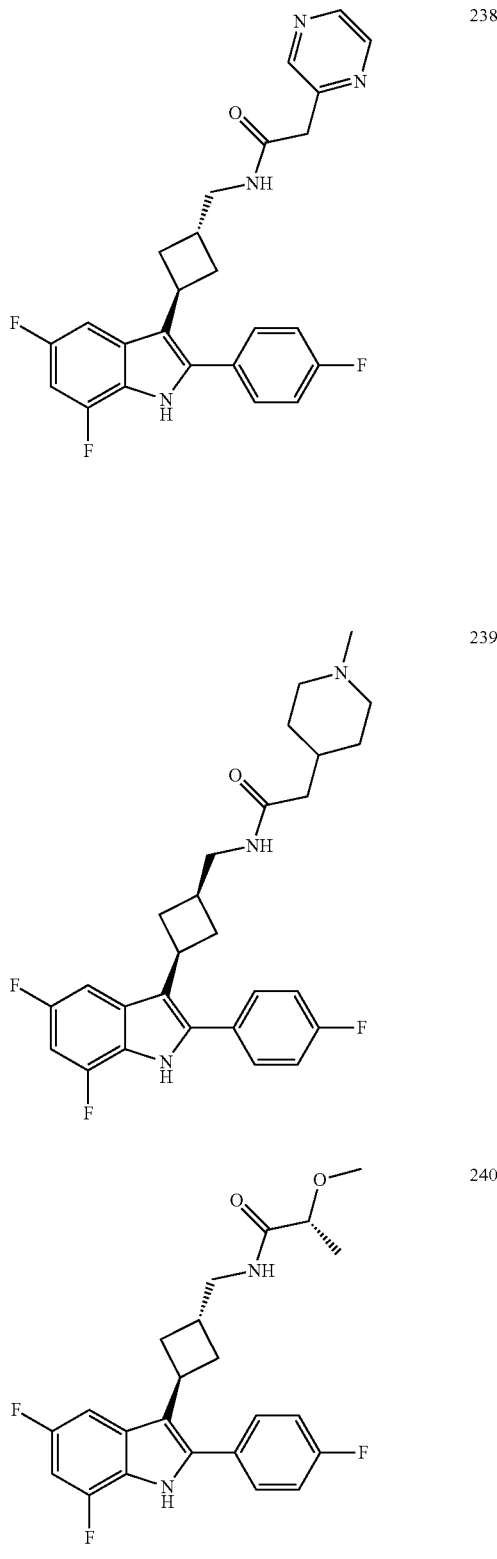

TABLE 1-continued

Compounds 1 to 456

TABLE 1-continued
Compounds 1 to 456
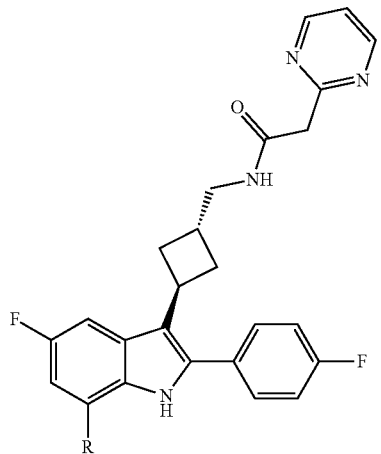
248
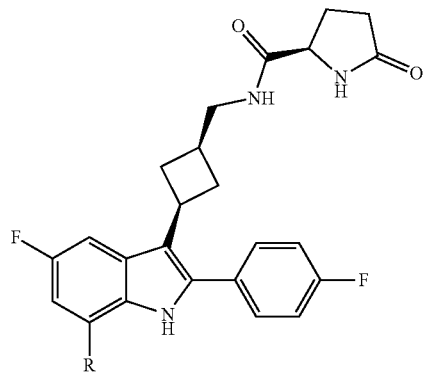
249
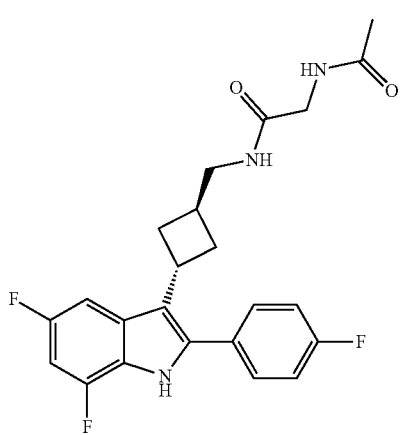 [SMILES: CC(=O)NCC(=O)NC[C@H]1C[C@H](c2c(-c3ccc(F)cc3)[nH]c3c(F)cc(F)cc32)C1]
250
TABLE 1-continued
Compounds 1 to 456
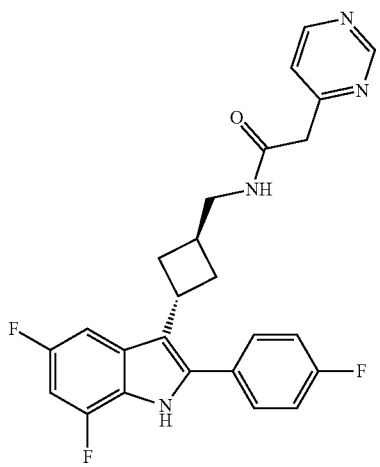 [SMILES: O=C(Cc1ccncn1)NC[C@H]1C[C@H](c2c(-c3ccc(F)cc3)[nH]c3c(F)cc(F)cc32)C1]
251
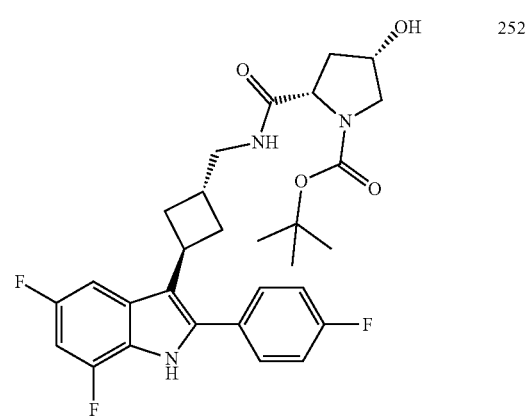
252
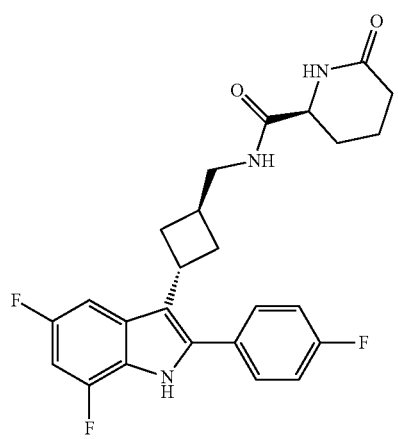 [SMILES: O=C1CCC[C@@H](C(=O)NC[C@H]2C[C@H](c3c(-c4ccc(F)cc4)[nH]c4c(F)cc(F)cc43)C2)N1]
253

TABLE 1-continued
Compounds 1 to 456
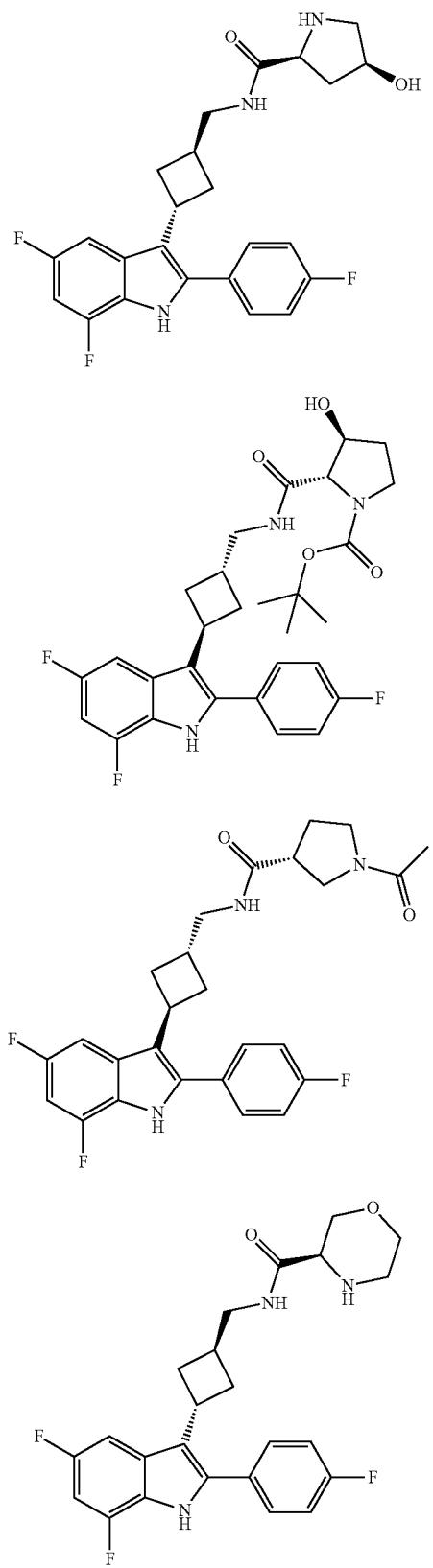
254
255
256
257
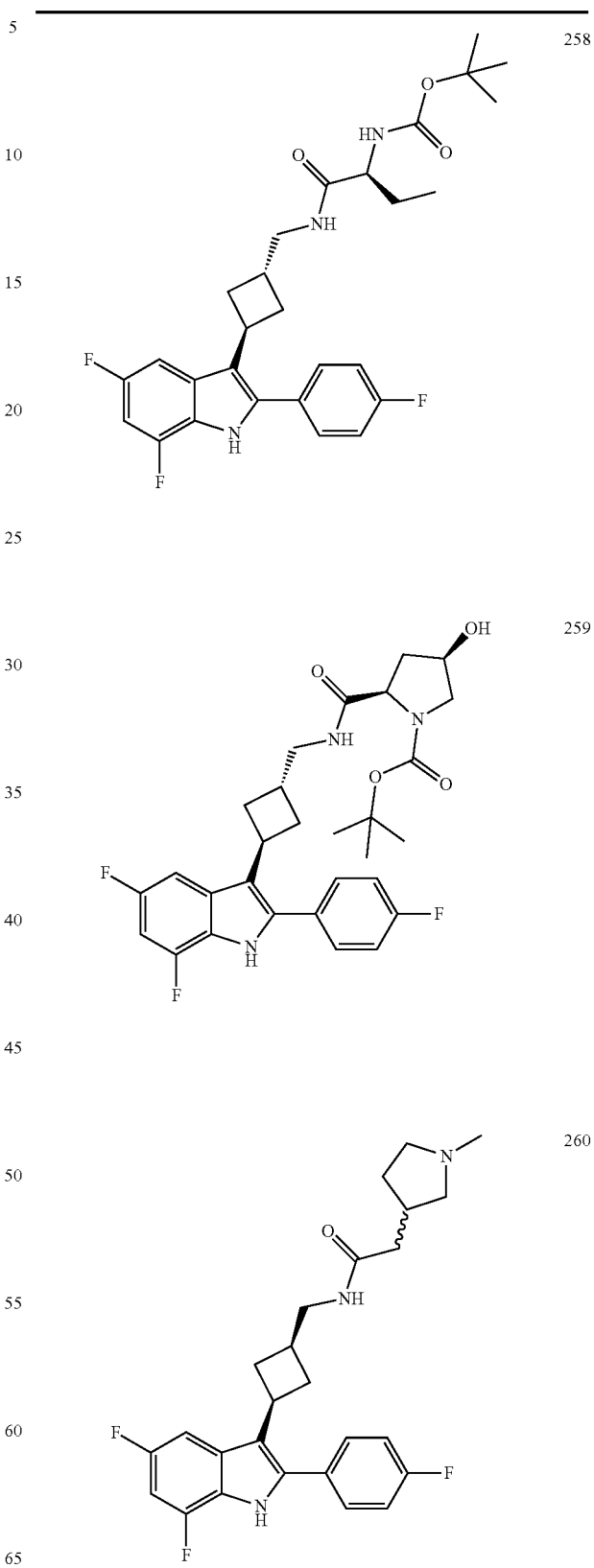
258
259
260

TABLE 1-continued
Compounds 1 to 456
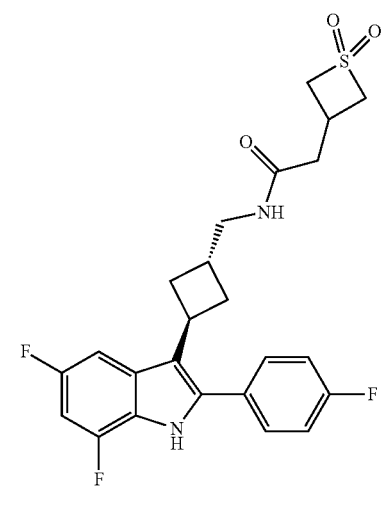 [SMILES: O=C(CC1CS(=O)(=O)C1)NC[C@H]1C[C@H](c2c(-c3ccc(F)cc3)[nH]c3c(F)cc(F)cc32)C1]
261
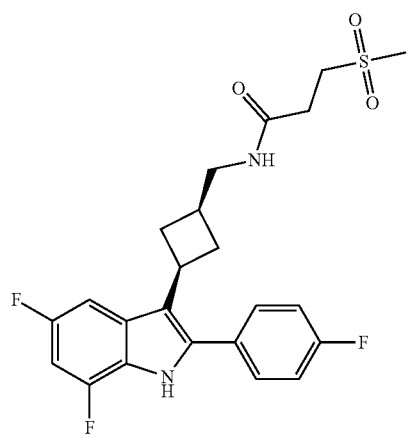 [SMILES: CS(=O)(=O)CCC(=O)NC[C@H]1C[C@@H](c2c(-c3ccc(F)cc3)[nH]c3c(F)cc(F)cc32)C1]
262
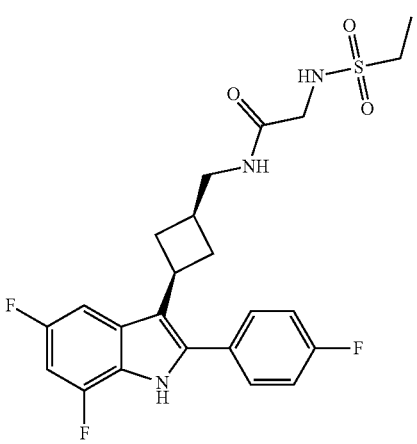 [SMILES: CCS(=O)(=O)NCC(=O)NC[C@H]1C[C@@H](c2c(-c3ccc(F)cc3)[nH]c3c(F)cc(F)cc32)C1]
263
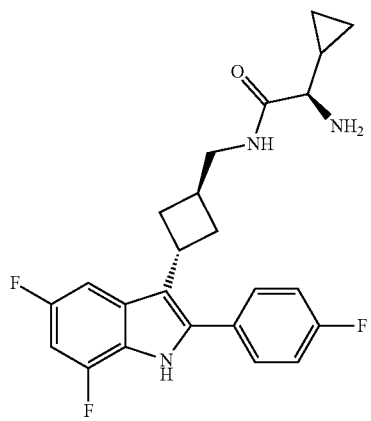 [SMILES: N[C@@H](C(=O)NC[C@H]1C[C@H](c2c(-c3ccc(F)cc3)[nH]c3c(F)cc(F)cc32)C1)C1CC1]
264
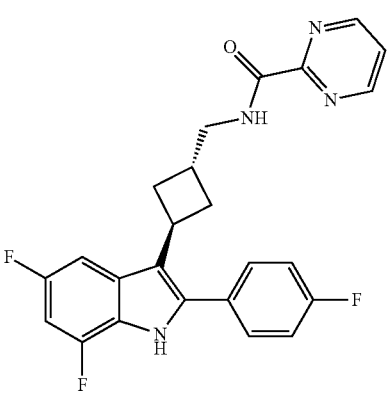 [SMILES: O=C(NC[C@H]1C[C@H](c2c(-c3ccc(F)cc3)[nH]c3c(F)cc(F)cc32)C1)c1ncccn1]
265
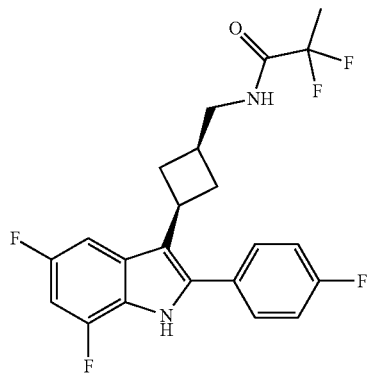 [SMILES: CC(F)(F)C(=O)NC[C@H]1C[C@@H](c2c(-c3ccc(F)cc3)[nH]c3c(F)cc(F)cc32)C1]
266
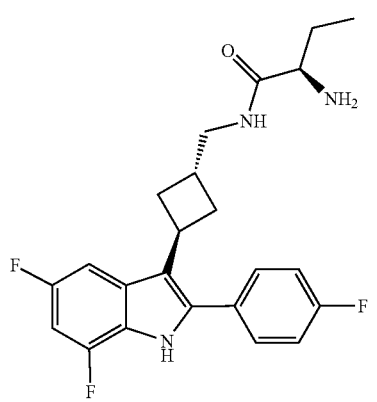 [SMILES: CC[C@@H](N)C(=O)NC[C@H]1C[C@H](c2c(-c3ccc(F)cc3)[nH]c3c(F)cc(F)cc32)C1]
267

TABLE 1-continued
Compounds 1 to 456
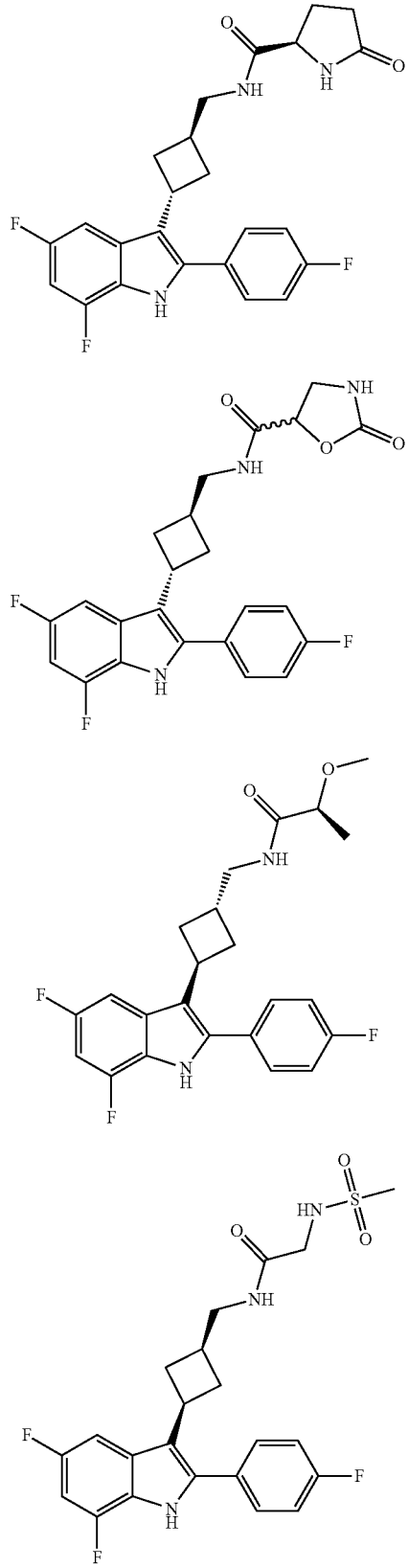
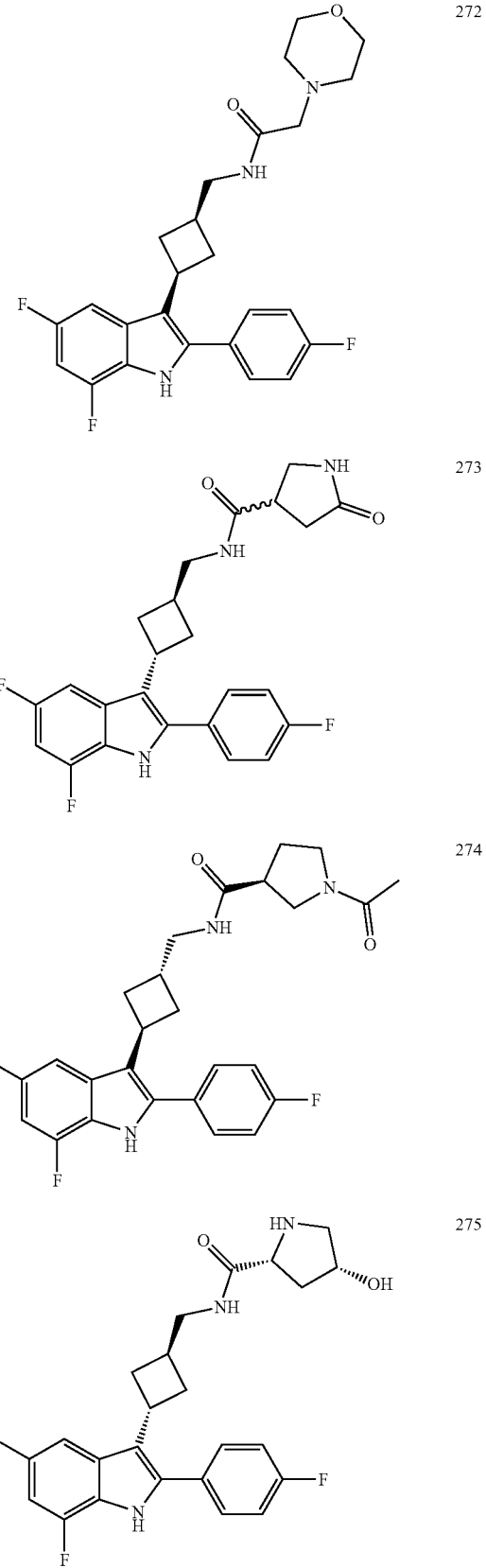

TABLE 1-continued
Compounds 1 to 456
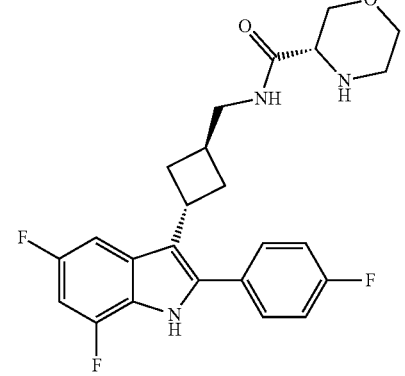
276
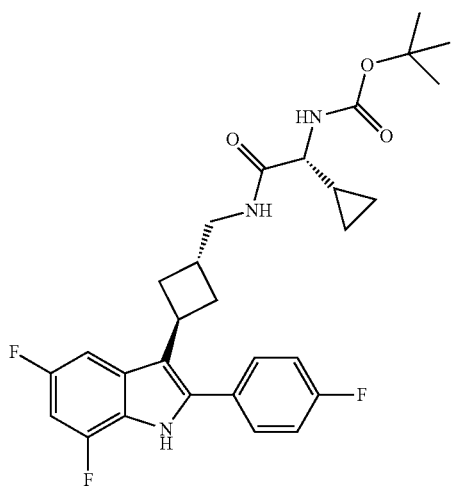 [SMILES: CC(C)(C)OC(=O)N[C@@H](C(=O)NC[C@H]1C[C@H](c2c(-c3ccc(F)cc3)[nH]c3c(F)cc(F)cc32)C1)C1CC1]
277
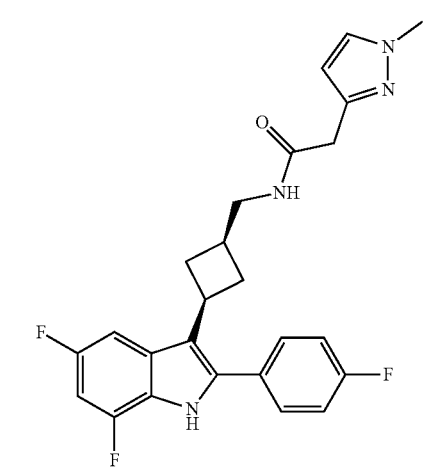 [SMILES: Cn1ccc(CC(=O)NC[C@H]2C[C@@H](c3c(-c4ccc(F)cc4)[nH]c4c(F)cc(F)cc43)C2)n1]
278
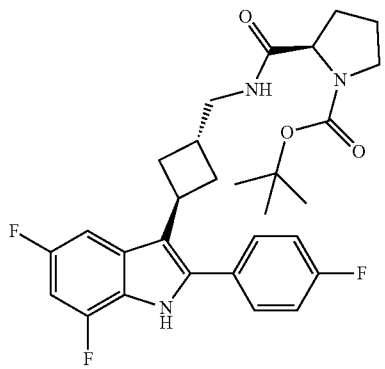 [SMILES: CC(C)(C)OC(=O)N1CCC[C@@H]1C(=O)NC[C@H]1C[C@H](c2c(-c3ccc(F)cc3)[nH]c3c(F)cc(F)cc32)C1]
279
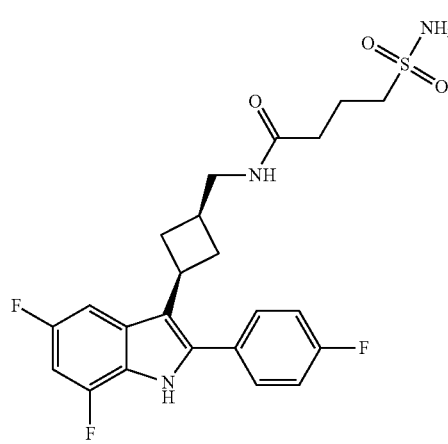 [SMILES: NS(=O)(=O)CCCC(=O)NC[C@H]1C[C@@H](c2c(-c3ccc(F)cc3)[nH]c3c(F)cc(F)cc32)C1]
280
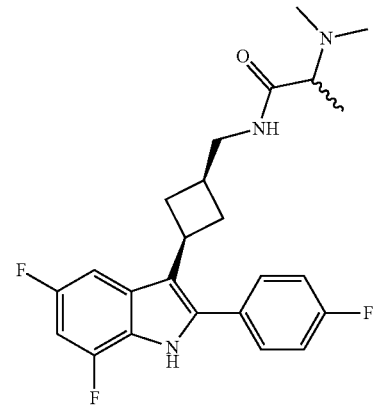 [SMILES: CC(C(=O)NC[C@H]1C[C@@H](c2c(-c3ccc(F)cc3)[nH]c3c(F)cc(F)cc32)C1)N(C)C]
281
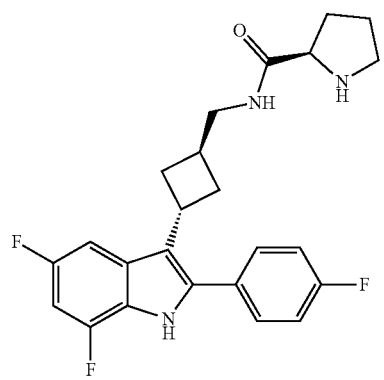 [SMILES: O=C(NC[C@H]1C[C@H](c2c(-c3ccc(F)cc3)[nH]c3c(F)cc(F)cc32)C1)[C@H]1CCCN1]
282

TABLE 1-continued
Compounds 1 to 456
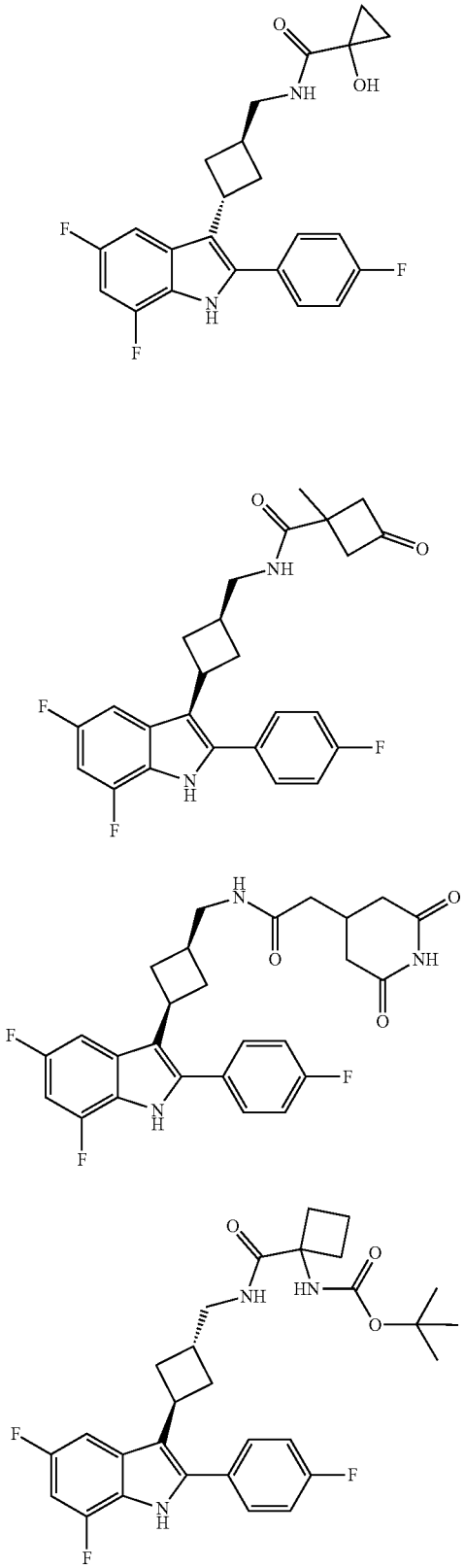
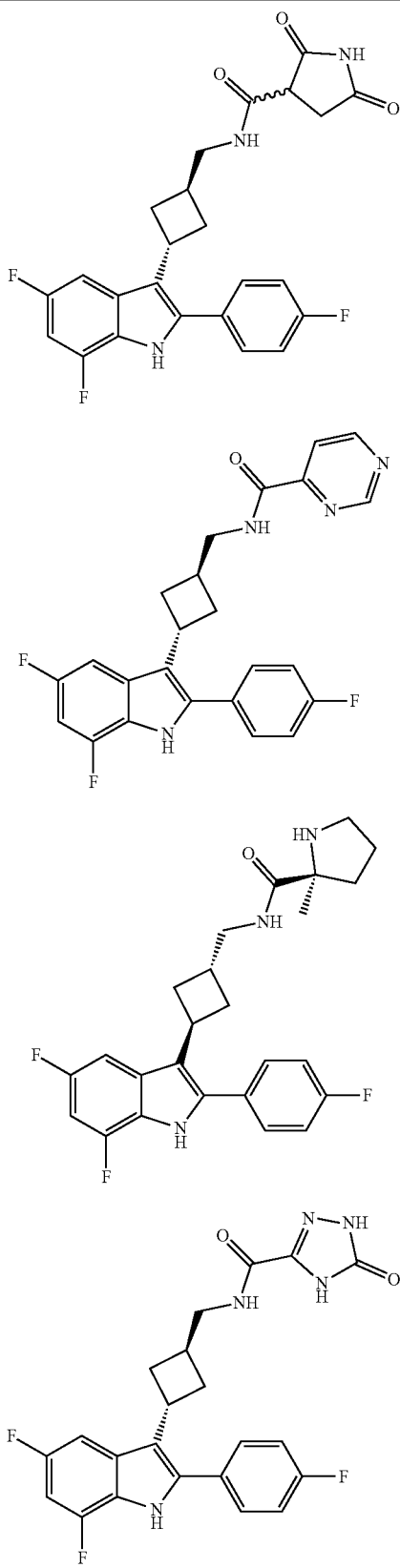

TABLE 1-continued
Compounds 1 to 456
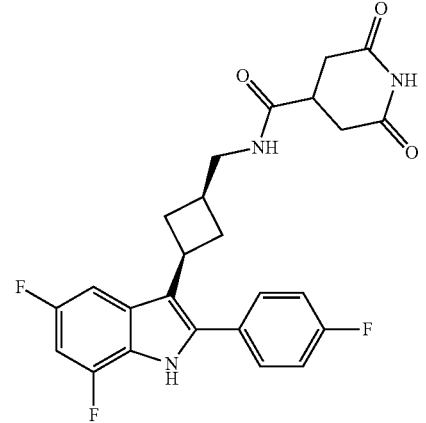 [SMILES: O=C1CC(C(=O)NC[C@H]2C[C@@H](c3c(-c4ccc(F)cc4)[nH]c4c(F)cc(F)cc43)C2)CC(=O)N1]
291
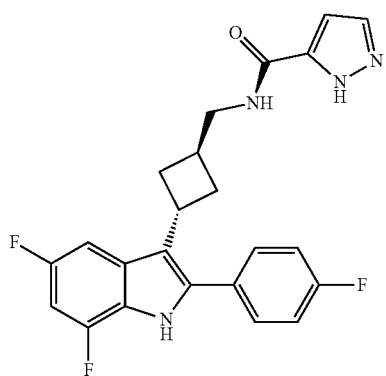
292
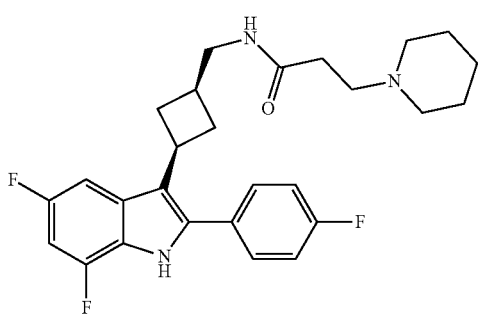 [SMILES: O=C(CCN1CCCCC1)NC[C@H]1C[C@@H](c2c(-c3ccc(F)cc3)[nH]c3c(F)cc(F)cc32)C1]
293
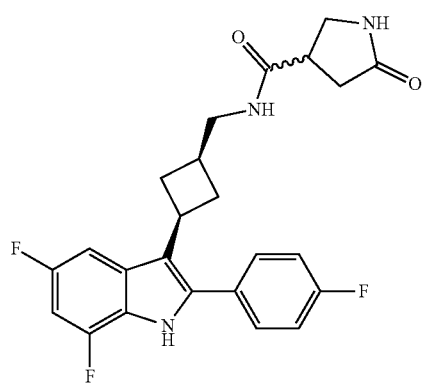 [SMILES: O=C1CC(C(=O)NC[C@H]2C[C@@H](c3c(-c4ccc(F)cc4)[nH]c4c(F)cc(F)cc43)C2)CN1]
294
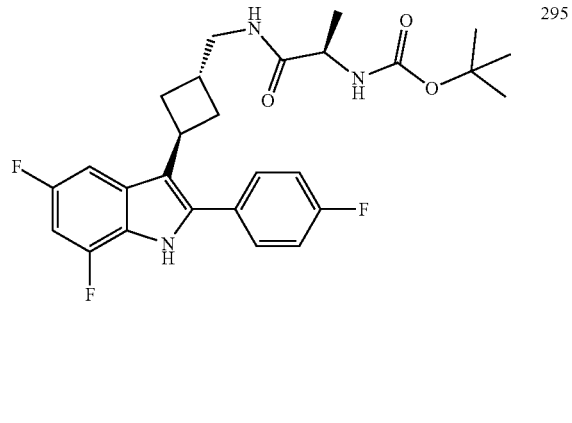
295
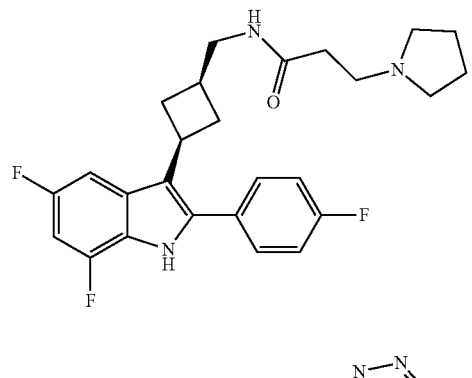
296
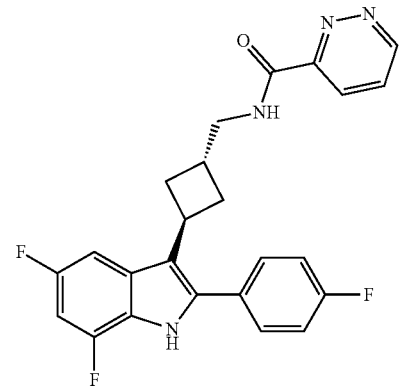 [SMILES: O=C(NC[C@H]1C[C@H](c2c(-c3ccc(F)cc3)[nH]c3c(F)cc(F)cc32)C1)c1cccnn1]
297
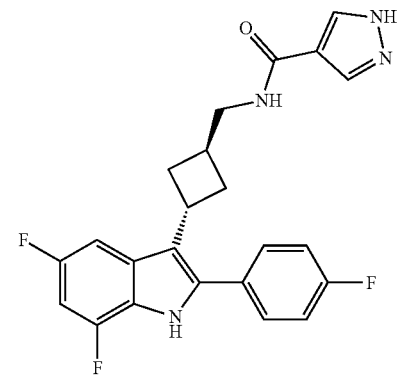 [SMILES: O=C(NC[C@H]1C[C@H](c2c(-c3ccc(F)cc3)[nH]c3c(F)cc(F)cc32)C1)c1cn[nH]c1]
298

TABLE 1-continued
Compounds 1 to 456
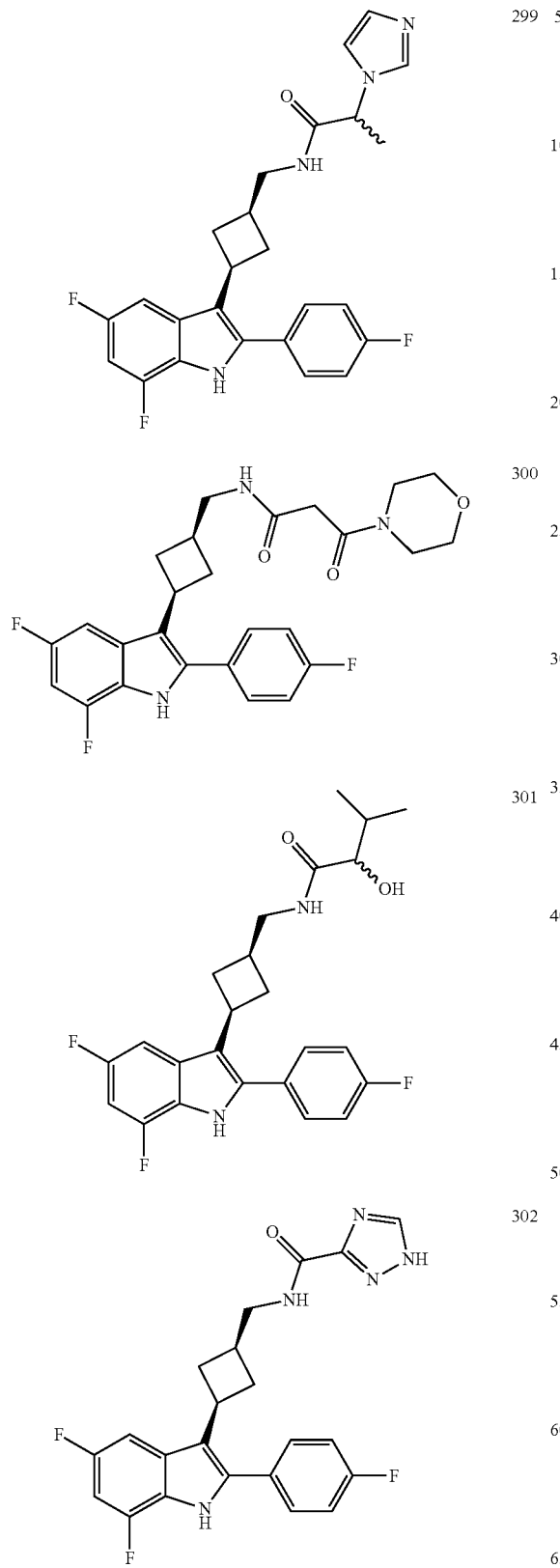
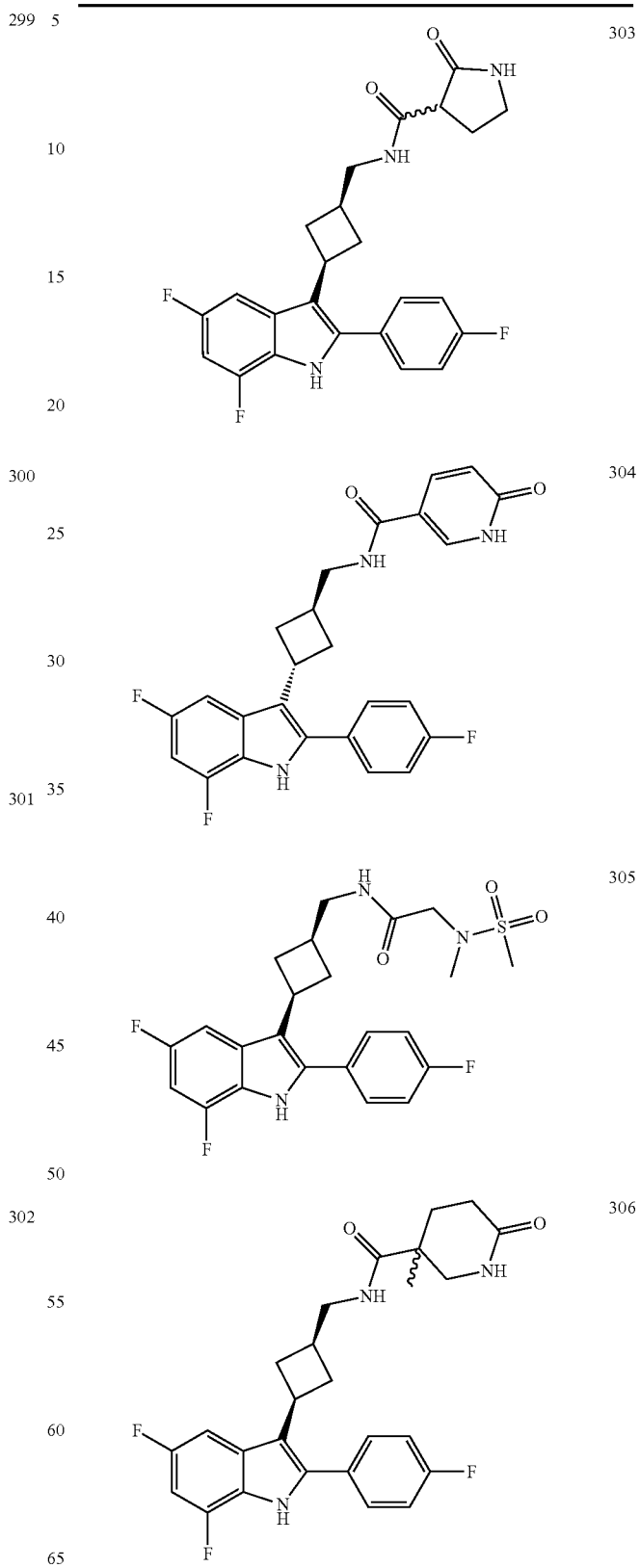

TABLE 1-continued
Compounds 1 to 456
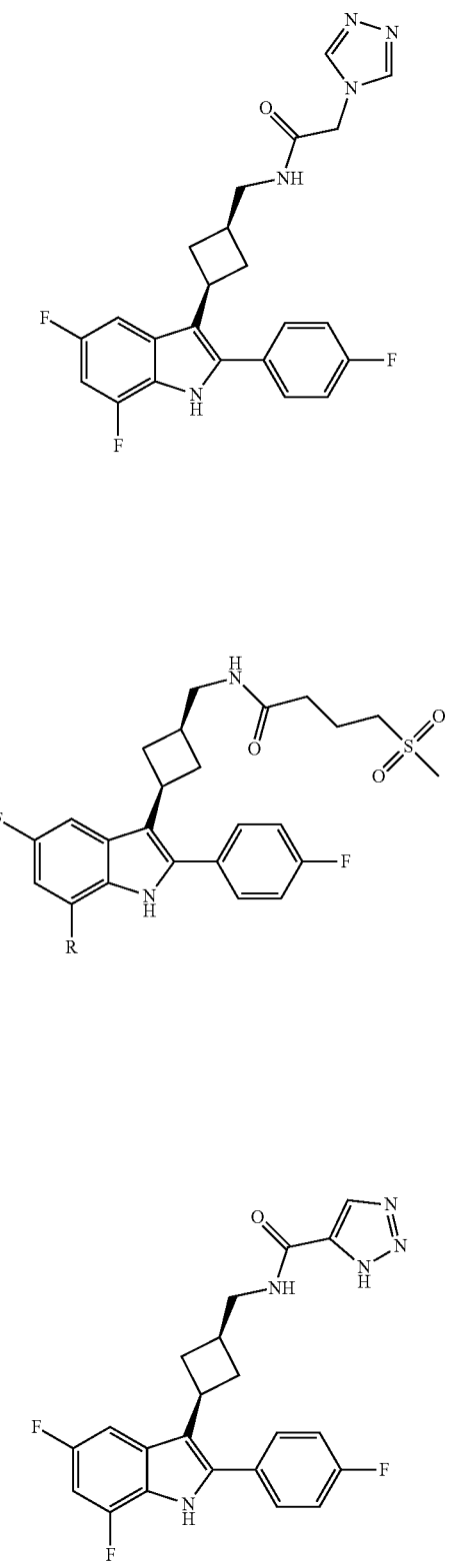
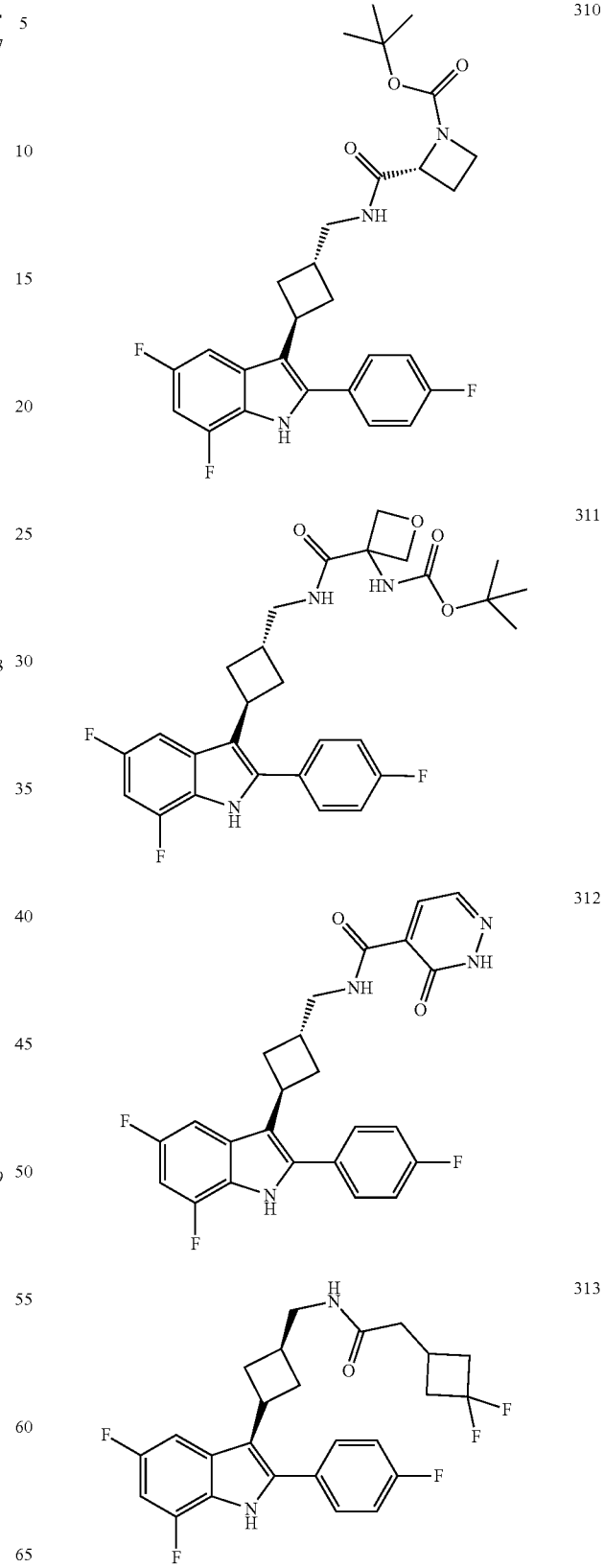

TABLE 1-continued
Compounds 1 to 456
| | |
|---|---|
| 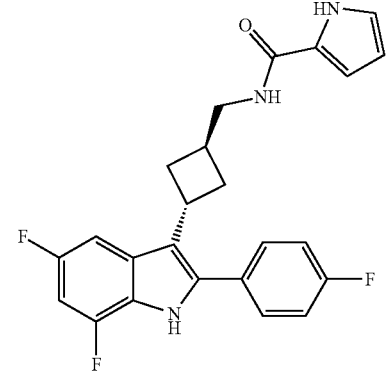 [SMILES: O=C(NC[C@H]1C[C@H](c2c(-c3ccc(F)cc3)[nH]c3c(F)cc(F)cc32)C1)c1ccc[nH]1] | 314 |
| 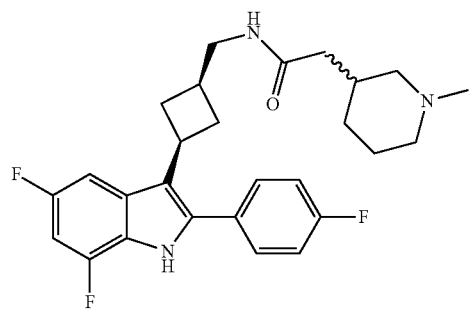 [SMILES: CN1CCCC(CC(=O)NC[C@H]2C[C@@H](c3c(-c4ccc(F)cc4)[nH]c4c(F)cc(F)cc43)C2)C1] | 315 |
| 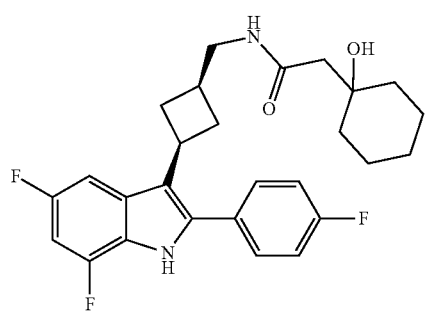 [SMILES: O=C(CC1(O)CCCCC1)NC[C@H]1C[C@@H](c2c(-c3ccc(F)cc3)[nH]c3c(F)cc(F)cc32)C1] | 316 |
| 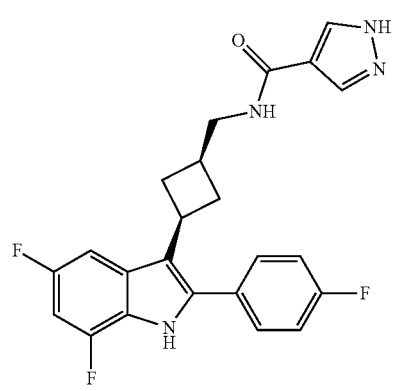 [SMILES: O=C(NC[C@H]1C[C@@H](c2c(-c3ccc(F)cc3)[nH]c3c(F)cc(F)cc32)C1)c1cn[nH]c1] | 317 |
| 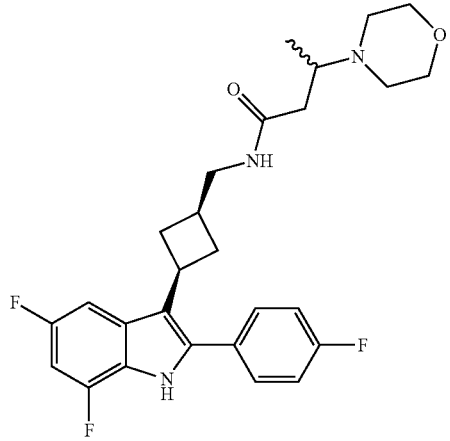 [SMILES: CC(CC(=O)NC[C@H]1C[C@@H](c2c(-c3ccc(F)cc3)[nH]c3c(F)cc(F)cc32)C1)N1CCOCC1] | 318 |
| 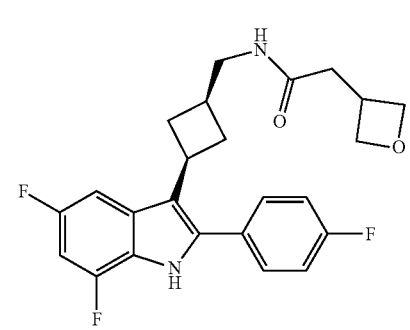 [SMILES: O=C(CC1COC1)NC[C@H]1C[C@@H](c2c(-c3ccc(F)cc3)[nH]c3c(F)cc(F)cc32)C1] | 319 |
| 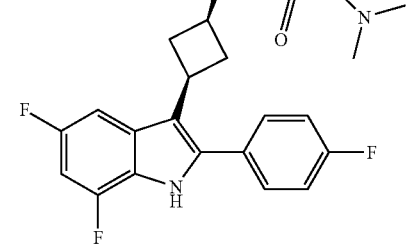 | 320 |
| 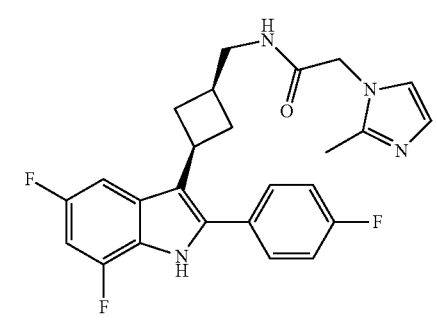 [SMILES: Cc1nccn1CC(=O)NC[C@H]1C[C@@H](c2c(-c3ccc(F)cc3)[nH]c3c(F)cc(F)cc32)C1] | 321 |

TABLE 1-continued
Compounds 1 to 456
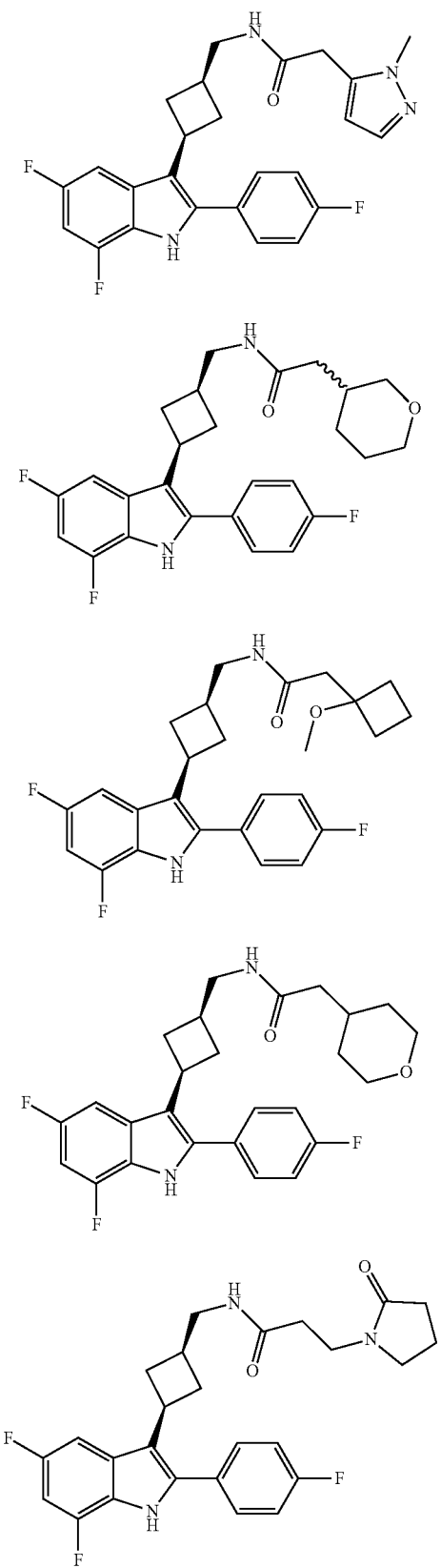
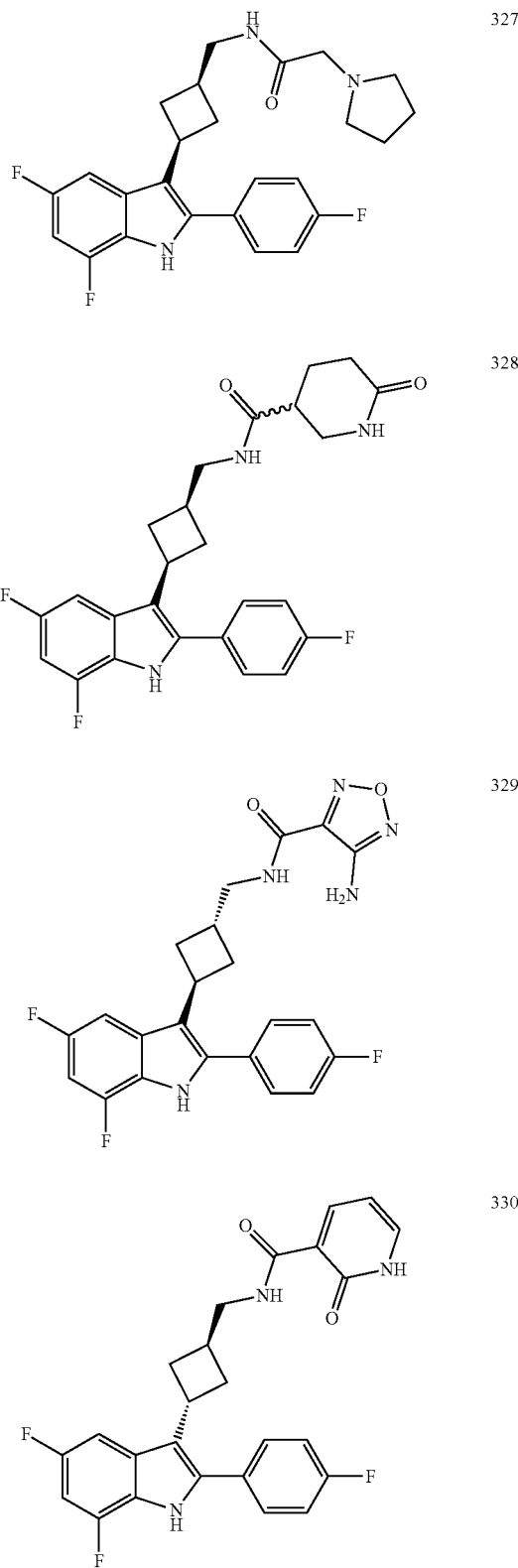

TABLE 1-continued
Compounds 1 to 456
331 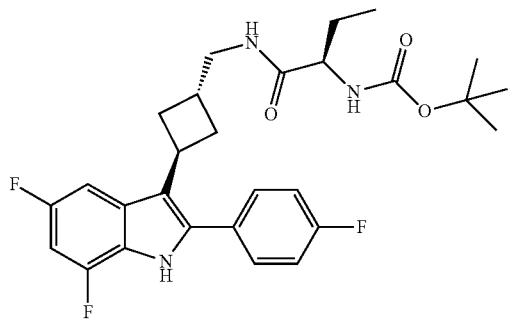 [SMILES: CC[C@@H](NC(=O)OC(C)(C)C)C(=O)NC[C@H]1C[C@H](c2c(-c3ccc(F)cc3)[nH]c3c(F)cc(F)cc32)C1]
332 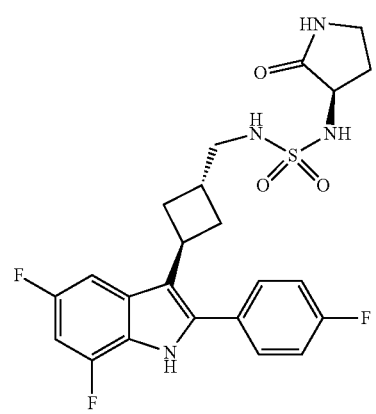 [SMILES: O=C1NCC[C@H]1NS(=O)(=O)NC[C@H]1C[C@H](c2c(-c3ccc(F)cc3)[nH]c3c(F)cc(F)cc32)C1]
333 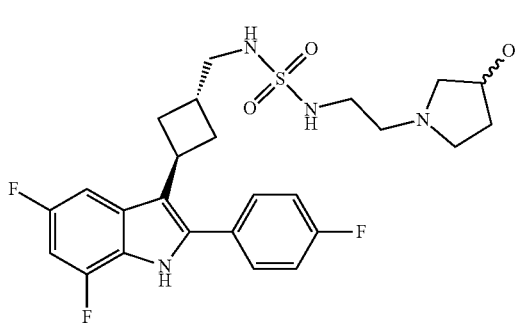
334 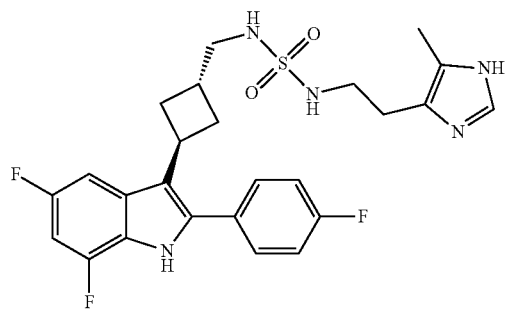 [SMILES: Cc1[nH]cnc1CCNS(=O)(=O)NC[C@H]1C[C@H](c2c(-c3ccc(F)cc3)[nH]c3c(F)cc(F)cc32)C1]
TABLE 1-continued
Compounds 1 to 456
335 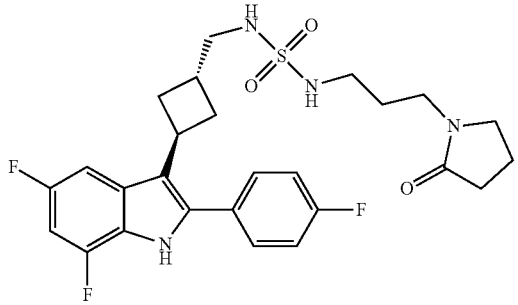 [SMILES: O=C1CCCN1CCCNS(=O)(=O)NC[C@H]1C[C@H](c2c(-c3ccc(F)cc3)[nH]c3c(F)cc(F)cc32)C1]
336 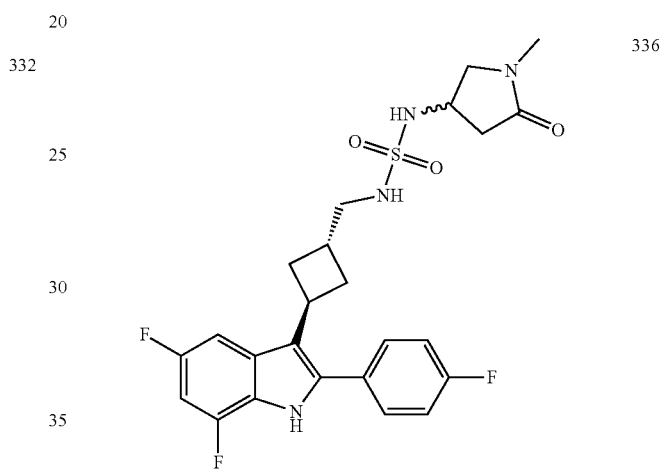
337 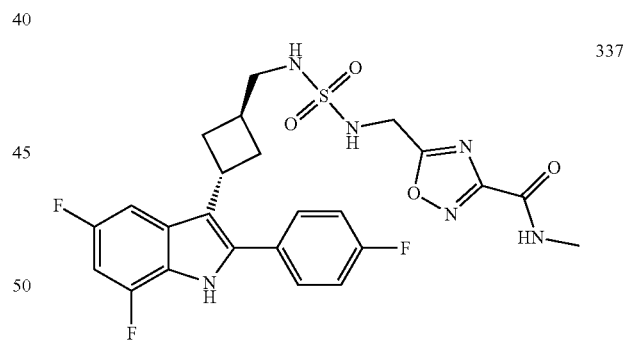
338 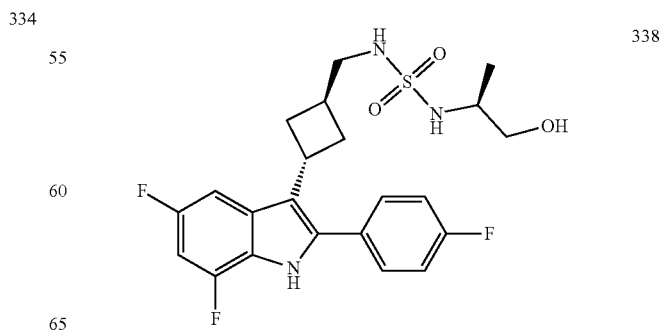

115
TABLE 1-continued
Compounds 1 to 456
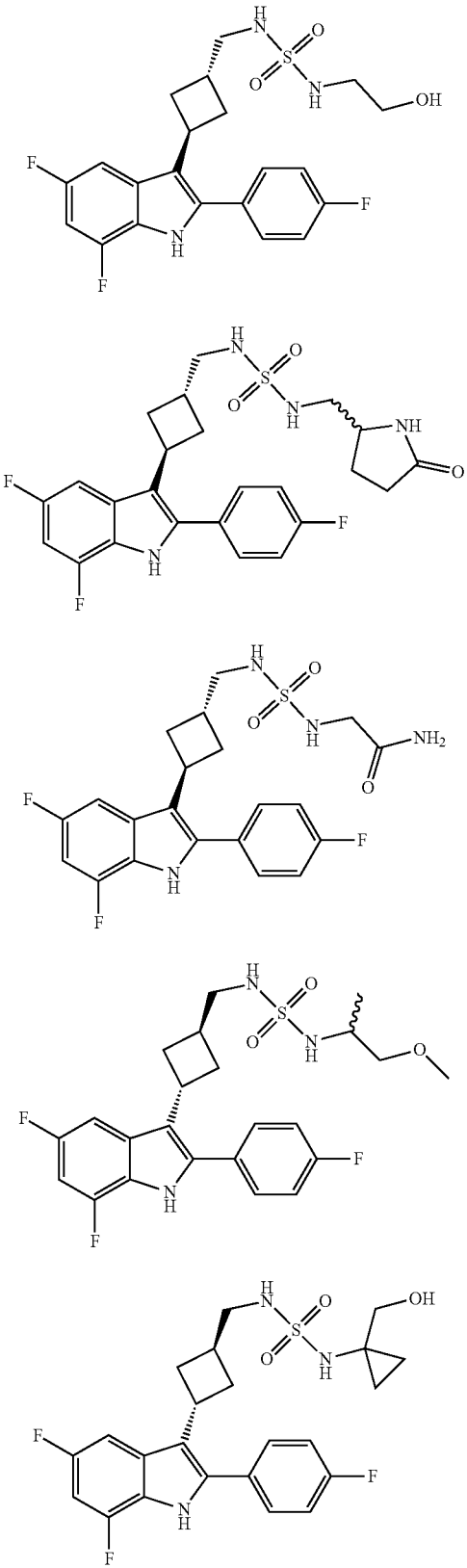
116
TABLE 1-continued
Compounds 1 to 456
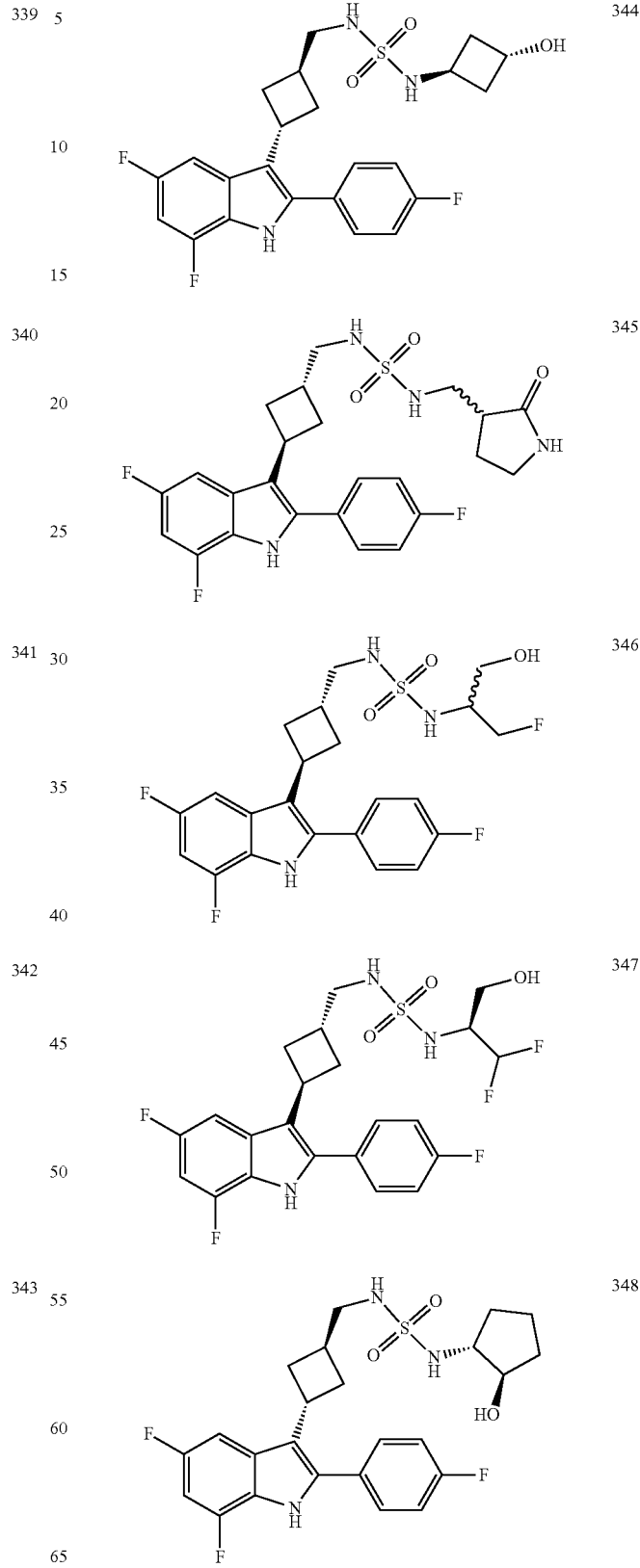

TABLE 1-continued
Compounds 1 to 456
349 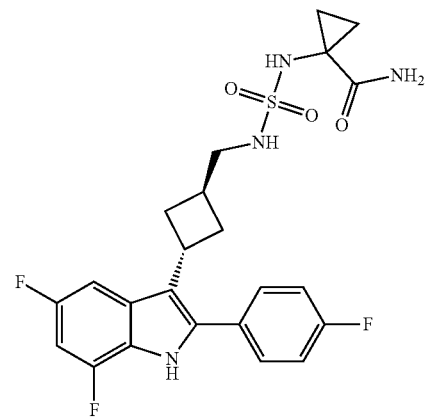 [SMILES: NC(=O)C1(NS(=O)(=O)NC[C@H]2C[C@H](c3c(-c4ccc(F)cc4)[nH]c4c(F)cc(F)cc43)C2)CC1]
350 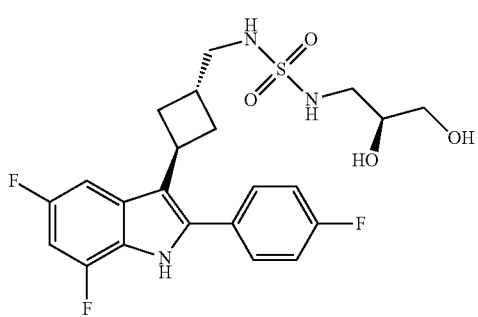 [SMILES: O=S(=O)(NC[C@H](O)CO)NC[C@H]1C[C@H](c2c(-c3ccc(F)cc3)[nH]c3c(F)cc(F)cc32)C1]
351 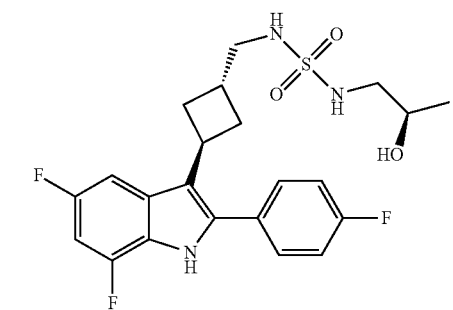 [SMILES: C[C@@H](O)CNS(=O)(=O)NC[C@H]1C[C@H](c2c(-c3ccc(F)cc3)[nH]c3c(F)cc(F)cc32)C1]
352 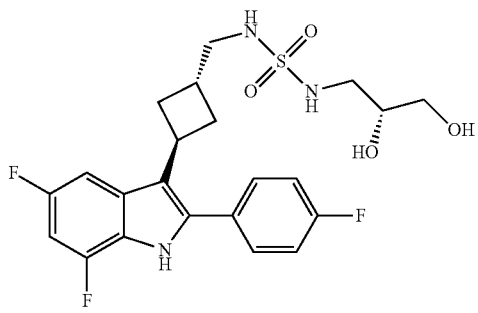 [SMILES: O=S(=O)(NC[C@@H](O)CO)NC[C@H]1C[C@H](c2c(-c3ccc(F)cc3)[nH]c3c(F)cc(F)cc32)C1]
353 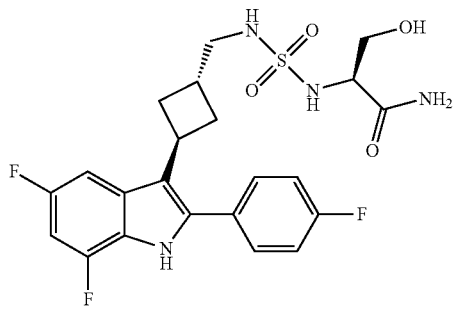 [SMILES: NC(=O)[C@H](CO)NS(=O)(=O)NC[C@H]1C[C@H](c2c(-c3ccc(F)cc3)[nH]c3c(F)cc(F)cc32)C1]
354 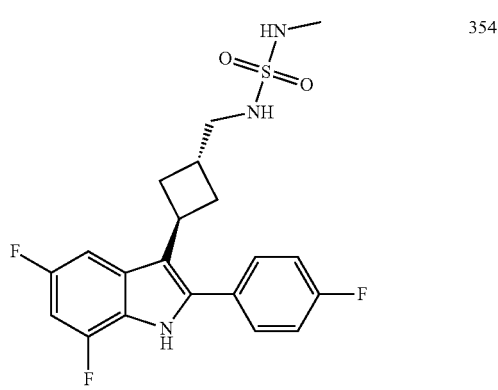
355 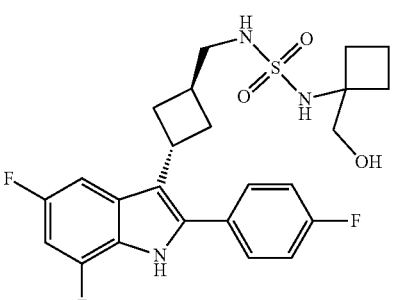
356 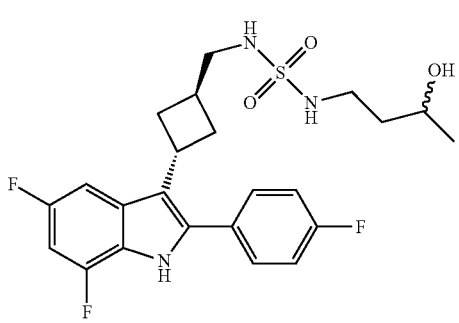 [SMILES: CC(O)CCNS(=O)(=O)NC[C@H]1C[C@H](c2c(-c3ccc(F)cc3)[nH]c3c(F)cc(F)cc32)C1]

TABLE 1-continued
Compounds 1 to 456
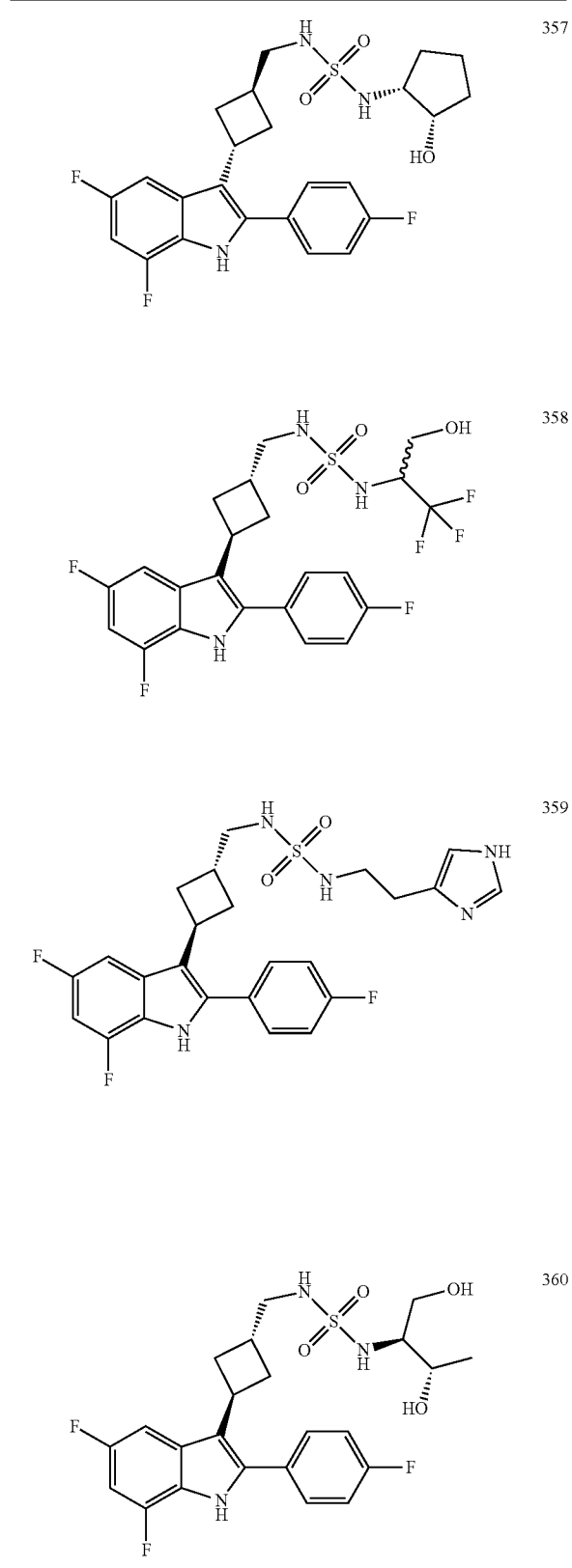
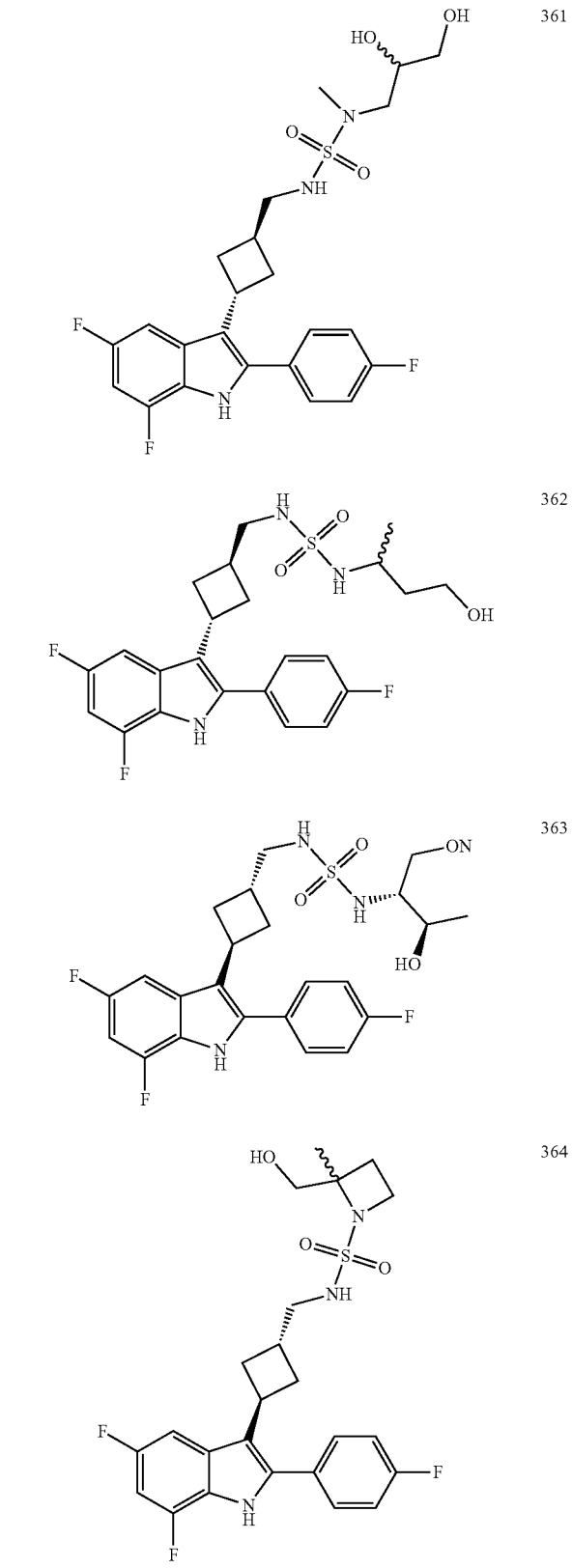

TABLE 1-continued
Compounds 1 to 456
365 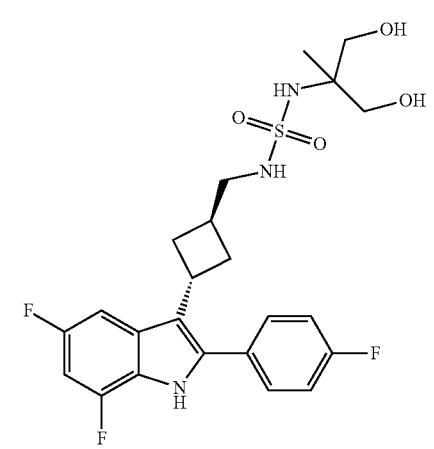 [SMILES: CC(CO)(CO)NS(=O)(=O)NC[C@H]1C[C@H](c2c(-c3ccc(F)cc3)[nH]c3c(F)cc(F)cc32)C1]
366 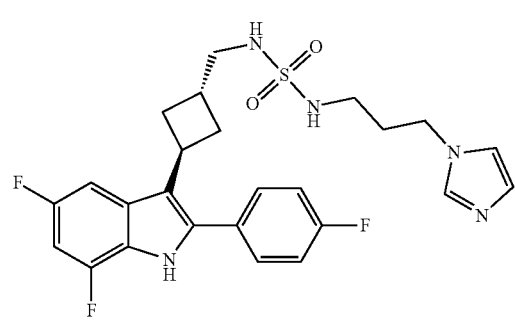 [SMILES: O=S(=O)(NCCCn1ccnc1)NC[C@H]1C[C@H](c2c(-c3ccc(F)cc3)[nH]c3c(F)cc(F)cc32)C1]
367 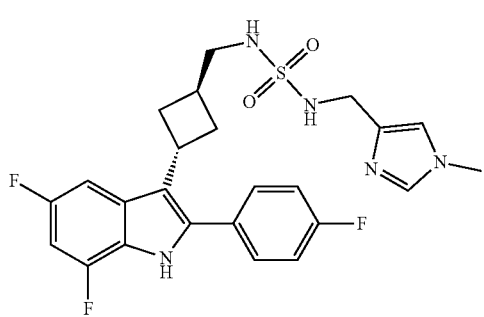 [SMILES: Cn1cnc(CNS(=O)(=O)NC[C@H]2C[C@H](c3c(-c4ccc(F)cc4)[nH]c4c(F)cc(F)cc43)C2)c1]
368 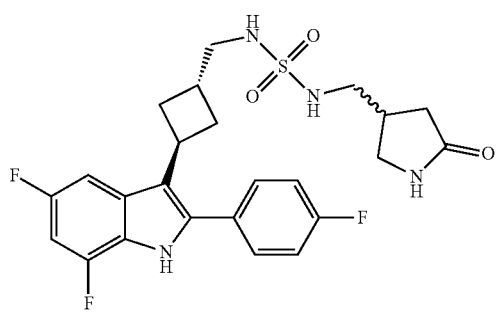 [SMILES: O=C1CC(CNS(=O)(=O)NC[C@H]2C[C@H](c3c(-c4ccc(F)cc4)[nH]c4c(F)cc(F)cc43)C2)CN1]
369 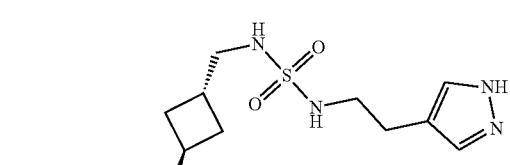
370 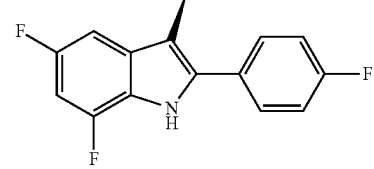
371 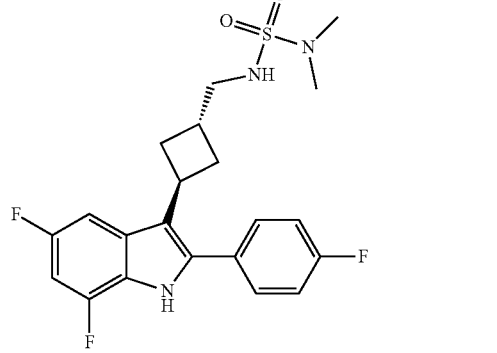
372 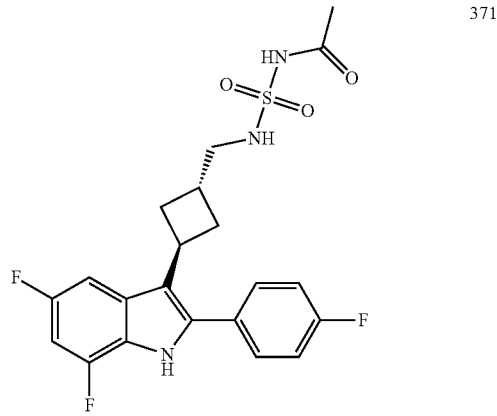

TABLE 1-continued
Compounds 1 to 456
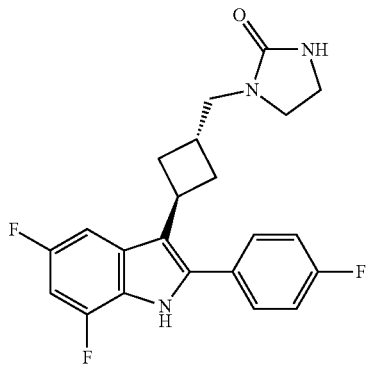 [SMILES: O=C1NCCN1C[C@H]1C[C@H](c2c(-c3ccc(F)cc3)[nH]c3c(F)cc(F)cc32)C1] 373
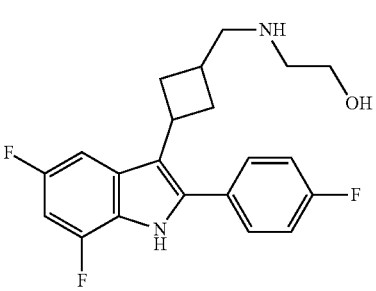 [SMILES: OCCNCC1CC(c2c(-c3ccc(F)cc3)[nH]c3c(F)cc(F)cc23)C1] 374
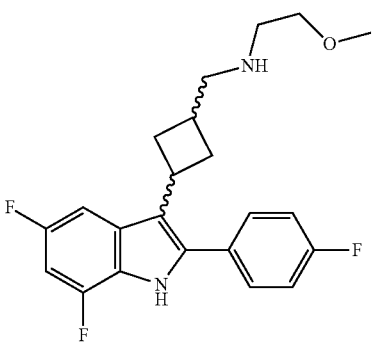 [SMILES: COCCNCC1CC(c2c(-c3ccc(F)cc3)[nH]c3c(F)cc(F)cc23)C1] 375
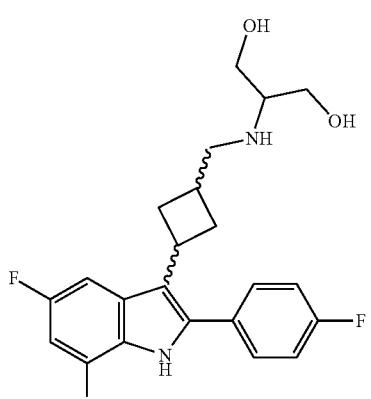 376
TABLE 1-continued
Compounds 1 to 456
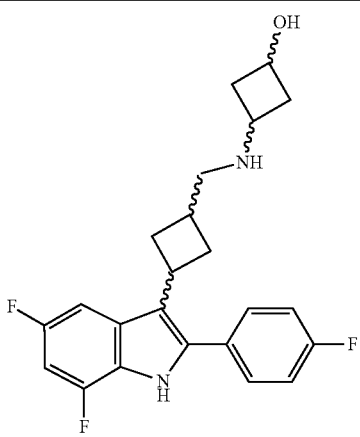 377
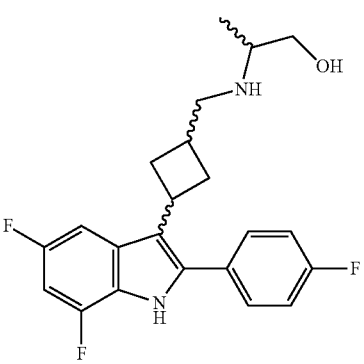 [SMILES: CC(CO)NCC1CC(c2c(-c3ccc(F)cc3)[nH]c3c(F)cc(F)cc23)C1] 378
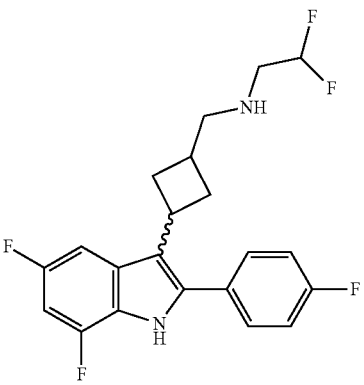 [SMILES: Fc1ccc(-c2[nH]c3c(F)cc(F)cc3c2C2CC(CNCC(F)F)C2)cc1] 379
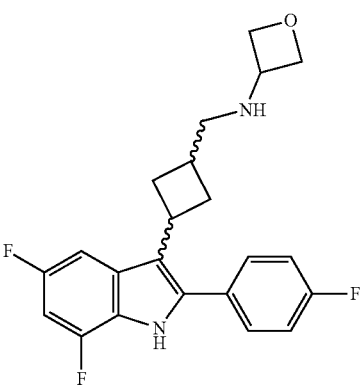 [SMILES: Fc1ccc(-c2[nH]c3c(F)cc(F)cc3c2C2CC(CNC3COC3)C2)cc1] 380

TABLE 1-continued
Compounds 1 to 456
381
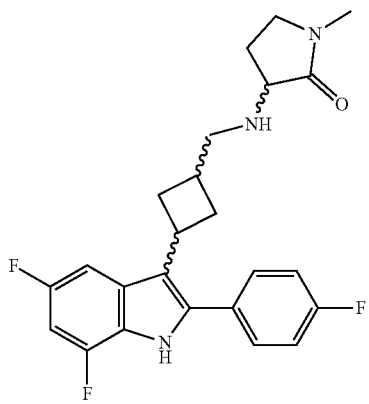 [SMILES: CN1CCC(NCC2CC(c3c(-c4ccc(F)cc4)[nH]c4c(F)cc(F)cc34)C2)C1=O]
382
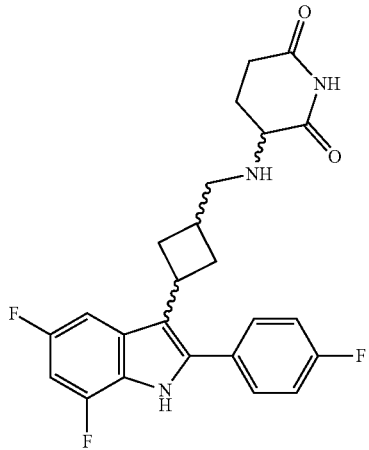 [SMILES: O=C1CCC(NCC2CC(c3c(-c4ccc(F)cc4)[nH]c4c(F)cc(F)cc34)C2)C(=O)N1]
383
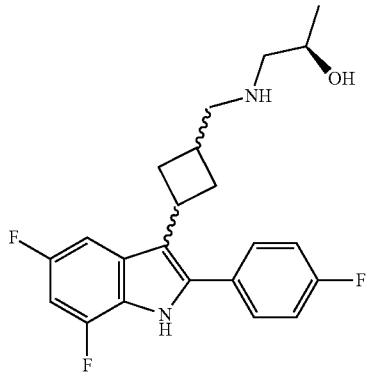 [SMILES: C[C@@H](O)CNCC1CC(c2c(-c3ccc(F)cc3)[nH]c3c(F)cc(F)cc23)C1]
TABLE 1-continued
Compounds 1 to 456
384
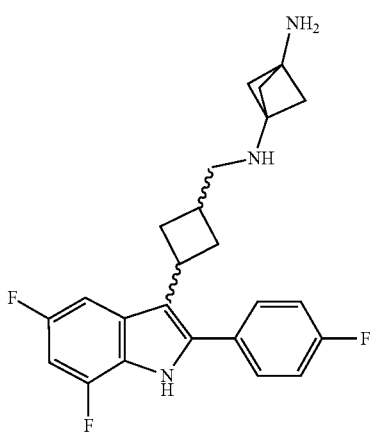 [SMILES: NC12CC(NCC3CC(c4c(-c5ccc(F)cc5)[nH]c5c(F)cc(F)cc45)C3)(C1)C2]
385
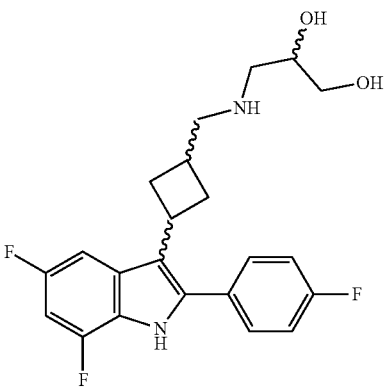 [SMILES: OCC(O)CNCC1CC(c2c(-c3ccc(F)cc3)[nH]c3c(F)cc(F)cc23)C1]
386
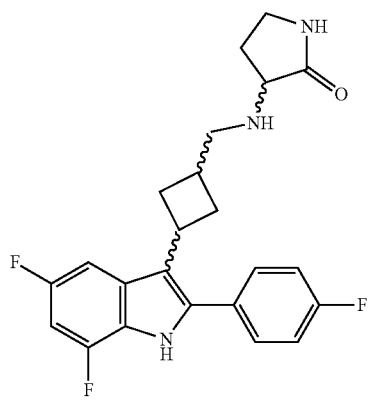 [SMILES: O=C1NCCC1NCC1CC(c2c(-c3ccc(F)cc3)[nH]c3c(F)cc(F)cc23)C1]

TABLE 1-continued
Compounds 1 to 456
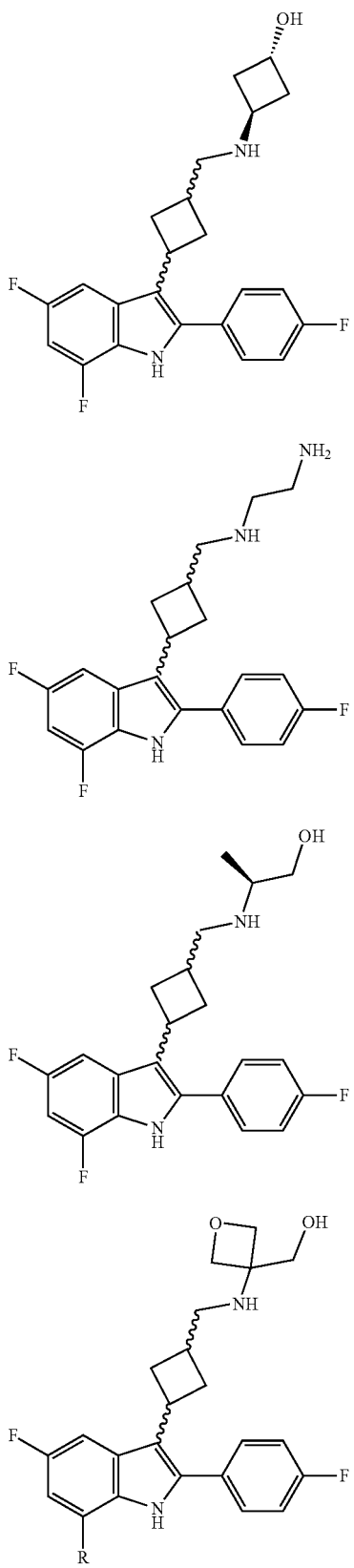
387
388
389
390
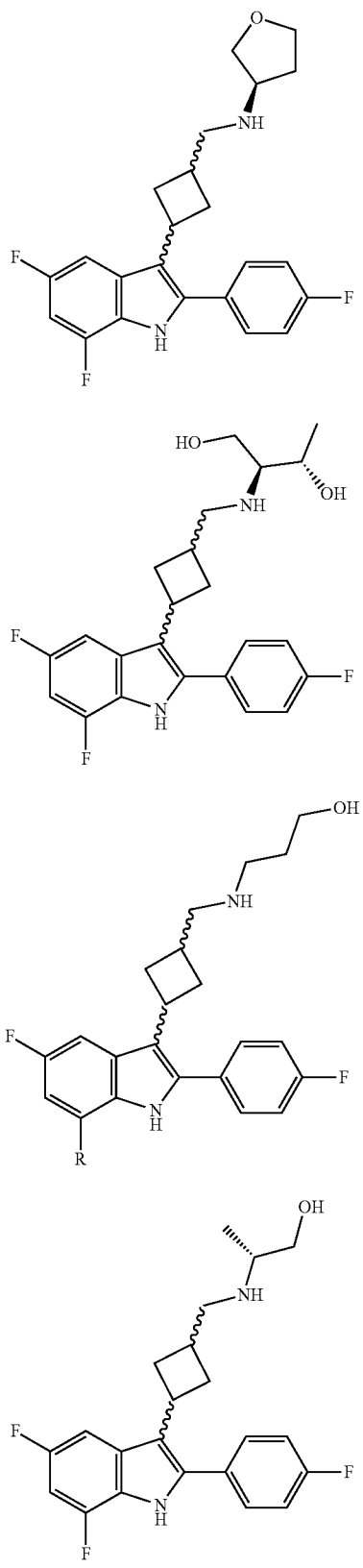
391
392
393
394

TABLE 1-continued
Compounds 1 to 456
| | |
|---|---|
| 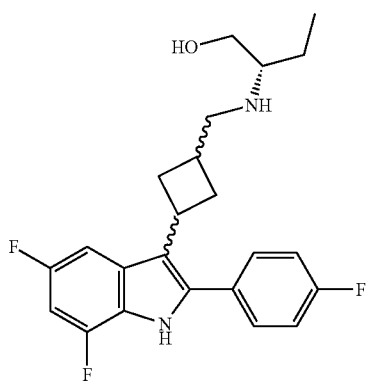 [SMILES: CC[C@@H](CO)NCC1CC(c2c(-c3ccc(F)cc3)[nH]c3c(F)cc(F)cc23)C1] | 395 |
| 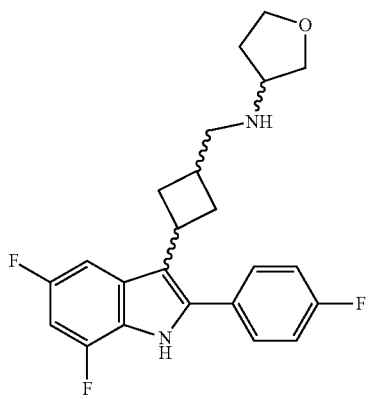 [SMILES: Fc1ccc(-c2[nH]c3c(F)cc(F)cc3c2C2CC(CNC3CCOC3)C2)cc1] | 396 |
| 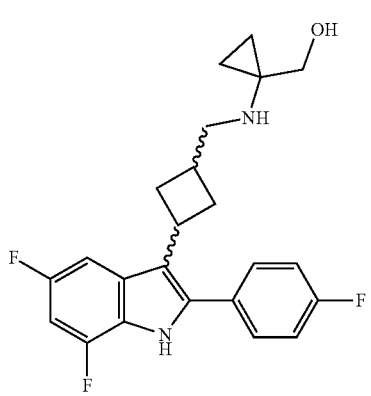 [SMILES: OCC1(NCC2CC(c3c(-c4ccc(F)cc4)[nH]c4c(F)cc(F)cc34)C2)CC1] | 397 |
| 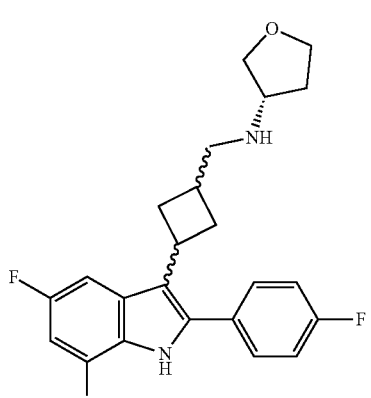 | 398 |
| 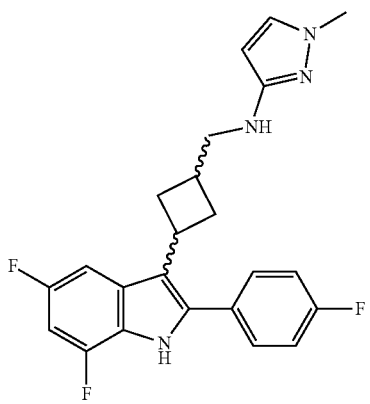 [SMILES: Cn1ccc(NCC2CC(c3c(-c4ccc(F)cc4)[nH]c4c(F)cc(F)cc34)C2)n1] | 399 |
| 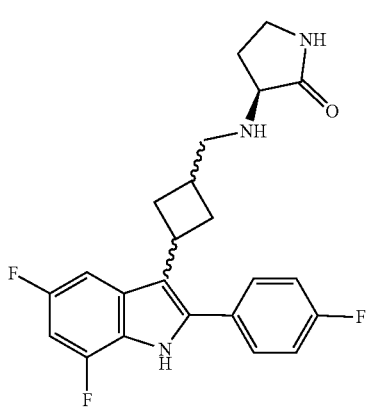 [SMILES: O=C1NCC[C@@H]1NCC1CC(c2c(-c3ccc(F)cc3)[nH]c3c(F)cc(F)cc23)C1] | 400 |
| 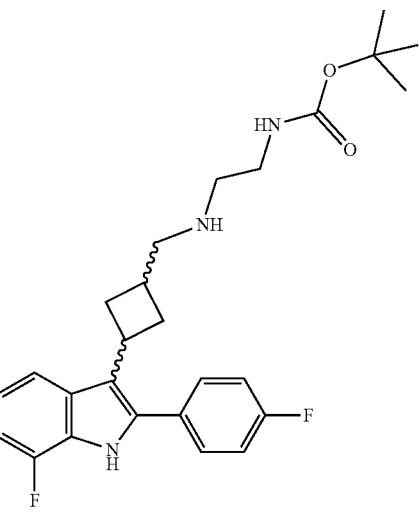 | 401 |

TABLE 1-continued
Compounds 1 to 456
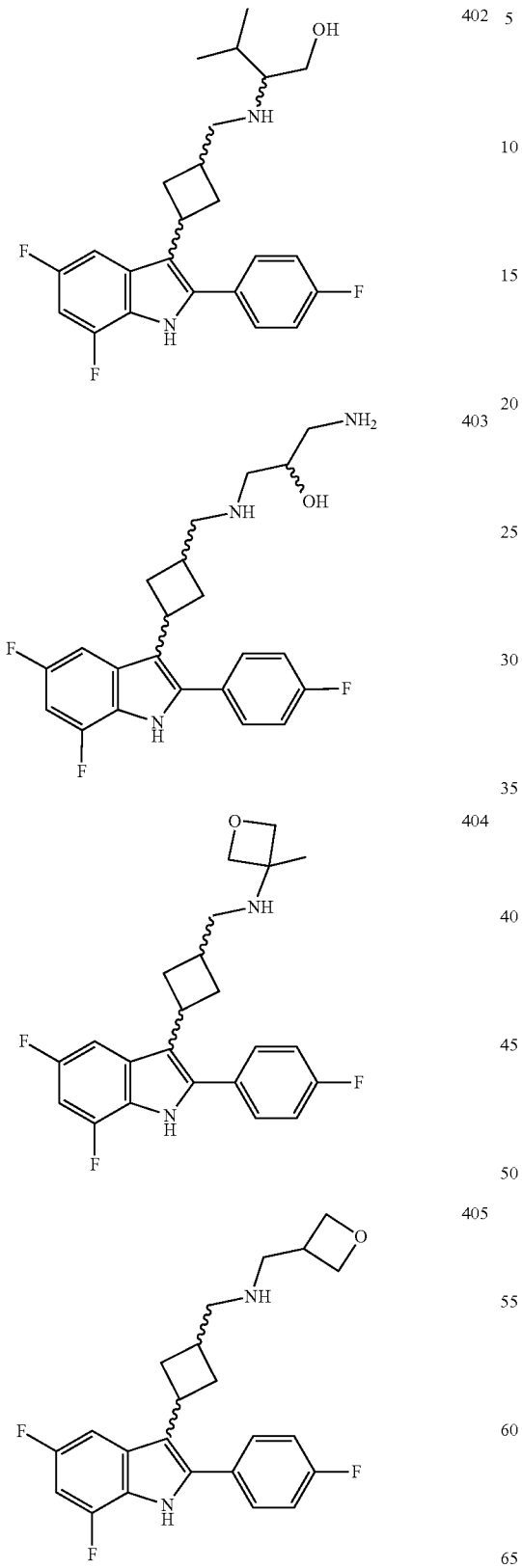
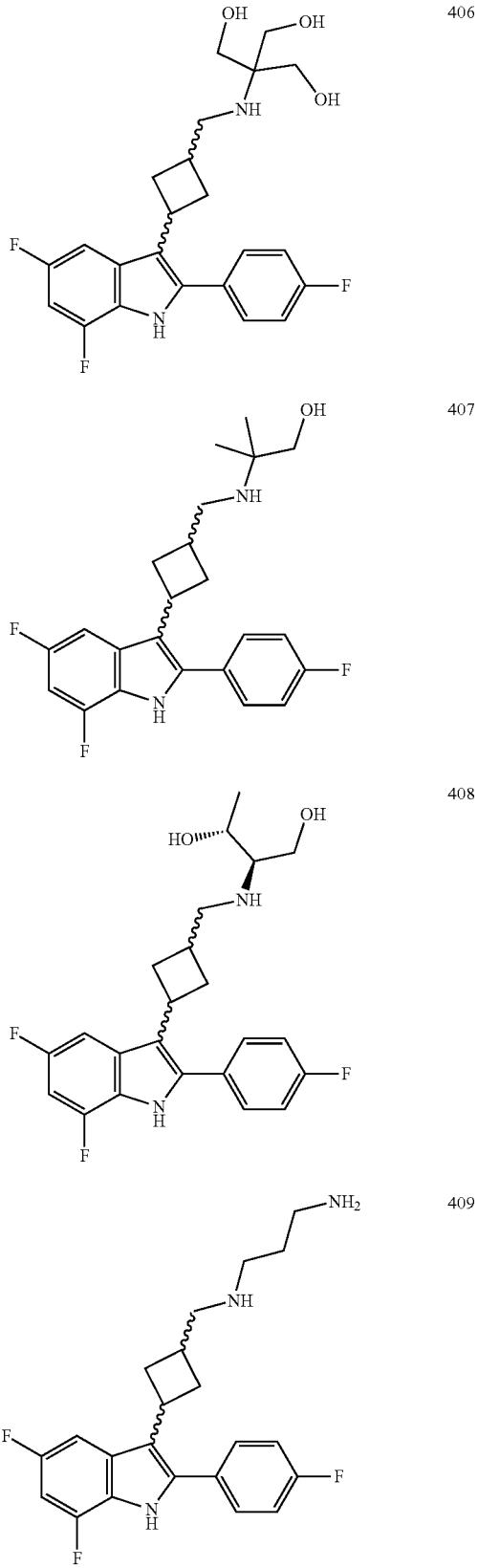

TABLE 1-continued
Compounds 1 to 456
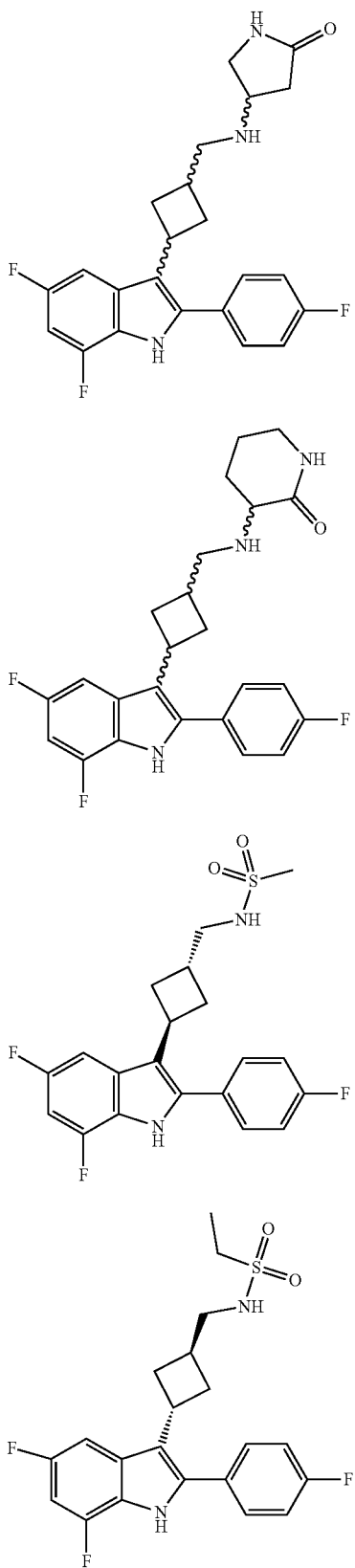
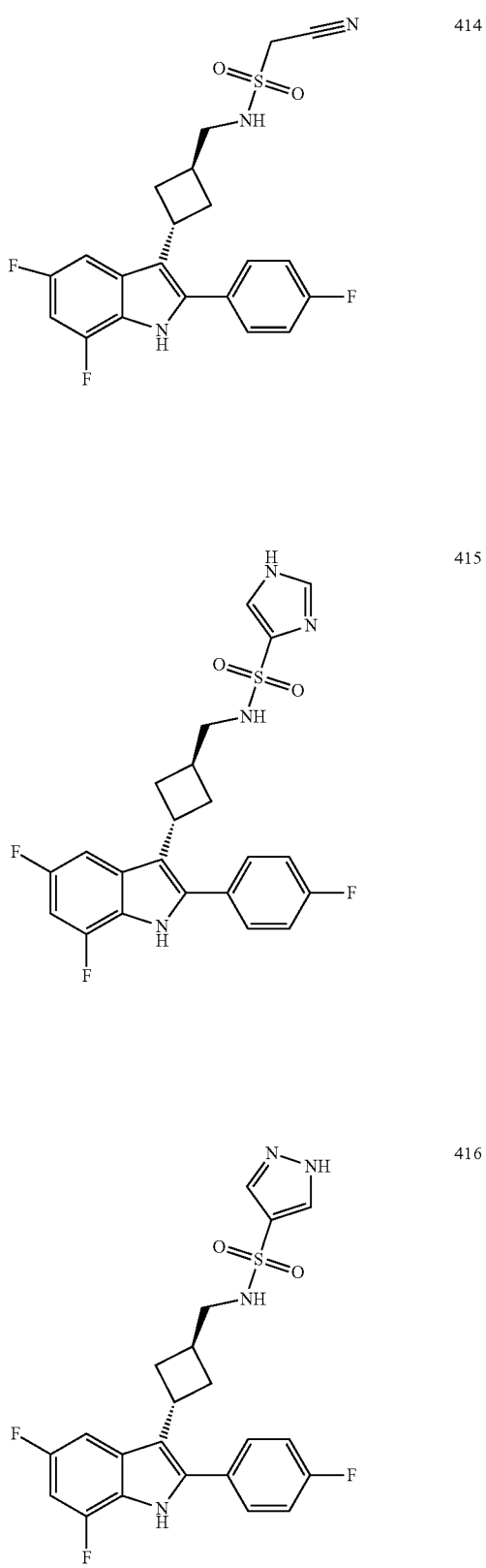

TABLE 1-continued
Compounds 1 to 456
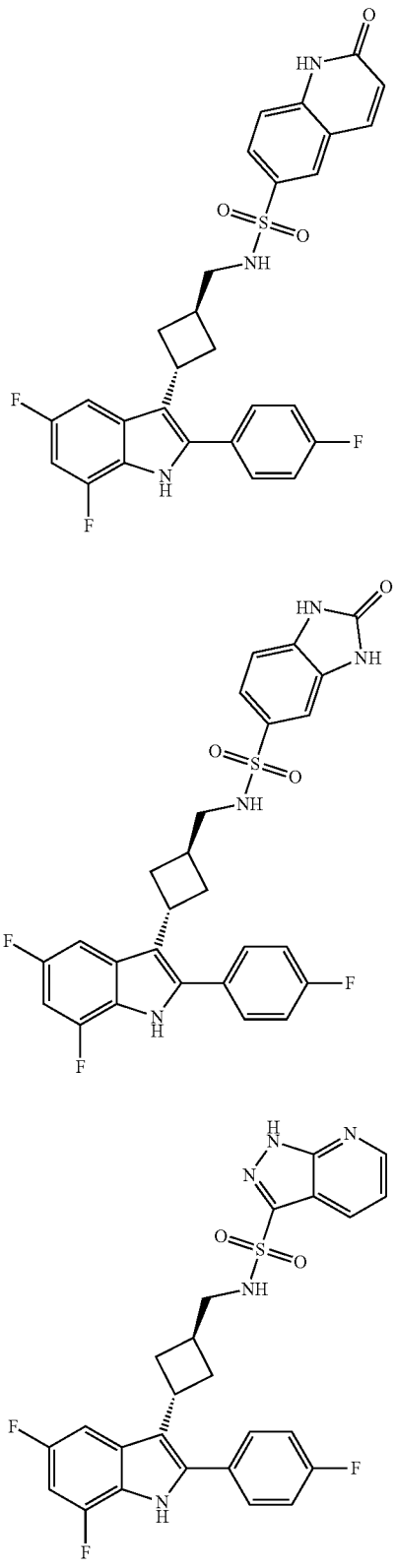
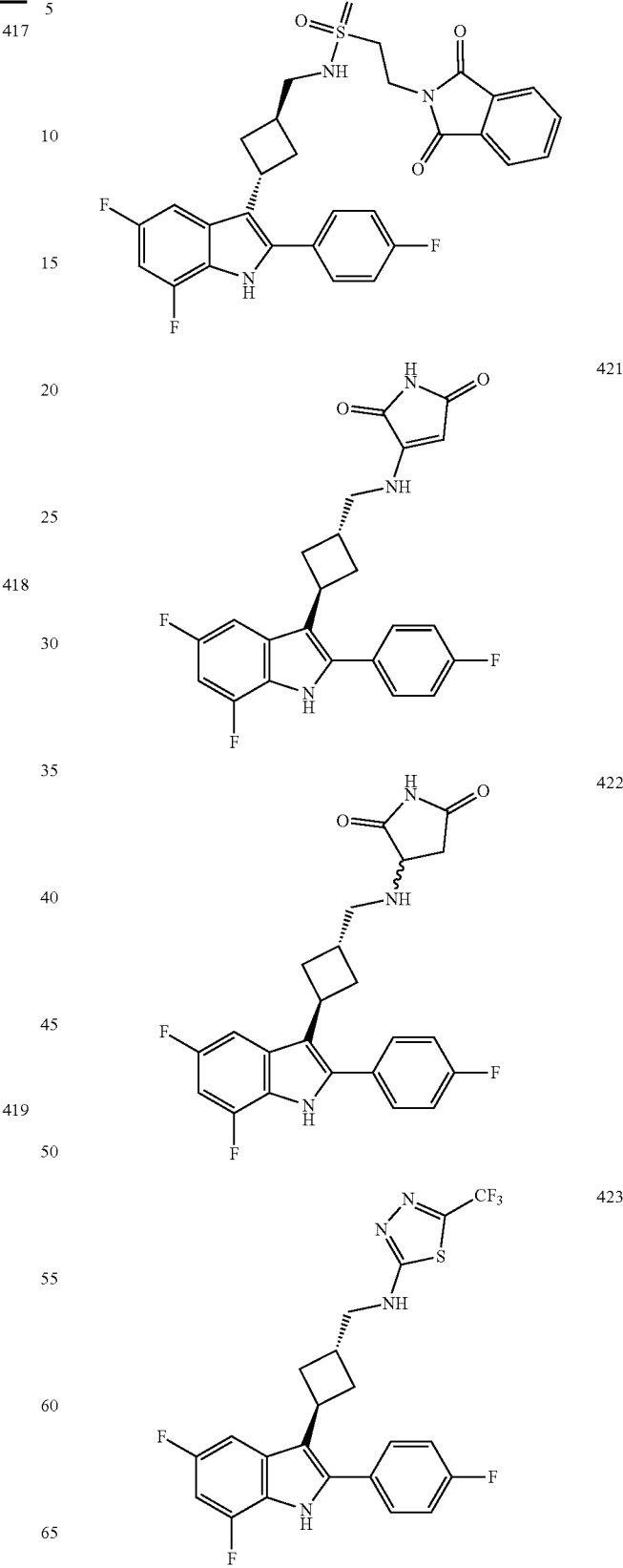

TABLE 1-continued
Compounds 1 to 456
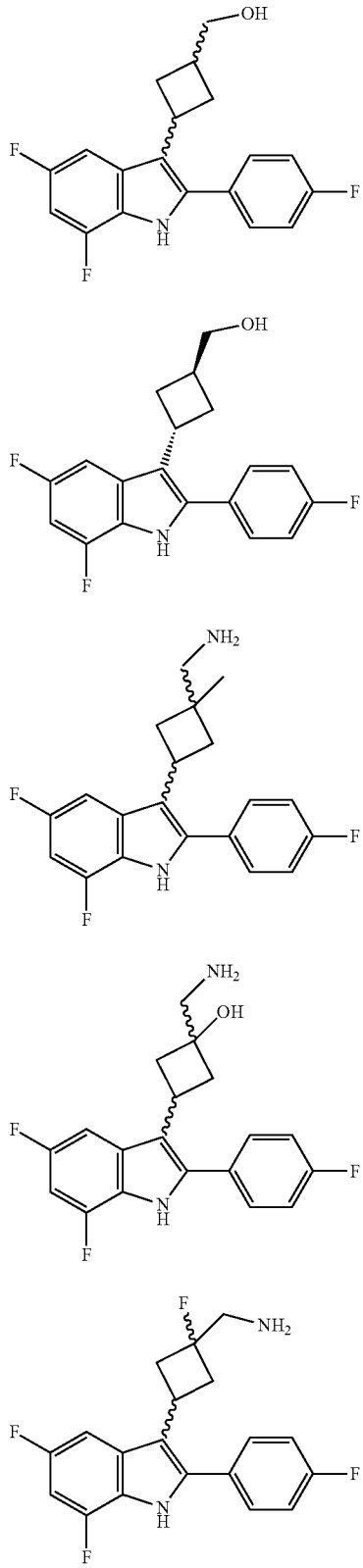
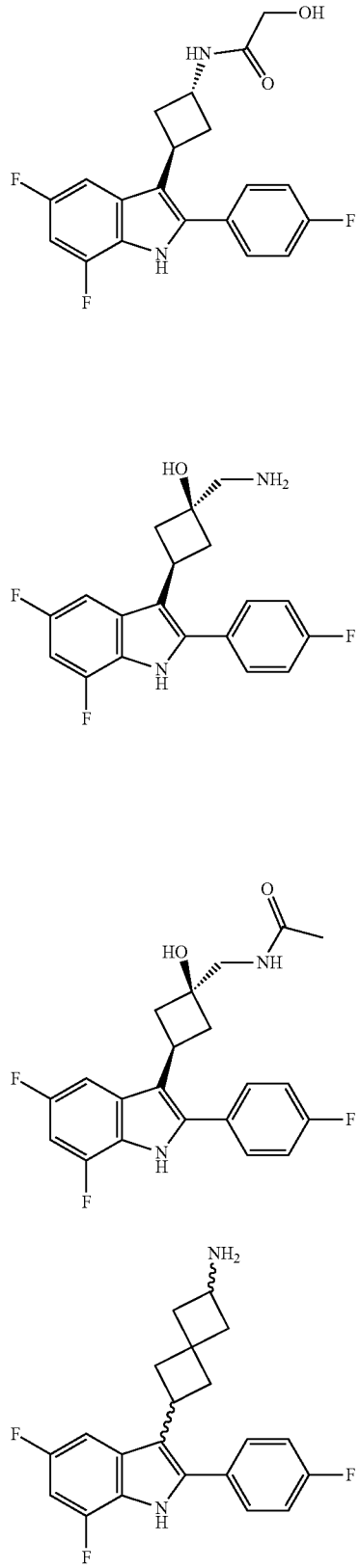

TABLE 1-continued
Compounds 1 to 456
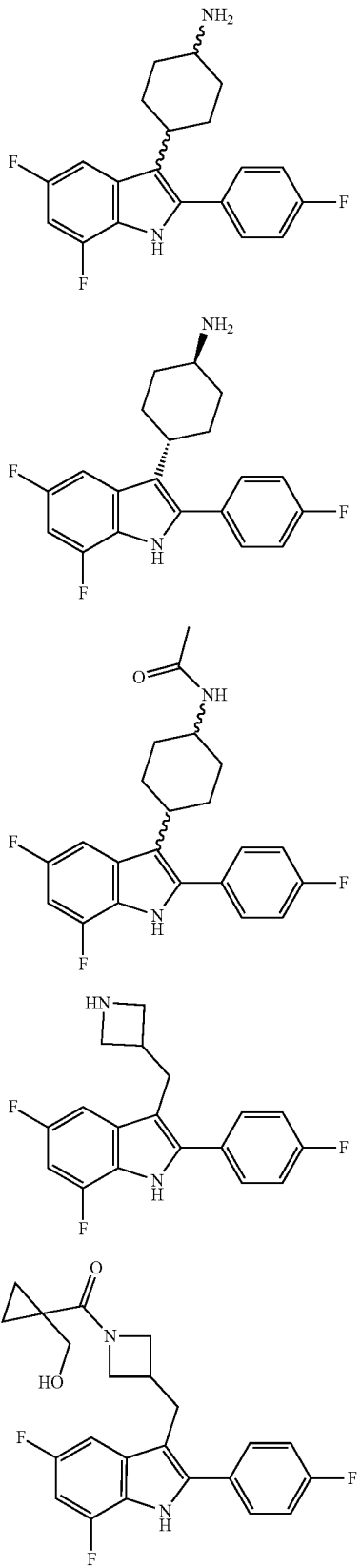
433
434
435
436
437
TABLE 1-continued
Compounds 1 to 456
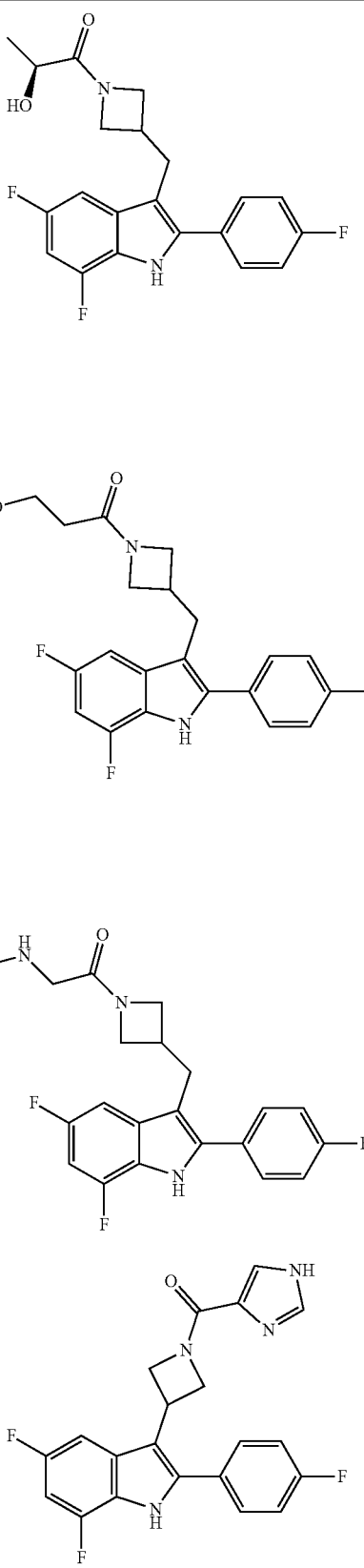
438
439
440
441

TABLE 1-continued
Compounds 1 to 456
| | |
|---|---|
| 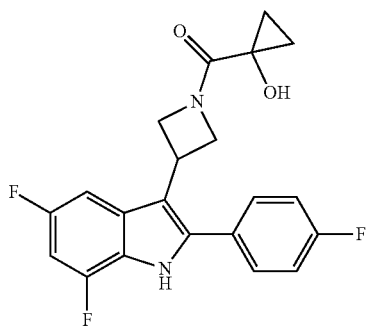 [SMILES: O=C(N1CC(c2c(-c3ccc(F)cc3)[nH]c3c(F)cc(F)cc23)C1)C1(O)CC1] | 442 |
| 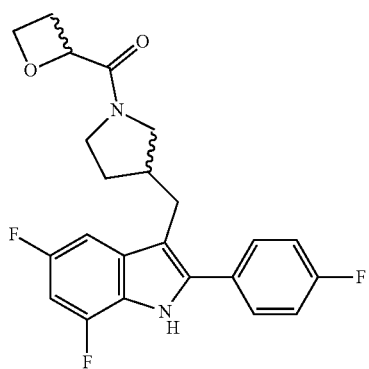 | 443 |
| 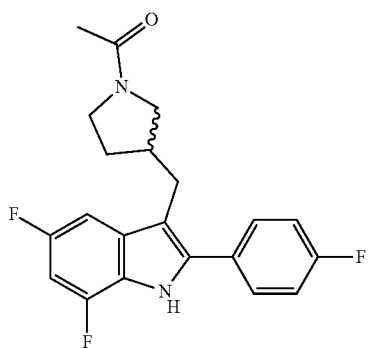 | 444 |
| 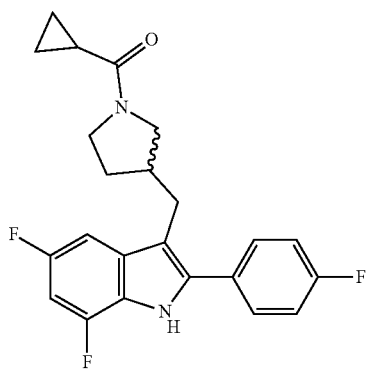 | 445 |
TABLE 1-continued
Compounds 1 to 456
| | |
|---|---|
| 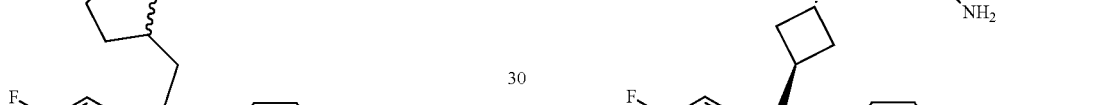 | 446 |
| 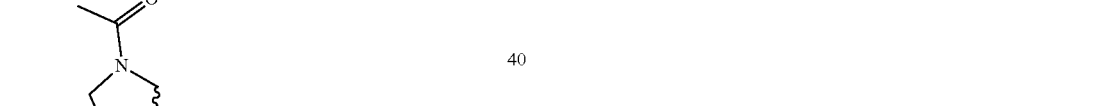 | 447 |
| 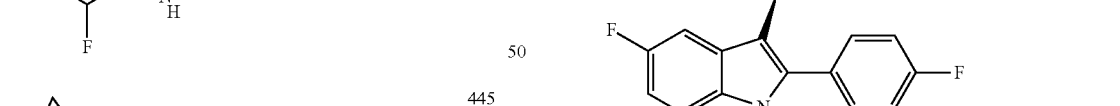 | 448 |
| 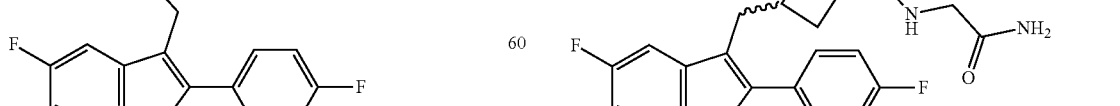 | 449 |

TABLE 1-continued

Compounds 1 to 456

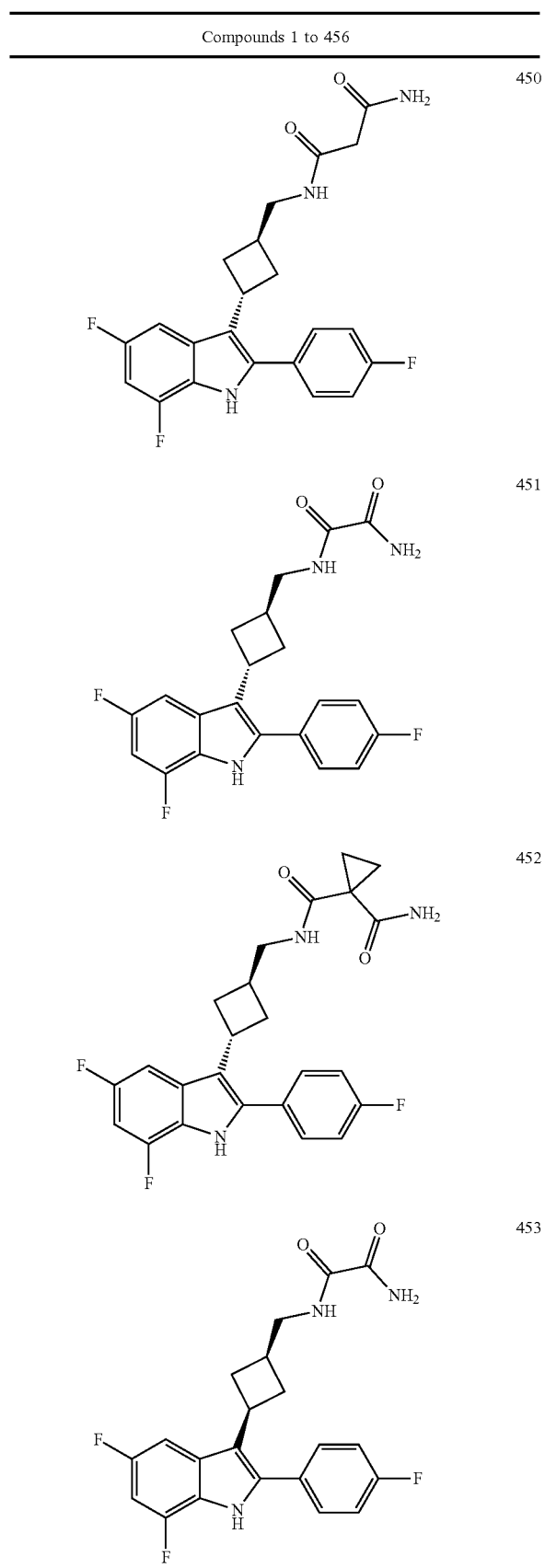

450

451

452

453

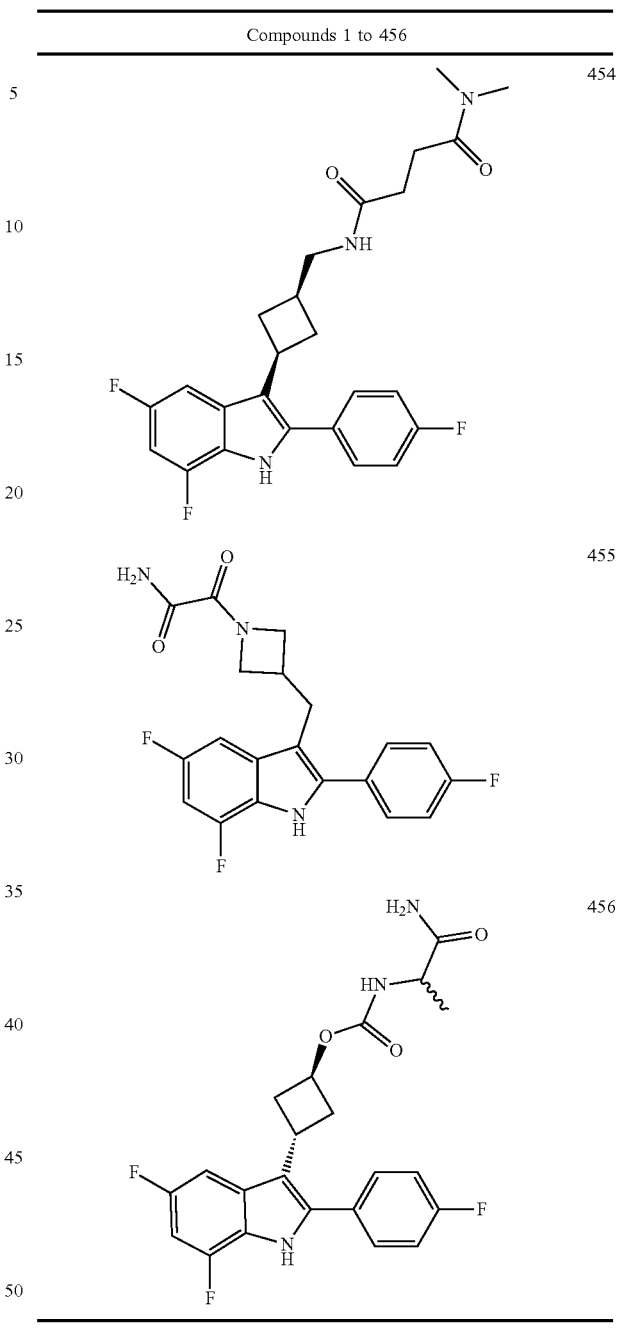

454

455

456

Another aspect of the disclosure provides methods for making compounds of Formulae I, I-A, I-B, I-C, I-D, I-E, and I-F, Compounds 1 to 456, deuterated derivatives of those compounds, and pharmaceutically acceptable salts of any of foregoing. The disclosure also provides intermediates for making any of the compounds, deuterated derivatives, or pharmaceutically acceptable salts of the disclosure.

Another aspect of the disclosure provides pharmaceutical compositions comprising at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing. In some embodiments, the pharmaceutical composition comprising at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing can be administered as a separate pharmaceutical composition concurrently with, prior to, or subsequent to, a composition comprising at least one other active therapeutic agent. In some embodiments, a pharmaceutical composition comprising at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing can be administered as a separate pharmaceutical composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as, e.g., human serum albumin), buffer substances (such as, e.g., phosphates, glycine, sorbic acid, and potassium sorbate), partial glyceride mixtures of saturated vegetable fatty acids, water, salts, and electrolytes (such as, e.g., protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as, e.g., lactose, glucose and sucrose), starches (such as, e.g., corn starch and potato starch), cellulose and its derivatives (such as, e.g., sodium carboxymethyl cellulose, ethyl cellulose, and cellulose acetate), powdered tragacanth, malt, gelatin, talc, excipients (such as, e.g., cocoa butter and suppository waxes), oils (such as, e.g., peanut oil, cottonseed oil, safflower oil, sesame oil, olive oil, corn oil, and soybean oil), glycols (such as, e.g., propylene glycol and polyethylene glycol), esters (such as, e.g., ethyl oleate and ethyl laurate), agar, buffering agents (such as, e.g., magnesium hydroxide and aluminum hydroxide), alginic acid, pyrogen-free water, isotonic saline, Ringer's solution, ethyl alcohol, phosphate buffer solutions, non-toxic compatible lubricants (such as, e.g., sodium lauryl sulfate and magnesium stearate), coloring agents, releasing agents, coating agents, sweetening agents, flavoring agents, perfuming agents, preservatives, and antioxidants.

In some embodiments of the disclosure, the compounds and the pharmaceutical compositions described herein are used to treat APOL1 mediated kidney disease. In some embodiments, the APOL1 mediated kidney disease is chosen from ESKD, FSGS, HIV-associated nephropathy, NDKD, arterionephrosclerosis, lupus nephritis, microalbuminuria, and chronic kidney disease. In some embodiments, the APOL1 mediated kidney disease treated with the compound, deuterated derivative, pharmaceutically acceptable salt, and/or composition of the disclosure is FSGS. In some embodiments, the APOL1 mediated kidney disease treated with the compound, deuterated derivative, pharmaceutically acceptable salt, and/or composition of the disclosure is NDKD. In some embodiments, the APOL1 mediated kidney disease treated with the compound, deuterated derivative, pharmaceutically acceptable salt, and/or composition of the disclosure is ESKD. In some embodiments, the patient with APOL1 mediated kidney disease to be treated with the compound, deuterated derivative, pharmaceutically acceptable salt, and/or composition of the disclosure has two APOL1 risk alleles. In some embodiments, the patient with APOL1 mediated kidney disease is homozygous for APOL1 genetic risk alleles G1: S342G:I384M. In some embodiments, the patient with APOL1 mediated kidney disease is homozygous for APOL1 genetic risk alleles G2: N388del:Y389del. In some embodiments, the patient with APOL1 mediated kidney disease is heterozygous for APOL1 genetic risk alleles G1: S342G:I384M and G2: N388del:Y389del.

In some embodiments, the methods of the disclosure comprise administering to a patient in need thereof at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing. In some embodiments, the at least one compound, deuterated derivative, or pharmaceutically acceptable salt is chosen from Compounds 1 to 456, deuterated derivatives of those compounds, and pharmaceutically acceptable salts of any of foregoing. In some embodiments, said patient in need thereof possesses APOL1 genetic variants, i.e., G1: S342G:I384M and G2: N388del:Y389del.

Another aspect of the disclosure provides methods of inhibiting APOL1 activity comprising contacting said APOL1 with at least one compound, deuterated derivative, or pharmaceutically acceptable salt chosen from compounds of Formulae I, I-A, I-B, I-C, I-D, I-E, and I-F, Compounds 1 to 456, deuterated derivatives of those compounds, and pharmaceutically acceptable salts of any of foregoing. In some embodiments, the methods of inhibiting APOL1 activity comprise contacting said APOL1 with at least one compound, deuterated derivative, or pharmaceutically acceptable salt chosen from Compounds 1 to 456, deuterated derivatives of those compounds, and pharmaceutically acceptable salts of any of foregoing.

Non-Limiting Exemplary Embodiments

Without limitation, some example embodiments of this disclosure include:
1. A compound, deuterated derivative, or pharmaceutically acceptable salt selected from Formula I:

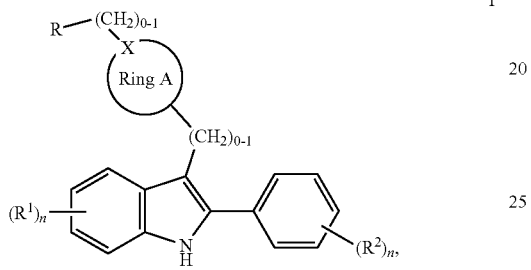

deuterated derivatives thereof, and pharmaceutically acceptable salts of any of the foregoing, wherein:
(i) R is selected from hydrogen, —$NR^3R^4$, —$C(O)R^3$, —$OR^3$, —$NR^5C(O)R^3$, —$NR^5C(O)OR^3$, —$NR^5SO_2R^3$, and —$NR^5SO_2NR^3R^4$;
(ii) X is selected from N and $CR^X$;
(iii) $R^X$ is absent or is selected from hydrogen, hydroxy, halogen, and $C_1$-$C_3$ linear and branched alkyl groups, wherein when $R^X$ is absent, X is a bridgehead atom;
(iv) Ring A is a 3- to 7-membered ring, wherein the ring is a cyclic alkyl or a heterocycle;
(v) each n is independently selected from 0, 1, 2, and 3;
(vi) each $R^1$ is independently selected from:
hydrogen,
halogen,
hydroxy,
amino,
$C_1$-$C_6$ linear and branched alkyl groups,
$C_1$-$C_6$ linear, branched, and cyclic alkoxy groups, and
$C_1$-$C_6$ linear and branched haloalkyl groups;
(vii) each $R^2$ is independently selected from:
hydrogen,
halogen,
hydroxy,
amino,
cyano,
$C_1$-$C_4$ linear, branched, and cyclic alkyl groups (e.g., $C_1$-$C_4$ linear, $C_3$-$C_4$ branched, and $C_3$-$C_4$ cyclic alkyl groups),
$C_1$-$C_4$ linear, branched, and cyclic hydroxyalkyl groups (e.g., $C_1$-$C_4$ linear, $C_3$-$C_4$ branched, and $C_3$-$C_4$ cyclic hydroxyalkyl groups),
$C_1$-$C_4$ linear, branched, and cyclic alkoxy groups (e.g., $C_1$-$C_4$ linear, $C_2$-$C_4$ branched, and $C_1$-$C_4$ cyclic alkoxy groups),
$C_1$-$C_4$ linear, branched, and cyclic haloalkyl groups (e.g., $C_1$-$C_4$ linear, $C_3$-$C_4$ branched, and $C_3$-$C_4$ cyclic haloalkyl groups), and
$C_1$-$C_4$ linear, branched, and cyclic haloalkoxy groups (e.g., $C_1$-$C_4$ linear, $C_2$-$C_4$ branched, and $C_1$-$C_4$ cyclic haloalkoxy groups);
(viii) $R^3$ and $R^4$ are independently selected from:
hydrogen,
$C_1$-$C_6$ linear and branched alkylsulfonyl groups optionally substituted with amino (e.g., optionally substituted with one amino group),
$C_1$-$C_6$ linear and branched alkoxy groups optionally substituted with 1-4 groups independently selected from hydroxy, amino, halogen, and oxo,
$C_1$-$C_3$ linear and branched aminoalkyl groups optionally substituted with 1-2 independently selected from amido,
$C_3$-$C_6$ cyclic alkyl groups optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with $C_1$-$C_6$ linear or branched alkyl,
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups, and
$C_1$-$C_3$ hydroxyalkyl,
3- to 6-membered heterocyclyl optionally substituted with 1-3 groups independently selected from:
halogen,
oxo,
hydroxy,
amido optionally substituted with $C_1$-$C_3$ alkyl,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups,
$C_1$-$C_3$ hydroxyalkyl and $C_1$-$C_3$ haloalkyl, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
3- to 10-membered heteroaryl optionally substituted with 1-2 groups independently selected from amino, hydroxy, oxo, and $C_1$-$C_6$ linear alkyl optionally substituted with 1-3 groups independently selected from halogen and amino,
$C_1$-$C_6$ linear and branched alkyl groups optionally substituted with 1-4 groups independently selected from:

$C_1$-$C_4$ alkyl groups,
amino optionally substituted with 1-2 groups independently selected from $C_1$-$C_6$ linear and branched alkylsulfonyl groups and $C_1$-$C_6$ linear, branched, and $C_3$-$C_6$ cyclic alkyl groups (optionally substituted with 1-2 groups independently selected from oxo, hydroxy, amido, and $C_1$-$C_6$ linear and branched alkylsulfonyl groups),
hydroxy,
oxo,
cyano,
carboxylic acid,
carbamate optionally substituted with 1-2 groups independently selected from $C_1$-$C_6$ linear, branched, and $C_3$-$C_6$ cyclic alkyl groups,
halogen,
amido optionally substituted with 1-2 groups independently selected from $C_1$-$C_6$ linear, branched, and cyclic alkyl groups (e.g., $C_1$-$C_6$ linear, $C_3$-$C_6$ branched, and $C_3$-$C_6$ cyclic alkyl groups) and $C_1$-$C_6$ linear, branched, and cyclic hydroxyalkyl groups (e.g., $C_1$-$C_6$ linear, $C_3$-$C_6$ branched, and $C_3$-$C_6$ cyclic hydroxyalkyl groups),
$C_3$-$C_6$ cyclic alkyl optionally substituted with 1-2 groups independently selected from amino, halogen, hydroxy, oxo, $C_1$-$C_3$ alkyl, $C_1$-$C_6$ linear and branched alkoxy groups, and carbamate (which may be further substituted with $C_1$-$C_4$ linear or branched alkyl),
$C_1$-$C_6$ linear and branched alkoxy groups optionally substituted with hydroxy,
$C_1$-$C_6$ linear and branched alkylsulfonyl groups,
aryl optionally substituted with 1-2 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
4- to 10-membered heterocyclyl optionally substituted with 1-2 groups independently selected from halogen groups, oxo, hydroxy, amido optionally substituted with $C_1$-$C_3$ alkyl, and $C_1$-$C_6$ linear and branched alkyl groups optionally substituted with 1-2 groups independently selected from hydroxy and $C_1$-$C_6$ linear and branched alkoxy groups, and
4- to 10-membered heteroaryl optionally substituted with 1-3 groups independently selected from halogen groups, oxo, hydroxy, $C_1$-$C_6$ linear, branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, branched, and $C_3$-$C_6$ cyclic alkyl,
or $R^3$ and $R^4$, together with the nitrogen atom to which they are attached, form a 3- to 10-membered heterocyclyl or heteroaryl optionally substituted with 1-3 groups independently selected from:
amino optionally substituted with 1-2 groups independently selected from $C_1$-$C_6$ linear, branched, and $C_3$-$C_6$ cyclic alkyl groups, which are optionally substituted with oxo,
halogen,
hydroxy,
oxo,
$C_1$-$C_6$ linear, branched, and $C_3$-$C_6$ cyclic alkyl groups optionally substituted with at 1-2 groups independently selected from hydroxy, amino, and $C_1$-$C_6$ linear and branched alkoxy groups,
$C_1$-$C_3$ linear or branched hydroxyalkyl, and
amide optionally substituted with 1-2 groups independently selected from $C_1$-$C_6$ linear, branched, and $C_3$-$C_6$ cyclic alkyl groups; and
(ix) $R^5$ is selected from hydrogen, hydroxy, halogen, and $C_1$-$C_3$ linear and branched alkyl groups.

2. The compound, deuterated derivative, or pharmaceutically acceptable salt according to Embodiment 1, wherein $R^3$ and $R^4$ are independently selected from:
hydrogen,
$C_1$-$C_6$ linear and branched alkylsulfonyl groups optionally substituted with amino (e.g., optionally substituted with one amino group),
$C_1$-$C_6$ linear and branched alkoxy groups optionally substituted with 1-4 groups independently selected from hydroxy, amino, halogen, and oxo,
$C_1$-$C_3$ linear and branched aminoalkyl groups optionally substituted with 1-2 groups independently selected from amido,
$C_3$-$C_6$ cyclic alkyl optionally substituted with 1-2 groups independently selected from:
halogen,
hydroxy,
oxo,
amido,
amino substituted with 1-2 groups independently selected from $C_1$-$C_6$ linear, branched, and $C_3$-$C_6$ cyclic alkyl groups,
aryl optionally substituted with 1-2 groups independently selected from halogen,
$C_1$-$C_6$ linear and branched alkoxy groups,
carbamate optionally substituted with $C_1$-$C_6$ linear or branched alkyl,
$C_1$-$C_6$ linear, branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups,
3- to 6-membered heterocyclyl optionally substituted with 2-3 groups independently selected from:
halogen,
oxo,
hydroxy,
$C_1$-$C_6$ linear and branched alkoxy groups optionally substituted with oxo,
$C_1$-$C_6$ linear, branched, and $C_3$-$C_6$ cyclic alkyl groups optionally substituted with 1-2 groups independently selected from hydroxy, oxo, and $C_1$-$C_6$ linear and branched alkoxy groups, and
carbamate optionally substituted with 1-2 groups independently selected from $C_1$-$C_6$ linear, branched, and $C_3$-$C_6$ cyclic alkyl groups,
aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups,
3- to 6-membered heteroaryl optionally substituted with 1-2 groups independently selected from amino, hydroxy, oxo, and C₁-C₆ linear alkyl optionally substituted with 1-3 groups independently selected from halogen and amino, C₁-C₆ linear and branched alkyl groups optionally substituted with 1-4 groups independently selected from:
  amino optionally substituted with 1-2 groups independently selected from C₁-C₆ linear and branched alkylsulfonyl groups and C₁-C₆ linear, branched, and C₃-C₆ cyclic alkyl groups (optionally substituted with 1-2 groups independently selected from oxo, hydroxy, amido, and C₁-C₆ linear and branched alkylsulfonyl groups),
  hydroxy,
  oxo,
  cyano,
  carboxylic acid,
  carbamate optionally substituted with 1-2 groups independently selected from C₁-C₆ linear, branched, and C₃-C₆ cyclic alkyl groups,
  halogen,
  amido optionally substituted with 1-2 groups independently selected from C₁-C₆ linear, branched, and cyclic alkyl groups (e.g., C₁-C₆ linear, C₃-C₆ branched, and C₃-C₆ cyclic alkyl groups) and C₁-C₆ linear, branched, and cyclic hydroxyalkyl groups (e.g., C₁-C₆ linear, C₃-C₆ branched, and C₃-C₆ cyclic hydroxyalkyl groups),
  C₃-C₆ cyclic alkyl optionally substituted with 1-2 groups independently selected from halogen, C₁-C₆ linear and branched alkoxy groups, hydroxy, amino, oxo, C₁-C₃ alkyl, and carbamate (which may be further substituted with C₁-C₄ linear or branched alkyl);
  C₁-C₆ linear and branched alkoxy groups optionally substituted with hydroxy,
  C₁-C₆ linear and branched alkylsulfonyl groups,
  aryl optionally substituted with 1-2 groups independently selected from halogen, hydroxy, and C₁-C₆ linear and branched alkyl groups optionally substituted with 1-2 groups independently selected from hydroxy and C₁-C₆ linear and branched alkoxy groups,
  4- to 10-membered heterocyclyl optionally substituted with 1-2 groups independently selected from halogen groups, oxo, hydroxy, and C₁-C₆ linear and branched alkyl groups optionally substituted with 1-2 groups independently selected from hydroxy and C₁-C₆ linear and branched alkoxy groups, and
  4- to 10-membered heteroaryl optionally substituted with 1-3 groups independently selected from halogen groups, oxo, hydroxy, C₁-C₆ linear, branched, and C₃-C₆ cyclic alkyl groups optionally substituted with 1-3 groups independently selected from halogen, hydroxy, and C₁-C₆ linear and branched alkoxy groups, and amido groups optionally substituted with 1-2 groups independently selected from C₁-C₆ linear, branched, and C₃-C₆ cyclic alkyl groups,
or $R^3$ and $R^4$, together with the nitrogen atom to which they are attached, form a 4- to 10-membered heterocyclyl or heteroaryl optionally substituted with 1-3 groups independently selected from:
  amino optionally substituted with 1-2 groups independently selected from C₁-C₆ linear, branched, and C₃-C₆ cyclic alkyl groups, which are optionally substituted with oxo,
  halogen,
  hydroxy,
  oxo,
  C₁-C₆ linear, branched, and C₃-C₆ cyclic alkyl groups optionally substituted with 1-2 groups independently selected from hydroxy, amino, and C₁-C₆ linear and branched alkoxy groups, and
  amide optionally substituted with 1-2 groups independently selected from C₁-C₆ linear, branched, and C₃-C₆ cyclic alkyl groups.

3. The compound, deuterated derivative, or pharmaceutically acceptable salt according to Embodiment 1 or 2, wherein $R^5$ is selected from hydrogen and C₁-C₃ linear and branched alkyl groups.

4. The compound, deuterated derivative, or pharmaceutically acceptable salt according to any one of Embodiments 1-3, wherein Ring A is selected from:

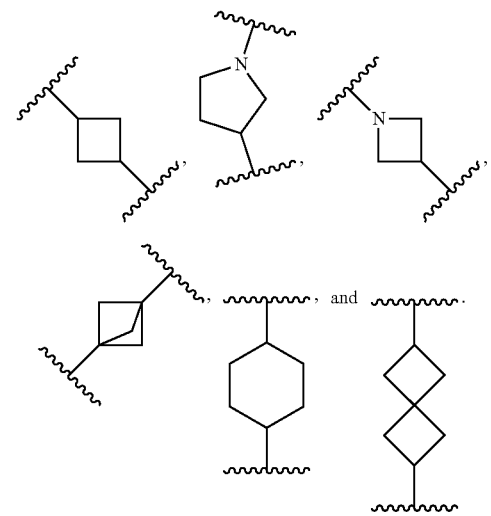

5. The compound, deuterated derivative, or pharmaceutically acceptable salt according to any one of Embodiments 1-3, wherein X is $CR^X$.

6. The compound, deuterated derivative, or pharmaceutically acceptable salt according to according to any one of Embodiments 1-3 or 5, wherein $R^X$ is selected from hydrogen, hydroxy, fluorine, and methyl.

7. The compound, deuterated derivative, or pharmaceutically acceptable salt according to Embodiment 1 or 2, wherein the compound, deuterated derivative, or pharmaceutically acceptable salt is selected from compounds of Formula I-A, Formula I-B, or Formula I-C:

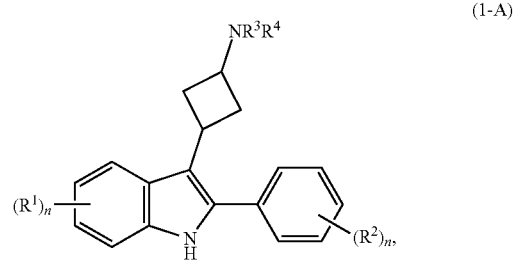

(1-A)

-continued

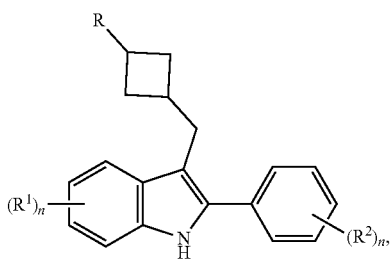
(I-B)

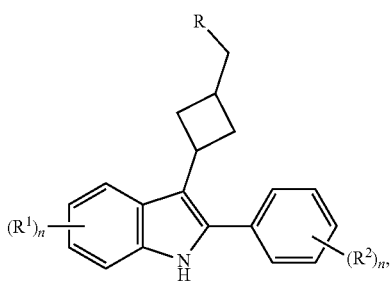
(I-C)

deuterated derivatives thereof, and pharmaceutically acceptable salts of any of the foregoing, wherein R, $R^1$, $R^2$, $R^3$, $R^4$, and n are as defined for Formula I in Embodiment 1 or 2.

8. The compound, deuterated derivative, or pharmaceutically acceptable salt according to any one of Embodiments 1-7, wherein each n is 1 or 2.

9. The compound, deuterated derivative, or pharmaceutically acceptable salt according to Embodiment 1 or 2, wherein the compound, reiterated derivative, or pharmaceutically acceptable salt is selected from compounds of Formula I-D, Formula I-E, or Formula I-F:

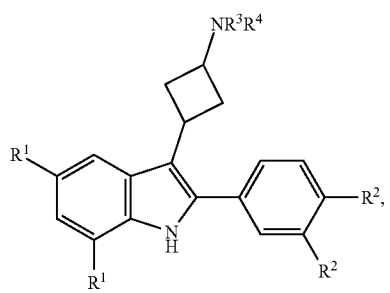
(I-D)

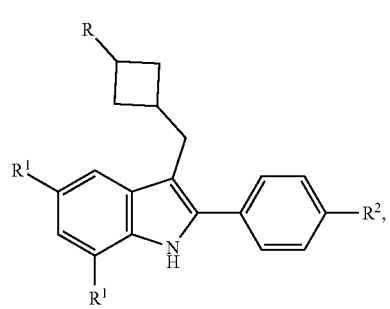
(I-E)

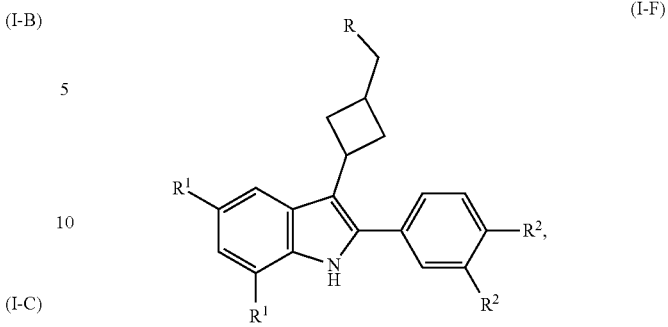
(I-F)

deuterated derivatives thereof, and pharmaceutically acceptable salts of any of the foregoing, wherein each R, $R^1$, $R^2$, $R^3$, and $R^4$ are as defined for Formula I in Embodiment 1 or 2.

10. The compound, deuterated derivative, or pharmaceutically acceptable salt according to any one of Embodiments 1-9, wherein each $R^1$ is independently selected from hydrogen, fluorine, and trifluoromethyl.

11. The compound, deuterated derivative, or pharmaceutically acceptable salt according to any one of Embodiments 1-10, wherein each $R^2$ is independently selected from hydrogen and fluorine.

12. The compound, deuterated derivative, or pharmaceutically acceptable salt according to any one of Embodiments 1-11, wherein R is selected from hydrogen and —$NH_2$.

13. The compound, deuterated derivative, or pharmaceutically acceptable salt according to any one of Embodiments 1-11, wherein R is —$NR^3R^4$.

14. The compound, deuterated derivative, or pharmaceutically acceptable salt according to Embodiment 13, wherein $R^3$ and $R^4$ are independently selected from
hydrogen,
$C_3$-$C_6$ cyclic alkyl groups (optionally substituted with hydroxy or amino),
$C_1$-$C_6$ linear and branched alkyl groups (optionally substituted with 1-3 groups independently selected from amino, halogen, hydroxy, methylamide, isopropyl, $C_3$-$C_6$ cyclic alkyl, and carbamate (which may be further substituted with $C_1$-$C_4$ linear or branched alkyl)),
$C_1$-$C_6$ linear and branched alkoxy,
3- to 6-membered heterocycle (optionally substituted with 1-2 groups independently selected from oxo, methyl, $C_1$-$C_3$ hydroxyalkyl, and trifluoromethyl), and
3- to 6-membered heteroaryl (optionally substituted with $C_1$-$C_3$ alkyl),
or $R^3$ and $R^4$ are taken together to form a 3- to 6-membered heterocycle (optionally substituted with oxo or methylamide).

15. The compound, deuterated derivative, or pharmaceutically acceptable salt according to any one of Embodiments 1-11, wherein R is —$NR^5C(O)R^3$.

16. The compound, deuterated derivative, or pharmaceutically acceptable salt according to Embodiment 15, wherein:
$R^3$ is selected from:
$C_1$-$C_6$ linear and branched alkoxy groups,
$C_1$-$C_6$ linear and branched alkylsulfonyl groups optionally substituted with amino,
$C_1$-$C_6$ linear and branched alkyl groups optionally substituted with 1-4 groups independently selected from:

hydroxy,
oxo,
cyano,
amido (which may be further substituted with 1-2 groups independently selected from $C_1$-$C_3$ alkyl and $C_1$-$C_3$ hydroxyalkyl),
amino (which may be further substituted with 1-2 groups independently selected from $C_1$-$C_3$ alkylsulfonyl and $C_1$-$C_3$ alkyl (which may be further substituted with hydroxy)),
carbamate (which may be further substituted with $C_1$-$C_4$ linear or branched alkyl),
$C_3$-$C_6$ cycloalkyl (which may be further substituted with 1-2 groups independently selected from amino, halogen, hydroxy, oxo, $C_1$-$C_3$ alkyl, $C_1$-$C_3$ alkoxy, and carbamate (which may be further substituted with $C_1$-$C_4$ linear or branched alkyl)),
3- to 6-membered heterocyclyl (which may be further substituted with 1-2 groups independently selected from halogen, oxo, and $C_1$-$C_3$ alkyl),
3- to 6-membered heteroaryl groups (which may be further substituted with 1-2 groups independently selected from oxo and $C_1$-$C_3$ alkyl),
$C_3$-$C_6$ cycloalkyl optionally substituted with 1-2 groups independently selected from halogen, hydroxy, amino (which may be further substituted with $C_1$-$C_3$ alkyl), $C_1$-$C_3$ alkoxy, $C_1$-$C_3$ alkyl (which may be further substituted with hydroxy), and carbamate (which may be further substituted with $C_1$-$C_4$ linear or branched alkyl),
$C_1$-$C_6$ linear and branched alkylsulfonyl groups optionally substituted with amino,
3- to 6-membered heterocyclyl optionally substituted with 1-2 groups independently selected from halogen, hydroxy, oxo, $C_1$-$C_3$ alkyl (which may be further substituted with oxo), $C_1$-$C_3$ alkoxy (which may be further substituted with oxo), and carbamate (which may be further substituted with $C_1$-$C_4$ linear or branched alkyl),
3- to 6-membered heteroaryl (which may be further optionally substituted by oxo or amino); and
$R^5$ is selected from hydrogen, hydroxy, halogen, and $C_1$-$C_3$ linear or branched alkyl.

17. The compound, deuterated derivative, or pharmaceutically acceptable salt according to Embodiment 15 or 16, wherein $R^5$ is hydrogen.

18. The compound, deuterated derivative, or pharmaceutically acceptable salt according to any one of Embodiments 1-11, wherein R is —$NR^5C(O)OR^3$.

19. The compound, deuterated derivative, or pharmaceutically acceptable salt according to Embodiment 18, wherein:
$R^3$ is selected from $C_1$-$C_6$ linear and branched alkyl groups (optionally substituted with 1-3 groups independently selected from hydroxy and aryl); and
$R^5$ is selected from hydrogen, hydroxy, halogen, and $C_1$-$C_3$ linear and branched alkyl groups.

20. The compound, deuterated derivative, or pharmaceutically acceptable salt according to Embodiment 18 or 19, wherein $R^5$ is hydrogen.

21. The compound, deuterated derivative, or pharmaceutically acceptable salt according to any one of Embodiments 1-11, wherein R is —$NR^5SO_2R^3$.

22. The compound, deuterated derivative, or pharmaceutically acceptable salt according to Embodiment 21, wherein
$R^3$ is selected from $C_1$-$C_6$ linear and branched alkyl (optionally substituted with 1-3 groups independently selected from halogen, hydroxy, amino, and cyano), 3- to 10-membered heteroaryl (optionally substituted with 1-2 groups independently selected from oxo and $C_1$-$C_3$ alkyl), $C_3$-$C_6$ cycloalkyl, 3- to 6-membered heterocyclyl; and
$R^5$ is selected from hydrogen, hydroxy, halogen, and $C_1$-$C_3$ linear and branched alkyl groups.

23. The compound, deuterated derivative, or pharmaceutically acceptable salt according to Embodiment 21 or 22, wherein $R^5$ is selected from hydrogen and propyl.

24. The compound, deuterated derivative, or pharmaceutically acceptable salt according to any one of Embodiments 1-11, wherein R is —$NR^5SO_2NR^3R^4$.

25. The compound, deuterated derivative, or pharmaceutically acceptable salt according to Embodiment 24, wherein $R^3$ and $R^4$ are independently selected from:
hydrogen,
$C_1$-$C_6$ linear and branched alkoxy groups,
$C_1$-$C_6$ linear and branched alkyl groups optionally substituted with 1-4 groups independently selected from:
$C_1$-$C_3$ alkyl,
amino,
amido,
halogen,
hydroxy,
3- to 6-membered heterocyclyl (which may be further substituted with 1-2 groups independently selected from oxo, hydroxy, amido (which may be further substituted with $C_1$-$C_3$ alkyl), and $C_1$-$C_3$ alkyl),
$C_3$-$C_6$ heteroaryl (which may be further substituted with $C_1$-$C_3$ alkyl), and
oxo,
$C_3$-$C_6$ cycloalkyl (optionally substituted with 1-2 groups independently selected from amido, hydroxy, and $C_1$-$C_3$ hydroxyalkyl),
3- to 6-membered heterocyclyl (optionally substituted with 1-2 groups independently selected from oxo, hydroxy, and $C_1$-$C_3$ alkyl), and
3- to 6-membered heteroaryl;
or $R^3$ and $R^4$, together with the nitrogen atom to which they are attached, form a 4- to 6-membered heterocyclyl optionally substituted with 1-2 groups independently selected from $C_1$-$C_3$ linear and branched alkyl groups and $C_1$-$C_3$ linear or branched hydroxyalkyl groups;
and
$R^5$ is selected from hydrogen, hydroxy, halogen, and $C_1$-$C_3$ linear and branched alkyl groups.

26. The compound, deuterated derivative, or pharmaceutically acceptable salt according to Embodiment 24 or 25, wherein $R^5$ is hydrogen or propyl.

27. The compound, deuterated derivative, or pharmaceutically acceptable salt according to any one of Embodiments 1-11, wherein R is —$OR^3$.

28. The compound, deuterated derivative, or pharmaceutically acceptable salt according to Embodiment 26, wherein:
$R^3$ is selected from hydrogen and $C_1$-$C_6$ linear and branched alkyl groups (optionally substituted with hydroxy or oxo).

29. The compound, deuterated derivative, or pharmaceutically acceptable salt according to any one of Embodiments 1-11, wherein R is —$C(O)R^3$.

30. The compound, deuterated derivative, or pharmaceutically acceptable salt according to Embodiment 29, wherein R³ is selected from hydrogen, C₁-C₆ linear and branched alkyl groups (optionally substituted with 1-2 groups independently selected from amino (which may be further substituted with C₁-C₃ alkyl), halogen, and hydroxy), C₃-C₆ cycloalkyl (which may be further substituted with hydroxy or C₁-C₃ hydroxyalkyl), 3- to 6-membered heteroaryl, and 3- to 6-membered heterocyclyl.

31. The compound, deuterated derivative, or pharmaceutically acceptable salt according to any one of Embodiments 1-30, wherein the optionally substituted heterocyclyl is a 4-membered heterocyclyl selected from:

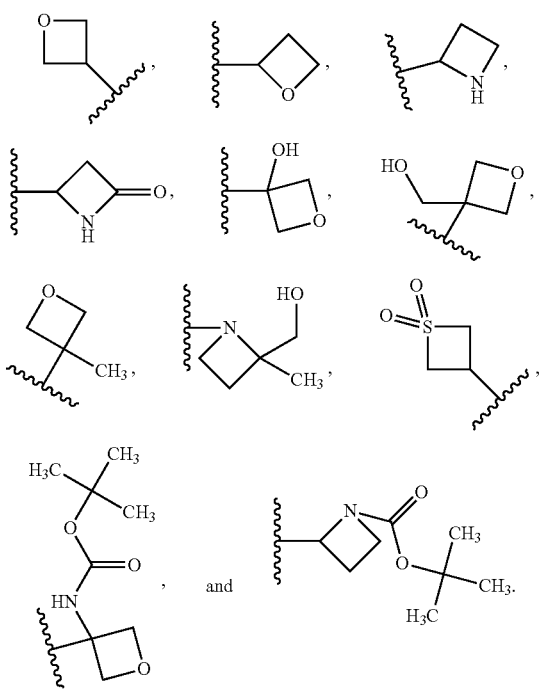

32. The compound, deuterated derivative, or pharmaceutically acceptable salt according to any one of Embodiments 1 and 3-30, wherein the optionally substituted heterocyclyl is a 5-membered heterocyclyl selected from:

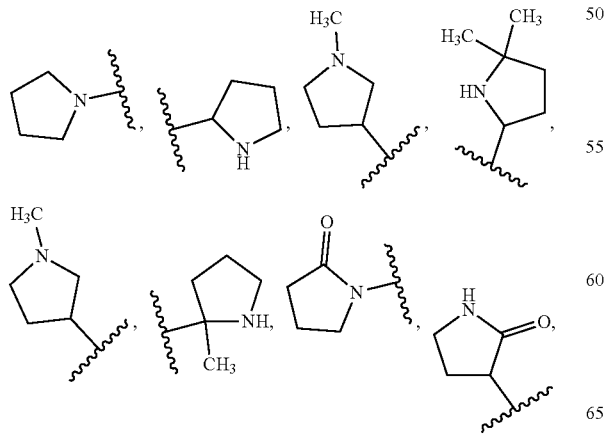

-continued

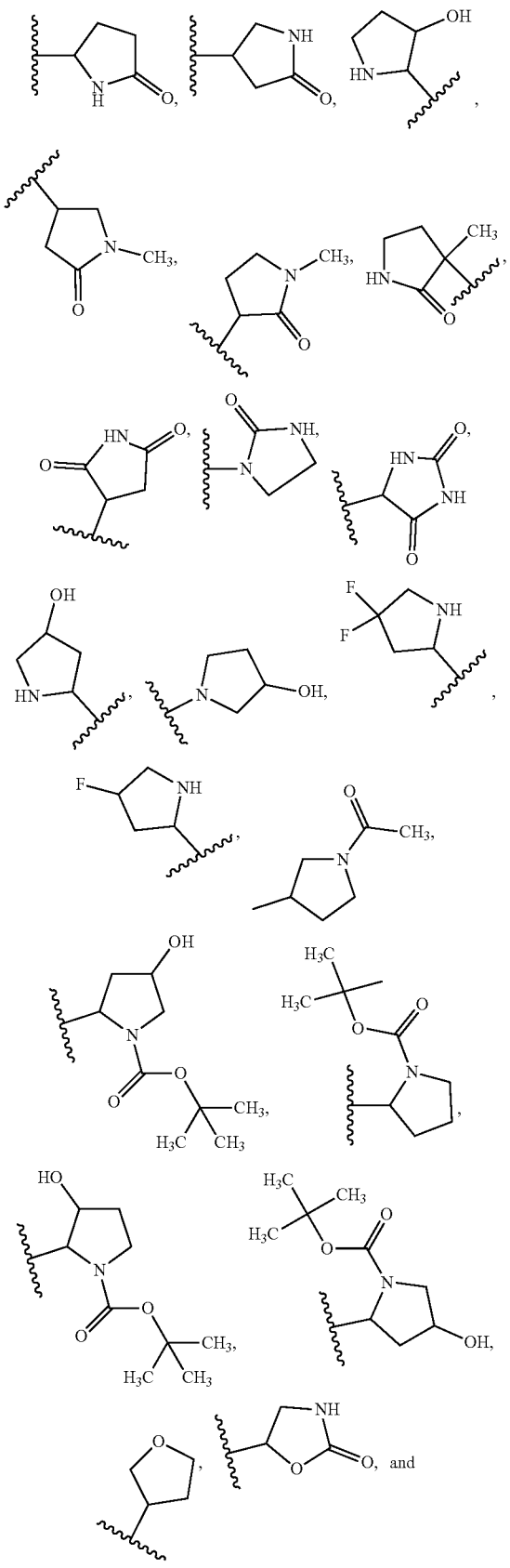

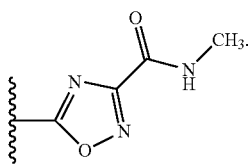

33. The compound, deuterated derivative, or pharmaceutically acceptable salt according to any one of Embodiments 1 and 3-30, wherein the optionally substituted heterocyclyl is a 6-membered heterocyclyl selected from:

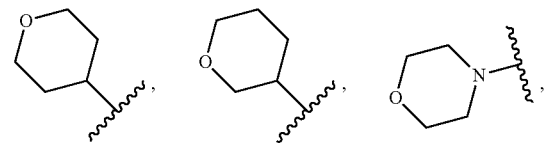

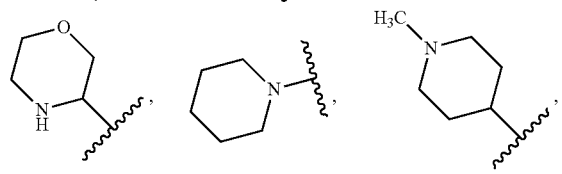


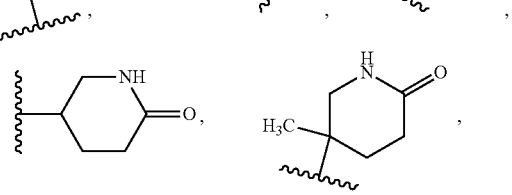

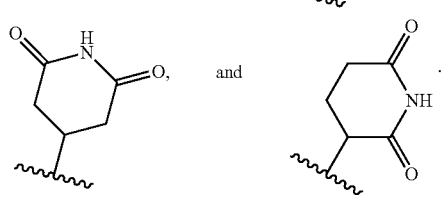

34. The compound, deuterated derivative, or pharmaceutically acceptable salt according to any one of Embodiments 1 and 3-30, wherein the optionally substituted 3- to 6- or 3- to 10-membered heteroaryl is selected from:

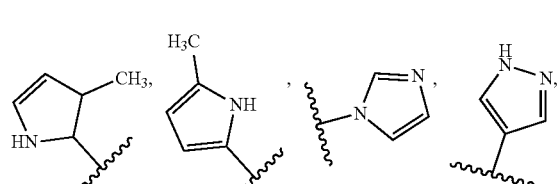

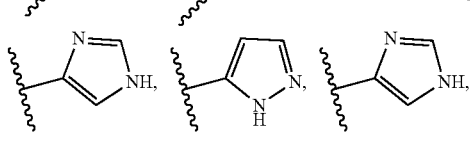

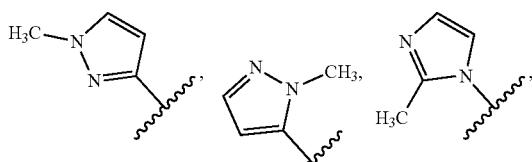

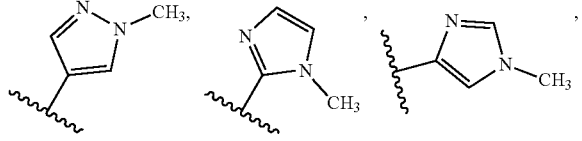

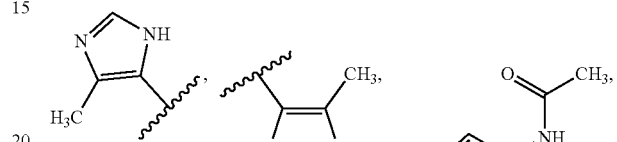

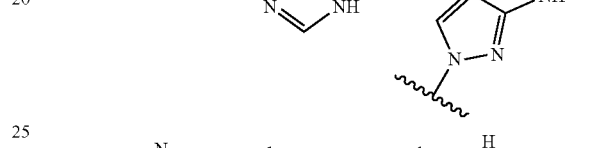

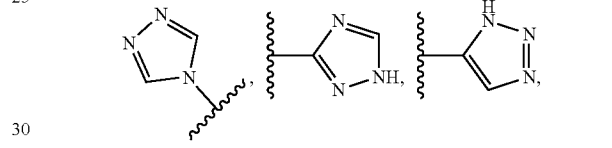

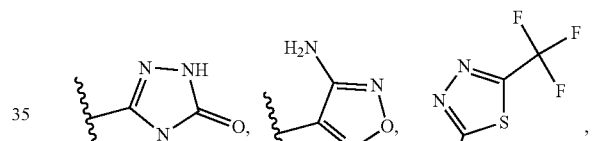

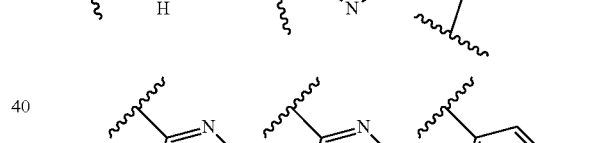

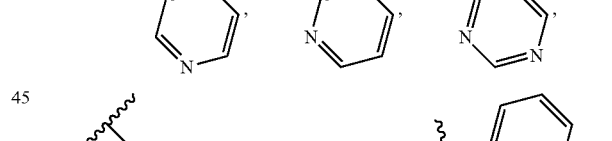

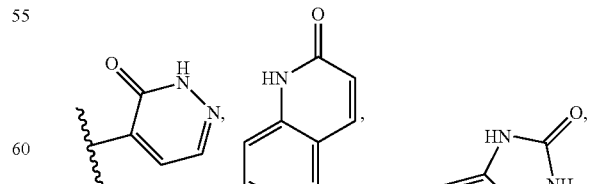

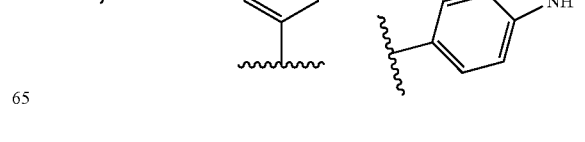

-continued

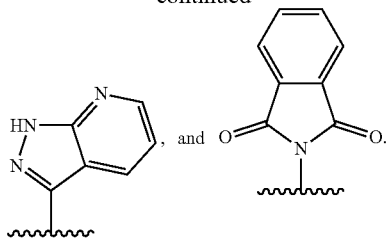

35. A compound, deuterated derivative, or pharmaceutically acceptable salt selected from Compounds 1 to 456 (Table 1), deuterated derivatives thereof, or pharmaceutically acceptable salts of any of the foregoing.

36. A pharmaceutical composition comprising the compound, deuterated derivative, or pharmaceutically acceptable salt according to any one of Embodiments 1-35 and 56-66 and a pharmaceutically acceptable carrier.

37. A method of treating APOL1 mediated kidney disease comprising administering to a patient in need thereof the compound, deuterated derivative, or pharmaceutically acceptable salt according to any one of Embodiments 1-35 or the pharmaceutical composition according to Embodiment 36.

38. The method according to Embodiment 37, wherein the APOL1 mediated kidney disease is chosen from ESKD, NDKD, FSGS, HIV-associated nephropathy, arterionephrosclerosis, lupus nephritis, microalbuminuria, and chronic kidney disease.

39. The method according to Embodiment 37, wherein the APOL1 mediated kidney disease is FSGS.

40. The method according to Embodiment 37, wherein the APOL1 mediated kidney disease is NDKD.

41. The method according to Embodiment 37, wherein the APOL1 mediated kidney disease is ESKD.

42. The method according to any one of Embodiments 37-41, wherein the APOL1 mediated kidney disease is associated with APOL1 genetic alleles chosen from homozygous G1: S342G:I384M and homozygous G2: N388del:Y389del.

43. The method according to any one of Embodiments 37-41, wherein the APOL1 mediated kidney disease is associated with compound heterozygous G1: S342G:I384M and G2: N388del:Y389del APOL1 genetic alleles.

44. A method of inhibiting APOL1 activity comprising contacting said APOL1 with the compound, deuterated derivative, or pharmaceutically acceptable salt according to any one of Embodiments 1-35 or the pharmaceutical composition according to Embodiment 36.

45. The method according to Embodiment 44, wherein the APOL1 is associated with APOL1 genetic alleles chosen from homozygous G1: S342G:I384M and homozygous G2: N388del:Y389del.

46. The method according to Embodiment 44, wherein the APOL1 is associated with APOL1 genetic alleles chosen from homozygous G1: S342G:I384M and homozygous G2: N388del:Y389del.

47. The method according to Embodiment 44, wherein the APOL1 is associated with compound heterozygous G1: S342G:I384M and G2: N388del:Y389del APOL1 genetic alleles.

48. The compound, deuterated derivative, or pharmaceutically acceptable salt according to any one of Embodiments 1-35 or the pharmaceutical composition according to Embodiment 36 for use in treating APOL1 mediated kidney disease.

49. Use of the compound, deuterated derivative, or pharmaceutically acceptable salt according to any one of Embodiments 1-35 in the manufacture of a medicament for treating APOL1 mediated kidney disease.

50. The compound for use or use according to Embodiment 48 or 49, wherein the APOL1 mediated kidney disease is selected from ESKD, NDKD, FSGS, HIV-associated nephropathy, sickle cell nephropathy, diabetic neuropathy, arterionephrosclerosis, lupus nephritis, microalbuminuria, and chronic kidney disease.

51. The compound for use or use according to Embodiment 48 or 49, wherein the APOL1 mediated kidney disease is FSGS.

52. The compound for use or use according to Embodiment 48 or 49, wherein the APOL1 mediated kidney disease is NDKD.

53. The compound for use or use according to Embodiment 48 or 49, wherein the APOL1 mediated kidney disease is ESKD.

54. The compound for use or use according to any one of Embodiments 48-53, wherein the APOL1 is associated with APOL1 genetic alleles chosen from homozygous G1: S342G:I384M and homozygous G2: N388del:Y389del.

55. The compound for use or use according to any one of Embodiments 48-53, wherein the APOL1 is associated with compound heterozygous G1: S342G:I384M and G2: N388del:Y389del APOL1 alleles.

56. The compound, deuterated derivative, or pharmaceutically acceptable salt according to Embodiment 2, wherein R is —$NR^3R^4$.

57. The compound, deuterated derivative, or pharmaceutically acceptable salt according to Embodiment 56, wherein $R^3$ and $R^4$ are independently selected from
 hydrogen,
 $C_3$-$C_6$ cyclic alkyl groups (optionally substituted with hydroxy or amino),
 $C_1$-$C_6$ linear and branched alkyl groups (optionally substituted with 1-3 groups independently selected from amino, halogen, hydroxy, methylamide, $C_3$-$C_6$ cyclic alkyl, and carbamate (which may be further substituted with $C_1$-$C_4$ linear or branched alkyl)),
 $C_1$-$C_6$ linear and branched alkoxy groups,
 3- to 6-membered heterocyclyl groups (optionally substituted with 2-3 groups independently selected from oxo and methyl), and
 3- to 6-membered heteroaryl groups (optionally substituted with $C_1$-$C_3$ alkyl),
 or $R^3$ and $R^4$ are taken together to form a 4- to 6-membered heterocyclyl group (optionally substituted with oxo or methylamide).

58. The compound, deuterated derivative, or pharmaceutically acceptable salt according to Embodiment 2, wherein R is —$NR^5C(O)R^3$.

59. The compound, deuterated derivative, or pharmaceutically acceptable salt according to Embodiment 58, wherein:
 $R^3$ is selected from:
  $C_1$-$C_6$ linear and branched alkoxy groups,
  $C_1$-$C_6$ linear and branched alkylsulfonyl groups optionally substituted with amino,
  $C_1$-$C_6$ linear and branched alkyl groups optionally substituted with 1-4 groups independently selected from:
   hydroxy,
   oxo,
   cyano, amido (which may be further substituted with 1-2 groups independently selected from $C_1$-$C_3$ alkyl and $C_1$-$C_3$ hydroxyalkyl), amino (which may be further substituted with 1-2 groups independently selected from $C_1$-$C_3$ alkylsulfonyl and $C_1$-$C_3$ alkyl (which may be further substituted with hydroxy)), carbamate (which may be further substituted with $C_1$-$C_4$ linear or branched alkyl), $C_3$-$C_6$ cyclic alkyl (which may be further substituted with 1-2 groups independently selected from halogen, hydroxy, and $C_1$-$C_3$ alkoxy), 4- to 6-membered heterocyclyl (which may be further substituted with 1-2 groups independently selected from halogen, oxo, and $C_1$-$C_3$ alkyl), 4- to 6-membered heteroaryl groups (which may be further substituted with 1-2 groups independently selected from oxo and $C_1$-$C_3$ alkyl), $C_3$-$C_6$ cyclic alkyl groups optionally substituted with 1-2 groups independently selected from halogen, hydroxy, amino (which may be further substituted with $C_1$-$C_3$ alkyl), $C_1$-$C_3$ alkoxy, $C_1$-$C_3$ alkyl (which may be further substituted with hydroxy), and carbamate (which may be further substituted with $C_1$-$C_4$ linear or branched alkyl), 3- to 6-membered heterocyclyl groups optionally substituted with 2-3 groups independently selected from halogen, hydroxy, oxo, $C_1$-$C_3$ alkyl (which may be further substituted with oxo), $C_1$-$C_3$ alkoxy (which may be further substituted with oxo), and carbamate (which may be further substituted with $C_1$-$C_4$ linear or branched alkyl), 3- to 6-membered heteroaryl groups (which may be further optionally substituted by oxo or amino); and $R^5$ is selected from hydrogen and $C_1$-$C_3$ linear or branched alkyl groups.

60. The compound, deuterated derivative, or pharmaceutically acceptable salt according to Embodiment 2, wherein R is —$NR^5SO_2R^3$.

61. The compound, deuterated derivative, or pharmaceutically acceptable salt according to Embodiment 60, wherein:

$R^3$ is selected from $C_1$-$C_6$ linear and branched alkyl groups (optionally substituted with 1-3 groups independently selected from halogen, hydroxy, amino, and cyano), 3- to 6-membered heteroaryl groups (optionally substituted with 1-2 groups independently selected from oxo and $C_1$-$C_3$ alkyl), $C_3$-$C_6$ cyclic alkyl groups, 3- to 6-membered heterocyclyl groups; and $R^5$ is selected from hydrogen and $C_1$-$C_3$ linear and branched alkyl groups.

62. The compound, deuterated derivative, or pharmaceutically acceptable salt according to Embodiment 2, wherein R is —$NR^5SO_2NR^3R^4$.

63. The compound, deuterated derivative, or pharmaceutically acceptable salt according to Embodiment 62, wherein $R^3$ and $R^4$ are independently selected from:

hydrogen, $C_1$-$C_6$ linear and branched alkoxy groups, $C_1$-$C_6$ linear and branched alkyl groups optionally substituted with 1-4 groups independently selected from:
amino,
amido,
halogen,
hydroxy, 4- to 6-membered heterocyclyl (which may be further substituted with 1-2 groups independently selected from oxo, hydroxy, and $C_1$-$C_3$ alkyl), 4- to 6-membered heteroaryl (which may be further substituted with $C_1$-$C_3$ alkyl), and oxo, $C_3$-$C_6$ cyclic alkyl groups optionally substituted with 1-2 groups independently selected from amido, hydroxy, and $C_1$-$C_3$ alkyl (which may be further substituted with 1-3 hydroxy groups), 3- to 6-membered heterocyclyl groups (optionally substituted with 2-3 groups independently selected from oxo, hydroxy, and $C_1$-$C_3$ alkyl), and 3- to 6-membered heteroaryl groups;

or $R^3$ and $R^4$, together with the nitrogen atom to which they are attached, form a 4- to 6-membered heterocyclyl group optionally substituted with 1-2 groups independently selected from $C_1$-$C_3$ linear and branched alkyl groups (which may be further substituted with at 1-2 hydroxy groups);

and $R^5$ is selected from hydrogen and $C_1$-$C_3$ linear and branched alkyl groups.

64. The compound, deuterated derivative, or pharmaceutically acceptable salt according to Embodiment 2, wherein R is —$C(O)R^3$.

65. The compound, deuterated derivative, or pharmaceutically acceptable salt according to Embodiment 64, wherein:

$R^3$ is selected from hydrogen, $C_1$-$C_6$ linear and branched alkyl groups (optionally substituted with 1-2 groups independently selected from amino (which may be further substituted with $C_1$-$C_3$ alkyl), halogen, and hydroxy), $C_3$-$C_6$ cyclic alkyl groups (which may be further substituted with hydroxy), 3- to 6-membered heteroaryl groups, and 3- to 6-membered heterocyclyl groups.

66. The compound, deuterated derivative, or pharmaceutically acceptable salt according to Embodiment 1 or 2, wherein, when R is —$C(O)R^3$, X is N or $R^3$ is not bonded to the rest of the molecule through a nitrogen atom.

EXAMPLES

In order that the disclosure described herein may be more fully understood, the following examples are set forth. It should be understood that these examples are for illustrative purposes only and are not to be construed as limiting this disclosure in any manner.

Throughout the synthetic schemes and descriptions for preparing compounds of Formulae I, I-A, I-B, I-C, I-D, I-E, and I-F, Compounds 1 to 456, deuterated derivatives of any of those compounds, and pharmaceutically acceptable salts of any of the foregoing, the following abbreviations are used:

Abbreviations

AIBN=Azobisisobutyronitrile
ARP=assay ready plate
BBBPY=4,4'-Di-tert-butyl-2,2'-dipyridyl
CBzCl=Benzyl chloroformate
CDMT=2-Chloro-4,6-dimethoxy-1,3,5-triazine
DIPEA=N,N-Diisopropylethylamine or N-ethyl-N-isopropyl-propan-2-amine
DMAP=dimethylamino pyridine
DMA=dimethyl acetamide DME=dimethoxyethane
DMEM=Dulbecco's modified Eagle's medium
DMF'=dimethylformamide
DMSO=dimethyl sulfoxide
DPPA=diphenylphosphoryl azide
EtOAc=Ethyl Acetate
EtOH=ethanol
FBS=fetal bovine serum
FLU=fluorescent values
HATU=[dimethylamino(triazolo[4,5-b]pyridin-3-yloxy)methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
LDA=lithium diisopropyl amide
LED=light emitting diode
MeOH=methanol
MTBE=Methyl tert-butyl ether
NMM=N-methyl morpholine
NMP=N-methyl pyrrolidine
PBS=phosphate-buffered saline
Pd(dppf)$_2$Cl$_2$=[1,1'-Bis(diphenylphosphino)ferrocene]dichloropalladium(II)
PdCl$_2$(PPh$_3$)$_2$=Bis(triphenylphosphine)palladium(II) dichloride
PP=polypropylene
PTSA=p-Toluenesulfonic acid monohydrate
T3P=2,4,6-Tripropyl-1,3,5,2,4,6-trioxatriphosphorinane-2,4,6-trioxide
TEA=triethylamine
Tet=tetracycline
TFA=trifluoroacetic acid
THF=tetrahydrofuran
THP=tetrahydropyran
TMSS=Tris(trimethylsilyl)silane Example 1. Synthesis of Compounds General Schemes:

Scheme 1 provides processes suitable for the preparation of indoles of Formula 1-4. In some embodiments, $X^1$ is a halogen. In some embodiments, the halogen is Cl, I, or Br. $R^1$, $R^2$, m, and n are as defined above. Any suitable conditions for coupling an alkyne can be used to convert aryl halides of Formula 1-1 and alkynes of Formula 1-2 to afford an amino aryl alkyne of Formula 1-3. For example, in some embodiments, the coupling is performed in the presence of a CuI and Pd(PPh$_3$)$_2$Cl$_2$ catalyst system. In some embodiments, the reaction is performed in the presence of at least one base. In some embodiments, the at least one base is DIPEA or NEt$_3$. In some embodiments, conversion of compounds of Formula 1-3 to indoles of Formula 1-4 is accomplished by treatment with CuI or PdCl$_2$ in at least one polar solvent in the presence of added heat. In some embodiments, the at least one polar solvent is chosen from DMF and MeCN. In some embodiments, the added heat is greater than 100° C.

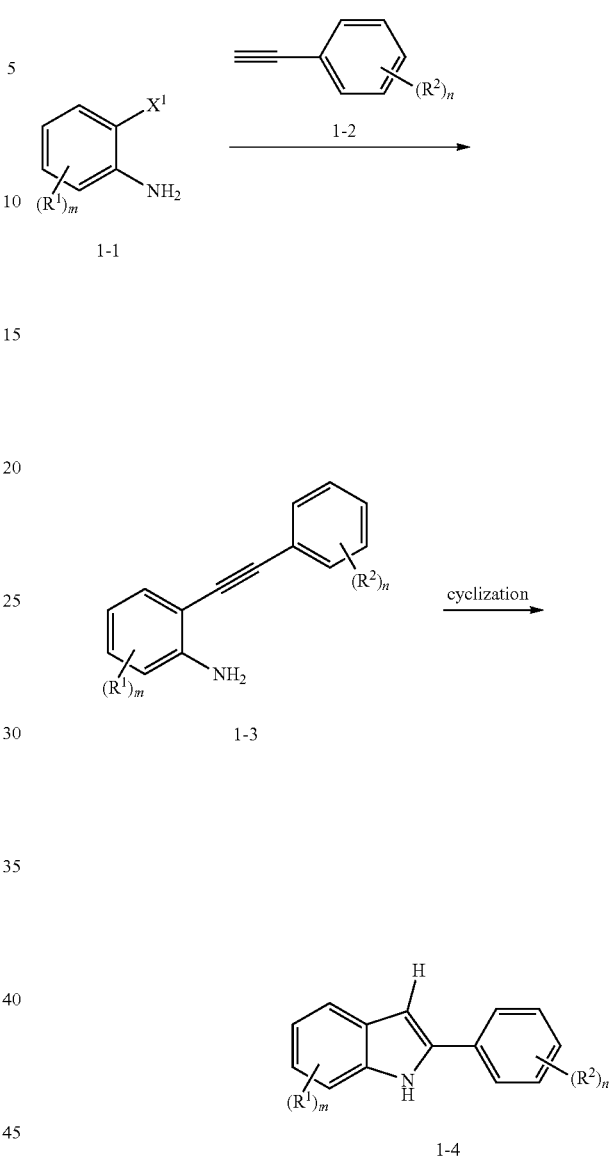

Scheme 1

Scheme 2 refers to a process for preparation of compounds of Formula 1-4 from an indole such as that represented by Formula 2-1, and an aryl halide of Formula 2-2, where $X^3$ is a halogen (e.g., I or Br). $R^{20}$ is an alkyl group, such as, e.g., Me or Et. The two $R^{20}$ groups may be linked by a carbon carbon bond to form a cyclic boronate ester. In some embodiments, the reaction is performed in the presence of a catalyst such as PdCl$_2$CN$_2$, a ligand such as norbornylene, and a base (e.g., K$_2$CO$_3$). The reaction may be performed in a solvent, such as, e.g., dimethylacetamide at elevated temperature (e.g., 90° C.). Compounds of Formula 1-4 may also be prepared from indoles of Formula 2-1 and aryl boronic acids or esters of Formula 2-3. In some embodiments, the reaction is performed in the presence of a palladium catalyst (e.g., Pd(OAc)$_2$ trimer) in a solvent such as, e.g., AcOH. The reaction is performed in the presence of oxygen.

Scheme 2

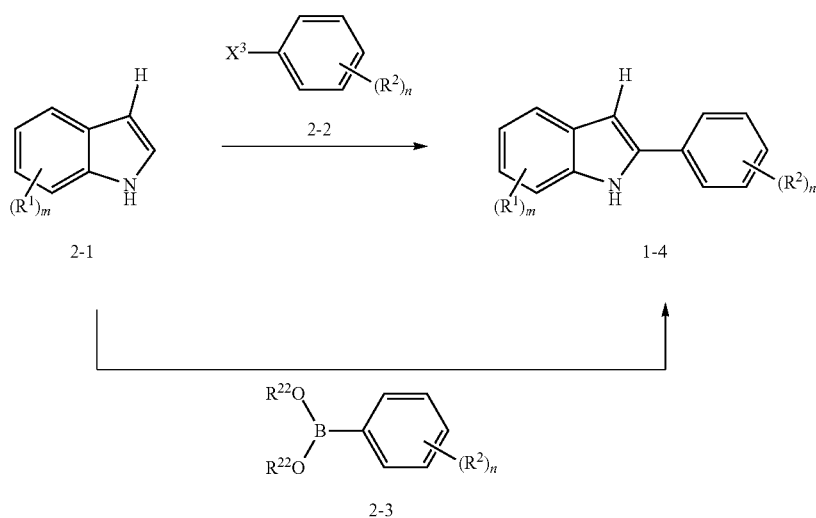

Scheme 3 describes processes for the preparation of Formula I. Indoles of Formula 1-4 may react with carbonyl compounds of Formula 3-1, to afford compounds of Formula I. Compound 3-1 are any ketones or aldehydes which are suitable to form a compound of Formula I upon reductive coupling with a compound of Formula 1-4. For example, compounds of Formula 3-1 may be an aldehyde, or a ketone in which the carbonyl group of the ketone is a substituent of ring A. In some embodiments, the reaction is performed in the presence of at least one acid and at least one reducing agent. In some embodiments, the acid is chosen from trifluoroacetic acid and methanesulfonic acid. In some embodiments, the reducing agent is $Et_3SiH$. The reaction may be performed in a solvent such as dichloromethane.

Scheme 4 refers to processing for the preparation of amines of Formula 4-3, which may be used in the preparation of further compounds of Formula I. $PG^1$ is any suitable nitrogen protecting group, for example, CBz or Boc. Compounds of Formula 4-2 may be prepared from indoles of Formula 1-4 and ketones of Formula 4-1 using any condition suitable for performing a reductive alkylation. An acid and a reducing agent may be used in the reductive alkylation step. In some embodiments, the acid used is trifluoroacetic acid or methanesulfonic acid. In some embodiments, the reducing agent may be triethylsilane. A compound of Formula 4-3 may be prepared from a compound of Formula 4-2 using any suitable condition for removal of a nitrogen protecting group. For example, where $PG^1$ is CBz, hydrogenolysis using hydrogen gas and a palladium on carbon catalyst affords compounds of Formula 4-3. In some embodiments, the reaction is performed in a solvent mixture such as, e.g., THF and methanol.

Scheme 3

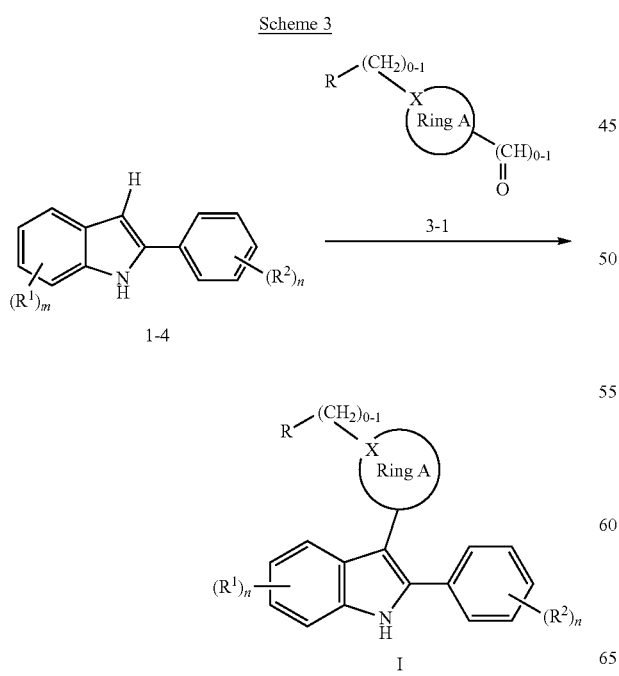

Scheme 4

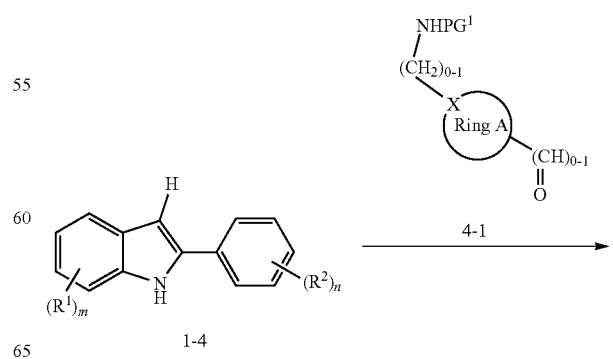

-continued

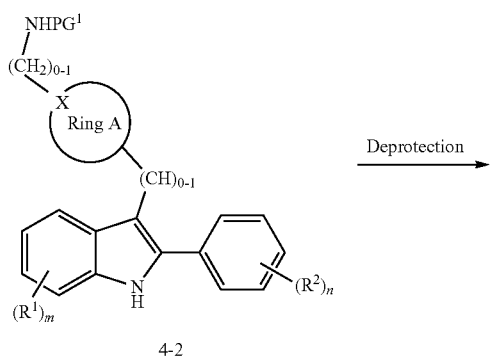

4-2

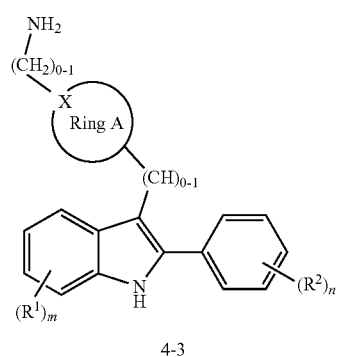

4-3

Scheme 5 shows processes for the preparation of compounds of Formula 5-3. Compounds of Formula 5-2 may be prepared from 1-4 and 5-1 using any suitable conditions for reductive alkylation. Compounds of Formula 5-3 may be prepared using any suitable method for the reduction of a nitrile group to an amine. In some embodiments, hydrogenation using a catalyst such as Raney Nickel may be used. The reaction may be performed in a solvent such as, e.g., a solution of ammonia in methanol. The reaction may be performed at elevated pressure, for example 60 psi hydrogen atmosphere. In some alterative embodiments, reduction with LiAlH$_4$ may be used. The reaction may be performed in a solvent such as THF. The reaction may be performed in the presence of added heat (e.g., 60° C.). Compounds of Formula 5-3 may be used as compounds of Formula 4-3.

-continued

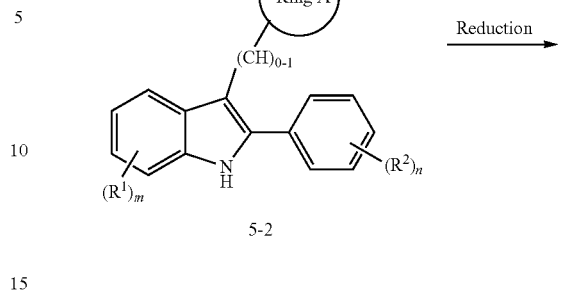

5-2

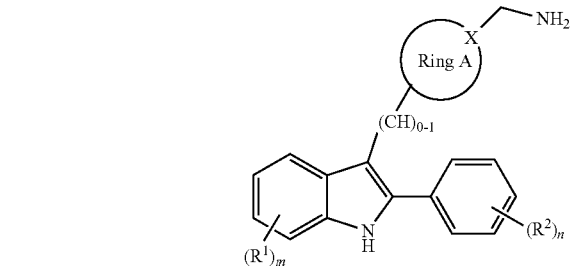

5-3

Processes for the preparation of a compound of Formula 6-2 involves coupling of amines of Formula 4-3 and a carboxylic acid of Formula 6-1, using any suitable method for the formation of an amide bond. In some embodiments, processes for preparing compounds of Formula 6-2, comprise reacting a compound of Formula 6-1 with an amine of Formula 4-3 in the presence of at least one amide coupling agent (e.g., HATU, CDMT, HDMC, or T3P) and at least one suitable base (e.g., DIPEA or TEA). In some embodiments, the amide coupling agent is chosen from HATU, CDMT, HDMC, and T3P. In some embodiments, a suitable base is chosen from DIPEA and TEA. In some embodiments, HATU and triethylamine in at least one solvent is used. In some embodiments, the solvent is DMF. Other suitable conditions for amide bond formation may be used to prepare compounds of Formula 6-2.

Scheme 5

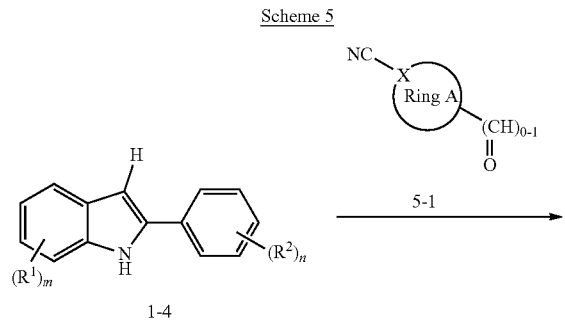

Scheme 6

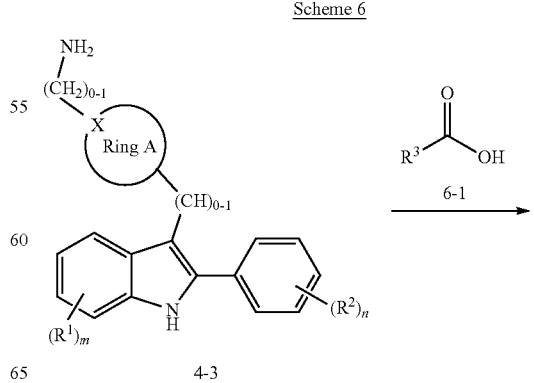

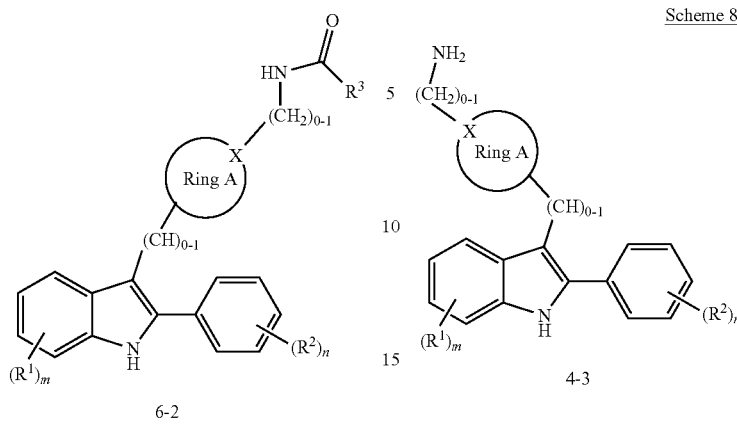

6-2

Scheme 7 shows processes for the preparation of sulfonamides of Formula 7-2. LG$^1$ represents any suitable leaving group atom or group. For example, LG$^1$ may be a chlorine atom. Reaction of an amine of Formula 4-3 with a sulfonyl reagent of Formula 7-1 in the presence of a base such as, e.g., DIPEA and in a solvent such as, e.g., DMF.

Scheme 7

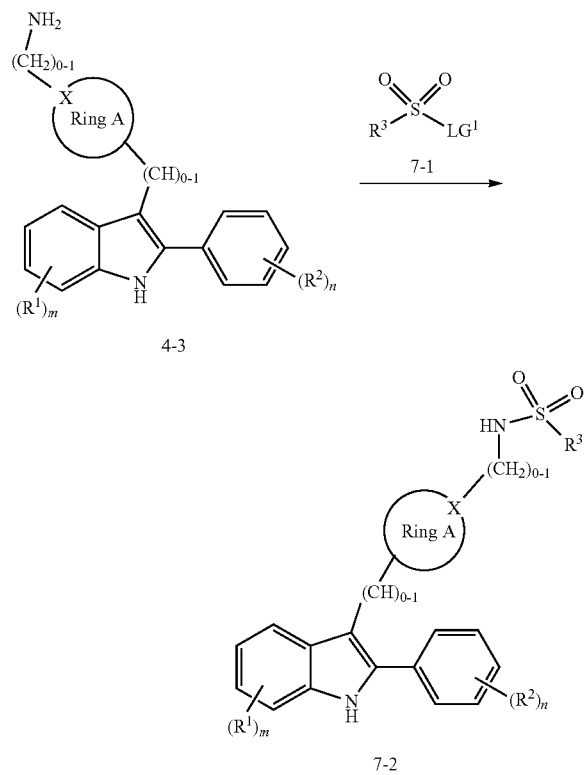

Scheme 8 shows processes for the preparation of a compound of Formula 8-2. An amine of Formula 4-3 may be treated with a sulfamoyl chloride of Formula 8-1. The reaction may be performed in a solvent such as, e.g., dichloromethane and a base such as, e.g., triethylamine. Any other suitable conditions for the preparation of a sulfamide may be used.

Scheme 8

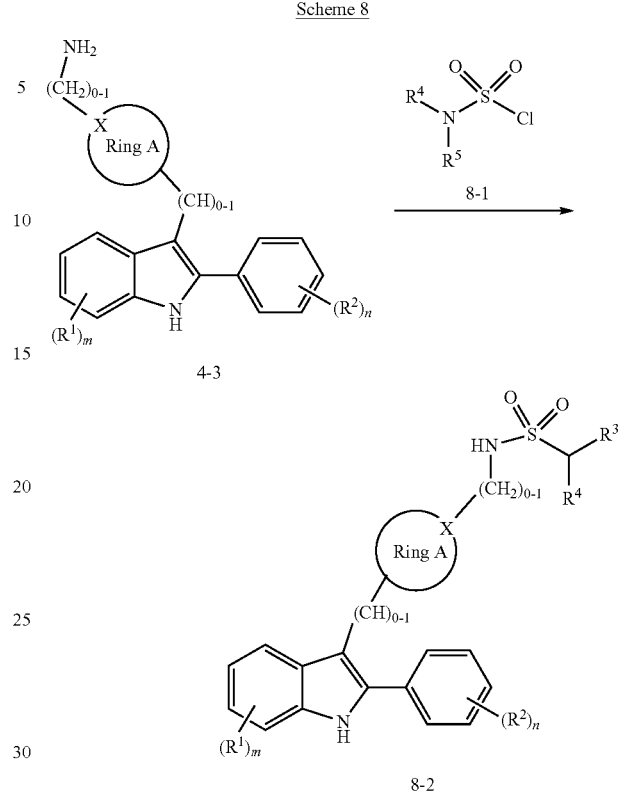

Scheme 9 shows processes for the preparation of compounds of Formula 9-5. Compounds of Formula 9-2 may be prepared by reductive alkylation of an indole of Formula 1-4 and a carbonyl compound of Formula 9-1. PG$^2$ is any suitable nitrogen protecting group, such as, e.g., CBz or Boc. Ring A contains a nitrogen atom. Removal of the nitrogen protecting group from 9-2 affords amines of Formula 9-3. Compounds of Formula 9-5 may be prepared from 9-3 by coupling with carboxylic acids of Formula 9-4 using any suitable method for coupling an amine and carboxylic acid. In some embodiments, an amide coupling agent may be used. For example, the reagent may be HATU, CDMT, T3P, or any other suitable coupling reagent. The reaction may be performed in the presence of a base, such as, e.g., TEA or DIPEA. The reaction may be performed in a solvent, such as, e.g., DMF or dichloromethane.

Scheme 9

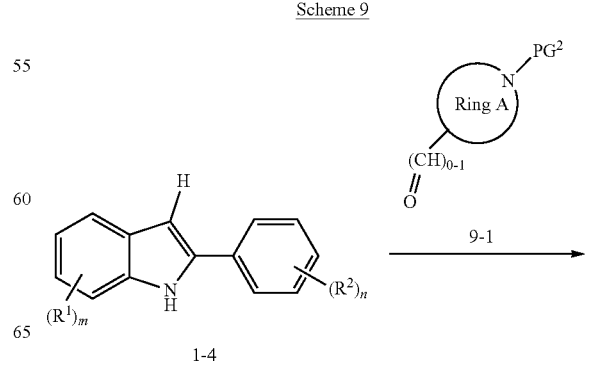

-continued

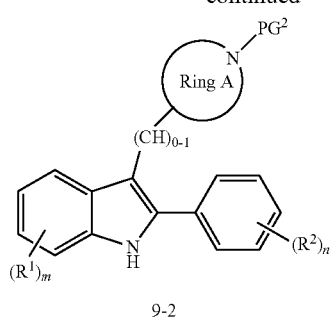

9-2

Deprotection →

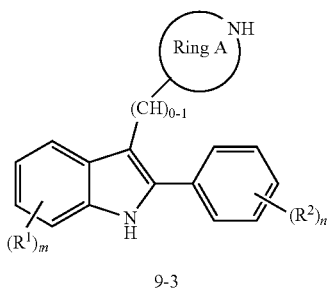 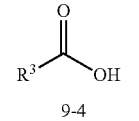

9-3      9-4

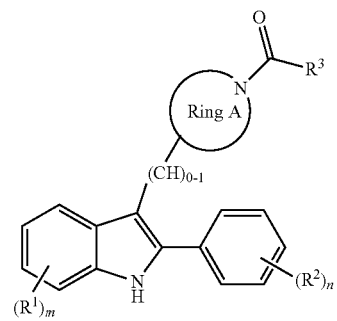

9-5

Scheme 10 shows processes for the preparation of a compound of Formula 10-3 from a ketone of Formula 10-1 and an amine of Formula 10-2. Any suitable method for reductive amination may be used. For example, the reaction may be performed in the presence of a reducing system such as, e.g., sodium triacetoxyborohydride and acetic acid. The reaction may be performed in a solvent such as, e.g., dichloromethane or dimethylformamide.

Scheme 10

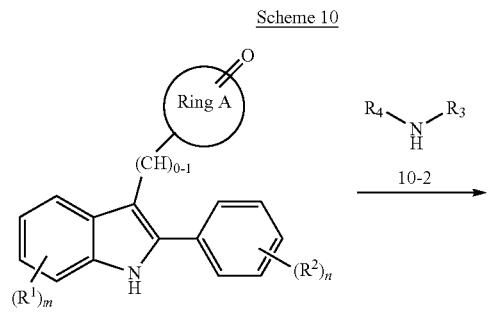

10-1

-continued

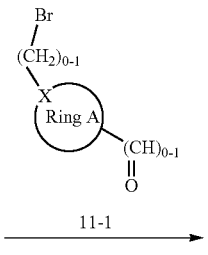

10-3

Scheme 11 shows processes for the preparation of compounds of Formula 11-4 from alkyl halides of Formula 11-2 and amines of Formula 11-3. In some embodiments, the reaction may be performed in the presence of a base such as, e.g., potassium carbonate. In some embodiments, the reaction may be performed in the presence of a solvent such as, e.g., DMF. The reaction may be performed in the presence of added heat (e.g. 80° C.).

Scheme 11

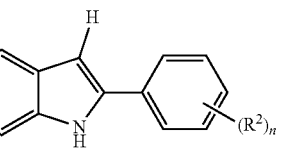

1-4      11-1

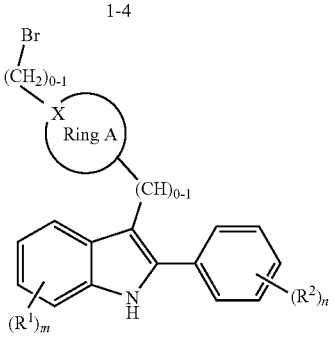 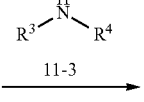

11-2     11-3

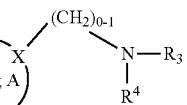

11-4

General Purification and Analysis Methods

Unless otherwise stated, all final products were purified, as necessary, by reversed-phase HPLC (Method: C18 Waters Sunfire column (30×150 mm, 5 micron). Gradient: 10-100% MeCN in H$_2$O. Modifier: 0.2% formic acid or 0.1% Trifluoroacetic acid).

Products were analyzed by LCMS methods A, B, or C. LCMS m/z and retention times were collected.

LCMS Method A: HPLC Sunfire C18 column. Gradient: 2-98% MeCN/H$_2$O over 3.8 minutes. TFA Modifier.

LCMS Method B: UPLC CSH C18 column. Gradient: 5-95% MeCN/H$_2$O. TFA Modifier.

LCMS Method C: UPLC CSH C18 column. Gradient: 10-60% MeCN/H$_2$O. TFA Modifier.

Compound 1

3-[7-fluoro-2-(4-fluorophenyl)-5-(trifluoromethyl)-1H-indol-3-yl]cyclobutanamine (1)

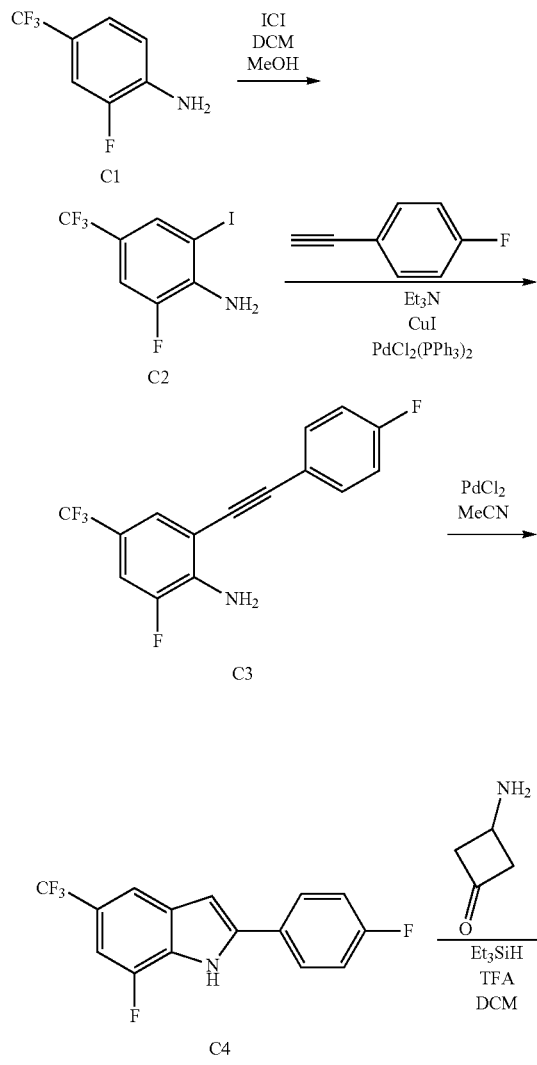

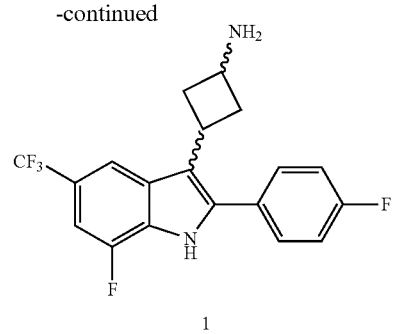

Step 1. Synthesis of 2-fluoro-6-iodo-4-(trifluoromethyl)aniline (C2)

To a solution of 2-fluoro-4-(trifluoromethyl)aniline C1 (5.0 g, 28 mmol) in DCM (100 mL) and MeOH (50 mL) was added iodine monochloride (8.9 g, 55 mmol) dropwise over 30 min. After stirring at room temperature for 48 hours, the mixture was quenched with 1 M NaOH (150 mL), and the aqueous layer was removed. The organic layer was washed with brine, dried over anhydrous magnesium sulfate, filtered and concentrated in vacuo. The crude material was purified by vacuum distillation to afford the product as an orange oil (6.0 g, 71%). $^1$H NMR (300 MHz, DMSO-d$_6$) δ 7.70 (s, 1H), 7.46 (d, J=11.3 Hz, 1H), 5.93 (s, 2H).

Step 2. Synthesis of 2-fluoro-6-[2-(4-fluorophenyl)ethynyl]-4-(trifluoromethyl)aniline (C3)

To a suspension of 1-ethynyl-4-fluoro-benzene (3.08 g, 25.4 mmol), CuI (630 mg, 3.2 mmol), PdCl$_2$(PPh$_3$)$_2$ (728 mg, 1.01 mmol), and Et$_3$N (6.0 mL, 43 mmol) in DMF (119 mL) was added 2-fluoro-6-iodo-4-(trifluoromethyl)aniline C2 (5.96 g, 19.5 mmol). After stirring at room temperature for 2 hours, water (200 mL) was added to the reaction. The resulting precipitate was filtered, washed with water (100 mL), and dried under reduced pressure to afford the product as a brown solid which was used without any further purification (6.5 g, quantitative). $^1$H NMR (300 MHz, DMSO-d$_6$) δ 7.81-7.72 (m, 2H), 7.45 (d, J=8.5 Hz, 2H), 7.28 (t, J=8.8 Hz, 2H), 6.34 (s, 2H). LCMS m/z 296.1 [M−H]$^-$.

Step 3. Synthesis of 7-fluoro-2-(4-fluorophenyl)-5-(trifluoromethyl)-1H-indole (C4)

A suspension of 2-fluoro-6-[2-(4-fluorophenyl)ethynyl]-4-(trifluoromethyl)aniline C3 (5.8 g, 19 mmol) and PdCl$_2$ (332 mg, 1.85 mmol) in MeCN (580 mL) was stirred at 80° C. for 5 hours. The reaction was cooled to room temperature and concentrated in vacuo. Purification by silica gel chromatography (Gradient: 0-15% EtOAc in hexane) yielded the product as an orange solid (4.02 g, 68%). $^1$H NMR (300 MHz, DMSO-d$_6$) δ 12.36 (s, 1H), 8.02 (dd, J=8.6, 5.4 Hz, 2H), 7.79 (s, 1H), 7.39-7.25 (m, 3H), 7.13 (d, J=3.2 Hz, 1H). LCMS m/z 296.1 [M−H]$^-$.

Step 4. Synthesis of 3-[7-fluoro-2-(4-fluorophenyl)-5-(trifluoromethyl)-1H-indol-3-yl]cyclobutanamine (1)

To a mixture of 7-fluoro-2-(4-fluorophenyl)-5-(trifluoromethyl)-1H-indole C4 (125 mg, 0.40 mmol), 3-aminocyclobutanone (51 mg, 0.60 mmol), Et$_3$SiH (230 mg, 2.0 mmol), and DCM (1.8 mL) was added TFA (226 mg, 2.0 mmol). After stirring overnight at room temperature, the reaction was concentrated in vacuo. Purification by reversed phase chromatography (C18 column; Gradient: MeCN in H$_2$O with 0.1% trifluoroacetic acid) yielded the product (85 mg, 44%) as a mixture of cis and trans isomers. LCMS m/z 367.09 [M+H]$^+$.

Compound 2

N-[3-[7-fluoro-2-(4-fluorophenyl)-5-(trifluoromethyl)-1H-indol-3-yl]cyclobutyl]-3-hydroxy-propanamide (2)

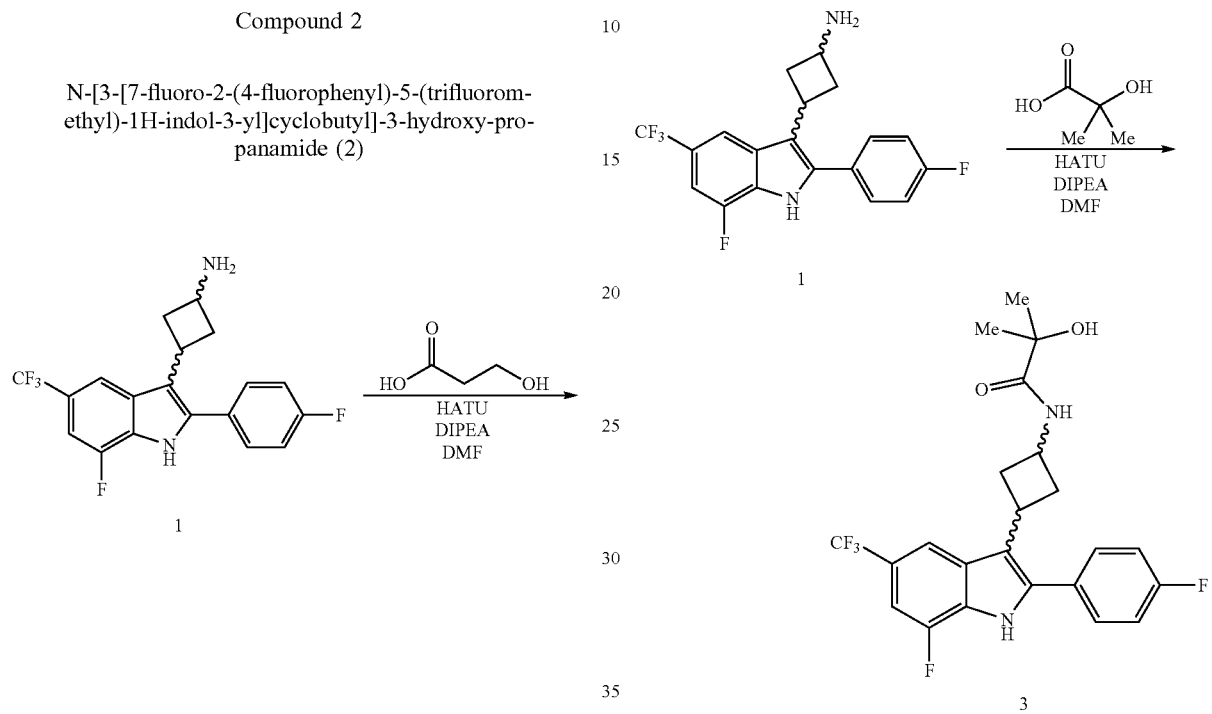

A mixture of 3-[7-fluoro-2-(4-fluorophenyl)-5-(trifluoromethyl)-1H-indol-3-yl]cyclobutanamine 1 (30 mg, 0.082 mmol), 3-hydroxypropanoic acid (25 mg, 0.28 mmol), HATU (62 mg, 0.16 mmol), DIPEA (60 mg, 0.5 mmol), and DMF (400 μL) was stirred at room temperature. Purification by reversed phase chromatography (C18 column; Gradient: MeCN in H$_2$O with 0.1% trifluoroacetic acid) yielded the product (14 mg, 39%) as a mixture of cis and trans isomers. LCMS m/z 439.1 [M+H]$^+$.

Compound 3

N-[3-[7-fluoro-2-(4-fluorophenyl)-5-(trifluoromethyl)-1H-indol-3-yl]cyclobutyl]-2-hydroxy-2-methyl-propanamide (3)

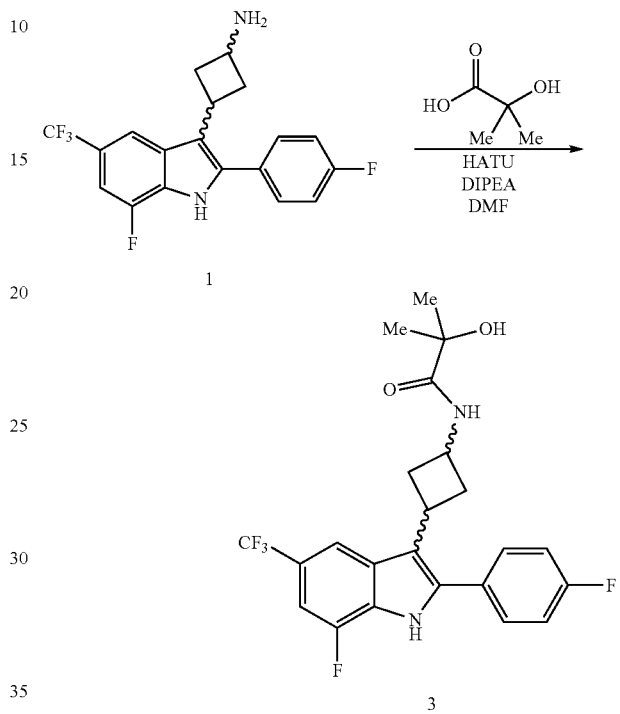

A mixture of 3-[7-fluoro-2-(4-fluorophenyl)-5-(trifluoromethyl)-1H-indol-3-yl]cyclobutanamine 1 (30 mg, 0.082 mmol), 2-hydroxy-2-methyl-propanoic acid (26 mg, 0.25 mmol), HATU (62 mg, 0.16 mmol), DIPEA (60 mg, 0.46 mmol), and DMF (400 μL) was stirred at room temperature. Purification by reversed phase chromatography (C18 column; Gradient: MeCN in H$_2$O with 0.1% trifluoroacetic acid) yielded the product (17 mg, 44%) as a mixture of cis and trans isomers. LCMS m/z 452.98 [M+H]$^+$.

Compound 4

3-[5,7-difluoro-2-(p-tolyl)-1H-indol-3-yl]cyclobutanamine (4)

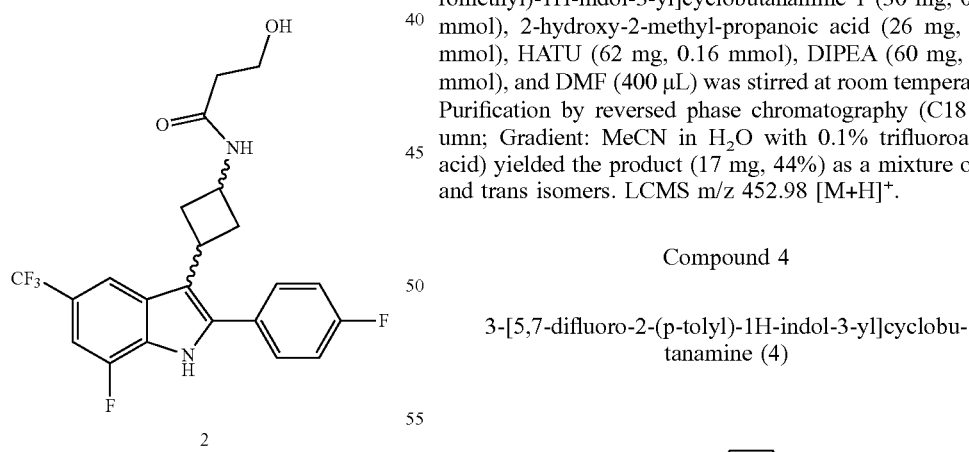

180

Compound 5

3-[5,7-difluoro-2-(m-tolyl)-1H-indol-3-yl]cyclobutanamine (5)

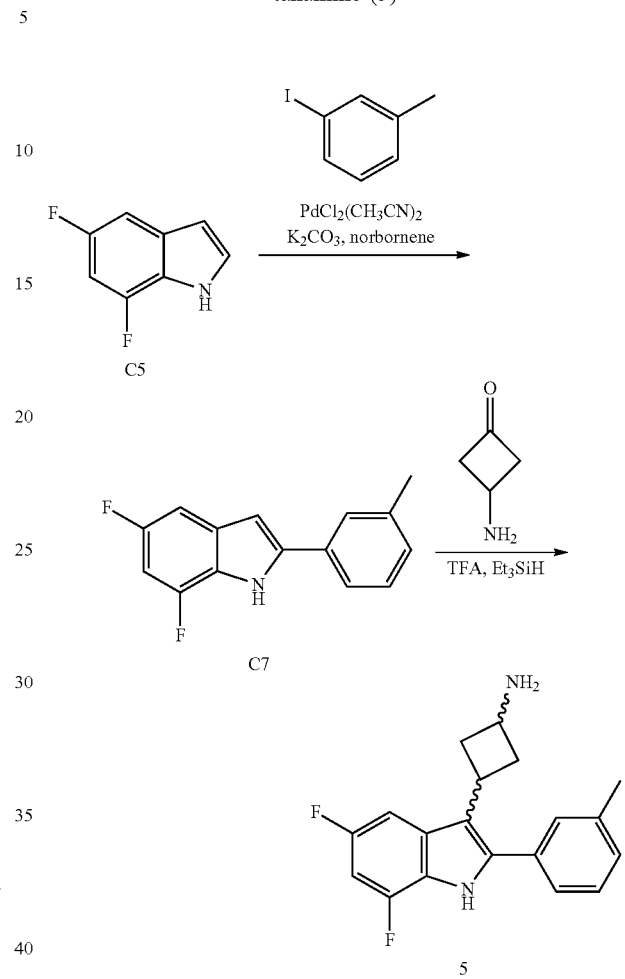

Step 1. Synthesis of 5,7-difluoro-2-(m-tolyl)-1H-indole (C7)

A 30 mL vial was charged with a magnetic sir bar, 5,7-difluoro-1H-indole C5 (500 mg, 3.3 mmol), 1-iodo-3-methyl-benzene (750 mg, 3.4 mmol), DMA (3 mL), water (500 $K_2CO_3$ (1.15 g, 8.32 mmol), norbornene (620 mg, 6.5 mmol), and bis(acetonitrile)palladium dichloride (84 mg, 0.32 mmol). The reaction mixture was heated to 90° C. for 14 hours. After cooling to room temperature, the mixture was diluted with water and extracted with EtOAc. The organic extract was dried with $MgSO_4$, filtered and concentrated in vacuo. Purification by silica gel chromatography (Gradient: 10% EtOAc in heptane) afforded the product (444 mg, 35%). LCMS 244.11 [M+H]$^+$.

Step 2. Synthesis of 3-[5,7-difluoro-2-(m-tolyl)-1H-indol-3-yl]cyclobutanamine (5)

A 30 mL vial was charged with a magnetic stir bar, 5,7-difluoro-2-(m-tolyl)-1H-indole C7 (75 mg, 0.29 mmol), DCM (1.1 mL), 3-aminocyclobutanone (30 mg, 0.35 mmol) and $Et_3SiH$ (200 mg, 1.7 mmol). To the mixture was then added trifluoroacetic acid (200 mg, 1.7 mmol), and the

179

-continued

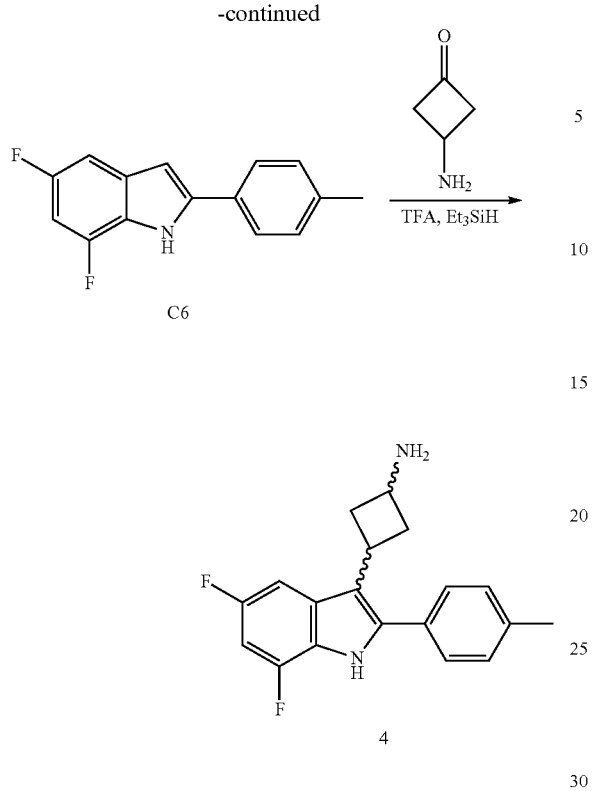

Step 1. Synthesis of 5,7-difluoro-2-(p-tolyl)-1H-indole (C6)

A 30 mL vial was charged with a magnetic sir bar, 5,7-difluoro-1H-indole C5 (500 mg, 3.3 mmol), 1-iodo-4-methyl-benzene (750 mg, 3.4 mmol), DMA (3 mL), water (500 μL), $K_2CO_3$ (1.12 g, 8.10 mmol), norbornene (620 mg, 6.6 mmol), and bis(acetonitrile)palladium dichloride (83 mg, 0.32 mmol). The reaction mixture was heated to 90° C. for 14 hours. After cooling to room temperature, the mixture was diluted with water and extracted with EtOAc. The organic extract was dried with $MgSO_4$, filtered and concentrated in vacuo. Purification by silica gel chromatography (Gradient: 10% EtOAc in heptane) afforded the product (301 mg, 30%). LCMS m/z 244.16 [M+H]$^+$.

Step 2. Synthesis of 3-[5,7-difluoro-2-(p-tolyl)-1H-indol-3-yl]cyclobutanamine (4)

A 30 mL vial was charged with a magnetic stir bar, 5,7-difluoro-2-(p-tolyl)-1H-indole C6 (75 mg, 0.29 mmol), DCM (1.1 mL), 3-aminocyclobutanone (40 mg, 0.5 mmol) and $Et_3SiH$ (200 mg, 1.7 mmol). To the mixture was then added trifluoroacetic acid (200 mg, 1.8 mmol), and the reaction was allowed to stir overnight. The mixture was then concentrated in vacuo. Purification by reversed phase chromatography (C18 column; Gradient: MeCN in $H_2O$ with 0.1% trifluoroacetic acid) yielded the product (33 mg, 27%) as a mixture of cis and trans isomers. $^1$H NMR (300 MHz, DMSO-$d_6$) δ 11.69 (s, 1H), 8.02 (d, J=25.7 Hz, 2H), 7.80-7.58 (m, 1H), 7.58-7.19 (m, 3H), 6.99 (t, J=10.5 Hz, 1H), 3.55 (dd, J=22.9, 14.6 Hz, 3H), 2.38 (s, 4H). LCMS m/z 312.98 [M+H]$^+$.

reaction was allowed to stir overnight. The mixture was then concentrated in vacuo. Purification by reversed phase chromatography (C18 column; Gradient: MeCN in H₂O with 0.1% trifluoroacetic acid) yielded the product (55 mg, 44%) as a mixture of cis and trans isomers. $^1$H NMR (300 MHz, DMSO-$d_6$) δ 11.72 (s, 1H), 8.08 (d, J=29.9 Hz, 3H), 7.68 (d, J=9.8 Hz, 1H), 7.35 (tt, J=21.2, 7.1 Hz, 4H), 7.01 (ddd, J=11.5, 9.7, 2.1 Hz, 1H), 3.55 (t, J=9.0 Hz, 2H), 2.74 (s, 1H), 2.40 (s, 6H). LCMS m/z 312.93 [M+H]$^+$.

Compound 6

3-[7-fluoro-2-(4-fluorophenyl)-1H-indol-3-yl]cyclobutanamine (6)

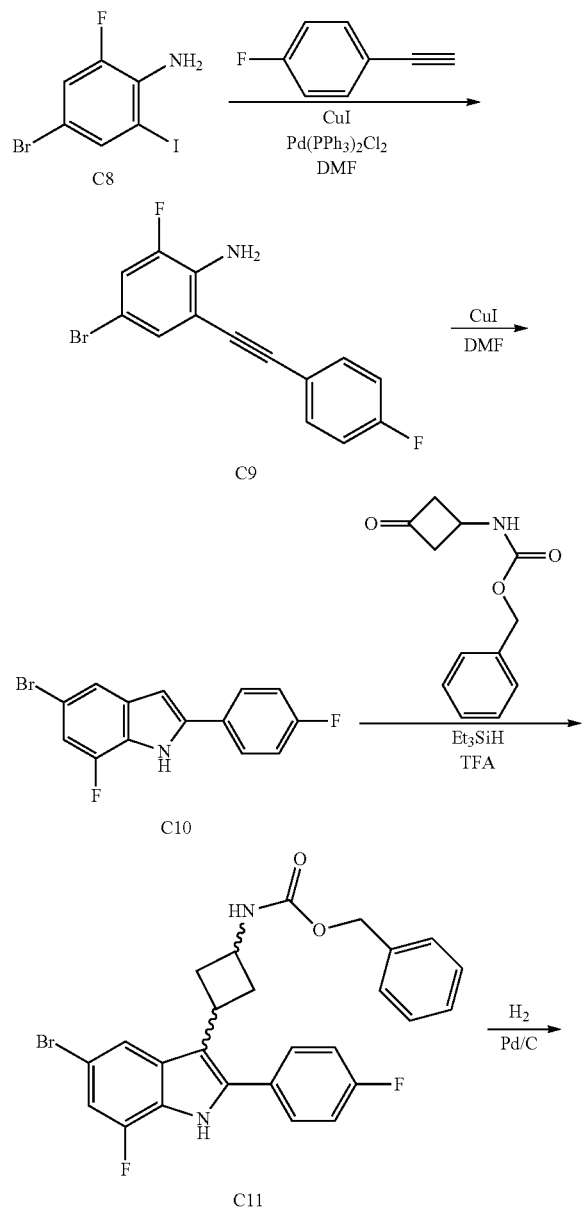

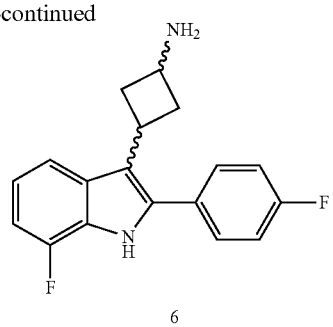

Step 1. Synthesis of 4-bromo-2-fluoro-6-[2-(4-fluorophenyl)ethynyl]aniline (C9)

To a solution of 4-bromo-2-fluoro-6-iodo-aniline C8 (40 g, 130 mmol) in DMF (80 mL) and NEt₃ (400 mL) was added 1-ethynyl-4-fluoro-benzene (20 g, 170 mmol), CuI (4 g, 21 mmol), and bis(triphenylphosphine)palladium(II) dichloride (4.6 g, 6.6 mmol). The mixture was allowed to stir at room temperature for 5 hours. Water (1000 mL) was added, and the mixture was extracted with MTBE, filtered and concentrated in vacuo. The product mixture was filtered through a silica gel plug (Eluent: 20% EtOAc in heptane). Silica gel chromatography (Gradient: 0-15% EtOAc in heptane) afforded the product as an orange solid. (32 g, 60%). $^1$H NMR (300 MHz, Chloroform-d) δ 7.63-7.42 (m, 2H), 7.34-7.25 (m, 1H), 7.22-6.97 (m, 3H), 4.31 (s, 2H). LCMS m/z 308.21 [M+H]$^+$.

Step 2. Synthesis of 5-bromo-7-fluoro-2-(4-fluorophenyl)-1H-indole (C10)

A solution of 4-bromo-2-fluoro-6-[2-(4-fluorophenyl)ethynyl]aniline C9 (32 g, 100 mmol) in DMF (400 mL) was heated to 150° C. for 4 hours. Next, CuI (2 g, 10 mmol) was added, and the reaction was heated to 150° C. for 3 hours. After cooling to room temperature, water (800 mL) was added, and the mixture was extracted with MTBE. The organic phase was then washed with brine, dried over Na₂SO₄, filtered, and then concentrated in vacuo. The product mixture was filtered through a silica gel plug (Eluent: 20% EtOAc in heptane). Subsequent silica gel chromatography (Gradient: 0-20% EtOAc in heptane) afforded the product as a pink solid. (14.4 g, 45%). $^1$H NMR (300 MHz, Chloroform-d) δ 8.47 (s, 1H), 7.73-7.59 (m, 2H), 7.55 (dd, J=1.5, 0.7 Hz, 1H), 7.26-7.14 (m, 2H), 7.08 (dd, J=10.2, 1.6 Hz, 1H), 6.73 (dd, J=3.4, 2.3 Hz, 1H). LCMS m/z 307.01 [M+H]$^+$.

Step 3. Synthesis of benzyl N-[3-[5-bromo-7-fluoro-2-(4-fluorophenyl)-1H-indol-3-yl]cyclobutyl]-carbamate (C11)

To a solution of 5-bromo-7-fluoro-2-(4-fluorophenyl)-1H-indole C10 (227 mg, 0.737 mmol) in DCM (3 mL) was added benzyl N-(3-oxocyclobutyl)carbamate (194 mg, 0.885 mmol) followed by Et₃SiH (514 mg, 4.42 mmol) and trifluoroacetic acid (505 mg, 4.43 mmol). The mixture was stirred at room temperature for 4 hours. The mixture was then partitioned between DCM and aqueous sat. sodium bicarbonate solution. The organic phase was separated and dried over magnesium sulfate, filtered, and concentrated in vacuo. The residue was purified by silica gel chromatography (17% EtOAc in heptane) to afford the product (351 mg, 73%). LCMS m/z 511.18 [M+H]$^+$.

Step 4. Synthesis of 3-[7-fluoro-2-(4-fluorophenyl)-1H-indol-3-yl]cyclobutanamine (6)

To a suspension of benzyl N-[3-[5-bromo-7-fluoro-2-(4-fluorophenyl)-1H-indol-3-yl]cyclobutyl]carbamate C11 (140 mg, 0.27 mmol) in MeOH (2.75 mL) was added 10% palladium on carbon catalyst (25 mg). The mixture was subjected to hydrogenation conditions of 1 atm H$_2$ for 24 hours. Filtration through a pad of Celite®, then concentration of the filtrate in vacuo and washing with DCM afforded the product, which was further purified by reversed phase chromatography (C18 column; Gradient: MeCN in H$_2$O with 5 mM hydrochloric acid) to afford the product (42 mg, 44%). LCMS m/z 299.16 [M+H]$^+$.

Compound 7

3-[2-(4-cyclopropylphenyl)-5-fluoro-1H-indol-3-yl] (7)

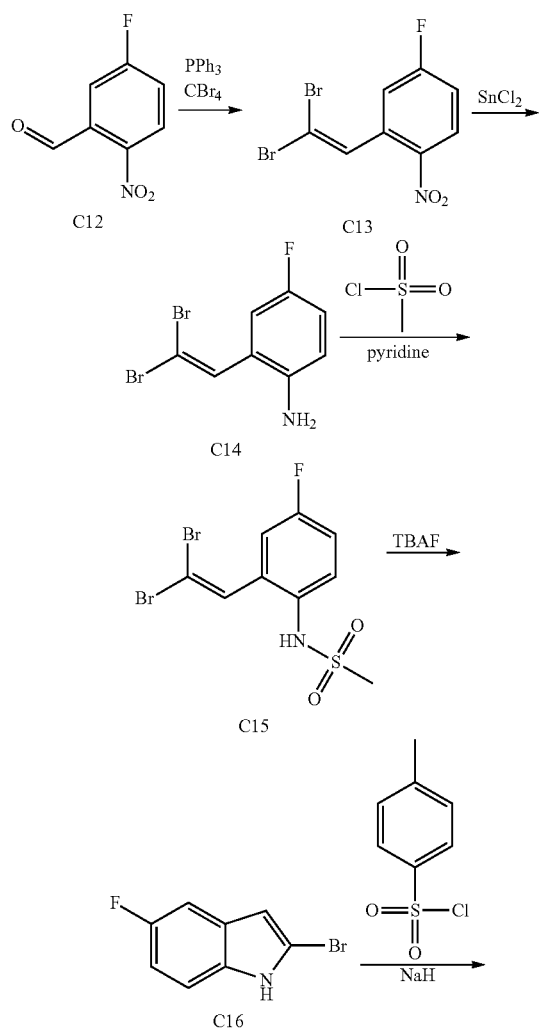

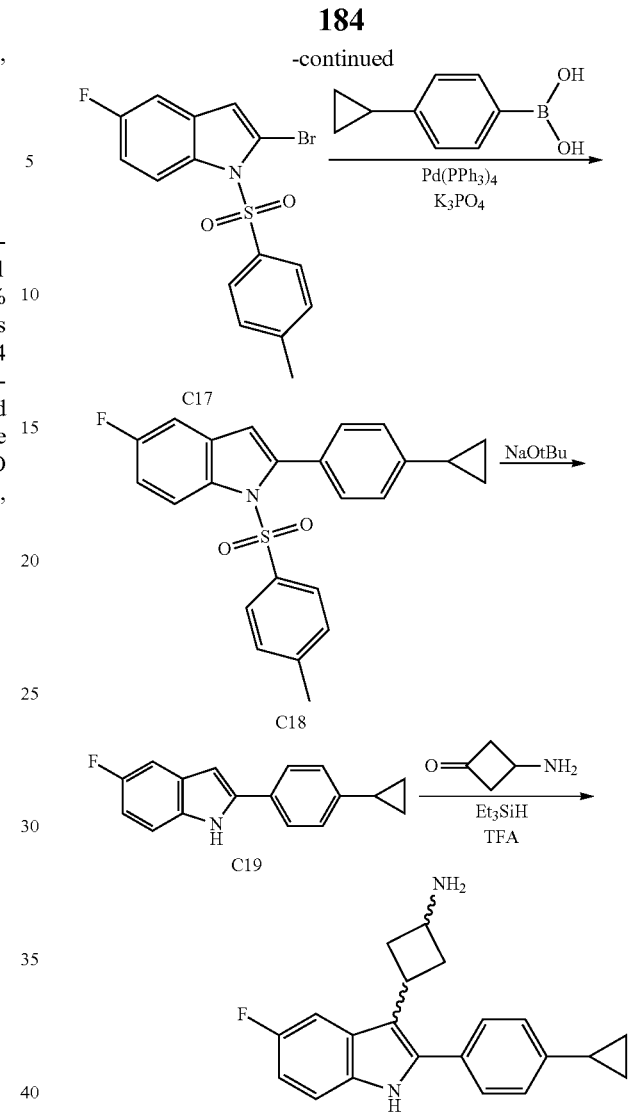

Step 1. Synthesis of 2-(2,2-dibromovinyl)-4-fluoro-1-nitro-benzene (C13)

To a stirred solution of 5-fluoro-2-nitro-benzaldehyde C12 (20 g, 120 mmol) and tetrabromomethane (78.443 g, 236.54 mmol) in DCM (800 mL) at 0° C. was added dropwise a solution of PPh$_3$ (124.08 g, 473.08 mmol) in DCM (400 mL). The mixture was kept stirring at 0° C. for 30 minutes. Then, the mixture was warmed to room temperature and stirred for another 1.5 hours. The mixture was cooled to 0° C. and diluted with hexane (~500 mL). The precipitate was filtered through a silica gel plug (Eluent: hexane). The filtrate was concentrated in vacuo to give the product (20 g, 52%) $^1$H NMR (400 MHz, Chloroform-d) δ 8.19 (dd, J=9.1, 5.0 Hz, 1H), 7.75 (s, 1H), 7.34-7.26 (m, 1H), 7.22-7.17 (m, 1H).

Step 2. Synthesis of 2-(2,2-dibromovinyl)-4-fluoro-aniline (C14)

To a stirred solution of 2-(2,2-dibromovinyl)-4-fluoro-1-nitro-benzene C13 (35 g, 110 mmol) in ethanol (700 mL) was added SnCl$_2$(H$_2$O) (121.53 g, 538.60 mmol). The mixture was refluxed for 1.5 hours. The mixture was then concentrated in vacuo and partitioned between water (500 mL) and EtOAc (1 L). Solid K₂CO₃ was added to the mixture to adjust the pH to 10. The organic phase was separated and dried over sodium sulfate, filtered, and concentrated in vacuo. Silica gel chromatography (Gradient: 15-20% EtOAc in heptane) afforded the product as red oil (25 g, 79%), $^1$H NMR (400 MHz, Chloroform-d) δ 7.28 (s, 1H), 7.06 (dd, J=9.4, 2.9 Hz, 1H), 6.90-6.85 (m, 1H), 6.64 (dd, J=8.8, 4.7 Hz, 1H), 3.57 (bs, 2H). LCMS m/z 295.35 $[M+H]^+$.

Step 3. Synthesis of N-[2-(2,2-dibromovinyl)-4-fluoro-phenyl]methanesulfonamide (C15)

To a solution of 2-(2,2-dibromovinyl)-4-fluoro-aniline C14 (25 g, 85 mmol) in DCM (230 mL) was added pyridine (13.409 g, 13.711 mL, 169.52 mmol). The mixture was cooled to 0° C., and methanesulfonyl chloride (14.564 g, 9.8405 mL, 127.14 mmol) was added dropwise. The mixture was allowed to stir for 12 hours at room temperature. The mixture was then partitioned between DCM and 20% aqueous NaHSO₄ solution. The organic layer was washed once more with 20% aqueous NaHSO₄ solution and aqueous sat. sodium bicarbonate solution, dried over sodium sulfate, and concentrated in vacuo. Silica gel chromatography (Eluent: 20% EtOAc in heptane) afforded the product as a yellow solid. (25 g, 79%). $^1$H NMR (400 MHz, DMSO-d₆) δ 9.35 (s, 1H), 7.77 (s, 1H), 7.46-7.38 (m, 2H), 7.31-7.26 (m, 1H), 2.97 (s, 3H).

Step 4. Synthesis of 2-bromo-5-fluoro-1H-indole (C16)

To a solution of N-[2-(2,2-dibromovinyl)-4-fluoro-phenyl]methanesulfonamide C15 (3 g, 8 mmol) in THF (180 mL) was added TBAF (16 mL of 1 M, 16 mmol). The reaction mixture was heated to 100° C. for 12 hours. The mixture was then partitioned between ethyl acetate (200 mL) and water (20 mL). The organic layer was separated, washed with brine (30 mL), dried over sodium sulfate and concentrated in vacuo. Silica gel chromatography (Eluent: 0.3% EtOAc in hexanes) afforded the product as a yellow solid (1.4 g, 81%). $^1$H NMR (400 MHz, Chloroform-d) δ 8.09 (bs, 1H), 7.25-7.16 (m, 2H), 6.96-6.86 (m, 2H), 6.49 (d, J=2.1 Hz, 1H). LCMS m/z 212.0 $[M+H]^+$.

Step 5. Synthesis of 2-bromo-5-fluoro-1-(p-tolylsulfonyl)indole (C17)

To a solution of 2-bromo-5-fluoro-1H-indole C16 (5 g, 23 mmol) in THF (50 mL) was added sodium hydride (2.4293 g, 60% w/w, 60.738 mmol) at 0° C. The reaction mixture was stirred at 0° C. for 30 minutes. 4-toluenesulfonyl chloride (4.8991 g, 25.697 mmol) was added, and the reaction mixture was stirred at room temperature for 16 h. The mixture was then partitioned between ethyl acetate (100 mL) and water (50 mL). The organic layer was separated, washed with water (50 mL) and brine (50 mL), dried over sodium sulfate, and concentrated in vacuo. Silica gel chromatography (Eluent: 10% EtOAc in hexane) afforded the product as an off-white solid (3 g, 35%). $^1$H NMR (400 MHz, Chloroform-d) δ 8.21 (dd, J=8.9, 4.4 Hz, 1H), 7.74 (d, J=8.3 Hz, 2H), 7.22 (d, J=8.1 Hz, 2H), 7.09-6.95 (m, 2H), 6.67 (s, 1H), 2.36 (s, 3H). LCMS m/z 368.0 $[M+H]^+$.

Step 6. Synthesis of 2-(4-cyclopropylphenyl)-5-fluoro-1-(p-tolylsulfonyl)indole (C18)

To a stirred solution of 2-bromo-5-fluoro-1-(p-tolylsulfonyl)indole C17 (500 mg, 1.4 mmol) in 1,4-dioxane (10 mL) was added (4-cyclopropylphenyl)boronic acid (241.97 mg, 1.4937 mmol), followed by a solution of K₃PO₄ (720.60 mg, 3.3948 mmol) in water. The reaction mixture was degassed for 5 minutes, and Pd(PPh₃)₄ (39.2 mg, 0.0339 mmol) was added. The reaction mixture was heated to 100° C. for 16 hours. After cooling to room temperature, the mixture was filtered through a pad of Celite® and concentrated in vacuo. The residue was diluted with DCM (20 mL), washed with water, aqueous sat. sodium bicarbonate solution, and brine (20 mL). The organic layer was dried over sodium sulfate, filtered, and concentrated in vacuo. Silica gel chromatography (Eluent: 30% EtOAc in hexane) afforded the product as a light brown solid (405 mg, 74%). $^1$H NMR (400 MHz, Chloroform-d) δ 8.23 (dd, J=9.6, 4.7 Hz, 1H), 7.38-7.36 (m, 2H), 7.26-7.22 (m, 2H), 7.12-7.09 (m, 2H), 7.07-7.03 (m, 4H), 6.44 (s, 1H), 2.29 (s, 3H), 1.98-1.94 (m, 1H), 1.06-1.01 (m, 2H), 0.8-0.76 (m, 2H). LCMS m/z 406.0 $[M+H]^+$.

Step 7. Synthesis of 2-(4-cyclopropylphenyl)-5-fluoro-1H-indole (C19)

To a solution of 2-(4-cyclopropylphenyl)-5-fluoro-1-(p-tolylsulfonyl)indole C18 (400 mg, 0.99 mmol) in 1,4-dioxane (10 mL) was added NaOtBu (284.42 mg, 2.9595 mmol). The reaction mixture was heated to reflux for 16 hours. The reaction mixture was cooled to room temperature and concentrated in vacuo. To the residue was added water and EtOAc. The organic phase was separated, washed with water and brine, dried over sodium sulfate, and concentrated in vacuo. Silica gel chromatography (Eluent: 10% EtOAc in hexane) afforded the product as a yellow solid (165 mg, 64%). $^1$H NMR (400 MHz, Chloroform-d) δ 8.26 (bs, 1H), 7.57-7.49 (m, 2H), 7.32-7.20 (m, 2H), 7.14 (d, J=8.2 Hz, 2H), 6.91 (td, J=9.1, 2.5 Hz, 1H), 6.72 (d, J=2.2 Hz, 1H), 1.96-1.89 (m, 1H), 1.03-0.96 (m, 2H), 0.76-0.72 (m, 2H). LCMS m/z 250.0 $[M-H]^-$.

Step 8. Synthesis of 3-[2-(4-cyclopropylphenyl)-5-fluoro-1H-indol-3-yl]cyclobutanamine (7)

To a solution of 3-aminocyclobutanone (15 mg, 0.18 mmol) and 2-(4-cyclopropylphenyl)-5-fluoro-1H-indole C19 (30 mg, 0.1 mmol), Et₃SiH (70 mg, 0.6 mmol) in DCM (0.5 mL) was added trifluoroacetic acid (70 mg, 0.6 mmol). The mixture was allowed to stir overnight. The mixture was then concentrated in vacuo and purified by reversed phase chromatography (C18 column; Gradient: MeCN in H₂O with 0.1% trifluoroacetic acid) to afford the product (10 mg, 18%). LCMS m/z 321.17 $[M+H]^+$.

Compound 8

3-[5,7-difluoro-2-[4-(trifluoromethoxy)phenyl]-1H-indol-3-yl]cyclobutanamine (8)

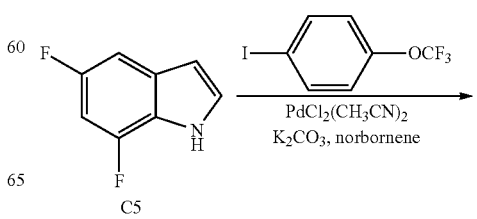

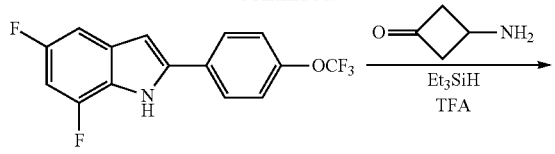

Compound 9

3-[5,7-difluoro-2-[4-(trifluoromethoxy)phenyl]-1H-indol-3-yl]cyclobutanamine (9)

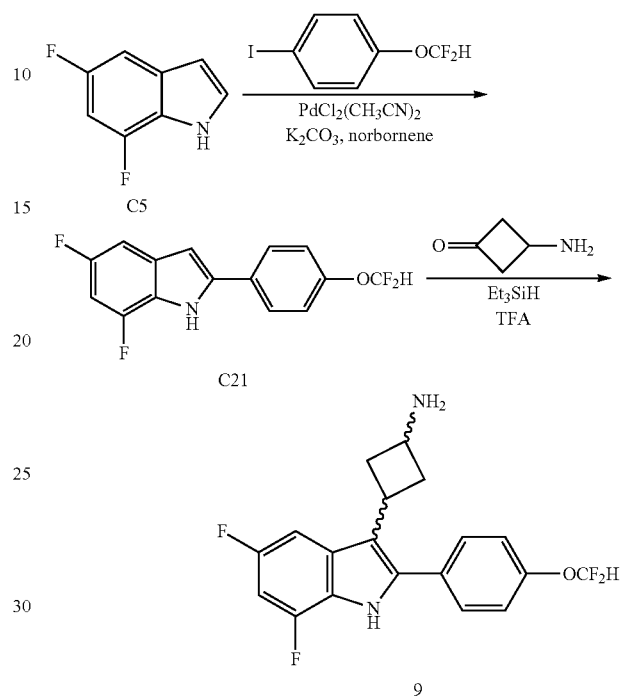

Step 1. Synthesis of 5,7-difluoro-2-[4-(trifluoromethoxy)phenyl]-1H-indole (C20)

A 30 mL vial was charged with a magnetic sir bar, 5,7-difluoro-1H-indole C5 (250 mg, 1.6 mmol), 1-iodo-4-(trifluoromethoxy)benzene (495 mg, 1.72 mmol), DMA (1.5 mL), water (250 μL), $K_2CO_3$ (566 mg, 4.10 mmol), norbornene (310 mg, 3.3 mmol), and bis(acetonitrile)palladium dichloride (42 mg, 0.16 mmol). The mixture was heated to 90° C. for 4 hours. After cooling to room temperature, the mixture was diluted with water and extracted with EtOAc. The organic extract was dried with $MgSO_4$, filtered, and concentrated in vacuo. Silica gel chromatography (Eluent: 10% EtOAc in heptane) afforded the product (250 mg, 43%) LCMS m/z 314.01 $[M+H]^+$.

Step 2. Synthesis of 3-[5,7-difluoro-2-[4-(trifluoromethoxy)phenyl]-1H-indol-3-yl]cyclobutan-amine (8)

A 30 mL vial was charged with a magnetic stir bar, 5,7-difluoro-2-[4-(trifluoromethoxy)phenyl]-1H-indole C20 (80 mg, 0.24 mmol), 3-aminocyclobutanone (33 mg, 0.39 mmol), DCM (800 μL), and $Et_3SiH$ (168 mg, 1.445 mmol). To the stirring mixture was added trifluoroacetic acid (165 mg, 1.45 mmol), and the mixture was allowed to stir overnight. The mixture was then concentrated in vacuo and purified by reversed phase chromatography (C18 column; Gradient: MeCN in $H_2O$ with 0.1% trifluoroacetic acid) to afford the product (25 mg, 21%). $^1$H NMR (300 MHz, DMSO-$d_6$) δ 11.82 (s, 1H), 7.98 (s, 2H), 7.82-7.60 (m, 2H), 7.53 (d, J=8.2 Hz, 1H), 7.04 (t, J=10.5 Hz, 1H), 3.53 (d, J=10.1 Hz, 2H), 2.58 (d, J=7.8 Hz, 2H), 2.40 (d, J=10.2 Hz, 2H). LCMS m/z 383.1 $[M+H]^+$.

Step 1. Synthesis of 2-[4-(difluoromethoxy)phenyl]-5,7-difluoro-1H-indole (C21)

A 30 mL vial was charged with a magnetic sir bar, 5,7-difluoro-1H-indole C5 (500 mg, 3.3 mmol), 1-(difluoromethoxy)-4-iodo-benzene (1.15 g, 4.26 mmol), DMA (2.2 mL), water (300 μL), $K_2CO_3$ (1.2 g, 8.7 mmol), norbornene (615 mg, 6.53 mmol), and bis(acetonitrile)palladium dichloride (85 mg, 0.33 mmol). The mixture was heated to 90° C. for 4 hours. After cooling to room temperature, the mixture was diluted with water and extracted with EtOAc. The organic extract was dried with $MgSO_4$, filtered, and concentrated in vacuo. Silica gel chromatography (Eluent: 10% EtOAc in heptane) afforded the product (509 mg, 53%). $^1$H NMR (300 MHz, Chloroform-d) δ 8.38 (s, 1H), 7.82-7.56 (m, 2H), 7.35-7.19 (m, 2H), 7.10 (dd, J=9.0, 2.2 Hz, 1H), 6.89-6.74 (m, 2H), 6.74-6.28 (m, 1H). LCMS m/z 295.93 $[M+H]^+$.

Step 2. Synthesis of 3-[5,7-difluoro-2-[4-(trifluoromethoxy)phenyl]-1H-indol-3-yl]cyclobutan-amine (9)

A 30 mL vial was charged with a magnetic stir bar, 2-[4-(difluoromethoxy)phenyl]-5,7-difluoro-1H-indole C21 (50 mg, 0.16 mmol), 3-aminocyclobutanone (21 mg, 0.25 mmol), dichloroethane (700 μL) and $Et_3SiH$ (111 mg, 0.955 mmol). To the stirring mixture was added trifluoroacetic acid (110 mg, 0.97 mmol), and the mixture was allowed to stir overnight. The mixture was then concentrated in vacuo and purified by reversed phase chromatography (C18 column;

Gradient: MeCN in H₂O with 0.1% trifluoroacetic acid) to afford the product (10.1 mg, 13%). LCMS m/z 365.11 [M+H]⁺.

Compound 10

3-[2-(4-chlorophenyl)-5,7-difluoro-1H-indol-3-yl]cyclobutanamine (10)

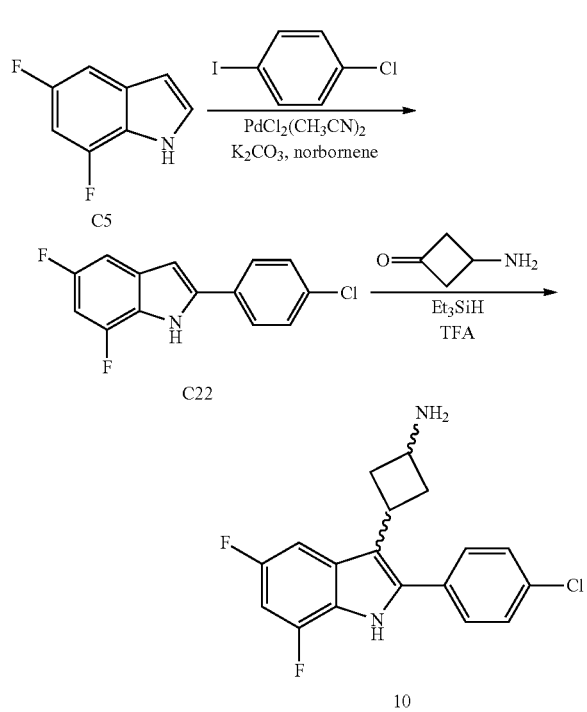

Step 1. Synthesis of 5,7-difluoro-2-(4-chlorophenyl)-1H-indole (C22)

A mixture of 5,7-difluoro-1H-indole C5 (250 mg, 1.6 mmol), 1-iodo-4-methoxy-benzene (410 mg, 1.7 mmol), PdCl₂(MeCN)₂ (43 mg, 0.17 mmol), norbornene (310 mg, 3.3 mmol), K₂CO₃ (565 mg, 4.09 mmol), water (0.25 mL), and DMA (1.5 mL) was stirred at 90° C. for 4 hours. After cooling to room temperature, the mixture was diluted with water and extracted with EtOAc. The organic layer was dried over anhydrous magnesium sulfate, filtered, and concentrated in vacuo. Purification by silica gel chromatography (10% EtOAc in heptane) yielded the product (181 mg, 40% yield). LCMS m/z 264.05 [M+H]⁺.

Step 2. Synthesis of 3-[2-(4-chlorophenyl)-5,7-difluoro-1H-indol-3-yl]cyclobutanamine (10)

To a mixture of 5,7-difluoro-2-(4-chlorophenyl)-1H-indole C22 (80 mg, 0.3 mmol), 3-aminocyclobutanone (40 mg, 0.5 mmol), Et₃SiH (200 mg, 1.7 mmol), and DCM (0.8 mL) was added trifluoroacetic acid (200 mg, 1.8 mmol). After stirring overnight at room temperature, the mixture was concentrated in vacuo. Purification by reversed phase chromatography (C18 column; Gradient: MeCN in H₂O with 0.1% trifluoroacetic acid) yielded the product (35 mg, 27% yield) as a mixture of cis and trans isomers. ¹H NMR (300 MHz, DMSO-d₆) δ 11.82 (s, 1H), 8.03 (d, J=30.2 Hz, 2H), 7.82-7.42 (m, 4H), 7.04 (t, J=10.8 Hz, 1H), 3.64 (s, 2H), 2.60 (s, 1H), 2.38 (s, 3H). LCMS m/z 333.1 [M+H]⁺.

Compound 11

3-[5,7-difluoro-2-(4-fluoro-3-methyl-phenyl)-1H-indol-3-yl]cyclobutanamine (11)

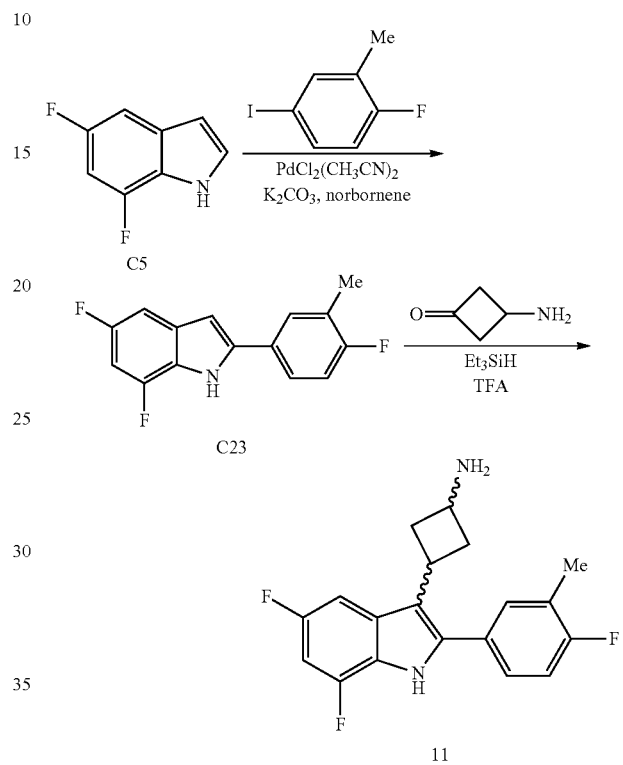

Step 1. Synthesis of 5,7-difluoro-2-(4-fluoro-3-methyl-phenyl)-1H-indole (C23)

A mixture of 5,7-difluoro-1H-indole C5 (225 mg, 1.47 mmol), 1-fluoro-4-iodo-2-methyl-benzene (350 mg, 1.5 mmol), PdCl₂(MeCN)₂ (40 mg, 0.15 mmol), norbornene (277 mg, 2.94 mmol), K₂CO₃ (508 mg, 3.68 mmol), water (0.3 mL), and DMA (3.4 mL) was stirred at 90° C. overnight. After cooling to room temperature, the reaction was diluted with water (75 mL) and extracted with EtOAc (2×50 mL). The organic layer was washed with brine, dried over anhydrous magnesium sulfate, filtered, and concentrated in vacuo. Purification by silica gel chromatography (10% EtOAc in heptane) yielded the product as an off-white solid (180 mg, 44% yield). ¹H NMR (300 MHz, DMSO-d₆) δ 11.92 (s, 1H), 7.85 (d, J=33.9 Hz, 2H), 7.45-7.09 (m, 2H), 6.97 (d, J=14.8 Hz, 2H), 2.31 (s, 3H). LCMS m/z 262.16 [M+H]⁺.

Step 2. Synthesis of 3-[5,7-difluoro-2-(4-fluoro-3-methyl-phenyl)-1H-indol-3-yl]cyclobutanamine (11)

To a mixture of 5,7-difluoro-2-(4-fluoro-3-methyl-phenyl)-1H-indole C23 (75 mg, 0.27 mmol), 3-aminocyclobutanone (30 mg, 0.35 mmol), Et₃SiH (200 mg, 1.7 mmol), and DCM (1.1 mL) was added trifluoroacetic acid (200 mg, 1.8 mmol). After stirring overnight at room temperature, the reaction was concentrated in vacuo. Purification by reversed phase chromatography (C18 column; Gradient: MeCN in H₂O with 0.1% trifluoroacetic acid) yielded the product (54 mg, 45% yield) as a mixture of cis and trans isomers. LCMS m/z 331.08 [M+H]⁺.

Compound 12

3-[5,7-difluoro-2-(4-methoxyphenyl)-1H-indol-3-yl]cyclobutanamine (12)

50% yield) as a mixture of cis and trans isomers. $^1$H NMR (300 MHz, DMSO-$d_6$) δ 11.66 (s, 1H), 8.05 (d, J=28.2 Hz, 2H), 7.66 (d, J=9.8 Hz, 1H), 7.45 (d, J=6.6 Hz, 2H), 7.04 (d, J=32.9 Hz, 2H), 3.93-3.73 (m, 3H), 3.63 (s, 2H), 2.41 (s, 2H). LCMS m/z 329.09 [M+H]⁺.

Compound 13 benzyl N-[3-[5,7-difluoro-2-(4-fluorophenyl)-1H-indol-3-yl]cyclobutyl]carbamate (13)

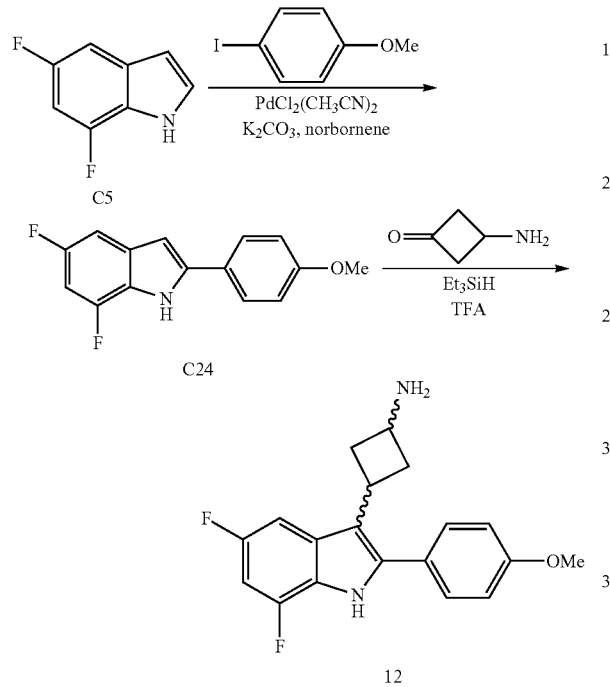

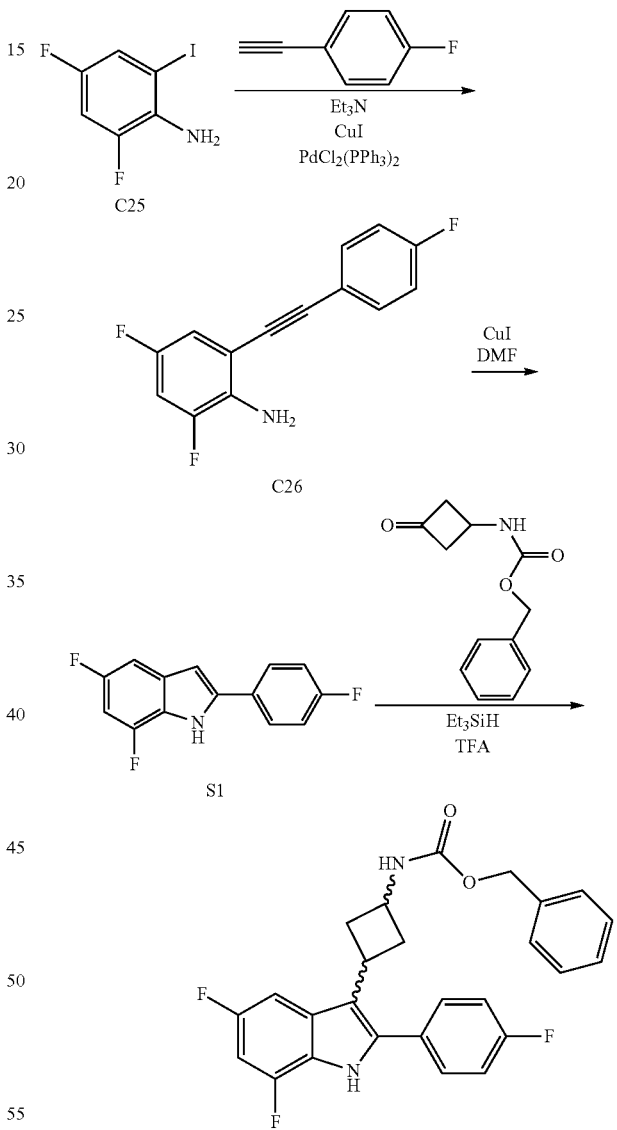

Step 1. Synthesis of 5,7-difluoro-2-(4-methoxyphenyl)-1H-indole (C24)

A mixture of 5,7-difluoro-1H-indole C5 (250 mg, 1.6 mmol), 1-iodo-4-methoxy-benzene (402 mg, 1.72 mmol), PdCl₂(MeCN)₂ (43 mg, 0.17 mmol), norbornene (310 mg, 3.3 mmol), K₂CO₃ (565 mg, 4.09 mmol), water (0.25 mL), and DMA (1.5 mL) was stirred at 90° C. for 4 hours. After cooling to room temperature, the reaction was diluted with water and extracted with EtOAc. The organic layer was dried over anhydrous magnesium sulfate, filtered, and concentrated in vacuo. Purification by silica gel chromatography (10% EtOAc in heptane) yielded the product (220 mg, 46% yield). LCMS m/z 260.14 [M+H]⁺.

Step 2. Synthesis of 3-[5,7-difluoro-2-(4-methoxyphenyl)-1H-indol-3-yl]cyclobutanamine (12)

To a mixture of 5,7-difluoro-2-(4-methoxyphenyl)-1H-indole C24 (80 mg, 0.3 mmol), 3-aminocyclobutanone (40 mg, 0.47 mmol), Et₃SiH (200 mg, 1.7 mmol), and DCM (0.8 mL) was added trifluoroacetic acid (200 mg, 1.8 mmol). After stirring overnight at room temperature, the reaction was concentrated in vacuo. Purification by reversed phase chromatography (C18 column; Gradient: MeCN in H₂O with 0.1% trifluoroacetic acid) yielded the product (65 mg, Step 1. Synthesis of 2,4-difluoro-6-[2-(4-fluorophenyl)ethynyl]aniline (C26)

To a flask containing 2,4-difluoro-6-iodo-aniline C25 (134 g, 526 mmol) was added NEt₃ (1.3 L), followed by DMF (250 mL), 1-ethynyl-4-fluoro-benzene (83.5 g, 695 mmol), CuI (20.5 g, 108 mmol), and PdCl₂(PPh₃)₂ (25 g, 36 mmol). The mixture was allowed to stir at room temperature for 2 hours. Solvent was removed under reduced pressure and water (500 mL) was added. The mixture was extracted with EtOAc, filtered, and concentrated in vacuo. The product mixture was filtered through a silica gel plug (Eluent: DCM), followed by a second silica plug filtration (Eluent: 30-40% EtOAc in heptane). Silica gel chromatography (Gradient: 0-20% EtOAc in heptane) afforded the product as a pale yellow solid. (87 g, 60%). $^1$H NMR (300 MHz, Chloroform-d) δ 7.58-7.45 (m, 2H), 7.14-7.02 (m, 2H), 6.92 (ddd, J=8.8, 2.8, 1.7 Hz, 1H), 6.87-6.71 (m, 1H), 4.15 (s, 2H). LCMS m/z 248.0 [M+H]$^+$.

Step 2. Synthesis of 5,7-difluoro-2-(4-fluorophenyl)-1H-indole (S1)

To a solution of 2,4-difluoro-6-[2-(4-fluorophenyl)ethynyl]aniline C26 (46 g, 170 mmol) in DMF (600 mL) was added CuI (1.9 g, 10 mmol), and the reaction was heated at reflux. Water (800 mL) was added, and the mixture was extracted with MTBE. The mixture was then washed with sat. NaCl solution, dried over Na$_2$SO$_4$, and then concentrated in vacuo to afford the product, which was used in subsequent steps without further purification (41 g, 87%). $^1$H NMR (300 MHz, Chloroform-d) δ 8.43 (s, 1H), 7.72-7.58 (m, 2H), 7.27-7.15 (m, 2H), 7.09 (dd, J=9.0, 2.1 Hz, 1H), 6.85-6.63 (m, 2H). LCMS m/z 248.0 [M+H]$^+$.

Step 3. Synthesis of benzyl N-[3-[5,7-difluoro-2-(4-fluorophenyl)-1H-indol-3-yl]cyclobutyl]carbamate (13)

To a solution of 5,7-difluoro-2-(4-fluorophenyl)-1H-indole S1 (1000 mg, 4.05 mmol) in dichloromethane (20 mL) was added benzyl N-(3-oxocyclobutyl)carbamate (450 mg, 2.1 mmol) followed by Et$_3$SiH (4.0 g, 34 mmol) and trifluoroacetic acid (1.5 g, 13 mmol). The mixture was stirred at room temperature overnight. The mixture was then concentrated in vacuo and partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-100% EtOAc in heptane) to afford the product (1.9 g, 79%). $^1$H NMR (300 MHz, Methanol-d$_4$) δ 7.73-7.09 (m, 9H), 6.72 (ddd, J=11.3, 9.6, 2.2 Hz, 1H), 5.06 (s, 2H), 4.16-3.90 (m, 1H), 3.63-3.37 (m, 1H), 2.79-2.52 (m, 2H), 2.30 (q, J=10.4 Hz, 2H). LCMS m/z 451.1 [M+H]$^+$.

Compound 14

3-[5,7-difluoro-2-(4-fluorophenyl)-1H-indol-3-yl]cyclobutanamine (14)

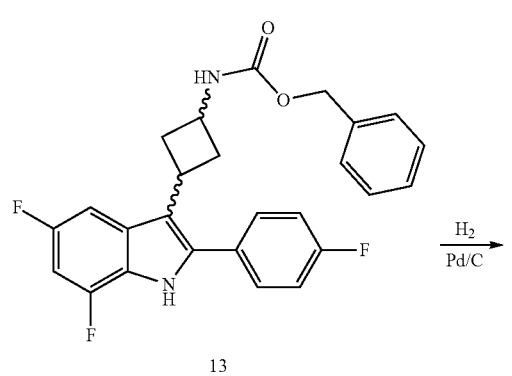

13

To a suspension of benzyl N-[3-[5,7-difluoro-2-(4-fluorophenyl)-1H-indol-3-yl]cyclobutyl]carbamate 13 (2 g, 3 mmol) in MeOH (20 mL) was added 10% palladium on carbon catalyst (300 mg). The mixture was subjected to hydrogenation conditions of 1 atm H$_2$ for 3 hours. Filtration through a pad of Celite®, then concentration of the filtrate in vacuo afforded the product (845 mg, 73%) which was used in subsequent steps without further purification. $^1$H NMR (300 MHz, Methanol-d$_4$) δ 7.64-7.48 (m, 2H), 7.43-7.18 (m, 3H), 6.77 (ddt, J=11.1, 9.6, 3.4 Hz, 1H), 3.81-3.56 (m, 2H), 3.07-2.25 (m, 5H). LCMS m/z 316.7 [M+H]$^+$.

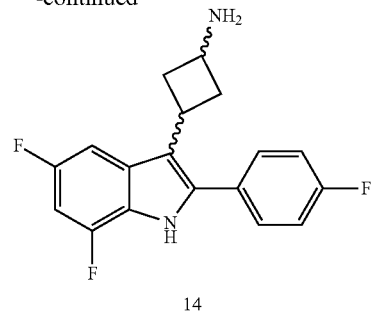

14

Compound 15

N-[3-[5,7-difluoro-2-(4-fluorophenyl)-1H-indol-3-yl]cyclobutyl]-2-hydroxy-acetamide (15)

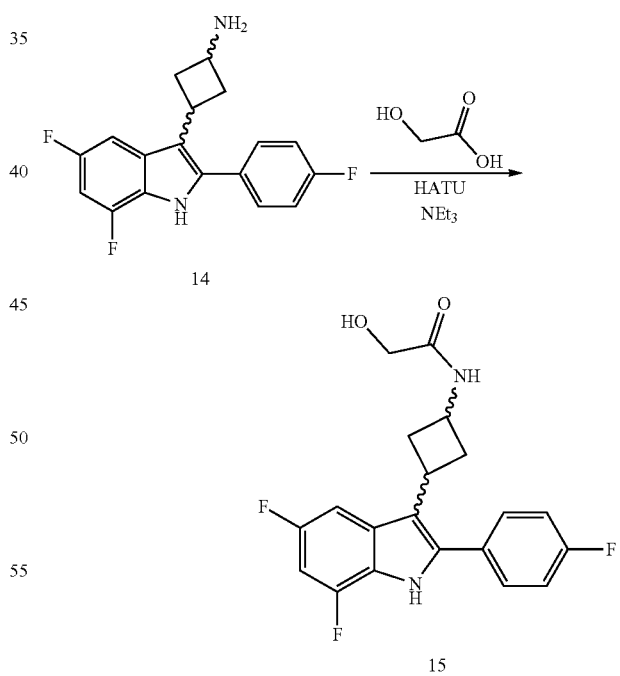

Synthesis of N-[3-[5,7-difluoro-2-(4-fluorophenyl)-1H-indol-3-yl]cyclobutyl]-2-hydroxy-acetamide (15)

To a solution of 3-[5,7-difluoro-2-(4-fluorophenyl)-1H-indol-3-yl]cyclobutanamine 14 (100 mg, 0.316 mmol) and 2-hydroxyacetic acid (25 mg, 0.329 mmol) in DMF (3 mL)

was added HATU (145 mg, 0.3813 mmol), and NEt₃ (90 µL, 0.642 mmol). The mixture was allowed to stir at room temperature overnight. The mixture was then Concentrated and purified by normal phase ISCO 12 g column, Hexane/Ethyl acetate (0-100%) to afford the product (14 mg, 11%). ¹H NMR (300 MHz, Methanol-d₄) δ 7.53 (ddd, J=9.3, 5.2, 2.5 Hz, 2H), 7.40 (dd, J=9.9, 2.2 Hz, 1H), 7.26-7.09 (m, 2H), 6.97-6.53 (m, 1H), 4.28 (tt, J=9.4, 7.4 Hz, 1H), 3.97 (d, J=13.4 Hz, 2H), 3.52 (tt, J=10.5, 7.7 Hz, 1H), 2.91-2.55 (m, 2H), 2.53-2.23 (m, 2H). LCMS m/z 375.2 [M+H]⁺.

Compound 16

N-[3-[5,7-difluoro-2-(4-fluorophenyl)-1H-indol-3-yl]cyclobutyl]-3-hydroxy-3-methyl-butanamide (16)

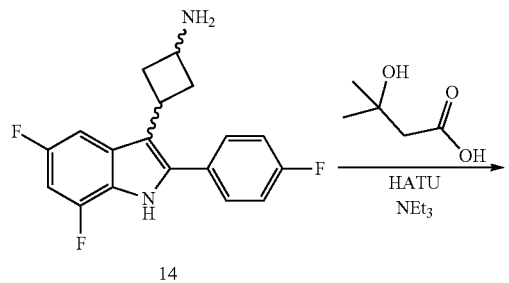

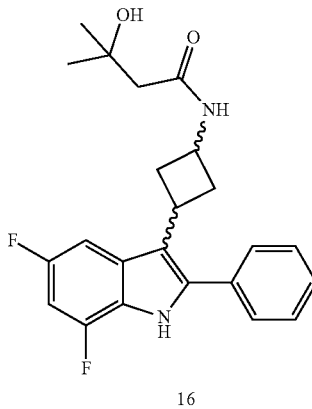

Synthesis of N-[3-[5,7-difluoro-2-(4-fluorophenyl)-1H-indol-3-yl]cyclobutyl]-3-hydroxy-3-methyl-butanamide (16)

Compound 16 was synthesized from compound 14 and 3-hydroxy-3-methylbutanoic acid using the method used to prepare compound 15. The crude mixture was then purified by reversed phase chromatography (C18 column; Gradient: MeCN in H₂O with 0.1% trifluoroacetic acid) to afford the product. ¹H NMR (300 MHz, Methanol-d₄) δ 7.62-7.42 (m, 2H), 7.38 (dd, J=9.8, 2.2 Hz, 1H), 7.29-7.08 (m, 2H), 6.74 (ddd, J=11.1, 9.6, 2.1 Hz, 1H), 4.39-4.13 (m, 1H), 3.69-3.39 (m, 1H), 2.70 (qd, J=7.7, 2.8 Hz, 2H), 2.32 (s, 3H), 2.03 (s, 1H), 1.25 (s, 6H). LCMS m/z 417.0 [M+H]⁺.

Compound 17

N-[3-[5,7-difluoro-2-(4-fluorophenyl)-1H-indol-3-yl]cyclobutyl]acetamide (17)

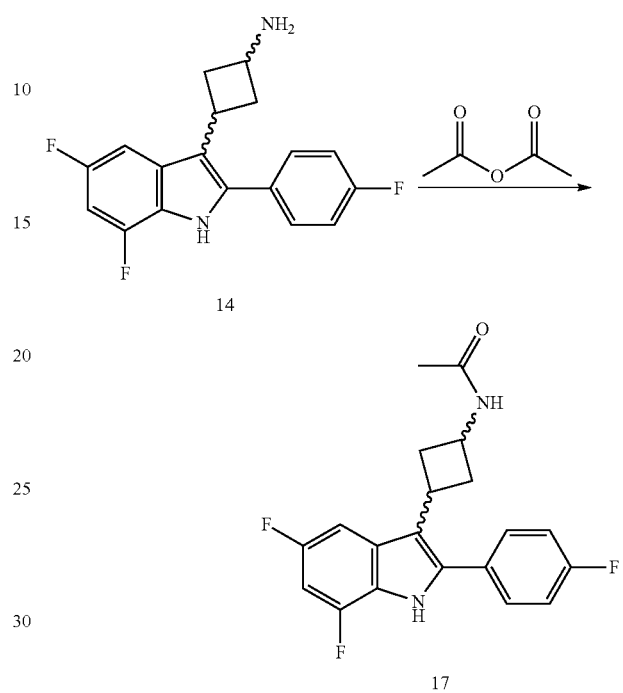

To a solution of 3-[5,7-difluoro-2-(4-fluorophenyl)-1H-indol-3-yl]cyclobutanamine 14 (20 mg, 0.063 mmol) in dichloromethane (3 mL) was added acetyl acetate (10 mg, 0.098 mmol) followed by pyridine (10 mg, 0.13 mmol). The mixture was allowed to stir at room temperature for 2 hours. The reaction mixture was concentrated under reduced pressure and purified by reversed phase chromatography (C18 column; Gradient: MeCN in H₂O with 0.1% trifluoroacetic acid) to afford the product (10 mg, 33%). ¹H NMR (300 MHz, Methanol-d₄) δ 7.62-7.43 (m, 2H), 7.45-7.29 (m, 1H), 7.27-7.00 (m, 2H), 6.73 (ddd, J=11.0, 9.6, 2.2 Hz, 1H), 4.38-4.07 (m, 1H), 3.49 (tt, J=10.5, 7.7 Hz, 1H), 2.66 (dtd, J=8.5, 7.6, 2.8 Hz, 2H), 2.40-2.13 (m, 2H), 1.92 (s, 3H). LCMS m/z 359.3 [M+H]⁺.

Compound 18

N-[3-[5,7-difluoro-2-(4-fluorophenyl)-1H-indol-3-yl]cyclobutyl]-2-methoxy-acetamide (18)

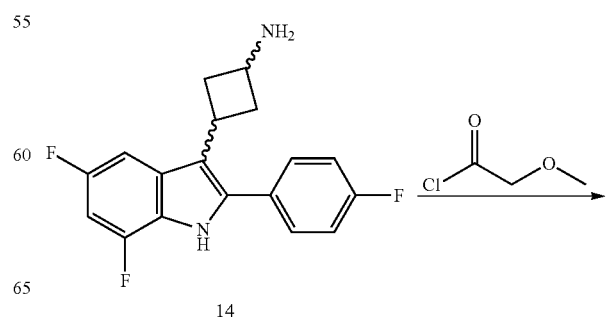

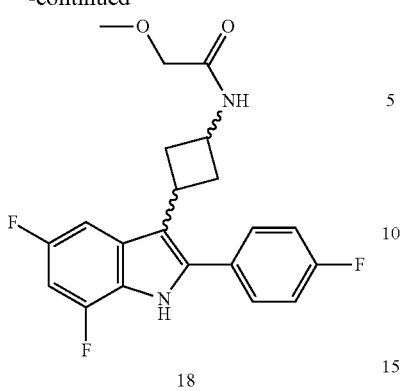

18

To a solution of 3-[5,7-difluoro-2-(4-fluorophenyl)-1H-indol-3-yl]cyclobutanamine 14 (20 mg, 0.063 mmol) in dichloromethane (3 mL) was added 2-methoxyacetyl chloride (10 mg, 0.09 mmol) followed by triethylamine (15 mg, 0.15 mmol). The mixture was allowed to stir at room temperature for 1 hour. The reaction mixture was concentrated under reduced pressure and purified by reversed phase chromatography (C18 column; Gradient: MeCN in H$_2$O with 0.1% trifluoroacetic acid) to afford the product (15 mg, 46%). $^1$H NMR (300 MHz, Methanol-d$_4$) δ 7.59-7.47 (m, 2H), 7.46-7.38 (m, 1H), 7.28-7.16 (m, 2H), 6.79-6.66 (m, 1H), 4.28 (ddd, J=16.9, 9.5, 7.4 Hz, 1H), 3.51 (ddd, J=10.5, 7.6, 2.9 Hz, 1H), 3.44-3.37 (m, 3H), 2.67 (dtd, J=8.6, 7.6, 2.8 Hz, 2H), 2.43-2.30 (m, 2H). LCMS m/z 389.2 [M+H]$^+$.

Compound 19

N-[1-[3-[5,7-difluoro-2-(4-fluorophenyl)-1H-indol-3-yl]cyclobutyl]pyrazol-3-yl]acetamide (19)

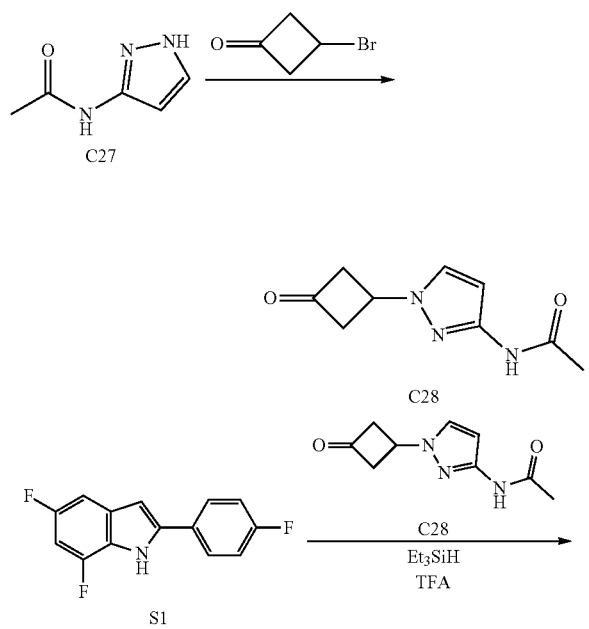

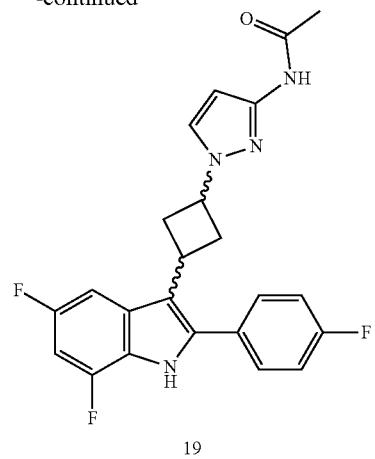

19

Step 1. Synthesis of N-[1-(3-oxocyclobutyl)pyrazol-3-yl]acetamide (C28)

To a solution of 3-bromocyclobutanone (500 mg, 3.4 mmol) in CDCl$_3$ (10 mL) was added Et$_3$N (375 mg, 3.71 mmol). The mixture was allowed to stir at room temperature for 10 minutes. To the reaction mixture was then added N-(1H-pyrazol-3-yl)acetamide C27 (420 mg, 3.36 mmol). The mixture was allowed to stir for another 1 hour. The mixture was concentrated in vacuo, and the residue was purified by silica gel chromatography (EtOAc in heptane gradient) to afford the product (600 mg, 55%). $^1$H NMR (300 MHz, DMSO-d$_6$) δ 10.50 (s, 1H), 7.79 (d, J=2.3 Hz, 1H), 6.49 (d, J=2.4 Hz, 1H), 5.09 (tt, J=8.0, 5.4 Hz, 1H), 3.67-3.28 (m, 5H), 1.98 (s, 3H). LCMS m/z 137.42 [M+H]$^+$.

Step 2. Synthesis of N-[1-[3-[5,7-difluoro-2-(4-fluorophenyl)-1H-indol-3-yl]cyclobutyl]pyrazol-3-yl]acetamide (19)

To a solution of N-[1-(3-oxocyclobutyl)pyrazol-3-yl]acetamide C28 (300 mg, 1.6 mmol) in dichloromethane (10 mL) was added 5,7-difluoro-2-(4-fluorophenyl)-1H-indole S1 (255 mg, 1.03 mmol) followed by triethylsilane (600 mg, 5.2 mmol) and trifluoroacetic acid (600 mg, 5.3 mmol). The mixture was allowed to stir at room temperature overnight. The mixture was then concentrated in vacuo and partitioned between ethyl acetate and aqueous sat. sodium bicarbonate solution. The organic phase was separated, concentrated in vacuo, and purified by reversed phase chromatography (C18 column; Gradient: MeCN in H$_2$O with 0.1% trifluoroacetic acid) to afford the product (100 mg, 17%). $^1$H NMR (300 MHz, DMSO-d$_6$) δ 11.74 (s, 1H), 10.34 (s, 1H), 7.70-7.53 (m, 3H), 7.50-7.23 (m, 3H), 7.01 (ddd, J=11.7, 9.8, 2.1 Hz, 1H), 6.40 (d, J=2.3 Hz, 1H), 4.72 (p, J=8.5 Hz, 1H), 3.74-3.46 (m, 1H), 2.91-2.53 (m, 5H), 2.08 (s, 1H), 1.97 (s, 3H). LCMS m/z 425.2 [M+H]$^+$.

Compound 20

(3S)-3-[[3-[5,7-difluoro-2-(4-fluorophenyl)-1H-indol-3-yl]cyclobutyl]amino]pyrrolidin-2-one (20)

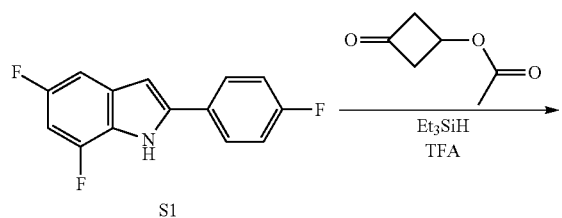

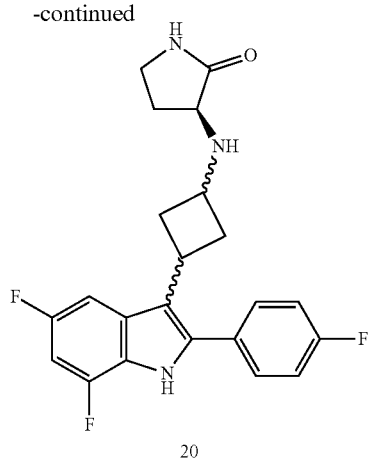

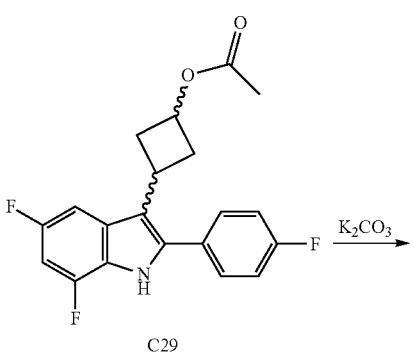

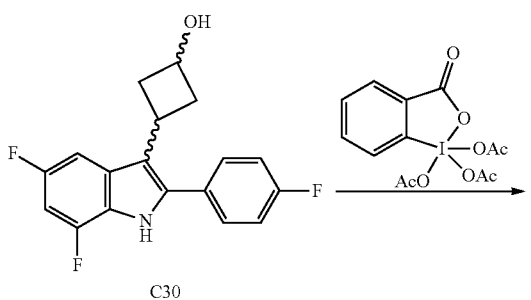

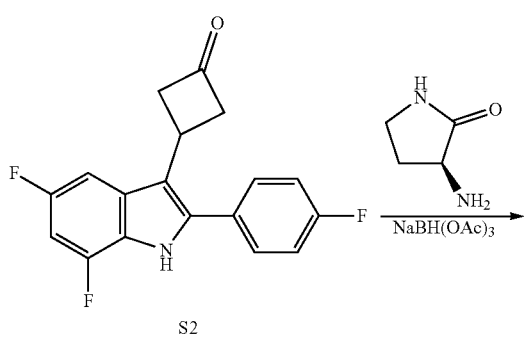

Step 1. Synthesis of [3-[5,7-difluoro-2-(4-fluorophenyl)-1H-indol-3-yl]cyclobutyl]acetate (C29)

To a solution of 5,7-difluoro-2-(4-fluorophenyl)-1H-indole S1 (5 g, 20 mmol) in dichloromethane (25 mL) was added (3-oxocyclobutyl) acetate (3.8 g, 0.030 mol) followed by Et₃SiH (12 g, 100 mmol) and trifluoroacetic acid (12 g, 110 mmol). The mixture was stirred at room temperature overnight. The mixture was then partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-40% EtOAc in heptane) to afford the product (7 g, 67%). LCMS m/z 360.2 [M+H]⁺.

Step 2. Synthesis of 3-[5,7-difluoro-2-(4-fluorophenyl)-1H-indol-3-yl]cyclobutanol (C30)

To a solution of [3-[5,7-difluoro-2-(4-fluorophenyl)-1H-indol-3-yl]cyclobutyl]acetate C29 (7 g, 12 mmol) in methanol (60 mL) was added potassium carbonate (2.2 g, 16 mmol). The mixture was stirred at room temperature for 4 hours. The mixture was then partitioned between ethyl acetate and brine. The organic phase was separated and dried over sodium sulfate, filtered, and concentrated in vacuo. The residue was purified by silica gel chromatography (EtOAc in heptane) to afford the product (4 g, 95%). ¹H NMR (300 MHz, DMSO-d₆) δ 11.67 (d, J=7.4 Hz, 1H), 7.75-7.15 (m, 5H), 6.99 (t, J=10.5 Hz, 1H), 4.43 (d, J=7.0 Hz, 1H), 3.99 (dd, J=13.0, 7.0 Hz, 1H), 2.57 (d, J=8.5 Hz, 2H), 2.21 (p, J=10.8, 10.2 Hz, 2H). LCMS m/z 318.2 [M+H]⁺.

Step 3. Synthesis of 3-[5,7-difluoro-2-(4-fluorophenyl)-1H-indol-3-yl]cyclobutanone (S2)

To a solution of 3-[5,7-difluoro-2-(4-fluorophenyl)-1H-indol-3-yl]cyclobutanol C30 (500 mg, 1.1 mmol) in dichloromethane (25 mL) was added 3-oxo-1,3-dihydro-1λ5,2-benziodoxole-1,1,1-triyltriacetate (580 mg, 1.4 mmol). The mixture was stirred at room temperature for 3 hours. The precipitate was removed by filtration, and the filtrate was concentrated in vacuo. The residue was purified by silica gel chromatography (Gradient: 0-50% EtOAc in heptane) to afford the product (200 mg, 37%). ¹H NMR (400 MHz, DMSO-d₆) δ 11.83 (s, 1H), 7.67-7.59 (m, 2H), 7.37 (t, J=8.8 Hz, 2H), 7.16 (dd, J=9.8, 2.2 Hz, 1H), 7.07-6.97 (m, 1H), 3.92 (p, J=8.2 Hz, 1H), 3.53-3.41 (m, 2H), 3.31-3.25 (m, 1H). LCMS m/z 316.3 [M+H]⁺.

Step 4. Synthesis of (3S)-3-[[3-[5,7-difluoro-2-(4-fluorophenyl)-1H-indol-3-yl]cyclobutyl]-amino]pyrrolidin-2-one (20)

Standard Method A: Reductive Amination Method

To a solution of (3S)-3-aminopyrrolidin-2-one (12 mg, 0.12 mmol) and 3-[5,7-difluoro-2-(4-fluorophenyl)-1H-indol-3-yl]cyclobutanone S2 (50 mg, 0.1 mmol) in DMF (2 mL) was added triacetoxy(sodio)boron (65 mg, 0.31 mmol) followed by acetic acid (5 mg, 0.01 mmol) The mixture was allowed to stir at room temperature overnight. The reaction mixture was then filtered, and the filtrate was purified by reversed phase chromatography (C18 column; Gradient: MeCN in H$_2$O with 0.1% trifluoroacetic acid) to afford the product (20 mg, 36%). $^1$H NMR (400 MHz, DMSO-d$_6$) δ 11.80 (d, J=3.3 Hz, 1H), 9.47 (d, J=117.9 Hz, 2H), 8.46 (s, 1H), 7.79 (dd, J=10.2, 2.2 Hz, 1H), 7.65-7.25 (m, 4H), 7.03 (ddt, J=11.8, 9.9, 2.3 Hz, 1H), 4.17 (dd, J=19.0, 9.8 Hz, 1H), 3.79 (s, 1H), 3.48 (ddd, J=18.2, 10.5, 7.7 Hz, 1H), 3.39-3.14 (m, 2H), 2.86-2.67 (m, 1H), 2.44-2.25 (m, 1H), 2.11-1.92 (m, 1H). LCMS m/z 400.2 [M+H]⁺.

Compounds 21-26

Compounds 21-26 (see Table 2) were prepared from intermediate S2 using the appropriate amine and using the reductive amination method as described for compound 20. Amines were obtained from commercial sources. Any modifications to methods are noted in Table 2 and accompanying footnotes.

TABLE 2

Structure and physicochemical data for compounds 21-26

| Cmpd | Product | Amine reagent | $^1$H NMR; LCMS m/z [M + H]⁺ |
|---|---|---|---|
| 21 | [structure] | [structure] | $^1$H NMR (300 MHz, Methanol-d$_4$) δ 7.53 (ddd, J = 10.3, 7.6, 5.3 Hz, 2H), 7.47-7.16 (m, 3H), 6.77 (dddd, J = 11.0, 9.6, 6.4, 2.1 Hz, 1H), 4.35-4.07 (m, 1H), 3.97 (tt, J = 9.3, 7.2 Hz, 1H), 3.72 (ddd, J = 10.6, 7.5, 3.1 Hz, 1H), 3.60 (d, J = 8.3 Hz, 2H), 3.03-2.63 (m, 3H), 2.49 (qd, J = 9.3, 2.8 Hz, 1H), 1.25-0.76 (m, 4H). LCMS m/z 387.18 [M + H]⁺. |
| 22 | [structure] | [structure] | LCMS m/z 373.07 [M + H]⁺. |
| 23 | [structure] | [structure] | LCMS m/z 402.02 [M + H]⁺. |

TABLE 2-continued
Structure and physicochemical data for compounds 21-26
| Cmpd | Product | Amine reagent | $^1$H NMR; LCMS m/z [M + H]$^+$ |
|---|---|---|---|
| 24 | 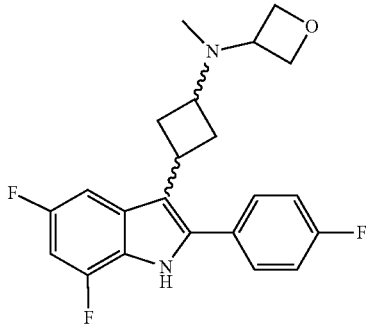 [SMILES: CN(C1COC1)C1CC(c2c(-c3ccc(F)cc3)[nH]c3c(F)cc(F)cc23)C1] | 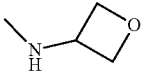 | LCMS m/z 387.18 [M + H]$^+$. |
| 25 | 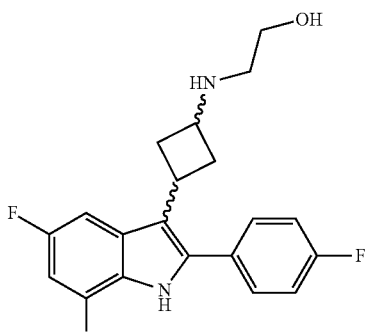 |  | LCMS m/z 361.3 [M + H]$^+$. |
| 26 | 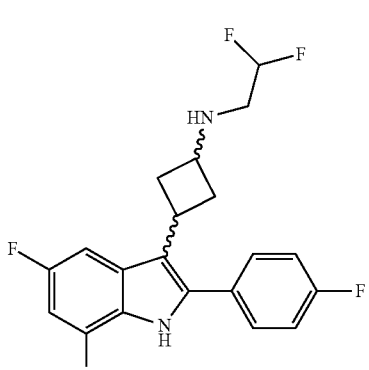 | 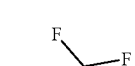 | LCMS m/z 381.15 [M + H]$^+$. |

Compound 27 benzyl((1s,3s)-3-(5,7-difluoro-2-(4-fluorophenyl)-1H-indol-3-yl)cyclobutyl)carbamate (27)

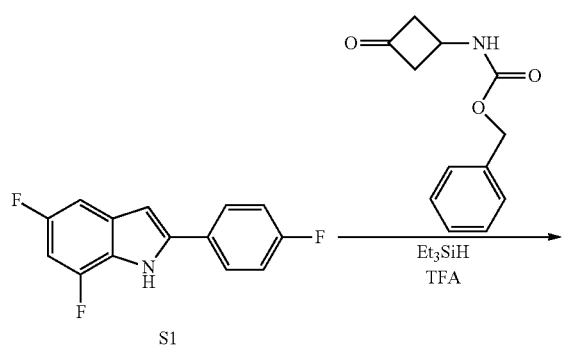

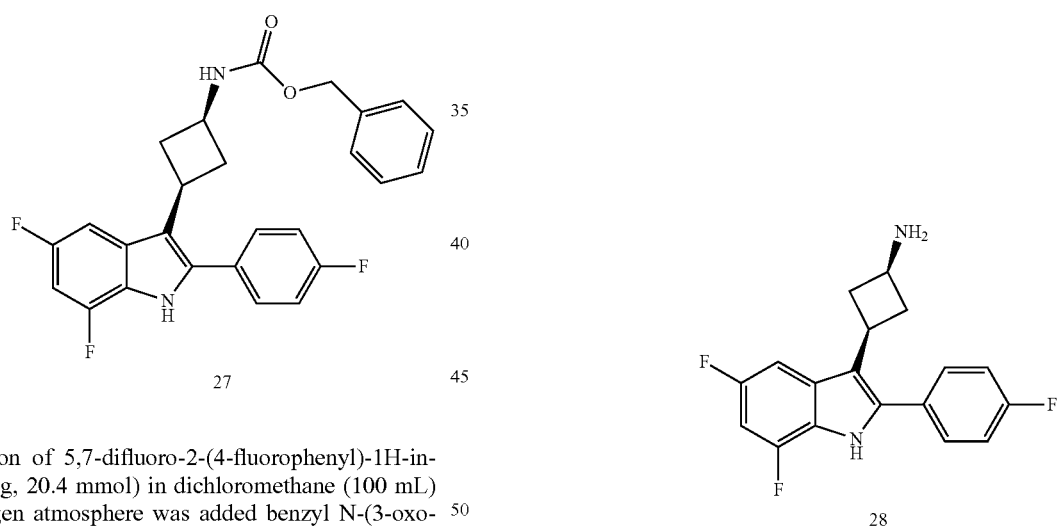

To a solution of 5,7-difluoro-2-(4-fluorophenyl)-1H-indole S1 (5.05 g, 20.4 mmol) in dichloromethane (100 mL) under a nitrogen atmosphere was added benzyl N-(3-oxocyclobutyl)carbamate (4.9 g, 22 mmol) followed by Et$_3$SiH (20 mL, 130 mmol) and trifluoroacetic acid (9.5 mL, 120 mmol). The mixture was stirred at room temperature overnight. The mixture was then concentrated in vacuo and partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-100% EtOAc in heptane) to afford the isomeric mixture of product. The isomeric mixture (6.5 g, 14 mmol) was separated into cis isomer by chiral SFC separation (3.9 g, 51%). Column: Daicel Chiralpak® AD-H, 20×250 mm; Mobile Phase: 40% methanol (containing 5 mM ammonia), 60% carbon dioxide. Flow: 75 mL/min. $^1$H NMR (300 MHz, Acetone-d$_6$) δ 7.69-7.56 (m, 3H), 7.40-7.25 (m, 7H), 6.93-6.77 (m, 2H), 5.10 (s, 2H), 4.14 (h, J=8.6 Hz, 1H), 3.51 (tt, J=10.6, 7.7 Hz, 1H), 2.68 (qd, J=7.7, 2.7 Hz, 2H), 2.50 (q, J=10.4 Hz, 2H). LCMS m/z 451.44 [M+H]$^+$.

Compound 28

(1s,3s)-3-(5,7-difluoro-2-(4-fluorophenyl)-1H-indol-3-yl)cyclobutan-1-amine (28)

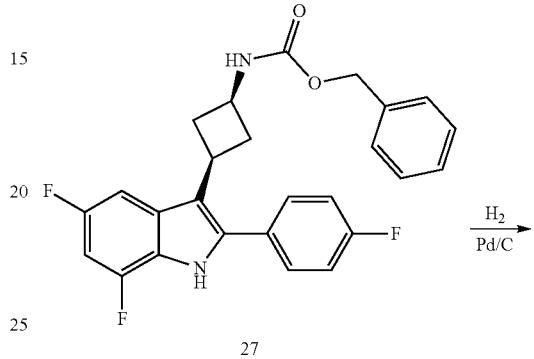

To a suspension of benzyl ((1s,3s)-3-(5,7-difluoro-2-(4-fluorophenyl)-1H-indol-3-yl)cyclobutyl)carbamate 27 (1000 mg, 1.51 mmol) in MeOH (20 mL) was added 10% palladium on carbon catalyst (1.6 mg). The mixture was subjected to hydrogenation conditions of 1 atm H$_2$ for 3 hours. Filtration through a pad of Celite®, then concentration of the filtrate in vacuo and washing with dichloromethane afforded the product (667 mg, 96%) which was used in subsequent steps without further purification. $^1$H NMR (300 MHz, Acetone-d$_6$) δ 10.68 (s, 1H), 7.67-7.55 (m, 3H), 7.34-7.22 (m, 2H), 6.83 (ddd, J=11.1, 9.6, 2.2 Hz, 1H), 4.10-3.97 (m, 1H), 3.70-3.57 (m, 1H), 2.79-2.68 (m, 2H), 2.51-2.39 (m, 2H). LCMS m/z 317.4 [M+H]$^+$.

Compound 29

N-((1s,3s)-3-(5,7-difluoro-2-(4-fluorophenyl)-1H-indol-3-yl)cyclobutyl)-2-hydroxyacetamide (29)

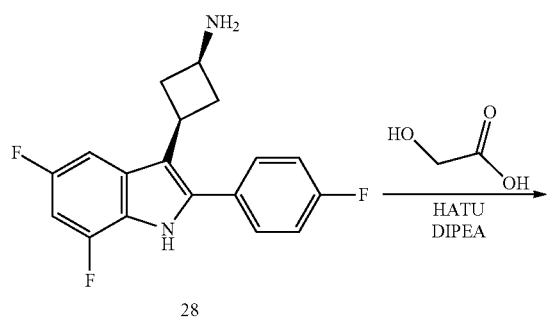

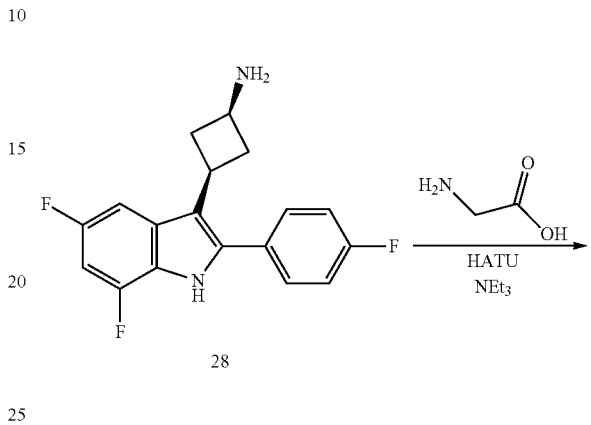

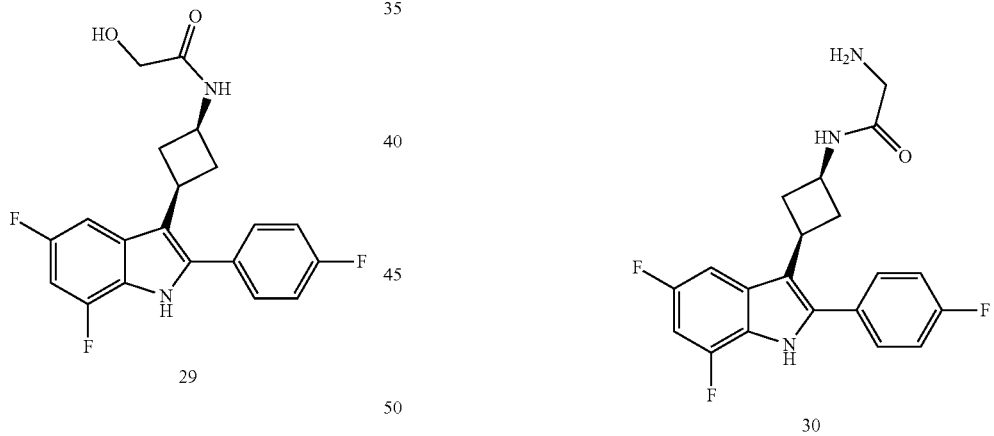

Standard Method B: Amide Coupling with HATU

To a solution of 2-hydroxyacetic acid (179 mg, 2.35 mmol) and HATU (1.12 g, 2.95 mmol) in DMF (9 mL) was added (1s,3s)-3-(5,7-difluoro-2-(4-fluorophenyl)-1H-indol-3-yl)cyclobutan-1-amine 28 (700 mg, 1.9 mmol) followed by DIPEA (674 µL, 3.87 mmol). The mixture was allowed to stir at room temperature for 4 hours. The mixture was then partitioned between ethyl acetate and aqueous sat. sodium bicarbonate solution. The organic phase was separated and washed with brine. The organic layer was dried over sodium sulfate, filtered, and concentrated in vacuo. The residue was then purified by reversed phase chromatography (C18 column; Gradient: MeCN in $H_2O$ with 0.1% trifluoroacetic acid) to afford the product (483.9 mg, 64%). $^1$H NMR (300 MHz, Acetone-$d_6$) δ 10.69 (s, 1H), 7.69-7.55 (m, 4H), 7.34-7.25 (m, 2H), 6.83 (ddd, J=11.1, 9.7, 2.2 Hz, 1H), 4.38 (q, J=7.7 Hz, 1H), 3.90 (s, 2H), 3.59-3.49 (m, 1H), 2.73-2.63 (m, 2H), 2.58-2.45 (m, 2H). LCMS m/z 375.34 [M+H]$^+$.

Compound 30

2-amino-N-((1s,3s)-3-(5,7-difluoro-2-(4-fluorophenyl)-1H-indol-3-yl)cyclobutyl)acetamide (30)

Compound 30 was prepared from compound 28, $Et_3N$ was used in place of DIPEA, and 2-aminoacetic acid in place of 2-hydroxyacetic acid using the method used to synthesize compound 29. LCMS m/z 416.24 [M+H]$^+$.

Compounds 31-78

Compounds 31-78 (see Table 3) were prepared from compound 28 using the appropriate reagent and using the standard amide coupling method as described for compound 30. Carboxylic acids were obtained from commercial sources. Any modifications to methods are noted in Table 3 and accompanying footnotes.

US 12,281,102 B2
209                                                                                                                              210
TABLE 3
Structure and physicochemical data for compounds 31-78
| Compound | Product | Carboxylic acid | $^1$H NMR; LCMS m/z [M + H]$^+$ |
|---|---|---|---|
| 31 | 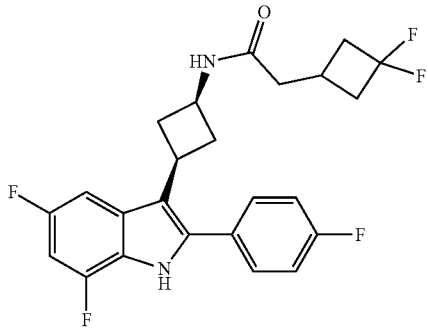 [SMILES: O=C(CC1CC(F)(F)C1)N[C@H]1C[C@@H](c2c(-c3ccc(F)cc3)[nH]c3c(F)cc(F)cc32)C1] | 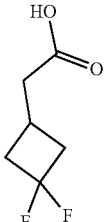 | LCMS m/z 449.1 [M + H]$^+$. |
| 32 | 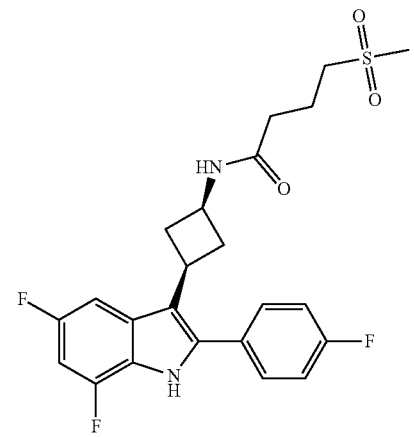 [SMILES: CS(=O)(=O)CCCC(=O)N[C@H]1C[C@@H](c2c(-c3ccc(F)cc3)[nH]c3c(F)cc(F)cc32)C1] | 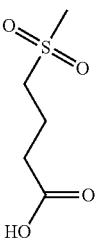 | LCMS m/z 465.13 [M + H]$^+$. |
| 33 | 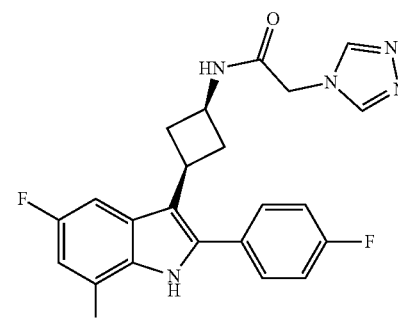 | 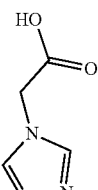 | LCMS m/z 426.17 [M + H]$^+$. |
| 34 | 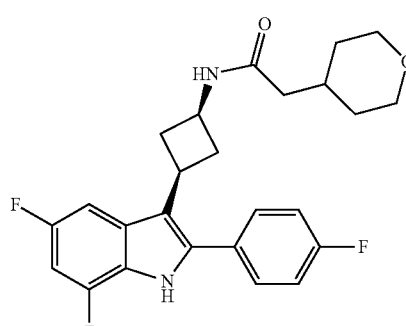 | 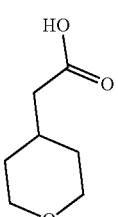 | LCMS m/z 443.18 [M + H]$^+$. |

TABLE 3-continued
Structure and physicochemical data for compounds 31-78
| Compound | Product | Carboxylic acid | $^1$H NMR; LCMS m/z [M + H]$^+$ |
|---|---|---|---|
| 35 | 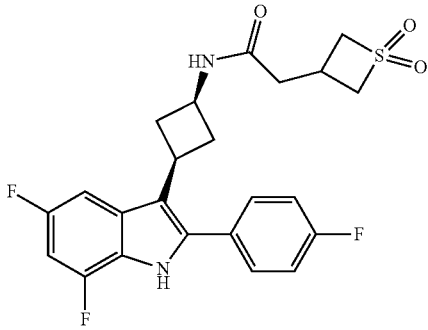 | 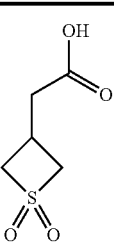 | LCMS m/z 443.18 [M + H]$^+$. |
| 36 | 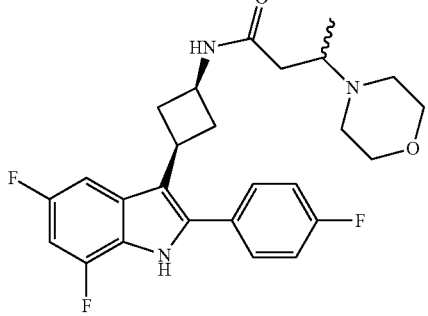 | 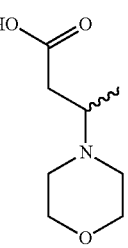 | LCMS m/z 472.2 [M + H]$^+$ |
| 37 | 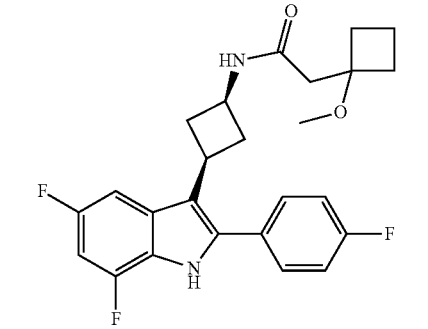 [SMILES: COC1(CC(=O)N[C@H]2C[C@@H](c3c(-c4ccc(F)cc4)[nH]c4c(F)cc(F)cc43)C2)CCC1] | 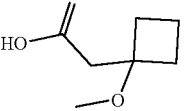 | LCMS m/z 443.31 [M + H]$^+$ |
| 38 | 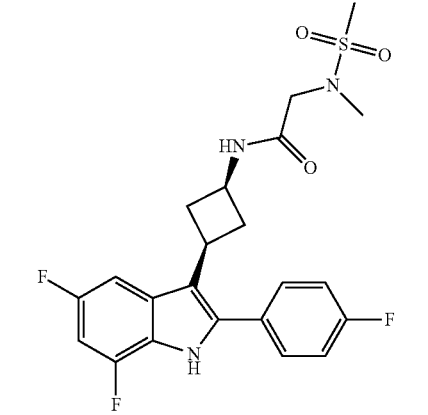 [SMILES: CN(CC(=O)N[C@H]1C[C@@H](c2c(-c3ccc(F)cc3)[nH]c3c(F)cc(F)cc32)C1)S(C)(=O)=O] | 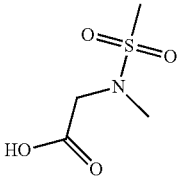 | LCMS m/z 466.11 [M + H]$^+$ |

TABLE 3-continued
Structure and physicochemical data for compounds 31-78
| Compound | Product | Carboxylic acid | $^1$H NMR; LCMS m/z [M + H]$^+$ |
|---|---|---|---|
| 39 | 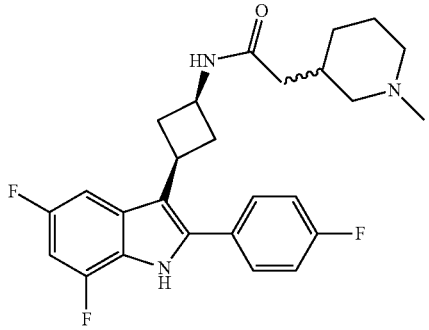 [SMILES: CN1CCCC(CC(=O)N[C@H]2C[C@@H](c3c(-c4ccc(F)cc4)[nH]c4c(F)cc(F)cc43)C2)C1] |  | LCMS m/z 456.2 [M + H]$^+$ |
| 40 | 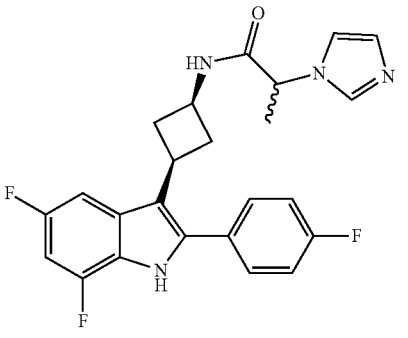 | 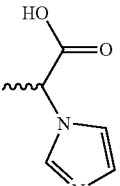 | LCMS m/z 439.17 [M + H]$^+$ |
| 41 | 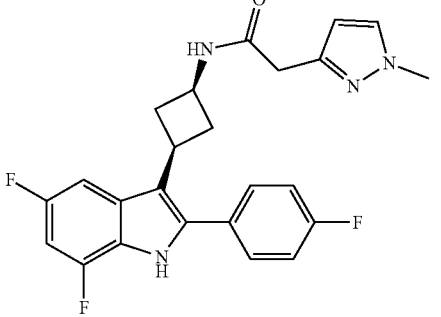 | 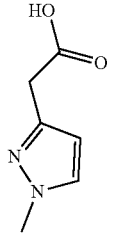 | LCMS m/z 439.17 [M + H]$^+$ |
| 42 | 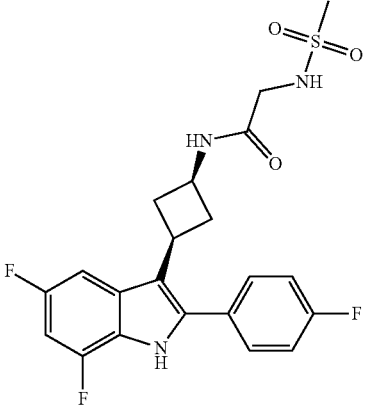 [SMILES: CS(=O)(=O)NCC(=O)N[C@H]1C[C@@H](c2c(-c3ccc(F)cc3)[nH]c3c(F)cc(F)cc32)C1] | 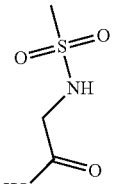 | LCMS m/z 452.1 [M + H]$^+$ |

TABLE 3-continued

Structure and physicochemical data for compounds 31-78

| Compound | Product | Carboxylic acid | $^1$H NMR; LCMS m/z [M + H]$^+$ |
|---|---|---|---|
| 43 | | | LCMS m/z 466.11 [M + H]$^+$ |
| 44 | | | LCMS m/z 442.23 [M + H]$^+$ |
| 45 | | | LCMS m/z 442.2 [M + H]$^+$ |
| 46 | | | LCMS m/z 428.19 [M + H]$^+$ |

TABLE 3-continued
Structure and physicochemical data for compounds 31-78
| Compound | Product | Carboxylic acid | $^1$H NMR; LCMS m/z [M + H]$^+$ |
|---|---|---|---|
| 47 | 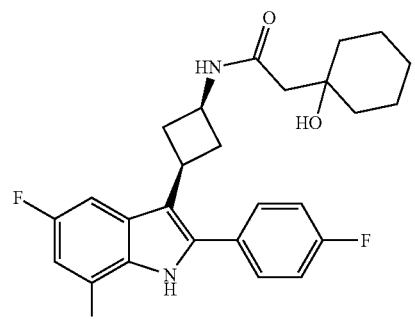 | 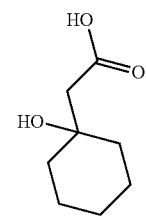 | LCMS m/z 457.29 [M + H]$^+$ |
| 48 | 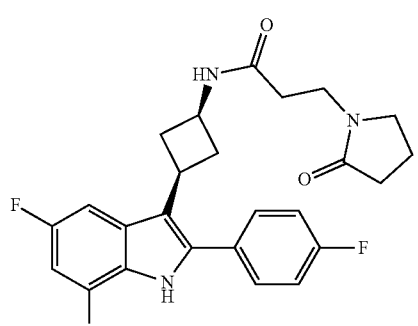 | 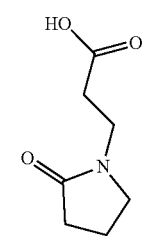 [SMILES: O=C(O)CCN1CCCC1=O] | LCMS m/z 456.3 [M + H]$^+$ |
| 49 | 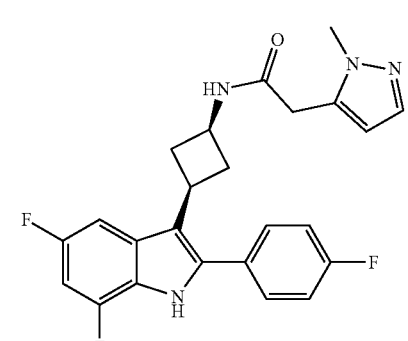 | 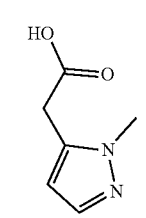 | LCMS m/z 439.33 [M + H]$^+$ |
| 50 | 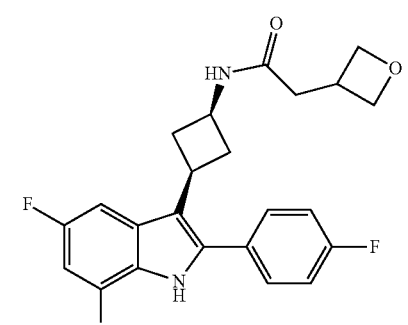 | 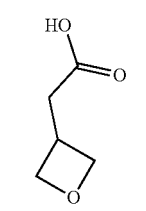 | LCMS m/z 415.35 [M + H]$^+$ |

TABLE 3-continued
Structure and physicochemical data for compounds 31-78
| Compound | Product | Carboxylic acid | $^1$H NMR; LCMS m/z [M + H]$^+$ |
|---|---|---|---|
| 51 | 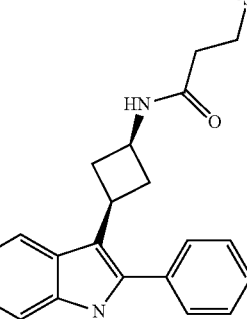 | 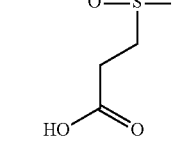 | LCMS m/z 452.29 [M + H]$^+$ |
| 52 |  | 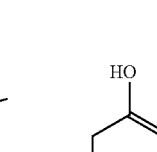 | LCMS m/z 456.34 [M + H]$^+$ |
| 53 | 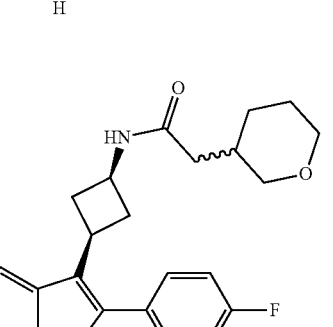 |  | LCMS m/z 443.38 [M + H]$^+$ |
| 54 | 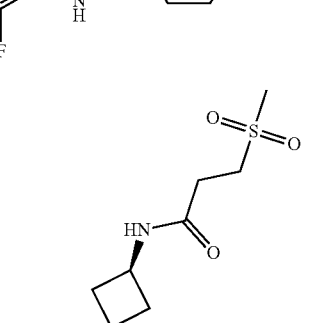 | 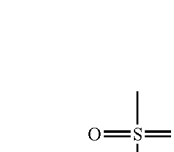 | LCMS m/z 451.26 [M + H]$^+$ |

TABLE 3-continued
Structure and physicochemical data for compounds 31-78
| Compound | Product | Carboxylic acid | ¹H NMR; LCMS m/z [M + H]⁺ |
|---|---|---|---|
| 55 | 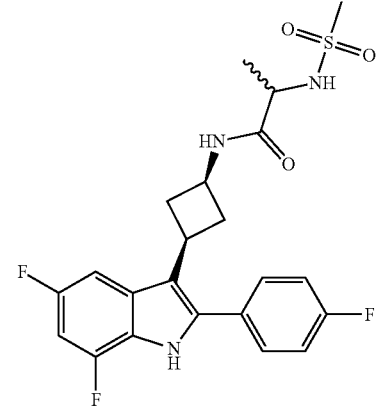 [SMILES: CC(NS(C)(=O)=O)C(=O)N[C@H]1C[C@@H](c2c(-c3ccc(F)cc3)[nH]c3c(F)cc(F)cc32)C1] | 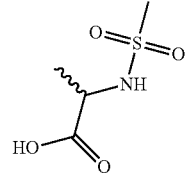 | LCMS m/z 466.24 [M + H]⁺ |
| 56 | 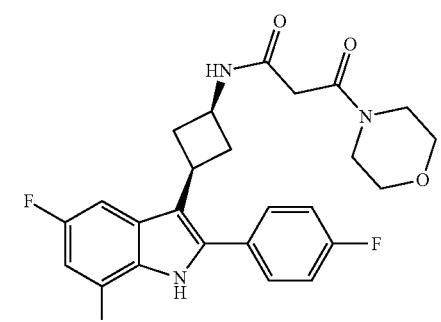 | 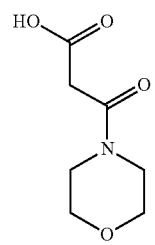 | LCMS m/z 472.32 [M + H]⁺ |
| 57 | 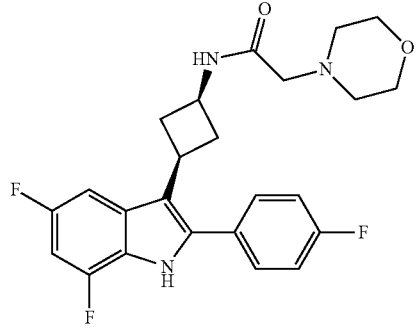 | 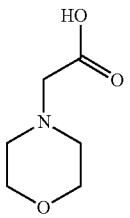 | LCMS m/z 444.37 [M + H]⁺ |
| 58 | 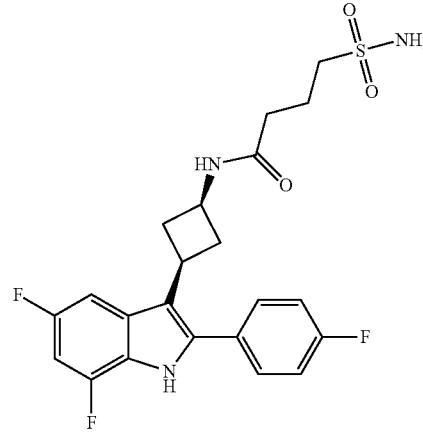 | 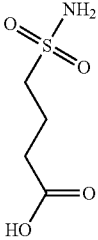 | LCMS m/z 466.29 [M + H]⁺ |

TABLE 3-continued
Structure and physicochemical data for compounds 31-78
| Compound | Product | Carboxylic acid | ¹H NMR; LCMS m/z [M + H]⁺ |
|---|---|---|---|
| 59 | 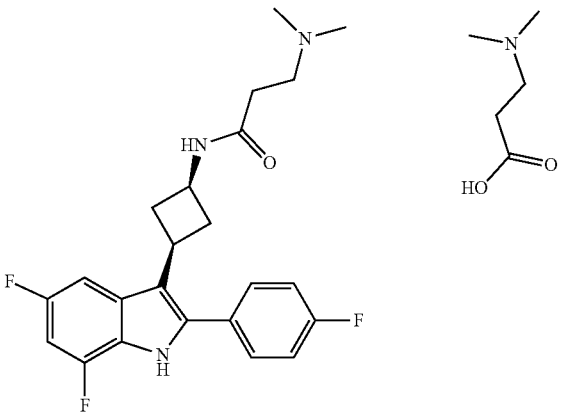 | 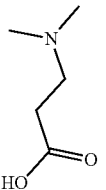 | LCMS m/z 416.34 [M + H]⁺ |
| 60 | 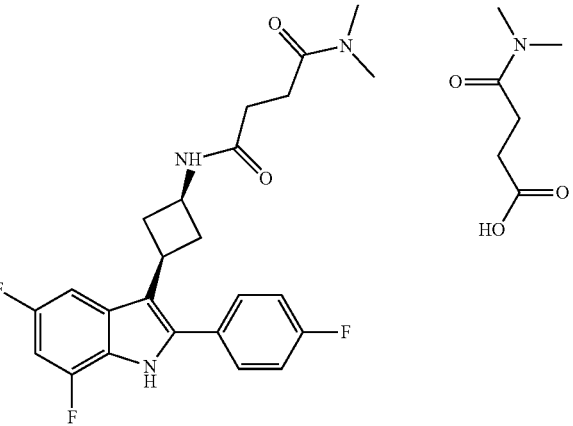 | 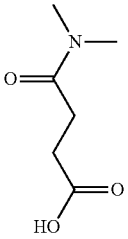 | LCMS m/z 444.37 [M + H]⁺ |
| 61 | 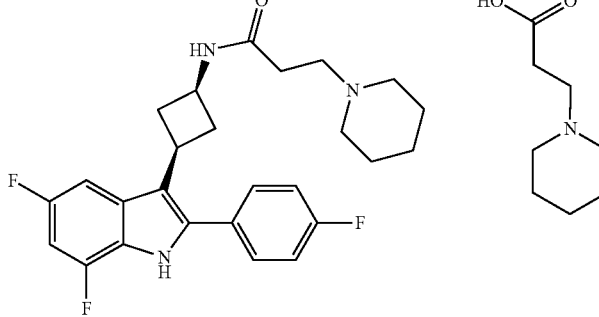 | 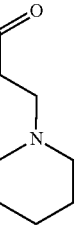 | LCMS m/z 456.39 [M + H]⁺ |

TABLE 3-continued

Structure and physicochemical data for compounds 31-78

| Compound | Product | Carboxylic acid | ¹H NMR; LCMS m/z [M + H]⁺ |
|---|---|---|---|
| 62 | | | LCMS m/z 403.33 [M + H]⁺ |
| 63 | | | LCMS m/z 439.33 [M + H]⁺ |
| 64 | | | LCMS m/z 442.23 [M + H]⁺ |
| 65 | | | LCMS m/z 442.23 [M + H]⁺ |

TABLE 3-continued

Structure and physicochemical data for compounds 31-78

| Compound | Product | Carboxylic acid | ¹H NMR; LCMS m/z [M + H]⁺ |
|---|---|---|---|
| 66 | | | LCMS m/z 456.17 [M + H]⁺ |
| 67 | | | LCMS m/z 384.15 [M + H]⁺ |
| 68 | | | LCMS m/z 409.14 [M + H]⁺ |
| 69 | | | LCMS m/z 428.16 [M + H]⁺ |

TABLE 3-continued
Structure and physicochemical data for compounds 31-78
| Compound | Product | Carboxylic acid | $^1$H NMR; LCMS m/z [M + H]$^+$ |
|---|---|---|---|
| 70 | 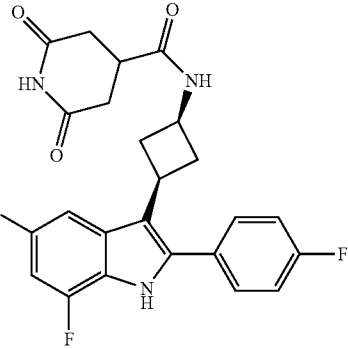 | 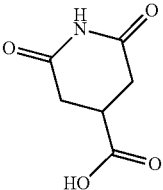 [SMILES: O=C1CC(C(=O)O)CC(=O)N1] | LCMS m/z 456.14 [M + H]$^+$ |
| 71 | 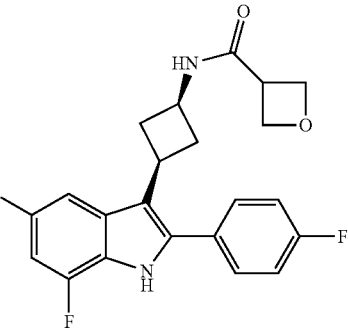 | 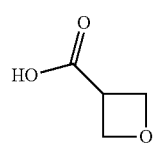 | LCMS m/z 401.15 [M + H]$^+$ |
| 72 | 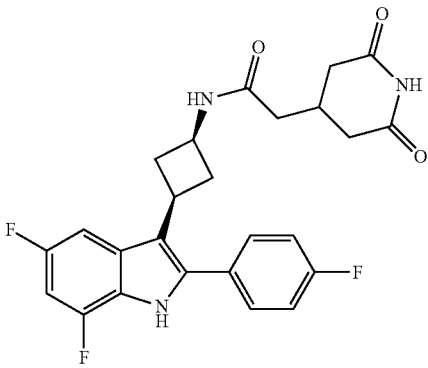 [SMILES: O=C1CC(CC(=O)N[C@H]2C[C@@H](c3c(-c4ccc(F)cc4)[nH]c4c(F)cc(F)cc43)C2)CC(=O)N1] | 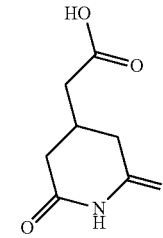 | LCMS m/z 470.15 [M + H]$^+$ |
| 73 | 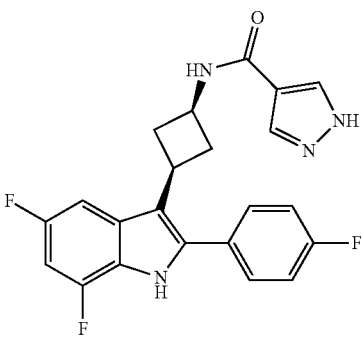 [SMILES: O=C(N[C@H]1C[C@@H](c2c(-c3ccc(F)cc3)[nH]c3c(F)cc(F)cc32)C1)c1cn[nH]c1] | 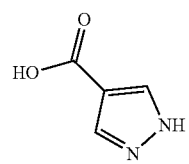 | LCMS m/z 411.12 [M + H]$^+$ |

TABLE 3-continued

Structure and physicochemical data for compounds 31-78

| Compound | Product | Carboxylic acid | $^1$H NMR; LCMS m/z [M + H]$^+$ |
|---|---|---|---|
| 74 | (structure: 3-(cyclobutyl-NHC(O)C(CH$_3$)$_2$OH)-2-(4-fluorophenyl)-5,7-difluoroindole) | 2-hydroxy-2-methylpropanoic acid | LCMS m/z 403.17 [M + H]$^+$ |
| 75 | (structure: 3-(cyclobutyl-NHC(O)CH$_2$CH$_2$NHCH$_3$)-2-(4-fluorophenyl)-5,7-difluoroindole) | 3-(methylamino)propanoic acid | LCMS m/z 402.2 [M + H]$^+$ |
| 76 | (structure: 3-(cyclobutyl-NHC(O)-1-hydroxycyclopropyl)-2-(4-fluorophenyl)-5,7-difluoroindole) | 1-hydroxycyclopropane-1-carboxylic acid | LCMS m/z 401.15 [M + H]$^+$ |

TABLE 3-continued
Structure and physicochemical data for compounds 31-78
| Compound | Product | Carboxylic acid | ¹H NMR; LCMS m/z [M + H]⁺ |
|---|---|---|---|
| 77 | 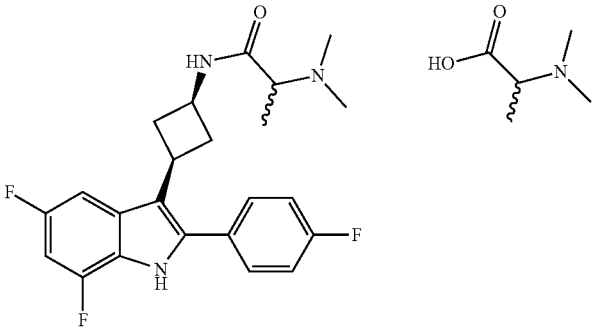 | 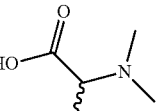 | LCMS m/z 416.24 [M + H]⁺ |
| 78 | 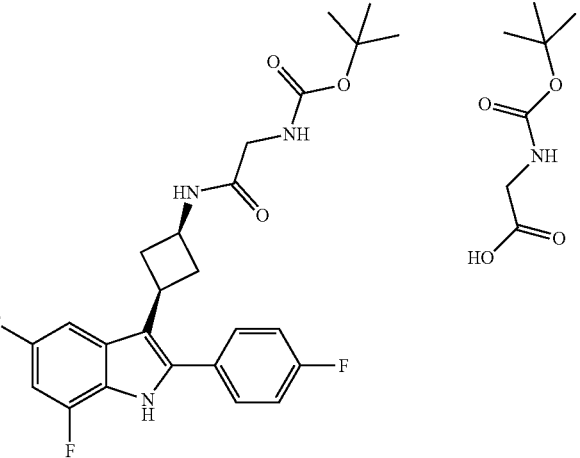 | 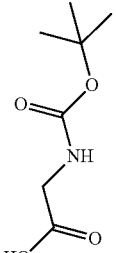 | LCMS m/z 474.3 [M + H]⁺ |
Compound 79
N-((1s,3s)-3-(5,7-difluoro-2-(4-fluorophenyl)-1H-indol-3-yl)cyclobutyl)propane-1-sulfonamide (79)
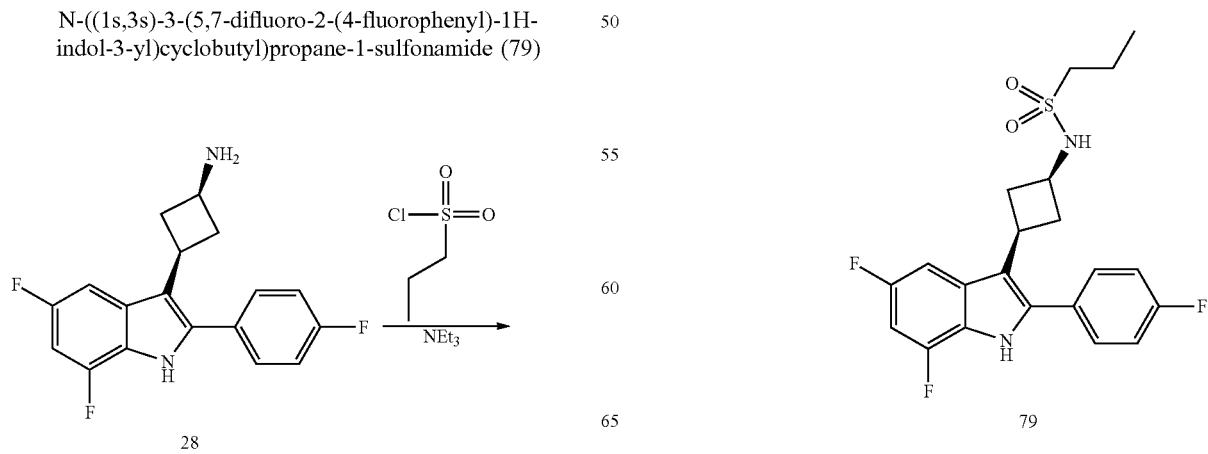

Standard Method C: Sulfonamide Coupling Method

To a solution of (1s,3s)-3-(5,7-difluoro-2-(4-fluorophenyl)-1H-indol-3-yl)cyclobutan-1-amine 28 (30 mg, 0.10 mmol) in dichloromethane (3 mL) was added propane-1-sulfonyl chloride (17 mg, 0.12 mmol) and NEt$_3$ (28 µL, 0.20 mmol). The mixture was allowed to stir at room temperature overnight. The mixture was then concentrated in vacuo, and the residue was purified by reversed phase chromatography (C18 column; Gradient: MeCN in H$_2$O with 0.1% trifluoroacetic acid) to afford the product (15.7 mg, 37%). LCMS m/z 423.11 [M+H]$^+$.

Compounds 80-87

Compounds 80-87 (see Table 4) were prepared from compound 28 using the appropriate reagent and using the standard sulfonamide coupling method as described for compound 79. Sulfonyl chlorides were obtained from commercial sources. Any modifications to methods are noted in Table 4 and accompanying footnotes.

TABLE 4

Structure and physicochemical data for compounds 80-87

| Compound | Product | Sulfonyl chloride | $^1$H NMR; LCMS m/z [M + H]$^+$ |
|---|---|---|---|
| 80 | 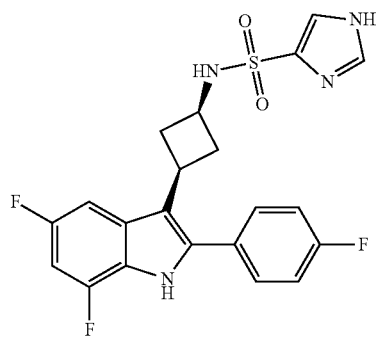 [SMILES: O=S(=O)(N[C@H]1C[C@@H](c2c(-c3ccc(F)cc3)[nH]c3c(F)cc(F)cc32)C1)c1c[nH]cn1] | 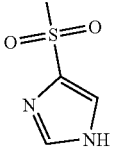 | LCMS m/z 447.05 [M + H]$^+$ |
| 81 | 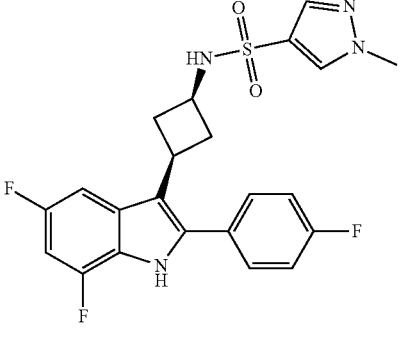 [SMILES: Cn1cc(S(=O)(=O)N[C@H]2C[C@@H](c3c(-c4ccc(F)cc4)[nH]c4c(F)cc(F)cc43)C2)cn1] | 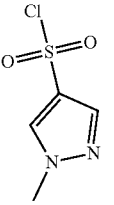 | LCMS m/z 461.09 [M + H]$^+$ |
| 82 | 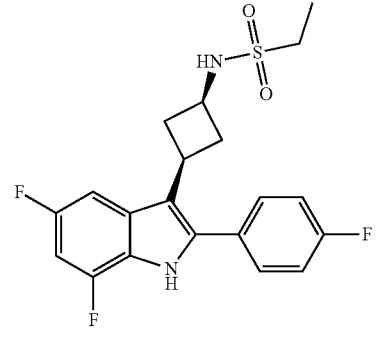 [SMILES: CCS(=O)(=O)N[C@H]1C[C@@H](c2c(-c3ccc(F)cc3)[nH]c3c(F)cc(F)cc32)C1] | 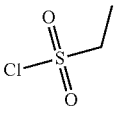 | LCMS m/z 409.1 [M + H]$^+$ |

TABLE 4-continued

Structure and physicochemical data for compounds 80-87

| Compound | Product | Sulfonyl chloride | ¹H NMR; LCMS m/z [M + H]⁺ |
|---|---|---|---|
| 83 | [structure: N-(cyclobutyl)oxetane-3-sulfonamide with 5,7-difluoro-2-(4-fluorophenyl)indole] | [oxetane-3-sulfonyl chloride] | ¹H NMR (300 MHz, Acetone-d₆) δ 10.73 (s, 1H), 7.81-7.45 (m, 3H), 7.30 (td, J = 9.3, 8.8, 2.4 Hz, 2H), 7.15-6.74 (m, 2H), 4.96-4.72 (m, 4H), 4.66-4.39 (m, 1H), 3.93 (qd, J = 9.4, 4.6 Hz, 1H), 3.51 (tt, J = 10.5, 7.6 Hz, 1H), 2.83-2.37 (m, 4H). LCMS m/z 437.08 [M + H]⁺ |
| 84 | [structure: N-(cyclobutyl)-1H-pyrazole-4-sulfonamide with 5,7-difluoro-2-(4-fluorophenyl)indole] | [1H-pyrazole-4-sulfonyl chloride] | ¹H NMR (300 MHz, Acetone-d₆) δ 10.68 (s, 1H, 7.74-7.42 (m, 3H), 7.36-7.18 (m, 2H), 7.03-6.75 (m, 2H), 3.86 (td, J = 9.3, 4.4 Hz, 1H), 3.47 (tt, J = 10.7, 7.7 Hz, 1H), 2.62-2.28 (m, 4H). LCMS m/z 447.08 [M + H]⁺ |
| 85 | [structure: N-(cyclobutyl)-1-methyl-1H-imidazole-2-sulfonamide with 5,7-difluoro-2-(4-fluorophenyl)indole] | [1-methyl-1H-imidazole-2-sulfonyl chloride] | LCMS m/z 461.09 [M + H]⁺ |
| 86 | [structure: N-(cyclobutyl)tetrahydro-2H-pyran-4-sulfonamide with 5,7-difluoro-2-(4-fluorophenyl)indole] | [tetrahydro-2H-pyran-4-sulfonyl chloride] | LCMS m/z 465.0 [M + H]⁺ |

TABLE 4-continued

Structure and physicochemical data for compounds 80-87

| Compound | Product | Sulfonyl chloride | ¹H NMR; LCMS m/z [M + H]⁺ |
|---|---|---|---|
| 87 | 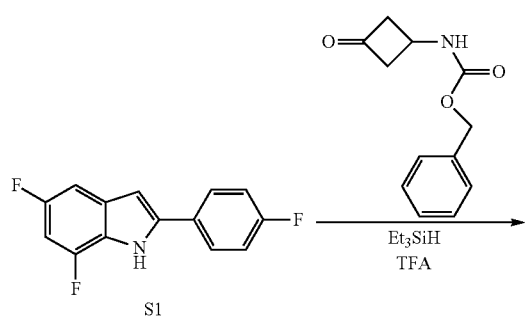 | | ¹H NMR (300 MHz, Acetone-$d_6$) δ 10.74 (s, 1H), 7.83-7.49 (m, 4H), 7.48-7.18 (m, 2H), 6.85 (ddd, J = 11.0, 9.7, 2.1 Hz, 1H), 4.49 (s, 2H), 4.13-3.92 (m, 1H), 3.55 (tt, J = 10.6, 7.6 Hz, 1H), 2.84 (dddd, J = 11.4, 7.5, 4.8, 2.7 Hz, 2H), 2.76-2.49 (m, 2H). LCMS m/z 420.08 [M + H]⁺ |

Compound 88

Benzyl (1r,3r)-3-(5,7-difluoro-2-(4-fluorophenyl)-1H-indol-3-yl)cyclobutyl)carbamate (88)

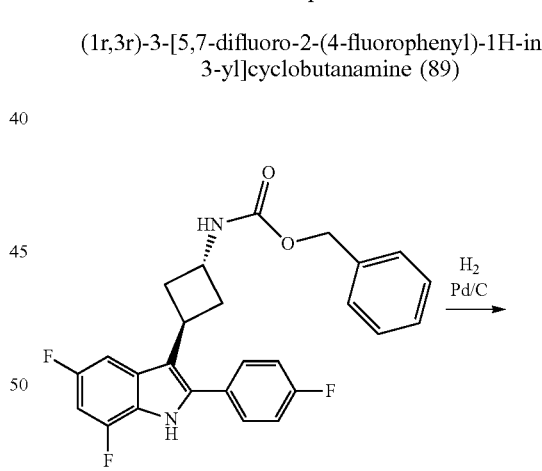

To a solution of 5,7-difluoro-2-(4-fluorophenyl)-1H-indole S1 (5.05 g, 20.4 mmol) in dichloromethane (100 mL) under a nitrogen atmosphere was added benzyl N-(3-oxocyclobutyl)carbamate (4.9 g, 22 mmol) followed by Et₃SiH (20 mL, 130 mmol) and trifluoroacetic acid (9.5 mL, 120 mmol). The mixture was stirred at room temperature overnight. The mixture was then concentrated in vacuo and partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-100% EtOAc in heptane) to afford the isomeric mixture of product. The isomeric mixture (6.5 g, 14 mmol) was separated into trans isomer by chiral SFC separation (1.1 g, 52%). Column: Daicel Chiralpak® AD-H, 20×250 mm; Mobile Phase: 40% methanol (containing 5 mM ammonia), 60% carbon dioxide. Flow: 75 mL/min. ¹H NMR (300 MHz, Acetone-$d_6$) δ 7.64-7.57 (m, 2H), 7.43-7.24 (m, 7H), 6.90-6.80 (m, 2H), 5.10 (2, 2H), 4.35 (d, J=6.9 Hz, 1H), 4.21-4.07 (m, 1H), 2.81-2.74 (m, 2H), 2.50-2.40 (m, 2H). LCMS m/z 451.24 [M+H]⁺.

Compound 89

(1r,3r)-3-[5,7-difluoro-2-(4-fluorophenyl)-1H-indol-3-yl]cyclobutanamine (89)

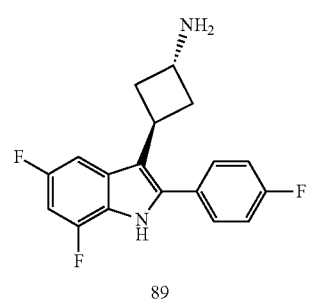

To a solution of benzyl N-[(1r,3r)-3-[5,7-difluoro-2-(4-fluorophenyl)-1H-indol-3-yl]cyclobutyl]carbamate 88 (1.7 g, 3.8 mmol) in MeOH (20 mL) and THF (5 mL) was added 10% palladium on carbon catalyst (1 g, 50% water). The reaction mixture was placed on Parr shaker at 30 psi for 6 hours. Then the mixture was filtered through Celite®. The filtrate was removed in vacuo, and the resulting mixture was triturated with DCM (10 mL) to provide the product (948.2 mg, 75%) $^1$H NMR (300 MHz, Methanol-$d_4$) δ 7.51 (ddt, J=8.3, 5.2, 2.5 Hz, 2H), 7.26 (dtd, J=8.8, 6.8, 2.2 Hz, 3H), 6.78 (ddd, J=11.1, 9.6, 2.1 Hz, 1H), 4.25 (p, J=9.0 Hz, 1H), 3.96 (dddt, J=8.2, 7.0, 3.5, 1.9 Hz, 1H), 2.97-2.80 (m, 2H), 2.50 (ddt, J=12.5, 9.6, 3.3 Hz, 2H). LCMS m/z 317.13 [M+H]$^+$.

Compound 90

N-[3-[5,7-difluoro-2-(4-fluorophenyl)-1H-indol-3-yl]cyclobutyl]-2-hydroxy-acetamide (90)

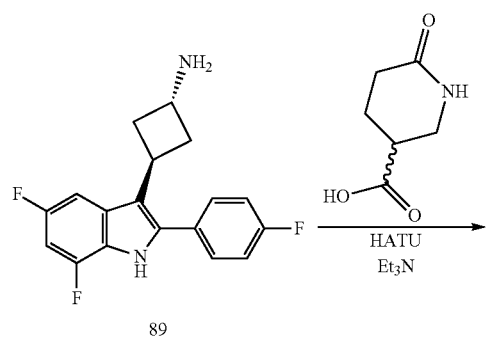

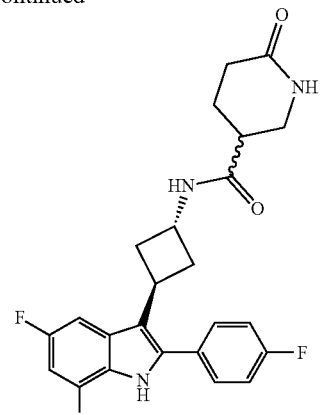

90

Standard Method D: Amide Coupling with HATU

To a solution of 6-oxopiperidine-3-carboxylic acid (11 mg, 0.079 mmol) and (1r,3r)-3-[5,7-difluoro-2-(4-fluorophenyl)-1H-indol-3-yl]cyclobutanamine 89 (25 mg, 0.079 mmol) in DMF (2 mL) was added HATU (36 mg, 0.095 mmol) followed by Et$_3$N (16 mg, 0.16 mmol). The reaction mixture was stirred at room temperature overnight. Purification by reversed phase chromatography (C18 column; Gradient: MeCN in H$_2$O with 0.1% trifluoroacetic acid) afforded the product (13.5 mg, 31%). LCMS m/z 442.13 [M+H]$^+$.

Compounds 91-144

Compounds 91-144 (see Table 5) were prepared in a single step from compound 89 using the amide coupling method described for the synthesis of compound 90. Carboxylic acids were obtained from commercial sources. Any modifications to methods are noted in Table 5 and accompanying footnotes.

TABLE 5

Structure and physicochemical data for compounds 91-144

| Compound | Product | Carboxylic acid | $^1$H NMR; LCMS m/z [M + H]$^+$ |
|---|---|---|---|
| 91 | | | LCMS m/z 402.16 [M + H]$^+$ |

TABLE 5-continued
Structure and physicochemical data for compounds 91-144
| Compound | Product | Carboxylic acid | ¹H NMR; LCMS m/z [M + H]⁺ |
|---|---|---|---|
| 92 | 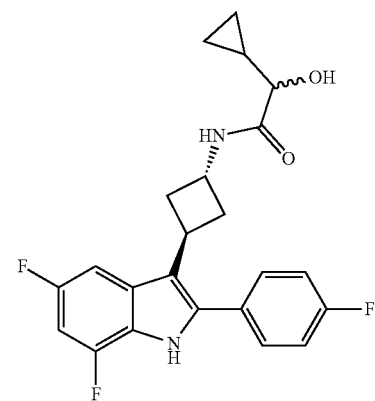 [SMILES: O=C(N[C@H]1C[C@H](c2c(-c3ccc(F)cc3)[nH]c3c(F)cc(F)cc32)C1)C(O)C1CC1] | 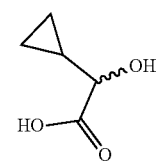 | LCMS m/z 415.16 [M + H]⁺ |
| 93 | 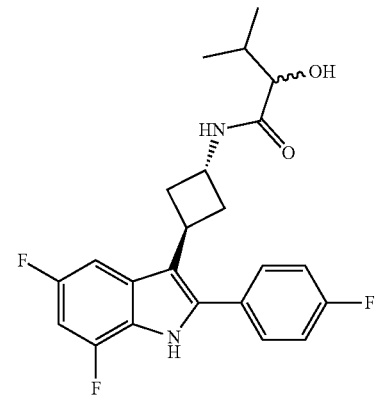 [SMILES: CC(C)C(O)C(=O)N[C@H]1C[C@H](c2c(-c3ccc(F)cc3)[nH]c3c(F)cc(F)cc32)C1] | 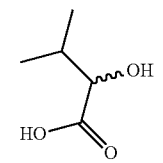 | LCMS m/z 417.18 [M + H]⁺ |
| 94 | 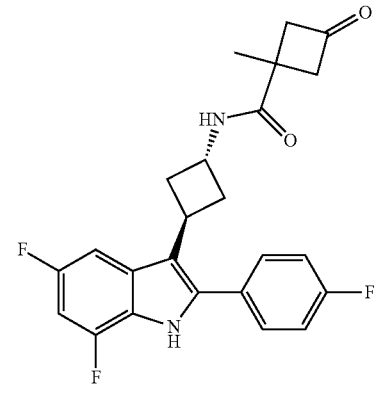 [SMILES: CC1(C(=O)N[C@H]2C[C@H](c3c(-c4ccc(F)cc4)[nH]c4c(F)cc(F)cc43)C2)CC(=O)C1] | 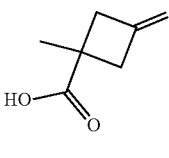 | LCMS m/z 427.18 [M + H]⁺ |
| 95 | 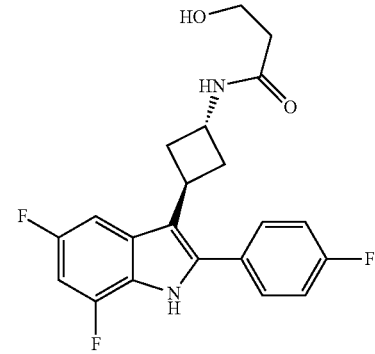 [SMILES: O=C(CCO)N[C@H]1C[C@H](c2c(-c3ccc(F)cc3)[nH]c3c(F)cc(F)cc32)C1] | 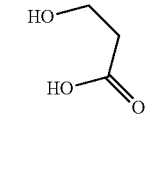 | LCMS m/z 389.17 [M + H]⁺ |

TABLE 5-continued
Structure and physicochemical data for compounds 91-144
| Compound | Product | Carboxylic acid | $^1$H NMR; LCMS m/z [M + H]$^+$ |
|---|---|---|---|
| 96 | 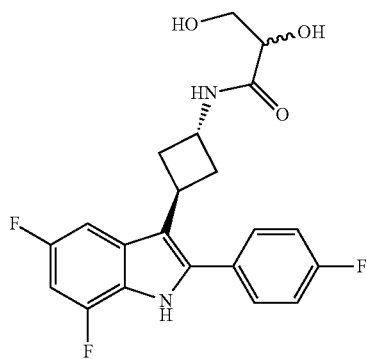 [SMILES: O=C(N[C@H]1C[C@H](c2c(-c3ccc(F)cc3)[nH]c3c(F)cc(F)cc32)C1)C(O)CO] | 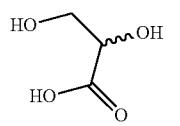 | LCMS m/z 405.13 [M + H]$^+$ |
| 97 | 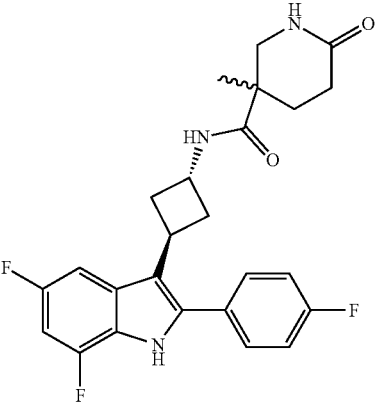 [SMILES: CC1(C(=O)N[C@H]2C[C@H](c3c(-c4ccc(F)cc4)[nH]c4c(F)cc(F)cc43)C2)CCC(=O)NC1] | 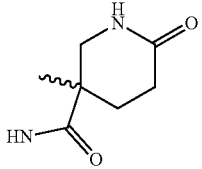 | LCMS m/z 456.17 [M + H]$^+$ |
| 98 | 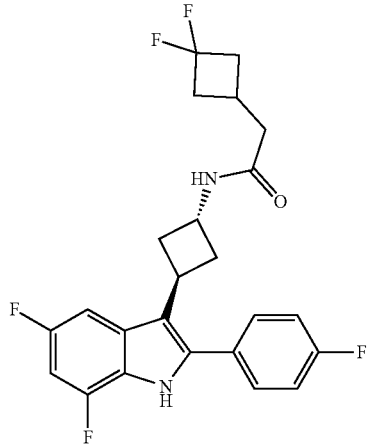 | 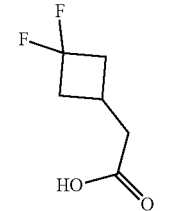 | LCMS m/z 449.14 [M + H]$^+$ |

US 12,281,102 B2
247                                                                 248
TABLE 5-continued
Structure and physicochemical data for compounds 91-144
| Compound | Product | Carboxylic acid | $^1$H NMR; LCMS m/z [M + H]$^+$ |
|---|---|---|---|
| 99 | 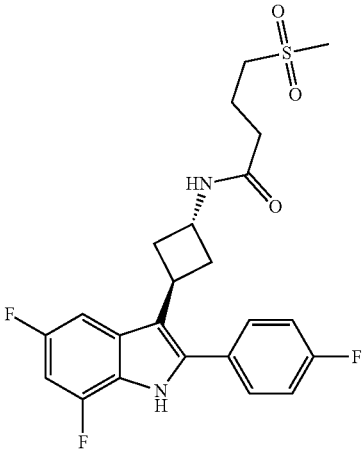 [SMILES: CS(=O)(=O)CCCC(=O)N[C@H]1C[C@H](c2c(-c3ccc(F)cc3)[nH]c3c(F)cc(F)cc32)C1] | 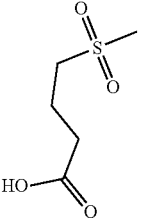 | LCMS m/z 465.13 [M + H]$^+$ |
| 100 | 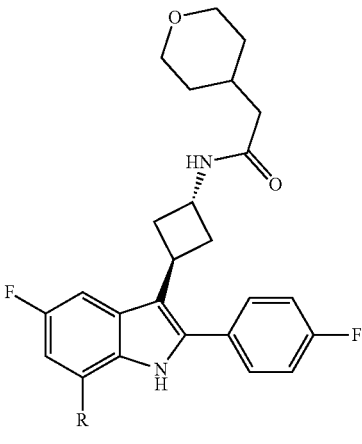 | 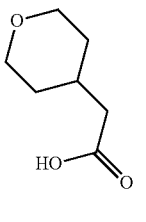 | LCMS m/z 443.18 [M + H]$^+$ |
| 101 | 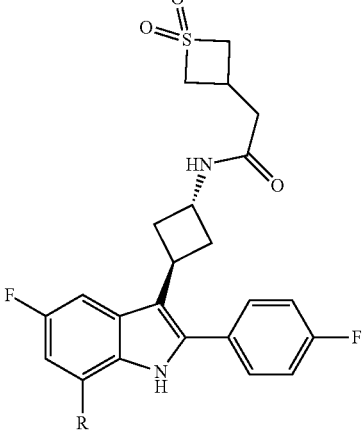 | 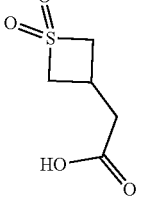 | LCMS m/z 463.11 [M + H]$^+$ |

TABLE 5-continued
Structure and physicochemical data for compounds 91-144
| Compound | Product | Carboxylic acid | $^1$H NMR; LCMS m/z [M + H]$^+$ |
|---|---|---|---|
| 102 | 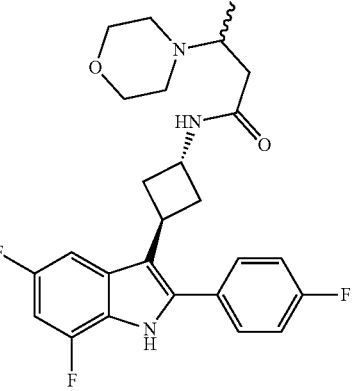 | 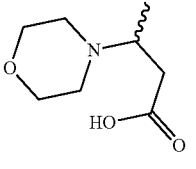 | LCMS m/z 472.2 [M + H]$^+$ |
| 103 | 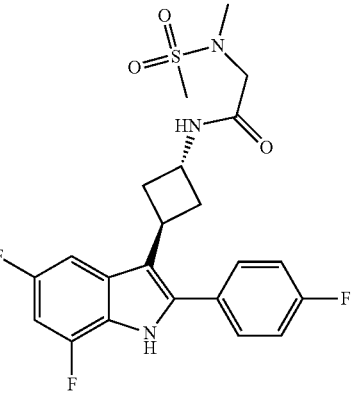 | 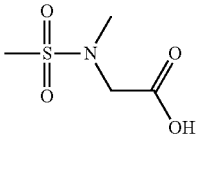 | LCMS m/z 466.11 [M + H]$^+$ |
| 104 | 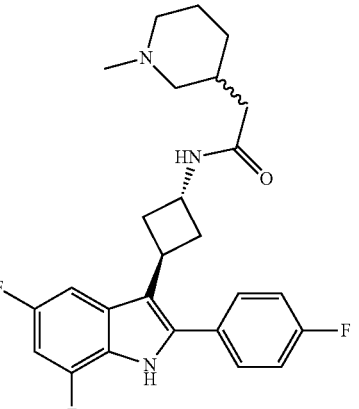 | 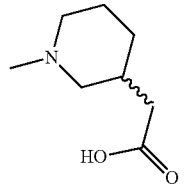 | LCMS m/z 456.2 [M + H]$^+$ |

TABLE 5-continued
Structure and physicochemical data for compounds 91-144
| Compound | Product | Carboxylic acid | $^1$H NMR; LCMS m/z [M + H]$^+$ |
|---|---|---|---|
| 105 | 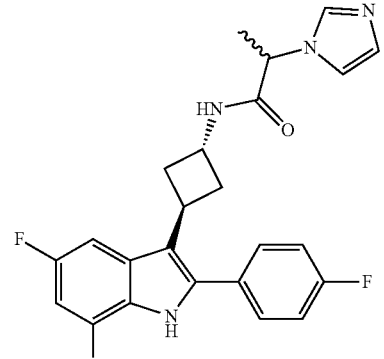 | 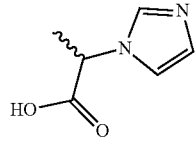 | LCMS m/z 439.17 [M + H]$^+$ |
| 106 | 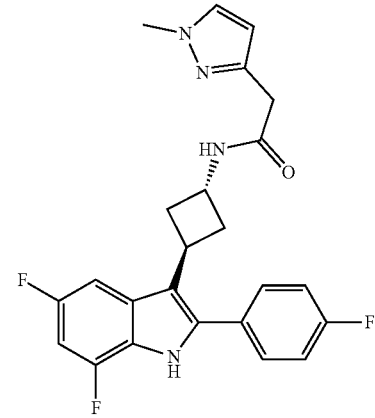 [SMILES: Cn1ccc(CC(=O)N[C@H]2C[C@H](c3c(-c4ccc(F)cc4)[nH]c4c(F)cc(F)cc43)C2)n1] | 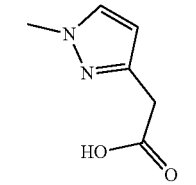 | LCMS m/z 439.17 [M + H]$^+$ |
| 107 | 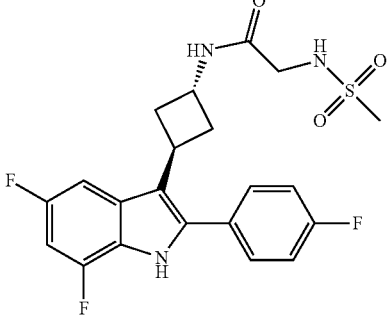 | 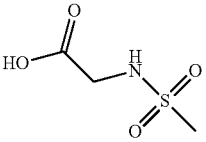 | LCMS m/z 452.1 [M + H]$^+$ |

TABLE 5-continued
Structure and physicochemical data for compounds 91-144
| Compound | Product | Carboxylic acid | $^1$H NMR; LCMS m/z [M + H]$^+$ |
|---|---|---|---|
| 108 | 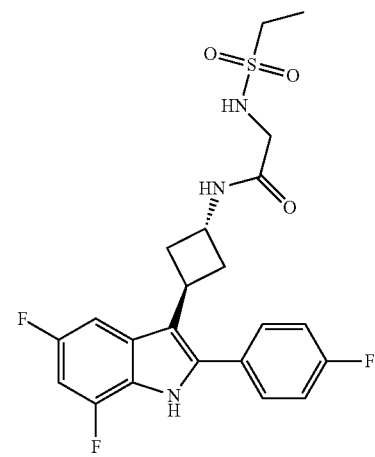 [SMILES: CCS(=O)(=O)NCC(=O)N[C@H]1C[C@H](c2c(-c3ccc(F)cc3)[nH]c3c(F)cc(F)cc32)C1] | 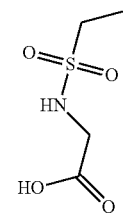 | LCMS m/z 466.11 [M + H]$^+$ |
| 109 | 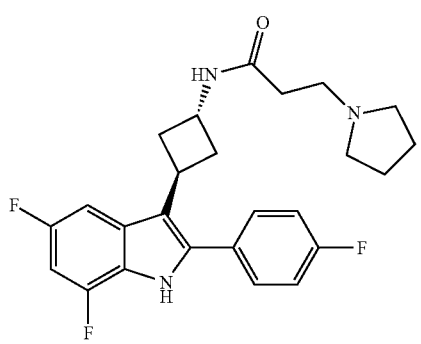 [SMILES: O=C(CCN1CCCC1)N[C@H]1C[C@H](c2c(-c3ccc(F)cc3)[nH]c3c(F)cc(F)cc32)C1] | 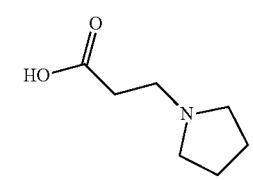 | LCMS m/z 442.2 [M + H]$^+$ |
| 110 | 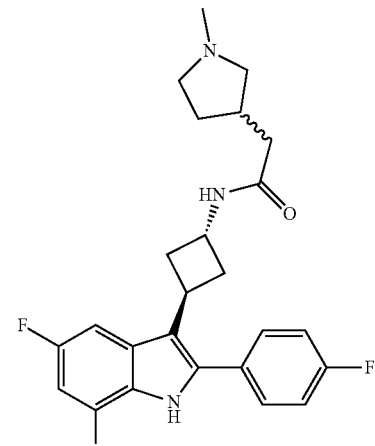 | 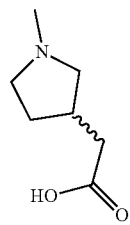 | LCMS m/z 442.2 [M + H]$^+$ |

TABLE 5-continued
Structure and physicochemical data for compounds 91-144
| Compound | Product | Carboxylic acid | $^1$H NMR; LCMS m/z [M + H]$^+$ |
|---|---|---|---|
| 111 | 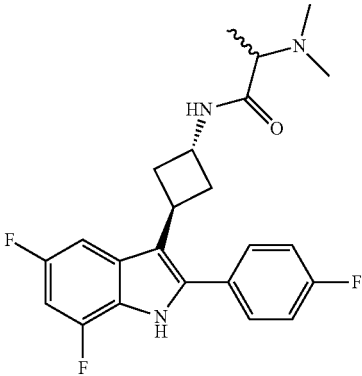 [SMILES: CC(C(=O)N[C@H]1C[C@H](c2c(-c3ccc(F)cc3)[nH]c3c(F)cc(F)cc32)C1)N(C)C] | 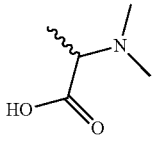 | LCMS m/z 416.2 [M + H]$^+$ |
| 112 | 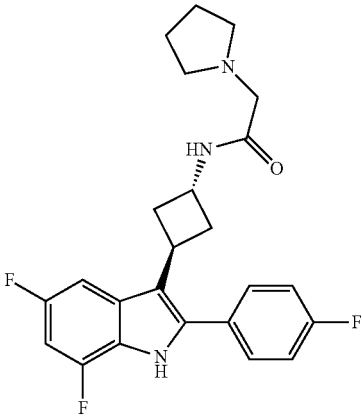 [SMILES: O=C(CN1CCCC1)N[C@H]1C[C@H](c2c(-c3ccc(F)cc3)[nH]c3c(F)cc(F)cc32)C1] | 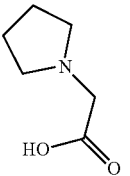 | LCMS m/z 428.19 [M + H]$^+$ |
| 113 | 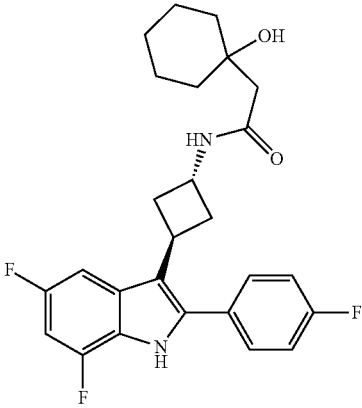 [SMILES: O=C(CC1(O)CCCCC1)N[C@H]1C[C@H](c2c(-c3ccc(F)cc3)[nH]c3c(F)cc(F)cc32)C1] | 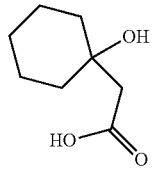 | LCMS m/z 457.18 [M + H]$^+$ |

TABLE 5-continued
Structure and physicochemical data for compounds 91-144
| Compound | Product | Carboxylic acid | ¹H NMR; LCMS m/z [M + H]⁺ |
|---|---|---|---|
| 114 | 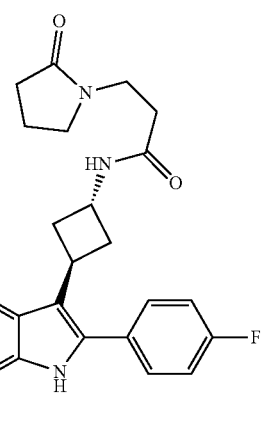 | 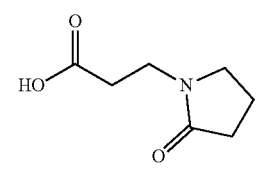 | LCMS m/z 456.17 [M + H]⁺ |
| 115 | 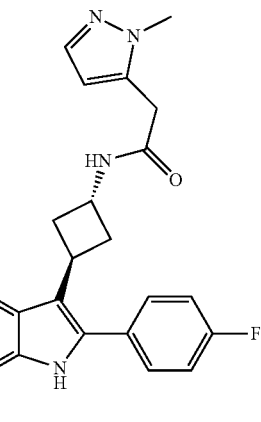 | 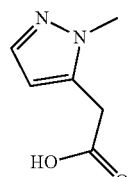 | LCMS m/z 439.17 [M + H]⁺ |
| 116 | 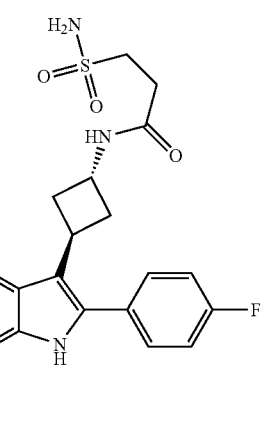 | 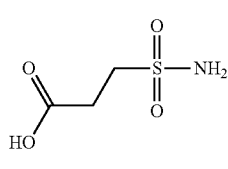 | LCMS m/z 452.1 [M + H]⁺ |

TABLE 5-continued
Structure and physicochemical data for compounds 91-144
| Compound | Product | Carboxylic acid | $^1$H NMR; LCMS m/z [M + H]$^+$ |
|---|---|---|---|
| 117 | 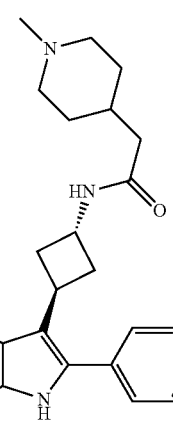 | 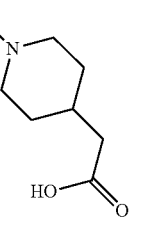 | LCMS m/z 456.2 [M + H]$^+$ |
| 118 | 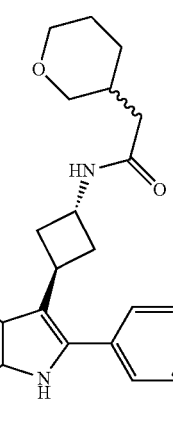 | 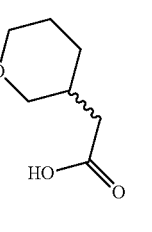 | LCMS m/z 443.18 [M + H]$^+$ |
| 119 | 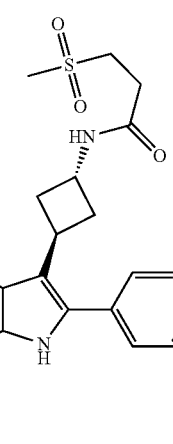 | 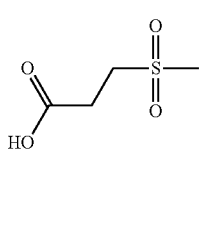 | LCMS m/z 451.12 [M + H]$^+$ |

TABLE 5-continued
Structure and physicochemical data for compounds 91-144
| Compound | Product | Carboxylic acid | $^1$H NMR; LCMS m/z [M + H]$^+$ |
|---|---|---|---|
| 120 | 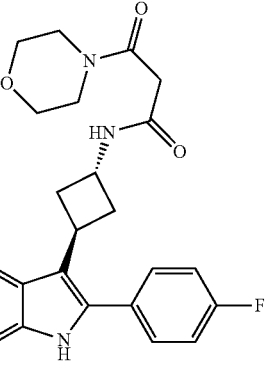 | 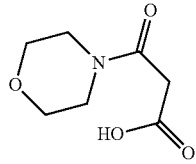 [SMILES: O=C(O)CC(=O)N1CCOCC1] | LCMS m/z 472.17 [M + H]$^+$ |
| 121 | 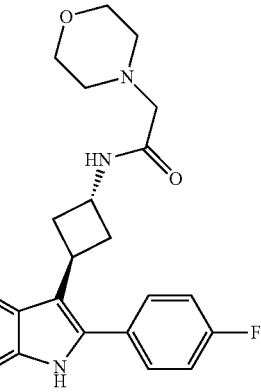 | 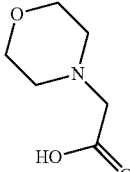 | LCMS m/z 444.19 [M + H]$^+$ |
| 122 | 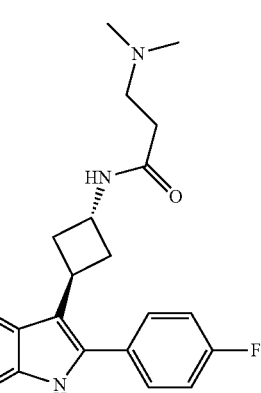 | 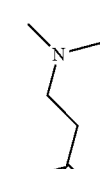 | LCMS m/z 416.2 [M + H]$^+$ |

TABLE 5-continued

Structure and physicochemical data for compounds 91-144

| Compound | Product | Carboxylic acid | ¹H NMR; LCMS m/z [M + H]⁺ |
|---|---|---|---|
| 123 | | | LCMS m/z 444.19 [M + H]⁺ |
| 124 | | | LCMS m/z 456.2 [M + H]⁺ |
| 125 | | | LCMS m/z 403.17 [M + H]⁺ |

US 12,281,102 B2
TABLE 5-continued
Structure and physicochemical data for compounds 91-144
| Compound | Product | Carboxylic acid | $^1$H NMR; LCMS m/z [M + H]$^+$ |
|---|---|---|---|
| 126 | 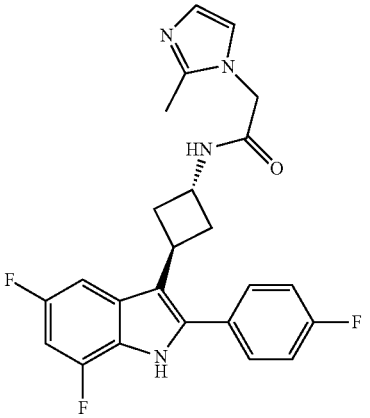 [SMILES: Cc1nccn1CC(=O)N[C@H]1C[C@H](c2c(-c3ccc(F)cc3)[nH]c3c(F)cc(F)cc32)C1] | 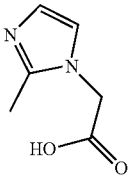 | LCMS m/z 439.17 [M + H]$^+$ |
| 127 | 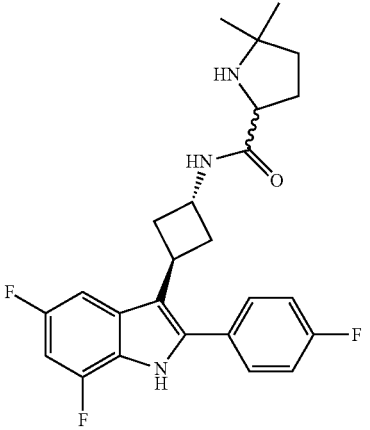 [SMILES: CC1(C)CCC(C(=O)N[C@H]2C[C@H](c3c(-c4ccc(F)cc4)[nH]c4c(F)cc(F)cc43)C2)N1] | 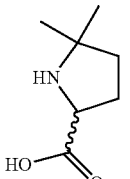 | LCMS m/z 442.2 [M + H]$^+$ |
| 128 | 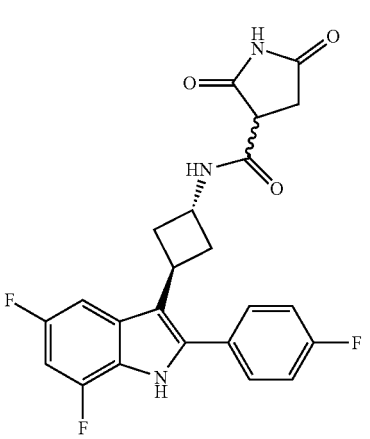 [SMILES: O=C1CC(C(=O)N[C@H]2C[C@H](c3c(-c4ccc(F)cc4)[nH]c4c(F)cc(F)cc43)C2)C(=O)N1] | 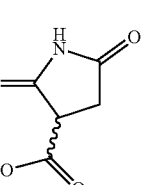 | LCMS m/z 442.1 [M + H]$^+$ |

TABLE 5-continued
Structure and physicochemical data for compounds 91-144
| Compound | Product | Carboxylic acid | ¹H NMR; LCMS m/z [M + H]⁺ |
|---|---|---|---|
| 129 | 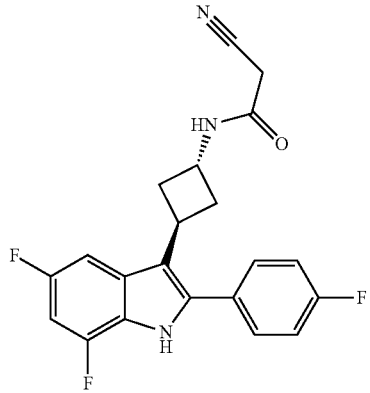 [SMILES: N#CCC(=O)N[C@H]1C[C@H](c2c(-c3ccc(F)cc3)[nH]c3c(F)cc(F)cc32)C1] | 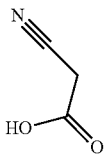 | LCMS m/z 384.02 [M + H]⁺ |
| 130 | 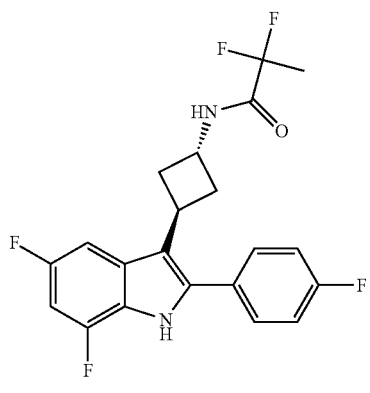 [SMILES: CC(F)(F)C(=O)N[C@H]1C[C@H](c2c(-c3ccc(F)cc3)[nH]c3c(F)cc(F)cc32)C1] | 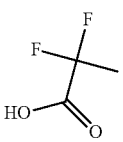 | LCMS m/z 409.2 [M + H]⁺ |
| 131 | 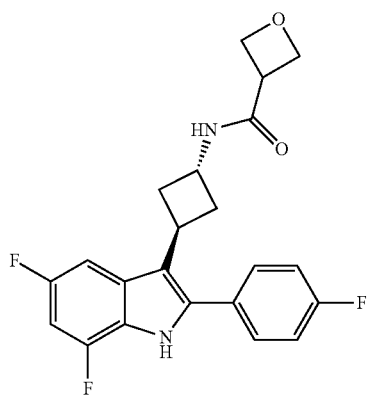 [SMILES: O=C(N[C@H]1C[C@H](c2c(-c3ccc(F)cc3)[nH]c3c(F)cc(F)cc32)C1)C1COC1] | 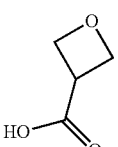 | LCMS m/z 401.15 [M + H]⁺ |

TABLE 5-continued
Structure and physicochemical data for compounds 91-144
| Compound | Product | Carboxylic acid | ¹H NMR; LCMS m/z [M + H]⁺ |
|---|---|---|---|
| 132 | 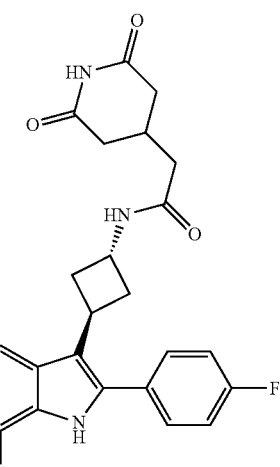 |  | LCMS m/z 470.15 [M + H]⁺ |
| 133 | 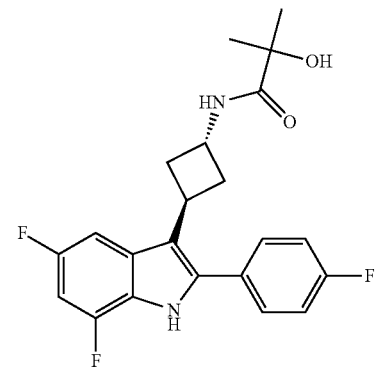 [SMILES: CC(C)(O)C(=O)N[C@H]1C[C@H](c2c(-c3ccc(F)cc3)[nH]c3c(F)cc(F)cc32)C1] | 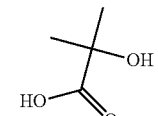 | LCMS m/z 403.17 [M + H]⁺ |
| 134 | 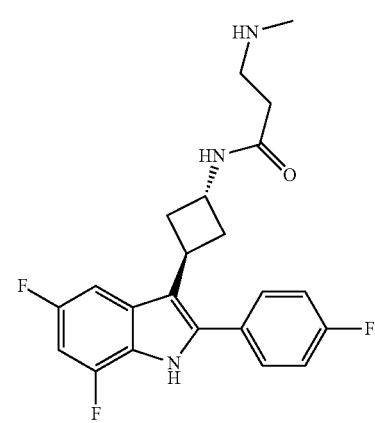 [SMILES: CNCCC(=O)N[C@H]1C[C@H](c2c(-c3ccc(F)cc3)[nH]c3c(F)cc(F)cc32)C1] | 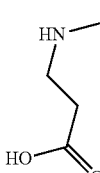 | LCMS m/z 402.16 [M + H]⁺ |

TABLE 5-continued
Structure and physicochemical data for compounds 91-144
| Compound | Product | Carboxylic acid | ¹H NMR; LCMS m/z [M + H]⁺ |
|---|---|---|---|
| 135 | 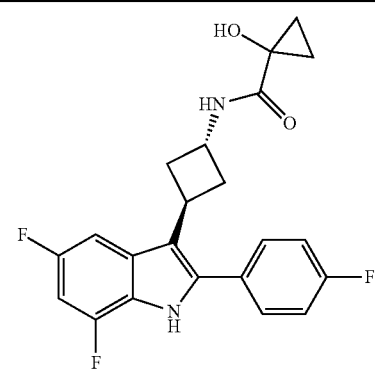 | 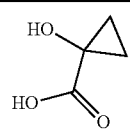 | LCMS m/z 401.15 [M + H]⁺ |
| 136 | 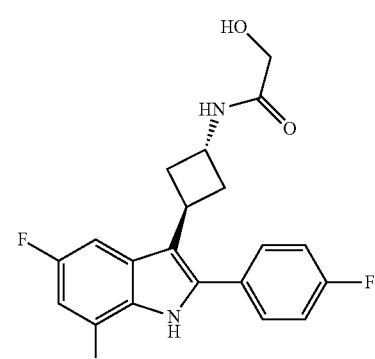 | 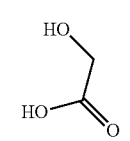 | ¹H NMR (400 MHz, Acetone-d₆) δ 10.72 (s, 1H), 7.65-7.58 (m, 2H), 7.47-7.37 (m, 1H), 7.32-7.25 (m, 2H), 6.86 (ddd, J = 11.0, 9.6, 2.2 Hz, 1H), 4.60 (dt, J = 12.8, 4.6 Hz, 1H), 4.20-4.09 (m, 1H), 3.94 (s, 2H), 2.84-2.76 (m, 2H), 2.54-2.44 (m, 2H); LCMS m/z 375.22 [M + H]⁺ |
| 137 | 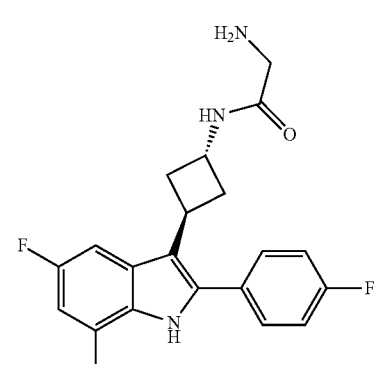 | 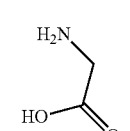 | LCMS m/z 374.18 [M + H]⁺ |
| 138 | 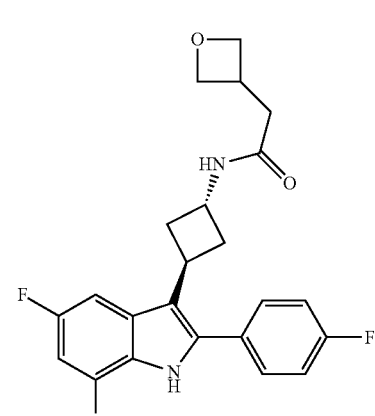 | 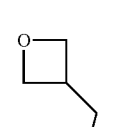 | LCMS m/z 415.23 [M + H]⁺ |

TABLE 5-continued
Structure and physicochemical data for compounds 91-144
| Compound | Product | Carboxylic acid | $^1$H NMR; LCMS m/z [M + H]$^+$ |
|---|---|---|---|
| 139 | 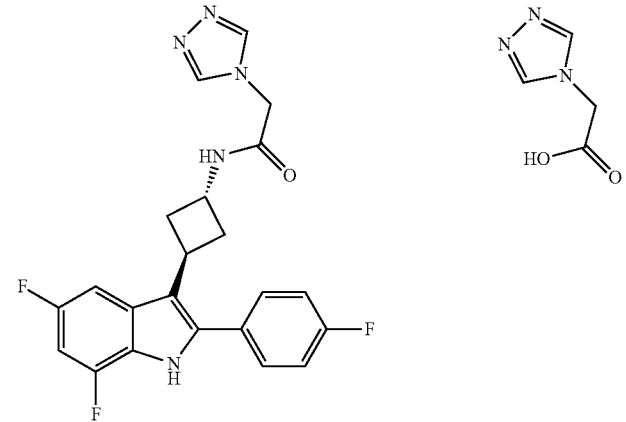 | 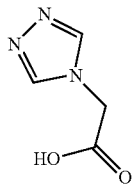 | LCMS m/z 426.14 [M + H]$^+$ |
| 140 | 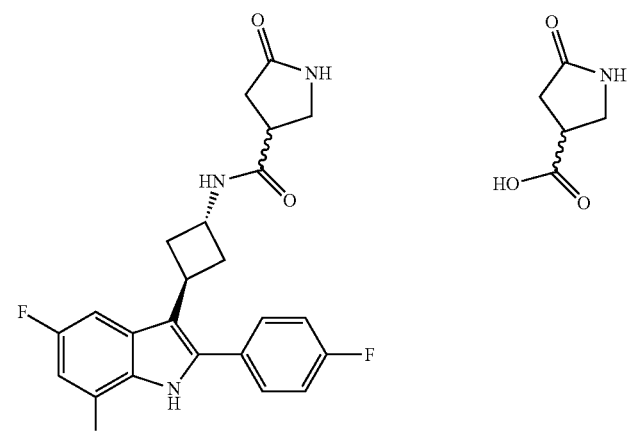 | 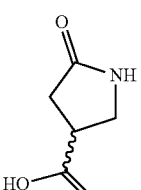 | LCMS m/z 428.28 [M + H]$^+$ |
| 141 | 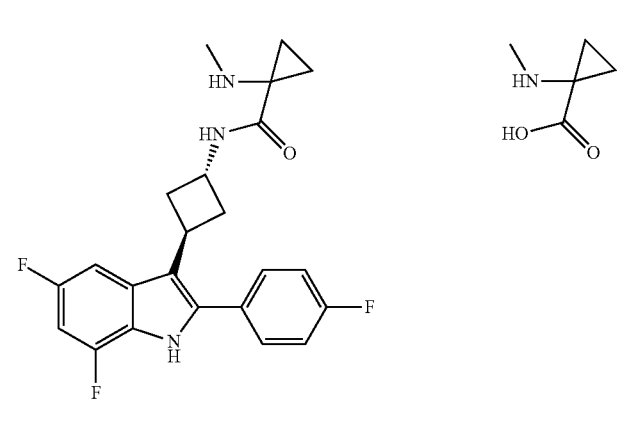 | 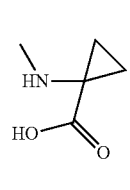 | LCMS m/z 414.18 [M + H]$^+$ |

TABLE 5-continued

Structure and physicochemical data for compounds 91-144

| Compound | Product | Carboxylic acid | ¹H NMR; LCMS m/z [M + H]⁺ |
|---|---|---|---|
| 142 | | | LCMS m/z 415.19 [M + H]⁺ |
| 143 | | | ¹H NMR (300 MHz, Acetone-d₆) δ 10.74 (s, 1H), 8.94 (t, J = 1.1 Hz, 1H), 8.24 (d, J = 6.6 Hz, 1H), 7.69-7.19 (m, 6H), 6.86 (dddd, J = 11.1, 9.7, 2.2, 1.5 Hz, 1H), 4.52 (td, J = 7.6, 4.0 Hz, 1H), 4.29-3.96 (m, 4H), 3.81 (d, J = 1.1 Hz, 2H), 2.92-2.67 (m, 2H), 2.42 (ddd, J = 13.4, 9.5, 3.7 Hz, 2H); LCMS m/z 439.2 [M + H]⁺ |
| 144 | | | LCMS m/z 395.23 [M + H]⁺ |

Compound 145

N-[(1r,3r)-3-[5,7-difluoro-2-(4-fluorophenyl)-1H-indol-3-yl]cyclobutyl]-1H-pyrazole-4-sulfonamide (145)

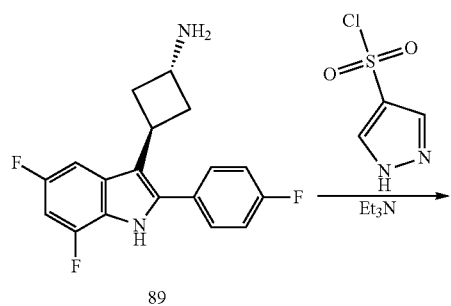

Standard Method E: Sulfonamide Coupling

To a solution of (1r,3r)-3-[5,7-difluoro-2-(4-fluorophenyl)-1H-indol-3-yl]cyclobutanamine 89 (30 mg, 0.09 mmol) in DMF (2 mL) was added 1H-pyrazole-4-sulfonyl chloride (20.5 mg, 0.123 mmol) followed by Et$_3$N (19 mg, 26 μL, 0.19 mmol). The reaction mixture was stirred at room temperature overnight. Purification by reversed phase chromatography (C18 column; Gradient: MeCN in H$_2$O with 0.1% trifluoroacetic acid) afforded the product (11.2 mg, 21%). $^1$H NMR (300 MHz, Acetone-d$_6$) δ 10.71 (s, 1H), 8.06-7.88 (m, 1H), 7.78-7.48 (m, 2H), 7.47-7.18 (m, 3H), 6.84 (dddd, J=10.9, 9.7, 5.0, 2.6 Hz, 2H), 4.20-3.99 (m, 2H), 2.81-2.66 (m, 2H), 2.49-2.32 (m, 2H); LCMS m/z 446.95 [M+H]$^+$.

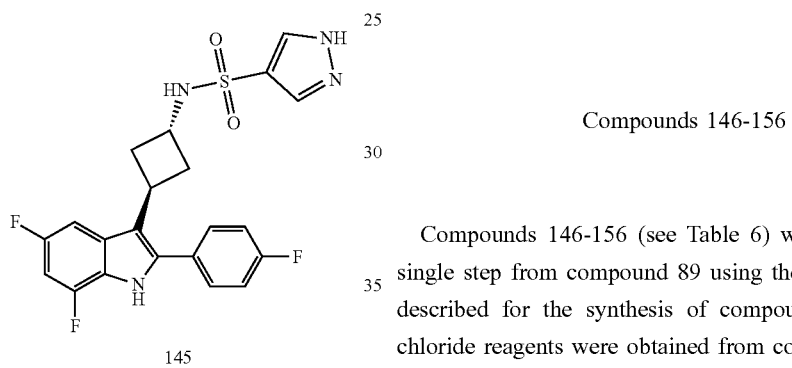

Compounds 146-156

Compounds 146-156 (see Table 6) were prepared in a single step from compound 89 using the standard method described for the synthesis of compound 145. Sulfonyl chloride reagents were obtained from commercial sources. Any modifications to methods are noted in Table 6 and accompanying footnotes.

TABLE 6

Structure and physicochemical data for compounds 146-156

| Cmpd | Product | Sulfonyl chloride | $^1$H NMR; LCMS m/z [M + H]$^+$ |
|---|---|---|---|
| 146 | ![structure] | ![structure] | $^1$H NMR (300 MHz, Acetone-d$_6$) δ 10.74 (s, 1H), 7.62 (ddd, J = 8.7, 4.9, 2.0 Hz, 2H), 7.42 (dd, J = 9.9, 2.1 Hz, 1H), 7.29 (tt, J = 8.9, 1.9 Hz, 2H), 6.86 (ddd, J = 11.5, 8.3, 2.1 Hz, 1H), 6.73-6.42 (m, 1H), 4.26 (dtd, J = 10.8, 7.9, 2.9 Hz, 1H), 4.20-4.06 (m, 1H), 3.97 (t, J = 6.3 Hz, 2H), 3.25 (t, J = 6.2 Hz, 2H), 2.95-2.74 (m, 2H), 2.58-2.50 (m, 2H). LCMS m/z 424.96 [M + H]$^+$ |

TABLE 6-continued
Structure and physicochemical data for compounds 146-156
| Cmpd | Product | Sulfonyl chloride | $^1$H NMR; LCMS m/z [M + H]$^+$ |
|---|---|---|---|
| 147 | 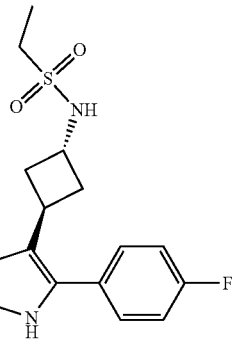 | 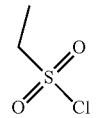 | LCMS m/z 409.1 [M + H]$^+$ |
| 148 | 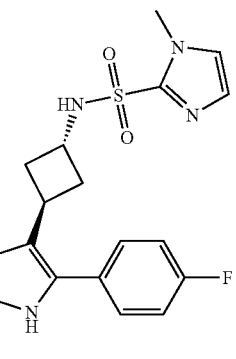 | 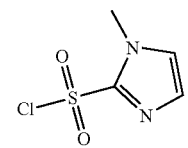 | LCMS m/z 461.09 [M + H]$^+$ |
| 149 | 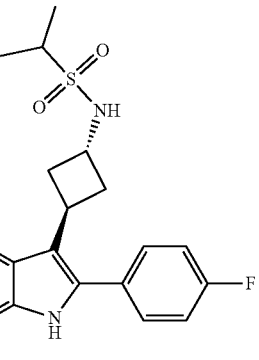 | 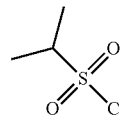 | LCMS m/z 423.04 [M + H]$^+$ |
| 150 | 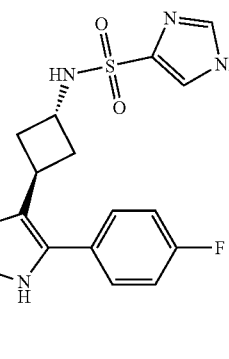 | 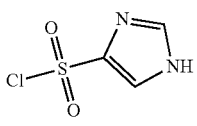 | LCMS m/z 446.95 [M + H]$^+$ |

TABLE 6-continued
Structure and physicochemical data for compounds 146-156
| Cmpd | Product | Sulfonyl chloride | $^1$H NMR; LCMS m/z [M + H]$^+$ |
|---|---|---|---|
| 151 | 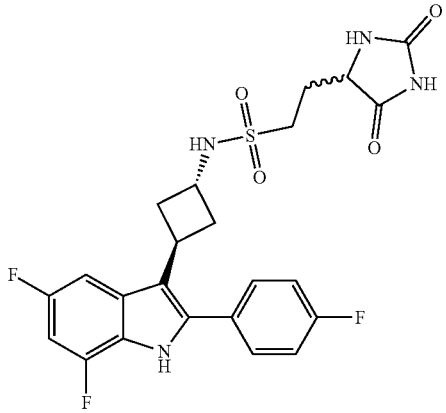 [SMILES: O=C1NC(=O)C(CCS(=O)(=O)N[C@H]2C[C@H](c3c(-c4ccc(F)cc4)[nH]c4c(F)cc(F)cc43)C2)N1] | 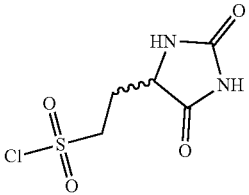 [SMILES: O=C1NC(=O)C(CCS(=O)(=O)Cl)N1] | LCMS m/z 507.31 [M + H]$^+$ |
| 152 | 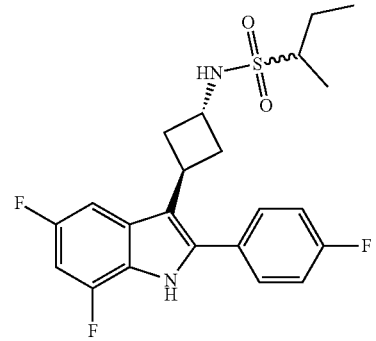 [SMILES: CCC(C)S(=O)(=O)N[C@H]1C[C@H](c2c(-c3ccc(F)cc3)[nH]c3c(F)cc(F)cc32)C1] | 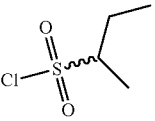 | LCMS m/z 437.01 [M + H]$^+$ |
| 153 | 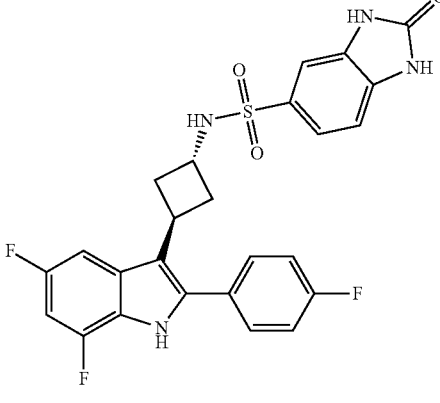 | 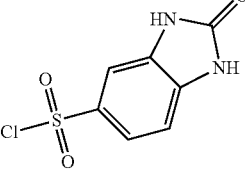 | LCMS m/z 513.17 [M + H]$^+$ |

TABLE 6-continued

Structure and physicochemical data for compounds 146-156

| Cmpd | Product | Sulfonyl chloride | ¹H NMR; LCMS m/z [M + H]⁺ |
|---|---|---|---|
| 154 | | | ¹H NMR (300 MHz, Acetone-$d_6$) δ 13.62 (s, 1H), 10.73 (s, 1H), 8.67 (d, J = 4.4 Hz, 1H), 8.44 (dd, J = 8.2, 1.7 Hz, 1H), 7.52 (td, J = 10.3, 9.5, 6.1 Hz, 3H), 7.42 (dd, J = 8.2, 4.5 Hz, 1H), 7.27 (dt, J = 17.7, 9.4 Hz, 3H), 6.95-6.67 (m, 1H), 4.30 (qt, J = 7.9, 4.1 Hz, 1H), 4.05 (dd, J = 17.6, 8.7 Hz, 1H), 2.66 (dd, J = 13.6, 7.0 Hz, 2H), 2.42 (ddd, J = 13.6, 9.5, 4.3 Hz, 2H); LCMS m/z 498.26 [M + H]⁺ |
| 155 | | | LCMS m/z 524.25 [M + H]⁺ |
| 156 | | | ¹H NMR (300 MHz, Acetone-$d_6$) δ 10.73 (s, 1H), 7.72-7.53 (m, 2H), 7.45-7.15 (m, 3H), 6.96-6.50 (m, 2H), 4.26 (tddd, J = 8.1, 4.7, 3.4, 1.2 Hz, 1H), 4.18-4.07 (m, 1H), 4.07-3.91 (m, 2H), 3.38 (td, J = 11.9, 2.2 Hz, 2H), 3.18 (tt, J = 12.0, 3.9 Hz, 1H), 2.96-2.73 (m, 2H), 2.68-2.43 (m, 2H), 2.04-1.87 (m, 2H), 1.73 (dtd, J = 13.2, 11.9, 4.6 Hz, 2H); LCMS m/z 465.09 [M + H]⁺ |

Preparation S3

3-((5,7-difluoro-2-(4-fluorophenyl)-1H-indol-3-yl)methyl)cyclobutan-1-amine (S3)

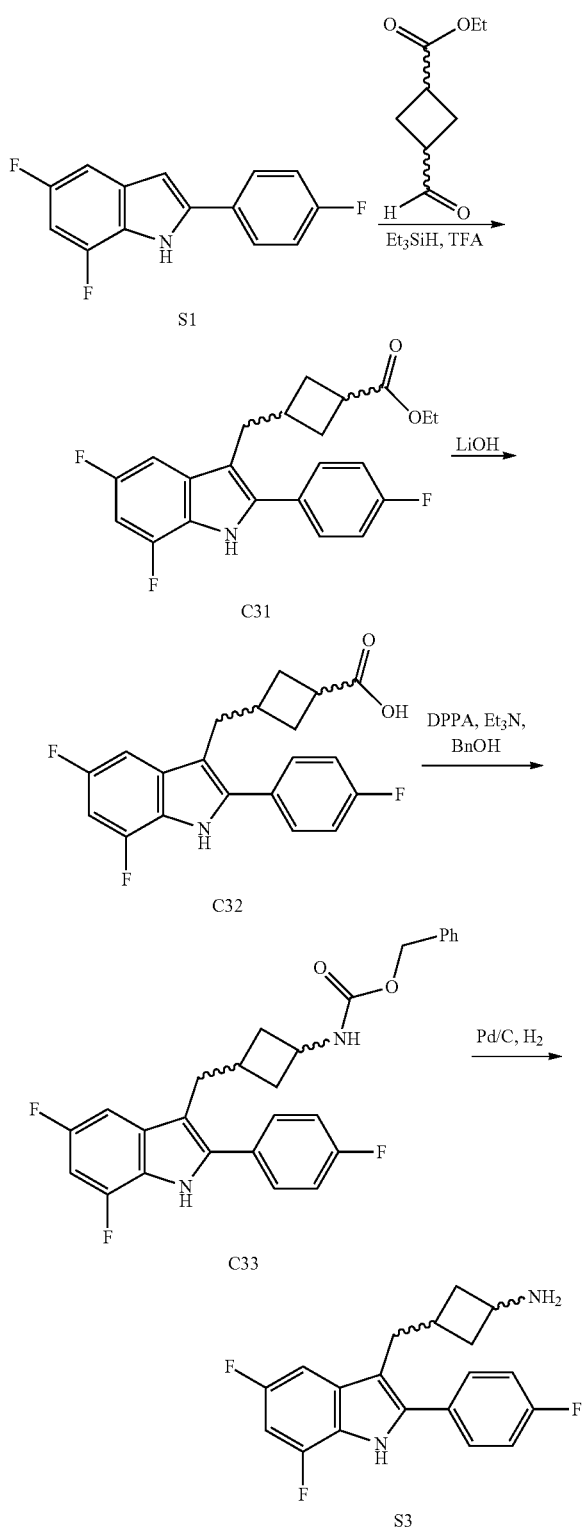

Step 1. Synthesis of ethyl 3-[[5,7-difluoro-2-(4-fluorophenyl)-1H-indol-3-yl]methyl]cyclobutanecarboxylate (C31)

5,7-difluoro-2-(4-fluorophenyl)-1H-indole S1 (750 mg, 3.034 mmol) and ethyl 3-formylcyclobutanecarboxylate (2.4 g, 15.37 mmol) were dissolved in $CH_2Cl_2$ (8 mL) and added $Et_3SiH$ (1.8 g, 15.48 mmol) and TFA (1.7 g, 14.91 mmol). The reaction mixture was stirred at room temperature overnight. The organic solvent (including TFA) was removed under reduced pressure. The resulting crude material was quenched with aqueous $NaHCO_3$ solution and extracted with EtOAc. The organic layer was washed with brine and dried over $Na_2SO_4$, concentrated and purified by silica gel column using hexane and EtOAc to provide ethyl 3-[[5,7-difluoro-2-(4-fluorophenyl)-1H-indol-3-yl]methyl]cyclobutanecarboxylate (1.1 g, 90%) as a mixture of diastereomers. $^1$H NMR (300 MHz, Acetone-$d_6$) δ 10.70 (s, 1H), 7.74 (dddd, J=8.4, 7.5, 5.2, 3.1 Hz, 2H), 7.39-7.15 (m, 3H), 6.82 (ddd, J=11.1, 9.7, 2.2 Hz, 1H), 4.03 (qd, J=7.1, 2.6 Hz, 2H), 3.11-2.93 (m, 2H), 2.93-2.78 (m, 1H), 2.79-2.48 (m, 1H), 2.26-2.10 (m, 2H), 1.97-1.77 (m, 2H), 1.43-1.20 (m, 1H), 1.16 (td, J=7.1, 1.5 Hz, 3H). LCMS m/z 388.35 $[M+H]^+$.

Step 2. Synthesis of 3-[[5,7-difluoro-2-(4-fluorophenyl)-1H-indol-3-yl]methyl]cyclobutanecarboxylic acid (C32)

Ethyl 3-[[5,7-difluoro-2-(4-fluorophenyl)-1H-indol-3-yl]methyl]cyclobutanecarboxylate C31 (1 g, 1.862 mmol) was dissolved in THF (10 mL), water (10 mL) and then LiOH (90 mg, 3.758 mmol) was added. The reaction mixture was stirred overnight. The reaction mixture was then concentrated, diluted with water and EtOAc. The organic layer was neutralized with 1N HCl and extracted with EtOAc. The combined organic layers were washed with brine and dried over $Na_2SO_4$. The organic layer was then concentrated and purified via column chromatography (Isco gradient 0-20% MeOH in DCM) to provide 3-[[5,7-difluoro-2-(4-fluorophenyl)-1H-indol-3-yl]methyl]cyclobutanecarboxylic acid (800 mg, quantitative) $^1$H NMR (300 MHz, Acetone-$d_6$) δ 10.71 (s, 1H), 7.88-7.64 (m, 2H), 7.43-7.08 (m, 3H), 6.82 (ddd, J=11.0, 9.7, 2.2 Hz, 1H), 3.15-3.04 (m, 1H), 3.01-2.94 (m, 1H), 2.94-2.79 (m, 1H), 2.79-2.48 (m, 1H), 2.29-2.11 (m, 2H), 1.90 (qdd, J=9.4, 5.3, 2.4 Hz, 2H). LCMS m/z 360.31 $[M+H]^+$.

Step 3. Synthesis of benzyl N-[3-[[5,7-difluoro-2-(4-fluorophenyl)-1H-indol-3-yl]methyl]cyclobutyl]carbamate (C33)

3-[[5,7-difluoro-2-(4-fluorophenyl)-1H-indol-3-yl]methyl]cyclobutanecarboxylic acid C32 (4000 mg, 7.888 mmol) was taken in toluene (40 mL). DPPA (2.6 g, 9.448 mmol) and $Et_3N$ (1000 mg, 9.882 mmol) were then added. The reaction mixture was heated at 90° C. for 6 hours. Then benzyl alcohol (2 mL) was added, and the reaction was heated overnight. The reaction mixture was cooled to room temperature, diluted with EtOAc and saturated $NaHCO_3$ solution. The organic layer was washed with brine and dried over $Na_2SO_4$. The crude material was purified via column chromatography to provide benzyl N-[3-[[5,7-difluoro-2-(4-fluorophenyl)-1H-indol-3-yl]methyl]cyclobutyl]carbamate (2 g, 30%). LCMS m/z 465.3 $[M+H]^+$.

Step 4. Synthesis of 3-[[5,7-difluoro-2-(4-fluorophenyl)-1H-indol-3-yl]methyl]cyclobutanamine (S3)

Under $N_2$, Pd/C (25 mg, 0.2349 mmol) was added to a round bottom flask, followed by MeOH (20 mL). Then benzyl N-[3-[[5,7-difluoro-2-(4-fluorophenyl)-1H-indol-3-yl]methyl]cyclobutyl]carbamate C33 (2000 mg, 2.364 mmol) was added. The reaction mixture was stirred under H₂ for 3 hours. The reaction mixture was filtered using Celite® pad, concentrated to provide the crude material as a white solid. The solid was further triturated with CH₂Cl₂ and filtered to provide 3-[[5,7-difluoro-2-(4-fluorophenyl)-1H-indol-3-yl]methyl]cyclobutanamine (700 mg, 69%). LCMS m/z 331.28 [M+H]⁺.

Compounds 157 and 158 trans-3-[[5,7-difluoro-2-(4-fluorophenyl)-1H-indol-3-yl]methyl]cyclobutanamine (157) and cis-3-[[5,7-difluoro-2-(4-fluorophenyl)-1H-indol-3-yl]methyl]cyclobutanamine (158)

2.180 mmol) and Et₃N (205 mg, 2.026 mmol) were then added. The reaction mixture was heated at 90° C. for 2 hours. Then benzyl alcohol (2 mL) was added, and the reaction was heated overnight. The reaction mixture was cooled to room temperature, diluted with EtOAc and saturated NaHCO₃ solution. The organic layer was washed with brine and dried over Na₂SO₄. The crude material was purified via silica gel column chromatography to provide a mixture of diastereomers (300 mg). The diastereomeric mixture was separated into constituent diastereomers by chiral SFC separation. Column: Daicel Chiralpak® AD-H, 20×250 mm; Mobile Phase: 40% ethyl alcohol (containing 5 mM Ammonia), 60% carbon dioxide. Flow: 80 mL/min.

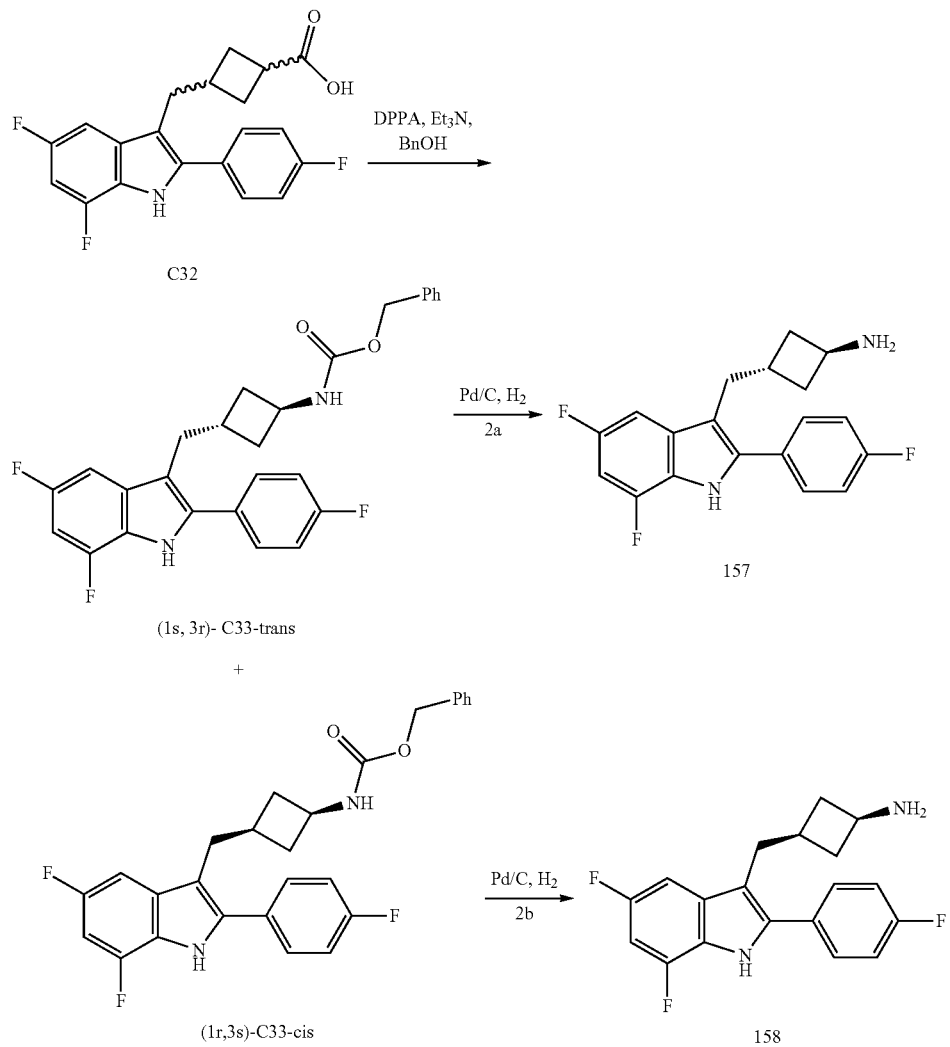

Step 1. Synthesis of trans and cis benzyl N-[3-[[5,7-difluoro-2-(4-fluorophenyl)-1H-indol-3-yl]methyl]cyclobutyl]carbamate (C33-trans and C33-cis)

3-[[5,7-difluoro-2-(4-fluorophenyl)-1H-indol-3-yl]methyl]cyclobutanecarboxylic acid C32 (800 mg, 1.688 mmol) was dissolved in toluene (20 mL). DPPA (600 mg, Products were isolated as: benzyl N-[(1s,3r)-3-[[5,7-difluoro-2-(4-fluorophenyl)-1H-indol-3-yl]methyl]cyclobutyl]carbamate C33-trans (96 mg, 22%) LCMS m/z 465.25 [M+H]⁺; benzyl N-[(1r,3 s)-3-[[5,7-difluoro-2-(4-fluorophenyl)-1H-indol-3-yl]methyl]cyclobutyl]carbamate C33-cis (93 mg, 22%) LCMS m/z 465.25 [M+H]⁺.

Step 2a. Synthesis of (1s,3r)-3-[[5,7-difluoro-2-(4-fluorophenyl)-1H-indol-3-yl]methyl]cyclobutanamine (157)

Standard Method F: Benzyl Carbamate Deprotection

Under $N_2$, Pd/C (5 mg, 0.04698 mmol) was added to a round bottom flask, followed by MeOH (20 mL). Then benzyl N-[(1s,3r)-3-[[5,7-difluoro-2-(4-fluorophenyl)-1H-indol-3-yl]methyl]cyclobutyl]carbamate C33-trans (100 mg, 0.1968 mmol) was added. The reaction mixture was stirred under $H_2$ for 3 hours. The reaction mixture was filtered through a pad of Celite®, concentrated in vacuo to provide the crude material as a white solid. The solid was further triturated with $CH_2Cl_2$ and filtered to provide (1s,3r)-3-[[5,7-difluoro-2-(4-fluorophenyl)-1H-indol-3-yl]methyl]cyclobutanamine (40 mg, 54%). LCMS m/z 331.24 $[M+H]^+$.

Step 2b. Synthesis of (1r,3s)-3-[[5,7-difluoro-2-(4-fluorophenyl)-1H-indol-3-yl]methyl]cyclobutanamine (158)

(1r,3s)-3-[[5,7-difluoro-2-(4-fluorophenyl)-1H-indol-3-yl]methyl]cyclobutanamine was prepared using standard method F. $^1$H NMR (300 MHz, Acetone-$d_6$) δ 11.21 (s, 1H), 7.32-7.09 (m, 2H), 7.05-6.87 (m, 2H), 6.77 (dd, J=9.6, 2.2 Hz, 1H), 6.50 (ddd, J=11.7, 9.8, 2.2 Hz, 1H), 3.19 (p, J=8.2, 7.8 Hz, 1H), 2.44 (d, J=6.2 Hz, 2H), 1.88-1.67 (m, 3H), 1.26-0.92 (m, 2H). LCMS m/z 331.28 $[M+H]^+$.

Compound 159

N-[3-[[5,7-difluoro-2-(4-fluorophenyl)-1H-indol-3-yl]methyl]cyclobutyl]-1-(hydroxymethyl)cyclopropanecarboxamide (159)

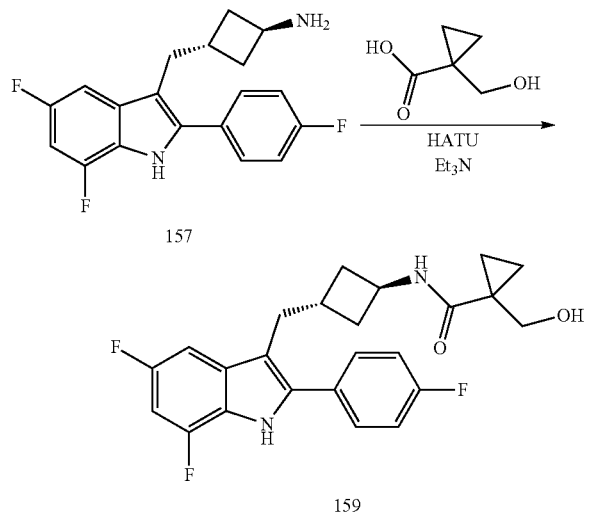

1-(Hydroxymethyl)cyclopropanecarboxylic acid (8 mg, 0.06890 mmol) was dissolved in DMF (2 mL), followed by the addition of (1s,3r)-3-[[5,7-difluoro-2-(4-fluorophenyl)-1H-indol-3-yl]methyl]cyclobutanamine 157 (20 mg, 0.06054 mmol), HATU (28 mg, 0.07364 mmol) and $Et_3N$ (15 mg, 0.1482 mmol). The reaction mixture was stirred overnight. The reaction mixture was filtered. Purification by reversed-phase HPLC. Method: C18 Waters Sunfire column (30×150 mm, 5 micron). Gradient: MeCN in $H_2O$ with 0.1% trifluoroacetic acid. The final product was isolated as N-[3-[[5,7-difluoro-2-(4-fluorophenyl)-1H-indol-3-yl]methyl]cyclobutyl]-1-(hydroxymethyl)cyclopropanecarboxamide (trifluoroacetate salt) (8 mg, 21%). $^1$H NMR (300 MHz, Acetone-$d_6$) δ 10.66 (s, 1H), 7.75 (dd, J=8.5, 5.5 Hz, 2H), 7.53-7.15 (m, 3H), 6.81 (td, J=10.4, 9.6, 2.1 Hz, 1H), 4.38 (q, J=7.4 Hz, 1H), 3.58 (s, 2H), 3.08 (d, J=8.0 Hz, 2H), 2.58 (td, J=8.3, 4.3 Hz, 1H), 2.03-1.78 (m, 4H), 0.97 (q, J=3.9 Hz, 2H), 0.56 (q, J=3.8 Hz, 2H). LCMS m/z 429.17 $[M+H]^+$.

Compound 160

N-[3-[[5,7-difluoro-2-(4-fluorophenyl)-1H-indol-3-yl]methyl]cyclobutyl]-3-hydroxy-3-methylbutanamide (160)

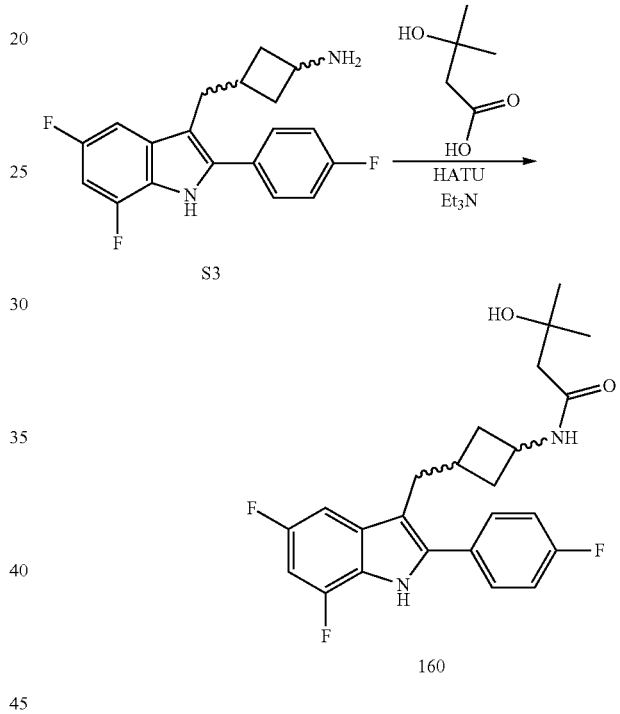

Standard Method G: Amide Coupling with HATU

3-[[5,7-difluoro-2-(4-fluorophenyl)-1H-indol-3-yl]methyl]cyclobutanamine S3 (20 mg, 0.061 mmol), 3-hydroxy-3-methyl-butanoic acid (10.7 mg, 0.091 mmol) were dissolved in DMF (2 mL). Then HATU (27.6 mg, 0.073 mmol) and $Et_3N$ (129 mg, 1.27 mmol). The reaction mixture was stirred at room temperature overnight. The reaction mixture was filtered. Purification by reversed-phase HPLC. Method: C18 Waters Sunfire column (30×150 mm, 5 micron). Gradient: MeCN in $H_2O$ with 0.1% trifluoroacetic acid. The final product was isolated as N-[3-[[5,7-difluoro-2-(4-fluorophenyl)-1H-indol-3-yl]methyl]cyclobutyl]-3-hydroxy-3-methylbutanamide (trifluoroacetic acid salt) (21.8 mg, 66%). LCMS m/z 431.18 $[M+H]^+$.

Compounds 161-172

Compounds 161-172 (see Table 7) were prepared in a single step from intermediate S3 using standard method G. Carboxylic acids were obtained from commercial sources. Any modifications to methods are noted in Table 7 and accompanying footnotes.

TABLE 7

Structure and physicochemical data for compounds 161-172

| Compound | Product | Carboxylic Acid | $^1$H NMR; LCMS m/z [M + H]$^+$ |
|---|---|---|---|
| 161 | | | LCMS m/z 403.14 [M + H]$^+$ |
| 162 | | | LCMS m/z 439.13 [M + H]$^+$ |
| 163 | | | LCMS m/z 442.13 [M + H]$^+$ |
| 164 | | | LCMS m/z 470.14 [M + H]$^+$ |
| 165 | | | LCMS m/z 416.04 [M + H]$^+$ |
| 166 | | | LCMS m/z 425.16 [M + H]$^+$ |

TABLE 7-continued
Structure and physicochemical data for compounds 161-172
| Compound | Product | Carboxylic Acid | $^1$H NMR; LCMS m/z [M + H]$^+$ |
|---|---|---|---|
| 167 | 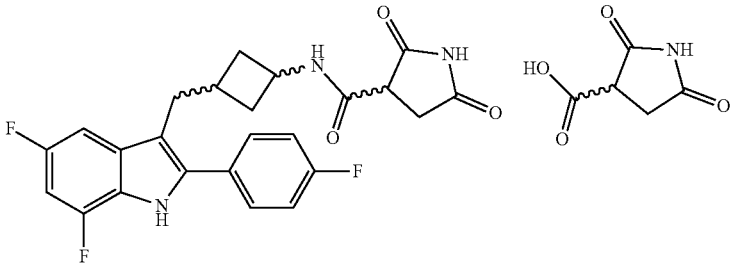 | 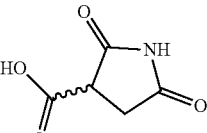 | LCMS m/z 456.23 [M + H]$^+$ |
| 168 | 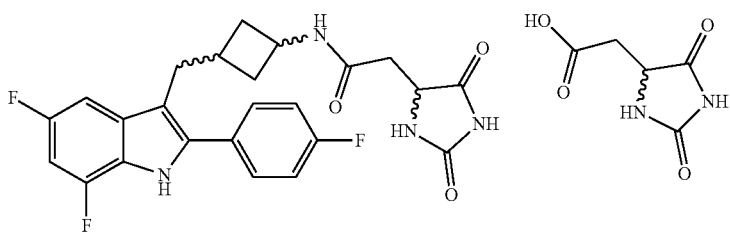 | 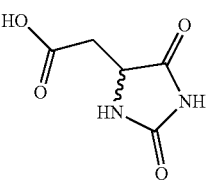 [SMILES: O=C(O)CC1NC(=O)NC1=O] | LCMS m/z 471.12 [M + H]$^+$ |
| 169 | 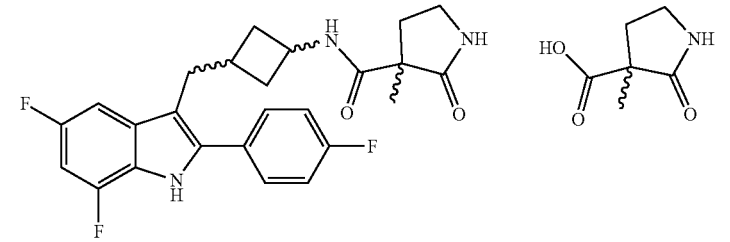 | 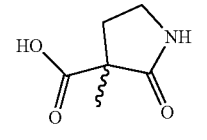 | LCMS m/z 456.17 [M + H]$^+$ |
| 170 | 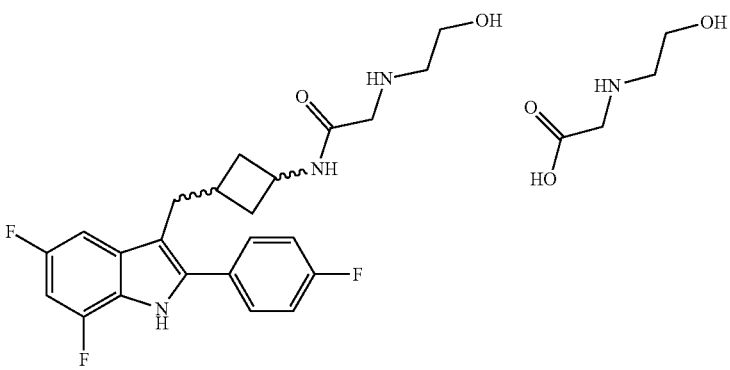 | 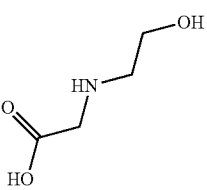 | LCMS m/z 430.21 [M + H]$^+$ |
| 171 | 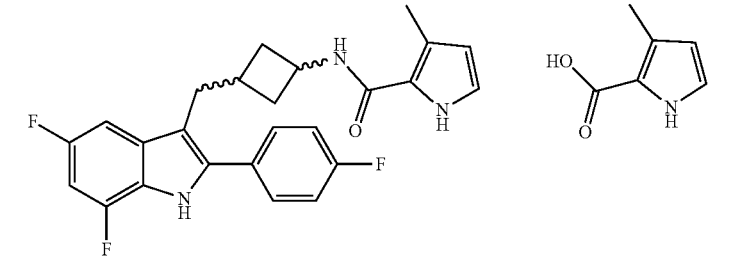 | 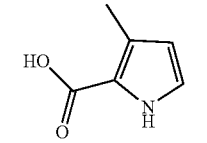 | LCMS m/z 438.12 [M + H]$^+$ |

TABLE 7-continued

Structure and physicochemical data for compounds 161-172

| Compound | Product | Carboxylic Acid | $^1$H NMR; LCMS m/z [M + H]$^+$ |
|---|---|---|---|
| 172 | 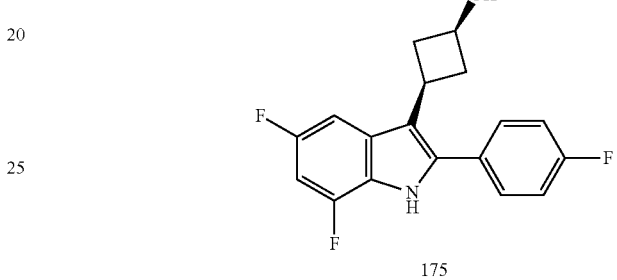 | | LCMS m/z 438.15 [M + H]$^+$ |

Compounds 173, 174, and 175

[3-[5,7-difluoro-2-(4-fluorophenyl)-1H-indol-3-yl]cyclobutyl]acetate (173), (1r,3r)-3-(5,7-difluoro-2-(4-fluorophenyl)-1H-indol-3-yl)cyclobutan-1-ol (174), and (1s,3s)-3-(5,7-difluoro-2-(4-fluorophenyl)-1H-indol-3-yl)cyclobutan-1-ol (175)

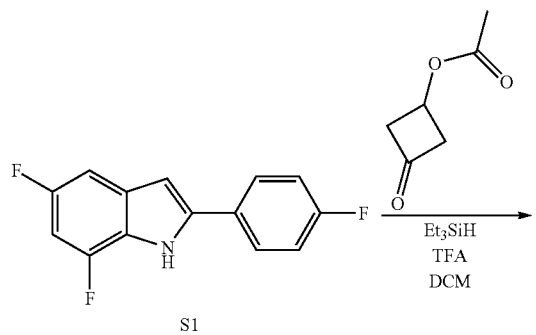

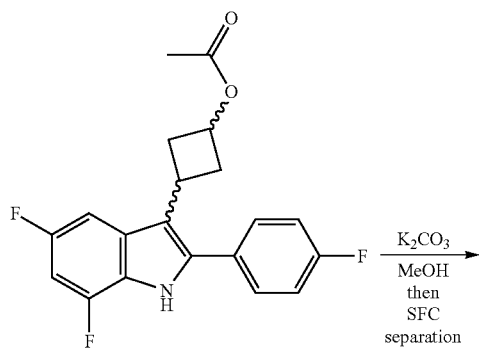

Step 1. Synthesis of [3-[5,7-difluoro-2-(4-fluorophenyl)-1H-indol-3-yl]cyclobutyl]acetate (173)

To a mixture of 5,7-difluoro-2-(4-fluorophenyl)-1H-indole S1 (100 mg, 0.40 mmol), (3-oxocyclobutyl) acetate (62 mg, 0.48 mmol), Et$_3$SiH (230 mg, 2.0 mmol), and DCM (1.8 mL) was added TFA (226 mg, 2.0 mmol). After stirring overnight at room temperature, the reaction was concentrated in vacuo. Purification by reversed phase chromatography (C18 column; Gradient: MeCN in H$_2$O with 0.1% trifluoroacetic acid) yielded the product (24.4 mg, 13%) as a mixture of cis and trans isomers. $^1$H NMR (300 MHz, Methanol-d$_4$) δ 7.67-7.40 (m, 2H), 7.33-7.10 (m, 3H), 6.74 (dddd, J=10.9, 9.6, 2.2, 1.0 Hz, 1H), 5.07-4.91 (m, 1H), 3.47 (tt, J=10.2, 7.9 Hz, 1H), 2.89-2.65 (m, 2H), 2.60-2.27 (m, 2H), 2.05 (d, J=10.2 Hz, 3H). LCMS m/z 360.18 [M+H]$^+$.

Step 2. Synthesis of (1r,3r)-3-(5,7-difluoro-2-(4-fluorophenyl)-1H-indol-3-yl)cyclobutan-1-ol (174) and (1s,3s)-3-(5,7-difluoro-2-(4-fluorophenyl)-1H-indol-3-yl)cyclobutan-1-ol (175)

To a solution of [3-[5,7-difluoro-2-(4-fluorophenyl)-1H-indol-3-yl]cyclobutyl]acetate 173 (700 mg, 1.2 mmol) in MeOH (10 mL) was added K$_2$CO$_3$ (200 mg, 1.4 mmol) at room temperature. The mixture was then partitioned between EtOAc and aqueous sat. sodium bicarbonate solution. The organic phase was separated, dried over magnesium sulfate, filtered, and concentrated in vacuo. The residue was purified by chiral SFC separation (Column: Daicel Chiralpak® OJ-H, 20×250 mm; Mobile Phase: 20% isopropanol (containing 5 mM Ammonia), 80% carbon dioxide. Flow: 75 mL/min.) to afford the trans isomer (1r,3r)-3-(5,7-difluoro-2-(4-fluorophenyl)-1H-indol-3-yl)cyclobutan-1-ol (100 mg, 46%) $^1$H NMR (300 MHz, Acetone-d$_6$) δ 10.67

(s, 1H), 7.81-7.51 (m, 2H), 7.51-7.07 (m, 3H), 6.99-6.62 (m, 1H), 4.58 (dt, J=6.9, 3.5 Hz, 1H), 4.13 (ttd, J=9.2, 7.9, 1.1 Hz, 2H), 2.79-2.55 (m, 2H), 2.50-2.25 (m, 2H). LCMS m/z 318.28 [M+H]⁺. and the cis isomer (1s,3s)-3-(5,7-difluoro-2-(4-fluorophenyl)-1H-indol-3-yl)cyclobutan-1-ol (180 mg, 81%) ¹H NMR (300 MHz, Acetone-d₆) δ 10.65 (s, 1H), 7.75-7.39 (m, 3H), 7.38-7.11 (m, 2H), 6.83 (ddd, J=11.0, 9.6, 2.2 Hz, 1H), 4.20 (dt, J=14.2, 7.1 Hz, 1H), 3.31 (tt, J=10.3, 7.8 Hz, 1H), 2.79-2.58 (m, 2H), 2.33 (dddd, J=10.5, 8.8, 7.9, 2.8 Hz, 2H). ¹H NMR (300 MHz, Chloroform-d) δ 8.04 (s, 1H), 7.46 (ddt, J=8.2, 5.1, 2.5 Hz, 2H), 7.37 (dd, J=9.6, 2.2 Hz, 1H), 7.24-7.10 (m, 2H), 6.77 (ddd, J=11.3, 9.4, 2.1 Hz, 1H), 4.43-4.22 (m, 1H), 3.27 (tt, J=10.2, 7.7 Hz, 1H), 2.86-2.66 (m, 2H), 2.45-2.17 (m, 2H), 1.79 (s, 1H). LCMS m/z 318.0 [M+H]⁺.

Compound 176

(3-(2-(4-chlorophenyl)-5,7-difluoro-1H-indol-3-yl)cyclobutyl)methanamine (176)

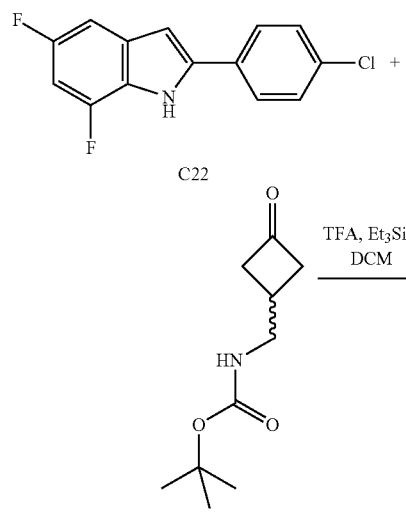

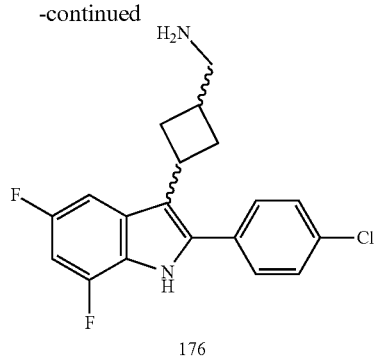

A 30 mL vial was charged with a magnetic stir bar, 2-(4-chlorophenyl)-5,7-difluoro-1H-indole (52 mg, 0.18 mmol) C22, tert-butyl N-[(3-oxocyclobutyl)methyl]carbamate (60 mg, 0.30 mmol) DCM (800 µL) and Et₃SiH (130 mg, 1.118 mmol). To the stirred mixture was then added TFA (130 mg, 1.14 mmol) and the reaction was allowed to stir overnight at room temperature before being concentrated in vacuo to afford the crude reaction product which was submitted for reverse phase HPLC purification (water/MeCN/0.1% TFA 5 to 95%) to afford a 1:1 cis/trans mixture of [3-[2-(4-chlorophenyl)-5,7-difluoro-1H-indol-3-yl]cyclobutyl]methanamine (Trifluoroacetate salt) (41 mg, 48%). LCMS m/z 347.09 [M+H]⁺.

Compounds 177-185

Compounds 177-185 (see Table 8) were prepared in a single step from the listed indole intermediates using the method used to synthesize compound 176. Indoles were obtained from commercial sources or synthesized as above. Any modifications to methods are noted in Table 8.

4-(5,7-difluoro-1H-indol-2-yl)benzonitrile (C34), listed in Table 8 below, was prepared using a similar method as C6 replacing the reagent 1-iodo-4-methyl-benzene with 1-iodobenzonitrile.

TABLE 8

Structure and physicochemical data for compounds 177-185

| Compound | Product | Indole Starting Material | ¹H NMR; LCMS m/z [M + H]⁺ |
|---|---|---|---|
| 177 | | | LCMS m/z 335.18 [M + H]⁺ |

TABLE 8-continued
Structure and physicochemical data for compounds 177-185
| Compound | Product | Indole Starting Material | $^1$H NMR; LCMS m/z [M + H]$^+$ |
|---|---|---|---|
| 178 | 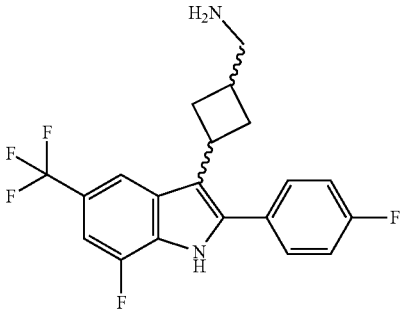 [SMILES: NCC1CC(c2c(-c3ccc(F)cc3)[nH]c3c(F)cc(C(F)(F)F)cc23)C1] | 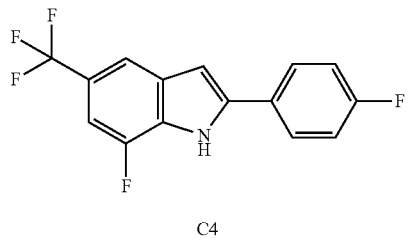 C4 | LCMS m/z 381.11 [M + H]$^+$ |
| 179 | 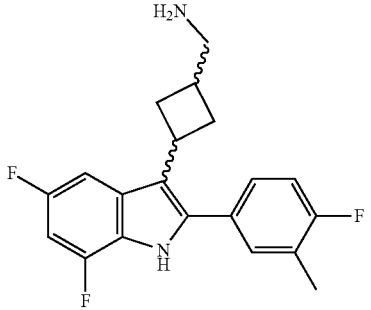 [SMILES: Cc1cc(-c2[nH]c3c(F)cc(F)cc3c2C2CC(CN)C2)ccc1F] | 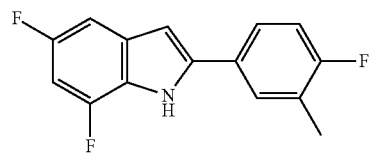 C23 | LCMS m/z 344.98 [M + H]$^+$ |
| 180 | 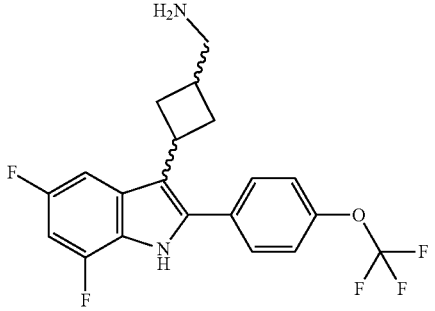 [SMILES: NCC1CC(c2c(-c3ccc(OC(F)(F)F)cc3)[nH]c3c(F)cc(F)cc23)C1] | 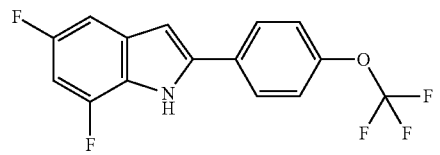 C20 | LCMS m/z 397.19 [M + H]$^+$ |
| 181 | 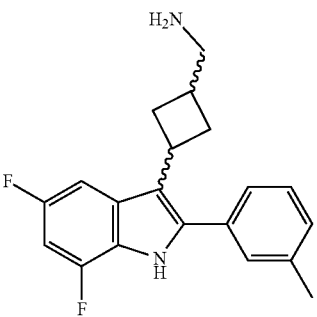 [SMILES: Cc1cccc(-c2[nH]c3c(F)cc(F)cc3c2C2CC(CN)C2)c1] | 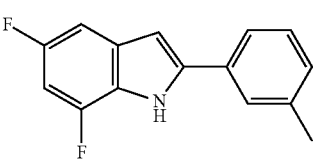 C7 | LCMS m/z 326.93 [M + H]$^+$ |

301
302
TABLE 8-continued
Structure and physicochemical data for compounds 177-185
| Compound | Product | Indole Starting Material | ¹H NMR; LCMS m/z [M + H]⁺ |
|---|---|---|---|
| 182 | 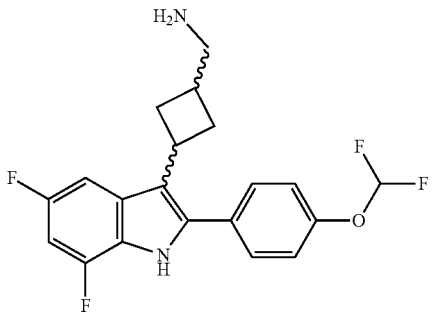 [SMILES: NCC1CC(c2c(-c3ccc(OC(F)F)cc3)[nH]c3c(F)cc(F)cc23)C1] | 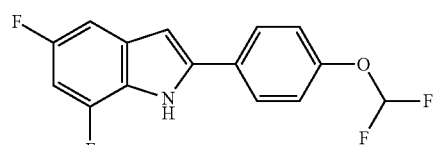 C21 | LCMS m/z 379.15 [M + H]⁺ |
| 183 | 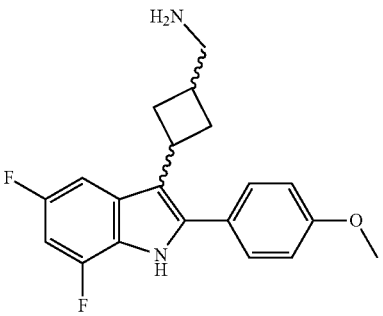 [SMILES: COc1ccc(-c2[nH]c3c(F)cc(F)cc3c2C2CC(CN)C2)cc1] | 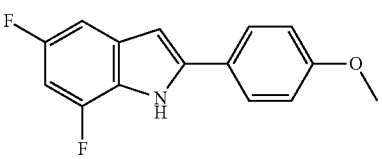 C24 | LCMS m/z 343.13 [M + H]⁺ |
| 184 | 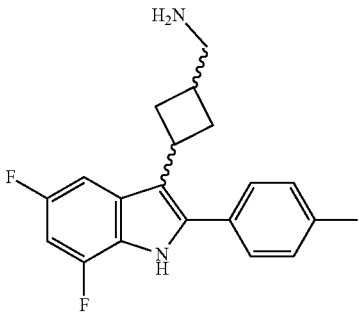 [SMILES: Cc1ccc(-c2[nH]c3c(F)cc(F)cc3c2C2CC(CN)C2)cc1] | 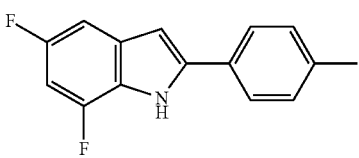 C6 | LCMS m/z 327.28 [M + H]⁺ |
| 185 | 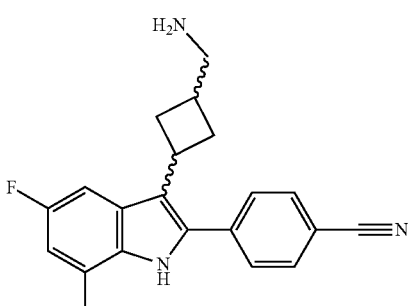 | 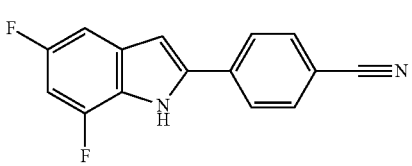 C34 | LCMS m/z 338.14 [M + H]⁺ |

Compound 186

(3-(5,7-difluoro-2-(4-fluorophenyl)-1H-indol-3-yl)cyclobutyl)methanamine (186)

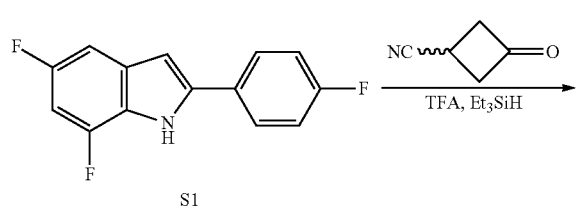

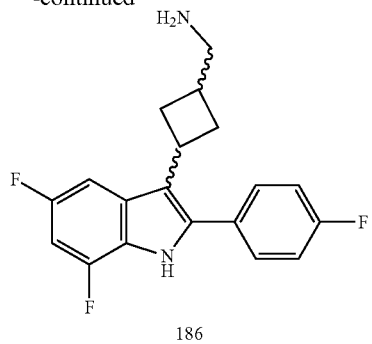

186

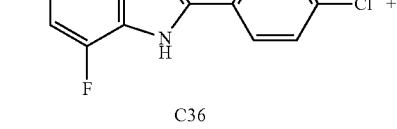

Step 1. Synthesis of 3-(5,7-difluoro-2-(4-fluorophenyl)-1H-indol-3-yl)cyclobutane-1-carbonitrile (C35)

A 250 mL round bottom flask was charged with a magnetic stir bar, 5,7-difluoro-2-(4-fluorophenyl)-1H-indole S1 (3.8 g, 13.8 mmol), 3-oxocyclobutanecarbonitrile (1.7 g, 17.8 mmol), DCM (100 mL), Et$_3$SiH (9.6 g, 82.5 mmol), and then TFA (9.5 g, 83.3 mmol) was added drop wise via syringe. After 16 h additional 3-oxocyclobutanecarbonitrile (1.7 g, 17.8 mmol), Et$_3$SiH (9.6 g, 82.5 mmol), and TFA (9.5 g, 83.3 mmol) were added and the mixture was allowed to stir for another 20 hours. The reaction was then judged to be complete by LCMS and was then carefully inverse quenched onto a solution of saturated aqueous NaHCO$_3$. Once a neutral pH was obtained the mixture was poured into a separatory funnel and extracted with DCM (2×500 mL). The organic extract was then combined, dried with MgSO$_4$, filtered through a bed of Celite® and concentrated in vacuo to afford the title compound C35 as a ~1:1 mixture of cis/trans.

Upon standing solids formed which were triturated with DCM (~50 mL). The resulting white solids were then collected via vacuum filtration using a Buchner funnel. The solids were determined to be the cis-product and the filtrate was mostly trans. The filtrate (trans) material was pre-absorbed onto Celite® and further purified via SiO$_2$ chromatography (120 g) using heptanes/ethyl acetate (8:1) as eluent to afford pure trans-3-[5,7-difluoro-2-(4-fluorophenyl)-1H-indol-3-yl]cyclobutanecarbonitrile C36 (1.7 g, 26%) LCMS m/z 327.28 [M+H]$^+$; and 3-[5,7-difluoro-2-(4-fluorophenyl)-1H-indol-3-yl]cyclobutanecarbonitrile C37 (2.2 g, 45%) LCMS m/z 327.28 [M+H]$^+$.

Step 2. Synthesis of (3-(5,7-difluoro-2-(4-fluorophenyl)-1H-indol-3-yl)cyclobutyl)methanamine (186)

A solution of 3-[5,7-difluoro-2-(4-fluorophenyl)-1H-indol-3-yl]cyclobutanecarbonitrile C35 (2.51 g, 6.388 mmol) in anhydrous THF (37 mL) was cooled to 0° C. in an ice bath under N$_2$. To the solution was added LiAlH$_4$ (16.5 mL of 2 M, 33.00 mmol) slowly. Upon complete addition the reaction was stirred at 0° C. for 10 minutes, then warmed to room temperature and then heated at 60° C. for 1 hour, after which time the reaction was complete. The reaction was then cooled to room temperature then slowly added to a cold solution of 1N aqueous Rochelle's salt (~200 mL). The reaction mixture was then poured into a separatory funnel partitioned with ethyl acetate (~200 mL). The organic phase was separated, washed with water, brine, and dried over anhydrous sodium sulfate. The solution was filtered through a bed of Celite® and concentrated in vacuo to afford the crude title compound as a solid. This material was purified by trituration with dichloromethane to afford white solids which were collected via vacuum filtration using a Buchner funnel and dried in vacuo to afford a ~1:1 cis/trans mixture of [3-[5,7-difluoro-2-(4-fluorophenyl)-1H-indol-3-yl]cyclobutyl]methanamine (2.01 g, 92%). LCMS m/z 331.16 [M+H]$^+$.

Compounds 187 and 188

Compounds 187 and 188 (see Table 9) were prepared in a single step from the listed nitriles using the method used to synthesize compound 186. Nitriles were synthesized as above.

TABLE 9

Structure and physicochemical data for compounds 187 and 188

| Compound | Product | Nitrile Starting Material | $^1$H NMR; LCMS m/z [M + H]$^+$ |
|---|---|---|---|
| 187 | [structure: H$_2$N-CH$_2$-cyclobutyl-3-yl attached to 5,7-difluoro-2-(4-fluorophenyl)-1H-indole] | [structure: NC-cyclobutyl-3-yl attached to 5,7-difluoro-2-(4-fluorophenyl)-1H-indole] C37 | $^1$H NMR (400 MHz, DMSO-d$_6$) δ 11.62 (s, 1H), 7.57 (dd, J = 8.5, 5.5 Hz, 2H), 7.46 (dd, J = 10.0, 2.2 Hz, 1H), 7.34 (t, J = 8.7 Hz, 2H), 7.01-6.91 (m, 1H), 3.59 (q, J = 9.6, 8.9 Hz, 1H), 2.56-2.50 (m, 2H), 2.3-2.22 (m, 3H), 2.02-1.97 (m, 2H). LCMS m/z 331.0 [M + H]$^+$ |
| 188 | [structure: H$_2$N-CH$_2$-cyclobutyl-3-yl attached to 5,7-difluoro-2-(4-fluorophenyl)-1H-indole] | [structure: NC-cyclobutyl-3-yl attached to 5,7-difluoro-2-(4-fluorophenyl)-1H-indole] C36 | $^1$H NMR (300 MHz, Acetone-d$_6$) δ 7.66-7.55 (m, 2H), 7.41 (ddd, J = 9.9, 5.6, 2.2 Hz, 1H), 7.32-7.24 (m, 2H), 6.84 (ddd, J = 11.1, 9.6, 2.2 Hz, 1H), 4.10-3.95 (m, 1H), 3.42 (s, 1H), 2.82 (d, J = 7.3 Hz, 1H), 2.68-2.48 (m, 3H), 2.25-2.16 (m, 2H); LCMS m/z 331.33 [M + H]$^+$ |

Compound 189

(S)-2-amino-N-(((1r,3S)-3-(5,7-difluoro-2-(4-fluoro-phenyl)-1H-indol-3-yl)cyclobutyl)methyl)propanamide (189)

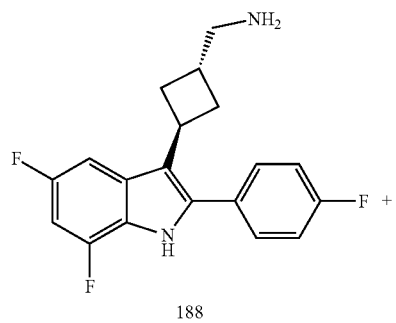

188

+

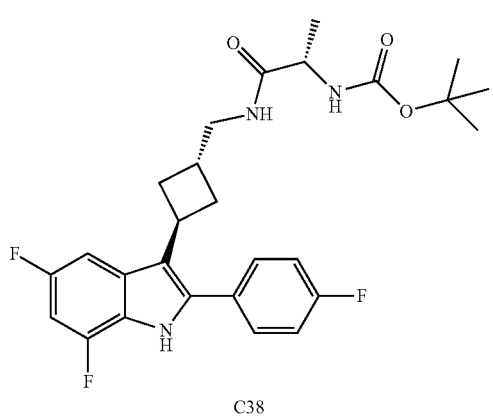

C38

$\xrightarrow{\text{HATU, Et}_3\text{N, DMF}}$ $\xrightarrow{\text{TFA}}$

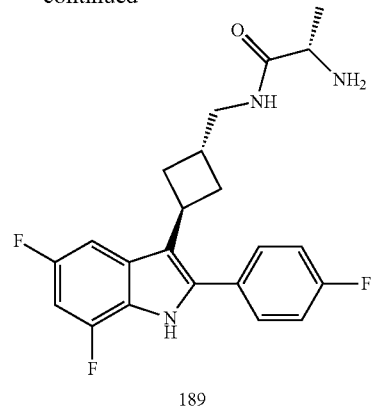

189

Step 1. Synthesis of tert-butyl N-[(1S)-2-[[3-[5,7-difluoro-2-(4-fluorophenyl)-1H-indol-3-yl]cyclobutyl]methylamino]-1-methyl-2-oxo-ethyl]carbamate (C38)

[3-[5,7-difluoro-2-(4-fluorophenyl)-1H-indol-3-yl]cyclobutyl]methanamine (35 mg, 0.105 mmol) 188 and (2S)-2-(tert-butoxycarbonylamino)propanoic acid (24 mg, 0.126 mmol) were mixed in DMF (1 mL). To this mixture was added HATU (48 mg, 0.126 mmol) and Et$_3$N (45 µL, 0.322 mmol). The reaction mixture was stirred at room temperature for 2 hours. Water was then added to the reaction mixture followed by extraction with EtOAc (3×2 mL). The combined organic fractions were washed with H$_2$O (1×2 mL), brine (1×2 mL), dried over anhydrous sodium sulfate, filtered, and concentrated in vacuo to obtain tert-butyl N-[(1S)-2-[[3-[5,7-difluoro-2-(4-fluorophenyl)-1H-indol-3-yl]cyclobutyl]methylamino]-1-methyl-2-oxo-ethyl]carbamate which was used in the next step without further purification.

Step 2. Synthesis of (2S)-2-amino-N-[[3-[5,7-difluoro-2-(4-fluorophenyl)-1H-indol-3-yl]cyclobutyl]methyl]propenamide (189)

The above material C38 was dissolved into DCM (0.5 mL) and TFA (500 µL, 6.490 mmol) was added. The mixture was stirred at room temperature for 30 minutes. and then concentrated in vacuo to afford (2S)-2-amino-N-[[3-[5,7-difluoro-2-(4-fluorophenyl)-1H-indol-3-yl]cyclobutyl]methyl]propenamide. LCMS m/z 402.43 [M+H]$^+$.

Compounds 190-331

Compounds 190-331 (see Table 10) were prepared in a single step or two steps from the listed indole intermediates and shown acid intermediates using either the method used to synthesize C38, the method used to synthesize 189 from C38, or the two-step method used to synthesize compound 189. Indoles were obtained from commercial sources or synthesized as above. Acid reagents were obtained from commercial sources. Any modifications to methods are noted in Table 10 and accompanying footnotes.

TABLE 10

Structure and physicochemical data for compounds 190-331

| Cmpd. | Method/Product | Starting materials | $^1$H NMR, LCMS m/z [M + H]$^+$ |
|---|---|---|---|
| 190 | As for compound 189 | | $^1$H NMR (400 MHz, Chloroform-d) δ 7.63-7.38 (m, 2H), 7.19 (ddt, J = 11.6, 8.9, 3.8 Hz, 3H), 6.84-6.61 (m, 1H), 4.13-3.67 (m, 1H), 3.30-3.11 (m, 3H), 2.95 (d, J = 6.0 Hz, 1H), 2.55 (td, J = 18.6, 13.5, 6.7 Hz, 3H), 2.22 (t, J = 9.5 Hz, 2H). LCMS m/z 388.44 [M + H]$^+$ |
| 191 | As for compound 189 | | $^1$H NMR (300 MHz, Methanol-d$_4$) δ 7.61-7.41 (m, 2H), 7.38-7.03 (m, 3H), 6.74 (ddd, J = 11.5, 9.7, 2.1 Hz, 1H), 4.09-3.86 (m, 1H), 3.76-3.67 (m, 2H), 3.49 (d, J = 6.0 Hz, 2H), 2.54 (d, J = 10.3 Hz, 3H), 2.16 (t, J = 9.1 Hz, 2H). LCMS m/z 388.39 [M + H]$^+$ |
| 192 | As for compound 189 | | $^1$H NMR (300 MHz, Methanol-d$_4$) δ 7.61-7.41 (m, 2H), 7.38-7.03 (m, 3H), 6.74 (ddd, J = 11.5, 9.7, 2.1 Hz, 1H), 4.09-3.86 (m, 1H), 3.76-3.67 (m, 2H), 3.49 (d, J = 6.0 Hz, 2H), 2.54 (d, J = 10.3 Hz, 3H), 2.16 (t, J = 9.1 Hz, 2H). LCMS m/z 415.16 [M + H]$^+$ |

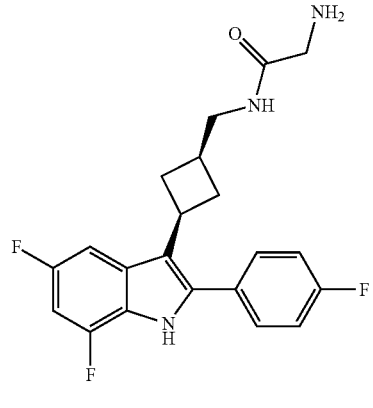
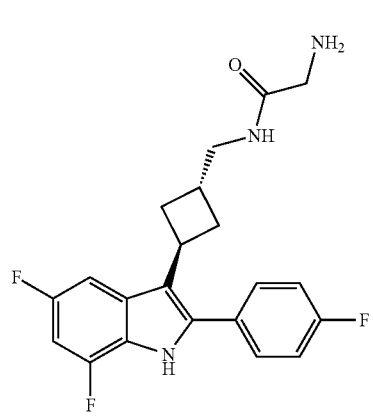
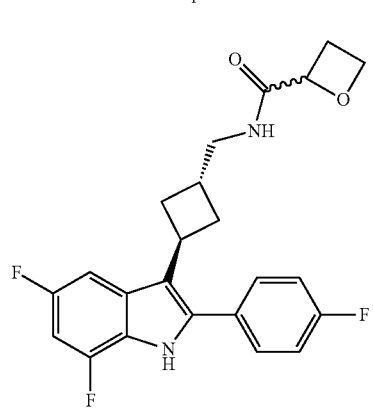

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 193 | As for compound C38 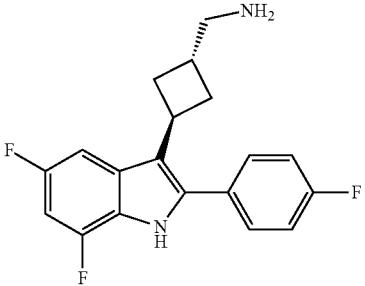 [SMILES: NC[C@H]1C[C@H](c2c(-c3ccc(F)cc3)[nH]c3c(F)cc(F)cc32)C1] | 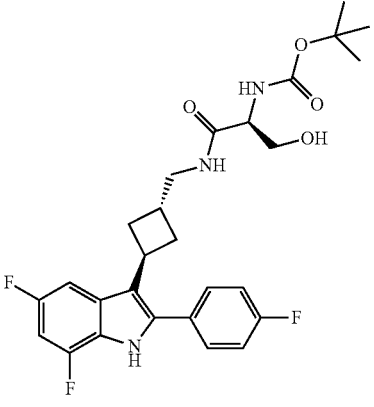 [SMILES: CC(C)(C)OC(=O)N[C@@H](CO)C(=O)NC[C@H]1C[C@H](c2c(-c3ccc(F)cc3)[nH]c3c(F)cc(F)cc32)C1] | LCMS m/z 518.22 [M + H]$^+$ |
| 194 | As for compound 189 from C38 | | LCMS m/z 418.36 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 195 | As for compound C38 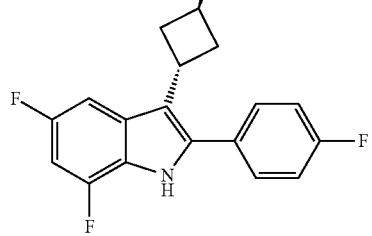 | 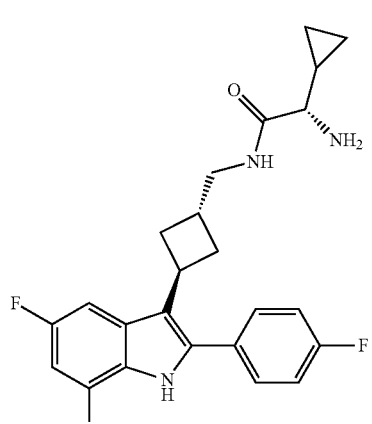 | LCMS m/z 373.21 [M + H]⁺ |
| 196 | As for compound 189 | | ¹H NMR (300 MHz, Methanol-d₄) δ 7.40 (dd, J = 8.2, 5.2 Hz, 2H), 7.26-7.00 (m, 3H), 6.64 (ddd, J = 11.2, 9.6, 1.9 Hz, 1H), 4.02-3.78 (m, 1H), 3.46 (s, 1H), 3.33 (dd, J = 13.6, 6.1 Hz, 1H), 3.07 (d, J = 9.3 Hz, 1H), 2.46 (t, J = 9.9 Hz, 3H), 2.10 (d, J = 9.9 Hz, 2H), 1.21-1.00 (m, 1H), 0.83-0.30 (m, 4H). LCMS m/z 428.31 [M + H]⁺ |
| 197 | As for compound 189 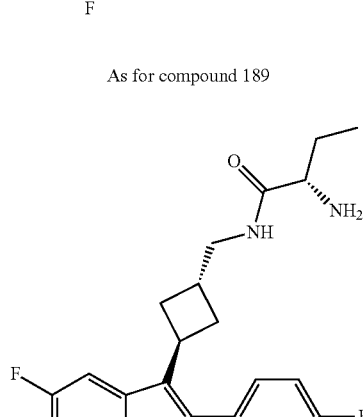 | | ¹H NMR (300 MHz, Methanol-d₄) δ 7.40 (dd, J = 8.4, 5.3 Hz, 2H), 7.26-7.01 (m, 3H), 6.64 (ddd, J = 11.4, 9.6, 2.0 Hz, 1H), 3.91 (q, J = 8.6, 8.1 Hz, 1H), 3.51-3.44 (m, 2H), 3.34 (dd, J = 13.1, 6.4 Hz, 1H), 2.56-2.34 (m, 3H), 2.06 (t, J = 9.6 Hz, 2H), 1.88-1.69 (m, 2H), 0.91 (t, J = 7.3 Hz, 3H). LCMS m/z 416.38 [M + H]⁺ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 198 | As for compound 189 | | LCMS m/z 414.14 [M + H]$^+$ |
| 199 | As for compound 189 | | LCMS m/z 428.44 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 200 | As for compound 189 | | ¹H NMR (300 MHz, Chloroform-d) δ 8.06 (s, 1H), 7.56-7.34 (m, 2H), 7.28 (dd, J = 9.5, 2.1 Hz, 1H), 7.25-7.16 (m, 2H), 6.78 (ddd, J = 10.8, 9.4, 2.2 Hz, 1H), 6.32 (s, 1H), 5.94 (t, J = 54.3 Hz, 1H), 3.99 (dt, J = 18.0, 8.9 Hz, 1H), 3.62 (t, J = 6.4 Hz, 2H), 2.77-2.53 (m, 3H), 2.16 (t, J = 9.1 Hz, 2H). LCMS m/z 409.14 [M + H]⁺ |
| 201 | As for compound 189 | | ¹H NMR (300 MHz, Methanol-d₄) δ 7.53-7.29 (m, 2H), 7.29-6.97 (m, 3H), 6.64 (ddd, J = 11.4, 9.6, 2.1 Hz, 1H), 3.91 (q, J = 8.7, 8.2 Hz, 1H), 3.82 (d, J = 8.7 Hz, 2H), 3.76-3.67 (m, 1H), 3.40 (d, J = 6.4 Hz, 2H), 2.44 (dd, J = 16.7, 7.8 Hz, 3H), 2.06 (t, J = 9.4 Hz, 2H). LCMS m/z 418.32 [M + H]⁺ |
| 202 | As for compound C38 | | ¹H NMR (300 MHz, Chloroform-d) δ 8.06 (s, 1H), 7.52-7.37 (m, 2H), 7.28-7.15 (m, 3H), 6.83-6.72 (m, 1H), 5.56 (d, J = 14.6 Hz, 1H), 5.11-4.63 (m, 4H), 4.07-3.90 (m, 1H), 3.81-3.65 (m, 1H), 3.65-3.50 (m, 2H), 2.73-2.48 (m, 3H), 2.14 (t, J = 9.3 Hz, 2H). LCMS m/z 415.19 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 203 | As for compound C38 | | LCMS m/z 389.17 [M + H]⁺ |
| 204 | As for compound C38 | | LCMS m/z 444.19 [M + H]⁺ |
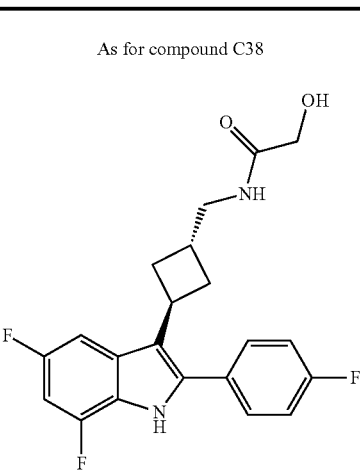
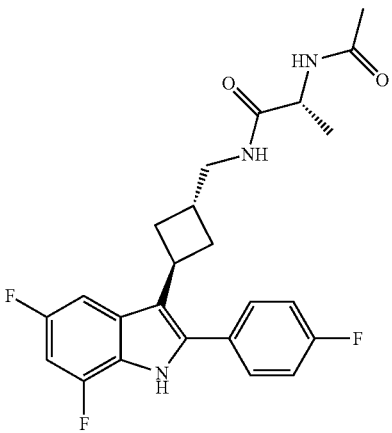

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 205 | As for compound 189 | | $^1$H NMR (300 MHz, Methanol-d$_4$) δ 7.40 (dd, J = 8.3, 5.2 Hz, 2H), 7.25-7.01 (m, 3H), 6.64 (ddd, J = 11.3, 9.6, 2.0 Hz, 1H), 5.38 (d, J = 51.6 Hz, 1H), 4.40 (q, J = 11.0, 8.6 Hz, 1H), 4.01-3.77 (m, 1H), 3.58 (s, 2H), 3.41 (d, J = 5.2 Hz, 2H), 2.69 (d, J = 14.3 Hz, 1H), 2.48 (s, 3H), 2.06 (t, J = 8.9 Hz, 3H). LCMS m/z 446.35 [M + H]$^+$ |
| 206 | As for compound C38 | | LCMS m/z 403.26 [M + H]$^+$ |
| 207 | As for compound C38 | | LCMS m/z 403.08 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 208 | As for compound C38 | | $^1$H NMR (300 MHz, Chloroform-d) δ 8.35 (s, 1H), 7.50-7.34 (m, 2H), 7.25 (dd, J = 9.5, 2.1 Hz, 1H), 7.20-7.03 (m, 2H), 6.83-6.68 (m, 2H), 6.63 (d, J = 7.6 Hz, 1H), 4.54 (p, J = 7.1 Hz, 1H), 4.09-3.78 (m, 1H), 3.66-3.37 (m, 2H), 2.54 (h, J = 5.3 Hz, 3H), 2.10 (t, J = 9.3 Hz, 2H), 2.00 (s, 3H), 1.38 (d, J = 7.0 Hz, 3H). LCMS m/z 444.33 [M + H]$^+$ |
| 209 | As for compound C38 | | LCMS m/z 417.21 [M + H]$^+$ |
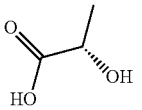
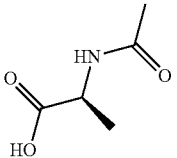

TABLE 10-continued
Structure and physicochemical data for compounds 190-331
| Cmpd. | Method/Product | Starting materials | ¹H NMR, LCMS m/z [M + H]⁺ |
|---|---|---|---|
| 210 | As for compound C38 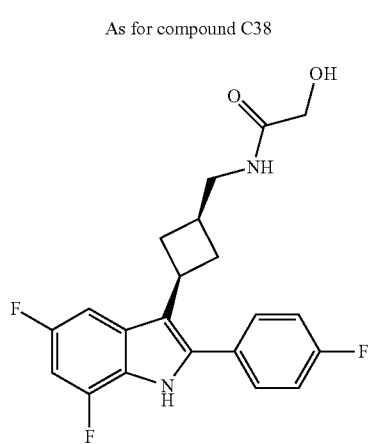 [SMILES: O=C(CO)NC[C@H]1C[C@@H](c2c(-c3ccc(F)cc3)[nH]c3c(F)cc(F)cc32)C1] | 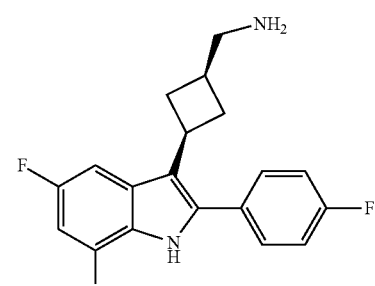 | LCMS m/z 389.25 [M + H]⁺ |
| 211 | As for compound C38 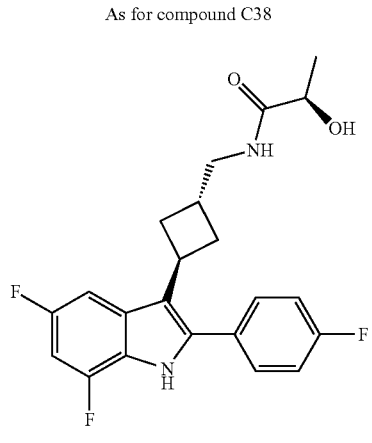 [SMILES: C[C@@H](O)C(=O)NC[C@H]1C[C@H](c2c(-c3ccc(F)cc3)[nH]c3c(F)cc(F)cc32)C1] | 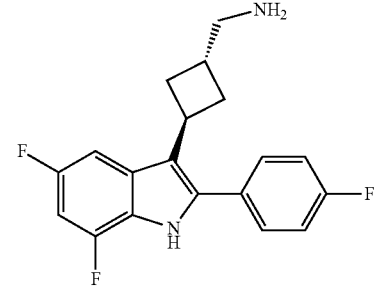 [SMILES: NC[C@H]1C[C@H](c2c(-c3ccc(F)cc3)[nH]c3c(F)cc(F)cc32)C1] | LCMS m/z 403.17 [M + H]⁺ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 212 | As for compound C38 | | LCMS m/z 488.19 [M + H]⁺ |
| 213 | As for compound C38 | | LCMS m/z 403.29 [M + H]⁺ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 214 | As for compound C38 | | $^1$H NMR (300 MHz, Methanol-d$_4$) δ 7.71-7.39 (m, 2H), 7.37-7.08 (m, 3H), 6.90-6.54 (m, 1H), 3.97 (s, 2H), 3.83-3.55 (m, 1H), 3.35 (s, 1H), 2.63-2.30 (m, 3H), 2.25-1.90 (m, 2H). LCMS m/z 389.38 [M + H]$^+$ |
| 215 | As for compound C38 | | LCMS m/z 488.19 [M + H]$^+$ |
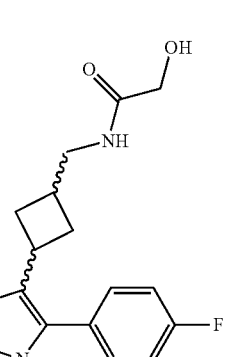
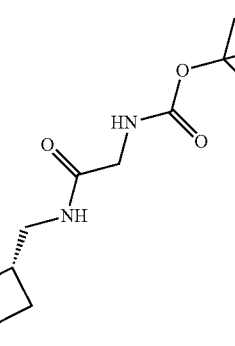

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 216 | As for compound C38 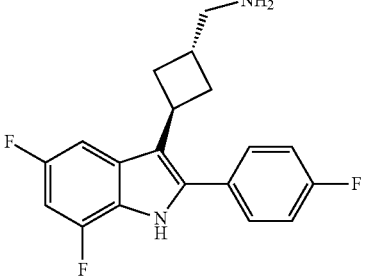 | 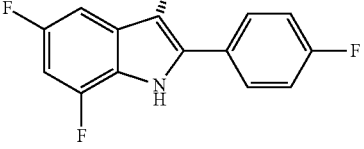 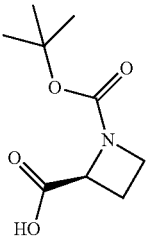 | LCMS m/z 514.35 [M + H]$^+$ |
| 217 | As for compound C38 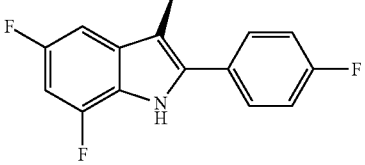 | 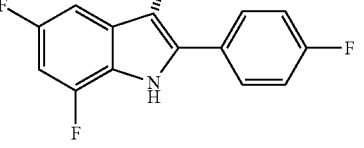 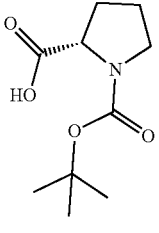 | LCMS m/z 528.29 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 218 | As for compound C38 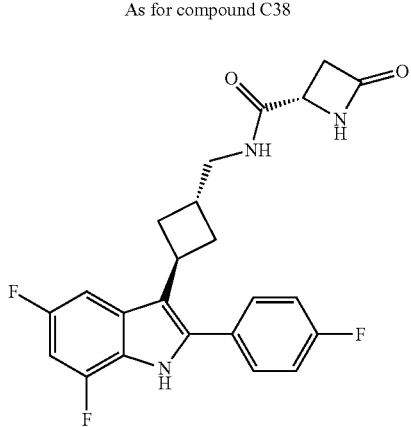 [SMILES: O=C1C[C@@H](C(=O)NC[C@H]2C[C@H](c3c(-c4ccc(F)cc4)[nH]c4c(F)cc(F)cc43)C2)N1] | 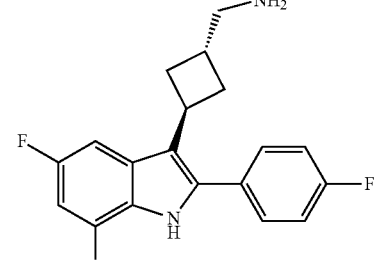 | LCMS m/z 428.29 [M + H]$^+$ |
| 219 | As for compound C38 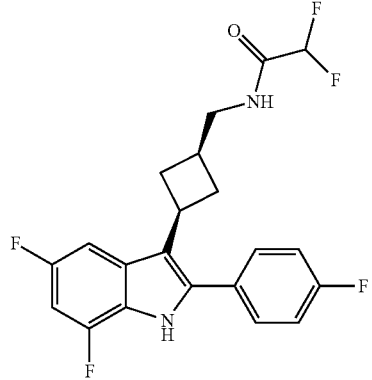 | 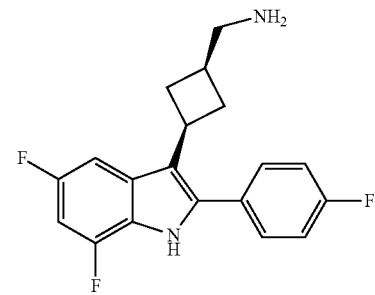 [SMILES: NC[C@H]1C[C@@H](c2c(-c3ccc(F)cc3)[nH]c3c(F)cc(F)cc32)C1] | LCMS m/z 409.23 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 220 | As for compound C38 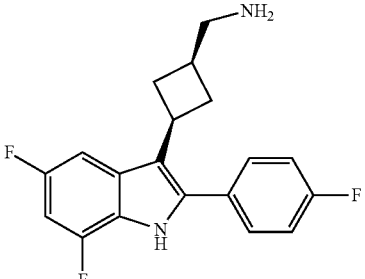 | 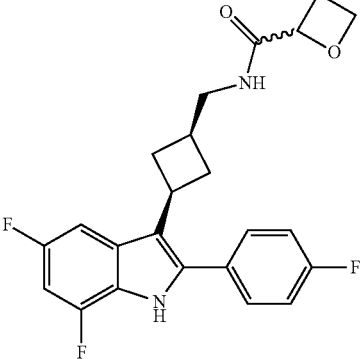 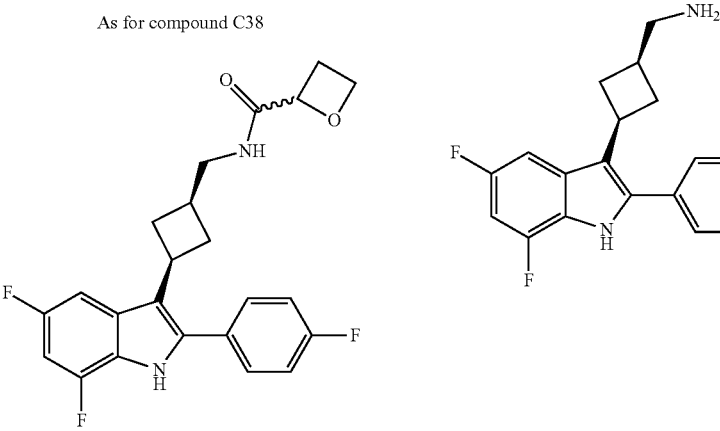 | LCMS m/z 415.28 [M + H]$^+$ |
| 221 | As for compound C38 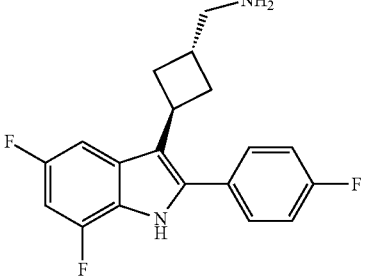 | 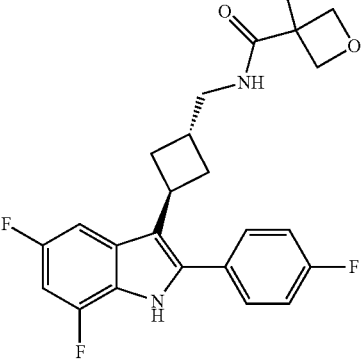 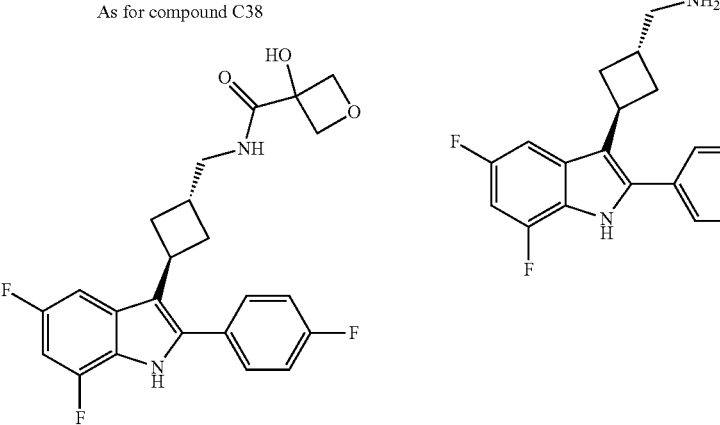 | LCMS m/z 431.09 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 222 | As for compound 189 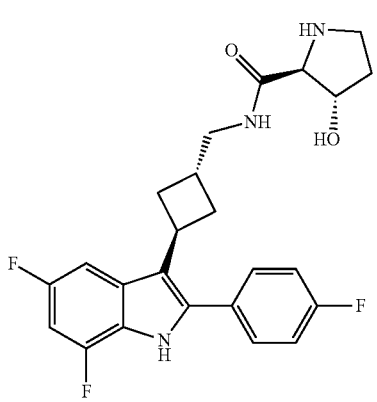 | 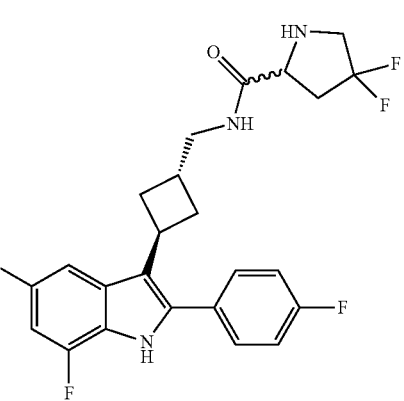 | ¹H NMR (300 MHz, Methanol-d₄) δ 7.63-7.45 (m, 2H), 7.38-7.19 (m, 3H), 6.77 (ddd, J = 11.5, 9.6, 2.1 Hz, 1H), 4.59-4.45 (m, 1H), 4.17 (d, J = 2.0 Hz, 1H), 4.02 (p, J = 9.3 Hz, 1H), 3.55 (ddd, J = 16.1, 7.0, 2.2 Hz, 4H), 2.57 (dd, J = 17.6, 7.7 Hz, 3H), 2.29-1.97 (m, 4H). LCMS m/z 444.33 [M + H]⁺ |
| 223 | As for compound 189 | | ¹H NMR (30 0MHz, Methanol-d₄) δ 7.61-7.38 (m, 2H), 7.37-7.09 (m, 3H), 6.74 (ddd, J = 11.3, 9.6, 1.9 Hz, 1H), 4.63 (s, 1H), 3.99 (t, J = 8.3 Hz, 1H), 3.94-3.79 (m, 2H), 3.53 (d, J = 5.8 Hz, 2H), 3.01 (s, 1H), 2.81-2.40 (m, 4H), 2.17 (t, J = 9.5 Hz, 2H). LCMS m/z 464.31 [M + H]⁺ |
| 224 | As for compound C38 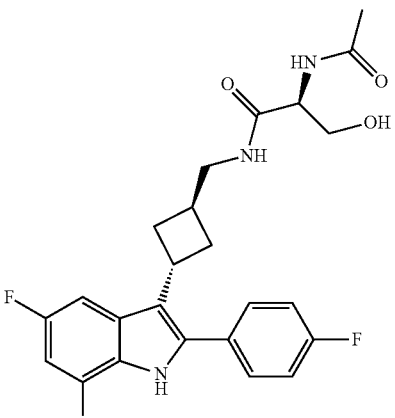 | | LCMS m/z 460.39 [M + H]⁺ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 225 | As for compound 189 | | $^1$H NMR (300 MHz, Methanol-d$_4$) δ 7.58-7.43 (m, 2H), 7.35-7.15 (m, 3H), 6.75 (ddd, J = 11.5, 9.7, 2.1 Hz, 1H), 4.59 (d, J = 3.6 Hz, 1H), 4.46 (dd, J = 10.5, 7.4 Hz, 1H), 4.01 (q, J = 8.8, 8.3 Hz, 1H), 3.82-3.67 (m, 1H), 3.61-3.37 (m, 3H), 2.67-2.41 (m, 4H), 2.27-1.96 (m, 3H). LCMS m/z 444.46 |
| 226 | As for compound C38 | | LCMS m/z 415.28 [M + H]$^+$ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 227 | As for compound C38 | | LCMS m/z 502.07 [M + H]$^+$ |
| 228 | As for compound C38 | | LCMS m/z 415.26 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 229 | As for compound 189 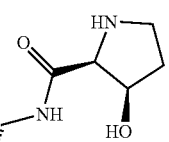 | 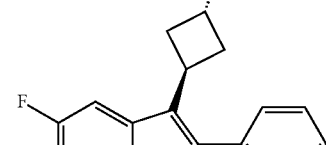 | $^1$H NMR (300 MHz, Methanol-d$_4$) δ 7.41 (dd, J = 8.4, 5.3 Hz, 2H), 7.14 (dt, J = 17.2, 8.6 Hz, 3H), 6.64 (td, J = 10.3, 9.5, 2.0 Hz, 1H), 4.60 (s, 1H), 4.09 (s, 1H), 4.01-3.81 (m, 1H), 3.64 (ddd, J = 5.9, 4.9, 1.2 Hz, 1H), 3.49 (dd, J = 5.2, 1.9 Hz, 1H), 3.47-3.38 (m, 2H), 2.66-2.32 (m, 3H), 2.09 (d, J = 12.6 Hz, 4H). LCMS m/z 444.42 [M + H]$^+$ |
| 230 | As for compound C38 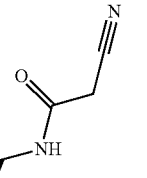 | 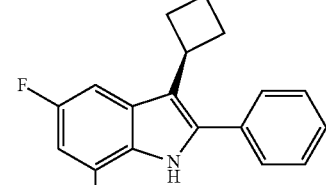 | LCMS m/z 398.25 |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 231 | As for compound C38 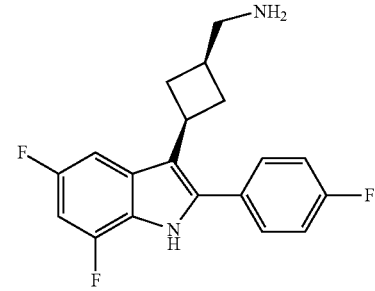 [SMILES: NC[C@H]1C[C@@H](c2c(-c3ccc(F)cc3)[nH]c3c(F)cc(F)cc32)C1] | 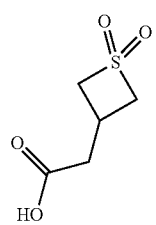 | LCMS m/z 477.21 [M + H]$^+$ |
| 232 | As for compound C38 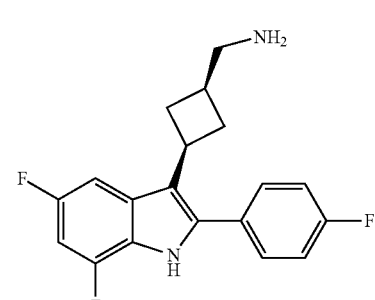 | 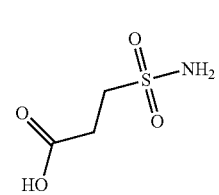 | LCMS m/z 466.14 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 233 | As for compound C38 | | LCMS m/z 455.98 [M + H]⁺ |
| 234 | As for compound C38 | | LCMS m/z 415.28 [M + H]⁺ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 235 | As for compound C38 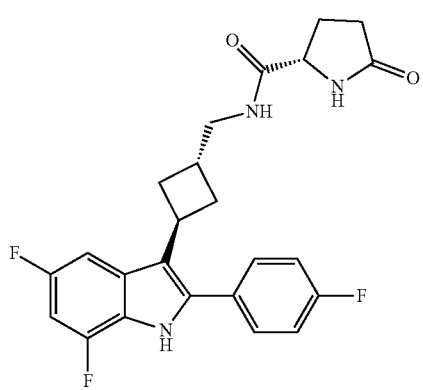 | 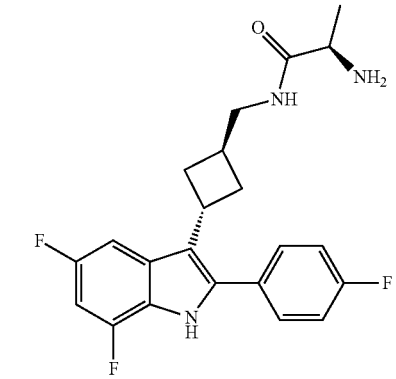 | $^1$H NMR (300 MHz, Methanol-d$_4$) δ 7.47-7.32 (m, 2H), 7.26-7.02 (m, 3H), 6.64 (ddd, J = 11.4, 9.6, 2.1 Hz, 1H), 4.07 (dd, J = 8.1, 4.7 Hz, 1H), 3.90 (q, J = 8.8, 8.3 Hz, 1H), 3.36 (d, J = 7.3 Hz, 2H), 2.55-2.13 (m, 6H), 2.13-1.85 (m, 3H). LCMS m/z 442.53 [M + H]$^+$ |
| 236 | As for compound C38 | | LCMS m/z 402.39 [M + H]$^+$ |
| 237 | As for compound C38 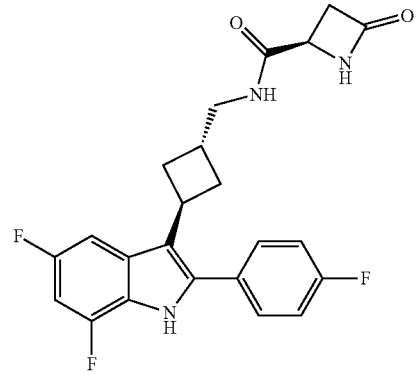 | | $^1$H NMR (300 MHz, Methanol-d$_4$) δ 7.64-7.40 (m, 2H), 7.38-7.11 (m, 3H), 6.75 (ddt, J = 11.0, 9.6, 2.4 Hz, 1H), 4.27-4.09 (m, 1H), 4.00 (p, J = 8.9 Hz, 1H), 3.62-3.38 (m, 2H), 3.30-2.80 (m, 2H), 2.69-2.43 (m, 3H), 2.30-2.07 (m, 2H). LCMS m/z 428.16 [M + H]$^+$ |

351
352
TABLE 10-continued
Structure and physicochemical data for compounds 190-331
| Cmpd. | Method/Product | Starting materials | $^1$H NMR, LCMS m/z [M + H]$^+$ |
|---|---|---|---|
| 238 | As for compound C38 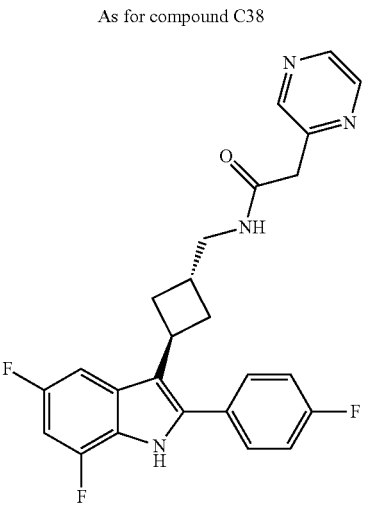 [SMILES: O=C(Cc1cnccn1)NC[C@H]1C[C@H](c2c(-c3ccc(F)cc3)[nH]c3c(F)cc(F)cc32)C1] | 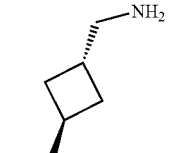 | LCMS m/z 451.15 [M + H]$^+$ |
| 239 | As for compound C38 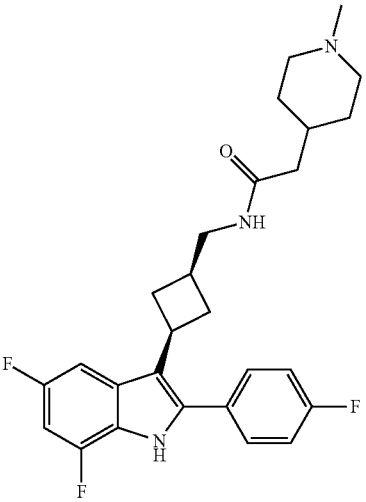 | 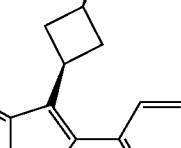 | LCMS m/z 470.21 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 240 | As for compound C38 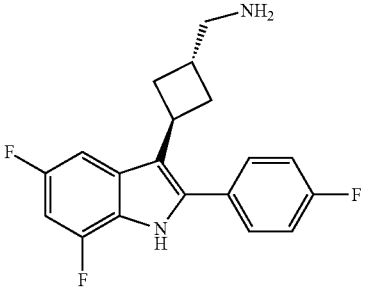 [SMILES: NC[C@H]1C[C@H](c2c(-c3ccc(F)cc3)[nH]c3c(F)cc(F)cc32)C1] | 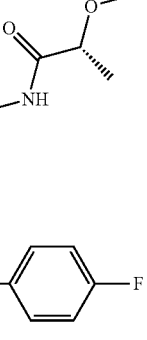 | LCMS m/z 417.20 [M + H]$^+$ |
| 241 | As for compound C38 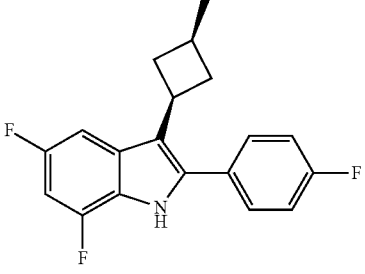 | 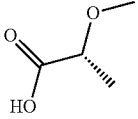 | LCMS m/z 428.28 [M + H]$^+$ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 242 | As for compound C38 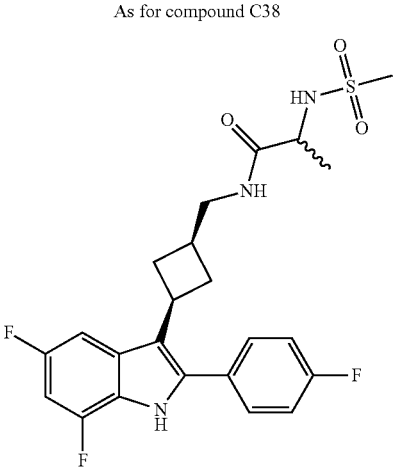 [SMILES: CC(NS(C)(=O)=O)C(=O)NC[C@H]1C[C@@H](c2c(-c3ccc(F)cc3)[nH]c3c(F)cc(F)cc32)C1] | 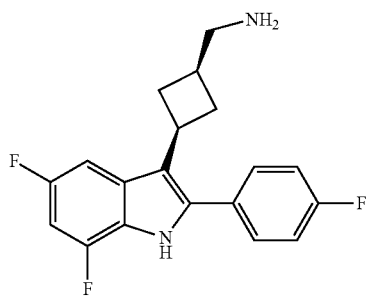 [SMILES: NC[C@H]1C[C@@H](c2c(-c3ccc(F)cc3)[nH]c3c(F)cc(F)cc32)C1] | LCMS m/z 480.15 [M + H]⁺ |
| 243 | As for compound C38 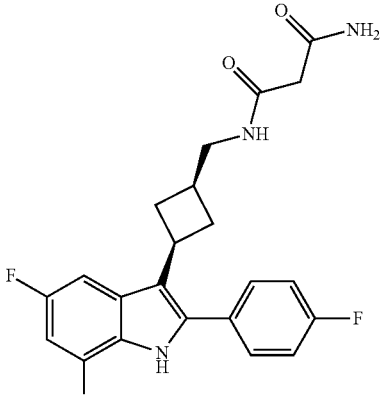 | 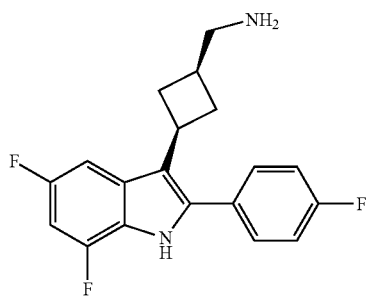 [SMILES: NC[C@H]1C[C@@H](c2c(-c3ccc(F)cc3)[nH]c3c(F)cc(F)cc32)C1] | LCMS m/z 416.26 [M + H]⁺ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 244 | As for compound C38 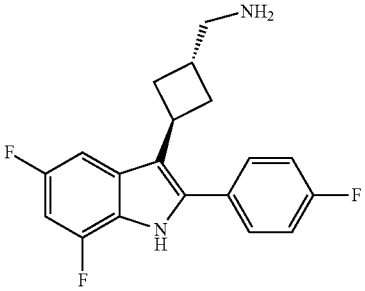 [SMILES: NC[C@H]1C[C@H](c2c(-c3ccc(F)cc3)[nH]c3c(F)cc(F)cc32)C1] | 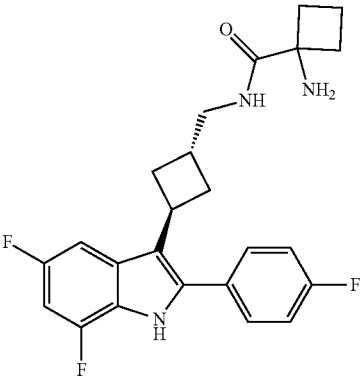 | LCMS m/z 428.44 [M + H]$^+$ |
| 245 | As for compound C38 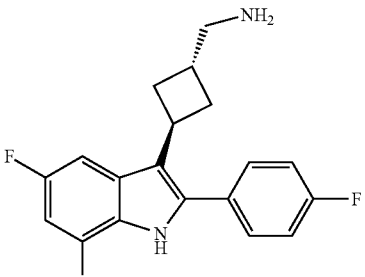 | 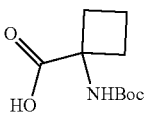 | $^1$H NMR (300 MHz, Methanol-d$_4$) δ 7.40 (t, J = 6.7 Hz, 2H), 7.28-6.97 (m, 3H), 6.74-6.51 (m, 1H), 4.90 (s, 1H), 4.03 (s, 1H), 3.88 (s, 2H), 3.45-3.34 (m, 2H), 2.73 (s, 1H), 2.46 (s, 4H), 2.07 (s, 2H). LCMS m/z 414.09 [M + H]$^+$ |
| 246 | As for compound C38 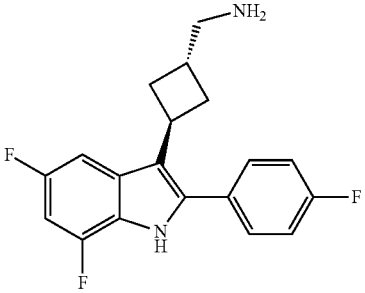 | 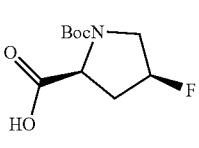 | $^1$H NMR (300 MHz, Methanol-d$_4$) δ 7.40 (t, J = 6.7 Hz, 2H), 7.28-6.97 (m, 3H), 6.74-6.51 (m, 1H), 4.90 (s, 1H), 4.03 (s, 1H), 3.88 (s, 2H), 3.45-3.34 (m, 2H), 2.73 (s, 1H), 2.46 (s, 4H), 2.07 (s, 2H). LCMS m/z 446.4 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 247 | As for compound C38 | | LCMS m/z 429.29 [M + H]⁺ |
| 248 | As for compound C38 | | LCMS m/z 451.19 [M + H]⁺ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 249 | As for compound C38 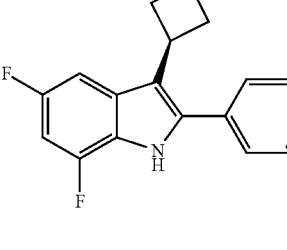 |  | LCMS m/z 442.29 [M + H]$^+$ |
| 250 | As for compound C38  |  | $^1$H NMR (300 MHz, Methanol-d$_4$) δ 7.58-7.39 (m, 2H), 7.35-7.06 (m, 3H), 6.73 (ddd, J = 11.4, 9.6, 2.2 Hz, 1H), 3.99 (q, J = 8.5, 7.7 Hz, 1H), 3.82 (s, 2H), 3.44 (d, J = 6.9 Hz, 2H), 2.52 (t, J = 8.6 Hz, 3H), 2.14 (t, J = 9.4 Hz, 2H), 2.00 (s, 3H). LCMS m/z 430.38 [M + H]$^+$ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 251 | As for compound C38 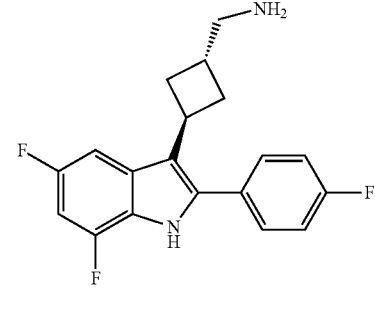 [SMILES: NC[C@H]1C[C@H](c2c(-c3ccc(F)cc3)[nH]c3c(F)cc(F)cc32)C1] | 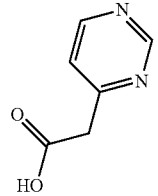 | LCMS m/z 451.12 [M + H]⁺ |
| 252 | As for compound C38 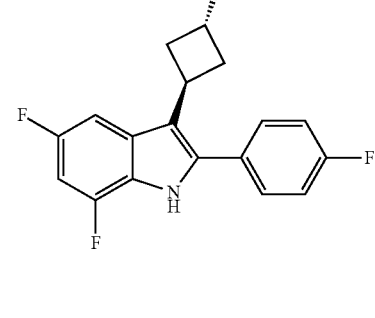 | 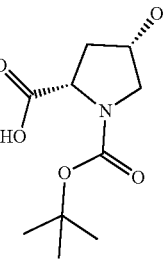 | LCMS m/z 544.38 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 253 | As for compound C38 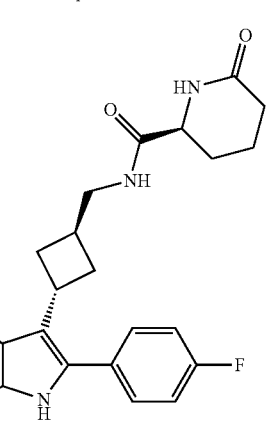 | 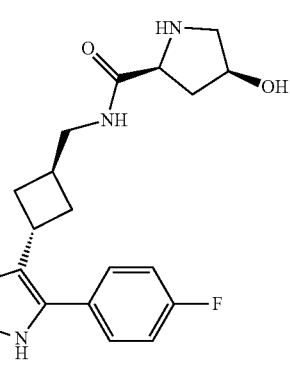 | ¹H NMR (300 MHz, Methanol-d₄) δ 7.59-7.37 (m, 2H), 7.33-7.08 (m, 3H), 6.73 (ddd, J = 11.0, 9.6, 2.1 Hz, 1H), 4.18-3.81 (m, 2H), 3.57-3.40 (m, 2H), 2.67-2.42 (m, 3H), 2.42-2.29 (m, 2H), 2.24-1.94 (m, 3H), 1.84 (dddd, J = 20.7, 14.6, 8.4, 3.9 Hz, 3H). LCMS m/z 456.17 [M + H]⁺ |
| 254 | As for compound C38 | | ¹H NMR (300 MHz, Methanol-d₄) δ 7.62-7.42 (m, 2H), 7.37-7.11 (m, 3H), 6.75 (ddd, J = 11.4, 9.6, 2.0 Hz, 1H), 4.53 (s, 1H), 4.34 (s, 1H), 4.03 (q, J = 8.9 Hz, 1H), 3.54 (d, J = 8.3 Hz, 2H), 3.39 (s, 2H), 2.55 (dd, J = 18.2, 8.3 Hz, 4H), 2.17 (d, J = 10.6 Hz, 3H). LCMS m/z 444.37 [M + H]⁺ |
| 255 | As for compound C38 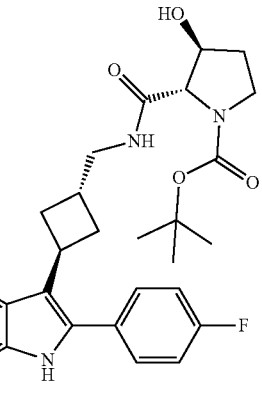 | | LCMS m/z 544.05 [M + H]⁺ |

TABLE 10-continued

Structure and physicochemical data for compounds 190-331

| Cmpd. | Method/Product | Starting materials | ¹H NMR, LCMS m/z [M + H]⁺ |
|---|---|---|---|

(Starting material structure at top: N-Boc-3-hydroxyproline)

| 256 | As for compound C38 (product: 1-acetyl-pyrrolidine-3-carboxamide linked via NH-CH₂-cyclobutyl to 5,7-difluoro-2-(4-fluorophenyl)-1H-indol-3-yl) | (aminomethyl-cyclobutyl-5,7-difluoro-2-(4-fluorophenyl)-1H-indole) and (1-acetylpyrrolidine-3-carboxylic acid) | LCMS m/z 470.2 [M + H]⁺ |
| 257 | As for compound C38 (product: morpholine-3-carboxamide linked via NH-CH₂-cyclobutyl to 5,7-difluoro-2-(4-fluorophenyl)-1H-indol-3-yl) | (aminomethyl-cyclobutyl-5,7-difluoro-2-(4-fluorophenyl)-1H-indole) and (N-Boc-morpholine-3-carboxylic acid) | ¹H NMR (300 MHz, Methanol-d₄) δ 7.40 (dd, J = 8.4, 5.2 Hz, 2H), 7.25-6.98 (m, 3H), 6.64 (ddd, J = 11.3, 9.7, 2.0 Hz, 1H), 4.10 (d, J = 12.4 Hz, 1H), 4.04-3.76 (m, 3H), 3.75-3.62 (m, 2H), 3.39 (d, J = 5.6 Hz, 2H), 3.28 (s, 1H), 3.18 (s, 1H), 2.44 (d, J = 10.4 Hz, 3H), 2.05 (t, J = 9.0 Hz, 2H). LCMS m/z 444.42 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 258 | As for compound C38 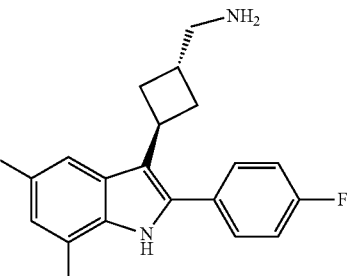 | 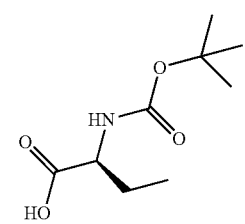 | LCMS m/z 516.14 [M + H]⁺ |
| 259 | As for compound C38 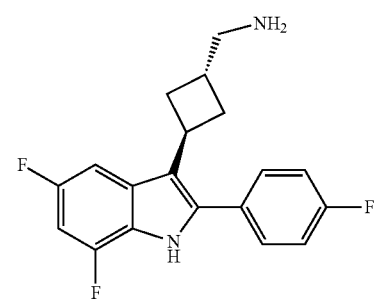 [SMILES: NC[C@H]1C[C@H](c2c(-c3ccc(F)cc3)[nH]c3c(F)cc(F)cc32)C1] | 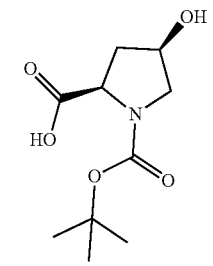 | LCMS m/z 430.18 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 260 | As for compound C38 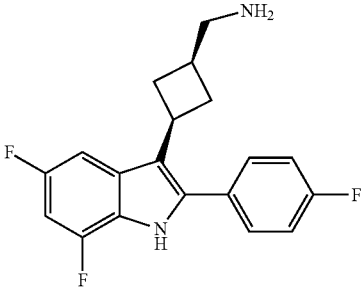 [SMILES: NC[C@H]1C[C@@H](c2c(-c3ccc(F)cc3)[nH]c3c(F)cc(F)cc32)C1] | 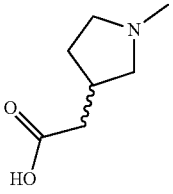 | LCMS m/z 456.24 [M + H]⁺ |
| 261 | As for compound C38 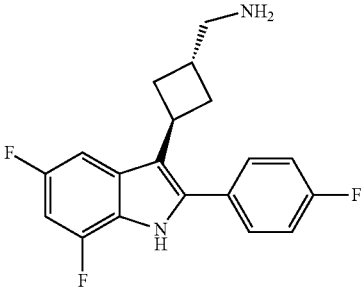 [SMILES: NC[C@H]1C[C@H](c2c(-c3ccc(F)cc3)[nH]c3c(F)cc(F)cc32)C1] | 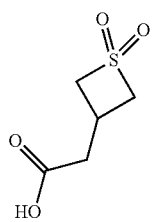 | LCMS m/z 477.15 [M + H]⁺ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 262 | As for compound C38 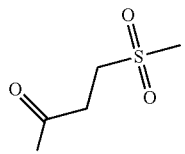 | 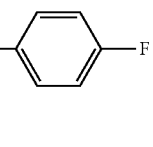 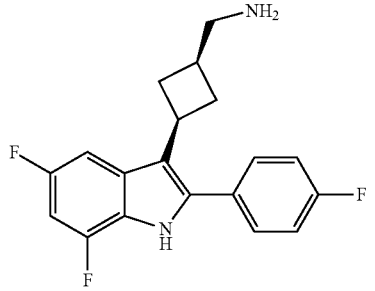 [SMILES: NC[C@H]1C[C@@H](c2c(-c3ccc(F)cc3)[nH]c3c(F)cc(F)cc32)C1] | LCMS m/z 465.16 [M + H]$^+$ |
| 263 | As for compound C38 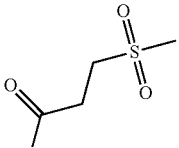 | 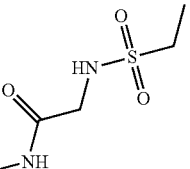 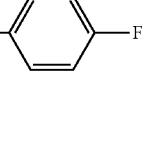 | LCMS m/z 480.15 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 264 | As for compound C38 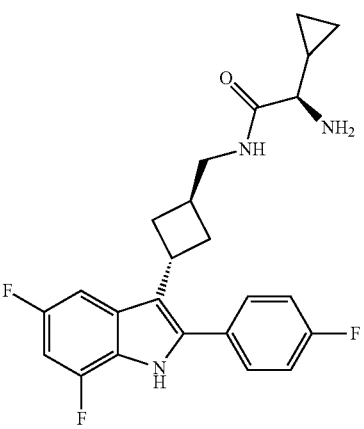 | 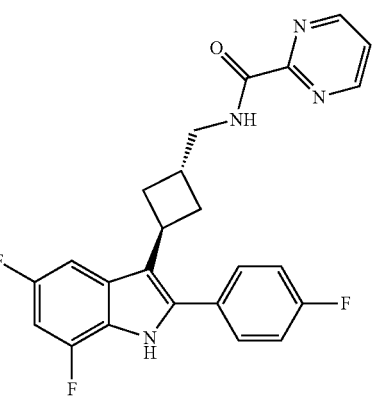 | ¹H NMR (300 MHz, Methanol-d₄) δ 7.40 (dd, J = 8.3, 5.2 Hz, 2H), 7.25-6.93 (m, 3H), 6.64 (ddd, J = 11.3, 9.5, 2.0 Hz, 1H), 4.01-3.80 (m, 1H), 3.45 (d, J = 6.6 Hz, 1H), 3.33 (dd, J = 13.4, 6.3 Hz, 1H), 3.07 (d, J = 9.5 Hz, 1H), 2.46 (t, J = 10.0 Hz, 3H), 2.10 (d, J = 9.7 Hz, 2H), 1.23-0.96 (m, 1H), 0.62 (dd, J = 17.0, 9.5 Hz, 4H). LCMS m/z 428.49 [M + H]⁺ |
| 265 | As for compound C38 | | ¹H NMR (300 MHz, Methanol-d₄) δ 8.93 (d, J = 4.9 Hz, 2H), 7.62 (d, J = 5.7 Hz, 1H), 7.54-7.40 (m, 2H), 7.31 (dd, J = 9.8, 2.2 Hz, 1H), 7.25-7.04 (m, 2H), 6.72 (ddd, J = 11.0, 9.6, 2.1 Hz, 1H), 4.04 (p, J = 9.0 Hz, 1H), 3.70 (d, J = 7.4 Hz, 2H), 2.88-2.45 (m, 3H), 2.23 (tt, J = 9.4, 2.8 Hz, 2H). LCMS m/z 437.15 [M + H]⁺ |
| 266 | As for compound C38 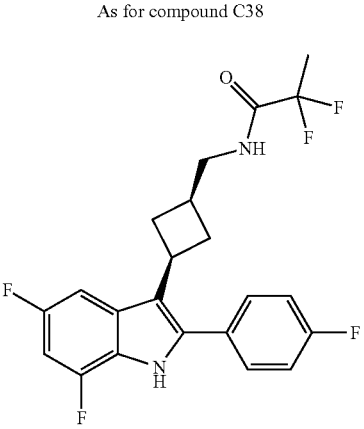 [SMILES: CC(F)(F)C(=O)NC[C@H]1C[C@@H](c2c(-c3ccc(F)cc3)[nH]c3c(F)cc(F)cc32)C1] | | LCMS m/z 423.24 [M + H]⁺ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 267 | As for compound C38 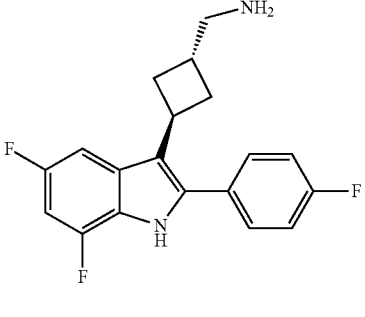 [SMILES: NC[C@H]1C[C@H](c2c(-c3ccc(F)cc3)[nH]c3c(F)cc(F)cc32)C1] | 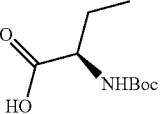 | ¹H NMR (300 MHz, Methanol-d₄) δ 7.40 (dd, J = 8.0, 5.5 Hz, 2H), 7.26-6.99 (m, 3H), 6.64 (ddd, J = 11.3, 9.6, 1.9 Hz, 1H), 4.03-3.81 (m, 1H), 3.58 (s, 2H), 3.33 (d, J = 13.9 Hz, 1H), 2.47 (d, J = 6.9 Hz, 3H), 2.08 (d, J = 9.3 Hz, 2H), 1.78 (s, 2H), 0.91 (t, J = 7.2 Hz, 3H). LCMS m/z 416.38 [M + H]⁺ |
| 268 | As for compound C38 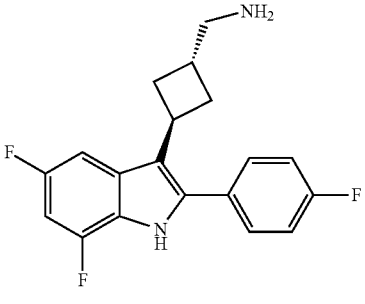 [SMILES: NC[C@H]1C[C@H](c2c(-c3ccc(F)cc3)[nH]c3c(F)cc(F)cc32)C1] | 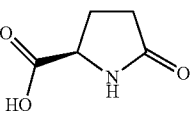 | ¹H NMR (300 MHz, Methanol-d₄) δ 7.62-7.39 (m, 2H), 7.39-7.12 (m, 3H), 6.75 (ddd, J = 11.0, 9.6, 2.2 Hz, 1H), 4.25-4.13 (m, 1H), 4.00 (p, J = 8.9 Hz, 1H), 3.55-3.40 (m, 2H), 2.66-2.23 (m, 6H), 2.23-1.95 (m, 3H). LCMS m/z 442.17 [M + H]⁺ |
| 269 | As for compound C38 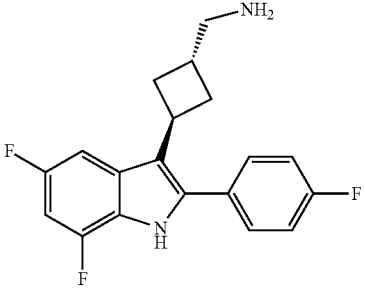 [SMILES: NC[C@H]1C[C@H](c2c(-c3ccc(F)cc3)[nH]c3c(F)cc(F)cc32)C1] | 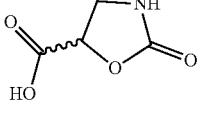 | ¹H NMR (300 MHz, Methanol-d₄) δ 7.63-7.37 (m, 2H), 7.36-7.10 (m, 3H), 6.73 (ddd, J = 11.1, 9.6, 2.2 Hz, 1H), 5.02 (dd, J = 9.7, 6.1 Hz, 1H), 4.00 (p, J = 8.9 Hz, 1H), 3.85 (dd, J = 9.7, 9.1 Hz, 1H), 3.60 (dd, J = 9.1, 6.1 Hz, 1H), 3.50 (d, J = 7.2 Hz, 2H), 2.74-2.41 (m, 3H), 2.15 (t, J = 9.6 Hz, 2H). LCMS m/z 444.05 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 270 | As for compound C38 | | H NMR (300 MHz, Methanol-d₄) δ 7.63-7.34 (m, 2H), 7.38-7.06 (m, 3H), 6.73 (ddd, J = 11.6, 9.6, 2.2 Hz, 1H), 3.99 (p, J = 9.0 Hz, 1H), 3.73 (q, J = 6.7 Hz, 1H), 3.53-3.41 (m, 2H), 3.34 (s, 3H), 2.71-2.40 (m, 3H), 2.25-2.05 (m, 2H), 1.31 (d, J = 6.7 Hz, 3H). LCMS m/z 417.18 [M + H]⁺ |
| 271 | As for compound C38 | | LCMS m/z 466.14 [M + H]⁺ |
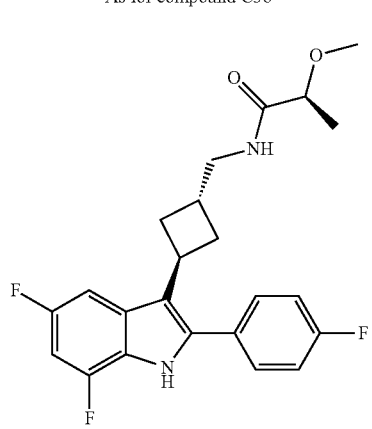

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 272 | As for compound C38 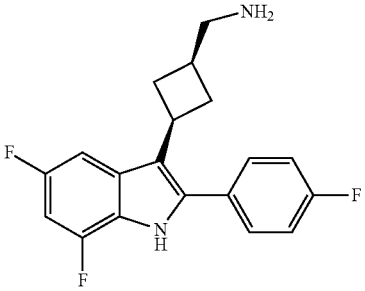 [SMILES: NC[C@H]1C[C@@H](c2c(-c3ccc(F)cc3)[nH]c3c(F)cc(F)cc32)C1] | 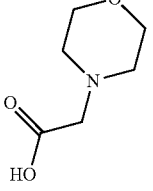 | LCMS m/z 458.22 [M + H]$^+$ |
| 273 | As for compound C38 | | LCMS m/z 442.39 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 274 | As for compound C38 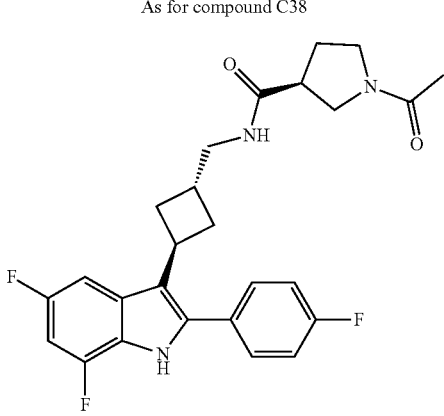 | 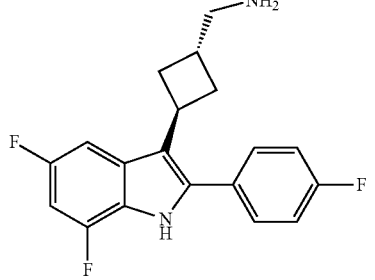 | LCMS m/z 470.2 [M + H]⁺ |
| 275 | As for compound C38 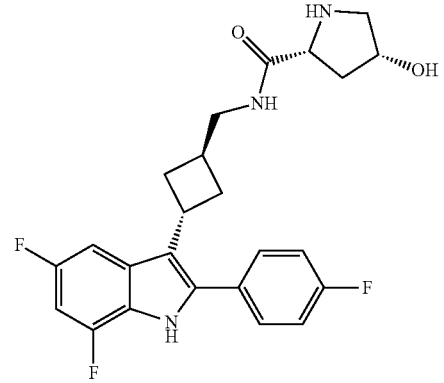 | 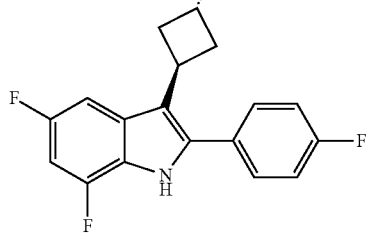 | ¹H NMR (300 MHz, Methanol-d₄) δ 7.52-7.29 (m, 2H), 7.24-7.00 (m, 3H), 6.64 (ddd, J = 11.5, 9.7, 2.1 Hz, 1H), 4.42 (s, 1H), 4.23 (d, J = 7.0 Hz, 1H), 3.91 (q, J = 8.7, 8.3 Hz, 1H), 3.44 (dt, J = 16.5, 7.7 Hz, 2H), 3.31 (d, J = 21.7 Hz, 2H), 2.45 (t, J = 9.3 Hz, 4H), 2.05 (q, J = 12.6, 11.2 Hz, 3H). LCMS m/z 444.37 [M + H]⁺ |
| 276 | As for compound 189 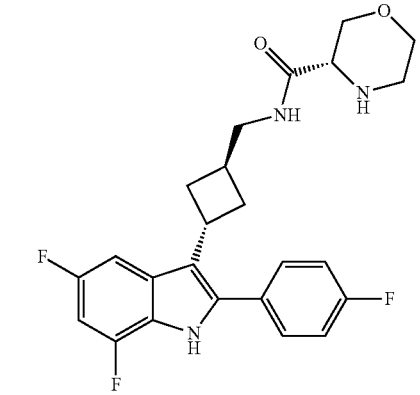 | 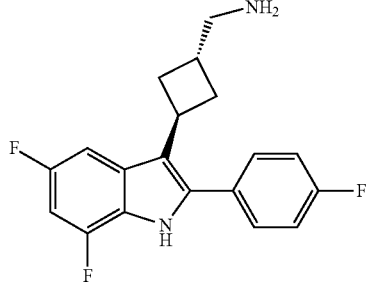 [SMILES: NC[C@H]1C[C@H](c2c(-c3ccc(F)cc3)[nH]c3c(F)cc(F)cc32)C1] | ¹H NMR (300 MHz, Methanol-d₄) δ 7.40 (dd, J = 8.3, 5.2 Hz, 2H), 7.25-6.99 (m, 3H), 6.64 (ddd, J = 11.3, 9.6, 2.0 Hz, 1H), 4.10 (d, J = 12.0 Hz, 1H), 4.04-3.75 (m, 3H), 3.75-3.64 (m, 2H), 3.48 (dd, J = 5.3, 3.9 Hz, 2H), 3.39 (d, J = 5.7 Hz, 2H), 3.28 (s, 1H), 2.44 (d, J = 10.3 Hz, 3H), 2.05 (t, J = 9.1 Hz, 2H). LCMS m/z 444.37 [M + H]⁺ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 277 | As for compound C38 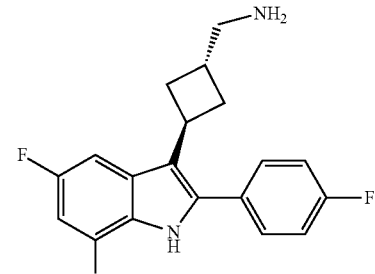 | 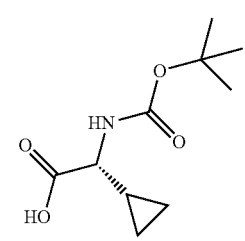 | LCMS m/z 528.35 [M + H]$^+$ |
| 278 | As for compound C38 | | LCMS m/z 453.18 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 279 | As for compound C38 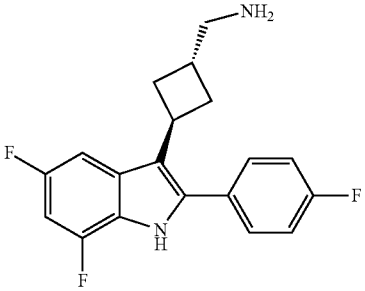 [SMILES: NC[C@H]1C[C@H](c2c(-c3ccc(F)cc3)[nH]c3c(F)cc(F)cc32)C1] | 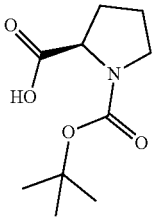 | LCMS m/z 528.26 [M + H]$^+$ |
| 280 | As for compound C38 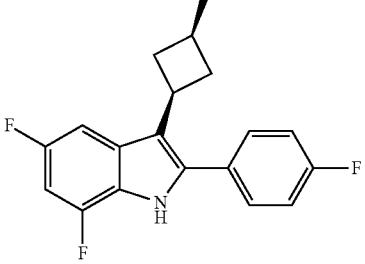 | 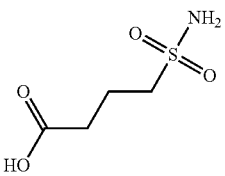 | LCMS m/z 480.28 [M + H]$^+$ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 281 | As for compound C38 | | $^1$H NMR (300 MHz, Methanol-d$_4$) δ 7.51 (ddd, J = 8.8, 6.6, 5.3 Hz, 2H), 7.32-7.11 (m, 3H), 6.84-6.59 (m, 1H), 4.10-3.59 (m, 2H), 3.51 (d, J = 6.8 Hz, 1H), 2.86 (d, J = 12.9 Hz, 6H), 2.50 (dp, J = 22.7, 7.8 Hz, 3H), 2.26-1.89 (m, 2H), 1.53 (dd, J = 14.1, 7.0 Hz, 3H). LCMS m/z 430.21 [M + H]$^+$ |
| 282 | As for compound C38 | | $^1$H NMR (300 MHz, Methanol-d$_4$) δ 7.61-7.40 (m, 2H), 7.37-7.10 (m, 3H), 6.76 (ddd, J = 11.1, 9.6, 2.2 Hz, 1H), 4.34-4.15 (m, 1H), 4.00 (p, J = 9.0 Hz, 1H), 3.64-3.34 (m, 4H), 2.70-2.32 (m, 4H), 2.27-1.88 (m, 5H). LCMS m/z 428.4 [M + H]$^+$ |
| 283 | As for compound C38 | | LCMS m/z 415.19 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 284 | As for compound C38 | | LCMS m/z 441.28 [M + H]⁺ |
| 285 | As for compound C38 | | LCMS m/z 484.26 [M + H]⁺ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 286 | As for compound C38 | | LCMS m/z 528.19 [M + H]⁺ |
| 287 | As for compound C38 | | LCMS m/z 456.12 [M + H]⁺ |

TABLE 10-continued

Structure and physicochemical data for compounds 190-331

| Cmpd. | Method/Product | Starting materials | $^{1}$H NMR, LCMS m/z [M + H]$^{+}$ |
|---|---|---|---|
| 288 | As for compound C38 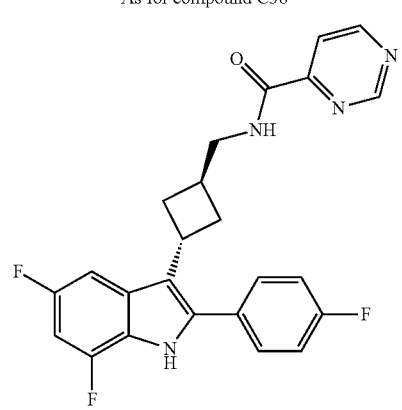 | 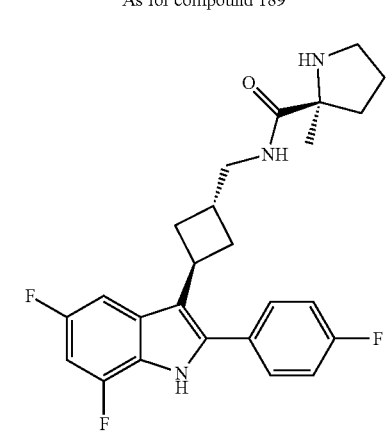 | $^{1}$H NMR (300 MHz, Methanol-d$_4$) δ 9.27 (d, J = 1.4 Hz, 1H), 9.04 (d, J = 5.1 Hz, 1H), 8.11 (dd, J = 5.1, 1.4 Hz, 1H), 7.63-7.42 (m, 2H), 7.33 (dd, J = 9.8, 2.2 Hz, 1H), 7.27-7.06 (m, 2H), 6.75 (ddd, J = 11.0, 9.6, 2.2 Hz, 1H), 4.06 (p, J = 9.0 Hz, 1H), 3.71 (d, J = 7.4 Hz, 2H), 2.88-2.51 (m, 3H), 2.33-2.13 (m, 2H). LCMS m/z 437.15 [M + H]$^{+}$ |
| 289 | As for compound 189 | | $^{1}$H NMR (300 MHz, Methanol-d$_4$) δ 7.52 (ddt, J = 8.3, 5.2, 2.6 Hz, 2H), 7.39-7.11 (m, 3H), 6.76 (ddd, J = 11.2, 9.7, 2.1 Hz, 1H), 4.00 (p, J = 8.7 Hz, 1H), 3.52 (d, J = 6.3 Hz, 2H), 3.47-3.35 (m, 2H), 2.60 (h, J = 8.2 Hz, 3H), 2.41-2.26 (m, 1H), 2.25-1.89 (m, 5H), 1.67 (s, 3H). LCMS m/z 442.23 [M + H]$^{+}$ |
| 290 | As for compound C38 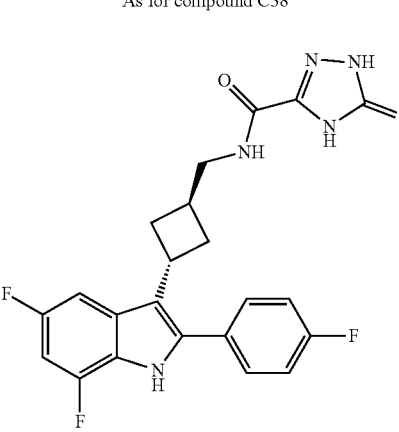 | | LCMS m/z 442.39 [M + H]$^{+}$ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 291 | As for compound C38 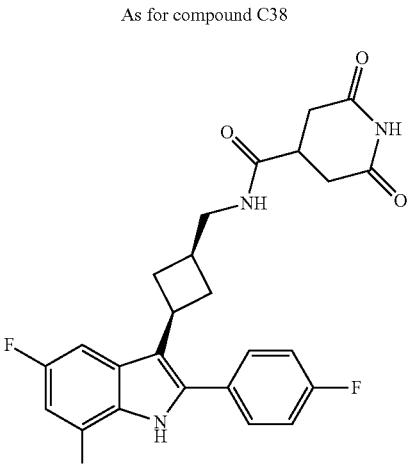 | 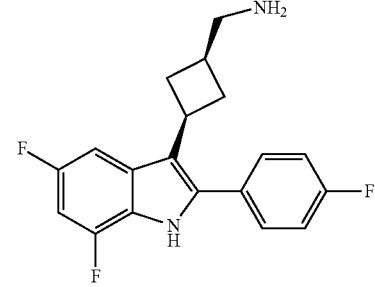 | LCMS m/z 470.26 [M + H]⁺ |
| 292 | As for compound C38 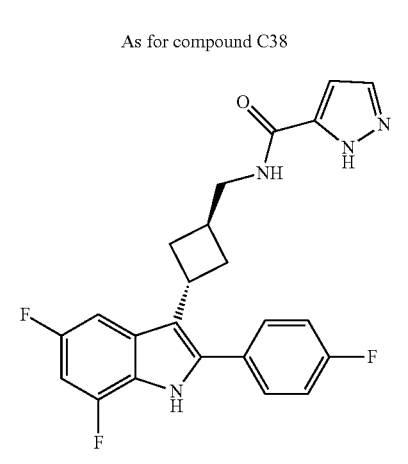 [SMILES: O=C(NC[C@H]1C[C@H](c2c(-c3ccc(F)cc3)[nH]c3c(F)cc(F)cc32)C1)c1ccn[nH]1] | 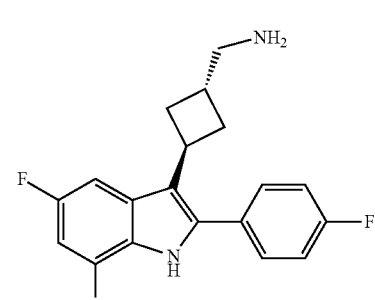 | ¹H NMR (300 MHz, Methanol-d₄) δ 7.69 (d, J = 2.4 Hz, 1H), 7.56-7.39 (m, 2H), 7.31 (dd, J = 9.8, 2.2 Hz, 1H), 7.25-7.06 (m, 2H), 6.87-6.57 (m, 2H), 4.02 (p, J = 8.9 Hz, 1H), 3.62 (d, J = 7.1 Hz, 2H), 2.61 (ddt, J = 19.3, 10.4, 7.8 Hz, 3H), 2.20 (tt, J = 9.5, 2.4 Hz, 2H). LCMS m/z 425.16 [M + H]⁺ |
| 293 | As for compound C38 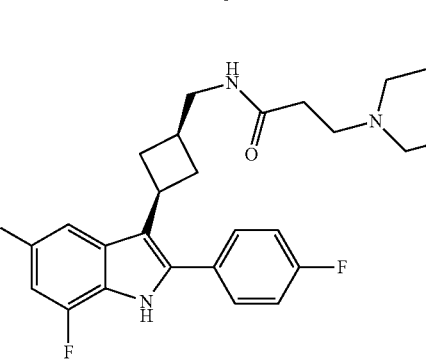 | 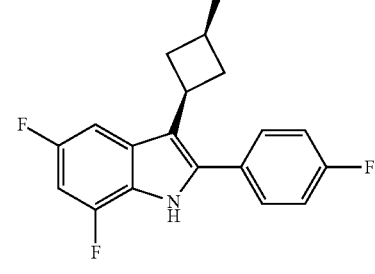 | LCMS m/z 470.24 [M + H]⁺ |

US 12,281,102 B2
TABLE 10-continued
Structure and physicochemical data for compounds 190-331
| Cmpd. | Method/Product | Starting materials | $^1$H NMR, LCMS m/z [M + H]$^+$ |
|---|---|---|---|
| 294 | As for compound C38 | | LCMS m/z 442.25 [M + H]$^+$ |
| 295 | As for compound C38 | | LCMS m/z 502.26 [M + H]$^+$ |
| 296 | As for compound C38 | | LCMS m/z 456.24 [M + H]$^+$ |
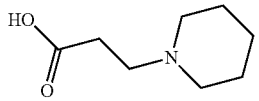

TABLE 10-continued

Structure and physicochemical data for compounds 190-331

| Cmpd. | Method/Product | Starting materials | ¹H NMR, LCMS m/z [M + H]⁺ |
|---|---|---|---|
| 297 | As for compound C38 | | ¹H NMR (300 MHz, Methanol-$d_4$) δ 9.31 (dd, J = 5.1, 1.7 Hz, 1H), 8.31 (dd, J = 8.5, 1.7 Hz, 1H), 7.89 (dd, J = 8.5, 5.1 Hz, 1H), 7.60-7.42 (m, 2H), 7.32 (dd, J = 9.8, 2.2 Hz, 1H), 7.25-7.05 (m, 2H), 6.72 (ddd, J = 11.1, 9.6, 2.2 Hz, 1H), 4.19-3.90 (m, 1H), 3.82-3.61 (m, 2H), 2.73 (q, J = 8.4, 7.6 Hz, 1H), 2.68-2.49 (m, 2H), 2.25 (ddd, J = 12.7, 9.4, 2.9 Hz, 2H). LCMS m/z 437.15 [M + H]⁺ |
| 298 | As for compound C38 | | ¹H NMR (300 MHz, Methanol-$d_4$) δ 8.07 (s, 2H), 7.58-7.40 (m, 2H), 7.32 (dd, J = 9.8, 2.2 Hz, 1H), 7.24-7.10 (m, 2H), 6.73 (ddd, J =11.1, 9.6, 2.2 Hz, 1H), 4.02 (p, J = 8.9 Hz, 1H), 3.59 (d, J = 7.1 Hz, 2H), 2.60 (dt, J = 19.9, 10.6 Hz, 3H), 2.20 (t, J = 9.6 Hz, 2H). LCSM m/z 425.16 [M + H]⁺ |
| 299 | As for compound C38 | | LCMS m/z 453.18 [M + H]⁺ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 300 | As for compound C38 | | LCMS m/z 486.2 [M + H]$^+$ |
| 301 | As for compound C38 | | LCMS m/z 431.3 [M + H]$^+$ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 302 | As for compound C38 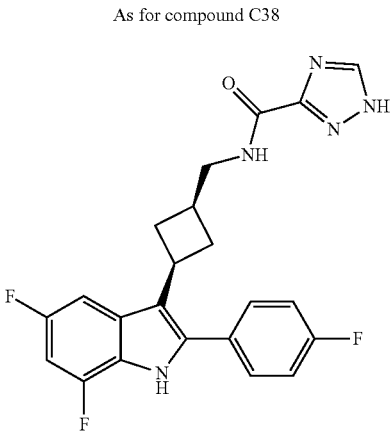 [SMILES: O=C(NC[C@H]1C[C@@H](c2c(-c3ccc(F)cc3)[nH]c3c(F)cc(F)cc32)C1)c1nc[nH]n1] | 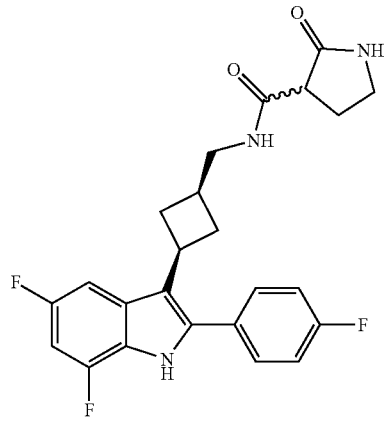 | LCMS m/z 426.26 [M + H]⁺ |
| 303 | As for compound C38 | | LCMS m/z 442.29 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 304 | As for compound C38 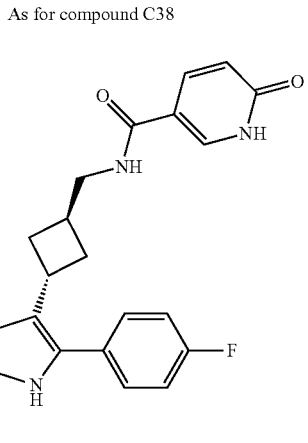 | 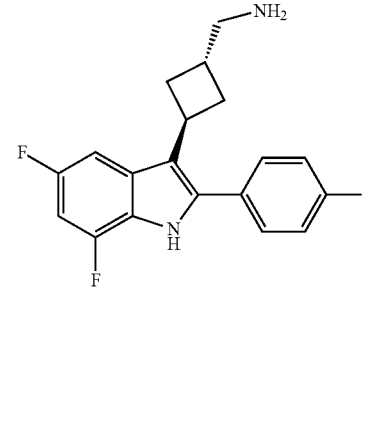 | LCMS m/z 452.16 [M + H]⁺ |
| 305 | As for compound C38 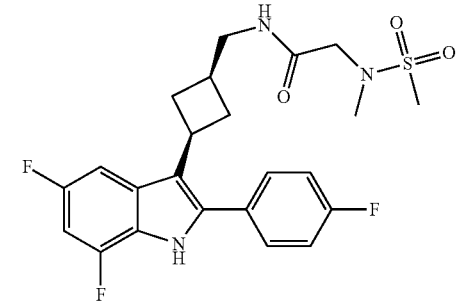 | 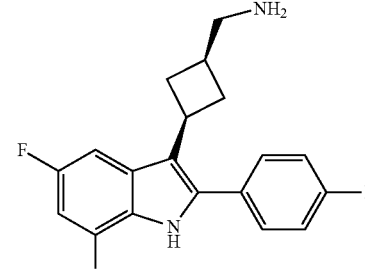 | LCMS m/z 490.15 [M + H]⁺ |
| 306 | As for compound C38 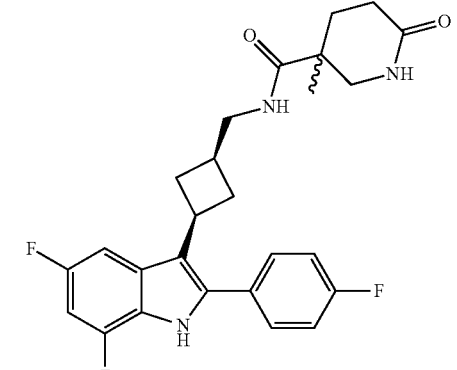 | 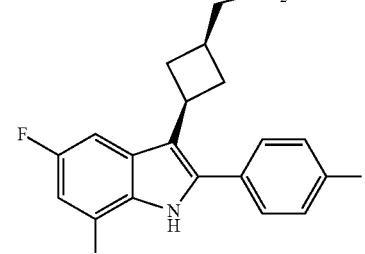 | LCMS m/z 470.33 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 307 | As for compound C38 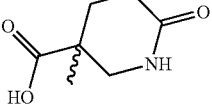 | 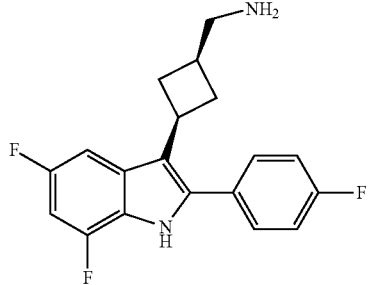 [SMILES: NC[C@H]1C[C@@H](c2c(-c3ccc(F)cc3)[nH]c3c(F)cc(F)cc32)C1] | LCMS m/z 440.18 [M + H]⁺ |
| 308 | As for compound C38 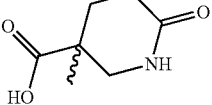 | 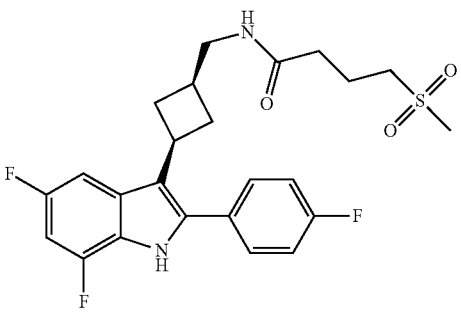 | LCMS m/z 479.17 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 309 | As for compound C38 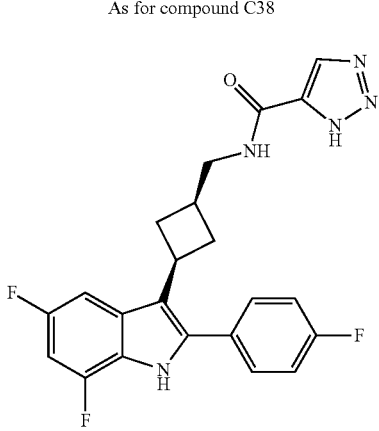 [SMILES: O=C(NC[C@H]1C[C@@H](c2c(-c3ccc(F)cc3)[nH]c3c(F)cc(F)cc32)C1)c1cnn[nH]1] | 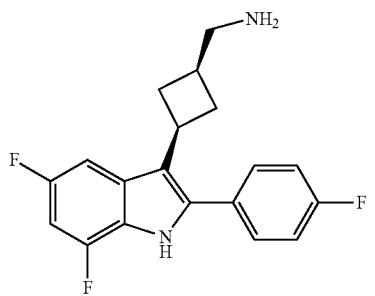 [SMILES: NC[C@H]1C[C@@H](c2c(-c3ccc(F)cc3)[nH]c3c(F)cc(F)cc32)C1] 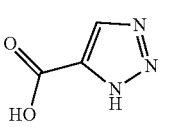 | LCMS m/z 426.26 [M + H]⁺ |
| 310 | As for compound C38 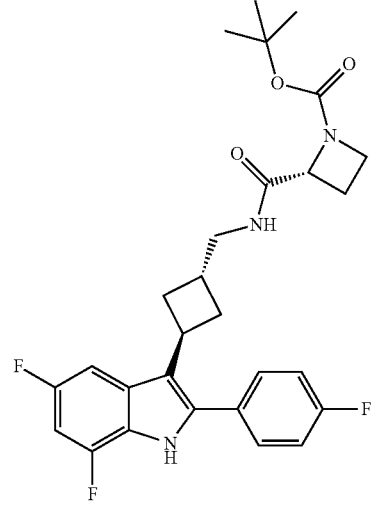 | 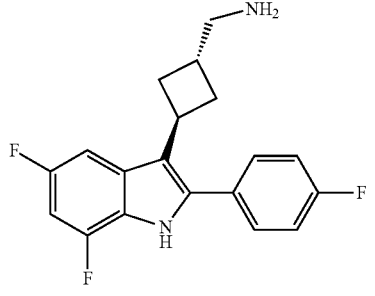 [SMILES: NC[C@H]1C[C@H](c2c(-c3ccc(F)cc3)[nH]c3c(F)cc(F)cc32)C1] 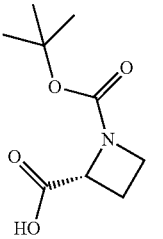 | LCMS m/z 514.18 [M + H]⁺ |

US 12,281,102 B2

TABLE 10-continued

Structure and physicochemical data for compounds 190-331

| Cmpd. | Method/Product | Starting materials | ¹H NMR, LCMS m/z [M + H]⁺ |
|---|---|---|---|
| 311 | As for compound C38 | | LCMS m/z 530.21 [M + H]⁺ |
| 312 | As for compound C38 | | LCMS m/z 453.13 [M + H]⁺ |
| 313 | As for compound C38 | | LCMS m/z 463.18 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 314 | As for compound C38 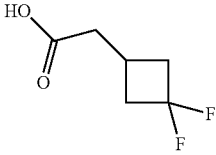 | 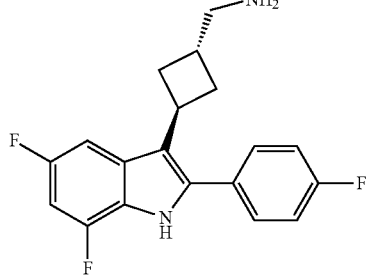 | ¹H NMR (300 MHz, Methanol-d₄) δ 7.58-7.39 (m, 2H), 7.32 (dd, J = 9.8, 2.2 Hz, 1H), 7.26-7.08 (m, 2H), 6.90 (dt, J = 2.9, 1.5 Hz, 1H), 6.81-6.61 (m, 2H), 6.24-6.03 (m, 1H), 4.02 (p, J = 8.9 Hz, 1H), 3.57 (d, J = 7.1 Hz, 2H), 2.79-2.47 (m, 3H), 2.33-2.09 (m, 2H). LCMS m/z 424.39 [M + H]⁺ |
| 315 | As for compound C38 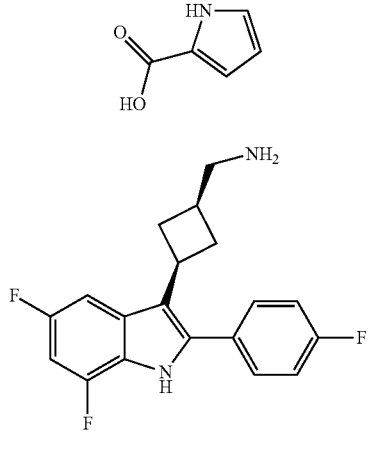 | | LCMS m/z 470.24 [M + H]⁺ |
| 316 | As for compound C38 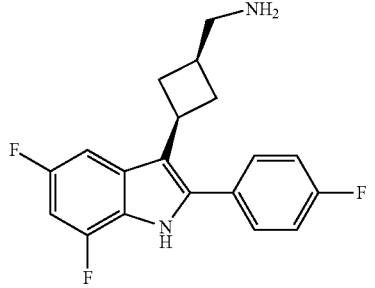 [SMILES: NC[C@H]1C[C@@H](c2c(-c3ccc(F)cc3)[nH]c3c(F)cc(F)cc32)C1] | | LCMS m/z 471.22 [M + H]⁺ |

US 12,281,102 B2
417                                                                 418
TABLE 10-continued
Structure and physicochemical data for compounds 190-331
| Cmpd. | Method/Product | Starting materials | $^1$H NMR, LCMS m/z [M + H]$^+$ |
|---|---|---|---|
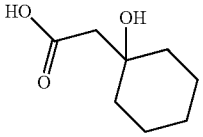 [SMILES: O=C(O)CC1(O)CCCCC1]
| 317 | As for compound C38 | 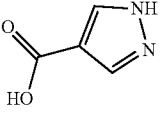 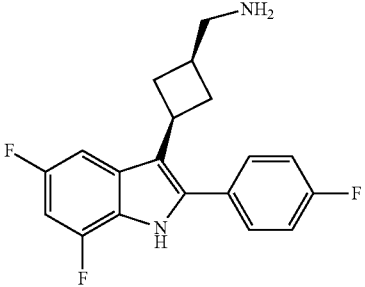 [SMILES: NC[C@H]1C[C@@H](c2c(-c3ccc(F)cc3)[nH]c3c(F)cc(F)cc32)C1] | LCMS m/z 425.26 [M + H]$^+$ |
| 318 | As for compound C38 | 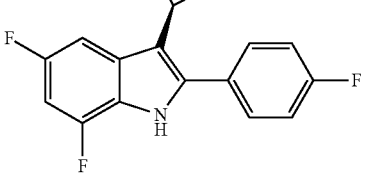 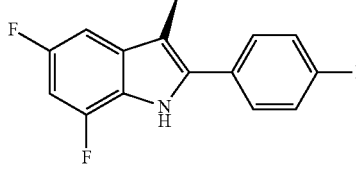  | LCMS m/z 486.2 [M + H]$^+$ |

TABLE 10-continued
Structure and physicochemical data for compounds 190-331
| Cmpd. | Method/Product | Starting materials | $^1$H NMR, LCMS m/z [M + H]$^+$ |
|---|---|---|---|
| 319 | As for compound C38 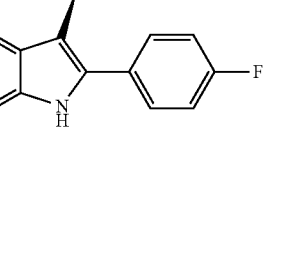 | 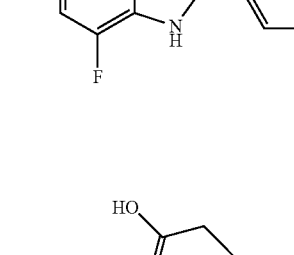  | LCMS m/z 429.23 [M + H]$^+$ |
| 320 | As for compound C38 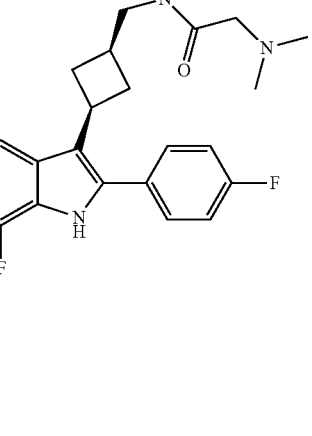 | 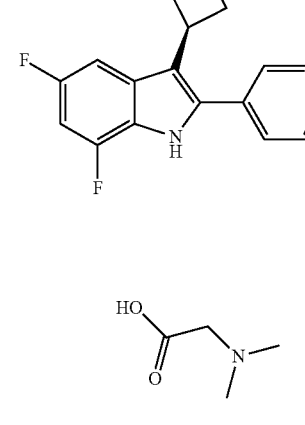  | LCMS m/z 416.24 [M + H]$^+$ |
| 321 | As for compound C38 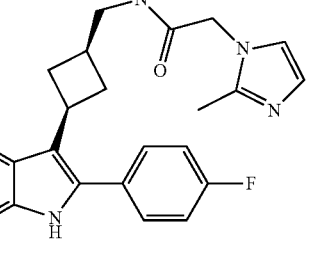 | 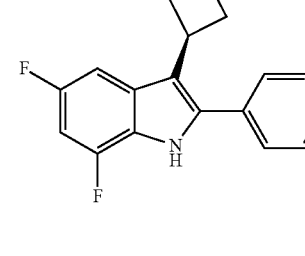 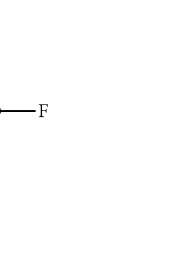 | LCMS m/z 453.18 [M + H]$^+$ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 322 | As for compound C38 | | LCMS m/z 453.21 [M + H]⁺ |
| 323 | As for compound C38 | | LCMS m/z 457.18 [M + H]⁺ |
| 324 | As for compound C38 | | LCMS m/z 457.18 [M + H]⁺ |

TABLE 10-continued
Structure and physicochemical data for compounds 190-331
| Cmpd. | Method/Product | Starting materials | ¹H NMR, LCMS m/z [M + H]⁺ |
|---|---|---|---|
| 325 | As for compound C38 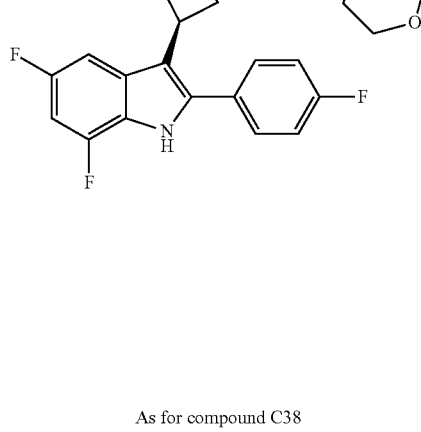 | 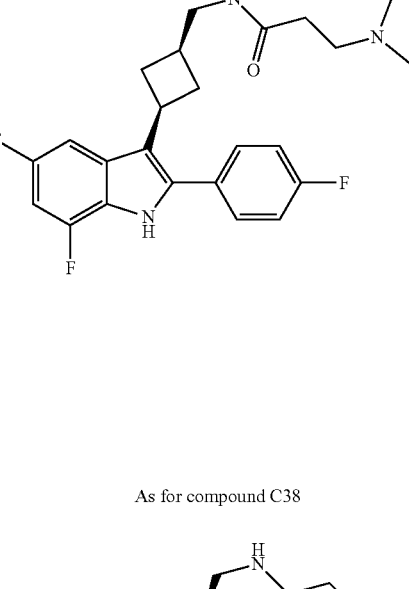 | LCMS m/z 457.08 [M + H]⁺ |
| 326 | As for compound C38 | | LCMS m/z 470.18 [M + H]⁺ |
| 327 | As for compound C38 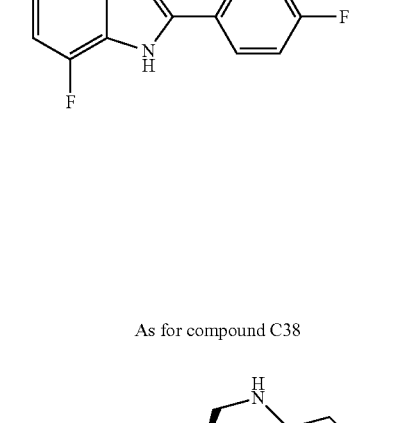 | | LCMS m/z 442.2 [M + H]⁺ |

TABLE 10-continued

Structure and physicochemical data for compounds 190-331

| Cmpd. | Method/Product | Starting materials | ¹H NMR, LCMS m/z [M + H]⁺ |
|---|---|---|---|
| 328 | As for compound C38 | | LCMS m/z 456.34 [M + H]⁺ |
| 329 | As for compound C38 | | ¹H NMR (300 MHz, Metahaol-d₄) δ 7.65-7.41 (m, 2H), 7.34 (dd, J = 9.8, 2.2 Hz, 1H), 7.29-7.11 (m, 2H), 6.75 (ddd, J = 11.5, 9.7, 2.2 Hz, 1H), 4.05 (p, J = 8.8 Hz, 1H), 3.64 (d, J = 7.3 Hz, 2H), 2.87-2.49 (m, 3H), 2.35-2.14 (m, 2H). LCMS m/z 442.15 [M + H]⁺ |

TABLE 10-continued

Structure and physicochemical data for compounds 190-331

| Cmpd. | Method/Product | Starting materials | $^1$H NMR, LCMS m/z [M + H]$^+$ |
|---|---|---|---|
| 330 | As for compound C38 | | LCMS m/z 452.16 [M + H]$^+$ |
| 331 | As for compound C38 | | LCMS m/z 516.23 [M + H]$^+$ |

Compound 332

(3R)-3-[[3-[5,7-difluoro-2-(4-fluorophenyl)-1H-indol-3-yl]cyclobutyl]methylsulfamoylamino]pyrrolidin-2-one (332)

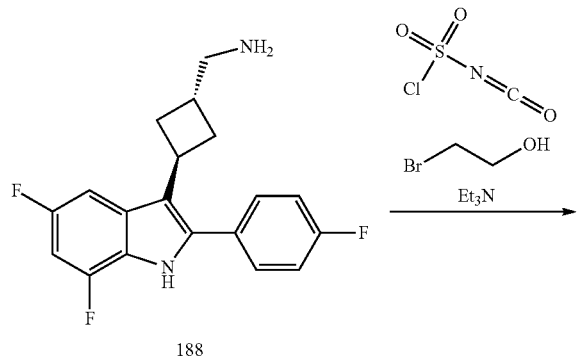

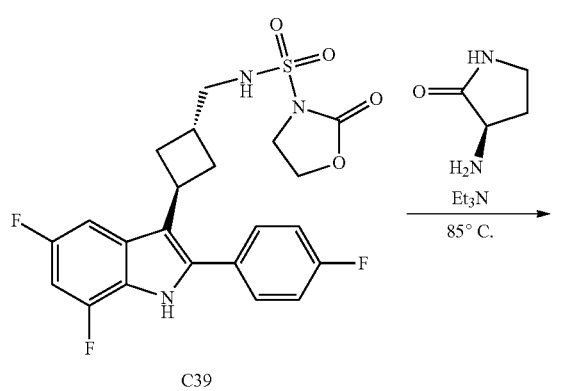

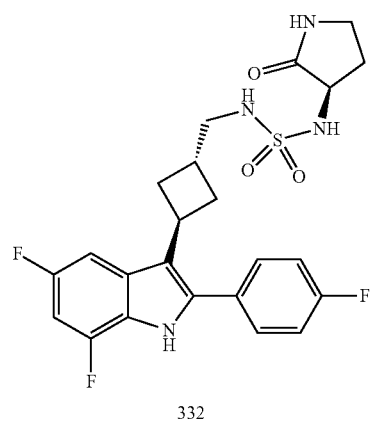

Step 1. Synthesis of N-[[3-[5,7-difluoro-2-(4-fluorophenyl)-1H-indol-3-yl]cyclobutyl]methyl]-2-oxo-oxazolidine-3-sulfonamide (C39)

To a solution of N-(oxomethylene)sulfamoyl chloride (262 µL, 3.01 mmol) in anhydrous DCM (20 mL) was slowly added 2-bromoethanol (1.9 mL, 26.8 mmol) in anhydrous $CH_2Cl_2$ (5 mL) at 0° C. After stirring for 2 h, the resulting mixture was added to a solution of [3-[5,7-difluoro-2-(4-fluorophenyl)-1H-indol-3-yl]cyclobutyl]methanamine 188 (800 mg, 2.42 mmol), $Et_3N$ (680 µL, 4.88 mmol) in anhydrous $CH_2Cl_2$ (10 mL) via cannula at 0° C. The mixture was warmed to room temperature and stirred for 12 hours. To the mixture was added 1.0 M aqueous HCl, and then the aqueous mixture was extracted with $CH_2Cl_2$. The organic extract was washed with water, dried over anhydrous $MgSO_4$ and conc in vacuo to afford the crude material which was purified via silica gel chromatography (40 g) eluting with 0-100% EtOAc in Hexanes to afford pure N-[[3-[5,7-difluoro-2-(4-fluorophenyl)-1H-indol-3-yl]cyclobutyl]methyl]-2-oxo-oxazolidine-3-sulfonamide (940 mg, 72%). $^1$H NMR (300 MHz, Acetone-$d_6$) δ 10.67 (s, 1H), 7.70-7.51 (m, 2H), 7.40 (dd, J=9.9, 2.2 Hz, 1H), 7.35-7.21 (m, 2H), 7.12 (t, J=6.0 Hz, 1H), 6.84 (ddd, J=11.5, 9.6, 2.2 Hz, 1H), 4.50 (dd, J=8.8, 6.8 Hz, 2H), 4.26-3.93 (m, 3H), 3.55-3.33 (m, 2H), 2.80-2.45 (m, 3H), 2.28 (tt, J=9.6, 2.9 Hz, 2H). LCMS m/z 480.38 [M+H]$^+$.

Step 2. Synthesis of (3R)-3-[[3-[5,7-difluoro-2-(4-fluorophenyl)-1H-indol-3-yl]cyclobutyl]methylsulfamoylamino]pyrrolidin-2-one (332)

To a of mixture of N-[[3-[5,7-difluoro-2-(4-fluorophenyl)-1H-indol-3-yl]cyclobutyl]methyl]-2-oxo-oxazolidine-3-sulfonamide C39 (19 mg) in acetonitrile (1.5 mL) and $Et_3N$ (0.25 mL) was added (R)-3-aminopyrrolidin-2-one. The reaction was then heated to 85° C. with stirring for 2.5 hours before being allowed to cool to ambient temperature. The reaction was then concentrated in vacuo and purified via reverse phase HPLC using a mobile phase of 5→95% MeCN in Water (0.1% TFA). The pure fractions which combined and concentrated in vacuo to afford pure title compound as its TFA salt. LCMS m/z 492.95 [M+H]$^+$.

Compounds 333-369

Compounds 333-369 (see Table 11) were prepared in two steps from 188 and the listed amine reagents using the method described in the synthesis of compound 332. Amine reagents were obtained from commercial sources.

TABLE 11
Structure and physicochemical data for compounds 333-369
| Compound | Product | Amine | ¹H NMR, LCMS m/z [M + H]+ |
|---|---|---|---|
| 333 | 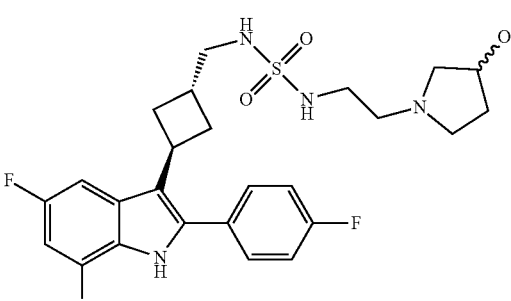 | 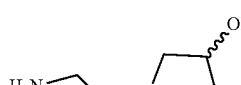 | LCMS m/z 523.3 [M + H]⁺ |
| 334 | 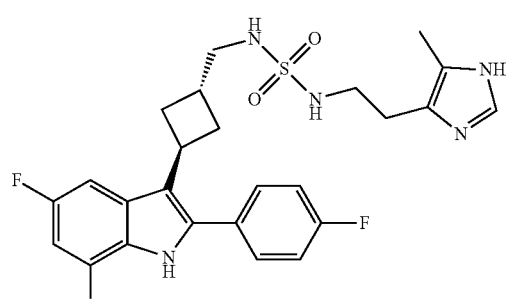 | 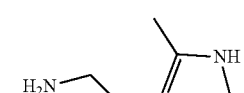 | LCMS m/z 518.35 [M + H]⁺ |
| 335 | 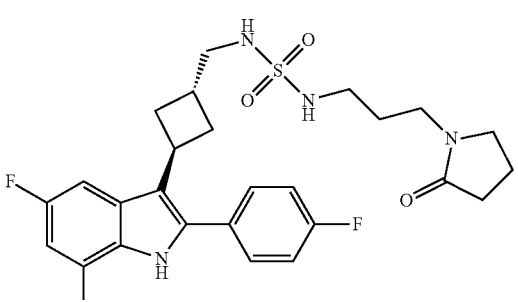 | 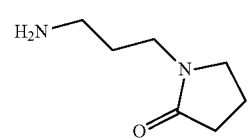 | LCMS m/z 535.06 [M + H]⁺ |
| 336 | 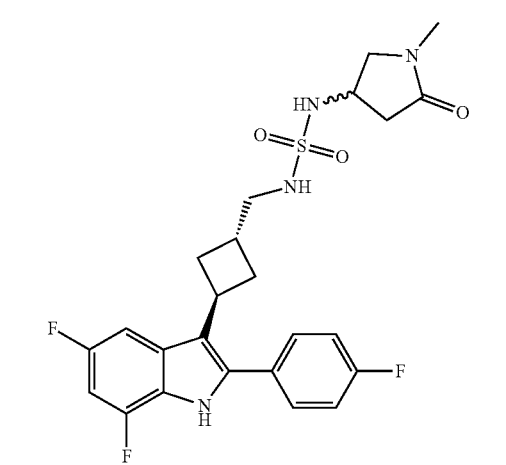 [SMILES: CN1CC(NS(=O)(=O)NC[C@H]2C[C@H](c3c(-c4ccc(F)cc4)[nH]c4c(F)cc(F)cc43)C2)CC1=O] |  | LCMS m/z 507.28 [M + H]⁺ |

TABLE 11-continued

Structure and physicochemical data for compounds 333-369

| Compound | Product | Amine | ¹H NMR, LCMS m/z [M + H]+ |
|---|---|---|---|
| 337 | | | LCMS m/z 549.4 [M + H]⁺ |
| 338 | | | LCMS m/z 468.06 [M + H]⁺ |
| 339 | | | LCMS m/z 454.25 [M + H]⁺ |
| 340 | | | LCMS m/z 507.31 [M + H]⁺ |

TABLE 11-continued
Structure and physicochemical data for compounds 333-369
| Compound | Product | Amine | ¹H NMR, LCMS m/z [M + H]+ |
|---|---|---|---|
| 341 | 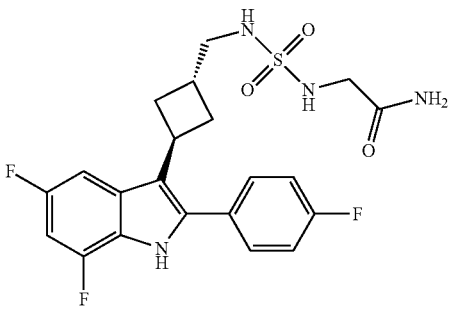 [SMILES: NC(=O)CNS(=O)(=O)NC[C@H]1C[C@H](c2c(-c3ccc(F)cc3)[nH]c3c(F)cc(F)cc32)C1] | 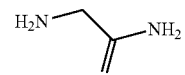 | LCMS m/z 467.24 [M + H]⁺ |
| 342 | 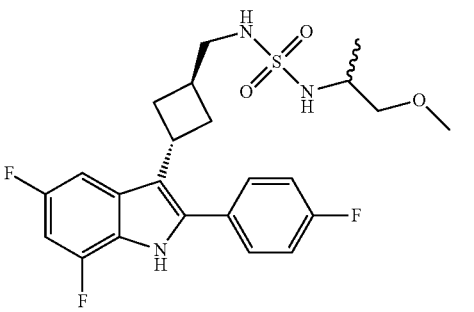 [SMILES: COCC(C)NS(=O)(=O)NC[C@H]1C[C@H](c2c(-c3ccc(F)cc3)[nH]c3c(F)cc(F)cc32)C1] | 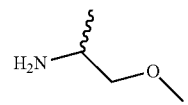 | LCMS m/z 481.97 [M + H]⁺ |
| 343 | 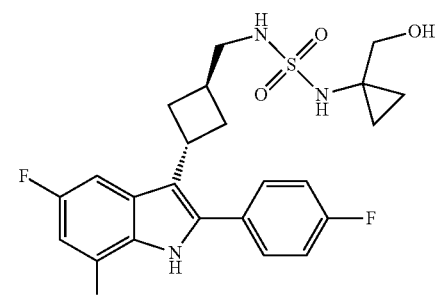 | 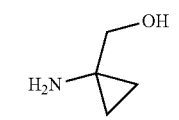 | LCMS m/z 480.31 [M + H]⁺ |
| 344 | 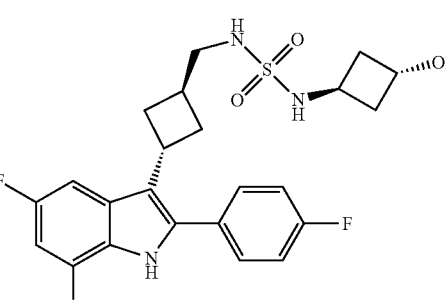 | 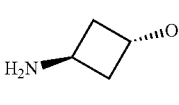 | LCMS m/z 480.14 [M + H]⁺ |

TABLE 11-continued
Structure and physicochemical data for compounds 333-369
| Compound | Product | Amine | ¹H NMR, LCMS m/z [M + H]+ |
|---|---|---|---|
| 345 | 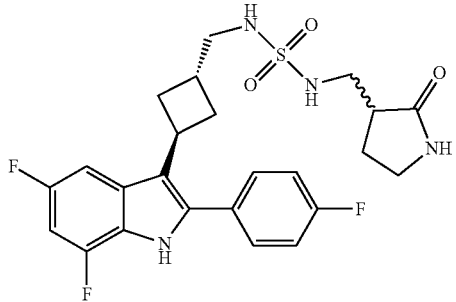 [SMILES: O=C1NCCC1CNS(=O)(=O)NC[C@H]1C[C@H](c2c(-c3ccc(F)cc3)[nH]c3c(F)cc(F)cc32)C1] | 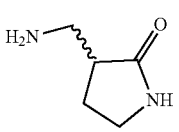 | LCMS m/z 507.21 [M + H]⁺ |
| 346 | 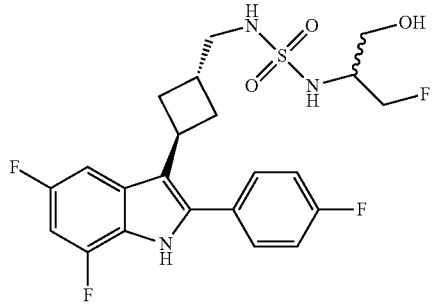 [SMILES: O=S(=O)(NC[C@H]1C[C@H](c2c(-c3ccc(F)cc3)[nH]c3c(F)cc(F)cc32)C1)NC(CO)CF] | 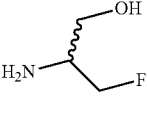 | LCMS m/z 486.14 [M + H]⁺ |
| 347 | 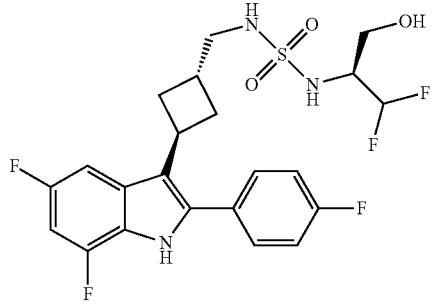 [SMILES: O=S(=O)(NC[C@H]1C[C@H](c2c(-c3ccc(F)cc3)[nH]c3c(F)cc(F)cc32)C1)N[C@@H](CO)C(F)F] | 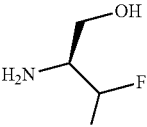 | LCMS m/z 504.35 [M + H]⁺ |
| 348 | 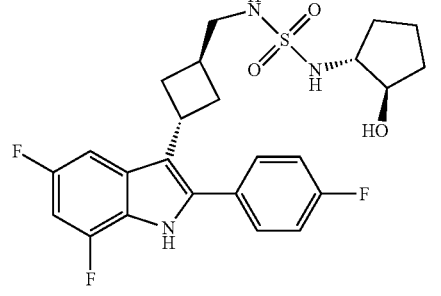 | 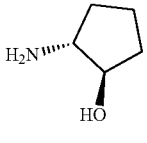 | LCMS m/z 494.31 [M + H]⁺ |

TABLE 11-continued
Structure and physicochemical data for compounds 333-369
| Compound | Product | Amine | $^1$H NMR, LCMS m/z [M + H]+ |
|---|---|---|---|
| 349 | 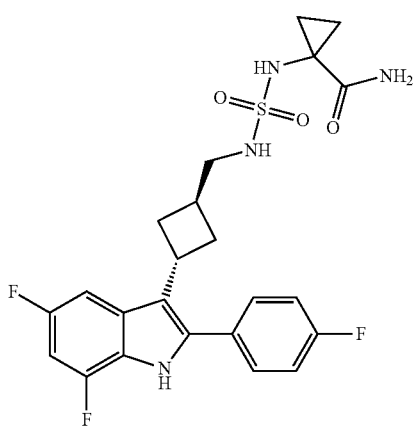 [SMILES: NC(=O)C1(NS(=O)(=O)NC[C@H]2C[C@H](c3c(-c4ccc(F)cc4)[nH]c4c(F)cc(F)cc43)C2)CC1] | 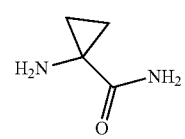 | LCMS m/z 493.11 [M + H]$^+$ |
| 350 | 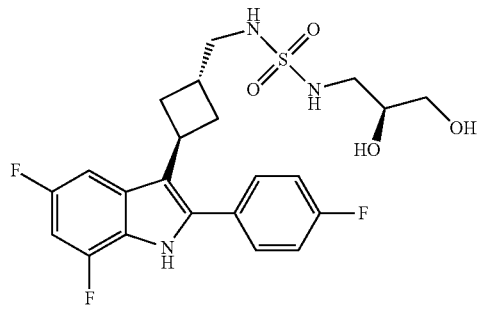 [SMILES: O=S(=O)(NC[C@H](O)CO)NC[C@H]1C[C@H](c2c(-c3ccc(F)cc3)[nH]c3c(F)cc(F)cc32)C1] | 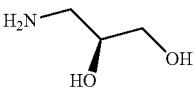 | LCMS m/z 484.35 [M + H]$^+$ |
| 351 | 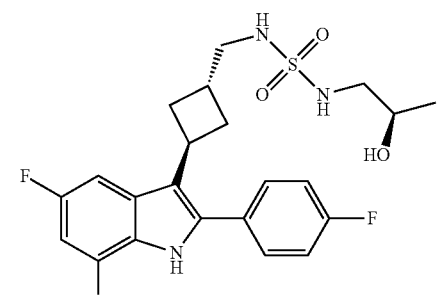 | 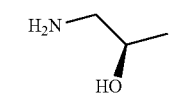 | LCMS m/z 486.12 [M + H]$^+$ |
| 352 | 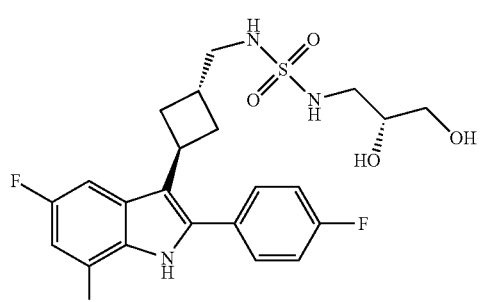 | 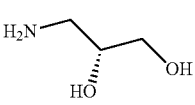 | LCMS m/z 483.89 [M + H]$^+$ |

441
442
TABLE 11-continued
Structure and physicochemical data for compounds 333-369
| Compound | Product | Amine | $^1$H NMR, LCMS m/z [M + H]+ |
|---|---|---|---|
| 353 | 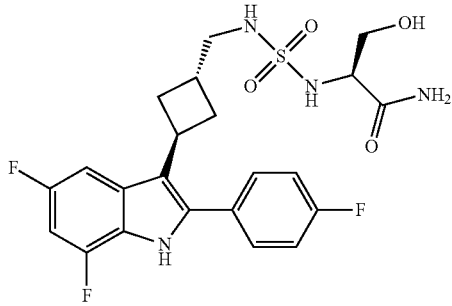 [SMILES: NC(=O)[C@H](CO)NS(=O)(=O)NC[C@H]1C[C@H](c2c(-c3ccc(F)cc3)[nH]c3c(F)cc(F)cc32)C1] | 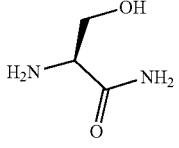 | LCMS m/z 497.28 [M + H]$^+$ |
| 354 | 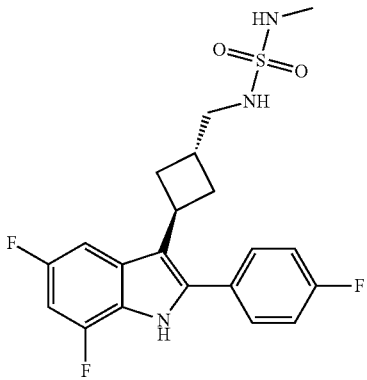 [SMILES: CNS(=O)(=O)NC[C@H]1C[C@H](c2c(-c3ccc(F)cc3)[nH]c3c(F)cc(F)cc32)C1] |  | LCMS m/z 424.34 [M + H]$^+$ |
| 355 | 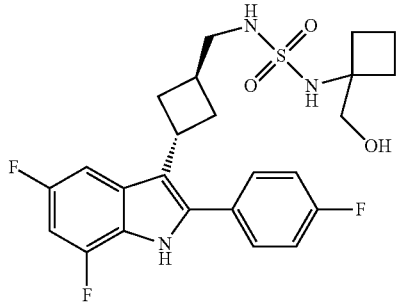 [SMILES: O=S(=O)(NC[C@H]1C[C@H](c2c(-c3ccc(F)cc3)[nH]c3c(F)cc(F)cc32)C1)NC1(CO)CCC1] | 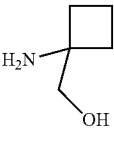 | LCMS m/z 494.28 [M + H]$^+$ |
| 356 | 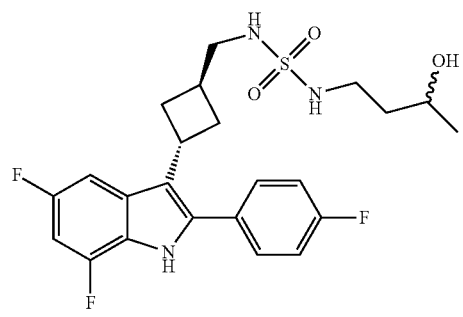 [SMILES: CC(O)CCNS(=O)(=O)NC[C@H]1C[C@H](c2c(-c3ccc(F)cc3)[nH]c3c(F)cc(F)cc32)C1] | 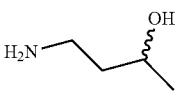 | LCMS m/z 482.03 [M + H]$^+$ |

TABLE 11-continued
Structure and physicochemical data for compounds 333-369
| Compound | Product | Amine | ¹H NMR, LCMS m/z [M + H]+ |
|---|---|---|---|
| 357 | 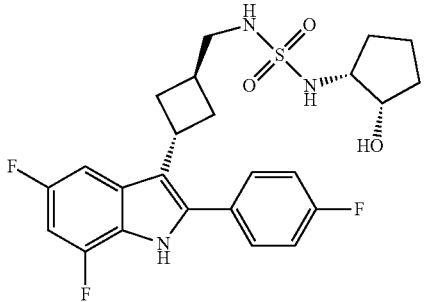 [SMILES: O=S(=O)(NC[C@H]1C[C@H](c2c(-c3ccc(F)cc3)[nH]c3c(F)cc(F)cc32)C1)N[C@@H]1CCC[C@@H]1O] | 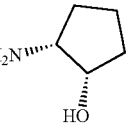 | LCMS m/z 494.15 [M + H]⁺ |
| 358 | 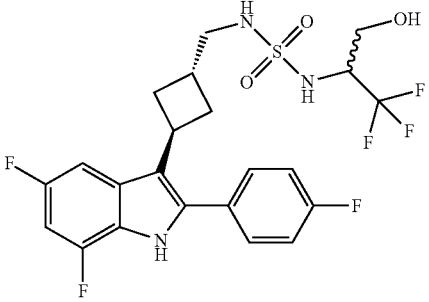 [SMILES: O=S(=O)(NC[C@H]1C[C@H](c2c(-c3ccc(F)cc3)[nH]c3c(F)cc(F)cc32)C1)NC(CO)C(F)(F)F] | 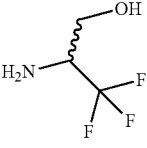 | LCMS m/z 522.23 [M + H]⁺ |
| 359 | 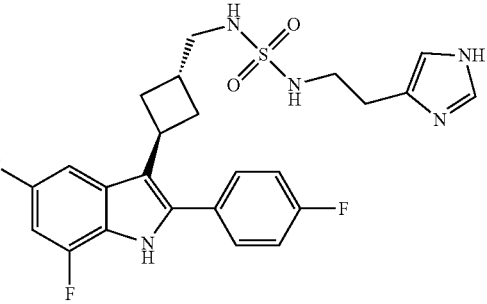 | 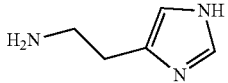 | LCMS m/z 504.22 [M + H]⁺ |
| 360 | 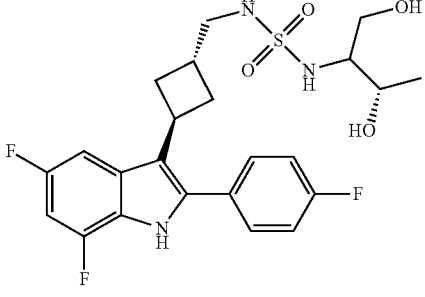 | 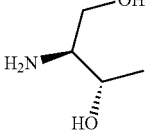 | LCMS m/z 498.16 [M + H]⁺ |

TABLE 11-continued
Structure and physicochemical data for compounds 333-369
| Compound | Product | Amine | ¹H NMR, LCMS m/z [M + H]+ |
|---|---|---|---|
| 361 | 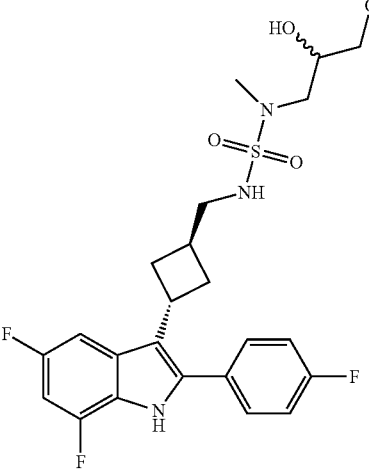 | 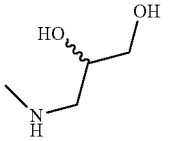 | LCMS m/z 498.32 [M + H]⁺ |
| 362 | 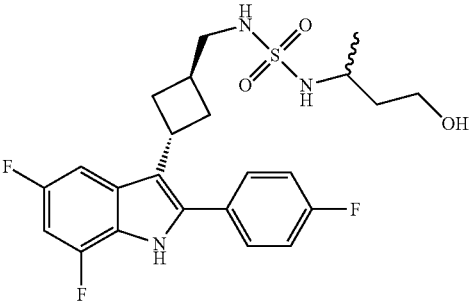 [SMILES: CC(CCO)NS(=O)(=O)NC[C@H]1C[C@H](c2c(-c3ccc(F)cc3)[nH]c3c(F)cc(F)cc32)C1] | 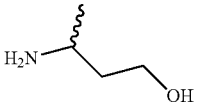 | LCMS m/z 482.16 [M + H]⁺ |
| 363 | 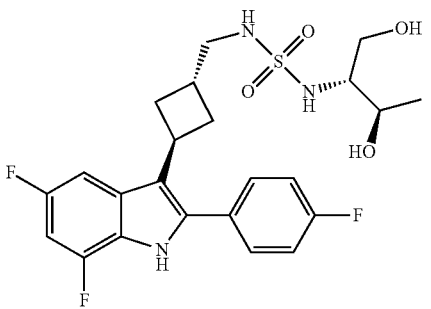 [SMILES: C[C@@H](O)[C@@H](CO)NS(=O)(=O)NC[C@H]1C[C@H](c2c(-c3ccc(F)cc3)[nH]c3c(F)cc(F)cc32)C1] | 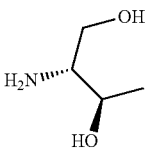 | LCMS m/z 498.39 [M + H]⁺ |

TABLE 11-continued
Structure and physicochemical data for compounds 333-369
| Compound | Product | Amine | ¹H NMR, LCMS m/z [M + H]+ |
|---|---|---|---|
| 364 | 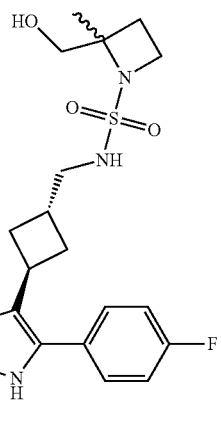 | 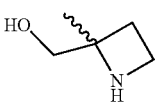 | LCMS m/z 494.35 [M + H]⁺ |
| 365 | 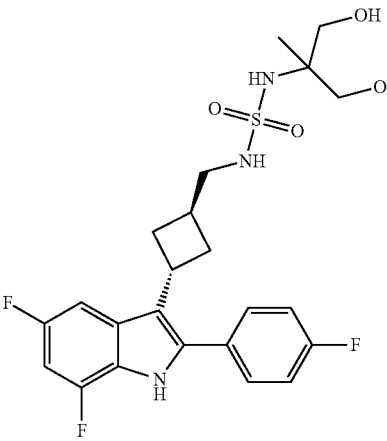 | 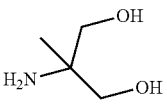 | LCMS m/z 498.09 [M + H]⁺ |
| 366 | 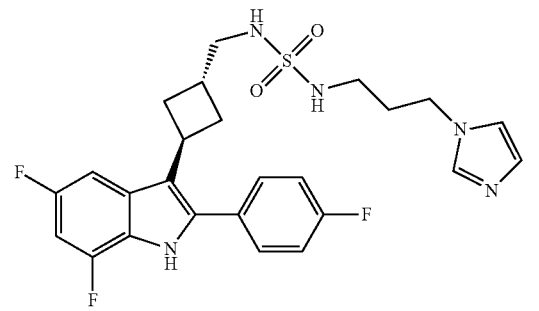 [SMILES: O=S(=O)(NCCCn1ccnc1)NC[C@H]1C[C@H](c2c(-c3ccc(F)cc3)[nH]c3c(F)cc(F)cc32)C1] | 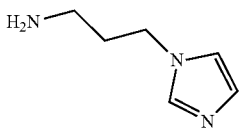 | LCMS m/z 418.19 [M + H]⁺ |
| 367 | 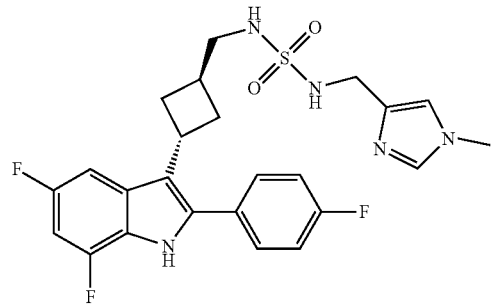 [SMILES: Cn1cnc(CNS(=O)(=O)NC[C@H]2C[C@H](c3c(-c4ccc(F)cc4)[nH]c4c(F)cc(F)cc43)C2)c1] | 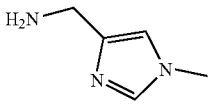 | LCMS m/z 504.15 [M + H]⁺ |

TABLE 11-continued

Structure and physicochemical data for compounds 333-369

| Compound | Product | Amine | ¹H NMR, LCMS m/z [M + H]+ |
|---|---|---|---|
| 368 | | | LCMS m/z 507.15 [M + H]⁺ |
| 369 | | | LCMS m/z 504.38 [M + H]⁺ |

Compound 370

3-[3-[(dimethylsulfamoylamino)methyl]cyclobutyl]-5,7-difluoro-2-(4-fluorophenyl)-1H-indole (370)

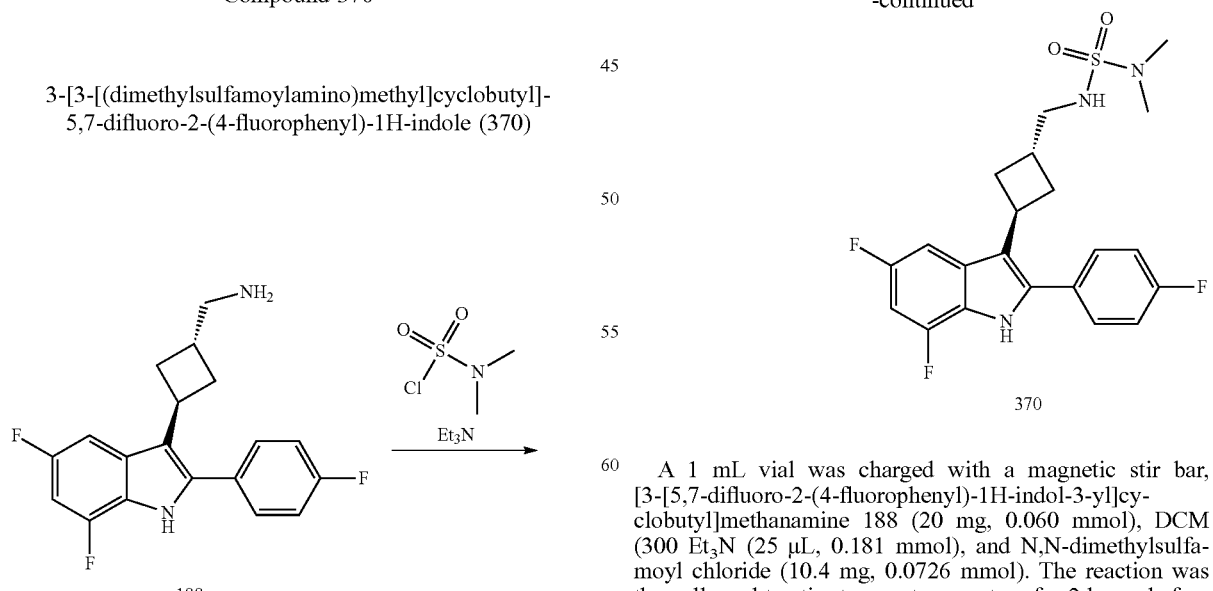

A 1 mL vial was charged with a magnetic stir bar, [3-[5,7-difluoro-2-(4-fluorophenyl)-1H-indol-3-yl]cyclobutyl]methanamine 188 (20 mg, 0.060 mmol), DCM (300 Et₃N (25 μL, 0.181 mmol), and N,N-dimethylsulfamoyl chloride (10.4 mg, 0.0726 mmol). The reaction was then allowed to stir at room temperature for 2 hours before being concentrated in vacuo to afford the crude title compound which was dissolved in DMSO (~1 mL). This was purified via reverse phase HPLC using a mobile phase of 5 to 95% MeCN in Water (0.1% TFA). The pure fractions which combined and concentrated in vacuo to afford pure 3-[3-[(dimethylsulfamoylamino)methyl]cyclobutyl]-5,7-difluoro-2-(4-fluorophenyl)-1H-indole. LCMS m/z 438.33 [M+H]+.

Compounds 371 and 372

Compounds 371 and 372 (see Table 12) were prepared in one step from 188 and the listed sulfonyl chloride reagents using the method described in the synthesis of compound 370. Sulfonyl chloride reagents were obtained from commercial sources.

TABLE 12

Structure and physicochemical data for compounds 371 and 372

| Compound | Product | Sulfonyl Chloride | $^1$H NMR, LCMS m/z [M + H]+ |
|---|---|---|---|
| 371 | 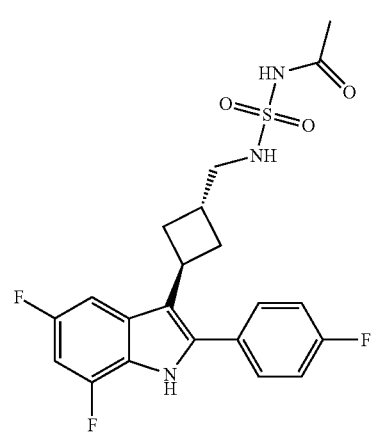 [SMILES: CC(=O)NS(=O)(=O)NC[C@H]1C[C@H](c2c(-c3ccc(F)cc3)[nH]c3c(F)cc(F)cc32)C1] | 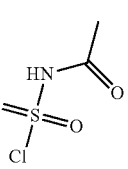 | $^1$H NMR (300 MHz, Methanol-$d_4$) δ 7.60-7.42 (m, 2H), 7.38-7.09 (m, 3H), 6.75 (ddd, J = 11.3, 9.6, 2.1 Hz, 1H), 3.96 (p, J = 8.9 Hz, 1H), 3.23 (d, J = 7.2 Hz, 2H), 2.71-2.40 (m, 3H), 2.19 (t, J = 9.3 Hz, 2H), 2.05 (s, 3H). LCMS m/z 452.33 [M + H]+ |
| 372 | 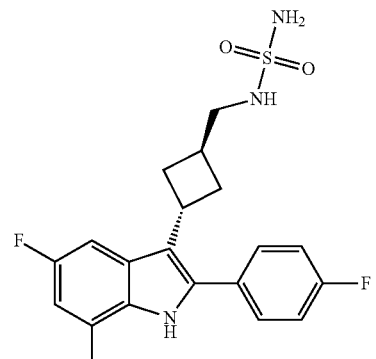 | 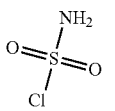 | LCMS m/z 410.31 [M + H]+ |

Compound 373

1-(((1r,3r)-3-(5,7-difluoro-2-(4-fluorophenyl)-1H-indol-3-yl)cyclobutyl)methyl)imidazolidin-2-one (373)

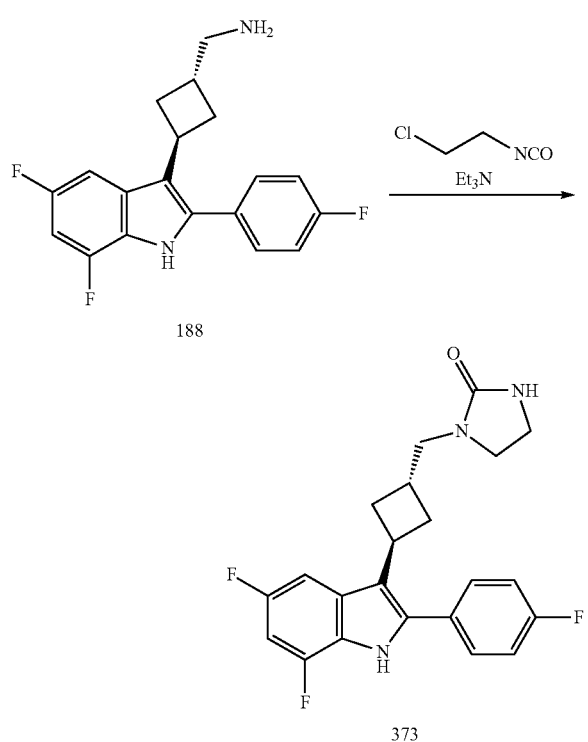

To a solution of ((1r,3r)-3-(5,7-difluoro-2-(4-fluorophenyl)-1H-indol-3-yl)cyclobutyl)methanamine 188 (27 mg, 0.72 mmol) in EtOH (1 mL) was added Et₃N (13 □L, 0.093 mmol) followed by 1-chloro-2-isocyanatoethane (8 mL, 0.094 mmol). The reaction mixture was stirred overnight at room temperature then concentrated in vacuo and purified via reverse phase chromatography (water/MeCN/0.1% TFA 5 to 95%) to afford 1-(((1r,3r)-3-(5,7-difluoro-2-(4-fluorophenyl)-1H-indol-3-yl)cyclobutyl)methyl)imidazolidin-2-one (21 mg, 73%). $^1$H NMR (300 MHz, Methanol-d₄) δ 7.60-7.40 (m, 2H), 7.42-7.11 (m, 3H), 6.76 (ddd, J=11.4, 9.6, 1.9 Hz, 1H), 4.89-4.74 (m, 2H), 3.98 (ddq, J=24.1, 16.1, 8.8 Hz, 3H), 3.53 (dd, J=19.5, 7.0 Hz, 2H), 2.63 (q, J=9.6, 9.0 Hz, 3H), 2.20 (q, J=12.6, 10.6 Hz, 2H). LCMS m/z 400.36 [M+H]⁺.

Compound 374

2-[[3-[5,7-difluoro-2-(4-fluorophenyl)-1H-indol-3-yl]cyclobutyl]methylamino]ethanol (374)

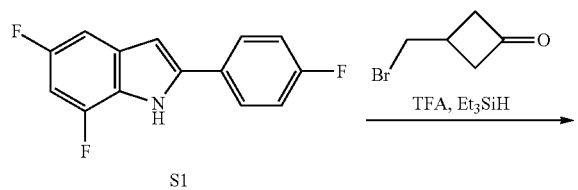

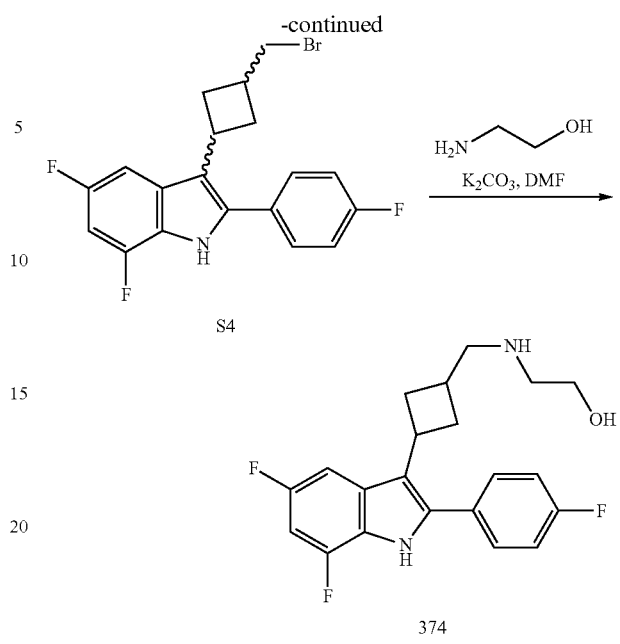

Step 1. Synthesis of 3-[3-(bromomethyl)cyclobutyl]-5,7-difluoro-2-(4-fluorophenyl)-1H-indole (S4)

A 200 mL round bottom flask was charged with a magnetic stir bar and 5,7-difluoro-2-(4-fluorophenyl)-1H-indole S1 (380 mg, 1.537 mmol). To this flask was added DCM (5 mL), followed by the addition of 3-(bromomethyl)cyclobutanone (250 mg, 1.53 mmol), Et₃SiH (900 mg, 7.74 mmol) and TFA (525 mg, 4.60 mmol). The reaction mixture was allowed to stir overnight at ambient temperature. The reaction mixture was then diluted with EtOAc (~100 mL) and then washed with saturated aqueous NaHCO₃. The organic layer then washed with brine, collected, dried with anhydrous Na₂SO₄, filtered through a bed of Celite®, and concentrated in vacuo to afford the crude title compound. The crude was purified by silica gel chromatography (80 g) using ethyl acetate/hexanes (1:10) as eluent to afford pure title compound as a 1:1 mixture of cis/trans (504 mg, 34%) $^1$H NMR (300 MHz, Methanol-d₄) δ 7.98-7.71 (m, 1H), 7.62-7.38 (m, 3H), 7.32-7.12 (m, 5H), 7.03 (dd, J=9.3, 2.2 Hz, 1H), 6.88-6.55 (m, 2H), 3.73-3.58 (m, 2H), 3.45 (d, J=6.8 Hz, 2H), 2.67-2.52 (m, 2H), 2.52-2.29 (m, 2H), 2.28-2.12 (m, 1H), 2.05 (dt d, J=11.8, 9.9, 4.9 Hz, 2H), 0.95 (t, J=7.9 Hz, 1H), 0.66-0.51 (m, 1H). LCMS m/z 394.38 [M+H]⁺.

Step 2. Synthesis of 2-[[3-[5,7-difluoro-2-(4-fluorophenyl)-1H-indol-3-yl]cyclobutyl]methylamino]ethanol (374)

A 1 mL vial was charged with a magnetic stir bar, 3-[3-(bromomethyl)cyclobutyl]-5,7-difluoro-2-(4-fluorophenyl)-1H-indole S4 (25 mg, 0.06342 mmol), DMF (317.1 µL), ethanolamine (approximately 3.874 mg, 3.828 µL, 0.06342 mmol), and K₂CO₃ (approximately 17.52 mg, 0.1268 mmol). The reaction was then heated to 80° C. with stirring for 12 hours before being allowed to cool to room temperature. The reaction mixture was diluted with DMSO (~0.5 mL) and this mixture was purified via reverse phase HPLC using a mobile phase of 5 to 95% MeCN in Water (0.1% TFA). The pure fractions which combined and concentrated in vacuo to afford pure title compound as its TFA salt. LCMS m/z 375.19 [M+H]⁺.

Compounds 375-411
Compounds 375-411 (see Table 13) were prepared in one step from S4 and the listed amine reagents using the method described in the synthesis of compound 374. Amine reagents were obtained from commercial sources.
TABLE 13
Structure and physicochemical data for compounds 375-411
| Compound | Product | Amine | $^1$H NMR, LCMS m/z [M + H]+ |
|---|---|---|---|
| 375 | 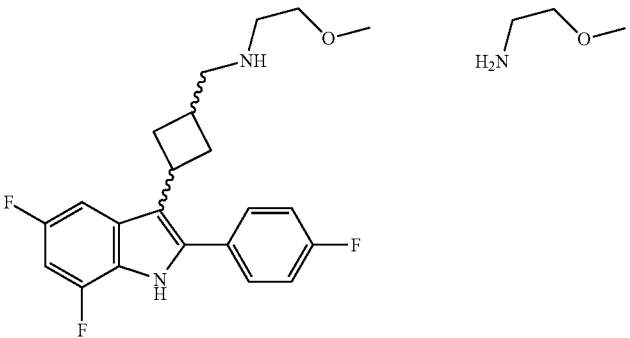 | 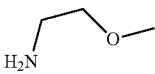 | LCMS m/z 389.2 [M + H]$^+$ |
| 376 | 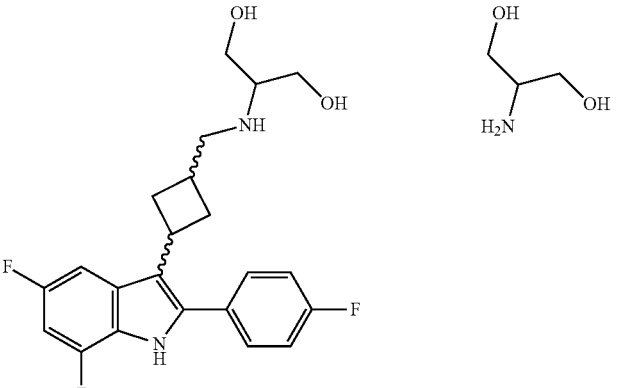 | 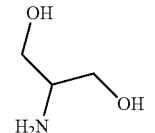 | LCMS m/z 405.19 [M + H]$^+$ |
| 377 | 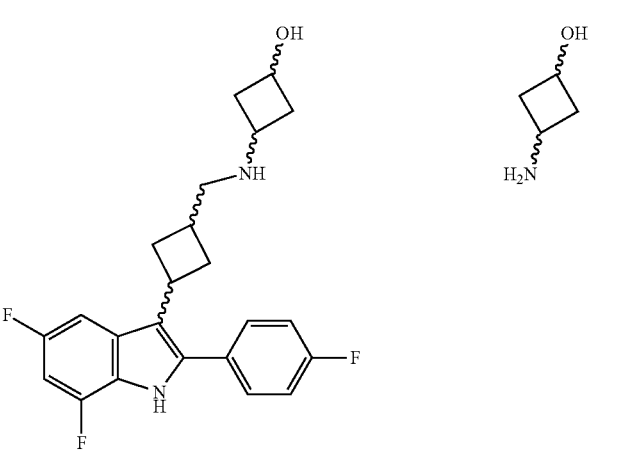 | 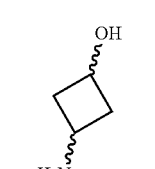 | LCMS m/z 401.23 [M + H]$^+$ |

TABLE 13-continued
Structure and physicochemical data for compounds 375-411
| Compound | Product | Amine | $^1$H NMR, LCMS m/z [M + H]+ |
|---|---|---|---|
| 378 | 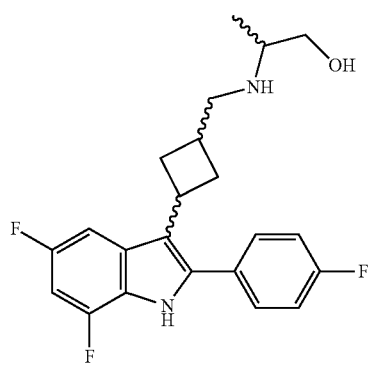 [SMILES: CC(CO)NCC1CC(c2c(-c3ccc(F)cc3)[nH]c3c(F)cc(F)cc23)C1] | 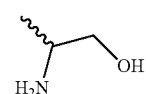 | LCMS m/z 389.2 [M + H]$^+$ |
| 379 | 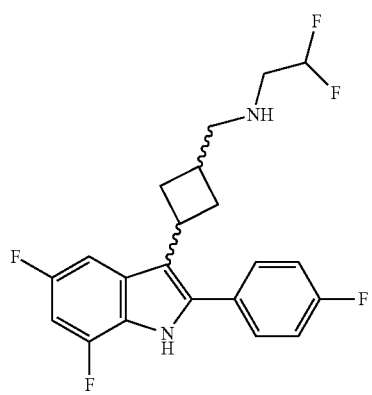 [SMILES: Fc1ccc(-c2[nH]c3c(F)cc(F)cc3c2C2CC(CNCC(F)F)C2)cc1] | 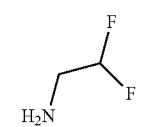 | LCMS m/z 395.18 [M + H]$^+$ |
| 380 | 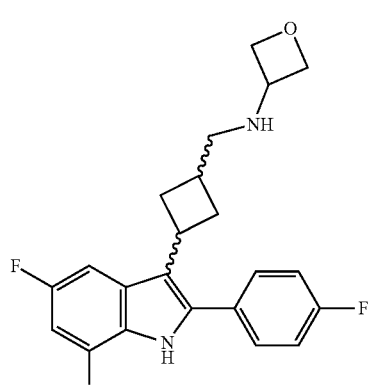 | 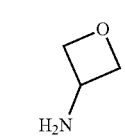 | $^1$H NMR (300 MHz, DMSO-d$_6$) δ 11.71 (s, 1H), 7.67-7.44 (m, 2H), 7.44-7.20 (m, 3H), 7.12-6.80 (m, 1H), 4.87-4.53 (m, 4H), 4.32 (d, J = 6.1 Hz, 1H), 3.84-3.60 (m, 1H), 2.97 (s, 2H), 1.99 (d, J = 9.8 Hz, 2H). LCMS m/z 387.28 [M + H]$^+$ |

TABLE 13-continued
Structure and physicochemical data for compounds 375-411
| Compound | Product | Amine | $^1$H NMR, LCMS m/z [M + H]+ |
|---|---|---|---|
| 381 | 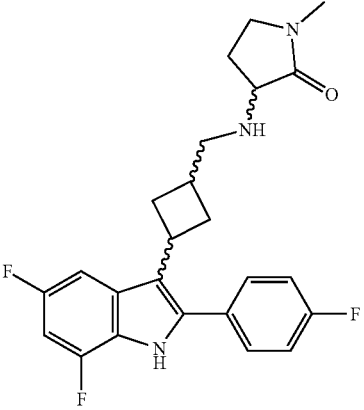 [SMILES: CN1CCC(NCC2CC(c3c(-c4ccc(F)cc4)[nH]c4c(F)cc(F)cc34)C2)C1=O] | 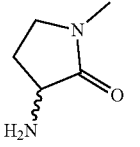 | LCMS m/z 428.2 [M + H]$^+$ |
| 382 | 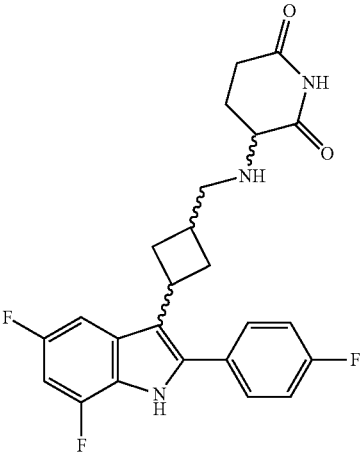 [SMILES: O=C1CCC(NCC2CC(c3c(-c4ccc(F)cc4)[nH]c4c(F)cc(F)cc34)C2)C(=O)N1] | 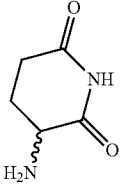 | LCMS m/z 442.17 [M + H]$^+$ |
| 383 | 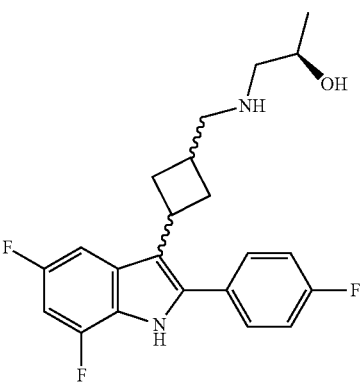 [SMILES: C[C@@H](O)CNCC1CC(c2c(-c3ccc(F)cc3)[nH]c3c(F)cc(F)cc23)C1] | 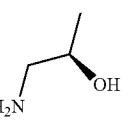 | LCMS m/z 389.2 [M + H]$^+$ |

TABLE 13-continued
Structure and physicochemical data for compounds 375-411
| Compound | Product | Amine | ¹H NMR, LCMS m/z [M + H]+ |
|---|---|---|---|
| 384 | 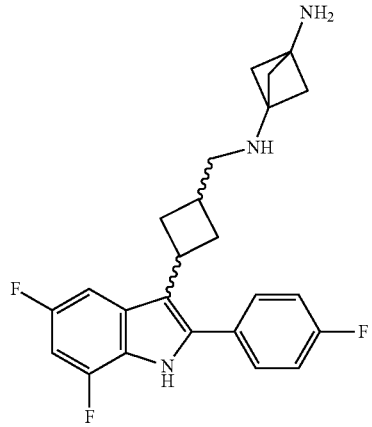 [SMILES: NC12CC(NCC3CC(c4c(-c5ccc(F)cc5)[nH]c5c(F)cc(F)cc45)C3)(C1)C2] | 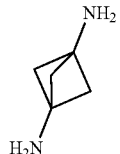 | LCMS m/z 412.24 [M + H]⁺ |
| 385 | 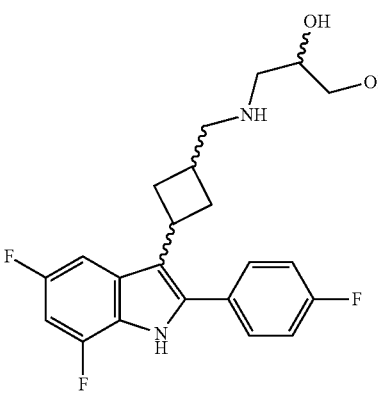 | 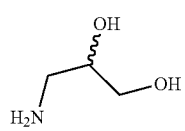 | LCMS m/z 405.19 [M + H]⁺ |
| 386 | 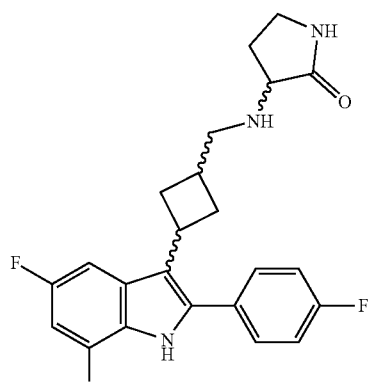 | 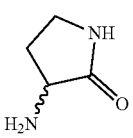 | LCMS m/z 414.0 [M + H]⁺ |

TABLE 13-continued

Structure and physicochemical data for compounds 375-411

| Compound | Product | Amine | ¹H NMR, LCMS m/z [M + H]+ |
|---|---|---|---|
| 387 | | | LCMS m/z 401.22 [M + H]⁺ |
| 388 | | | ¹H NMR (300 MHz, Methanol-d₄) δ 7.51 (td, J = 9.0, 5.5 Hz, 2H), 7.39-7.12 (m, 3H), 6.74 (dddd, J = 11.4, 9.6, 4.4, 2.1 Hz, 1H), 3.81 (tt, J = 10.0, 7.4 Hz, 1H), 3.50-3.35 (m, 1H), 3.15 (d, J = 6.7 Hz, 2H), 2.75-2.45 (m, 3H), 2.41-1.99 (m, 2H). LCMS m/z 374.44 [M + H]⁺ |
| 389 | | | LCMS m/z 389.2 [M + H]⁺ |

TABLE 13-continued

Structure and physicochemical data for compounds 375-411

| Compound | Product | Amine | ¹H NMR, LCMS m/z [M + H]+ |
|---|---|---|---|
| 390 | | | LCMS m/z 417.18 [M + H]⁺ |
| 391 | | | LCMS m/z 401.22 [M + H]⁺ |
| 392 | | | LCMS m/z 419.2 [M + H]⁺ |

TABLE 13-continued
Structure and physicochemical data for compounds 375-411
| Compound | Product | Amine | ¹H NMR, LCMS m/z [M + H]+ |
|---|---|---|---|
| 393 | 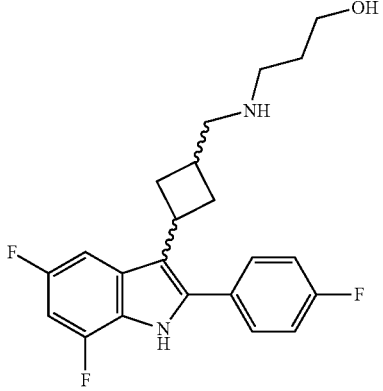 [SMILES: OCCCNCC1CC(c2c(-c3ccc(F)cc3)[nH]c3c(F)cc(F)cc23)C1] | 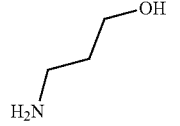 | LCMS m/z 389.23 [M + H]⁺ |
| 394 | 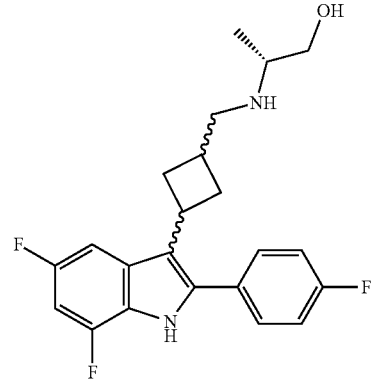 [SMILES: C[C@H](CO)NCC1CC(c2c(-c3ccc(F)cc3)[nH]c3c(F)cc(F)cc23)C1] | 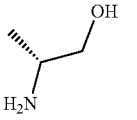 | LCMS m/z 389.2 [M + H]⁺ |
| 395 | 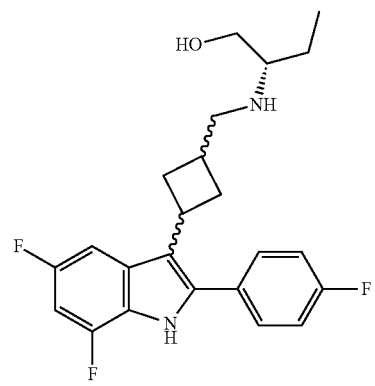 [SMILES: CC[C@@H](CO)NCC1CC(c2c(-c3ccc(F)cc3)[nH]c3c(F)cc(F)cc23)C1] | 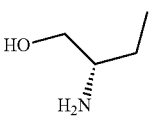 | LCMS m/z 403.34 [M + H]⁺ |

TABLE 13-continued
Structure and physicochemical data for compounds 375-411
| Compound | Product | Amine | ¹H NMR, LCMS m/z [M + H]+ |
|---|---|---|---|
| 396 | 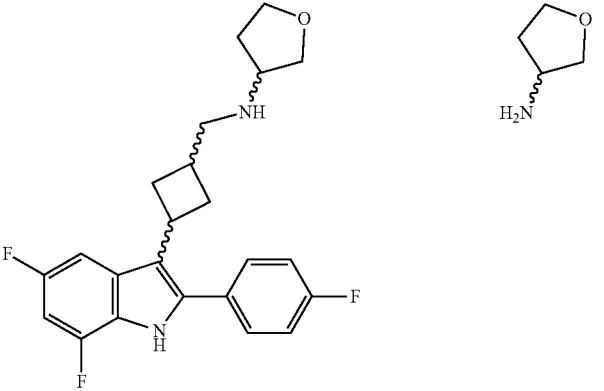 |  | LCMS m/z 401.19 [M + H]⁺ |
| 397 | 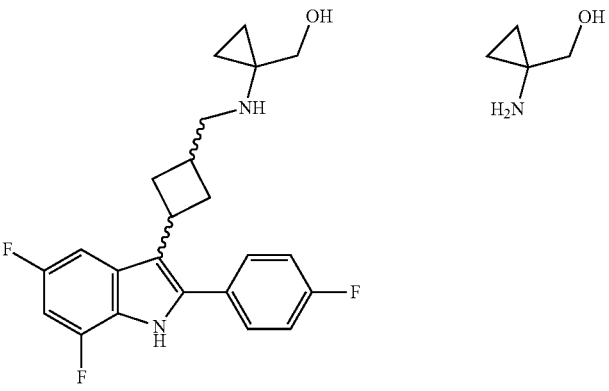 | 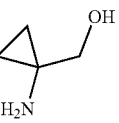 | LCMS m/z 401.19 [M + H]⁺ |
| 398 | 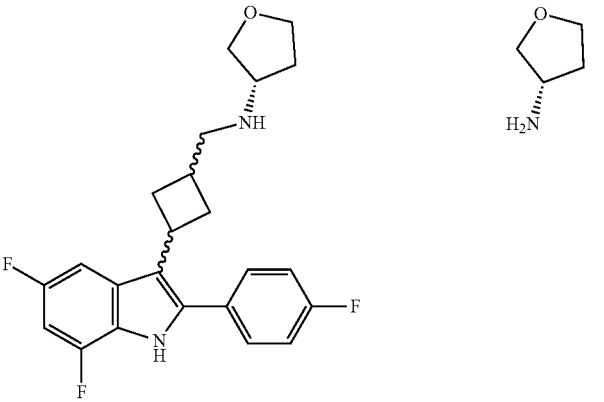 | 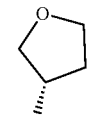 | LCMS m/z 401.22 [M + H]⁺ |

TABLE 13-continued
Structure and physicochemical data for compounds 375-411
| Compound | Product | Amine | ¹H NMR, LCMS m/z [M + H]+ |
|---|---|---|---|
| 399 | 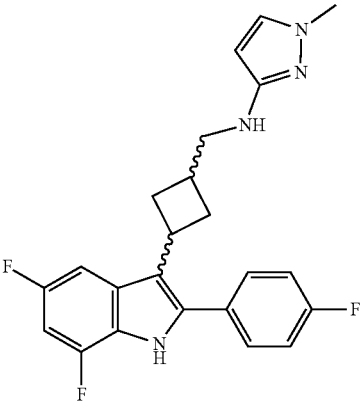 [SMILES: Cn1ccc(NCC2CC(c3c(-c4ccc(F)cc4)[nH]c4c(F)cc(F)cc34)C2)n1] | 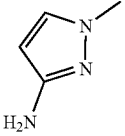 | LCMS m/z 411.19 [M + H]⁺ |
| 400 | 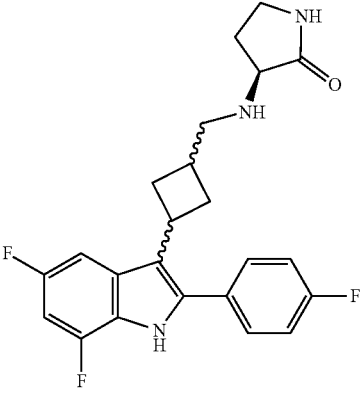 [SMILES: O=C1NCC[C@@H]1NCC1CC(c2c(-c3ccc(F)cc3)[nH]c3c(F)cc(F)cc23)C1] | 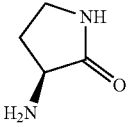 | ¹H NMR (300 MHz, Acetone-d₆) δ 7.62 (dddd, J = 8.8, 7.7, 5.3, 2.6 Hz, 2H), 7.45-7.19 (m, 3H), 6.92-6.75 (m, 1H), 4.32-4.00 (m, 1H), 3.93-3.73 (m, 1H), 3.73-3.35 (m, 4H), 3.13-2.78 (m, 2H), 2.78-2.57 (m, 3H), 2.58-2.36 (m, 2H), 2.34-2.14 (m, 2H). LCMS m/z 414.18 [M + H]⁺ |
| 401 | 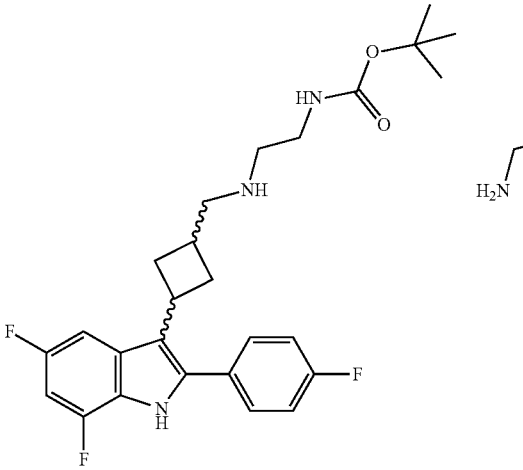 | 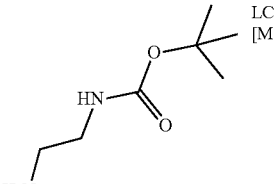 | LCMS m/z 474.22 [M + H]⁺ |

TABLE 13-continued
Structure and physicochemical data for compounds 375-411
| Compound | Product | Amine | ¹H NMR, LCMS m/z [M + H]+ |
|---|---|---|---|
| 402 | 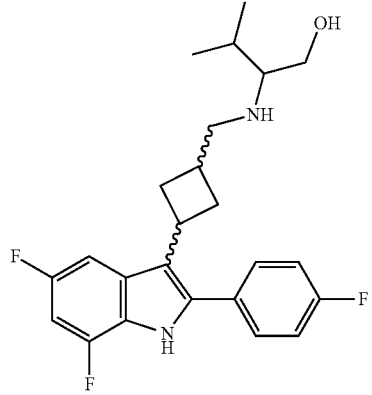 [SMILES: CC(C)C(CO)NCC1CC(c2c(-c3ccc(F)cc3)[nH]c3c(F)cc(F)cc23)C1] | 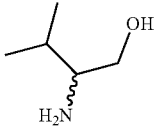 | LCMS m/z 417.21 [M + H]⁺ |
| 403 | 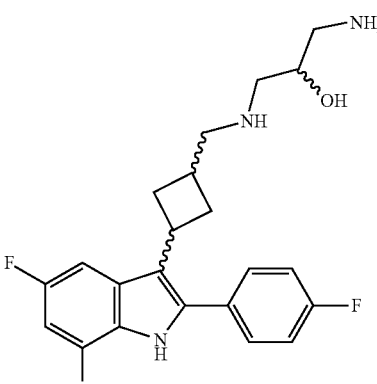 | 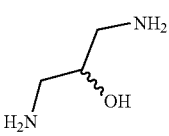 | LCMS m/z 404.22 [M + H]⁺ |
| 404 | 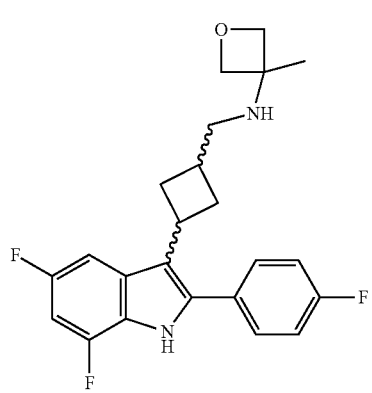 [SMILES: CC1(NCC2CC(c3c(-c4ccc(F)cc4)[nH]c4c(F)cc(F)cc34)C2)COC1] | 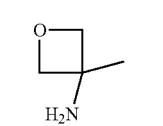 | H NMR (300 MHz, DMSO-d₆) δ 11.72 (d, J = 4.7 Hz, 1H), 9.08 (s, 3H), 7.73-7.47 (m, 3H), 7.36 (td, J = 9.2, 2.3 Hz, 4H), 7.17-6.76 (m, 1H), 4.70 (dd, J = 14.8, 7.4 Hz, 3H), 4.40 (dd, J = 16.0, 7.4 Hz, 3H), 3.72 (td, J = 15.2, 8.7 Hz, 1H), 3.22 (d, J = 7.7 Hz, 1H), 3.01 (s, 2H), 2.21 (d, J = 10.3 Hz, 1H), 1.99 (d, J = 10.0 Hz, 2H), 1.62 (s, 1H), 1.55 (s, 3H). LCMS m/z 401.25 [M + H]⁺ |

TABLE 13-continued
Structure and physicochemical data for compounds 375-411
| Compound | Product | Amine | ¹H NMR, LCMS m/z [M + H]+ |
|---|---|---|---|
| 405 | 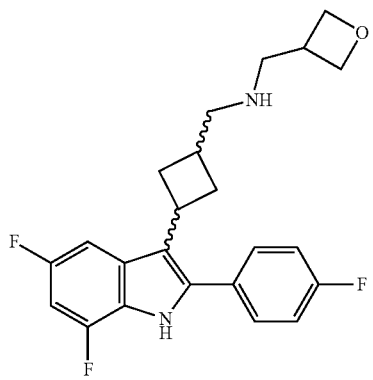 [SMILES: Fc1ccc(-c2[nH]c3c(F)cc(F)cc3c2C2CC(CNCC3COC3)C2)cc1] | 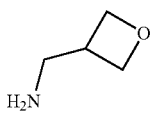 | LCMS m/z 401.22 [M + H]⁺ |
| 406 | 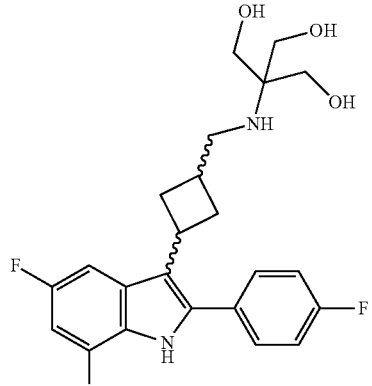 | 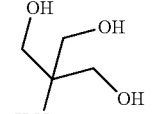 | LCMS m/z 435.2 [M + H]⁺ |
| 407 | 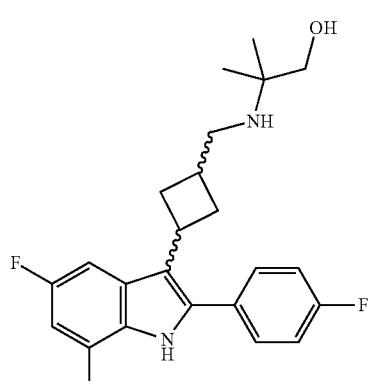 | 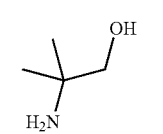 | LCMS m/z 403.21 [M + H]⁺ |

TABLE 13-continued
Structure and physicochemical data for compounds 375-411
| Compound | Product | Amine | ¹H NMR, LCMS m/z [M + H]+ |
|---|---|---|---|
| 408 | 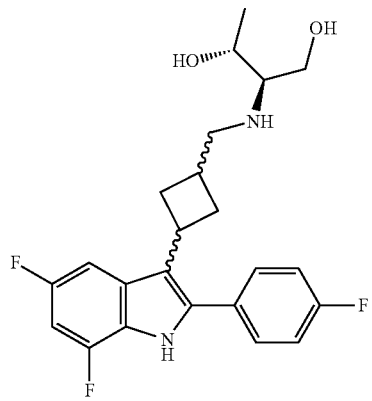 [SMILES: C[C@@H](O)[C@@H](CO)NCC1CC(c2c(-c3ccc(F)cc3)[nH]c3c(F)cc(F)cc23)C1] | 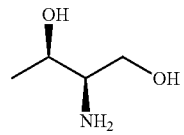 | LCMS m/z 419.22 [M + H]⁺ |
| 409 | 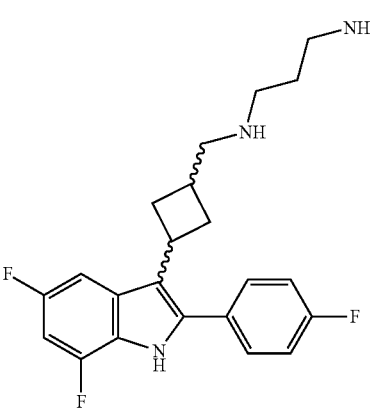 | 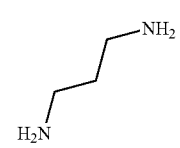 | LCMS m/z 388.23 [M + H]⁺ |

TABLE 13-continued

Structure and physicochemical data for compounds 375-411

| Compound | Product | Amine | ¹H NMR, LCMS m/z [M + H]+ |
|---|---|---|---|
| 410 | 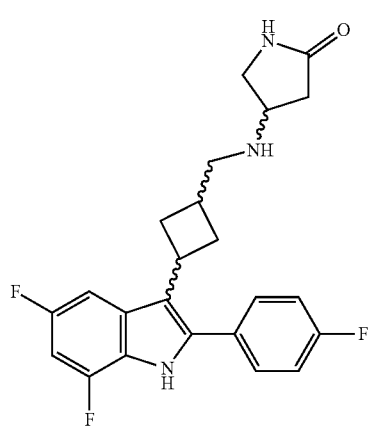 [SMILES: O=C1CC(NCC2CC(c3c(-c4ccc(F)cc4)[nH]c4c(F)cc(F)cc34)C2)CN1] | 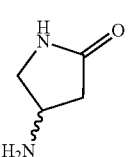 | LCMS m/z 414.18 [M + H]⁺ |
| 411 | 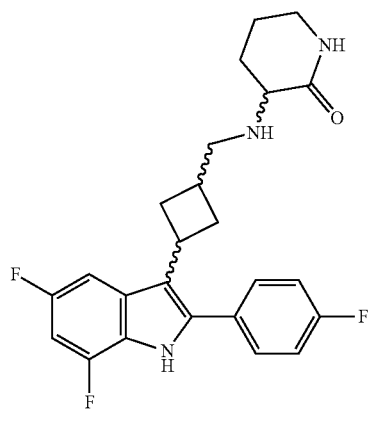 [SMILES: O=C1NCCCC1NCC1CC(c2c(-c3ccc(F)cc3)[nH]c3c(F)cc(F)cc23)C1] | 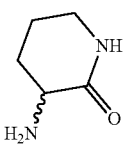 | LCMS m/z 428.22 [M + H]⁺ |

Compound 412

N-(((1r,3r)-3-(5,7-difluoro-2-(4-fluorophenyl)-1H-indol-3-yl)cyclobutyl)methyl)methanesulfonamide (412)

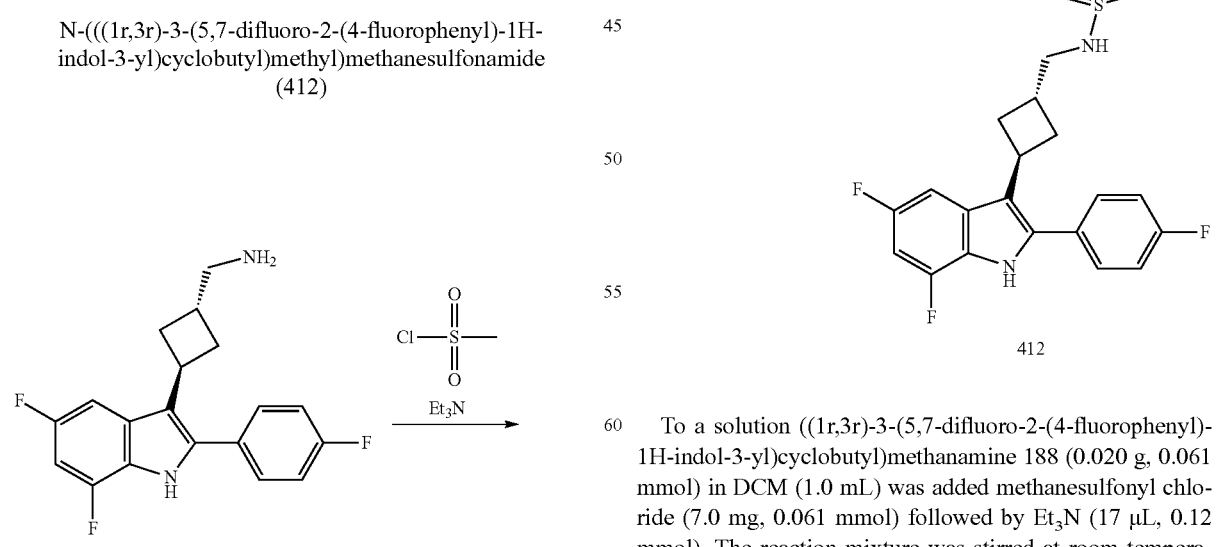

To a solution ((1r,3r)-3-(5,7-difluoro-2-(4-fluorophenyl)-1H-indol-3-yl)cyclobutyl)methanamine 188 (0.020 g, 0.061 mmol) in DCM (1.0 mL) was added methanesulfonyl chloride (7.0 mg, 0.061 mmol) followed by Et₃N (17 μL, 0.12 mmol). The reaction mixture was stirred at room temperature for 2 hours then concentrated in vacuo, and purified via reverse phase HPLC (water/MeCN/0.1% TFA 5 to 95%) to provide N-(((1r,3r)-3-(5,7-difluoro-2-(4-fluorophenyl)-1H-indol-3-yl)cyclobutyl)methyl)methanesulfonamide (14 mg, 33%). $^1$H NMR (300 MHz, Methanol-$d_4$) δ 7.64-7.41 (m, 2H), 7.32 (dd, J=9.8, 2.2 Hz, 1H), 7.28-7.15 (m, 2H), 6.75 (ddd, J=11.5, 9.6, 2.2 Hz, 1H), 3.98 (dt, J=18.0, 8.9 Hz, 1H), 3.29 (d, J=6.0 Hz, 2H), 2.97 (s, 3H), 2.69-2.47 (m, 3H), 2.35-2.08 (m, 2H). LCMS m/z 409.27 [M+H]$^+$.

Compounds 413-420

Compounds 413-420 (see Table 14) were prepared in one step from compound 188 and the listed sulfonyl chloride reagents using the method described in the synthesis of compound 412. Amine reagents were obtained from commercial sources.

TABLE 14

Structure and physicochemical data for compounds 413-420

| Cmpd | Product | Sulfonyl Chloride | $^1$H NMR, LCMS m/z [M + H]+ |
|---|---|---|---|
| 413 | 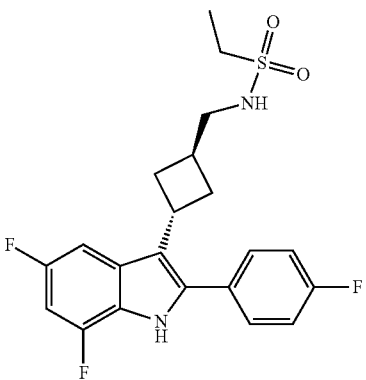 [SMILES: CCS(=O)(=O)NC[C@H]1C[C@H](c2c(-c3ccc(F)cc3)[nH]c3c(F)cc(F)cc32)C1] | 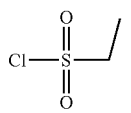 | $^1$H NMR (300 MHz, Methanol-$d_4$) δ 7.60-7.41 (m, 2H), 7.32 (dd, J = 9.8, 2.2 Hz, 1H), 7.27-7.11 (m, 2H), 6.75 (ddd, J = 11.1, 9.6, 2.2 Hz, 1H), 3.98 (dt, J = 17.6, 8.9 Hz, 1H), 3.27 (d, J = 6.0 Hz, 2H), 3.09 (q, J = 7.4 Hz, 2H), 2.67-2.45 (m, 3H), 2.34-2.10 (m, 2H), 1.35 (t, J = 7.4 Hz, 3H). LCMS m/z 423.35 [M + H]$^+$ |
| 414 | 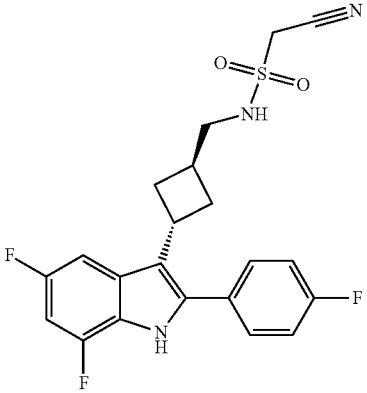 [SMILES: N#CCS(=O)(=O)NC[C@H]1C[C@H](c2c(-c3ccc(F)cc3)[nH]c3c(F)cc(F)cc32)C1] | 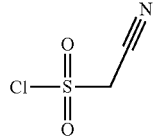 | LCMS m/z 434.37 [M + H]$^+$ |
| 415 | 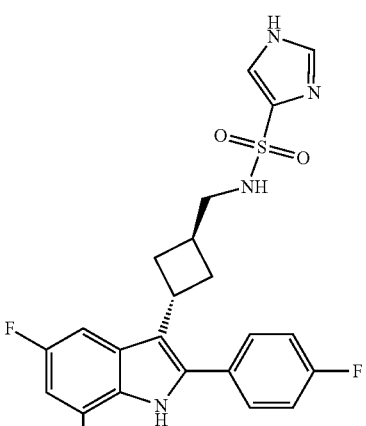 | 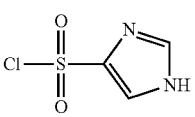 | LCMS m/z 561.33 [M + H]$^+$ |

TABLE 14-continued
Structure and physicochemical data for compounds 413-420
| Cmpd | Product | Sulfonyl Chloride | $^1$H NMR, LCMS m/z [M + H]+ |
|---|---|---|---|
| 416 | 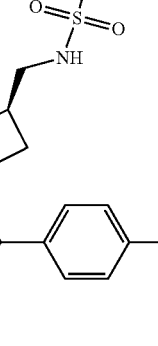 |  | LCMS m/z 461.33 [M + H]$^+$ |
| 417 | 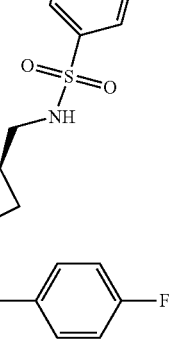 |  | LCMS m/z 538.37 [M + H]$^+$ |
| 418 | 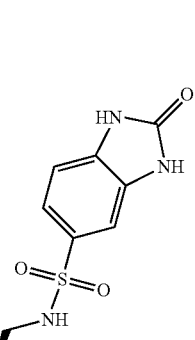 | 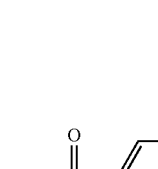 | LCMS m/z 527.36 [M + H]$^+$ |

TABLE 14-continued

Structure and physicochemical data for compounds 413-420

| Cmpd | Product | Sulfonyl Chloride | ¹H NMR, LCMS m/z [M + H]+ |
|---|---|---|---|
| 419 | | | LCMS m/z 512.35 [M + H]⁺ |
| 420 | | | LCMS m/z 568.4 [M + H]⁺ |

Preparation of 421

3-((((1r,3r)-3-(5,7-difluoro-2-(4-fluorophenyl)-1H-indol-3-yl)cyclobutyl)methyl)amino)-1H-pyrrole-2,5-dione (421)

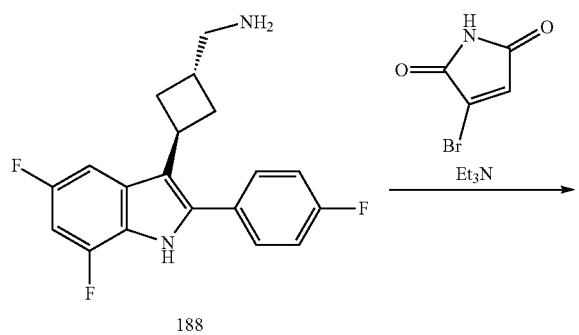

To a solution of ((1r,3r)-3-(5,7-difluoro-2-(4-fluorophenyl)-1H-indol-3-yl)cyclobutyl)methanamine 188 (0.026 g, 0.079 mmol) was added 3-bromo-1H-pyrrole-2,5-dione (17 mg, 0.097 mmol) followed by Et₃N (25 µL, 0.179 mmol). The reaction mixture was stirred at room temperature for 2 hours then concentrated in vacuo. Silica gel chromatography (Redi-Sep cartridge, 12 g) Gradient: 10-100% EtOAc in heptane) afforded the product 3-((((1r,3r)-3-(5,7-difluoro-2-(4-fluorophenyl)-1H-indol-3-yl)cyclobutyl)methyl)amino)-1H-pyrrole-2,5-dione (15 mg, 45%). ¹H NMR (300 MHz, Chloroform-d) δ 8.12 (s, 1H), 7.55-7.33 (m, 2H), 7.27-7.12 (m, 2H), 7.03 (s, 1H), 6.78 (ddd, J=10.8, 9.4, 2.1 Hz, 1H), 5.41 (s, 1H), 4.90 (d, J=1.4 Hz, 1H), 3.98 (p, J=9.0 Hz, 1H), 3.41 (dd, J=7.3, 5.7 Hz, 2H), 2.89-2.51 (m, 3H), 2.29-2.10 (m, 2H). LCMS m/z 426.33 [M+H]⁺.

Preparation of 422

3-((((1r,3r)-3-(5,7-difluoro-2-(4-fluorophenyl)-1H-indol-3-yl)cyclobutyl)methyl)amino)pyrrolidine-2,5-dione (422)

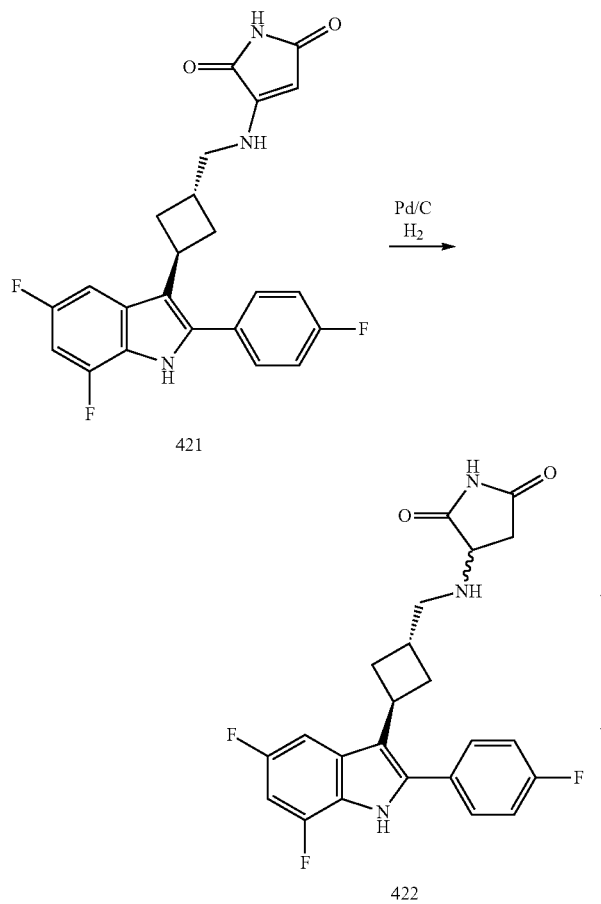

To 3-((((1r,3r)-3-(5,7-difluoro-2-(4-fluorophenyl)-1H-indol-3-yl)cyclobutyl)methyl)amino)-1H-pyrrole-2,5-dione 421 (7 mg, 0.017 mmol) was added 10% palladium on carbon (10 mg). followed by methanol (10 mL). The mixture was place under a balloon of hydrogen and was evacuated then backfilled with hydrogen. The reaction was stirred overnight. The catalyst was filtered, and the filtrate was concentrated in vacuo. Silica gel chromatography (Redi-Sep cartridge, 12 g) Gradient: 0-60% EtOAc in heptane) afforded the product 3-((((1r,3r)-3-(5,7-difluoro-2-(4-fluorophenyl)-1H-indol-3-yl)cyclobutyl)methyl)amino)pyrrolidine-2,5-dione (4.0 mg, 21%). ¹H NMR (300 MHz, Chloroform-d) δ 8.02 (s, 1H), 7.43-7.30 (m, 2H), 7.27-7.20 (m, 1H), 7.15-7.04 (m, 2H), 6.68 (ddd, J=11.2, 9.4, 2.2 Hz, 1H), 3.93-3.73 (m, 2H), 3.05-2.83 (m, 2H), 2.75 (dd, J=11.1, 7.0 Hz, 1H), 2.53 (ddd, J=18.9, 15.3, 6.6 Hz, 4H), 2.20-1.99 (m, 2H). LCMS m/z 428.35 [M+H]⁺.

Preparation of 423

N-(((1r,3r)-3-(5,7-difluoro-2-(4-fluorophenyl)-1H-indol-3-yl)cyclobutyl)methyl)-5-(trifluoromethyl)-1,3,4-thiadiazol-2-amine (423)

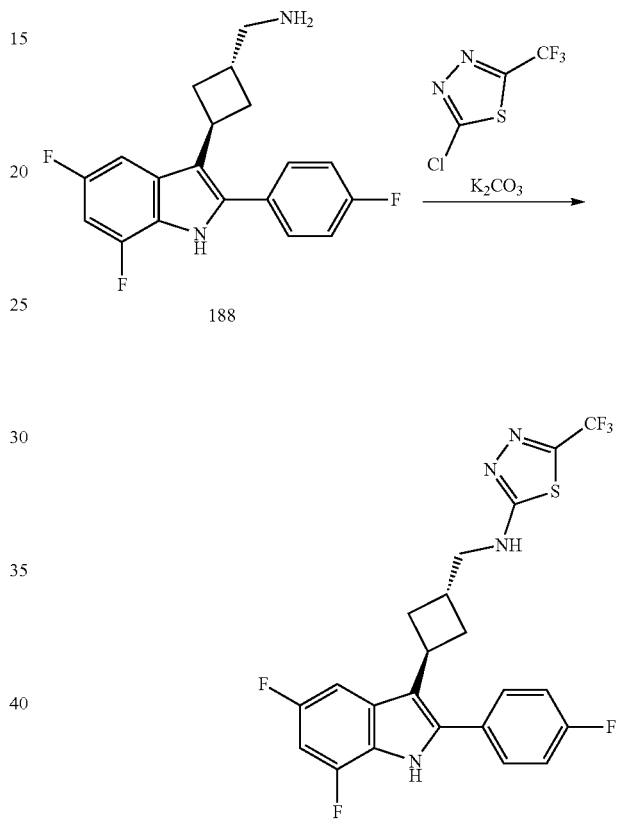

To a solution of ((1r,3r)-3-(5,7-difluoro-2-(4-fluorophenyl)-1H-indol-3-yl)cyclobutyl)methanamine 188 (0.020 g, 0.061 mmol) was added 2-chloro-5-(trifluoromethyl)-1,3,4-thiadiazole (12 mg, 0.064 mmol) followed by K₂CO₃. The reaction mixture was heated to 120° C. and stirred overnight. Water was added to the reaction mixture, followed by extraction with EtOAc (3×1 mL). The combined organic fractions were washed with water (1×1 mL), brine (1×1 mL), dried over sodium sulfate, and then concentrated in vacuo. Silica gel chromatography (Redi-Sep cartridge, 4 g) Gradient: 0-100% EtOAc in heptane) afforded the product N-(((1r,3r)-3-(5,7-difluoro-2-(4-fluorophenyl)-1H-indol-3-yl)cyclobutyl)methyl)-5-(trifluoromethyl)-1,3,4-thiadiazol-2-amine (28 mg, 96%). ¹H NMR (300 MHz, Methanol-d₄) δ 7.61-7.42 (m, 2H), 7.31 (dd, J=9.8, 2.2 Hz, 1H), 7.26-7.13 (m, 2H), 6.74 (ddd, J=11.1, 9.6, 2.2 Hz, 1H), 4.05 (p, J=8.9 Hz, 1H), 3.67 (d, J=7.6 Hz, 2H), 2.86-2.68 (m, 1H), 2.68-2.50 (m, 2H), 2.21 (tt, J=9.6, 2.8 Hz, 2H). LCMS m/z 483.62 [M+H]⁺.

Compound 424

[3-[5,7-difluoro-2-(4-fluorophenyl)-1H-indol-3-yl]cyclobutyl]methanol (424)

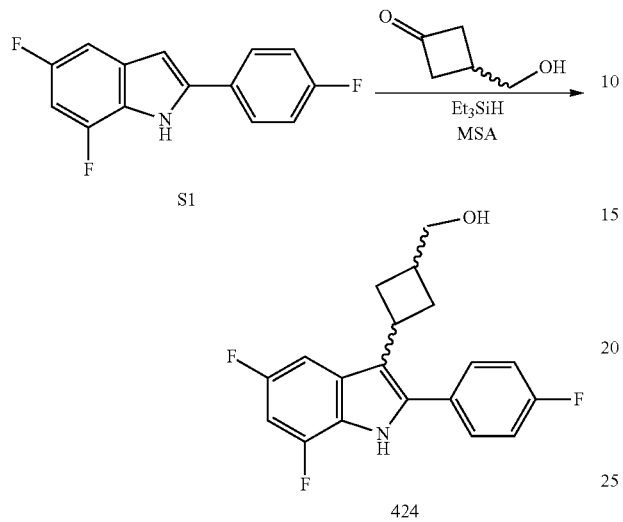

Synthesis of [3-[5,7-difluoro-2-(4-fluorophenyl)-1H-indol-3-yl]cyclobutyl]methanol (424)

To a solution of 5,7-difluoro-2-(4-fluorophenyl)-1H-indole S1 (1000 mg, 4.045 mmol), and 3-(hydroxymethyl)cyclobutanone (405 mg, 4.045 mmol) in DCM (10 mL) was added Et$_3$SiH (1.5 g, 12.90 mmol) followed by methanesulfonic acid (585 mg, 6.087 mmol). The reaction was stirred at room temperature overnight. The reaction was concentrated and washed with aqueous sat. NaHCO$_3$ and extracted with EtOAc. The organic layer was dried and purification by silica gel chromatography (Eluent: EtOAc in heptane) followed by purification by reversed-phase HPLC. Method: C18 Waters Sunfire column (30×150 mm, 5 micron). Gradient: MeCN in H$_2$O with 0.1% trifluoroacetic acid afforded the product. [3-[5,7-difluoro-2-(4-fluorophenyl)-1H-indol-3-yl]cyclobutyl]methanol 424 (Trifluoroacetate salt) (800 mg, 43%) $^1$H NMR (300 MHz, DMSO-d$_6$) δ 11.62 (s, 1H), 7.71-7.47 (m, 3H), 7.46-7.09 (m, 2H), 6.97 (ddd, J=11.2, 9.7, 2.2 Hz, 1H), 3.61 (p, J=9.2 Hz, 1H), 2.49 (2H obscured by the DMSO solvent peak) 2.43-2.29 (m, 1H), 2.22 (t, J=8.8 Hz, 4H). LCMS m/z 332.14 [M+H]$^+$.

Compound 425

[3-[5,7-difluoro-2-(4-fluorophenyl)-1H-indol-3-yl]cyclobutyl]methanol (425)

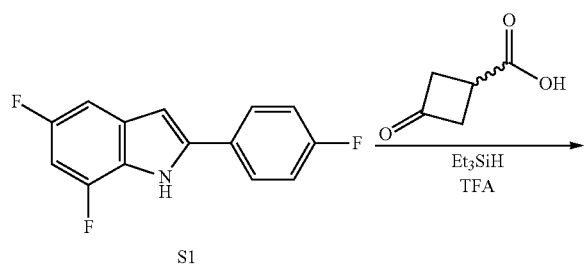

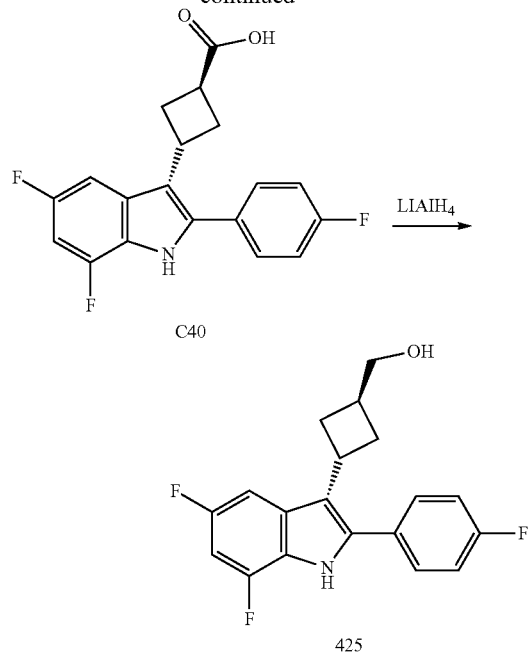

Step 1. Synthesis of 3-[5,7-difluoro-2-(4-fluorophenyl)-1H-indol-3-yl]cyclobutanecarboxylic acid (C40)

To a solution of 5,7-difluoro-2-(4-fluorophenyl)-1H-indole S1 (20 g, 80.90 mmol) and 3-oxocyclobutanecarboxylic acid (13.9 g, 121.8 mmol) in DCM (160 mL) was added Et$_3$SiH (65 mL, 407.0 mmol). TFA (31 mL, 402.4 mmol) was added via addition funnel while monitoring the temperature. Slight exotherm (2-3° C.) was observed during addition. The reaction was stirred at room temperature overnight. The solvent was removed in vacuo and the reaction was quenched with sat. NaHCO$_3$ adjusting to pH 7. The layers were separated and the organic layer was washed with brine. The solvent was removed in vacuo. DCM (25 mL) was added and the solids were triturated. The organic layer was filtered. The solid was cis isomer and discarded. The solvent was removed in vacuo. Purification by Silica gel chromatography (Column: 4 g Combiflash Isco. Gradient: 0-20% MeOH in dichloromethane) afforded the product. 3-[5,7-difluoro-2-(4-fluorophenyl)-1H-indol-3-yl]cyclobutanecarboxylic acid C40 (8.49 g, 59%) $^1$H NMR (300 MHz, Acetone-d$_6$) δ 10.71 (s, 1H), 7.79-7.56 (m, 2H), 7.45 (dd, J=9.8, 2.2 Hz, 1H), 7.39-7.21 (m, 2H), 6.85 (ddd, J=11.1, 9.6, 2.2 Hz, 1H), 4.14 (pd, J=9.3, 1.3 Hz, 1H), 3.29 (dddd, J=9.4, 7.3, 3.6, 1.3 Hz, 1H), 2.89-2.56 (m, 4H). LCMS m/z 346.07 [M+H]$^+$.

Step 2. Synthesis of [3-[5,7-difluoro-2-(4-fluorophenyl)-1H-indol-3-yl]cyclobutyl]methanol (425)

To a solution of 3-[5,7-difluoro-2-(4-fluorophenyl)-1H-indol-3-yl]cyclobutanecarboxylic acid C40 (2.5 g, 7.240 mmol) in THF (25 mL) at 0° C. was added LiAlH$_4$ (12.6 mL of 2.3 M, 28.98 mmol). The reaction was stirred at 0° C. for 1 hour and then stirred at room temperature for 3 hours. The reaction mixture was poured slowly into Rochelle salt. Reaction was extracted with ethyl acetate, washed with brine, separated, and dried with Na$_2$SO$_4$. The organic layer was concentrated in vacuo. Purification by reversed-phase HPLC. Method: C18 Waters Sunfire column (30×150 mm, 5 micron). Gradient: MeCN in H$_2$O with 0.1% trifluoroacetic acid afforded the product [3-[5,7-difluoro-2-(4-fluorophenyl)-1H-indol-3-yl]cyclobutyl]methanol 425 (Trifluoroacetate salt) (2.3 g, 68%) $^1$H NMR (300 MHz, Acetone-d$_6$) δ 10.66 (s, 1H), 7.72-7.50 (m, 2H), 7.42 (dd, J=9.9, 2.2 Hz, 1H), 7.34-7.15 (m, 2H), 6.94-6.75 (m, 1H), 4.00 (p, J=9.2 Hz, 1H), 3.79-3.55 (m, 3H), 2.64-2.47 (m, 3H), 2.24 (tq, J=9.9, 2.5 Hz, 2H). LCMS m/z 332.02 [M+1]$^+$.

Compound 426

[3-[5,7-difluoro-2-(4-fluorophenyl)-1H-indol-3-yl]-1-methyl-cyclobutyl]methanamine (426)

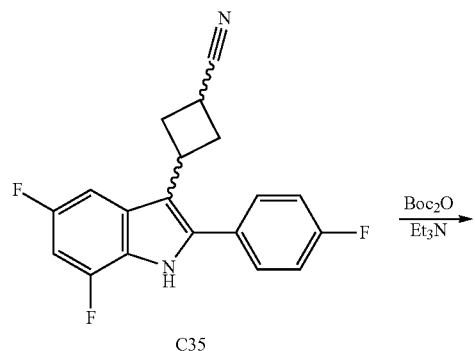

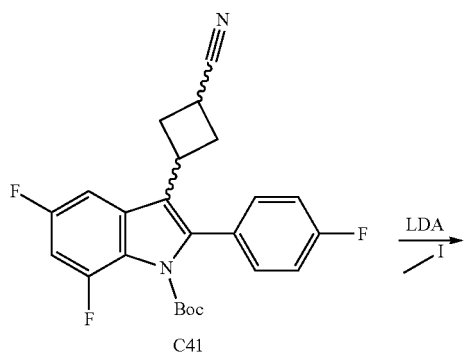

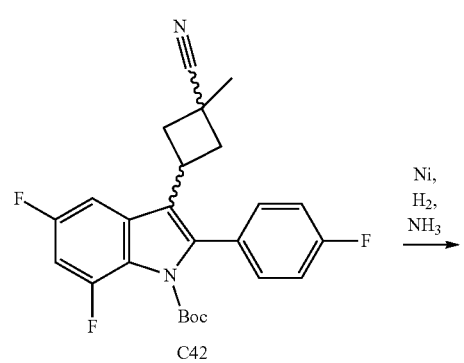

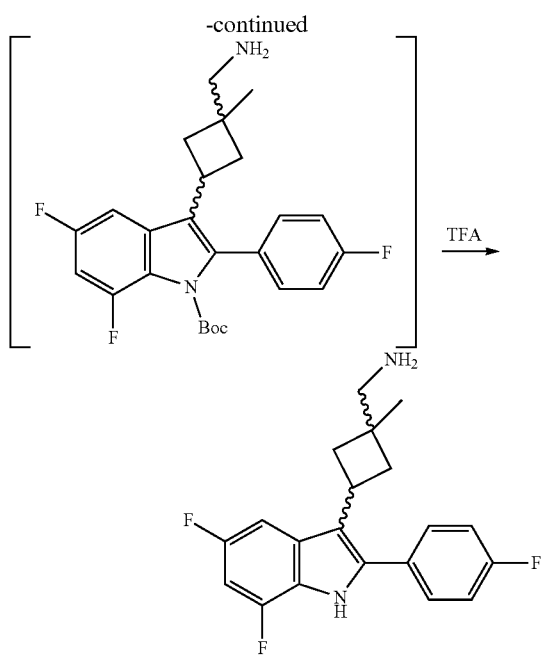

Step 1. Synthesis of tert-butyl 3-(3-cyanocyclobutyl)-5,7-difluoro-2-(4-fluorophenyl)indole-1-carboxylate (C41)

To a solution of 3-[5,7-difluoro-2-(4-fluorophenyl)-1H-indol-3-yl]cyclobutanecarbonitrile C35 (2000 mg, 4.184 mmol), and tert-butoxycarbonyl tert-butyl carbonate (1.1 g, 5.040 mmol) in THF (50 mL) was added Et$_3$N (850 mg, 8.400 mmol), and DMAP (50 mg, 0.4093 mmol). The reaction was stirred at room temperature overnight. The reaction was concentrated and quenched with water and EtOAc. Organic layer was washed with brine, separated, and dried with Na$_2$SO$_4$. The organic layer was concentrated in vacuo. Purification by silica gel chromatography (Eluent: EtOAc in heptane) afforded the product. tert-butyl 3-(3-cyanocyclobutyl)-5,7-difluoro-2-(4-fluorophenyl)indole-1-carboxylate C41 (800 mg, 41%) LCMS m/z 427.41 [M+H]$^+$.

Step 2. Synthesis of tert-butyl 3-(3-cyano-3-methyl-cyclobutyl)-5,7-difluoro-2-(4-fluorophenyl)-indole-1-carboxylate (C42)

To a solution of tert-butyl 3-(3-cyanocyclobutyl)-5,7-difluoro-2-(4-fluorophenyl)indole-1-carboxylate C41 (250 mg, 0.5863 mmol) in THF (25 mL) at −78° C. was added LDA (350 μL of 2 M, 0.7000 mmol). Reaction was stirred for 30 minutes at −78° C., and stirred at 0° C. for another 30 minutes. Reaction was cooled back to −78° C. and CH$_3$I (100 mg, 0.7045 mmol) was added. Reaction was stirred for 30 minutes. Reaction was quenched with aq. NH$_4$Cl, water, and EtOAc. Organic layer was washed with brine, separated, and dried with Na$_2$SO$_4$. The organic layer was concentrated in vacuo. Purification by silica gel chromatography (Eluent: EtOAc in heptane) afforded the product tert-butyl 3-(3-cyano-3-methyl-cyclobutyl)-5,7-difluoro-2-(4-fluorophenyl)indole-1-carboxylate C42 (60 mg, 14%). LCMS m/z 441.31 [M+H]$^+$.

493

Step 3. Synthesis of [3-[5,7-difluoro-2-(4-fluoro-phenyl)-1H-indol-3-yl]-1-methyl-cyclobutyl]-methanamine (426)

Ni (50 mg, 0.8519 mmol) was washed in methanol and added to a hydrogenation flask with MeOH (20 mL). Tert-butyl 3-(3-cyano-3-methyl-cyclobutyl)-5,7-difluoro-2-(4-fluorophenyl)indole-1-carboxylate (100 mg, 0.2270 mmol) C42 in MeOH (10 mL) was added to the reaction. 30 mL 7N Ammonia in methanol was added. The reaction was stirred overnight under $H_2$ at 60 psi. The reaction mixture was concentrated and filtered to give crude amine. To a solution of the amine in DCM (3 mL) was added TFA (3 mL). The reaction was stirred for two hours. Solvent was removed to give [3-[5,7-difluoro-2-(4-fluorophenyl)-1H-indol-3-yl]-1-methyl-cyclobutyl]methanamine (Trifluoroacetate salt) 426 (2.5 mg, 2%) $^1$H NMR (400 MHz, Methanol-$d_4$) δ 7.69-7.40 (m, 2H), 7.33-7.06 (m, 2H), 6.74 (ddd, J=11.1, 9.6, 2.2 Hz, 1H), 4.15-3.77 (m, 1H), 2.90 (s, 2H), 2.41-2.08 (m, 3H), 1.38 (s, 2H). LCMS m/z 345.5 [M+H]$^+$.

Compound 427

1-(aminomethyl)-3-[5,7-difluoro-2-(4-fluorophenyl)-1H-indol-3-yl]cyclobutanol (427)

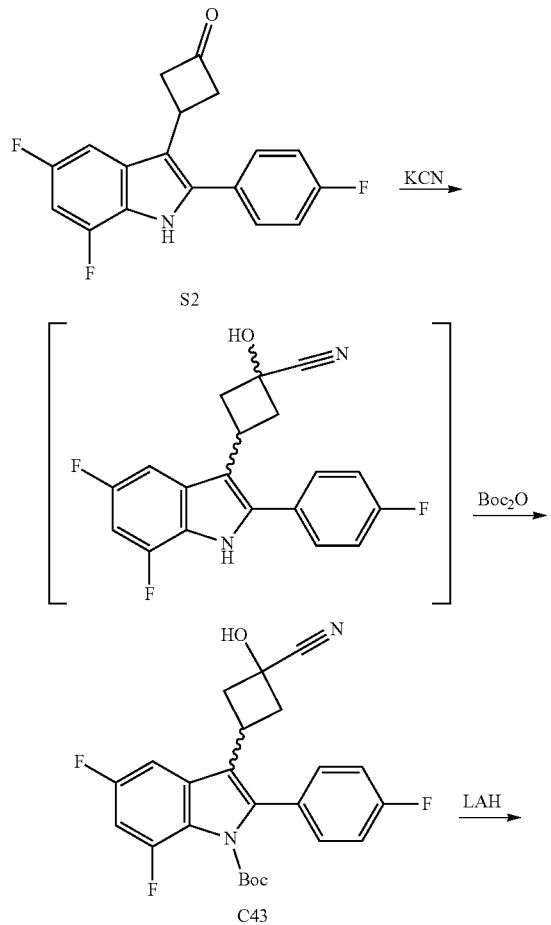

494

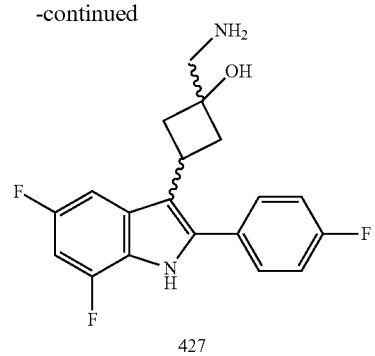

Steps 1 and 2. Synthesis of tert-butyl 3-(3-cyano-3-hydroxy-cyclobutyl)-5,7-difluoro-2-(4-fluoro-phenyl)indole-1-carboxylate (C43)

3-[5,7-difluoro-2-(4-fluorophenyl)-1H-indol-3-yl]cyclobutanone S2 (175 mg, 0.4593 mmol) was added to a vigorously stirred mixture of EtOAc (2 mL) and $H_2O$ (1.5 mL) containing hydrogen carbonate (Sodium salt) (77 mg, 0.9166 mmol) and KCN (45 mg, 0.6911 mmol). Reaction was stirred overnight to give 3-[5,7-difluoro-2-(4-fluorophenyl)-1H-indol-3-yl]-1-hydroxy-cyclobutanecarbonitrile intermediate which was used without further purification LCMS m/z 343.25 [M+H]$^+$.

Tert-butoxycarbonyl tert-butyl carbonate (106 μL, 0.4614 mmol) was added to the reaction mixture from the above step and stirred overnight at room temperature. The phases were separated and the organic layer was washed with water and brine. The organic layer was dried over $MgSO_4$ and concentrated under reduced pressure. Purification by silica gel chromatography (Gradient: 0-30% EtOAc in heptane) yielded the product tert-butyl 3-(3-cyano-3-hydroxy-cyclobutyl)-5,7-difluoro-2-(4-fluorophenyl)indole-1-carboxylate C43 (198 mg, 56%) $^1$H NMR (300 MHz, Chloroform-d) 7.32 (ddt, J=8.1, 5.1, 2.5 Hz, 2H), 7.23-7.13 (m, 2H), 7.07 (ddd, J=8.4, 2.3, 0.7 Hz, 1H), 6.88 (ddd, J=11.7, 9.3, 2.3 Hz, 1H), 3.96 (tt, J=9.8, 8.5 Hz, 1H), 2.80 (ddt, J=12.6, 9.9, 2.5 Hz, 2H), 2.60-2.44 (m, 2H), 1.35 (s, 9H). LCMS m/z 443.29 [M+H]$^+$.

Step 3. Synthesis of tert-butyl 3-[3-(aminomethyl)-3-hydroxy-cyclobutyl]-5,7-difluoro-2-(4-fluorophenyl)indole-1-carboxylate (427)

To a solution of tert-butyl 3-(3-cyano-3-hydroxy-cyclobutyl)-5,7-difluoro-2-(4-fluorophenyl)indole-1-carboxylate C43 (14 mg, 0.02712 mmol) in THF (0.5 mL) was added lithium aluminum hydride (approximately 67.80 μL of 2 M, 0.1356 mmol). The reaction mixture was stirred at room temperature for two hours. The reaction was quenched with 1N aqueous Rochelle's salt. The solution was partitioned with ethyl acetate. The combined organics were washed with water, brine, and dried over anhydrous sodium sulfate. The solution was filtered and concentrated in vacuo, Purification by reversed-phase chromatography (Column: C18. Gradient: 10-100% MeCN in water with 0.1% TFA) afforded the product. 1-(aminomethyl)-3-[5,7-difluoro-2-(4-fluorophenyl)-1H-indol-3-yl]cyclobutanol 427 (Trifluoroacetate salt) (9.7 mg, 72%) $^1$H NMR (400 MHz, Methanol-$d_4$) δ 7.60-7.48 (m, 2H), 7.28-7.16 (m, 2H), 7.13 (dd, J=9.7, 2.2 Hz, 1H), 6.75 (ddd, J=11.0, 9.6, 2.2 Hz, 1H), 4.20 (h, J=8.7 Hz, 1H), 2.97 (d, J=5.5 Hz, 2H), 2.56-2.34 (m, 4H). LCMS m/z found 347.3 [M+H]⁺.

Compound 428

[3-[5,7-difluoro-2-(4-fluorophenyl)-1H-indol-3-yl]-1-fluoro-cyclobutyl]methanamine (428)

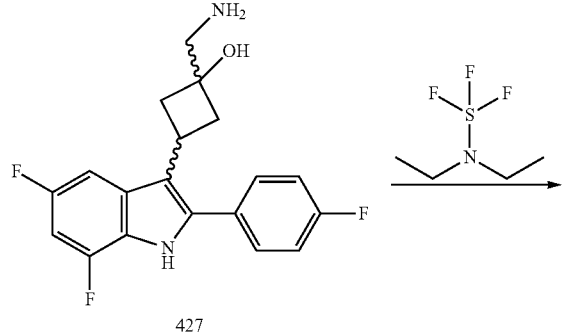

Preparation: [3-[5,7-difluoro-2-(4-fluorophenyl)-1H-indol-3-yl]-1-fluoro-cyclobutyl]methan-amine (428)

To a solution of 1-(aminomethyl)-3-[5,7-difluoro-2-(4-fluorophenyl)-1H-indol-3-yl]cyclobutanol 427 (78 mg, 0.2252 mmol) in DCM (2 mL) at −78° C., was added DAST (60 μL, 0.4541 mmol)). The reaction mixture was stirred under Argon at −78° C. for 10 minutes. The reaction was warmed to room temperature and quenched by addition of saturated aqueous NaHCO₃. The solution was diluted with EtOAc, washed with saturated aqueous NaHCO₃, saturated aqueous NaCl, dried over MgSO₄, filtered, and concentrated. Purification by reversed-phase chromatography (Column: C18. Gradient: 10-90% MeCN in water with 0.1% TFA) afforded the product [3-[5,7-difluoro-2-(4-fluorophenyl)-1H-indol-3-yl]-1-fluoro-cyclobutyl]methanamine 428 (Trifluoroacetate salt) (4.8 mg, 4%). ¹H NMR (300 MHz, Methanol-d₄) δ 7.76-7.46 (m, 2H), 7.47-7.01 (m, 3H), 6.98-6.63 (m, 1H), 4.23 (p, J=9.1 Hz, 1H), 3.17 (dd, J=33.0, 20.5 Hz, 2H), 2.98-2.25 (m, 4H). LCMS m/z 349.33 [M+H]⁺.

Compound 429

N-((1r,3r)-3-(5,7-difluoro-2-(4-fluorophenyl)-1H-indol-3-yl)cyclobutyl)-2-hydroxyacetamide (429)

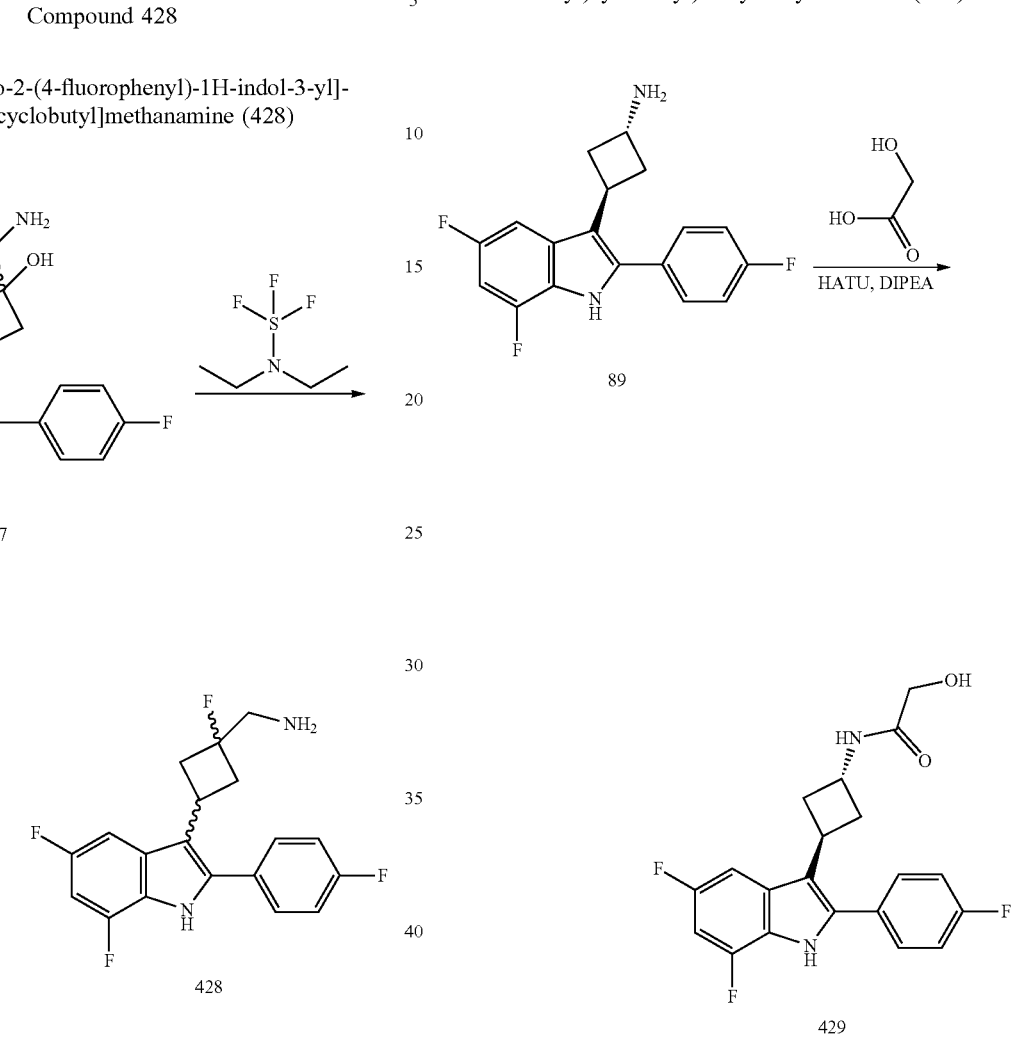

Synthesis of N-((1r,3r)-3-(5,7-difluoro-2-(4-fluorophenyl)-1H-indol-3-yl)cyclobutyl)-2-hydroxyacetamide (429)

To a solution of 2-hydroxyacetic acid (30 mg, 0.4 mmol) and HATU (181 mg, 0.476 mmol) in DMF (1.5 mL) was (1r,3r)-3-[5,7-difluoro-2-(4-fluorophenyl)-1H-indol-3-yl] cyclobutanamine 89 (100 mg, 0.32 mmol) followed by DIPEA (111 μL, 0.637 mmol). The mixture was stirred at room temperature for 4 hours. The mixture was then partitioned between water and ethyl acetate. The organic layer was separated, washed with brine, dried over sodium sulfate, filtered, and concentrated in vacuo Purification by reversed phase chromatography (C18 column; Gradient: MeCN in H₂O with 0.1% trifluoroacetic acid) yielded the product (55 mg, 45%). ¹H NMR (400 MHz, Acetone-d₆) δ 10.72 (s, 1H), 7.65-7.58 (m, 2H), 7.47-7.37 (m, 1H), 7.32-7.25 (m, 2H), 6.86 (ddd, J=11.0, 9.6, 2.2 Hz, 1H), 4.60 (dt, J=12.8, 4.6 Hz, 1H), 4.20-4.09 (m, 1H), 3.94 (s, 2H), 2.84-2.76 (m, 2H), 2.54-2.44 (m, 2H). LCMS m/z 375.22 [M+H]⁺.

Compound 430

(1s,3s)-1-(aminomethyl)-3-(5,7-difluoro-2-(4-fluorophenyl)-1H-indol-3-yl)cyclobutan-1-ol (430)

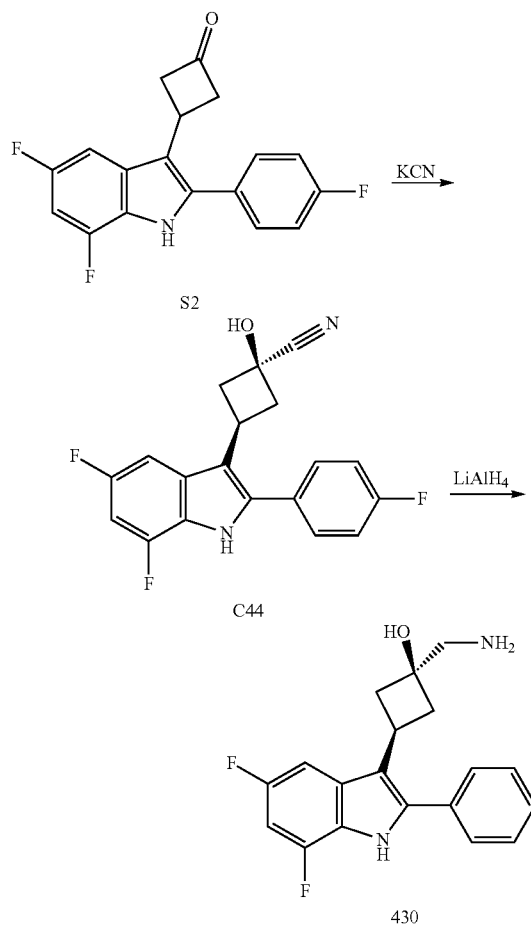

Step 1. Synthesis of (1s,3s)-3-(5,7-difluoro-2-(4-fluorophenyl)-1H-indol-3-yl)-1-hydroxycyclobutane-1-carbonitrile (C44)

To a solution of 3-[5,7-difluoro-2-(4-fluorophenyl)-1H-indol-3-yl]cyclobutanone S2 (1.17 g, 3.71 mmol) in EtOAc (17 mL) was added sodium bicarbonate (623 mg, 7.42 mmol) and KCN (363 mg, 5.58 mmol) in H$_2$O (13 mL). The reaction mixture was vigorously stirred at room temperature overnight. The organic phase was separated and washed with water then brine. The organic layer was dried over magnesium sulfate, filtered, and concentrated in vacuo. Silica gel chromatography (Gradient: 0-40% EtOAc in hexane) afforded the product (1.1 g, 78%). $^1$H NMR (300 MHz, Acetone-d$_6$) δ 10.81 (s, 1H), 7.75-7.55 (m, 2H), 7.46 (dd, J=9.8, 2.2 Hz, 1H), 7.38-7.24 (m, 2H), 6.88 (ddt, J=11.1, 9.6, 2.4 Hz, 1H), 3.79 (tt, J=10.3, 8.3 Hz, 1H), 3.19-3.03 (m, 2H), 2.73 (ddt, J=12.4, 10.1, 2.3 Hz, 2H). LCMS m/z 343.3 [M+H]$^+$.

Step 2. Synthesis of (1s,3s)-1-(aminomethyl)-3-(5,7-difluoro-2-(4-fluorophenyl)-1H-indol-3-yl)cyclobutan-1-ol (430)

To a solution of (1s,3s)-3-(5,7-difluoro-2-(4-fluorophenyl)-1H-indol-3-yl)-1-hydroxycyclobutane-1-carbonitrile C44 (608 mg, 1.78 mmol) in THF (10 mL) was added lithium aluminum hydride (approximately 3.552 mL of 2 M, 7.104 mmol) dropwise. The reaction mixture was stirred at room temperature for 2 hours and quenched with potassium sodium tartrate solution. EtOAc (20 mL) was added to the mixture, and the organic layer was separated and washed with water (20 mL), brine (20 mL), dried over sodium sulfate, filtered, and concentrated in vacuo. The residue was dissolved in DCM, and the resulting precipitate was collected to afford the product. (6 mg, 2%). $^1$H NMR (300 MHz, Methanol-d$_4$) δ 7.63-7.34 (m, 3H), 7.32-7.06 (m, 2H), 6.73 (ddd, J=11.4, 9.6, 2.2 Hz, 1H), 3.37 (d, J=9.2 Hz, 1H), 2.77 (s, 2H), 2.50 (ddt, J=10.5, 8.3, 2.4 Hz, 2H), 2.36 (td, J=9.9, 2.9 Hz, 2H). LCMS m/z 347.35 [M+H]$^+$.

Compound 431

N-(((1s,3s)-3-(5,7-difluoro-2-(4-fluorophenyl)-1H-indol-3-yl)-1-hydroxycyclobutyl)methyl)acetamide (431)

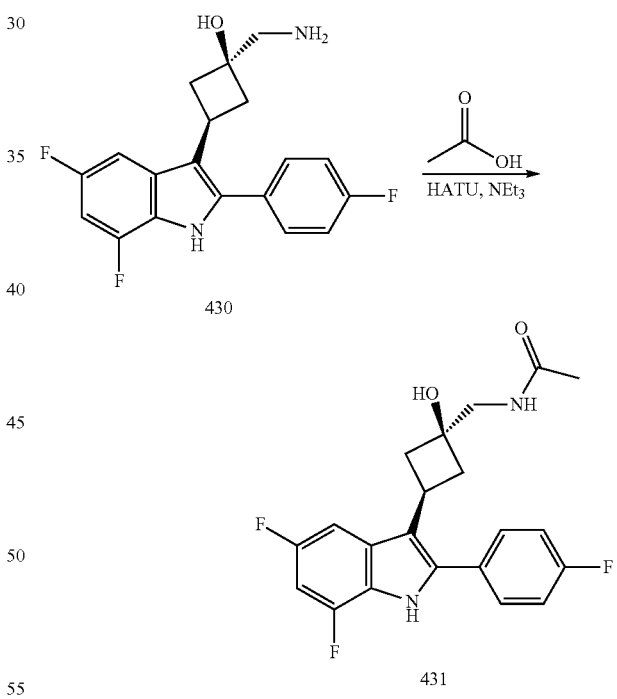

To a solution of compound 430 (17 mg, 0.043 mmol) and AcOH (3 μL, 0.05 mmol) in DMF (1 mL) was added HATU (18 mg, 0.047 mmol), followed by triethylamine (12 μL, 0.086 mmol). The reaction mixture was stirred at room temperature for 2 hours. Water was added, and the mixture was extracted with EtOAc (3×2 mL). The combined organic fractions were washed with H$_2$O (2 mL) and brine (2 mL), dried over sodium sulfate, filtered, and concentrated in vacuo. Silica gel chromatography (Gradient: 0-100% EtOAc in hexane) afforded the product (2 mg, 10%). $^1$H NMR (300 MHz, Chloroform-d) δ 8.11 (s, 1H), 7.52-7.39 (m, 2H), 7.34

(dd, J=9.5, 2.2 Hz, 1H), 7.24-7.10 (m, 2H), 6.77 (ddd, J=10.7, 9.4, 2.1 Hz, 1H), 5.99 (s, 1H), 3.53 (d, J=5.8 Hz, 2H), 3.34 (p, J=8.9 Hz, 1H), 3.20 (s, 1H), 2.54 (tt, J=8.3, 2.3 Hz, 2H), 2.41 (td, J=9.9, 2.7 Hz, 2H), 1.61 (s, 3H). LCMS m/z 389.25 [M+H]⁺.

Compound 432

6-[5,7-difluoro-2-(4-fluorophenyl)-1H-indol-3-yl]spiro[3.3]heptan-2-amine (432)

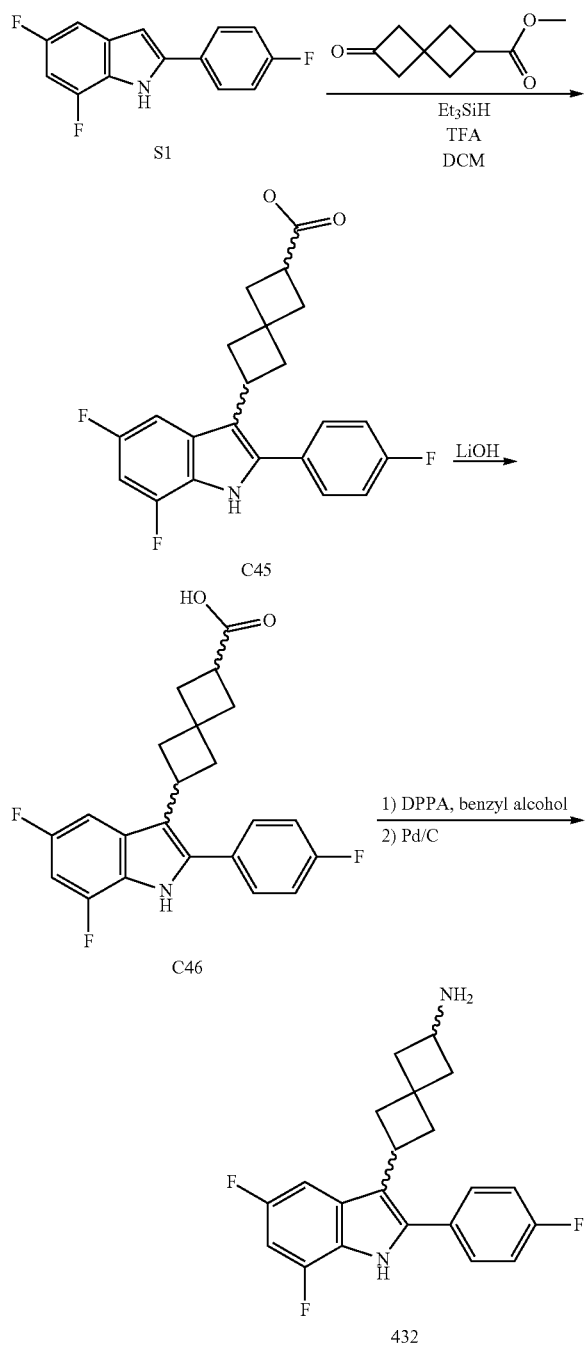

Step 1. Synthesis of methyl 6-(5,7-difluoro-2-(4-fluorophenyl)-1H-indol-3-yl)spiro[3.3]heptane-2-carboxylate (C45)

To a mixture of 5,7-difluoro-2-(4-fluorophenyl)-1H-indole S1 (200 mg, 0.81 mmol) in DCM (5 mL) was added Et₃SiH (1.1 mL, 6.9 mmol) and TFA (400 mg, 5.3 mmol). The mixture was stirred at room temperature overnight. The mixture was concentrated in vacuo, and water and ethyl acetate were added. The organic layer was separated and washed with aqueous sodium bicarbonate solution and brine. The organic layer was dried over sodium sulfate, filtered, and concentrated in vacuo to afford the product (100 mg, 28%). ¹H NMR (300 MHz, DMSO-d₆) δ 11.65 (s, 1H), 7.70-7.43 (m, 2H), 7.43-7.27 (m, 2H), 7.19 (dd, J=9.8, 2.2 Hz, 1H), 6.97 (ddd, J=11.2, 9.8, 2.2 Hz, 1H), 3.66 (ddd, J=10.0, 8.2, 1.7 Hz, 1H), 3.57 (s, 3H), 3.33 (s, 1H), 3.03 (p, J=8.5 Hz, 1H), 2.48-2.07 (m, 7H). LCMS m/z 400.07 [M+H]⁺.

Step 2. Synthesis of 6-[5,7-difluoro-2-(4-fluorophenyl)-1H-indol-3-yl]spiro[3.3]heptane-2-carboxylic acid (C46)

To a solution of methyl 6-(5,7-difluoro-2-(4-fluorophenyl)-1H-indol-3-yl)spiro[3.3]heptane-2-carboxylate C45 (100 mg, 0.23 mmol) in THF (5 mL) and water (2.5 mL) was added LiOH (20 mg, 0.84 mmol). The mixture was stirred at room temperature overnight. The mixture was concentrated in vacuo and purified by reversed phase chromatography (C18 column; Gradient: MeCN in H₂O with 0.1% trifluoroacetic acid) to afford the product. (15 mg, 11%). ¹H NMR (300 MHz, Methanol-d₄) δ 7.58-7.43 (m, 2H), 7.26-7.09 (m, 3H), 6.71 (ddd, J=11.1, 9.6, 2.1 Hz, 1H), 3.70 (tt, J=9.8, 8.3 Hz, 1H), 3.01 (p, J=8.5 Hz, 1H), 2.60-2.09 (m, 8H). LCMS m/z 386.17 [M+H]⁺.

Step 3. Synthesis of 6-[5,7-difluoro-2-(4-fluorophenyl)-1H-indol-3-yl]spiro[3.3]heptan-2-amine (432)

To a solution of 6-[5,7-difluoro-2-(4-fluorophenyl)-1H-indol-3-yl]spiro[3.3]heptane-2-carboxylic acid C46 (200 mg, 0.52 mmol) in toluene (10 mL) was added diphenylphosphoryl azide (215 mg, 0.781 mmol) and Et₃N (105 mg, 1.04 mmol). The mixture was heated at 80° C. for 6 h and benzyl alcohol (10 mL) was added. The mixture was heated overnight. The mixture was concentrated in vacuo, and water and ethyl acetate were added. The organic layer was separated, washed with brine, dried over sodium sulfate, filtered, and concentrated in vacuo. Silica gel chromatography afforded the intermediate carbamate as a solid. The solid was dissolved in MeOH (10 mL) and added Pd/C catalyst (50 mg of 10% w/w, 0.047 mmol). The mixture was stirred under stirred under an atmosphere of hydrogen overnight. The suspension was filtered, and the filtrate was concentrated in vacuo and reversed phase chromatography (C18 column; Gradient: MeCN in H₂O with 0.1% trifluoroacetic acid) to afford the product (40 mg, 15%). ¹H NMR (300 MHz, DMSO-d₆) δ 11.67 (s, 1H), 7.65-7.43 (m, 2H), 7.45-7.25 (m, 2H), 7.21 (dd, J=9.8, 2.2 Hz, 1H), 6.98 (ddd, J=11.6, 9.8, 2.1 Hz, 1H), 3.84-3.63 (m, 2H), 3.59 (d, J=7.5 Hz, 2H), 2.40-1.88 (m, 6H). LCMS m/z 357.38 [M+H]⁺.

Compound 433

4-[5,7-difluoro-2-(4-fluorophenyl)-1H-indol-3-yl]cyclohexanamine (433)

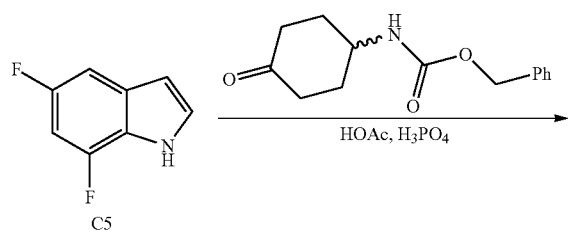

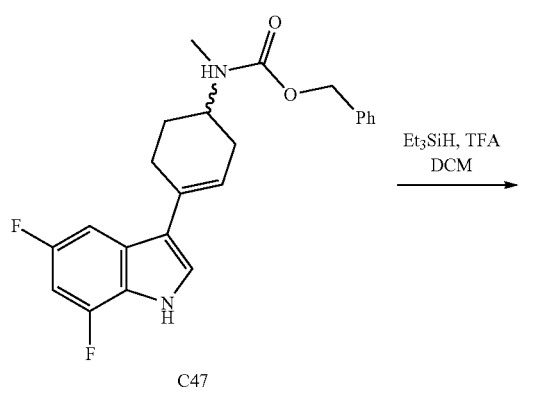

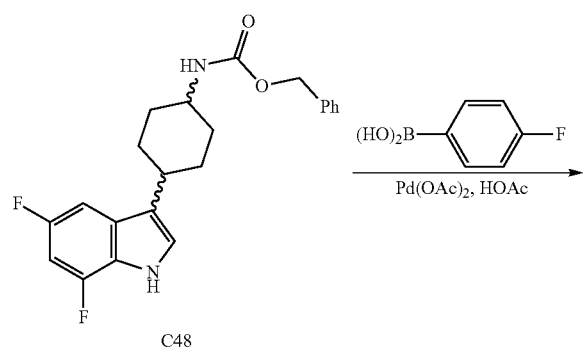

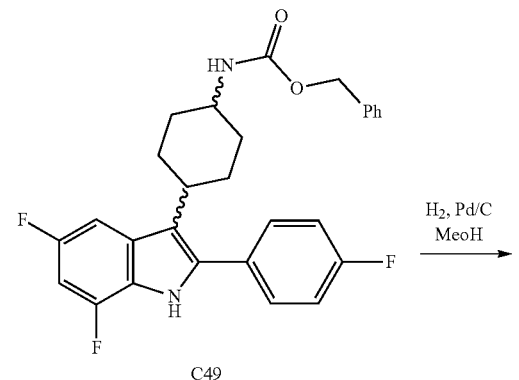

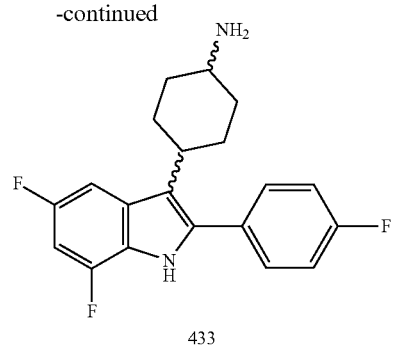

Step 1. Synthesis of benzyl (4-(5,7-difluoro-1H-indol-3-yl)cyclohex-3-en-1-yl)carbamate (C47)

To a 50 mL round bottom flask charged with a magnetic stir bar was added benzyl N-(4-oxocyclohexyl)carbamate (1 g, 4.04 mmol) and 5,7-difluoro-1H-indole C5 (680 mg, 4.44 mmol), acetic acid (10 mL), and phosphoric acid (5 mL). The reaction mixture was then heated at 60° C. with stirring for 8 h before the reaction was allowed to cool to room temperature. The reaction was then carefully inversed quenched onto cooled 2 M sodium hydroxide to obtain a neutral pH. The resulting mixture was then extracted with ethyl acetate (2×200 mL). The combined organic phase was washed with brine, dried with anhydrous MgSO$_4$, filtered and concentrated in vacuo to afford the title compound which was used directly without further purification. Benzyl (4-(5,7-difluoro-1H-indol-3-yl)cyclohex-3-en-1-yl)carbamate (1.5 g). $^1$H NMR (400 MHz, DMSO-d$_6$) δ 11.56 (d, J=2.5 Hz, 1H), 11.42 (d, J=2.6 Hz, 1H), 7.76 (d, J=2.6 Hz, 1H), 7.51 (d, J=2.6 Hz, 1H), 7.43-7.25 (m, 5H), 7.20 (d, J=7.7 Hz, 1H), 6.99-6.52 (m, 4H), 4.99 (s, 3H), 2.86 (d, J 13.5 Hz, 2H), 2.11-1.93 (m, 2H), 1.82-1.67 (m, 2H), 1.51 (q, J=11.8, 11.1 Hz, 2H). LCMS m/z 383.14 [M+H]$^+$.

Step 2. Synthesis of benzyl (4-(5,7-difluoro-1H-indol-3-yl)cyclohexyl)carbamate (C48)

To a 100 mL round bottom flask charged with a magnetic stir bar was added benzyl (4-(5,7-difluoro-1H-indol-3-yl)cyclohex-3-en-1-yl)carbamate C47 (1.5 g, 2.81 mmol), DCM (30 mL), Et$_3$SiH (675 mg, 5.80 mmol), and TFA (1 g, 8.77 mmol). The reaction was then allowed to stir at ambient temperature overnight before being quenched with saturated aqueous NaHCO$_3$. The mixture was then extracted with EtOAc (2×200 mL). The combined organic phase was washed with brine, dried with anhydrous MgSO$_4$, filtered and concentrated in vacuo to afford the crude title compound which was purified via silica gel chromatography (40 g) that was eluted with EtOAc in heptanes (0→100%) to afford pure title compound. Benzyl (4-(5,7-difluoro-1H-indol-3-yl)cyclohexyl)carbamate (950 mg, 78%). $^1$H NMR (300 MHz, DMSO-d$_6$) δ 11.38 (s, 1H), 7.58-7.15 (m, 7H), 7.04-6.77 (m, 1H), 5.03 (d, J=4.3 Hz, 2H), 4.03 (q, J=7.1 Hz, 2H), 3.75 (d, J=5.7 Hz, 1H), 3.58-3.31 (m, 1H), 2.73 (dt, J=40.3, 10.8 Hz, 1H), 2.08-1.24 (m, 8H). LCMS m/z 385.17 [M+H]$^+$.

Step 3. Synthesis of benzyl (4-(5,7-difluoro-2-(4-fluorophenyl)-1H-indol-3-yl)cyclohexyl)carbamate (C49)

A 50 mL round bottom flask was charged with a magnetic stir bar, (4-fluorophenyl)boronic acid (125 mg, 0.893 mmol), benzyl (4-(5,7-difluoro-1H-indol-3-yl)cyclohexyl) carbamate C48 (400 mg, 0.868 mmol), and HOAc (10 mL). The mixture was degassed with $O_2$ and $Pd(OAc)_2$ (195 mg, 0.868 mmol) was then added. The resulting reaction mixture was allowed to stir overnight under an atmosphere of $O_2$. The reaction mixture was then concentrated in vacuo and the crude material was then extracted with EtOAc (2×50 mL). The combined organic phase was washed with brine, dried with anhydrous $MgSO_4$, filtered and concentrated in vacuo to afford the crude title compound which was purified via silica gel chromatography (40 g) that was eluted with heptanes/EtOAc (0 to 100%) to afford pure title compound. Benzyl (4-(5,7-difluoro-2-(4-fluorophenyl)-1H-indol-3-yl) cyclohexyl)carbamate (200 mg, 25%). LCMS m/z 476.51 [M+H]⁺.

Step 4. Synthesis of 4-[5,7-difluoro-2-(4-fluorophenyl)-1H-indol-3-yl]cyclohexanamine (433)

To a 50 mL round bottom flask charged with a magnetic stir bar was added benzyl N-[4-[5,7-difluoro-2-(4-fluorophenyl)-1H-indol-3-yl]cyclohexyl]carbamate C49 (200 mg, 0.402 mmol), MeOH (~10 mL) and 10% Pd/C (~15 mg). The reaction mixture was purged with hydrogen and allowed to stir under an atmosphere of hydrogen for 3 hours. The reaction mixture was then purged with $N_2$, filtered, and concentrated in vacuo to afford the crude 4-[5,7-difluoro-2-(4-fluorophenyl)-1H-indol-3-yl]cyclohexanamine which was purified via reverse phase HPLC (5% to 95% MeCN in water, 0.1% TFA) to afford the pure title compound as its TFA salt. 4-[5,7-difluoro-2-(4-fluorophenyl)-1H-indol-3-yl] cyclohexanamine (98 mg, 46%). ¹H NMR (300 MHz, Methanol-d₄) δ 7.60-7.46 (m, 2H), 7.24 (tq, J=9.6, 3.0, 2.6 Hz, 3H), 6.88-6.61 (m, 1H), 2.98-2.78 (m, 1H), 2.31-2.04 (m, 4H), 2.04-1.72 (m, 2H), 1.72-1.32 (m, 2H). LCMS m/z 345.14 [M+H]⁺.

Compound 434

Trans-4-[5,7-difluoro-2-(4-fluorophenyl)-1H-indol-3-yl]cyclohexanamine (434)

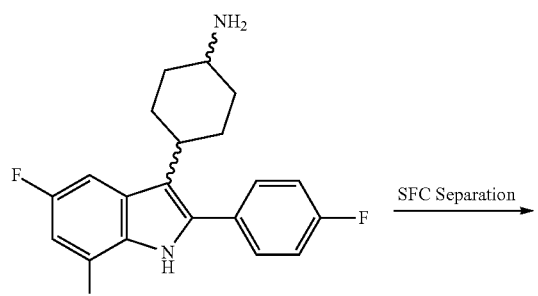

Preparation of Trans-4-[5,7-difluoro-2-(4-fluorophenyl)-1H-indol-3-yl]cyclohexanamine Racemic mixture of 4-[5,7-difluoro-2-(4-fluorophenyl)-1H-indol-3-yl]cyclohexanamine 433 (1.1 g, 3.194 mmol) was separated into constituent diastereomers by chiral SFC separation (Column: Daicel Chiralpak® AD-H, 10×250 mm; Mobile Phase: 30% EtOH (containing 5 mM Ammonia), 70% carbon dioxide. Flow: 75 mL/min) to afford two isomers. The second peak was assigned as trans-4-[5,7-difluoro-2-(4-fluorophenyl)-1H-indol-3-yl]cyclohexanamine (270 mg, 21%). ¹H NMR (400 MHz, Methanol-d₄) δ 7.63-7.44 (m, 2H), 7.34-7.13 (m, 3H), 6.72 (ddd, J=11.0, 9.6, 2.1 Hz, 1H), 3.35 (d, J=2.7 Hz, 1H), 2.96-2.80 (m, 1H), 2.14 (t, J=11.9 Hz, 4H), 1.92 (d, J=10.9 Hz, 2H), 1.50 (ddt, J=23.4, 14.9, 7.3 Hz, 2H). LCMS m/z 345.37 [M+H]⁺.

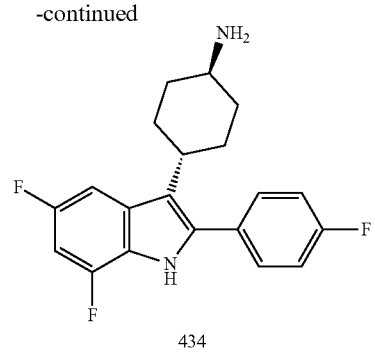

Compound 435

N-(4-(5,7-difluoro-2-(4-fluorophenyl)-1H-indol-3-yl)cyclohexyl)acetamide (435)

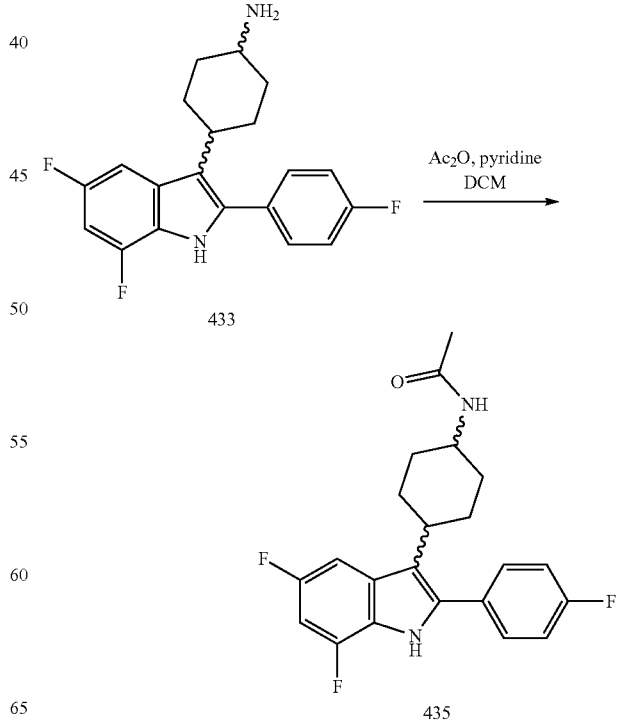

Preparation of N-(4-(5,7-difluoro-2-(4-fluorophenyl)-1H-indol-3-yl)cyclohexyl)acetamide (435)

To a 25 mL round bottom flask charged with a magnetic stir bar was added 4-[5,7-difluoro-2-(4-fluorophenyl)-1H-indol-3-yl]cyclohexanamine 433 (50 mg, 0.145 mmol), DCM (5 mL), acetic anhydride (approximately 14.8 mg, 0.145 mmol) and pyridine (~20 µL). The reaction mixture was allowed to stir at ambient temperature for 2 hours. The reaction mixture was then concentrated in vacuo and the crude product was dissolved in ~1 mL DMSO and purified via reverse phase HPLC (5 to 95% MeCN in water, 0.1% TFA) to afford the pure title compound as an off white solid. N-(4-(5,7-Difluoro-2-(4-fluorophenyl)-1H-indol-3-yl)cyclohexyl)acetamide. $^1$H NMR (300 MHz, Methanol-$d_4$) δ 7.63-7.38 (m, 2H), 7.24 (td, J=9.2, 2.4 Hz, 3H), 6.70 (ddd, J=11.3, 9.6, 2.1 Hz, 1H), 3.78 (tt, J=11.7, 3.9 Hz, 1H), 2.83 (tt, J=12.3, 3.7 Hz, 1H), 2.32-1.68 (m, 8H), 1.30 (qd, J=12.7, 3.6 Hz, 2H). LCMS m/z 387.32 [M+H]$^+$.

Compound 436

3-(azetidin-3-ylmethyl)-5,7-difluoro-2-(4-fluorophenyl)-1H-indole (436)

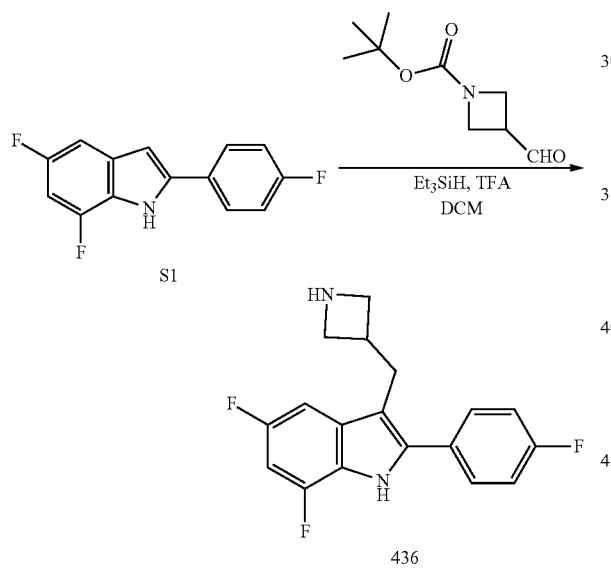

Preparation of 3-(azetidin-3-ylmethyl)-5,7-difluoro-2-(4-fluorophenyl)-1H-indole (436)

To a 25 mL round bottom flask charged with a magnetic stir bar, tert-butyl 3-formylazetidine-1-carboxylate (562 mg, 3.03 mmol), DCM (5 mL), 5,7-difluoro-2-(4-fluorophenyl)-1H-indole S1 (500 mg, 2.02 mmol), was added Et$_3$SiH (1.1 g, 9.46 mmol) and TFA (1.5 g, 13.16 mmol). The reaction mixture was stirred at ambient temperature for 12 h before being concentrated in vacuo. The resulting residue was dissolved in ~1 mL DMSO and then submitted directly to reverse phase HPLC purification (5 to 95% MECN in water, 0.1% TFA) to afford the pure title compound as its TFA salt. 3-(Azetidin-3-ylmethyl)-5,7-difluoro-2-(4-fluorophenyl)-1H-indole (400 mg, 41%). $^1$H NMR (400 MHz, Methanol-$d_4$) δ 7.73-7.52 (m, 2H), 7.41-7.12 (m, 3H), 6.78 (ddd, J=11.0, 9.6, 2.2 Hz, 1H), 3.89 (dd, J=10.6, 7.9 Hz, 2H), 3.71-3.51 (m, 2H), 3.24-3.18 (m, 2H). LCMS m/z 317.11 [M+H]$^+$.

Compound 437

[3-[[5,7-difluoro-2-(4-fluorophenyl)-1H-indol-3-yl]methyl]azetidin-1-yl]-[1-(hydroxymethyl)cyclopropyl]methanone (Trifluoroacetate salt) (437)

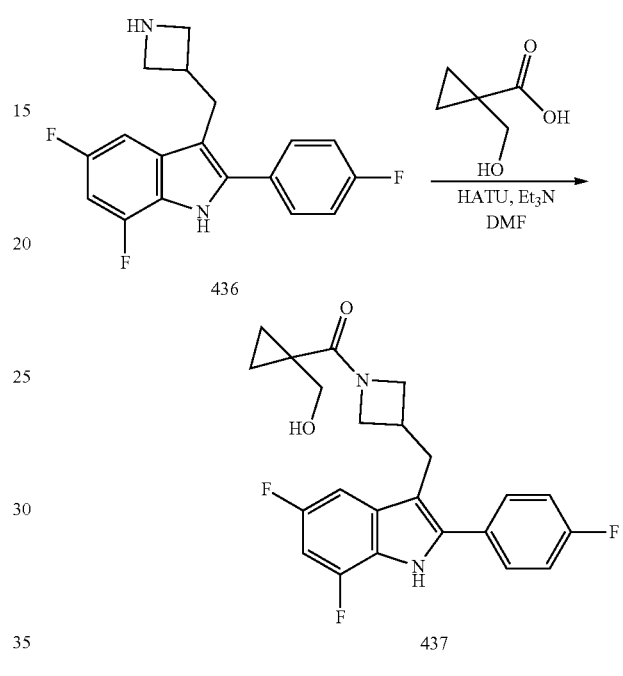

Preparation of [3-[[5,7-difluoro-2-(4-fluorophenyl)-1H-indol-3-yl]methyl]azetidin-1-yl]-[1-(hydroxymethyl)cyclopropyl]methanone (Trifluoroacetate salt) (437)

To a 10 mL vial charged with a magnetic stir bar was added 3-(azetidin-3-ylmethyl)-5,7-difluoro-2-(4-fluorophenyl)-1H-indole 436 (50 mg, 0.158 mmol), DMF (2 mL), 1-(hydroxymethyl)cyclopropanecarboxylic acid (22 mg, 0.189 mmol), and HATU (72 mg, 0.189 mmol), and Et$_3$N (32 mg, 0.316 mmol). The reaction was allowed to stir overnight at ambient temperature and was then submitted directly to reverse phase HPLC purification (water→MeCN 5 to 95%, 0.1% TFA) to afford the pure title compound as its TFA salt. [3-[[5,7-Difluoro-2-(4-fluorophenyl)-1H-indol-3-yl]methyl]azetidin-1-yl]-[1-(hydroxymethyl)cyclopropyl]methanone (35 mg, 38%). $^1$H NMR (300 MHz, Acetone-$d_6$) δ 10.86 (s, 1H), 7.75 (ddd, J=9.8, 4.8, 2.1 Hz, 2H), 7.30 (tq, J=9.3, 2.7, 2.1 Hz, 3H), 6.86 (ddt, J=11.2, 9.7, 3.8 Hz, 1H), 4.35 (d, J=45.1 Hz, 2H), 3.90 (d, J=77.0 Hz, 2H), 3.54 (s, 2H), 3.27 (d, J=7.7 Hz, 2H), 3.16-2.93 (m, 1H), 2.71 (s, 3H), 0.92 (t, J=3.2 Hz, 2H), 0.71 (t, J=3.3 Hz, 2H). LCMS m/z 415.19 [M+H]$^+$.

Compounds 438-440

Compounds 438-440 (see Table 15) were prepared in one step from 436 and the listed carboxylic acid reagents using the method described in the synthesis of compound 437. Carboxylic acid reagents were obtained from commercial sources.

TABLE 15
Structure and physicochemical data for compounds 438-440
| Compound | Product | Carboxylic Acid | ¹H NMR, LCMS m/z [M + H]⁺ |
|---|---|---|---|
| 438 | | | LCMS m/z 389.17 [M + H]⁺ |
| 439 | | | LCMS m/z 389.17 [M + H]⁺ |
| 440 | | | LCMS m/z 388.19 [M + H]⁺ |
Compound 441
(3-(5,7-difluoro-2-(4-fluorophenyl)-1H-indol-3-yl)azetidin-1-yl)(1H-imidazol-4-yl)methanone (441)
-continued
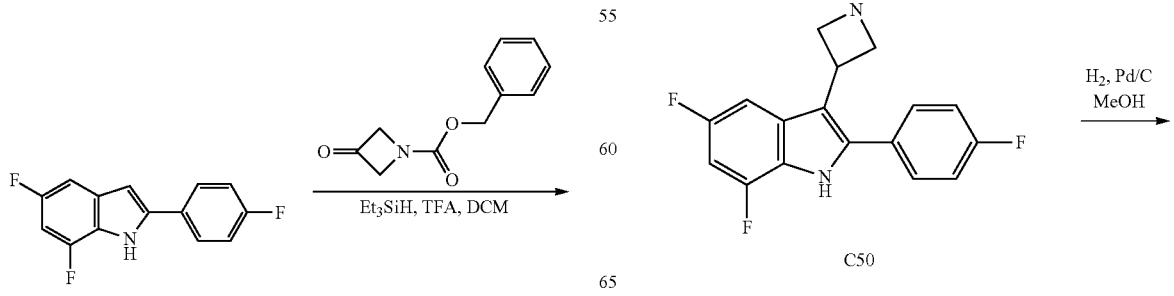

-continued

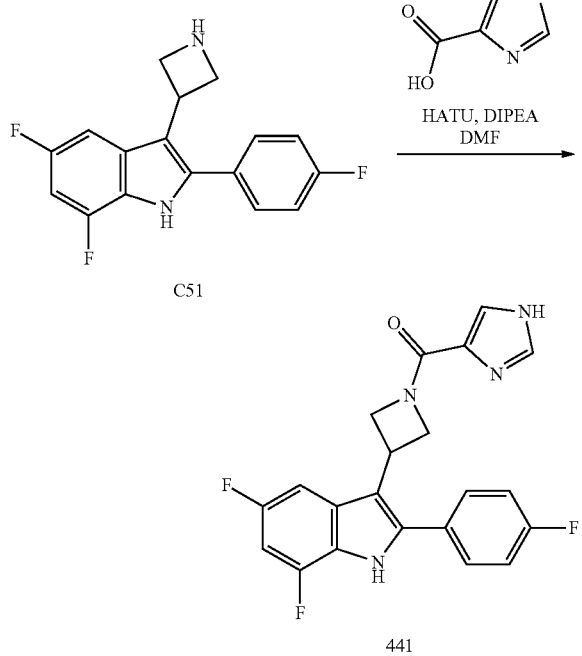

Step 1. Synthesis of benzyl 3-[5,7-difluoro-2-(4-fluorophenyl)-1H-indol-3-yl]azetidine-1-carboxylate (C50)

A 50 mL round bottom flask was charged with a magnetic stir bar, 5,7-difluoro-2-(4-fluorophenyl)-1H-indole S1 (500 mg, 1.35 mmol), DCM (15 mL), benzyl 3-oxoazetidine-1-carboxylate (277 mg, 1.35 mmol), Et₃SiH (470 mg, 4.04 mmol), and TFA (310 mg, 2.71 mmol). The reaction mixture was allowed to stir overnight at ambient temperature before being concentrated in vacuo. The resulting residue was dissolved in EtOAc (~50 mL) and the organic phase was washed with saturated aqueous NaHCO₃. The organic layer was separated, dried with anhydrous MgSO₄, filtered, and concentrated in vacuo to afford the crude title compound. This material was purified via silica gel chromatography (40 g) using a gradient of heptanes/EtOAc (0→100%) to afford pure title compound. Benzyl 3-[5,7-difluoro-2-(4-fluorophenyl)-1H-indol-3-yl]azetidine-1-carboxylate (536 mg, 84%). LCMS m/z 524.04 [M+H]⁺.

Step 2. Synthesis of 3-(azetidin-3-yl)-5,7-difluoro-2-(4-fluorophenyl)-1H-indole (C51)

To a 200 mL round bottom flask charged with a magnetic stir bar was added MeOH (10 mL), 10 wt % Pd/C (20 mg), and benzyl 3-[5,7-difluoro-2-(4-fluorophenyl)-1H-indol-3-yl]azetidine-1-carboxylate C50 (500 mg, 1.06 mmol) in MeOH (20 mL). The reaction was purged and placed under an atmosphere of hydrogen. The resulting mixture was stirred at ambient temperature for 3 hours before being filtered through a pad of Celite®. The solvent was removed in vacuo to afford the crude title compound which was dissolved in ~1 mL of DMSO and purified via reverse phase HPLC (water→MeCN 5 to 95%, 0.1% TFA) to afford the pure title compound as its TFA salt. 3-(Azetidin-3-yl)-5,7-difluoro-2-(4-fluorophenyl)-1H-indole (380 mg, 81%). ¹H NMR (300 MHz, Methanol-d₄) δ 7.63-7.48 (m, 2H), 7.41 (dd, J=9.5, 2.1 Hz, 1H), 7.37-7.18 (m, 2H), 6.85 (ddd, J=11.0, 9.6, 2.1 Hz, 1H), 4.70-4.52 (m, 1H), 4.45 (dd, J=11.0, 9.1 Hz, 2H), 4.36-4.17 (m, 2H). LCMS m/z 303.26 [M+H]⁺.

Step 3. Synthesis of (3-(5,7-difluoro-2-(4-fluorophenyl)-1H-indol-3-yl)azetidin-1-yl)(1H-imidazol-4-yl)methanone (441)

To a 5 mL vial charged with a magnetic stir bar was added 3-(azetidin-3-yl)-5,7-difluoro-2-(4-fluorophenyl)-1H-indole C51 (20 mg, 0.066 mmol), DMF (~300 μL), HATU (50 mg, 0.132 mmol), DIPEA (~40 μL), and 1H-imidazole-4-carboxylic acid (~10 mg). The reaction was allowed to stir overnight at room temperature, and then was diluted with additional DMF to ~1 mL total volume and purified via reverse phase HPLC (5 to 95% MeCN in water, 0.1% TFA) to afford the pure title compound as its TFA salt. (3-(5,7-difluoro-2-(4-fluorophenyl)-1H-indol-3-yl)azetidin-1-yl)(1H-imidazol-4-yl)methanone. LCMS m/z 397.11 [M+H]⁺.

Compound 442

(3-(5,7-difluoro-2-(4-fluorophenyl)-1H-indol-3-yl)azetidin-1-yl)(1-hydroxycyclopropyl)methanone (442)

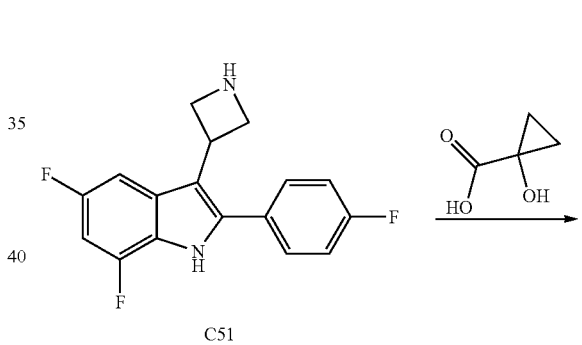

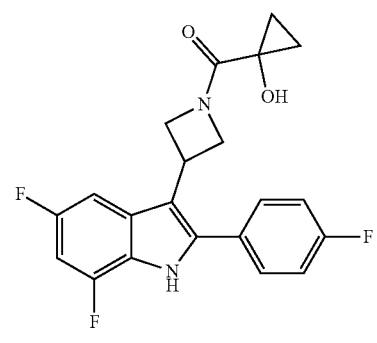

Compound 442 was prepared as 441 with substitution of the appropriate carboxylic acid (see above structure). LCMS m/z 387.14 [M+H]⁺.

Preparation S5

5,7-difluoro-2-(4-fluorophenyl)-3-(pyrrolidin-3-ylmethyl)-1H-indole (S5)

Compound 443

[3-[[5,7-difluoro-2-(4-fluorophenyl)-1H-indol-3-yl]methyl]pyrrolidin-1-yl]-(oxetan-2-yl)methanone (443)

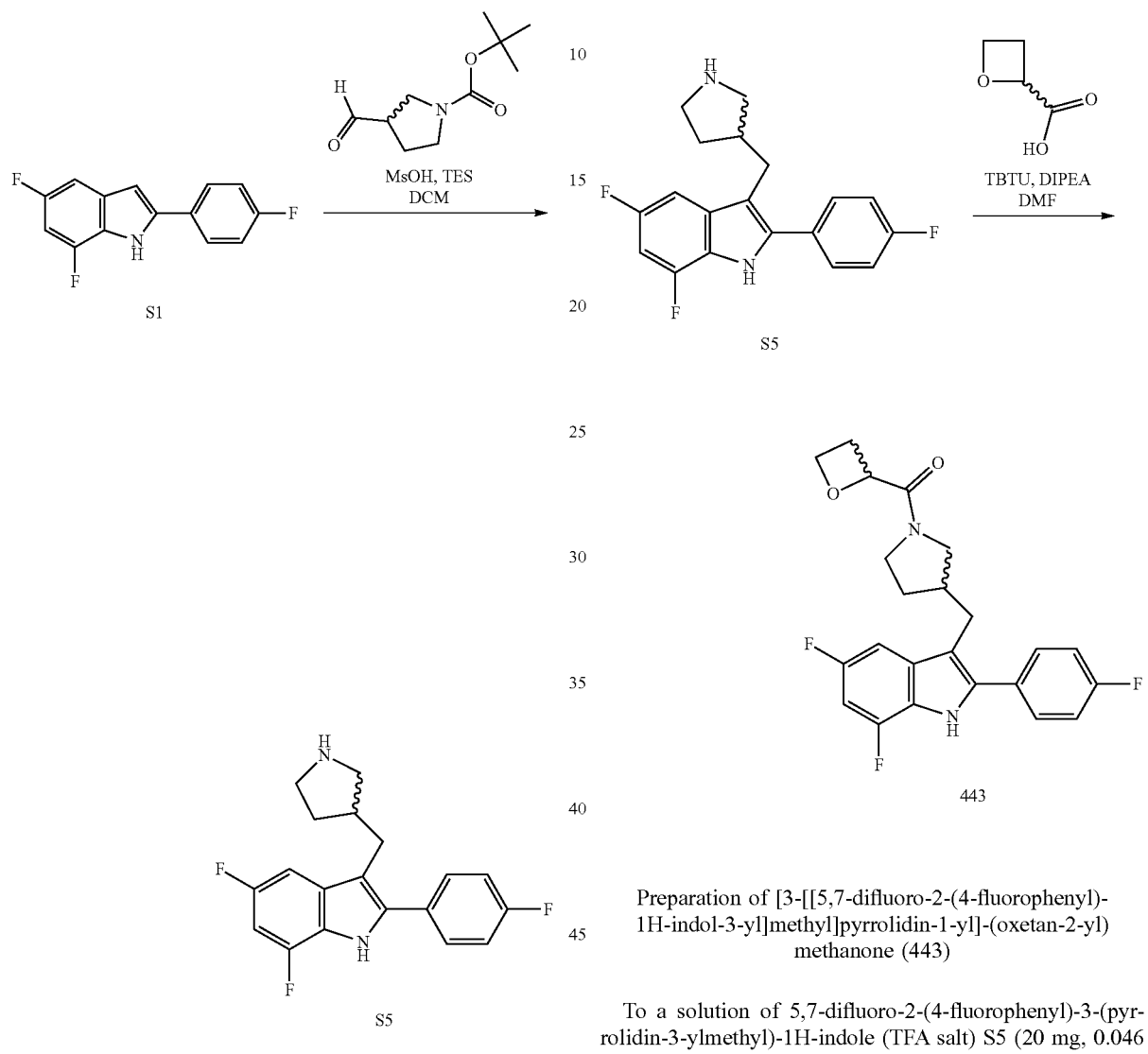

Preparation of 5,7-difluoro-2-(4-fluorophenyl)-3-(pyrrolidin-3-ylmethyl)-1H-indole (S5)

To a solution of 5,7-difluoro-2-(4-fluorophenyl)-1H-indole S1 (755 mg, 3.05 mmol) in DCM (20 mL) was added sequentially methanesulfonic acid (300 µL, 4.62 mmol), tert-butyl 3-formylpyrrolidine-1-carboxylate (730 mg, 3.66 mmol) and triethylsilane (1.5 mL, 9.39 mmol). The resulting mixture was stirred at ambient temperature overnight. The volatiles were removed and the crude was purified by reversed phase chromatography (C18 column; Gradient: MeCN in H$_2$O with 0.1% trifluoroacetic acid) to afford the title compound as a TFA salt. 5,7-Difluoro-2-(4-fluorophenyl)-3-(pyrrolidin-3-ylmethyl)-1H-indole (946 mg, 68%). LCMS m/z 331.25 [M+H]$^+$.

Preparation of [3-[[5,7-difluoro-2-(4-fluorophenyl)-1H-indol-3-yl]methyl]pyrrolidin-1-yl]-(oxetan-2-yl)methanone (443)

To a solution of 5,7-difluoro-2-(4-fluorophenyl)-3-(pyrrolidin-3-ylmethyl)-1H-indole (TFA salt) S5 (20 mg, 0.046 mmol) in DMF (2 mL) was added Hünig's base (40 µL, 0.23 mmol) and TBTU (20 mg, 0.06 mmol) followed by oxetane-2-carboxylic acid (25 mg, 0.24 mmol). The resulting mixture was stirred at ambient temperature overnight. The reaction was filtered and concentrated. The crude was purified by reversed phase chromatography (C18 column; Gradient: 5% to 95% MeCN in water with 0.1% trifluoroacetic acid) to afford the product. [3-[[5,7-Difluoro-2-(4-fluorophenyl)-1H-indol-3-yl]methyl]pyrrolidin-1-yl]-(oxetan-2-yl)methanone (9.7 mg, 49%). $^1$H NMR (300 MHz, Methanol-d$_4$) δ 7.62 (ddd, J=8.4, 6.3, 4.1 Hz, 2H), 7.23 (tdd, 8.8, 4.0, 2.2 Hz, 2H), 7.11 (dq, J=9.4, 2.1 Hz, 1H), 6.74 (ddt, J=11.3, 9.6, 2.0 Hz, 1H), 5.18 (dq, J=52.5, 7.8 Hz, 1H), 4.78-4.36 (m, 2H), 3.60-3.36 (m, 2H), 3.29-3.11 (m, 1H), 3.03 (td, J=11.4, 10.8, 7.0 Hz, 1H), 2.93 (dt, J=7.5, 2.8 Hz, 2H), 2.89-2.43 (m, 3H), 1.89 (dh, J=18.9, 6.0 Hz, 1H), 1.57 (dddd, J=26.4, 13.0, 8.0, 5.3 Hz, 1H). LCMS m/z 415.32 [M+H]$^+$.

513

Compound 444

1-(3-((5,7-difluoro-2-(4-fluorophenyl)-1H-indol-3-yl)methyl)pyrrolidin-1-yl)ethan-1-one (444)

514

Compound 445

Cyclopropyl-[3-[[5,7-difluoro-2-(4-fluorophenyl)-1H-indol-3-yl]methyl]pyrrolidin-1-yl]methanone (445)

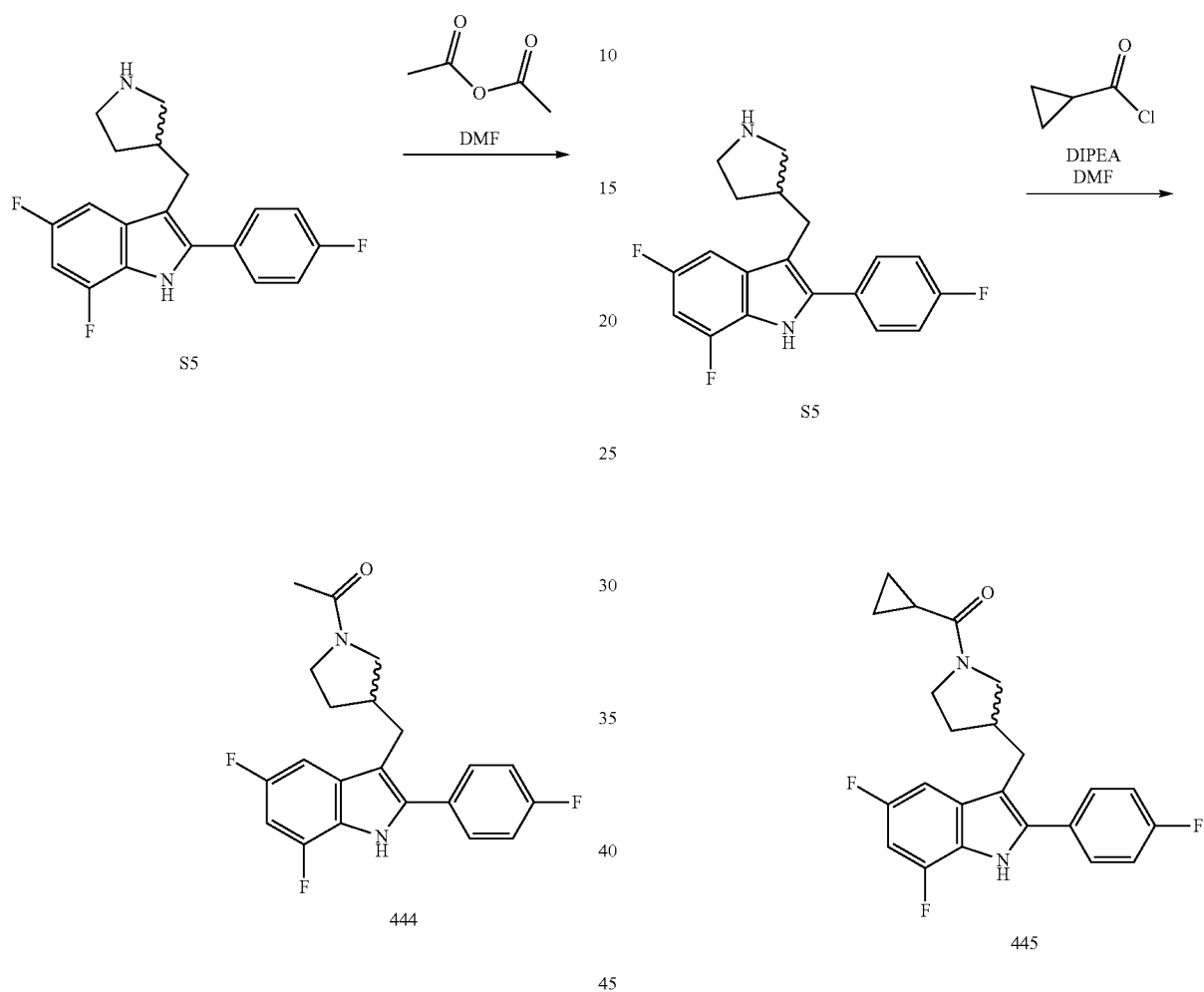

Preparation of 1-(3-((5,7-difluoro-2-(4-fluorophenyl)-1H-indol-3-yl)methyl)pyrrolidin-1-yl)ethan-1-one (444)

To a solution of 5,7-difluoro-2-(4-fluorophenyl)-3-(pyrrolidin-3-ylmethyl)-1H-indole (TFA salt) S5 (45 mg, 0.10 mmol) in DMF (2 mL) was added Hünig's base (100 µL, 0.57 mmol) and acetic anhydride (50 µL, 0.53 mmol). The resulting mixture was stirred at ambient temperature overnight. The mixture was purified by reversed phase chromatography (C18 column; Gradient: MeCN in H$_2$O with 0.1% trifluoroacetic acid) to afford the product. 1-(3-((5,7-Difluoro-2-(4-fluorophenyl)-1H-indol-3-yl)methyl)pyrrolidin-1-yl)ethan-1-one (20 mg, 49%). $^1$H NMR (300 MHz, Chloroform-d) δ 8.73 (d, J=5.3 Hz, 1H), 7.62-7.40 (m, 2H), 7.31-6.90 (m, 3H), 6.71 (dddd, J=10.7, 9.4, 5.8, 2.1 Hz, 1H), 3.66 (ddq, J=9.6, 6.7, 3.3, 2.9 Hz, 1H), 3.61-3.45 (m, 1H), 3.45-3.16 (m, 3H), 3.05-2.75 (m, 2H), 2.54 (ddt, J=33.4, 15.3, 8.3 Hz, 1H), 2.14 (s, 3H), 1.74-1.48 (m, 1H). LCMS m/z 373.2 [M+H]$^+$.

Preparation of cyclopropyl-[3-[[5,7-difluoro-2-(4-fluorophenyl)-1H-indol-3-yl]methyl]pyrrolidin-1-yl]methanone (445)

To a solution of 5,7-difluoro-2-(4-fluorophenyl)-3-(pyrrolidin-3-ylmethyl)-1H-indole (TFA salt) S5 (30 mg, 0.068 mmol) in DMF (2 mL) was added Hünig's base (50 µL, 0.29 mmol) and cyclopropanecarbonyl chloride (25 mg, 0.24 mmol). The resulting mixture was stirred at ambient temperature overnight. The reaction was filtered and purified by reversed phase chromatography (C18 column; Gradient: MeCN in H$_2$O with 0.1% trifluoroacetic acid) to afford the product. Cyclopropyl(3-((5,7-difluoro-2-(4-fluorophenyl)-1H-indol-3-yl)methyl)pyrrolidin-1-yl)methanone (11.3 mg, 40%). $^1$H NMR (300 MHz, Methanol-d$_4$) δ 7.73-7.52 (m, 2H), 7.23 (tdd, J=8.8, 3.9, 2.1 Hz, 2H), 7.12 (ddd, J=9.4, 3.6, 2.2 Hz, 1H), 6.85-6.59 (m, 1H), 3.73-3.50 (m, 1H), 3.47-3.17 (m, 3H), 2.97 (ddd, J=17.5, 10.9, 7.4 Hz, 2H), 2.73-2.43 (m, 1H), 2.00-1.78 (m, 1H), 1.75-1.43 (m, 2H), 0.90-0.61 (m, 4H). LCMS m/z 399.23 [M+H]$^+$.

515
Compound 446

N[1]'-[3-[5,7-difluoro-2-(4-fluorophenyl)-1H-indol-3-yl]cyclobutyl]cyclopropane-1,1-dicarboxamide (446)

516
Compound 447

N'-[3-[5,7-difluoro-2-(4-fluorophenyl)-1H-indol-3-yl]cyclobutyl]propanediamide (447)

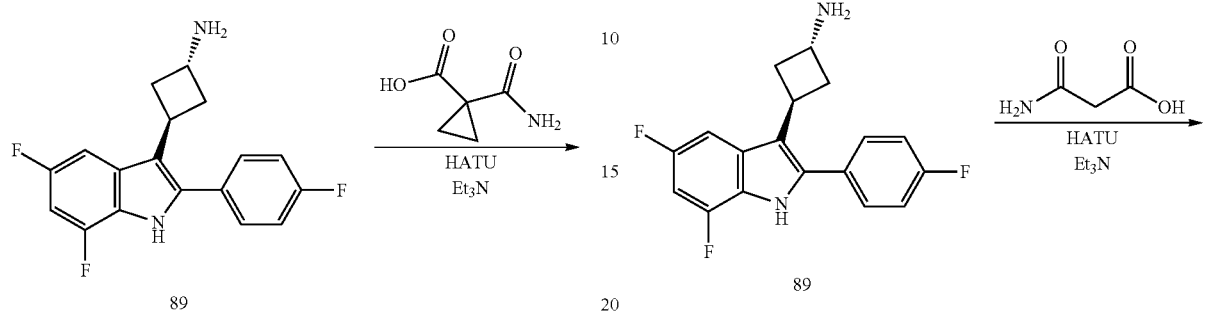

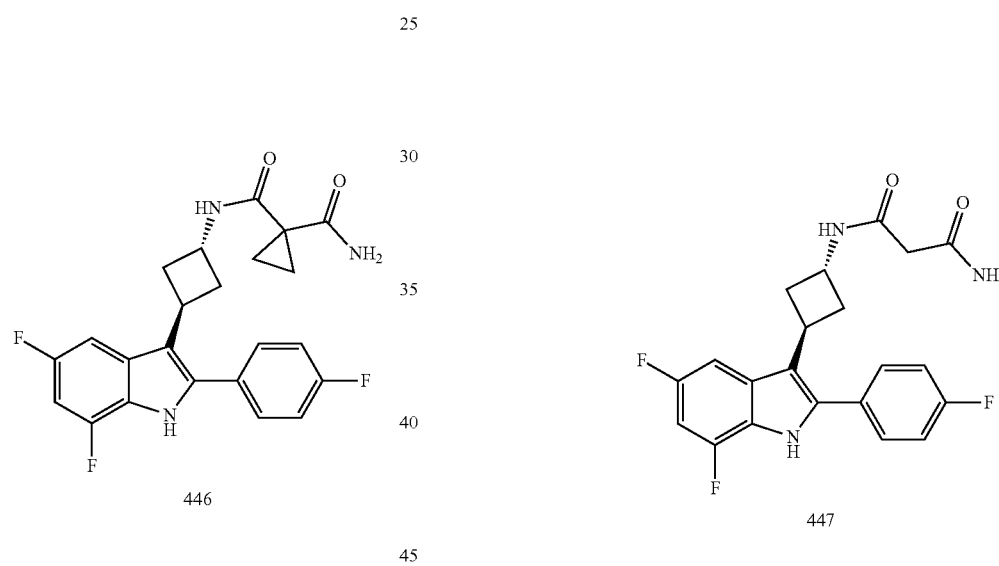

Preparation of N[1]'-[3-[5,7-difluoro-2-(4-fluorophenyl)-1H-indol-3-yl]cyclobutyl]cyclopropane-1,1-dicarboxamide (446)

To a solution of 1-carbamoylcyclopropanecarboxylic acid (10 mg, 0.08 mmol) and (1r,3r)-3-[5,7-difluoro-2-(4-fluorophenyl)-1H-indol-3-yl]cyclobutanamine 89 (25 mg, 0.079 mmol) in DMF (2 mL) was added HATU (36 mg, 0.095 mmol) followed by Et$_3$N (16 mg, 0.16 mmol). The reaction mixture was stirred at room temperature overnight. Purification by reversed-phase HPLC (Method: C18 Waters Sunfire column (30×150 mm, 5 micron). Gradient: MeCN in H$_2$O with 0.1% trifluoroacetic acid) afforded the product. N[1]'-[3-[5,7-Difluoro-2-(4-fluorophenyl)-1H-indol-3-yl]cyclobutyl]cyclopropane-1,1-dicarboxamide (6.4 mg, 15%). $^1$H NMR (300 MHz, Acetone-d$_6$) δ 10.67 (s, 1H), 8.68 (s, 1H), 7.69-7.37 (m, 4H), 7.35-7.21 (m, 2H), 6.90-6.73 (m, 2H), 4.52 (s, 1H), 4.28-3.89 (m, 1H), 2.88-2.64 (m, 2H), 2.55-2.39 (m, 2H), 1.63-1.28 (m, 4H). LCMS m/z 428.16 [M+H]$^+$.

Preparation of N'-[3-[5,7-difluoro-2-(4-fluorophenyl)-1H-indol-3-yl]cyclobutyl]propanediamide (447)

To a solution of 3-amino-3-oxopropanoic acid (10 mg, 0.1 mmol) and (1r,3r)-3-[5,7-difluoro-2-(4-fluorophenyl)-1H-indol-3-yl]cyclobutanamine 89 (25 mg, 0.079 mmol) in DMF (2 mL) was added HATU (37 mg, 0.097 mmol) followed by Et$_3$N (16 mg, 0.16 mmol). The reaction mixture was stirred at room temperature overnight. Purification by reversed-HPLC (Method: C18 Waters Sunfire column (30× 150 mm, 5 micron). Gradient: MeCN in H$_2$O with 0.1% trifluoroacetic acid) afforded the product. N'-[3-[5,7-Difluoro-2-(4-fluorophenyl)-1H-indol-3-yl]cyclobutyl]propanediamide (18 mg, 39%). $^1$H NMR (300 MHz, Acetone-d$_6$) δ 10.71 (s, 1H), 7.69-7.57 (m, 2H), 7.49-7.38 (m, 1H), 7.37-7.21 (m, 2H), 6.85 (ddd, J=11.0, 9.6, 2.2 Hz, 1H), 4.53 (tt, J=7.9, 3.9 Hz, 1H), 4.24-3.96 (m, 1H), 3.15 (s, 2H), 2.93-2.66 (m, 2H), 2.42 (ddd, J=13.3, 9.4, 3.7 Hz, 2H). LCMS m/z 402.13 [M+H]$^+$.

Compound 448

2-(3-((1r,3r)-3-(5,7-difluoro-2-(4-fluorophenyl)-1H-indol-3-yl)cyclobutyl)ureido)acetamide (448)

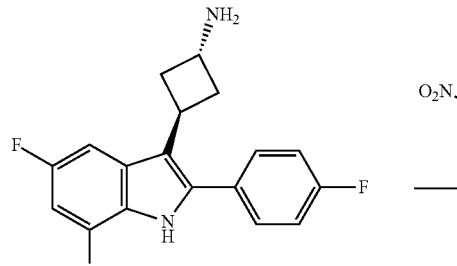
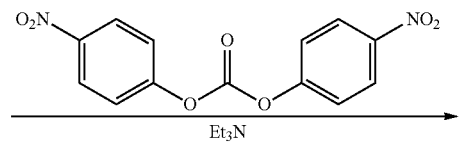
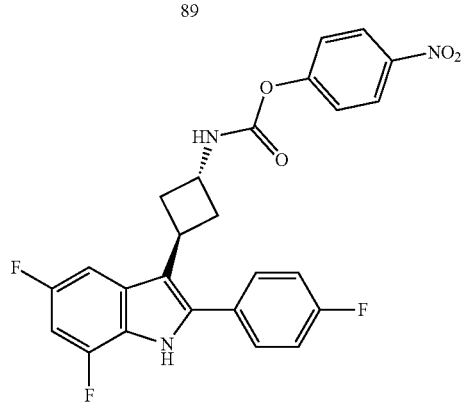
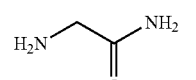
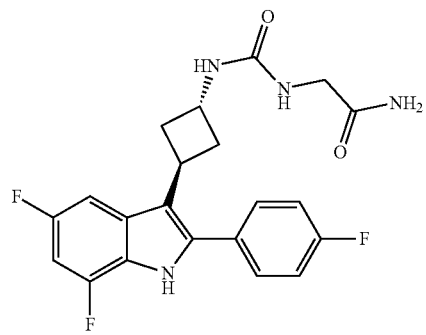

Step 1. Synthesis of 4-nitrophenyl ((1r,3r)-3-(5,7-difluoro-2-(4-fluorophenyl)-1H-indol-3-yl)cyclobutyl)carbamate (S6)

To a solution of 3-[5,7-difluoro-2-(4-fluorophenyl)-1H-indol-3-yl]cyclobutanamine 89 (600 mg, 1.9 mmol) in THF (20 mL) was added bis(4-nitrophenyl)carbonate (285 mg, 0.937 mmol), followed by Et$_3$N (200 mg, 2.0 mmol). The reaction mixture was stirred for a few hours. The mixture was then concentrated in vacuo to provide the product. 4-Nitrophenyl ((1r,3r)-3-(5,7-difluoro-2-(4-fluorophenyl)-1H-indol-3-yl)cyclobutyl)carbamate (600 mg, 12%). LCMS m/z 482.27 [M+H]$^+$.

Step 2. Synthesis of 2-(3-((1r,3r)-3-(5,7-difluoro-2-(4-fluorophenyl)-1H-indol-3-yl)cyclobutyl)ureido)acetamide (448)

Standard Method H: Urea Formation

To a solution of (4-nitrophenyl) N-[3-[5,7-difluoro-2-(4-fluorophenyl)-1H-indol-3-yl]cyclobutyl]carbamate S6 (50 mg, 0.1 mmol) in DMF (2 mL) was added 2-aminoacetamide (8 mg, 0.1039 mmol) followed by Et$_3$N (10.5 mg, 14.5 µL, 0.104 mmol). The reaction mixture was stirred at room temperature overnight. Purification by reversed-phase HPLC (Method: C18 Waters Sunfire column (30×150 mm, 5 micron). Gradient: MeCN in H$_2$O with 0.1% trifluoroacetic acid) afforded the product. 2-(3-((1r,3r)-3-(5,7-difluoro-2-(4-fluorophenyl)-1H-indol-3-yl)cyclobutyl)ureido)acetamide. LCMS m/z 417.42 [M+H]$^+$.

Compound 449

N-(2-amino-2-oxoethyl)-3-((5,7-difluoro-2-(4-fluorophenyl)-1H-indol-3-yl)methyl)cyclobutane-1-carboxamide (449)

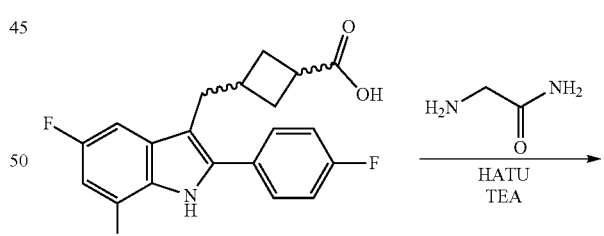
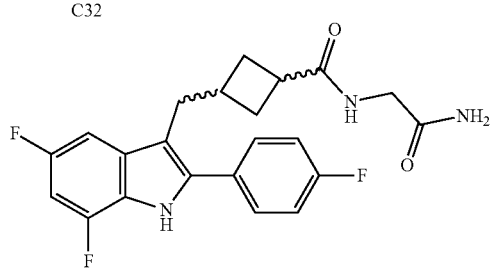

Preparation of N-(2-amino-2-oxoethyl)-3-((5,7-difluoro-2-(4-fluorophenyl)-1H-indol-3-yl)-methyl)cyclobutane-1-carboxamide (449)

To a solution of 3-[[5,7-difluoro-2-(4-fluorophenyl)-1H-indol-3-yl]methyl]cyclobutanecarboxylic acid C32 (30 mg), and 2-aminoacetamide in DMF (2 mL) was added HATU and Et$_3$N. The reaction mixture was stirred at room temperature overnight. Purification by reversed-phase HPLC (Method: C18 Waters Sunfire column (30×150 mm, 5 micron). Gradient: MeCN in H$_2$O with 0.1% trifluoroacetic acid) afforded the product. N-(2-amino-2-oxoethyl)-3-((5,7-difluoro-2-(4-fluorophenyl)-1H-indol-3-yl)methyl)cyclobutane-1-carboxamide. LCMS m/z 416.17 [M+H]$^+$.

Compound 450

N$^1$-(((1r,3r)-3-(5,7-difluoro-2-(4-fluorophenyl)-1H-indol-3-yl)cyclobutyl)methyl)malonamide (450)

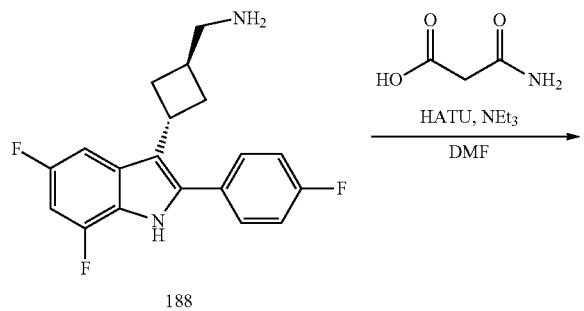

188

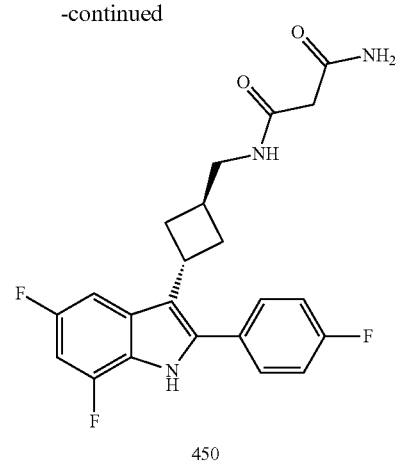

450

Preparation of N$^1$-(((1r,3r)-3-(5,7-difluoro-2-(4-fluorophenyl)-1H-indol-3-yl)cyclobutyl)-methyl)malonamide (450)

Standard Method I: Amide Coupling Method

To a solution of ((1r,3r)-3-(5,7-difluoro-2-(4-fluorophenyl)-1H-indol-3-yl)cyclobutyl)methanamine 188 (20 mg, 0.06 mmol) and 3-amino-3-oxopropanoic acid (8.1 mg, 0.079 mmol) in DMF (1 mL) was added HATU (32 mg, 0.085 mmol) followed by triethylamine (18 mg, 0.18 mmol). The mixture was stirred at room temperature for 2 hours. The mixture was then filtered and purified by reversed-phase HPLC (Method: C18 Waters Sunfire column (30×150 mm, 5 micron). Gradient: 5% to 95% MeCN in water with 0.1% trifluoroacetic acid) to yield the product. N$^1$-(((1r,3r)-3-(5,7-difluoro-2-(4-fluorophenyl)-1H-indol-3-yl)cyclobutyl)methyl)malonamide (3.4 mg, 11%). LCMS m/z 416.38 [M+H]$^+$.

Compounds 451-452

Compounds 451-452 were prepared from compound 188 using the appropriate amine and using the standard coupling method as described for compound 450. Carboxylic acids were obtained from commercial sources. Any modifications to methods are noted in Table 16 and accompanying footnotes.

TABLE 16

Structure and physicochemical data for compounds 451-452

| Compound | Product | Carboxylic Acid | $^1$H NMR; LCMS m/z [M + H]$^+$ |
|---|---|---|---|
| 451 | ![structure] | ![acid] | $^1$H NMR (300 MHz, Methanol-d$_4$) δ 7.58-7.38 (m, 2H), 7.29 (dd, J = 9.8, 2.2 Hz, 1H), 7.27-7.11 (m, 2H), 6.73 (ddd, J = 11.0, 9.6, 2.2 Hz, 1H), 4.01 (p, J = 9.0 Hz, 1H), 3.50 (d, J = 7.3 Hz, 2H), 2.73-2.42 (m, 3H), 2.28-2.06 (m, 2H); LCMS m/z 402.34 [M + H]$^+$ |

TABLE 16-continued

Structure and physicochemical data for compounds 451-452

| Compound | Product | Carboxylic Acid | ¹H NMR; LCMS m/z [M + H]⁺ |
|---|---|---|---|
| 452 | (structure) | (structure) | LCMS m/z 442.19 [M + H]⁺ |

Compound 453

$N^1$-(((1s,3s)-3-(5,7-difluoro-2-(4-fluorophenyl)-1H-indol-3-yl)cyclobutyl)methyl)oxalamide (453)

Preparation of $N^1$-(((1s,3s)-3-(5,7-difluoro-2-(4-fluorophenyl)-1H-indol-3-yl)cyclobutyl)methyl)-oxalamide (453)

To a solution of ((1s,3s)-3-(5,7-difluoro-2-(4-fluorophenyl)-1H-indol-3-yl)cyclobutyl)methanamine 187 (20 mg, 0.06 mmol) and oxamic acid (5.4 mg, 0.06 mmol) in DMF was added HATU (28 mg, 0.073 mmol) followed by DIPEA (23 mg, 0.18 mmol). The mixture was stirred at room temperature overnight. The mixture was then filtered and purified by reversed-phase HPLC (Method: C18 Waters Sunfire column (30×150 mm, 5 micron). Gradient: MeCN in H₂O with 0.1% trifluoroacetic acid) to yield the product. $N^1$-(((1s,3s)-3-(5,7-Difluoro-2-(4-fluorophenyl)-1H-indol-3-yl)cyclobutyl)methyl)oxalamide (15.6 mg, 50%). LCMS m/z 402.25 [M+H]⁺.

Compound 454

$N^1$-(((1s,3s)-3-(5,7-difluoro-2-(4-fluorophenyl)-1H-indol-3-yl)cyclobutyl)methyl)-$N^4$,$N^4$-dimethylsuccinamide (454)

-continued

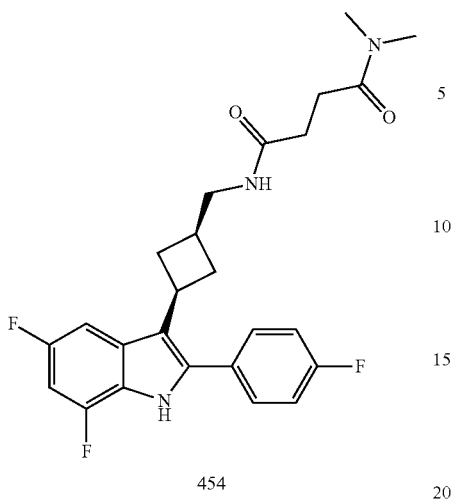

454

Preparation of N¹-(((1s,3s)-3-(5,7-difluoro-2-(4-fluorophenyl)-1H-indol-3-yl)cyclobutyl)methyl)-N⁴, N⁴-dimethylsuccinamide (454)

To a solution of ((1s,3s)-3-(5,7-difluoro-2-(4-fluorophenyl)-1H-indol-3-yl)cyclobutyl)methanamine 187 (21 mg, 0.064 mmol) and 4-(dimethylamino)-4-oxo-butanoic acid (0.477 mL, 2 M, 0.0954 mmol) in DMF (1 mL) was added HATU (30 mg, 0.08 mmol) followed by NEt₃ (0.027 mL, 0.19 mmol). The mixture was stirred at room temperature overnight. The mixture was then filtered and purified by reversed-phase HPLC (Method: C18 Waters Sunfire column (30×150 mm, 5 micron). Gradient: MeCN in H₂O with 0.1% trifluoroacetic acid) to yield the product. $N^1$-(((1s,3s)-3-(5, 7-Difluoro-2-(4-fluorophenyl)-1H-indol-3-yl)cyclobutyl) methyl)-$N^4$,$N^4$-dimethylsuccinamide (14.9 mg, 41%). LCMS m/z 458.22 [M+H]⁺.

Compound 455

2-[3-[[5,7-difluoro-2-(4-fluorophenyl)-1H-indol-3-yl]methyl]azetidin-1-yl]-2-oxo-acetamide (455)

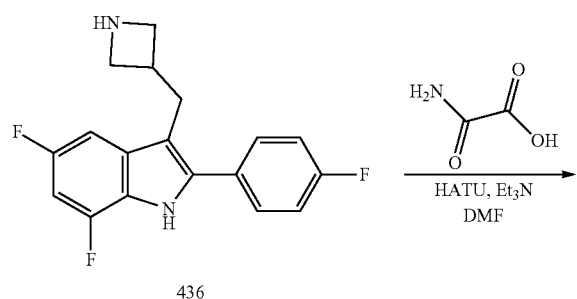

-continued

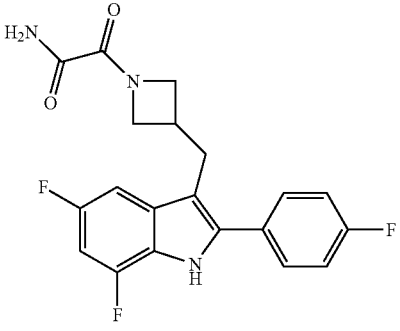

455

Preparation of 2-[3-[[5,7-difluoro-2-(4-fluorophenyl)-1H-indol-3-yl]methyl]azetidin-1-yl]-2-oxo-acetamide (455)

To a solution of 3-(azetidin-3-ylmethyl)-5,7-difluoro-2-(4-fluorophenyl)-1H-indole 436 (30 mg, 0.1 mmol) and 2-amino-2-oxoacetic acid (10 mg, 0.11 mmol) in DMF (2 mL) was added HATU (43 mg, 0.11 mmol), and Et₃N (19 mg, 0.19 mmol). The reaction was allowed to stir overnight at ambient temperature and purified by reversed-phase HPLC (Method: C18 Waters Sunfire column (30×150 mm, 5 micron). Gradient: MeCN in H₂O with 0.1% trifluoroacetic acid) to afford the product. 2-[3-[[5,7-Difluoro-2-(4-fluorophenyl)-1H-indol-3-yl]methyl]azetidin-1-yl]-2-oxo-acetamide (7.9 mg, 17%). LCMS m/z 388.16 [M+H]⁺.

Compound 456

[3-[5,7-difluoro-2-(4-fluorophenyl)-1H-indol-3-yl]cyclobutyl]N-(2-amino-1-methyl-2-oxo-ethyl)carbamate (456)

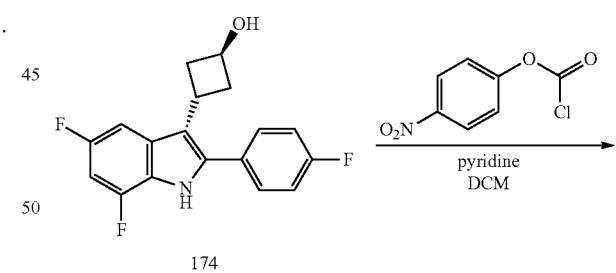

-continued

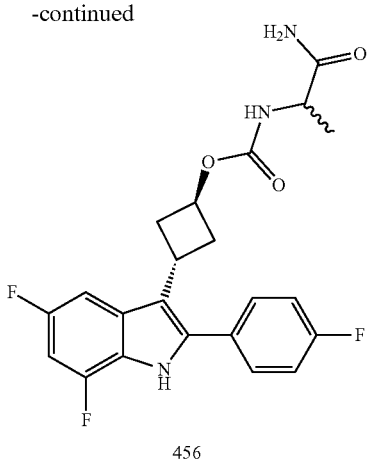

456

Step 1. Synthesis of (1r,3r)-3-(5,7-difluoro-2-(4-fluorophenyl)-1H-indol-3-yl)cyclobutyl (4-nitrophenyl)carbonate (C52)

To a solution of (1r,3r)-3-(5,7-difluoro-2-(4-fluorophenyl)-1H-indol-3-yl)cyclobutan-1-ol 174 (2000 mg, 6.30 mmol) in DCM (20 mL) was added (4-nitrophenyl) carbonochloridate (2 g, 10 mmol), followed by pyridine (750 mg, 9.5 mmol). The mixture was stirred for 5 hours at room temperature. The mixture was concentrated in vacuo, and the residue was dissolved in ethyl acetate. The solution was washed with 2 M aqueous NaOH (×3) and brine, dried over sodium sulfate, filtered, and concentrated in vacuo to afford the product. (1r,3r)-3-(5,7-Difluoro-2-(4-fluorophenyl)-1H-indol-3-yl)cyclobutyl (4-nitrophenyl) carbonate. LCMS m/z 483.26 [M+H]$^+$.

Step 2. Synthesis of [3-[5,7-difluoro-2-(4-fluorophenyl)-1H-indol-3-yl]cyclobutyl]N-(2-amino-1-methyl-2-oxo-ethyl)carbamate (456)

[3-[5,7-difluoro-2-(4-fluorophenyl)-1H-indol-3-yl]cyclobutyl](4-nitrophenyl)carbonate C52 (50 mg) was taken in DMF (2 mL). 2-aminopropanamide (14 mg) and pyridine were added. The reaction mixture was heated at 80° C. overnight. The reaction mixture was filtered. Purification by reversed-phase HPLC (Method: C18 Waters Sunfire column (30×150 mm, 5 micron). Gradient: MeCN in H$_2$O with 0.1% trifluoroacetic acid) afforded the product. [3-[5,7-Difluoro-2-(4-fluorophenyl)-1H-indol-3-yl]cyclobutyl] N-(2-amino-1-methyl-2-oxo-ethyl)carbamate. LCMS m/z 432.13 [M+H]$^+$.

Example 2. Assays for Detecting and Measuring APOL1 Inhibitor Properties of Compounds Acute APOL1 Thallium Assay with Inducible Stable Clones of HEK 293 Cells Apolipoprotein L1 (APOL1) proteins form potassium-permeable cation pores in the plasma membrane. APOL1 risk variants (G1 and G2) induce greater potassium flux than G0 in HEK293 cells. This assay exploits the permeability of thallium (T1+) through ligand-gated potassium channels. The dye produces a bright fluorescent signal upon binding to T1+ conducted through potassium channels. The intensity of the T1+ signal is proportional to the number of potassium channels in the open state. Therefore, it provides a functional indication of the potassium channel activities. During the initial dye-loading step, the T1+ indicator dye as an acetoxymethyl (AM) ester enters the cells through passive diffusion. Cytoplasm esterases cleave the AM ester and relieve its active thallium-sensitive form. The cells are then stimulated with T1+. The increase of fluorescence in the assay represents the influx of T1+ into the cell specifically through the potassium channel (i.e. through APOL1 pores), providing a functional measurement of potassium channel/pore activity. The Thallium assay is conducted with cells expressing G1 APOL1.

Reagents and Materials

APOL1 Cell Line (HEK T-Rex Stable Inducible Cell Line)

HEK T-Rex System

Tetracycline (Tet) inducible mammalian expression system.

Stably express the Tet repressor to regulate transcription.

Expression under the full-length CMV promoter.

APOL1 stable inducible cell line Clone used: G1 DC3.25

Tissue Culture Media

Cell Culture Medium

DMEM+10% FBS+P/S+5 µg/mL blasticidin+1 µg/mL puromycin.

500 mL DMEM+55 mL FBS+5 mL P/S+280 µL blasticidin S HCl (10 mg/mL)+56 µL puromycin (10 mg/mL).

Cell Assay Medium

DMEM with 2% FBS+penicillin streptomycin.

Reagents:

| | | |
|---|---|---|
| PBS | 7.4 pH no phenol red no sodium pyruvate Concentration: 1X | Gibco Cat. No. 10-010-49 |
| Trypsin | 0.25%/EDTA 2.21 mM in HBSS | Wisent, Cat. No. 325-043-EL |
| DMEM | High Glucose, no sodium pyruvate, with phenol red, with glutamine | GIBCO, Cat. No. 11960-051 |
| FBS | Tet System Approved FBS US Sourced | Takara Cat. No. 631101 |
| HEPES Buffer | 1M | Invitrogen, Cat. No. 15630-080 |
| HBSS | calcium magnesium no phenol red | Life Technologies, Cat. No. 14025-126 |
| DMSO | | |
| Penicillin Streptomycin (P/S) | Sterile filtered for cell culture Concentration: 100X | Wisent, Cat. No. 450-201-EL |
| Puromycin Dihydrochloride | Concentration: 10 mg/mL | Gibco, Cat. No. A11138-03 |
| Blasticidin S HCl | Concentration: 10 mg/mL | Gibco, Cat. No. A11139-03 |
| Ouabain | Prepare 100 mM stock in DMSO aliquot and store at −20° C. | Tocris, Cat. No. 1076 |
| Probenecid | Resuspend in 1 mL HBSS 20 mM HEPES | Invitrogen, Cat. No. P36400 |
| Tetracycline | Prepare 1 mg/mL stock in H$_2$O aliquot and store at −20° C. | Sigma-Aldrich, Cat. No. T7660 |

Materials

| | |
|---|---|
| Corning® BioCoat™ Poly-D-Lysine 384-well black, transparent, flat bottom tissue culture plates | Cat. No. 354663, Lot No. 31616006 |
| Corning® 384-well microplate, clear polypropylene, round bottom, sterile | Costar Cat. No.: 3656 |
| FLIPR pipette tips, 384-well | Molecular Devices, Cat. No. 9000-0764 |
| FLIPR Potassium Assay Kit | Molecular Devices, Cat. No. R8223 |

Instruments and Equipment
- Nuaire cell culture hood, Cat. No. 540-600
- 37° C./5% CO incubator link to robotic arm, Liconic: STX110
- Molecular Devices FLIPR$^{Tetra}$ High throughput cellular screening system, Cat. No. FT0324, Molecular Devices
- ThermoFisher MultiDrop 384, Cat. No. 5840300
- Biotek Microfill, Cat. No. ASF1000A-4145
- BioRad TC10 cell counter, Cat. No. 145-0010

Assay Procedures
Cells Scaled Up from Frozen Vials
- APOL1 G1 3.25 (HEK293 T-Rex) frozen vials: 5 million cells per vial
- Step 1, Day 1: Defrost frozen vial into T-225.
- Step 2, Day 5: (when 85% confluent): Split one T-225 at 3×10$^6$ cells per flask.
- Step 3, Day 8: Splits cells to set up for the assay plates as described below.

Cell Culture
T-Rex APOL1 HEK cells are split twice per week to keep the confluence state below 85% of the culture flask surface area. Cells can be kept until passage 25.

Cell Culture Medium
- DMEM high glucose+10% FBS, +P/S, +5 µg/mL blasticidin, +1 µg/mL puromycin.
- 500 mL DMEM, +55 mL FBS, +5 mL P/S, +280 µL blasticidin 10 mg/mL, +56 µL Puromycin 10 mg/mL.

Assay Media
- Opti-MEM reduced serum medium from Invitrogen.

Day 1
Preparation of Cell Assay Plates
- Culture medium is removed from the x cm$^2$ T-flask by aspiration.
- The cell monolayer is rinsed with PBS 1× at room temperature. PBS is removed by aspiration.
- Cells are trypsinized using Trypsin.
- The flasks are incubated at room temperature for 2-3 minutes.
- Complete DMEM medium is then added. Cell suspension is then transferred to a 50 mL Falcon polypropylene tube.
- Cells are then counted using a BioRad TC10 cell counter and the required amount of cells are centrifuged at 1200 RPM for 5 minutes. Required amount is 1.3×10$^6$ cells/mL APOL1 T-Rex HEK cells.
- The pellet is suspended in the assay medium.
- Using the MultiDrop, add 20 µL to each well (corresponds to 26000 cells total per well) of a 384-well black, transparent, flat bottom Poly-D coated plate.
- Tetracycline as prepared in the following section is added to the cells before plating to induce APOL1 expression.
- Plates are left at room temperature for 20 to 30 minutes before incubation at 37° C. and 5% CO$_2$.

Preparation of Tetracycline
Tetracycline stock is prepared at 1 mg/mL in H$_2$O, aliquoted and stored at −20° C.
On the day the cells are plated for the assay, the tetracycline working concentration is prepared as follows:
- Predilute tetracycline stock at 100× by transferring 50 µL stock in 5 mL assay media to give 10 µg/mL intermediate stock.
- Prepare tetracycline at 4× if added with Biomek to the cell plates or added directly on cells to give a 1× tetracycline concentration according to Table 17 below.

TABLE 17

Concentration of Tetracycline for cell plate.

| Clones | 1X Tet ng/mL | 5X Tet ng/mL | mL predilution | mL diluted cell suspension |
|---|---|---|---|---|
| G1 DC3.25 | 15 | 75 | 0.3 | 39.7 |

Day 2
Preparation of Thallium Loading Dye and Cells Loading FLIPR® Potassium Assay Kit R8223
Preparation of the Loading Buffer:
1. Remove one vial each of Component A (Dye) and Component C (Pluronic) from the freezer, and then equilibrate to room temperature.
2. For the Bulk Kit, prepare 200 mL of 20 mM HEPES plus 1×HBSS, pH 7.4 as Component B.
3. Dissolve the contents of the Component C vial in DMSO, and the mix thoroughly by vortexing.
4. Combine the vial of Component A (dye) with 10 mL of the Component B buffer (HBSS 20 mM HEPES).
5. Combine the Component C solution from step 3 to the Component A solution from step 4, and then mix by vortexing for 1 to 2 minutes until the contents of the vial are dissolved. Note: It is important that the contents are completely dissolved to ensure reproducibility between experiments.
6. For the Bulk Kit only, combine the solution from step 5 with the remaining 190 mL of the prepared Component B buffer, and then mix thoroughly.

For each 10 mL of prepared dye add: 200 µL Probenecid (equals 2.5 mM final in assay plate) and 20 µL of 100 mM ouabain (equals 100 µM in assay plate).
Add 25 µL loading dye to each well of assay plate containing 25 µL. Link to robotic arm (with multidrop or microfill).
Incubate for 30 minutes at room temperature.

Preparation of Drug Plates and Transfer of Compounds to Assay Plates
- The compounds are plated in assay ready plates (ARP). The plate layout in FIG. 1 shows the plate map for ARPs for dose response.
- The compounds are hydrated with 20 µL HBSS with 20 mM HEPES.
- The compounds are transferred to the assay plates 30 minutes after loading thallium sensitive dye as described in Preparation of Thallium Loading Dye described above.
- The compounds are diluted by a 1:500 ratio for the final concentration.
- The compound transfer is done using FLIPR. Mix: 3 strokes, 10 µL with speed @ 5 µL/sec, Height 20 µL. Aspirate: 10 µL with speed @ 5 µL/sec, Height 5 µL;

Tip up speed of 20 mm/sec. Dispense: 10 µL with speed @ 5 µL/sec, Height 10 µL; liquid removal speed of 20 mm/sec.

Incubate for 30 minutes at room temperature.

Preparation of the Thallium Sulfate Source Plate
  Prepare a 5× thallium sulfate solution in 1× chloride buffer.
  For 5 mL of 5× thallium source plate: 1 mL of Chloride Free 5×, 0.5 mL Tl$_2$SO$_4$ 50 mM (2 mM equivalent final), 3.5 mL H2O.
  Dispense in 384-well Corning PP round-bottom plates (Costar, Cat. No. 3656).
  Need 12.5 µL per well for each assay plate+dead volume. Spin briefly.

Start Assay on FLIPR 384-Head
Parameters
  Excitation: 470-495 nm; Emission: 515-575 nm.
  Addition volume: 12.5 µL.
  Aspirate: 12.5 µL with speed @ 20 µL/sec, Height 5 µL; Tip up speed of 20 mm/sec
  Dispense: 12.5 µL with speed @ 20 µL/sec, Height 40 µL; liquid removal speed of 20 mm/sec.
  Read baseline for 10 seconds; transfer 12.5 µL to assay plate.
  Read every second for 60 seconds.
  Keep tips on head for thallium addition.

Data Analysis
  Stat file: Export slope (rate) between 17 and 32 seconds.
  Analyze using (No Tet DMSO) and (Tet DMSO) controls (set up Stimulation and neutral controls, respectively).
  Calculate percent inhibition thallium rate versus controls.
  Data is reported as IC$_{50}$ (half maximum inhibitory concentration) and maximum percent inhibition.

*Trypanosoma brucei brucei* Lysis Assay Using APOL1 Recombinant Protein

*Trypanosoma brucei brucei* is a blood stream parasite to which human, gorillas and baboon are immune due to the presence of the APOL1 protein in their HDL particles. The protein is uptaken by the parasite via the TbHpHb receptor located in its flagellar pocket and is bonded by the Hpr protein contained in the HDL particles which triggers the receptor endocytosis by the parasite.

Following endocytosis, the formed vesicle containing the HDL particle matures from early to late endosome, and subsequently to lysosome. The concomitant pH change in the lumen of the vesicle triggers the insertion of the APOL1 protein into the membrane of the late endosome/lysosome and hereby triggers lysosomal membrane permeabilization and as a further downstream event, trypanosome lysis. *Trypanosoma brucei brucei* is sensitive to lysis by all three APOL1 variants (G0, G1, and G2).

The *Trypanosoma brucei brucei* lysis assay is a lysis assay of the parasite using recombinant APOL1 protein variant followed by a fluorescent detection method of viability by the addition of AlamarBlue reagent to the assay well, a general metabolic redox indicator (AlamarBlue assay).

Briefly, the AlamarBlue active compound, the resazurin, a blue, water soluble, non-toxic and cell permeable molecule, which can be followed by absorbance, is reduced by various metabolic pathways into resorufin, a red compound which can be followed by either absorbance or fluorescence. The assay allows the calculation of the percent viability (percent of living Trypanosomes remaining in each well) at the end of a lysis relative to the untreated condition by interpolation of fluorescent values (FLU) on a standard curve with a known amount of seeded trypanosome/well.

Reagents and Materials
*Trypanosoma brucei brucei* (ATCC, Cat. No. PRA-382)
  Lister 427 VSG 221 bloodstream form.
Thaw/Expansion Media (ATCC Medium 2834 Modified HMI-9 Medium)

| | | |
|---|---|---|
| IMDM | 250 mL | 76.3% |
| FBS | 25 mL | 7.63% |
| Serum Plus | 25 mL | 7.63% |
| HMI-9 | 25 mL | 7.63% |
| Hypoxanthine | 2.5 mL | 0.763% |
| 327 5 mL total | | |

Assay Media (No Phenol Red/No FBS): Make on Day of Use

| | | |
|---|---|---|
| IMDM No Phenol Red | 250 mL | 82.6% |
| Serum Plus | 25 mL | 8.26% |
| HMI-9 | 25 mL | 8.26% |
| Hypoxanthine | 2.5 mL | 0.826% |
| 302.5 mL total | | |

HMI-9 (10×)

| | |
|---|---|
| Bathocuproine disulfonic acid | 280 mg |
| Cysteine | 1820 mg |
| Sodium pyruvate (100x) | 100 mL |
| Uracil | 100 mg |
| Cytosine | 100 mg |
| 2-mercaptoethanol | 140 µL |
| Water | 900 mL |
| 1000 mL total | |

Hypoxanthine Stock (100×)–9 (10×)

| | |
|---|---|
| Sodium Hydroxide | 0.8 g |
| Hypoxanthine | 2.72 g |
| Water | 200 mL |
| 200 mL total | |

Media Reagents

| | | |
|---|---|---|
| IMDM | Phenol Red sodium pyruvate L-glutamine 25 mM HEPES | Life Technologies, Cat. No. 12440 |
| IMDM | NO Phenol Red sodium pyruvate L-glutamine 25 mM HEPES | Life Technologies, Cat. No. 21056 |
| FBS | Heat inactivated | Sigma-Aldrich, Cat. No. F8317-500 mL |
| Serum Plus | medium supplement | Sigma-Aldrich, Cat. No. 14008C |
| Bathocuproine disulfonic acid | | Sigma-Aldrich, Cat. No. B1125-1 G |
| Cysteine | | Sigma-Aldrich, Cat. No. C7352-25 G |
| Sodium Pyruvate Solution | 100x | Sigma-Aldrich, Cat. No. S8636-100 ml |
| Uracil | | Sigma-Aldrich, Cat. No. U1128-25 G |
| Cytosine | | Sigma-Aldrich, Cat. No. C3506-1 G |

-continued

| | | |
|---|---|---|
| 2-mercaptoethanol | Sigma-Aldrich, Cat. No. M3148-25 ml | |
| Hypoxanthine | Sigma, Cat. No. H9636 | |
| Sodium hydroxide | Sigma-Aldrich, Cat. No. S8045-500 G | |

Materials

| | | |
|---|---|---|
| T75/T175 | Nunc ™ Non-Treated flask Non-TC treated Vented/White lids with filter | T75 Thermo-Fisher Cat. No. 156800 T175 Thermo-Fisher Cat. No. 159926 |
| Assay Plates | 384 well black clear bottom Non-sterile Non-TC treated | Corning ® Cat. No. 3762 |
| Polypropylene storage plates | | Corning ® Cat. No. 3656 |
| Plate Lids | Clear universal sterile lids | Thermo-Fisher Cat. No. 250002 |
| Bravo Tips | 30 µL tips for 384 well | Axygen Cat. No. VT-384-31UL-R-S |
| E1-Clip Tip pipette 12 channel adjustable 2-125 µL | | Thermo-Fisher Cat. No. 4672070BT |
| Tips | 125 µL E1-Clip sterile filter | Thermo-Fisher Cat. No. 94420153 |
| Tips | 125 µL E1-Clip sterile (non-filter) | Thermo-Fisher Cat. No. 94410153 |

Equipment
  E1-Clip Tip pipette 12 channel adjustable 2-125 µL, Cat. No. 4672070BT
  ThermoFisher MultiDrop 384, Cat. No. 5840300
  Multidrop
  Agilent Bravo, Cat. No. G5409A
  Bravo
  SpectraMax M5
Assay Ready Plates (ARPs)
  ARPs comes in two formats:
    10 mM final top concentration with a 2.5 fold dilution down.
    5 mM final top concentration with a 3 fold dilution down.
    Both have a 10 point Dose response.
    0.1% DMSO final in the Black Assay Plate.
    Compounds are diluted 1000 fold in the Black Assay Plate.
    Each plate is designed for 14 compounds in duplicate.
  In the final Black Assay Plate:
    Column 1: Media only (no APOL1) (100% viable)
    Column 2-23: 0.05 µg/mL APOL1 (~$EC_{90}$) (10% viable with APOL1)
    Column 24: 0.1 µg/mL APOL1 ($EC_{100}$) (Approx. 0% viable)
Assay Procedures

*Trypanosoma brucei brucei* Culture

Protocol A
Step 1, Day 1
  That the cells at 35° C. for no more than 2 minutes.
  Resuspend one vial gently in 20 mL pre-warmed media and incubate in a T75 flask at 37° C. and 5% $CO_2$.
  Do not remove the cryoprotective agent.
Step 2, Day 4
  Centrifuge at 800×g for 5 minutes at room temperature.
  Resuspend in 1 mL media.
  Make a 1:25 fold dilution (10 µL/240 µL media).
  Count on a hemocytometer (after adding parasites).
    Let sit for 1-2 minutes for the parasites to settle.
    Count should be approximately 100 viable motile parasites/16 grid or approximately $25 \times 10^6$ parasites/flask.
  Passage the parasites by adding $1 \times 10^6$ parasites/T75 flask in 20 mL media.
  Passage the parasites by adding $2.33 \times 10^6$ parasites/T175 flask in 46.6 mL media.
    For every T75 flask should make enough for approximately 1.5×384 well assay plates.
    For every T175 flask should make enough for approximately 3.8×384 well assay plates.
Step 3, Day 6
  Centrifuge at 800×g for 5 minutes.
    Resuspend in 3 mL assay media (No phenol red, no FBS) per 75 starting flask.
    Resuspend in 7 mL assay media (No phenol red, no FBS) per 175 flask
  Make a 1:25 fold dilution.
  Count by hemocytometer.
    Every T75 flask set up should have approximately $75 \times 10^6$ parasites/flask (verify doubling time=8.7 hours±1 hour).
    Every T175 flask set up should have approximately $175 \times 10^6$ parasites/flask (verify doubling time=8.7 hours±1 hour).
    Require $46 \times 10^6$ parasites per 384 well plate (at 120,000 parasites per well).
Protocol B
Step 1, Day 1
  Thaw the cells at 35° C. for not more than 2 minutes.
  Resuspend one vial gently in 20 mL of pre-warmed mediate and incubate in a T75 flask at 37° C. and 5% $CO_2$.
  Do not remove the cryoprotective agent.
Step 2, Day 2
  Centrifuge at 800×g for 5 minutes at room temperature.
  Resuspend in 1 mL media.
  Make a 1:25 fold dilution (10 µL/240 µL media).
    Let sit for 1-2 minutes for the parasites to settle.
    Count should be approximately 100 viable motile parasites/16 grid or approximately $8 \times 10^6$ parasites per flask.
  Passage the parasites by adding $1.25 \times 10^6$ parasites per T75 flask in 20 mL media.
    For every T75 flask set up should have approximately 1.5×384 well assay plates.
    For every T175 flask set up should have approximately 3.8×384 well assay plates.
Step 3, Day 5
  Centrifuge at 800×g for 5 minutes.
    Resuspend in 3 mL assay media (No phenol red, no FBS) per T75 starting flask.
    Resuspend in 7 mL assay media (No phenol red, no FBS) per T175 starting flask.
  Make a 1:25 fold dilution.
  Count by hemocytometer.
    Every T75 flask should have approximately $75 \times 10^6$ parasites per flask (verify doubling time: 7.7 hours±1 hour).

Lysis Assay Setup

APOL1 G1 Protein
  Remove an aliquot of the 1.2 mg/mL APOL1 protein stock from −70° C.
  Determine amount required for the experiment:
    Need 11.5 mL of 0.1 µg/mL APOL1 per 384 well plate.
    Need 0.5 mL of 0.2 µg/mL APOL1 per 384 well plate for control.
  Make initial 1:10 dilution (10 µL/90 µL) into Assay media (now at 120 µg/mL).
    Using APOL1 at a final concentration of 0.05 µg/mL for an ~$EC_{50}$. Need to determine this value for each new lot of protein used.
    Adding 30 mL/well of 2×APOL1 concentration of 0.1 µg/mL.
      Solution A: Measure 8.33 µL (120 µg/mL) in 10 mL for a 0.1 µg/mL 2× stock.
      Solution B: Measure 16.67 µL (120 µg/mL) in 10 mL for a 0.2 µg/mL 2× stock control.
Multidrop
  Black Assay Plate (384 well black well clear bottom, Cat. No. 3762).
  Column 1: Dispense 30 µL/well of Assay media (no APOL1).
  Column 2-23: Dispense 30 µL/well of Solution A (0.1 µg/mL APOL1).
  Column 24: Dispense 30 µL/well of Solution B (0.2 µg/mL APOL1).
  Storage Plate (Polypropylene storage plate, Corning® Cat. No. 3656).
  Column 1-24: Dispense 80 µL Assay media (no APOL1) per well (30 mL media/plate).
Bravo: Compound Transfer
  Place the storage plate, the Assay Ready Plate (ARP), and Black Assay Plate on the deck.
    Transfer 20 µL from the storage plate to the ARP and mix.
    Transfer 6 µL from the ARP to the Black Assay Plate and mix.
    Black Assay Plates are now ready for Trypanosome addition.
Trypanosome Addition:
  Once the Black Assay Plates have compounds added, begin harvesting the Trypanosomes as described in Step 3 of the *Trypanosoma brucei brucei* Culture section.
  Count the Trypanosomes and prepare at $5\times10^6$/mL in Assay media (No Phenol red and no FBS).
    Requires 9.2 mL of $5\times10^6$ trypanosomes/mL for each 384 well plate ($46\times10^6$/plate).
  Add 24 µL of $5\times10^6$ trypanosomes mix to each well of a 384 well plate using the E1-Clip multichannel 12 channel 2-125 µL adjustable pipette.
  Once addition is complete, tap plate on the surface to ensure liquid is within each well.
  Place plates on the plate shaker for approximately 10 seconds and shake to ensure even distribution and that no drops are left on any edges.
  Place in incubator overnight (16 hours) at 37° C. and 5% $CO_2$.
  Each well should include 60 µL:
    30 µL 2×APOL1 media, 6 µL of 10× compounds, and 24 µL of trypanosome solution.
  Every T175 flask should have approximately $175\times10^6$ parasites per flask (verify doubling time: 7.7 hours±1 hour).

AlamarBlue Addition
  After 16 hours overnight in incubator, remove required amount of AlamarBlue (2.3 mL/plate) from the bottle stored in refrigerator, and warm up briefly in a 37° C. water bath.
  Add 6 µL/well using the E1-Clip Multichannel 12 channel 2-125 µL adjustable pipette.
  Protect from light and incubate the plate at 37° C. and 5% $CO_2$ for 2.5 hrs.
  Read on SpectraMax (Softmax Pro 6.4 software, excitation: 555 nm, emission: 585 nm)

Potency Data for Compounds 1 to 456

The compounds of Formulae I, I-A, I-B, I-C, I-D, I-E, and I-F, deuterated derivatives thereof and pharmaceutically acceptable salts of any of the foregoing are useful as inhibitors of APOL1 activity. Table 18 below illustrates the $IC_{50}$ of the compounds 1 to 456 using procedures described above (assays described above in Example 2A and 2B). In Table 18 below, the following meanings apply. For $IC_{50}$: "+++" means <0.25 µM; "++" means 0.25 µM to 1.0 µM; "+" means greater than 1.0 µM. N.D.=Not determined.

TABLE 18

Potency data for Compounds 1 to 456

| Compound No. | Thallium Assay ($IC_{50}$) | Trypanosoma Assay ($IC_{50}$) |
| --- | --- | --- |
| 1 | + | N.D. |
| 2 | ++ | N.D. |
| 3 | ++ | N.D. |
| 4 | +++ | +++ |
| 5 | ++ | N.D. |
| 6 | ++ | +++ |
| 7 | ++ | N.D. |
| 8 | ++ | N.D. |
| 9 | +++ | +++ |
| 10 | +++ | +++ |
| 11 | ++ | N.D. |
| 12 | ++ | +++ |
| 13 | + | N.D. |
| 14 | +++ | +++ |
| 15 | +++ | ++ |
| 16 | ++ | ++ |
| 17 | ++ | ++ |
| 18 | ++ | ++ |
| 19 | + | N.D. |
| 20 | +++ | N.D. |
| 21 | ++ | N.D. |
| 22 | + | N.D. |
| 23 | + | N.D. |
| 24 | + | N.D. |
| 25 | ++ | N.D. |
| 26 | ++ | N.D. |
| 27 | + | N.D. |
| 28 | +++ | +++ |
| 29 | ++ | ++ |
| 30 | ++ | +++ |
| 31 | + | N.D. |
| 32 | + | N.D. |
| 33 | + | N.D. |
| 34 | + | N.D. |
| 35 | + | N.D. |
| 36 | + | N.D. |
| 37 | + | N.D. |
| 38 | + | N.D. |
| 39 | + | N.D. |
| 40 | + | N.D. |
| 41 | + | N.D. |
| 42 | + | N.D. |
| 43 | + | N.D. |
| 44 | + | N.D. |
| 45 | + | N.D. |
| 46 | + | N.D. |
| 47 | + | N.D. |

TABLE 18-continued

Potency data for Compounds 1 to 456

| Compound No. | Thallium Assay (IC$_{50}$) | Trypanosoma Assay (IC$_{50}$) |
|---|---|---|
| 48 | + | N.D. |
| 49 | + | N.D. |
| 50 | + | N.D. |
| 51 | + | N.D. |
| 52 | + | N.D. |
| 53 | + | N.D. |
| 54 | + | N.D. |
| 55 | + | N.D. |
| 56 | ++ | N.D. |
| 57 | + | N.D. |
| 58 | ++ | N.D. |
| 59 | + | N.D. |
| 60 | + | N.D. |
| 61 | + | N.D. |
| 62 | + | N.D. |
| 63 | + | N.D. |
| 64 | + | N.D. |
| 65 | + | N.D. |
| 66 | + | N.D. |
| 67 | + | N.D. |
| 68 | ++ | N.D. |
| 69 | + | N.D. |
| 70 | + | N.D. |
| 71 | ++ | N.D. |
| 72 | + | N.D. |
| 73 | ++ | N.D. |
| 74 | ++ | N.D. |
| 75 | ++ | N.D. |
| 76 | ++ | N.D. |
| 77 | + | N.D. |
| 78 | + | N.D. |
| 79 | + | N.D. |
| 80 | + | N.D. |
| 81 | + | N.D. |
| 82 | + | N.D. |
| 83 | + | N.D. |
| 84 | + | N.D. |
| 85 | + | N.D. |
| 86 | + | N.D. |
| 87 | + | N.D. |
| 88 | + | N.D. |
| 89 | +++ | +++ |
| 90 | + | N.D. |
| 91 | + | N.D. |
| 92 | ++ | N.D. |
| 93 | ++ | N.D. |
| 94 | ++ | N.D. |
| 95 | +++ | N.D. |
| 96 | ++ | N.D. |
| 97 | + | N.D. |
| 98 | + | N.D. |
| 99 | + | N.D. |
| 100 | + | N.D. |
| 101 | + | N.D. |
| 102 | + | N.D. |
| 103 | + | N.D. |
| 104 | + | N.D. |
| 105 | + | N.D. |
| 106 | ++ | N.D. |
| 107 | + | N.D. |
| 108 | + | N.D. |
| 109 | + | N.D. |
| 110 | + | N.D. |
| 111 | + | N.D. |
| 112 | + | N.D. |
| 113 | + | N.D. |
| 114 | + | N.D. |
| 115 | + | N.D. |
| 116 | ++ | N.D. |
| 117 | + | N.D. |
| 118 | + | N.D. |
| 119 | + | N.D. |
| 120 | + | N.D. |
| 121 | + | N.D. |
| 122 | + | N.D. |
| 123 | ++ | N.D. |
| 124 | + | N.D. |
| 125 | +++ | N.D. |
| 126 | + | N.D. |
| 127 | + | N.D. |
| 128 | +++ | N.D. |
| 129 | +++ | N.D. |
| 130 | ++ | N.D. |
| 131 | ++ | N.D. |
| 132 | + | N.D. |
| 133 | +++ | N.D. |
| 134 | ++ | N.D. |
| 135 | +++ | N.D. |
| 136 | +++ | N.D. |
| 137 | +++ | N.D. |
| 138 | + | N.D. |
| 139 | + | N.D. |
| 140 | + | N.D. |
| 141 | ++ | N.D. |
| 142 | +++ | N.D. |
| 143 | ++ | N.D. |
| 144 | +++ | N.D. |
| 145 | ++ | N.D. |
| 146 | +++ | N.D. |
| 147 | +++ | N.D. |
| 148 | + | N.D. |
| 149 | ++ | N.D. |
| 150 | ++ | N.D. |
| 151 | ++ | N.D. |
| 152 | + | N.D. |
| 153 | + | N.D. |
| 154 | + | N.D. |
| 155 | + | N.D. |
| 156 | + | N.D. |
| 157 | +++ | N.D. |
| 158 | +++ | N.D. |
| 159 | + | N.D. |
| 160 | ++ | N.D. |
| 161 | ++ | N.D. |
| 162 | ++ | N.D. |
| 163 | + | N.D. |
| 164 | + | N.D. |
| 165 | + | N.D. |
| 166 | + | N.D. |
| 167 | + | N.D. |
| 168 | + | N.D. |
| 169 | + | N.D. |
| 170 | + | N.D. |
| 171 | + | N.D. |
| 172 | + | N.D. |
| 173 | ++ | +++ |
| 174 | +++ | +++ |
| 175 | ++ | N.D. |
| 176 | +++ | +++ |
| 177 | + | N.D. |
| 178 | ++ | N.D. |
| 179 | +++ | N.D. |
| 180 | +++ | +++ |
| 181 | +++ | +++ |
| 182 | +++ | +++ |
| 183 | +++ | +++ |
| 184 | +++ | +++ |
| 185 | +++ | +++ |
| 186 | +++ | +++ |
| 187 | +++ | +++ |
| 188 | +++ | +++ |
| 189 | +++ | N.D. |
| 190 | +++ | N.D. |
| 191 | +++ | N.D. |
| 192 | +++ | N.D. |
| 193 | +++ | N.D. |
| 194 | +++ | N.D. |
| 195 | +++ | N.D. |
| 196 | +++ | N.D. |
| 197 | +++ | N.D. |

TABLE 18-continued

Potency data for Compounds 1 to 456

| Compound No. | Thallium Assay (IC$_{50}$) | Trypanosoma Assay (IC$_{50}$) |
|---|---|---|
| 198 | +++ | N.D. |
| 199 | +++ | N.D. |
| 200 | +++ | N.D. |
| 201 | +++ | N.D. |
| 202 | +++ | N.D. |
| 203 | +++ | N.D. |
| 204 | +++ | N.D. |
| 205 | +++ | N.D. |
| 206 | ++ | N.D. |
| 207 | ++ | N.D. |
| 208 | ++ | N.D. |
| 209 | ++ | N.D. |
| 210 | ++ | N.D. |
| 211 | ++ | N.D. |
| 212 | ++ | N.D. |
| 213 | ++ | N.D. |
| 214 | ++ | ++ |
| 215 | ++ | N.D. |
| 216 | ++ | N.D. |
| 217 | ++ | N.D. |
| 218 | ++ | N.D. |
| 219 | ++ | N.D. |
| 220 | ++ | N.D. |
| 221 | ++ | N.D. |
| 222 | ++ | N.D. |
| 223 | ++ | N.D. |
| 224 | ++ | N.D. |
| 225 | ++ | N.D. |
| 226 | ++ | N.D. |
| 227 | + | N.D. |
| 228 | + | N.D. |
| 229 | + | N.D. |
| 230 | + | N.D. |
| 231 | + | N.D. |
| 232 | + | N.D. |
| 233 | + | N.D. |
| 234 | + | N.D. |
| 235 | + | N.D. |
| 236 | + | N.D. |
| 237 | + | N.D. |
| 238 | + | N.D. |
| 239 | + | N.D. |
| 240 | + | N.D. |
| 241 | + | N.D. |
| 242 | + | N.D. |
| 243 | + | N.D. |
| 244 | + | N.D. |
| 245 | + | N.D. |
| 246 | + | N.D. |
| 247 | + | N.D. |
| 248 | + | N.D. |
| 249 | + | N.D. |
| 250 | + | N.D. |
| 251 | + | N.D. |
| 252 | + | N.D. |
| 253 | + | N.D. |
| 254 | + | N.D. |
| 255 | + | N.D. |
| 256 | + | N.D. |
| 257 | + | N.D. |
| 258 | + | N.D. |
| 259 | + | N.D. |
| 260 | + | N.D. |
| 261 | + | N.D. |
| 262 | + | N.D. |
| 263 | + | N.D. |
| 264 | + | N.D. |
| 265 | + | N.D. |
| 266 | + | N.D. |
| 267 | + | N.D. |
| 268 | + | N.D. |
| 269 | + | N.D. |
| 270 | + | N.D. |
| 271 | + | N.D. |
| 272 | + | N.D. |
| 273 | + | N.D. |
| 274 | + | N.D. |
| 275 | + | N.D. |
| 276 | + | N.D. |
| 277 | + | N.D. |
| 278 | + | N.D. |
| 279 | + | N.D. |
| 280 | + | N.D. |
| 281 | + | N.D. |
| 282 | + | N.D. |
| 283 | + | N.D. |
| 284 | + | N.D. |
| 285 | + | N.D. |
| 286 | + | N.D. |
| 287 | + | N.D. |
| 288 | + | N.D. |
| 289 | + | N.D. |
| 290 | + | N.D. |
| 291 | + | N.D. |
| 292 | + | N.D. |
| 293 | + | N.D. |
| 294 | + | N.D. |
| 295 | + | N.D. |
| 296 | + | N.D. |
| 297 | + | N.D. |
| 298 | + | N.D. |
| 299 | + | N.D. |
| 300 | + | N.D. |
| 301 | + | N.D. |
| 302 | + | N.D. |
| 303 | + | N.D. |
| 304 | + | N.D. |
| 305 | + | N.D. |
| 306 | + | N.D. |
| 307 | + | N.D. |
| 308 | + | N.D. |
| 309 | + | N.D. |
| 310 | + | N.D. |
| 311 | + | N.D. |
| 312 | + | N.D. |
| 313 | + | N.D. |
| 314 | + | N.D. |
| 315 | + | N.D. |
| 316 | + | N.D. |
| 317 | + | N.D. |
| 318 | + | N.D. |
| 319 | + | N.D. |
| 320 | + | N.D. |
| 321 | + | N.D. |
| 322 | + | N.D. |
| 323 | + | N.D. |
| 324 | + | N.D. |
| 325 | + | N.D. |
| 326 | + | N.D. |
| 327 | + | N.D. |
| 328 | + | N.D. |
| 329 | + | N.D. |
| 330 | + | N.D. |
| 331 | + | N.D. |
| 332 | + | N.D. |
| 333 | + | N.D. |
| 334 | + | N.D. |
| 335 | + | N.D. |
| 336 | + | N.D. |
| 337 | ++ | N.D. |
| 338 | ++ | N.D. |
| 339 | +++ | N.D. |
| 340 | + | N.D. |
| 341 | ++ | N.D. |
| 342 | + | N.D. |
| 343 | ++ | N.D. |
| 344 | + | N.D. |
| 345 | + | N.D. |
| 346 | ++ | N.D. |
| 347 | + | N.D. |

TABLE 18-continued

Potency data for Compounds 1 to 456

| Compound No. | Thallium Assay (IC$_{50}$) | Trypanosoma Assay (IC$_{50}$) |
|---|---|---|
| 348 | + | N.D. |
| 349 | + | N.D. |
| 350 | + | N.D. |
| 351 | + | N.D. |
| 352 | + | N.D. |
| 353 | + | N.D. |
| 354 | + | N.D. |
| 355 | ++ | N.D. |
| 356 | ++ | N.D. |
| 357 | + | N.D. |
| 358 | + | N.D. |
| 359 | + | N.D. |
| 360 | + | N.D. |
| 361 | + | N.D. |
| 362 | ++ | N.D. |
| 363 | + | N.D. |
| 364 | + | N.D. |
| 365 | + | N.D. |
| 366 | + | N.D. |
| 367 | + | N.D. |
| 368 | ++ | N.D. |
| 369 | ++ | N.D. |
| 370 | + | N.D. |
| 371 | ++ | N.D. |
| 372 | +++ | N.D. |
| 373 | +++ | N.D. |
| 374 | +++ | +++ |
| 375 | +++ | +++ |
| 376 | ++ | N.D. |
| 377 | ++ | N.D. |
| 378 | ++ | N.D. |
| 379 | ++ | N.D. |
| 380 | ++ | N.D. |
| 381 | ++ | N.D. |
| 382 | ++ | N.D. |
| 383 | ++ | N.D. |
| 384 | ++ | N.D. |
| 385 | ++ | N.D. |
| 386 | ++ | N.D. |
| 387 | ++ | N.D. |
| 388 | ++ | N.D. |
| 389 | + | N.D. |
| 390 | + | N.D. |
| 391 | + | N.D. |
| 392 | + | N.D. |
| 393 | + | N.D. |
| 394 | + | N.D. |
| 395 | + | N.D. |
| 396 | + | N.D. |
| 397 | + | N.D. |
| 398 | + | N.D. |
| 399 | + | N.D. |
| 400 | + | N.D. |
| 401 | + | N.D. |
| 402 | + | N.D. |
| 403 | + | N.D. |
| 404 | + | N.D. |
| 405 | + | N.D. |
| 406 | + | N.D. |
| 407 | + | N.D. |
| 408 | + | N.D. |
| 409 | + | N.D. |
| 410 | + | N.D. |
| 411 | N.D. | N.D. |
| 412 | ++ | N.D. |
| 413 | ++ | N.D. |
| 414 | ++ | N.D. |
| 415 | ++ | N.D. |
| 416 | + | N.D. |
| 417 | + | N.D. |
| 418 | + | N.D. |
| 419 | + | N.D. |
| 420 | + | N.D. |
| 421 | + | N.D. |
| 422 | ++ | N.D. |
| 423 | + | N.D. |
| 424 | +++ | +++ |
| 425 | +++ | N.D. |
| 426 | ++ | +++ |
| 427 | ++ | +++ |
| 428 | ++ | N.D. |
| 429 | ++ | +++ |
| 430 | ++ | N.D. |
| 431 | + | N.D. |
| 432 | + | +++ |
| 433 | +++ | +++ |
| 434 | ++ | +++ |
| 435 | + | N.D. |
| 436 | +++ | N.D. |
| 437 | ++ | N.D. |
| 438 | +++ | N.D. |
| 439 | +++ | N.D. |
| 440 | ++ | N.D. |
| 441 | ++ | N.D. |
| 442 | ++ | N.D. |
| 443 | ++ | ++ |
| 444 | + | ++ |
| 445 | + | N.D. |
| 446 | ++ | N.D. |
| 447 | ++ | N.D. |
| 448 | ++ | N.D. |
| 449 | + | N.D. |
| 450 | ++ | N.D. |
| 451 | ++ | N.D. |
| 452 | + | N.D. |
| 453 | + | N.D. |
| 454 | + | N.D. |
| 455 | ++ | N.D. |
| 456 | + | N.D. |

OTHER EMBODIMENTS

This disclosure provides merely exemplary embodiments of the disclosed subject matter. One skilled in the art will readily recognize from the disclosure and embodiments, that various changes, modifications and variations can be made therein without departing from the spirit and scope of the disclosure as defined in the following claims.

What is claimed is:

1. A compound, deuterated derivative, or pharmaceutically acceptable salt selected from compounds of Formula I:

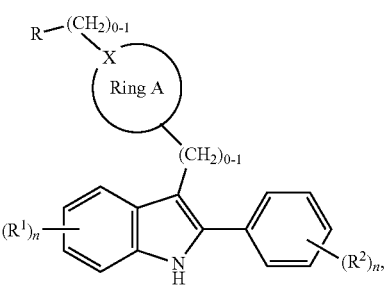

deuterated derivatives thereof, and pharmaceutically acceptable salts of any of the foregoing, wherein
(i) R is selected from —NR$^3$R$^4$, —C(O)R$^3$, —OR$^3$, —NRSC(O)R$^3$, —NRSC(O)OR$^3$, —NR$^5$SO$_2$R$^3$, and —NR$^5$SO$_2$NR$^3$R$^4$, wherein, when R is —C(O)R$^3$, X is N or R$^3$ is not bonded to the rest of the molecule through a nitrogen atom;
(ii) X is selected from N and CR$^X$;
(iii) R$^X$ is absent or is selected from hydrogen, hydroxy, halogen, and C$_1$-C$_3$ linear and branched alkyl groups, wherein, when R$^X$ is absent, X is a bridgehead atom;
(iv) Ring A is a 4- to 7-membered cyclic alkyl or heterocycle, wherein the 4- to 7-membered heterocycle has one heteroatom and wherein the heteroatom is a nitrogen atom;
(v) each n is independently selected from 1, 2, and 3;
(vi) each R$^1$ is independently selected from:
halogen,
amino, and
C$_1$-C$_6$ linear and branched haloalkyl groups;
(vii) each R$^2$ is independently selected from:
halogen,
hydroxy,
amino,
cyano,
C$_1$-C$_4$ linear, branched, and cyclic alkyl groups,
C$_1$-C$_4$ linear, branched, and cyclic hydroxyalkyl groups,
C$_1$-C$_4$ linear, branched, and cyclic alkoxy groups,
C$_1$-C$_4$ linear, branched, and cyclic haloalkyl groups, and
C$_1$-C$_4$ linear, branched, and cyclic haloalkoxy groups;
(viii) R$^3$ and R$^4$ are independently selected from:
hydrogen,
C$_1$-C$_6$ linear and branched alkylsulfonyl groups optionally substituted with amino,
C$_1$-C$_6$ linear and branched alkoxy optionally substituted with 1-4 groups independently selected from hydroxy, amino, halogen, and oxo,
C$_1$-C$_3$ linear and branched aminoalkyl groups optionally substituted with 1-2 groups independently selected from amido,
C$_3$-C$_6$ cycloalkyl optionally substituted with 1-2 groups independently selected from:
halogen,
hydroxy,
oxo,
amido,
amino substituted with 1-2 groups independently selected from C$_1$-C$_6$ linear, C$_3$-C$_6$ branched, and C$_3$-C$_6$ cyclic alkyl groups,
aryl optionally substituted with 1-2 groups independently selected from halogen,
C$_1$-C$_6$ linear and branched alkoxy groups,
carbamate optionally substituted with C$_1$-C$_6$ linear or branched alkyl,
C$_1$-C$_6$ linear, C$_3$-C$_6$ branched, and C$_3$-C$_6$ cyclic alkyl groups optionally substituted with 1-3 groups independently selected from hydroxy, oxo, halogen, C$_1$-C$_6$ linear and branched alkoxy groups, and carbamate optionally substituted with 1-3 groups independently selected from C$_1$-C$_6$ linear and branched alkyl groups, and
C$_1$-C$_3$ hydroxyalkyl,
3- to 6-membered heterocyclyl optionally substituted with 1-3 groups independently selected from:
halogen,
oxo,
hydroxy,
C$_1$-C$_6$ linear and branched alkoxy groups optionally substituted with oxo,
C$_1$-C$_6$ linear, C$_3$-C$_6$ branched, and C$_3$-C$_6$ cyclic alkyl groups optionally substituted with 1-2 groups independently selected from hydroxy, oxo, and C$_1$-C$_6$ linear and branched alkoxy groups,
C$_1$-C$_3$ hydroxyalkyl and C$_1$-C$_3$ haloalkyl groups, and
carbamate optionally substituted with 1-2 groups independently selected from C$_1$-C$_6$ linear, C$_3$-C$_6$ branched, and C$_3$-C$_6$ cyclic alkyl groups,
aryl optionally substituted with 1-4 groups independently selected from halogen, hydroxy, and C$_1$-C$_6$ linear and branched alkyl groups optionally substituted with 1-2 groups independently selected from hydroxy and C$_1$-C$_6$ linear and branched alkoxy groups,
3- to 10-membered heteroaryl optionally substituted with 1-2 groups independently selected from amino, hydroxy, oxo, and C$_1$-C$_6$ linear alkyl optionally substituted with 1-3 groups independently selected from halogen and amino,
C$_1$-C$_6$ linear and branched alkyl groups optionally substituted with 1-4 groups independently selected from:
C$_1$-C$_4$ alkyl groups,
amino optionally substituted with 1-2 groups independently selected from C$_1$-C$_6$ linear and branched alkylsulfonyl groups and C$_1$-C$_6$ linear, C$_3$-C$_6$ branched, and C$_3$-C$_6$ cyclic alkyl groups (optionally substituted with 1-2 groups independently selected from oxo, hydroxy, amido, and C$_1$-C$_6$ linear and branched alkylsulfonyl groups),
hydroxy,
oxo,
cyano,
carboxylic acid,
carbamate optionally substituted with 1-2 groups independently selected from C$_1$-C$_6$ linear, C$_3$-C$_6$ branched, and C$_3$-C$_6$ cyclic alkyl groups,
halogen,
amido optionally substituted with 1-2 groups independently selected from C$_1$-C$_6$ linear, C$_3$-C$_6$ branched, and C$_3$-C$_6$ cyclic alkyl groups and C$_1$-C$_6$ linear, C$_3$-C$_6$ branched, and C$_3$-C$_6$ cyclic hydroxyalkyl groups,
C$_3$-C$_6$ cyclic alkyl optionally substituted with 1-2 groups independently selected from amino, halogen, hydroxy, oxo, C$_1$-C$_3$ alkyl, C$_1$-C$_6$ linear and branched alkoxy groups, and carbamate (which may be further substituted with C$_1$-C$_4$ linear or branched alkyl),
C$_1$-C$_6$ linear and branched alkoxy groups optionally substituted with hydroxy,
C$_1$-C$_6$ linear and branched alkylsulfonyl groups,
aryl optionally substituted with 1-2 groups independently selected from halogen, hydroxy, and C$_1$-C$_6$ linear and branched alkyl groups optionally substituted with 1-2 groups independently selected from hydroxy and C$_1$-C$_6$ linear and branched alkoxy groups,
4- to 10-membered heterocyclyl optionally substituted with 1-2 groups independently selected from halogen groups, oxo, hydroxy, amido optionally substituted with C$_1$-C$_3$ alkyl, and C$_1$-C$_6$ linear and branched alkyl groups optionally substituted with 1-2 groups independently selected from hydroxy and C$_1$-C$_6$ linear and branched alkoxy groups, and
4- to 10-membered heteroaryl optionally substituted with 1-3 groups independently selected from halogen groups, oxo, hydroxy, $C_1$-$C_6$ linear, $C_3$-$C_6$ branched, or $C_3$-$C_6$ cyclic alkyl optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, $C_3$-$C_6$ branched, or $C_3$-$C_6$ cyclic alkyl, or $R^3$ and $R^4$, together with the nitrogen atom to which they are attached, form a 3- to 10-membered heterocyclyl or heteroaryl optionally substituted with 1-3 groups independently selected from:

amino optionally substituted with 1-2 groups independently selected from $C_1$-$C_6$ linear, $C_3$-$C_6$ branched, and $C_3$-$C_6$ cyclic alkyl groups, which are optionally substituted with oxo, halogen, hydroxy, oxo, $C_1$-$C_6$ linear, $C_3$-$C_6$ branched, and $C_3$-$C_6$ cyclic alkyl groups optionally substituted with 1-2 groups independently selected from hydroxy, amino, and $C_1$-$C_6$ linear and branched alkoxy groups, $C_1$-$C_3$ linear or branched hydroxyalkyl, and amide optionally substituted with 1-2 groups independently selected from $C_1$-$C_6$ linear, $C_3$-$C_6$ branched, and $C_3$-$C_6$ cyclic alkyl groups; and (ix) $R^5$ is selected from hydrogen, hydroxy, halogen, and $C_1$-$C_3$ linear and branched alkyl groups.

2. The compound, deuterated derivative, or pharmaceutically acceptable salt according to claim 1, wherein $R^3$ and $R^4$ are independently selected from:

hydrogen, $C_1$-$C_6$ linear and branched alkylsulfonyl groups optionally substituted with amino, $C_1$-$C_6$ linear and branched alkoxy groups optionally substituted with 1-4 groups independently selected from hydroxy, amino, halogen, and oxo, $C_1$-$C_3$ linear and $C_3$ branched aminoalkyl groups optionally substituted with 1-2 amido groups, $C_3$-$C_6$ cyclic alkyl optionally substituted with 1-2 groups independently selected from:

halogen, hydroxy, oxo, amido, amino substituted with 1-2 groups independently selected from $C_1$-$C_6$ linear, $C_3$-$C_6$ branched, and $C_3$-$C_6$ cyclic alkyl groups, aryl optionally substituted with 1-2 groups independently selected from halogen, $C_1$-$C_6$ linear and branched alkoxy groups, carbamate optionally substituted with $C_1$-$C_6$ linear or branched alkyl, and $C_1$-$C_6$ linear, $C_3$-$C_6$ branched, and $C_3$-$C_6$ cyclic alkyl groups optionally substituted with 1-3 groups independently selected from hydroxy, oxo, halogen, $C_1$-$C_6$ linear and branched alkoxy groups, and carbamate optionally substituted with 1-3 groups independently selected from $C_1$-$C_6$ linear and branched alkyl groups, 3- to 6-membered heterocyclyl optionally substituted with 2-3 groups independently selected from:

halogen, oxo, hydroxy, $C_1$-$C_6$ linear and branched alkoxy groups optionally substituted with oxo, $C_1$-$C_6$ linear, $C_3$-$C_6$ branched, and $C_3$-$C_6$ cyclic alkyl groups optionally substituted with 1-2 groups independently selected from hydroxy, oxo, and $C_1$-$C_6$ linear and branched alkoxy groups, and carbamate optionally substituted with 1-2 groups independently selected from $C_1$-$C_6$ linear, $C_3$-$C_6$ branched, and $C_3$-$C_6$ cyclic alkyl groups, aryl optionally substituted with 1-4 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups, 3- to 6-membered heteroaryl optionally substituted with 1-2 groups independently selected from amino, hydroxy, oxo, and $C_1$-$C_6$ linear alkyl optionally substituted with 1-3 groups independently selected from halogen and amino, $C_1$-$C_6$ linear and branched alkyl groups optionally substituted with 1-4 groups independently selected from:

amino optionally substituted with 1-2 groups independently selected from $C_1$-$C_6$ linear and branched alkylsulfonyl groups and $C_1$-$C_6$ linear, $C_3$-$C_6$ branched, and $C_3$-$C_6$ cyclic alkyl groups (optionally substituted with 1-2 groups independently selected from oxo, hydroxy, amido, and $C_1$-$C_6$ linear and branched alkylsulfonyl groups), hydroxy, oxo, cyano, carboxylic acid, carbamate optionally substituted with 1-2 groups independently selected from $C_1$-$C_6$ linear, $C_3$-$C_6$ branched, and $C_3$-$C_6$ cyclic alkyl groups, halogen, amido optionally substituted with 1-2 groups independently selected from $C_1$-$C_6$ linear, $C_3$-$C_6$ branched, and $C_3$-$C_6$ cyclic alkyl groups and $C_1$-$C_6$ linear, $C_3$-$C_6$ branched, and $C_3$-$C_6$ cyclic hydroxyalkyl groups, $C_3$-$C_6$ cyclic alkyl optionally substituted with 1-2 groups independently selected from halogen, $C_1$-$C_6$ linear and branched alkoxy groups, hydroxy, amino, oxo, $C_1$-$C_3$ alkyl, and carbamate (which may be further substituted with $C_1$-$C_4$ linear or branched alkyl), $C_1$-$C_6$ linear and branched alkoxy groups optionally substituted with hydroxy, $C_1$-$C_6$ linear and branched alkylsulfonyl groups, aryl optionally substituted with 1-2 groups independently selected from halogen, hydroxy, and $C_1$-$C_6$ linear and branched alkyl groups optionally substituted with 1-2 groups independently selected from hydroxy and $C_1$-$C_6$ linear and branched alkoxy groups, 4- to 10-membered heterocyclyl optionally substituted with 1-2 groups independently selected from halogen groups, oxo, hydroxy, and $C_1$-$C_6$ linear and branched alkyl groups optionally substituted with 1-2 groups independently selected from hydroxy and $C_1$-$C_6$ linear and branched alkoxy groups, and 4- to 10-membered heteroaryl optionally substituted with 1-3 groups independently selected from halogen groups, oxo, hydroxy, $C_1$-$C_6$ linear, $C_3$-$C_6$ branched, and $C_3$-$C_6$ cyclic alkyl groups optionally substituted with 1-3 groups independently selected from halogen, hydroxy, and $C_1$-$C_6$ linear and branched alkoxy groups, and amido groups optionally substituted with 1-2 groups independently selected from $C_1$-$C_6$ linear, $C_3$-$C_6$ branched, and $C_3$-$C_6$ cyclic alkyl groups, or $R^3$ and $R^4$, together with the nitrogen atom to which they are attached, form a 4- to 10-membered heterocyclyl or heteroaryl optionally substituted with 1-3 groups independently selected from:

amino optionally substituted with 1-2 groups independently selected from $C_1$-$C_6$ linear, $C_3$-$C_6$ branched, and $C_3$-$C_6$ cyclic alkyl groups, which are optionally substituted with oxo, halogen, hydroxy, oxo, $C_1$-$C_6$ linear, $C_3$-$C_6$ branched, and $C_3$-$C_6$ cyclic alkyl groups optionally substituted with 1-2 groups independently selected from hydroxy, amino, and $C_1$-$C_6$ linear and branched alkoxy groups, and amide optionally substituted with 1-2 groups independently selected from $C_1$-$C_6$ linear, $C_3$-$C_6$ branched, and $C_3$-$C_6$ cyclic alkyl groups.

3. The compound, deuterated derivative, or pharmaceutically acceptable salt according to claim 1, wherein $R^5$ is selected from hydrogen and $C_1$-$C_3$ linear and branched alkyl groups.

4. The compound, deuterated derivative, or pharmaceutically acceptable salt according to claim 1, wherein Ring A is selected from:

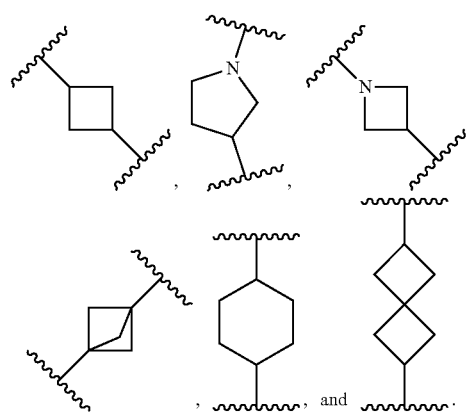

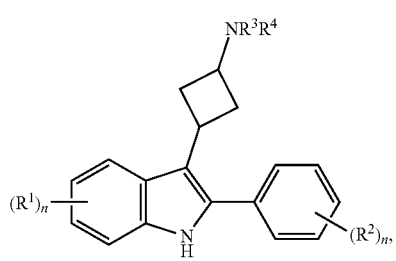

5. The compound, deuterated derivative, or pharmaceutically acceptable salt according to claim 1, wherein X is $CR^X$.

6. The compound, deuterated derivative, or pharmaceutically acceptable salt according to according to claim 5, wherein $R^X$ is selected from hydrogen, hydroxy, fluorine, and methyl.

7. The compound, deuterated derivative, or pharmaceutically acceptable salt according to claim 1, wherein the compound, deuterated derivative, or pharmaceutically acceptable salt is selected from compounds of Formula I-A, Formula I-B, or Formula I-C:

(I-A)

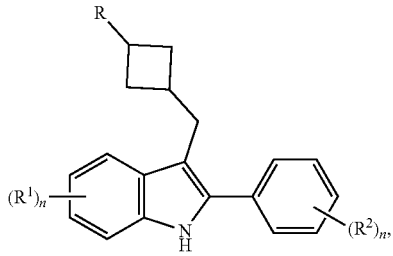

(I-B)

(I-C)

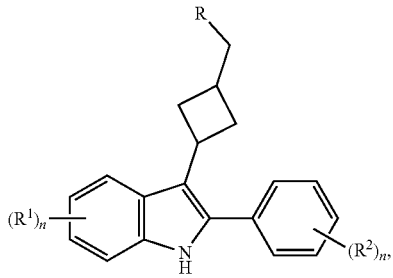

deuterated derivatives thereof, and pharmaceutically acceptable salts of any of the foregoing, wherein R, $R^1$, $R^2$, $R^3$, $R^4$, and n are as defined for Formula I in claim 1.

8. The compound, deuterated derivative, or pharmaceutically acceptable salt according to claim 1, wherein each n is 1 or 2.

9. The compound, deuterated derivative, or pharmaceutically acceptable salt according to claim 1, wherein the compound, deuterated derivative, or pharmaceutically acceptable salt is selected from compounds of Formula I-D, Formula I-E, or Formula I-F:

(I-D)

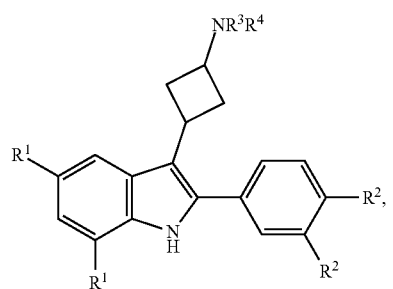

(I-E)

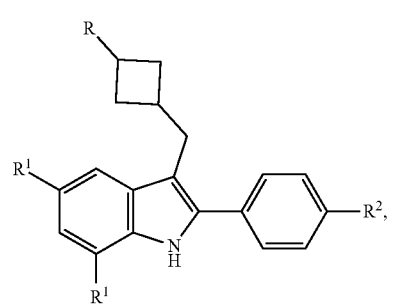

-continued

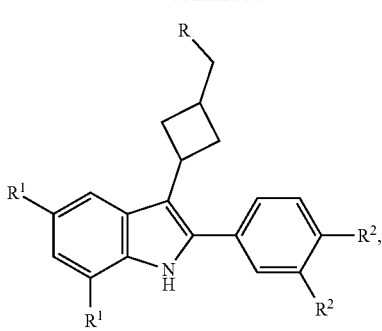

(I-F)

deuterated derivatives thereof, and pharmaceutically acceptable salts of any of the foregoing, wherein each R, $R^1$, $R^2$, $R^3$, and $R^4$ are as defined for Formula I in claim 1.

10. The compound, deuterated derivative, or pharmaceutically acceptable salt according to claim 1, wherein each $R^1$ is independently selected from fluorine and trifluoromethyl.

11. The compound, deuterated derivative, or pharmaceutically acceptable salt according to claim 1, wherein each $R^2$ is fluorine.

12. The compound, deuterated derivative, or pharmaceutically acceptable salt according to claim 1, wherein R is $-NH_2$.

13. The compound, deuterated derivative, or pharmaceutically acceptable salt according to claim 1, wherein R is $-NR^3R^4$.

14. The compound, deuterated derivative, or pharmaceutically acceptable salt according to claim 13, wherein $R^3$ and $R^4$ are independently selected from
 hydrogen,
 $C_3$-$C_6$ cyclic alkyl (optionally substituted with hydroxy or amino),
 $C_1$-$C_6$ linear and branched alkyl (optionally substituted with 1-3 groups independently selected from amino, halogen, hydroxy, methylamide, isopropyl, $C_3$-$C_6$ cyclic alkyl, and carbamate (which may be further substituted with $C_1$-$C_4$ linear or branched alkyl)),
 $C_1$-$C_6$ linear and branched alkoxy,
 3- to 6-membered heterocyclyl (optionally substituted with 1-2 groups independently selected from oxo, methyl, $C_1$-$C_3$ hydroxyalkyl, and trifluoromethyl), and
 3- to 6-membered heteroaryl (optionally substituted with $C_1$-$C_3$ alkyl),
or $R^3$ and $R^4$, together with the nitrogen atom to which they are attached, form a 3- to 6-membered heterocyclyl (optionally substituted with oxo or methylamide).

15. The compound, deuterated derivative, or pharmaceutically acceptable salt according to claim 1, wherein R is $-NRSC(O)R^3$.

16. The compound, deuterated derivative, or pharmaceutically acceptable salt according to claim 15, wherein $R^3$ is selected from:
 $C_1$-$C_6$ linear and branched alkoxy groups,
 $C_1$-$C_6$ linear and branched alkylsulfonyl groups optionally substituted with amino,
 $C_1$-$C_6$ linear and branched alkyl groups optionally substituted with 1-4 groups independently selected from:
  hydroxy,
  oxo,
  cyano,
  amido (which may be further substituted with 1-2 groups independently selected from $C_1$-$C_3$ alkyl and $C_1$-$C_3$ hydroxyalkyl),
  amino (which may be further substituted with 1-2 groups independently selected from $C_1$-$C_3$alkylsulfonyl and $C_1$-$C_3$ alkyl (which may be further substituted with hydroxy)),
  carbamate (which may be further substituted with $C_1$-$C_4$ linear or branched alkyl),
  $C_3$-$C_6$ cycloalkyl (which may be further substituted with 1-2 groups independently selected from amino, halogen, hydroxy, oxo, $C_1$-$C_3$ alkyl, $C_1$-$C_3$ alkoxy, and carbamate (which may be further substituted with $C_1$-$C_4$ linear or branched alkyl)),
  3- to 6-membered heterocyclyl (which may be further substituted with 1-2 groups independently selected from halogen, oxo, and $C_1$-$C_3$ alkyl), and
  3- to 6-membered heteroaryl groups (which may be further substituted with 1-2 groups independently selected from oxo and $C_1$-$C_3$ alkyl),
 $C_3$-$C_6$ cycloalkyl optionally substituted with 1-2 groups independently selected from halogen, hydroxy, amino (which may be further substituted with $C_1$-$C_3$ alkyl), $C_1$-$C_3$ alkoxy, $C_1$-$C_3$ alkyl (which may be further substituted with hydroxy) and carbamate (which may be further substituted with $C_1$-$C_4$ linear or branched alkyl),
 $C_1$-$C_6$ linear and branched alkylsulfonyl optionally substituted with amino,
 3- to 6-membered heterocyclyl optionally substituted with 1-2 groups independently selected from halogen, hydroxy, oxo, $C_1$-$C_3$ alkyl (which may be further substituted with oxo), $C_1$-$C_3$ alkoxy (which may be further substituted with oxo), and carbamate (which may be further substituted with $C_1$-$C_4$ linear or branched alkyl), and
 3- to 6-membered heteroaryl (which may be further optionally substituted by oxo or amino); and
 $R^5$ is selected from hydrogen, hydroxy, halogen, and $C_1$-$C_3$ linear and branched alkyl groups.

17. The compound, deuterated derivative, or pharmaceutically acceptable salt according to claim 15, wherein $R^5$ is hydrogen.

18. The compound, deuterated derivative, or pharmaceutically acceptable salt according to claim 1, wherein R is $-NRSC(O)OR^3$.

19. The compound, deuterated derivative, or pharmaceutically acceptable salt according to claim 18, wherein
 $R^3$ is selected from $C_1$-$C_6$ linear and branched alkyl groups (optionally substituted with 1-3 groups independently selected from hydroxy and aryl); and
 $R^5$ is selected from hydrogen, hydroxy, halogen, and $C_1$-$C_3$ linear and branched alkyl groups.

20. The compound, deuterated derivative, or pharmaceutically acceptable salt according to claim 18, wherein $R^5$ is hydrogen.

21. The compound, deuterated derivative, or pharmaceutically acceptable salt according to claim 1, wherein R is $-NR^5SO_2R^3$.

22. The compound, deuterated derivative, or pharmaceutically acceptable salt according to claim 21, wherein:
 $R^3$ is selected from $C_1$-$C_6$ linear and branched alkyl (optionally substituted with 1-3 groups independently selected from halogen, hydroxy, amino, and cyano), 3- to 10-membered heteroaryl (optionally substituted with 1-2 groups independently selected from oxo and $C_1$-$C_3$ alkyl), $C_3$-$C_6$ cycloalkyl, and 3- to 6-membered heterocyclyl; and $R^5$ is selected from hydrogen, hydroxy, halogen, and $C_1$-$C_3$ linear and branched alkyl groups.

23. The compound, deuterated derivative, or pharmaceutically acceptable salt according to claim 21, wherein $R^5$ is selected from hydrogen and propyl.

24. The compound, deuterated derivative, or pharmaceutically acceptable salt according to claim 1, wherein R is —$NR^5SO_2NR^3R^4$.

25. The compound, deuterated derivative, or pharmaceutically acceptable salt according to claim 24, wherein
$R^3$ and $R^4$ are independently selected from:
hydrogen,
$C_1$-$C_6$ linear and branched alkoxy groups,
$C_1$-$C_6$ linear and branched alkyl groups optionally substituted with 1-4 groups independently selected from:
$C_1$-$C_3$ alkyl groups,
amino,
amido,
halogen,
hydroxy,
3- to 6-membered heterocyclyl (which may be further substituted with 1-2 groups independently selected from oxo, hydroxy, amido (which may be further substituted with $C_1$-$C_3$ alkyl), and $C_1$-$C_3$ alkyl),
$C_3$-$C_6$ heteroaryl (which may be further substituted with $C_1$-$C_3$ alkyl), and
oxo,
$C_3$-$C_6$ cycloalkyl (optionally substituted with 1-2 groups independently selected from amido, hydroxy, and $C_1$-$C_3$ hydroxyalkyl),
3- to 6-membered heterocyclyl (optionally substituted with 1-2 groups independently selected from oxo, hydroxy, and $C_1$-$C_3$ alkyl), and
3- to 6-membered heteroaryl;
or $R^3$ and $R^4$, together with the nitrogen atom to which they are attached, form a 4- to 6-membered heterocyclyl optionally substituted with 1-2 groups independently selected from $C_1$-$C_3$ linear and branched alkyl groups and $C_1$-$C_3$ linear and branched hydroxyalkyl groups; and
$R^5$ is selected from hydrogen, hydroxy, halogen, and $C_1$-$C_3$ linear or branched alkyl.

26. The compound, deuterated derivative, or pharmaceutically acceptable salt according to claim 24, wherein $R^5$ is hydrogen or propyl.

27. The compound, deuterated derivative, or pharmaceutically acceptable salt according to claim 1, wherein R is —$OR^3$.

28. The compound, deuterated derivative, or pharmaceutically acceptable salt according to claim 27, wherein:
$R^3$ is selected from hydrogen and $C_1$-$C_6$ linear and branched alkyl groups (optionally substituted with hydroxy or oxo).

29. The compound, deuterated derivative, or pharmaceutically acceptable salt according to claim 1, wherein R is —$C(O)R^3$.

30. The compound, deuterated derivative, or pharmaceutically acceptable salt according to claim 29, wherein:
$R^3$ is selected from hydrogen, $C_1$-$C_6$ linear and branched alkyl groups (optionally substituted with 1-2 groups independently selected from amino (which may be further substituted with $C_1$-$C_3$ alkyl), halogen, and hydroxy), $C_3$-$C_6$ cycloalkyl (which may be further substituted with hydroxy or $C_1$-$C_3$ hydroxyalkyl), 3- to 6-membered heteroaryl, and 3- to 6-membered heterocyclyl.

31. A compound, deuterated derivative, or pharmaceutically acceptable salt selected from:

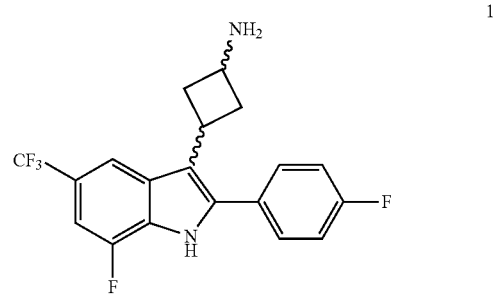

1

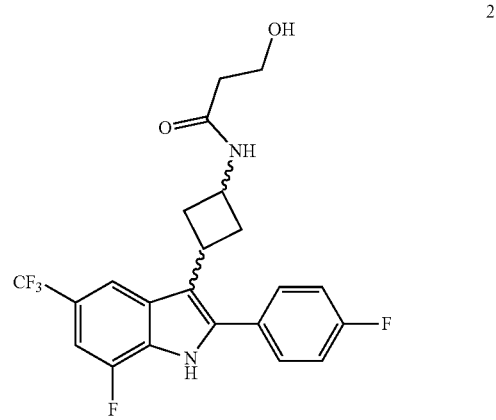

2

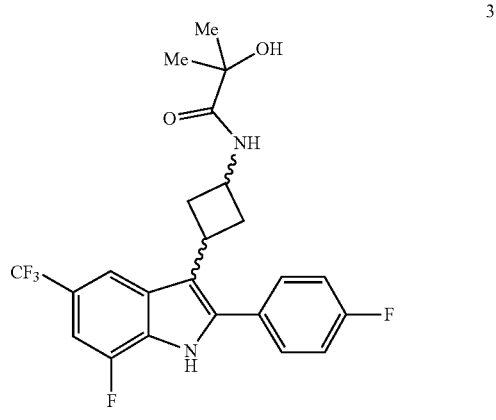

3

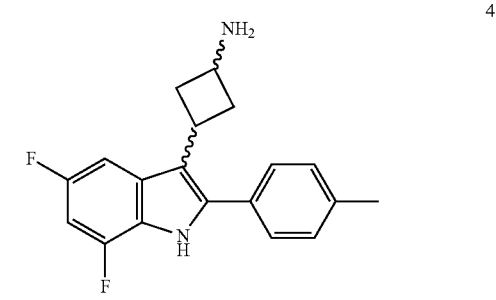

4

| | |
|---|---|
| 5 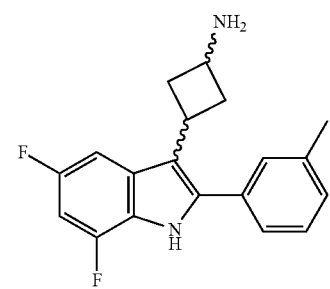 | 10 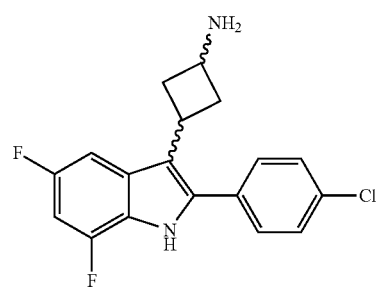 |
| 6 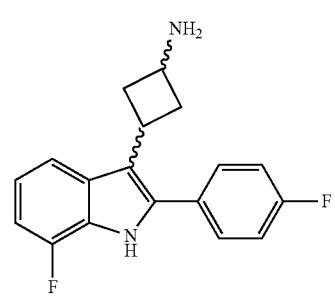 | 11 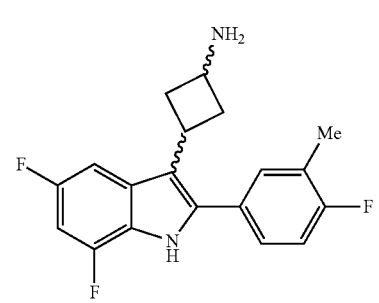 |
| 7 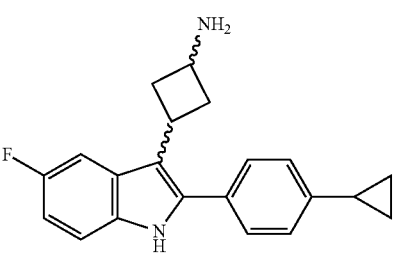 | 12 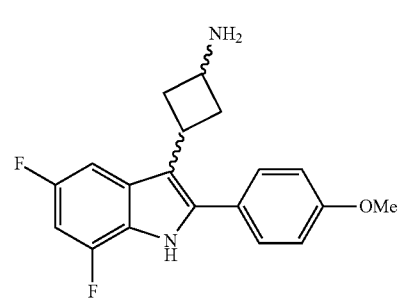 |
| 8 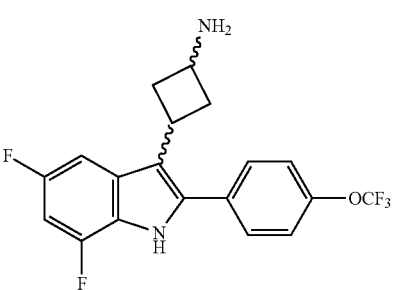 | 13 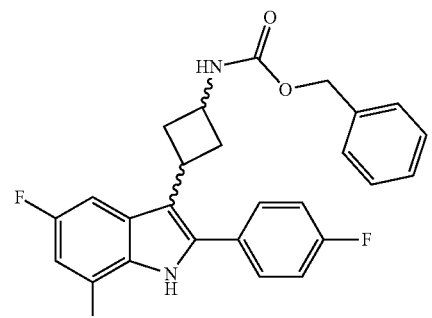 |
| 9 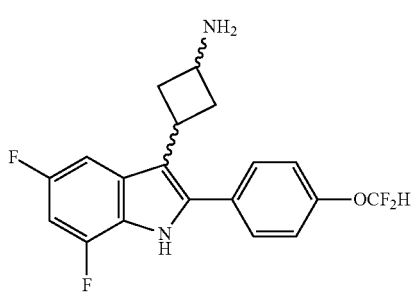 | 14 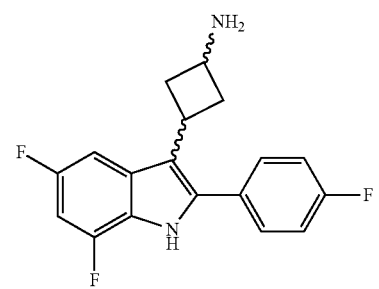 |

| 15 | 19 |
|---|---|
| 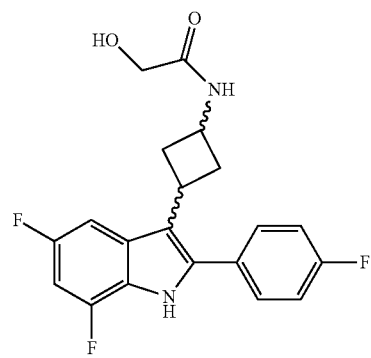 | 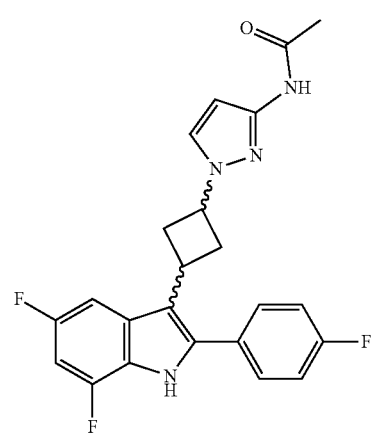 |
| 16 | 20 |
| 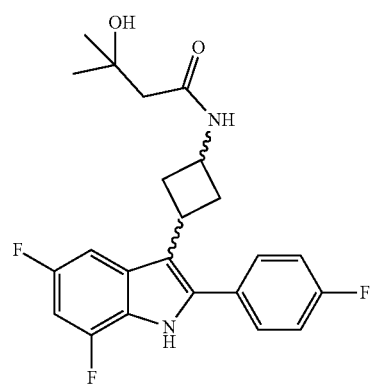 | 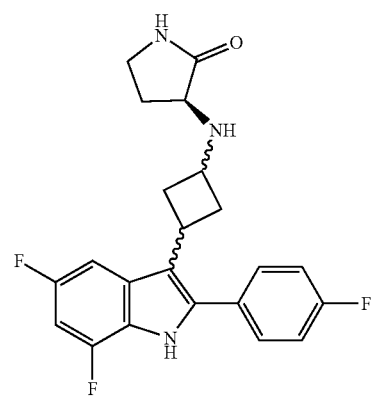 |
| 17 | 21 |
| 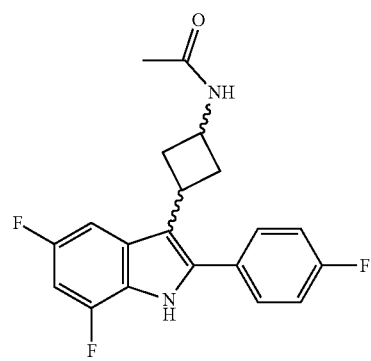 | 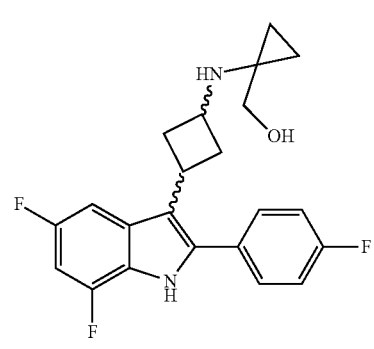 |
| 18 | 22 |
| 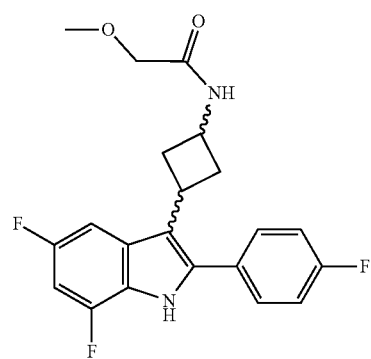 | 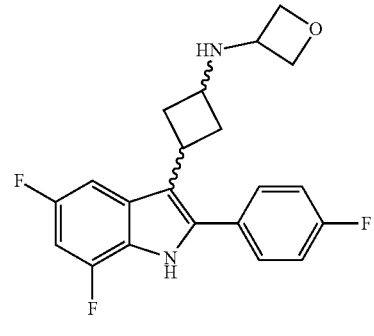 |

23
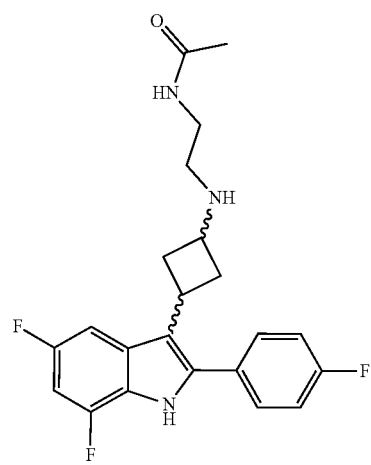
24
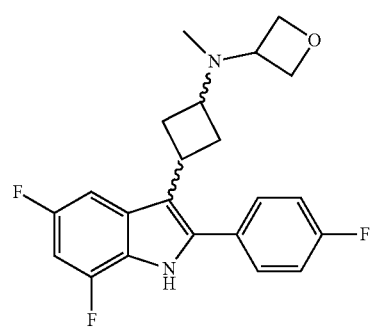
25
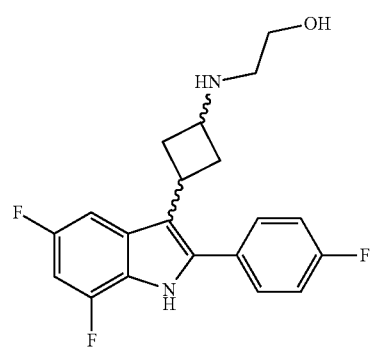
26
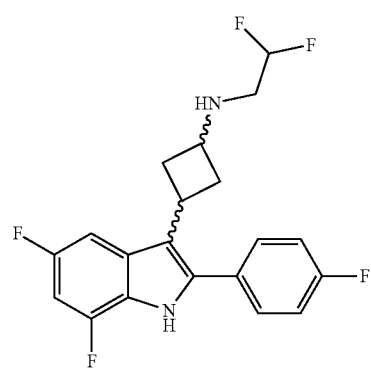
27
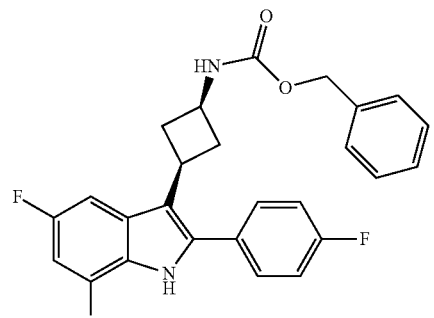
28
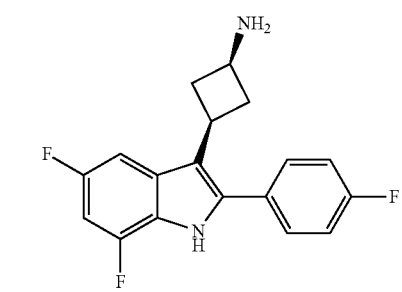
29
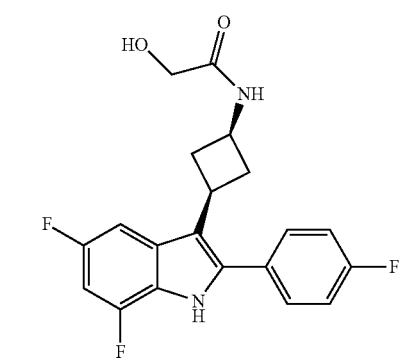
30
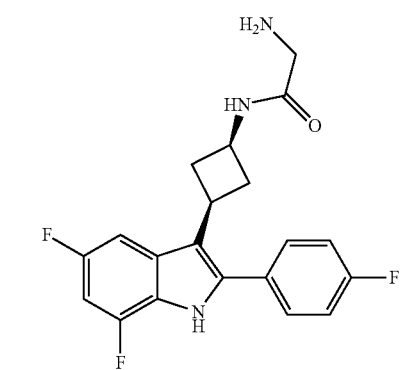

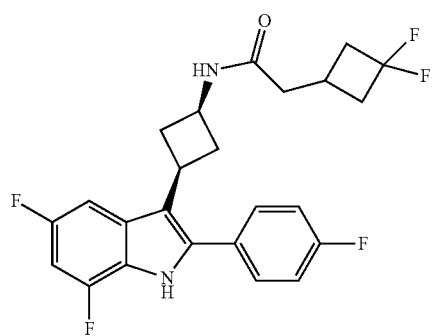
31
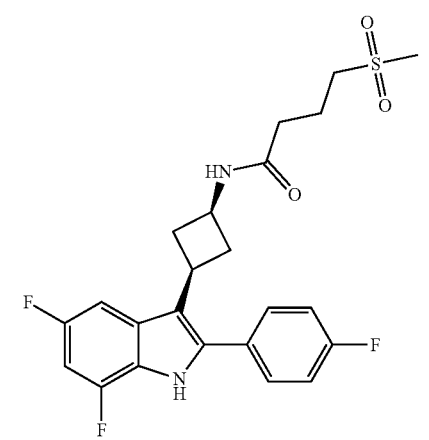
32
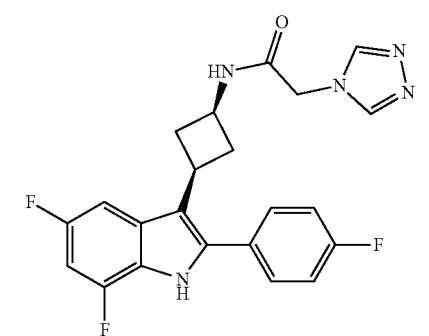
33
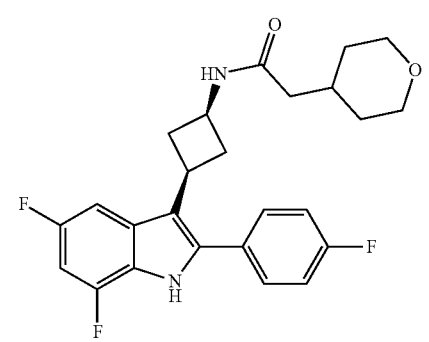
34
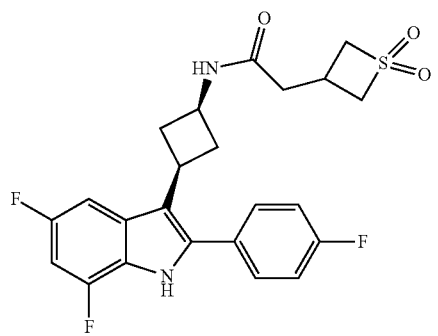
35
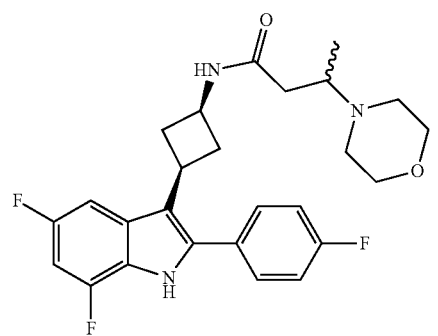
36
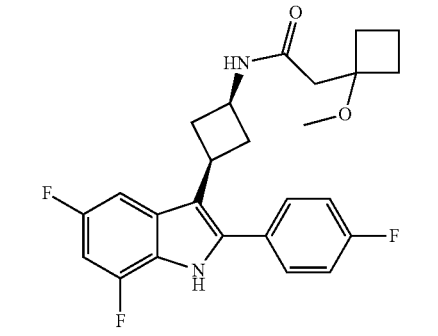
37
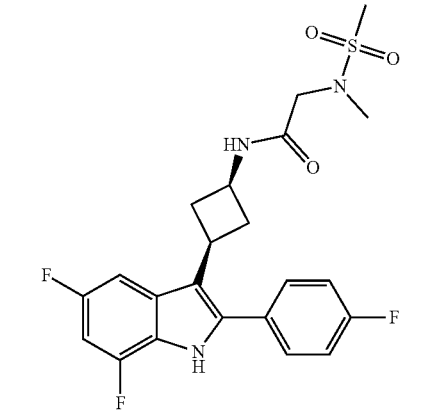
38

| 39 | 43 |
|---|---|
| 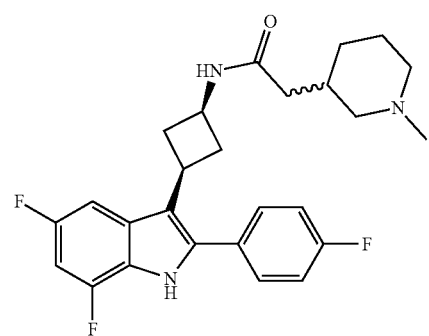 | 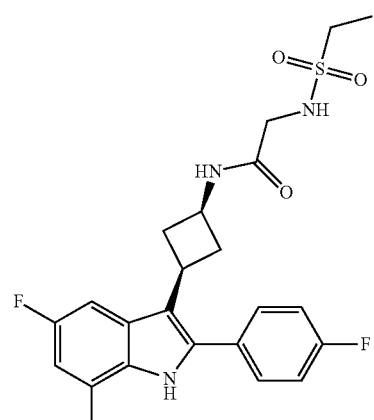 |
| 40 | 44 |
| 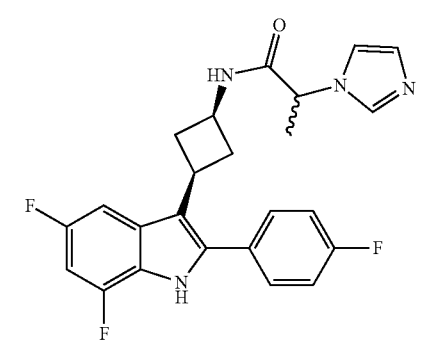 | 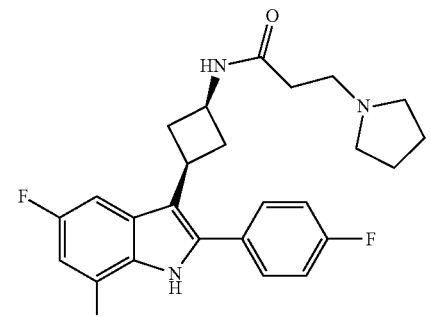 |
| 41 | 45 |
| 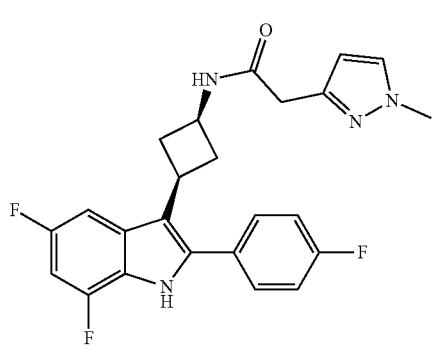 | 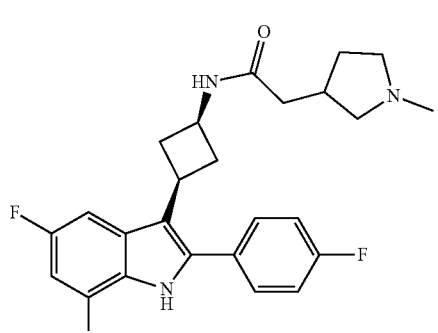 |
| 42 | 46 |
| 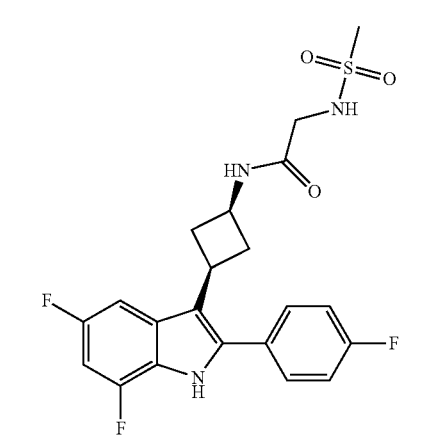 | 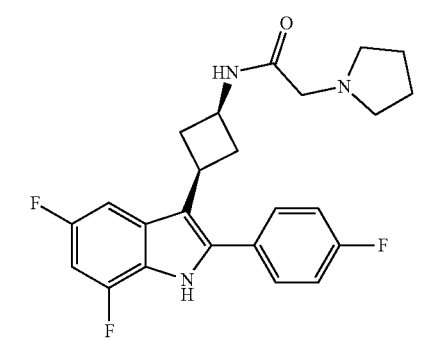 |

47
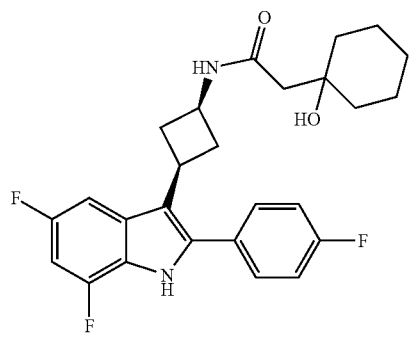
48
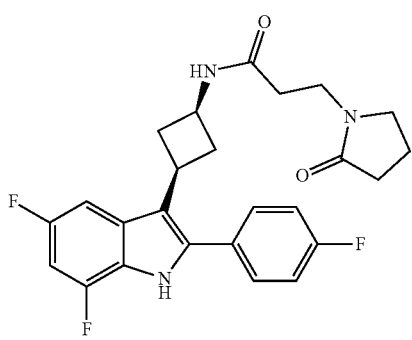
49
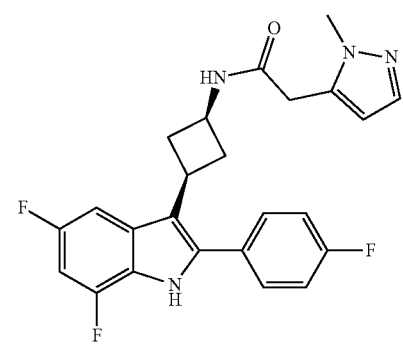
50
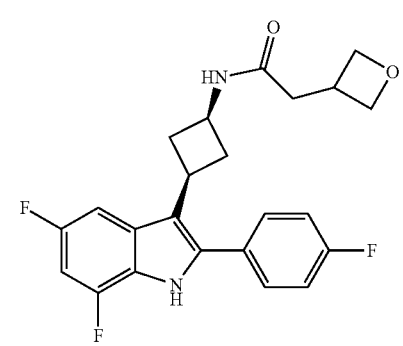
51
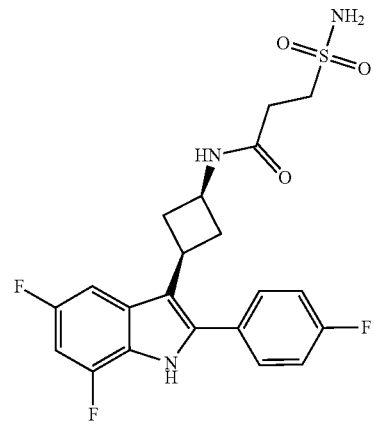
52
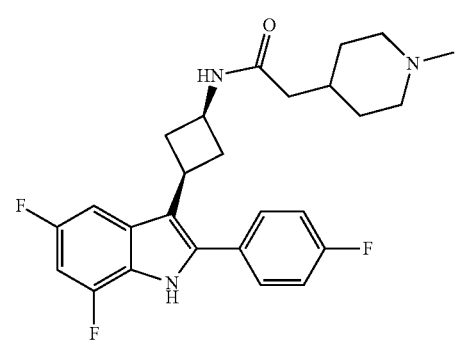
53
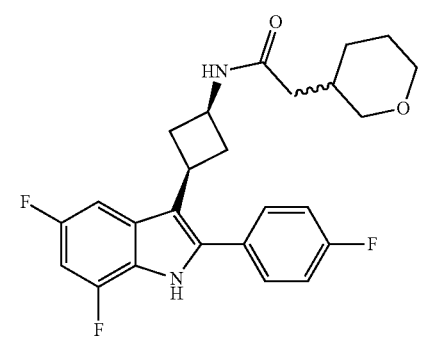
54
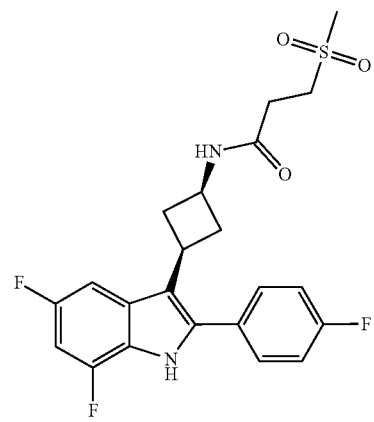

563
-continued
55
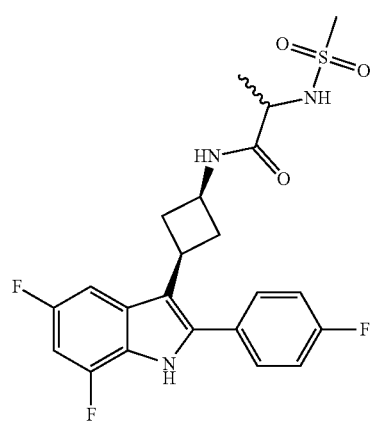
56
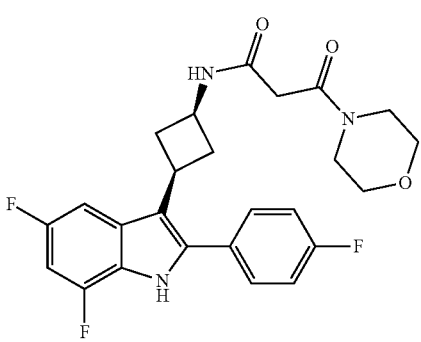
57
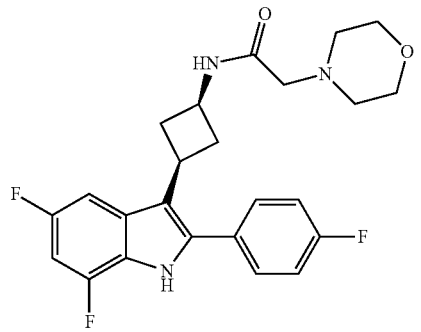
564
-continued
58
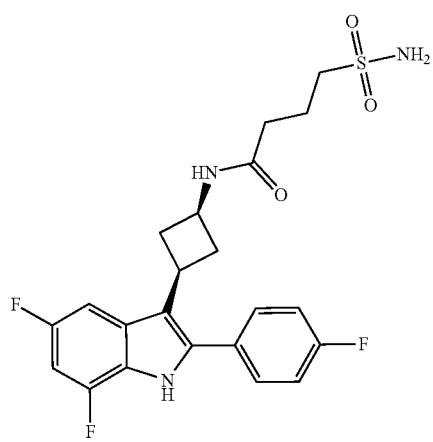
59
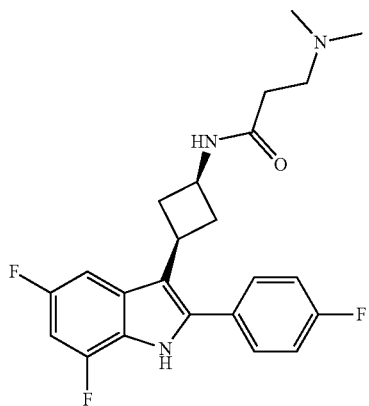
60
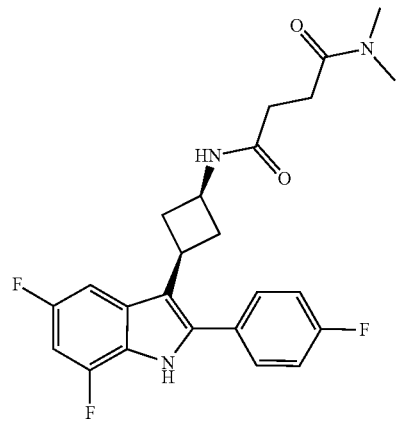

61
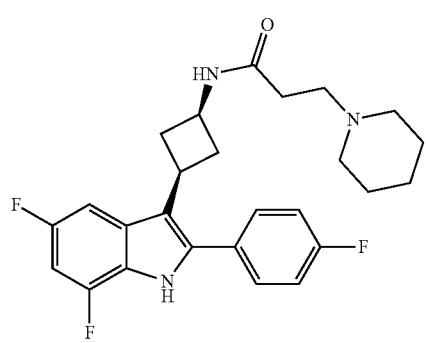
62
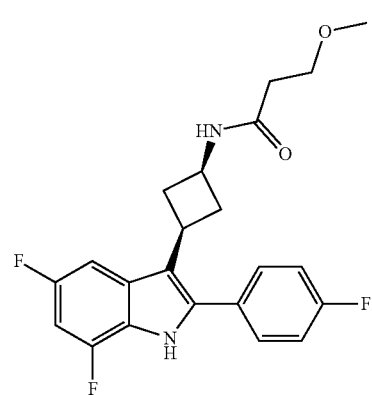
63
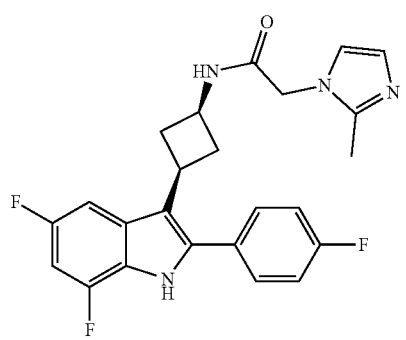
64
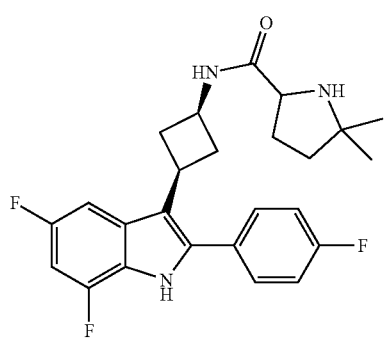
65
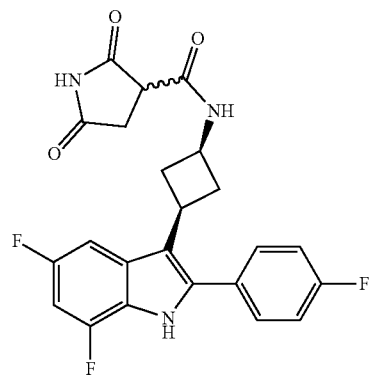
66
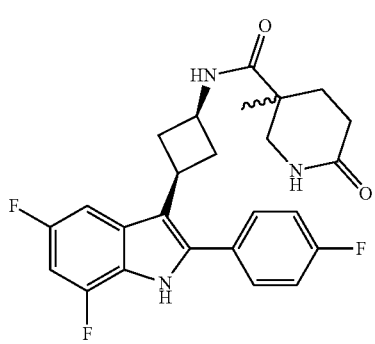
67
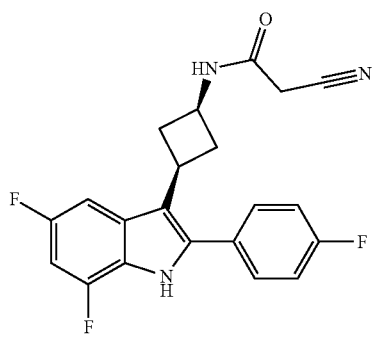
68
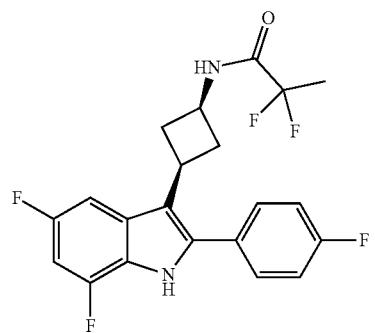

567
-continued
69
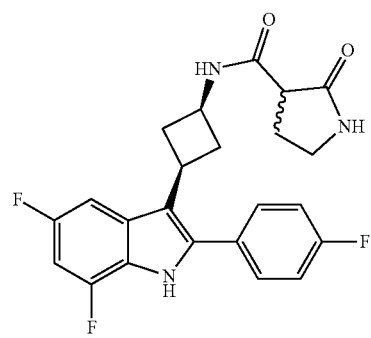
70
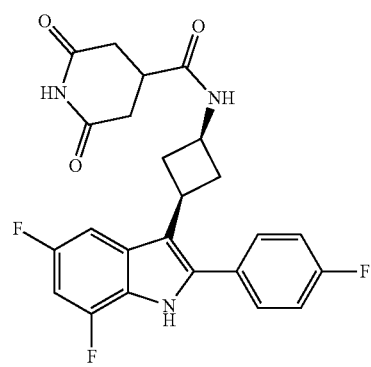
71
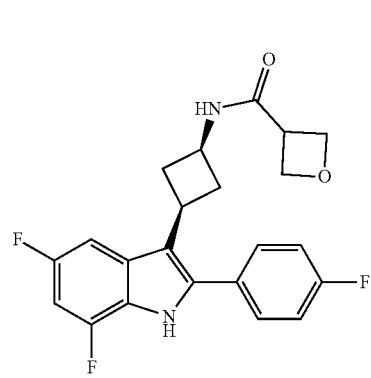
72
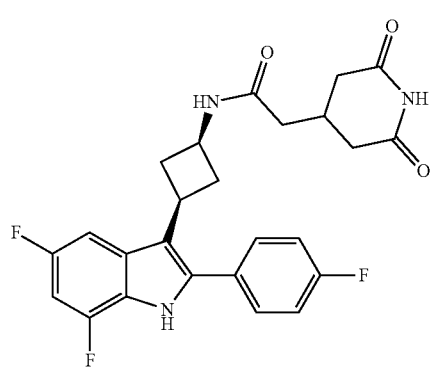
568
-continued
73
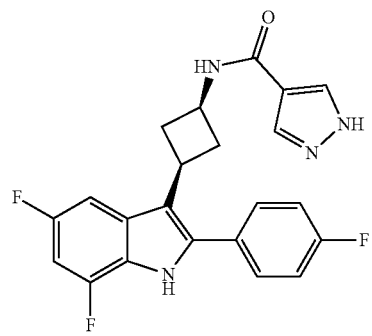
74
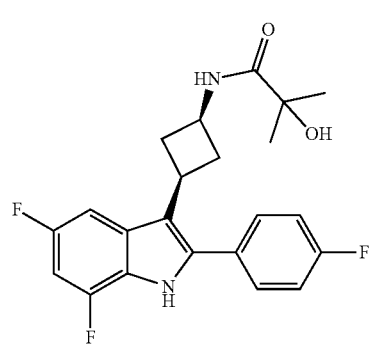
75
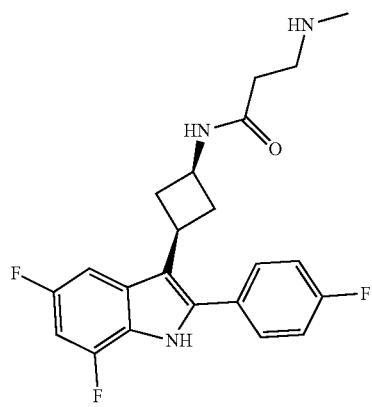
76
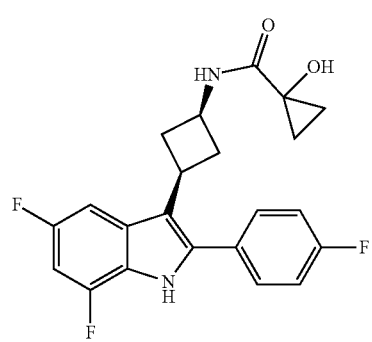

77
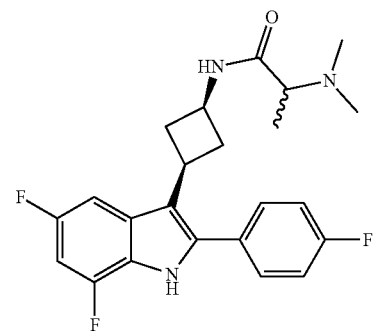
78
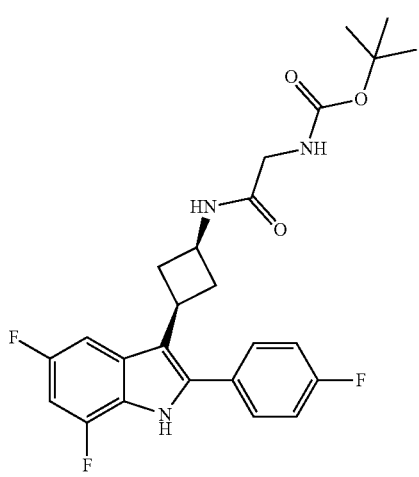
79
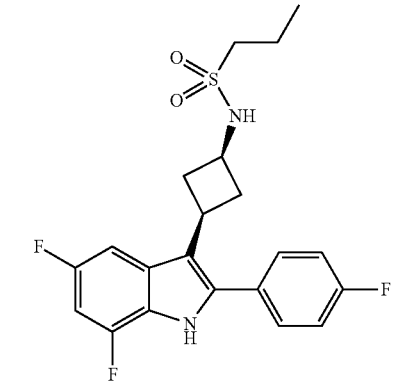
80
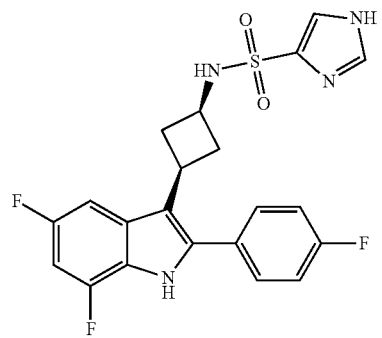
81
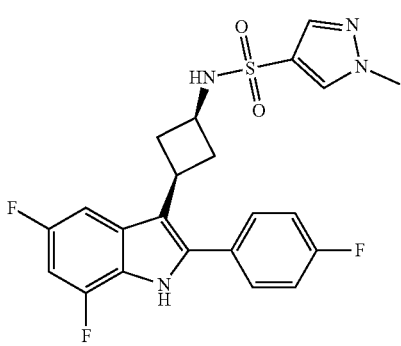
82
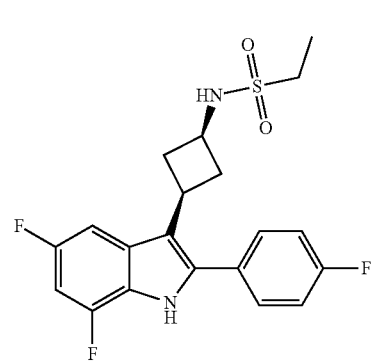
83
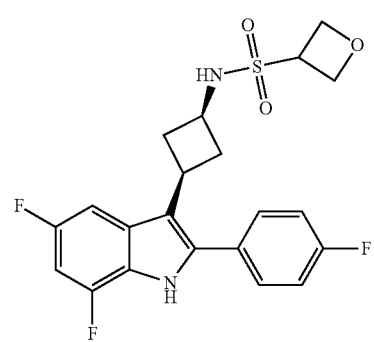
84
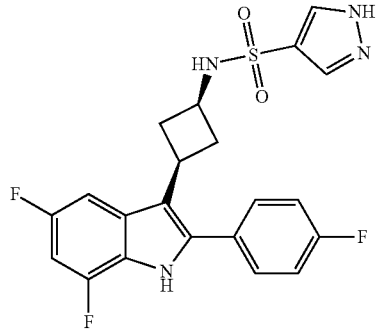

| 85 | 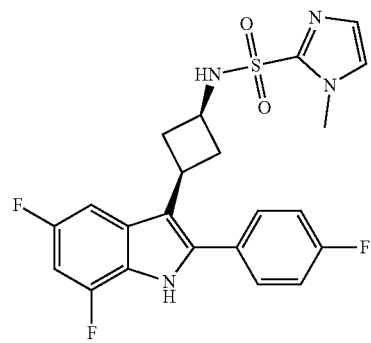 | 89 | 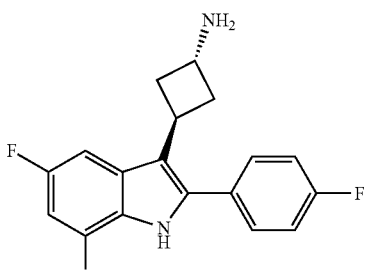 |
| 86 | 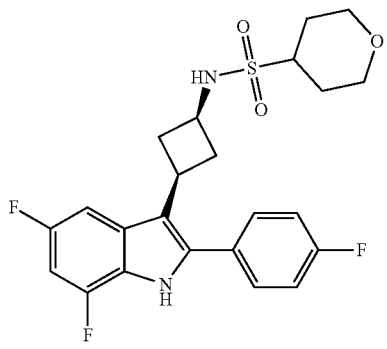 | 90 | 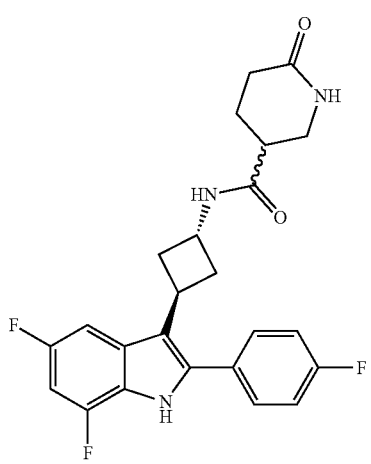 |
| 87 | 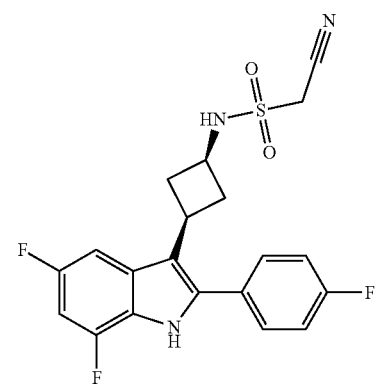 | 91 | 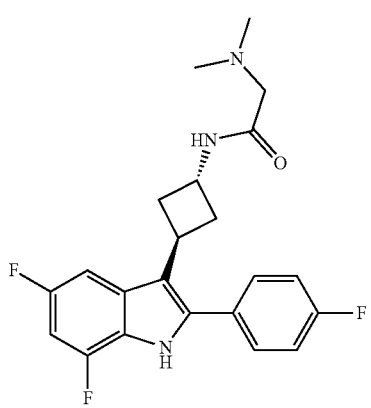 |
| 88 | 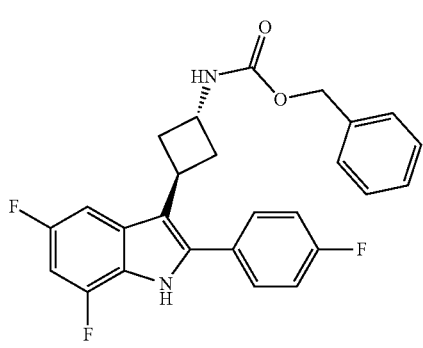 | 92 | 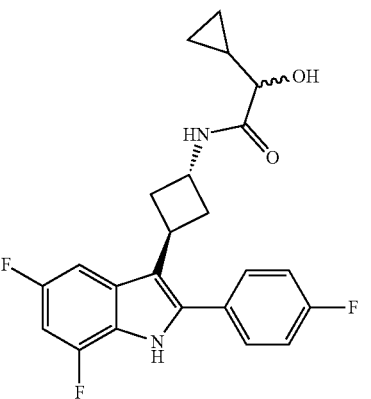 |

93
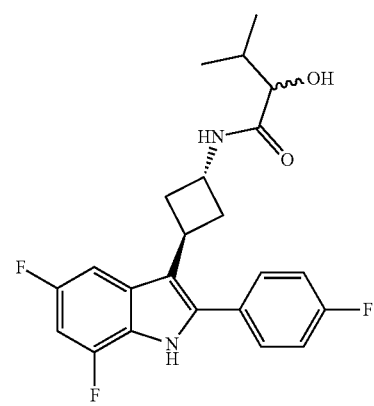
94
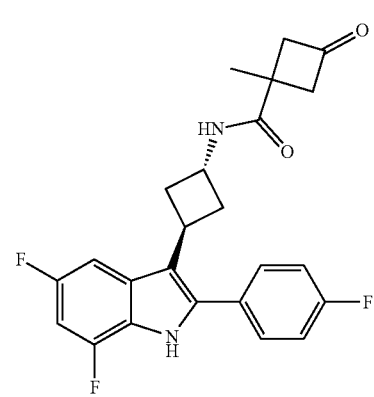
95
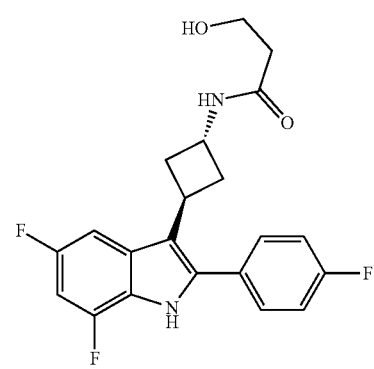
96
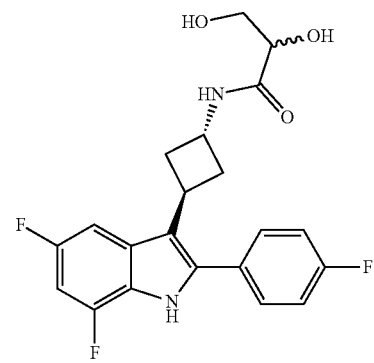
97
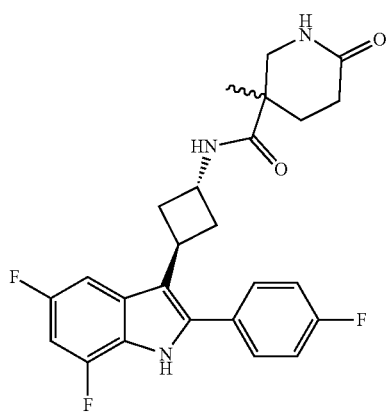
98
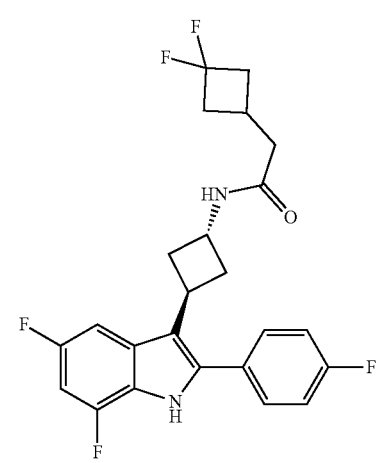
99
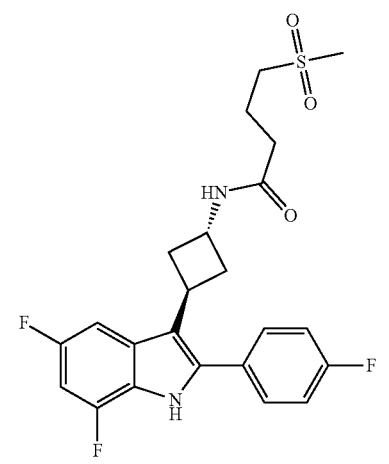

100
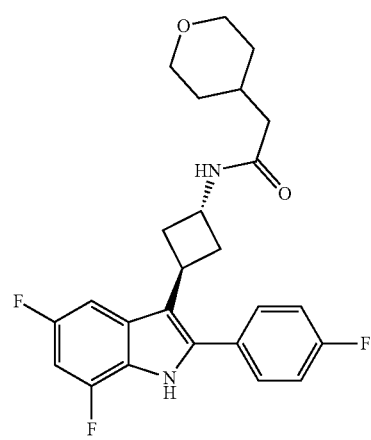
101
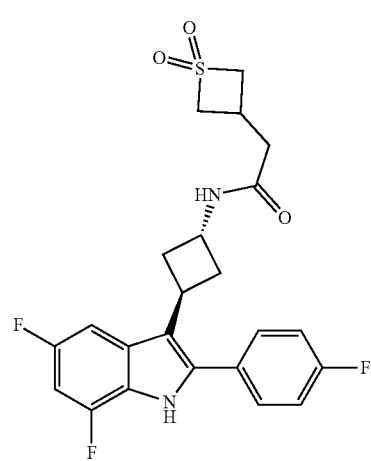
102
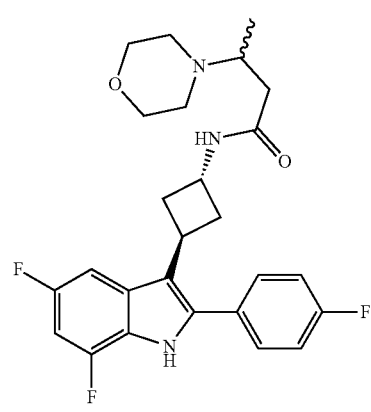
103
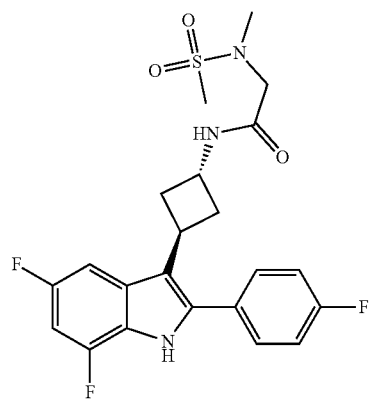
104
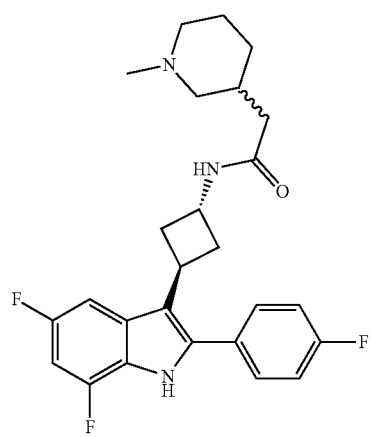
105
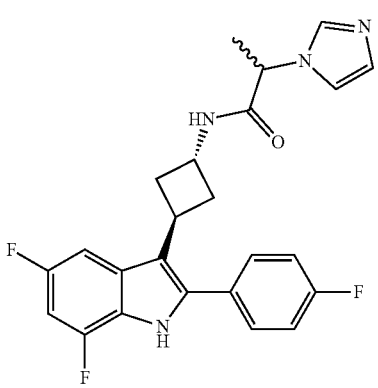
106
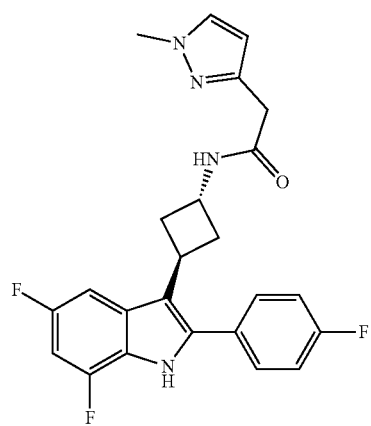

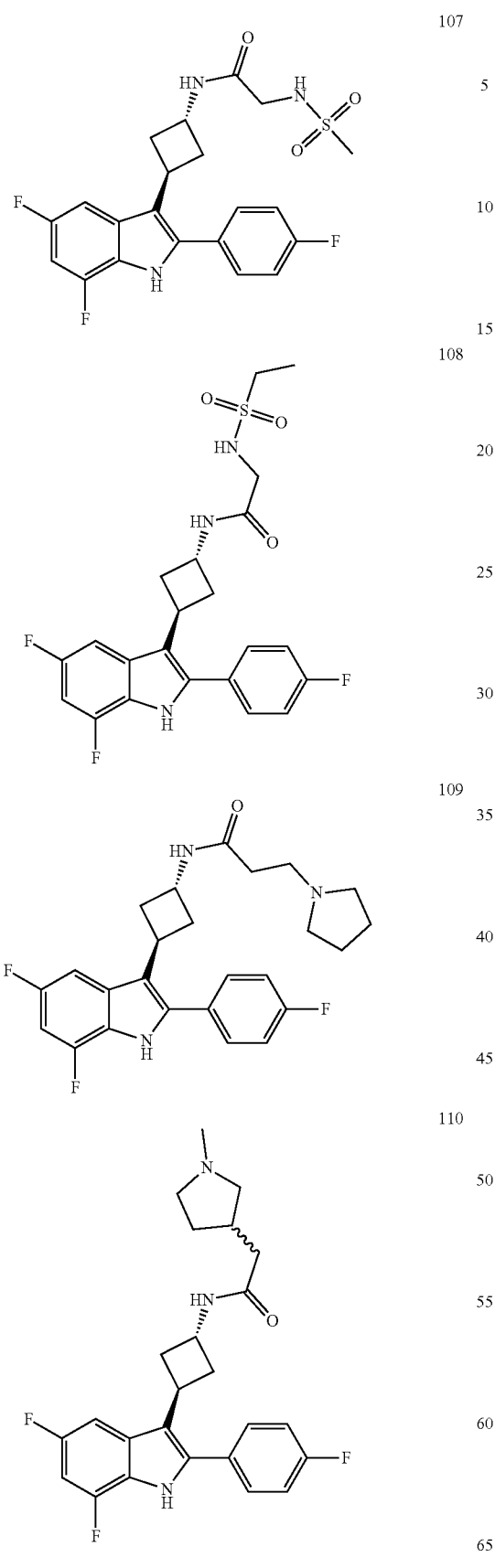
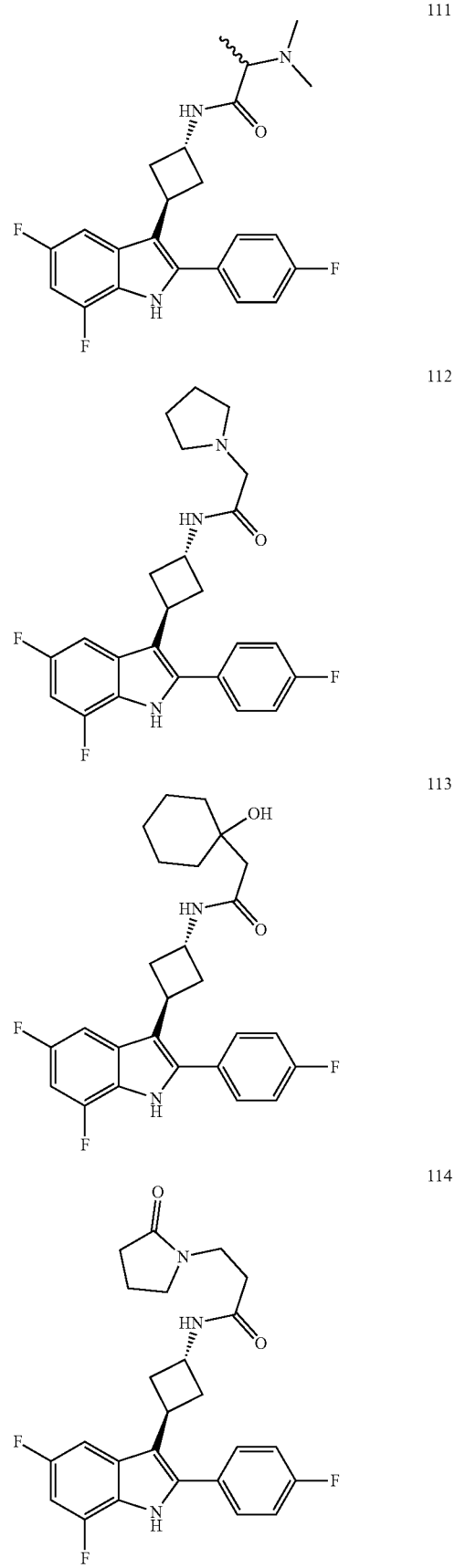

579
-continued
115
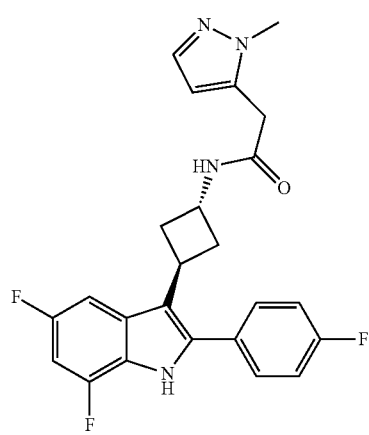
116
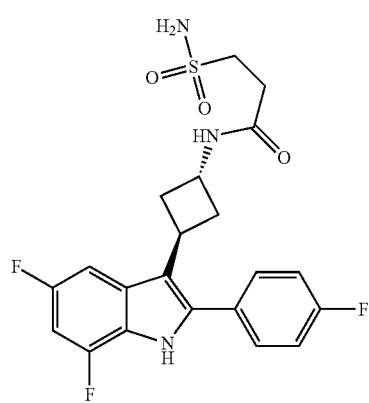
117
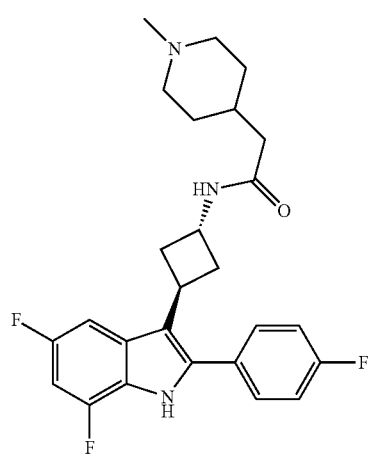
580
-continued
118
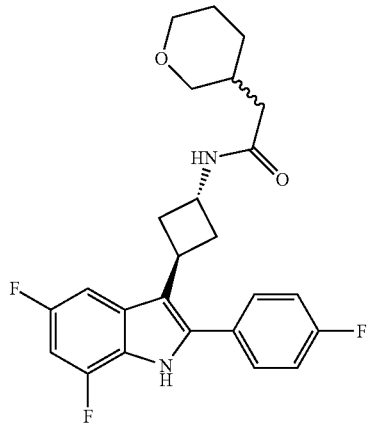
119
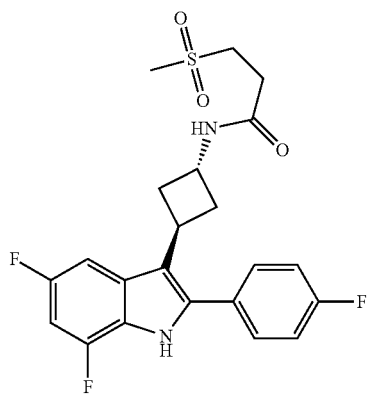
120
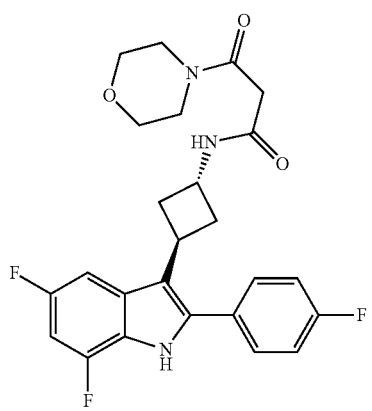
121
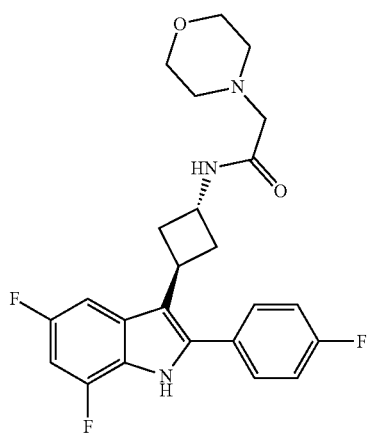

122
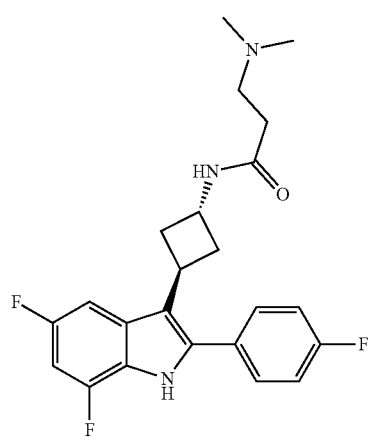
123
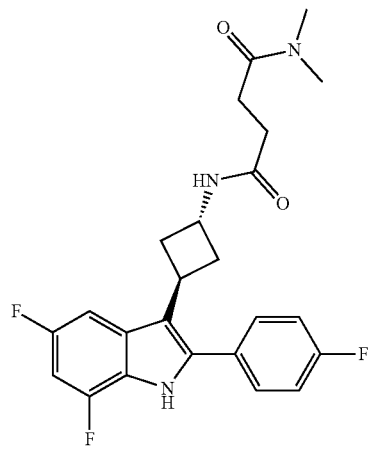
124
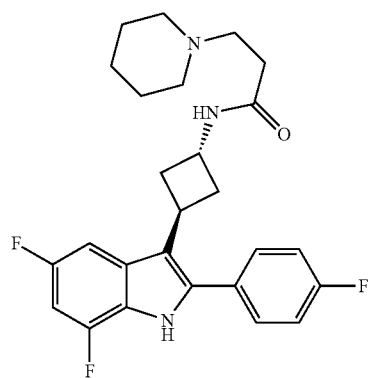
125
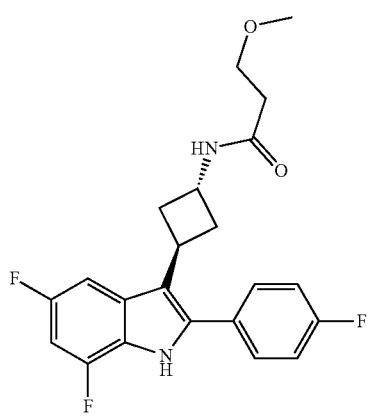
126
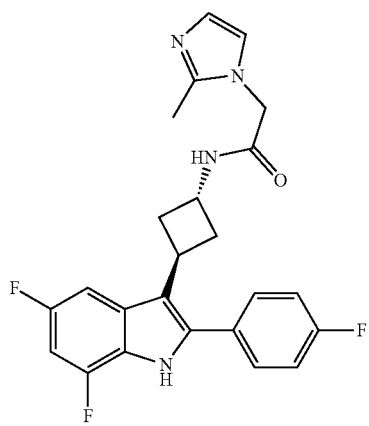
127
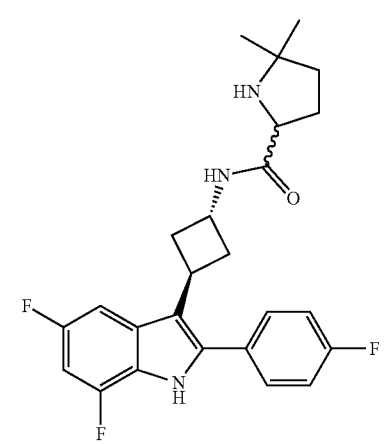

-continued
128
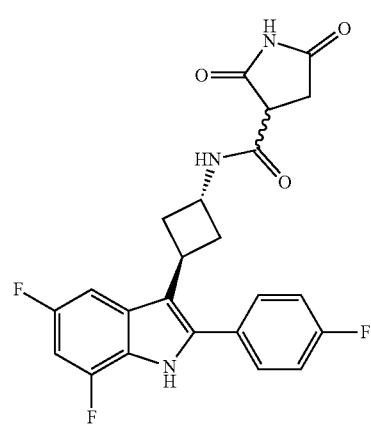
129
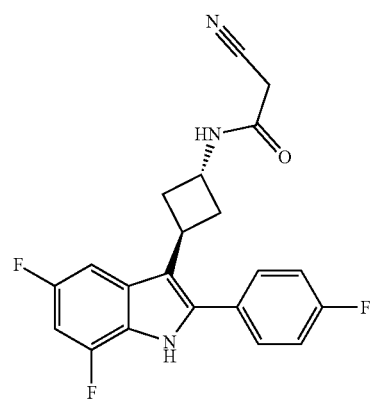
130
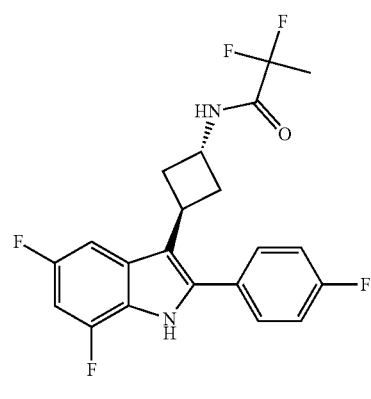
131
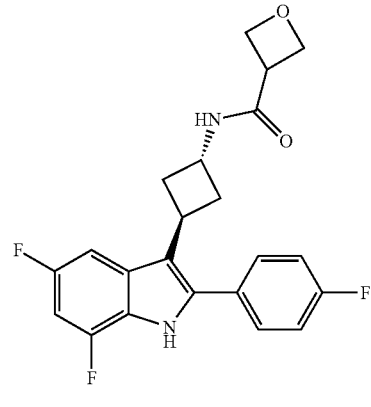
-continued
132
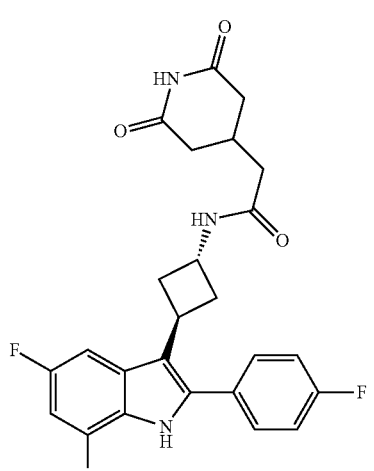
133
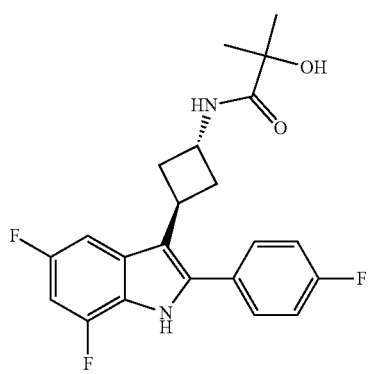
134
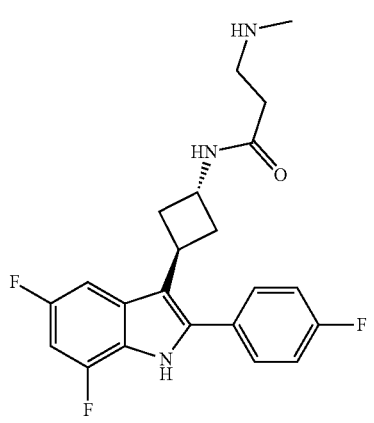
135
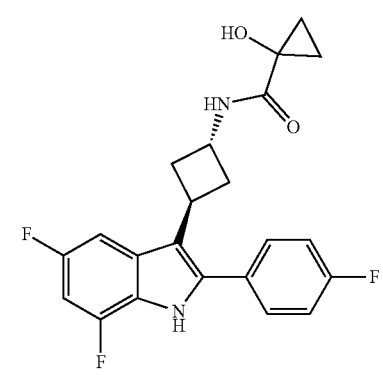

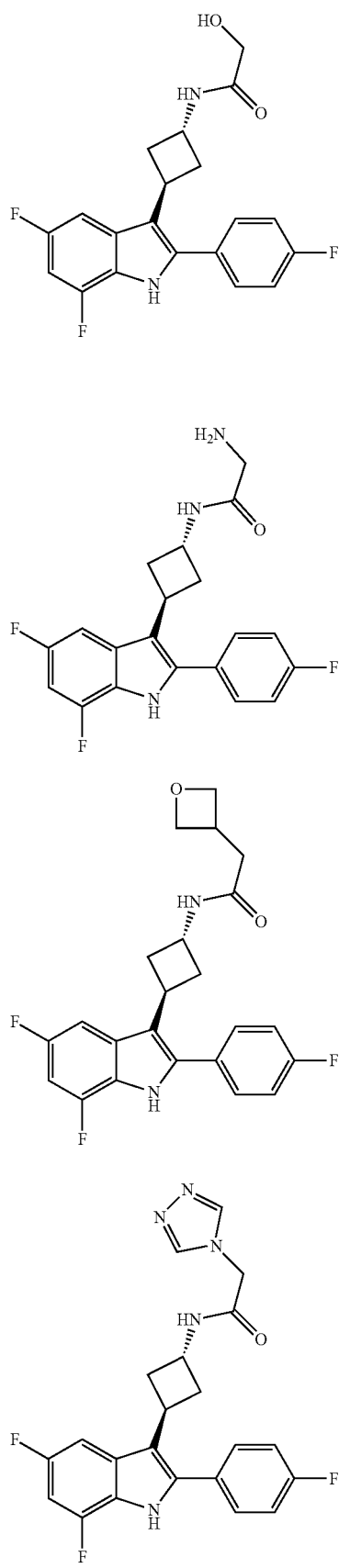
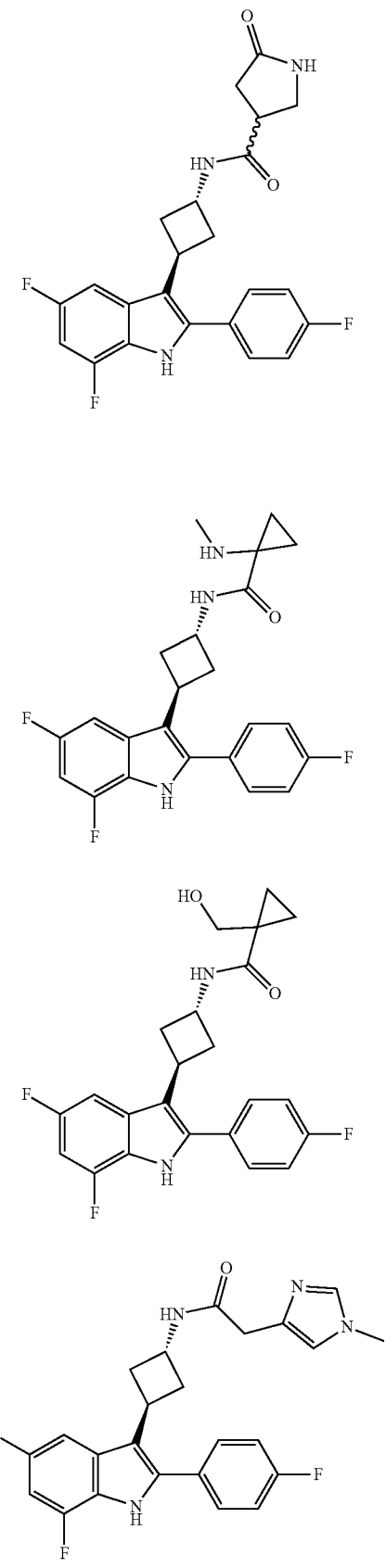

144 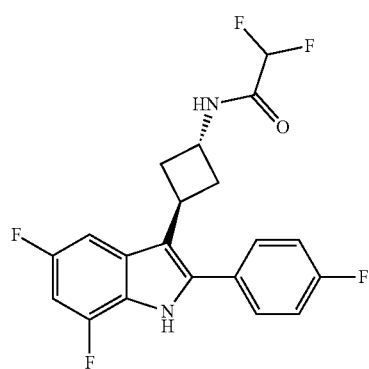
145 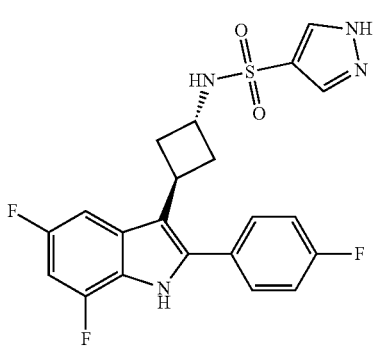
146 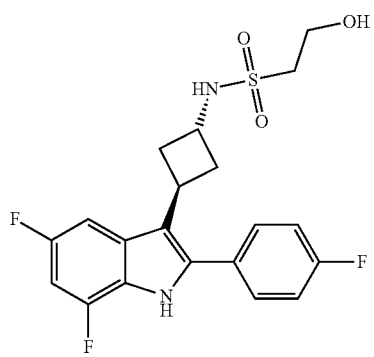
147 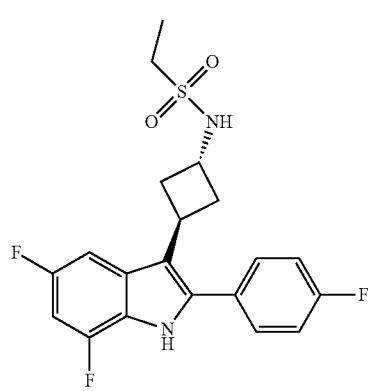
148 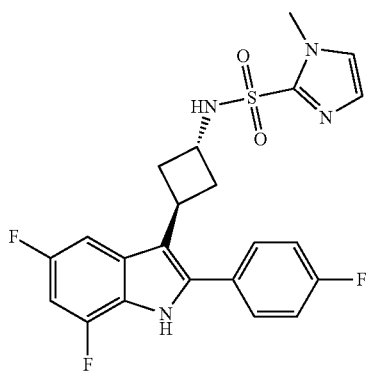
149 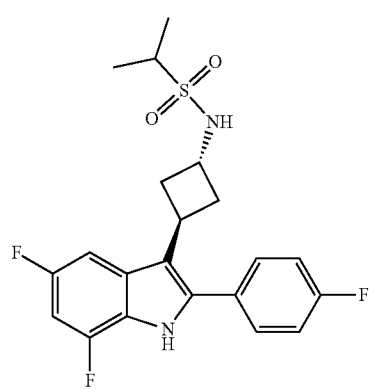
150 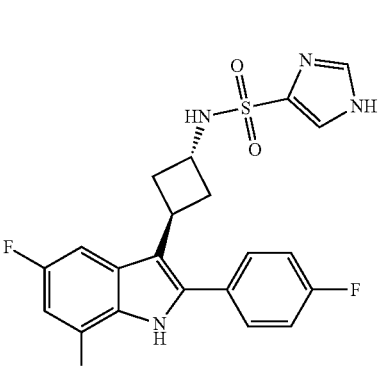
151 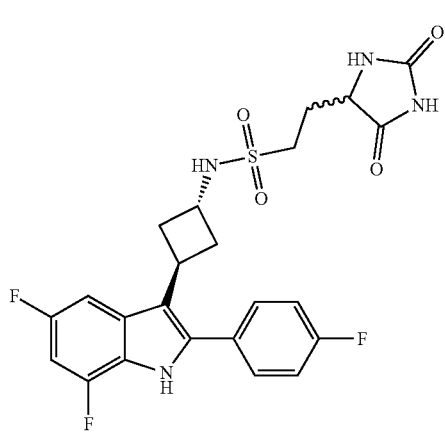

152
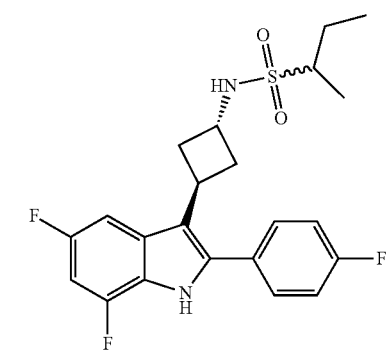
153
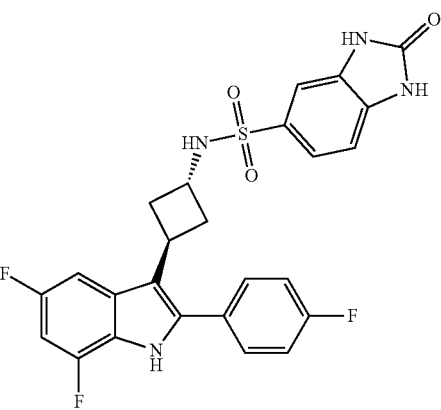
154
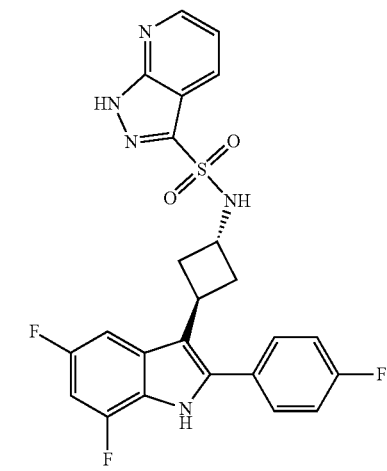
155
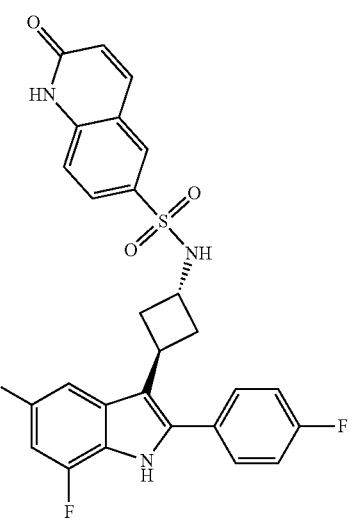
156
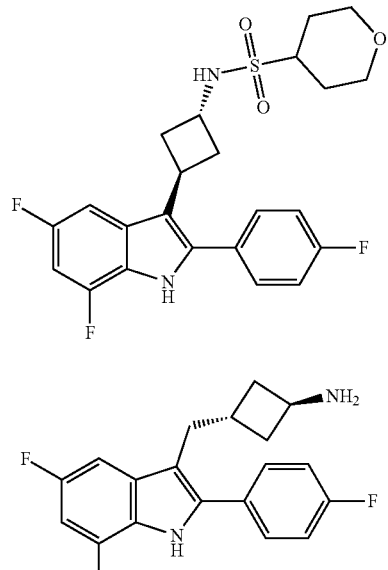
157
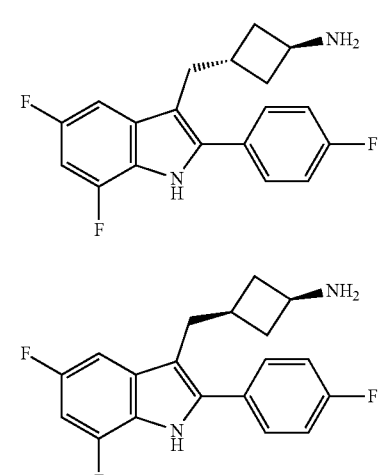
158
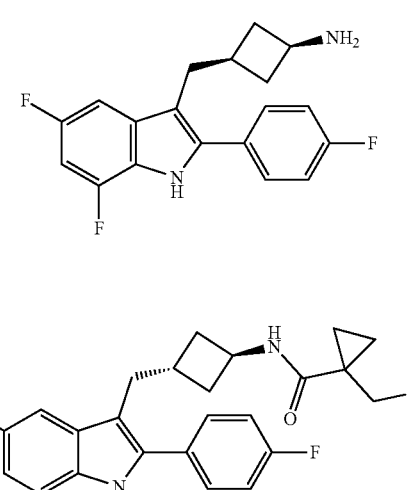
159

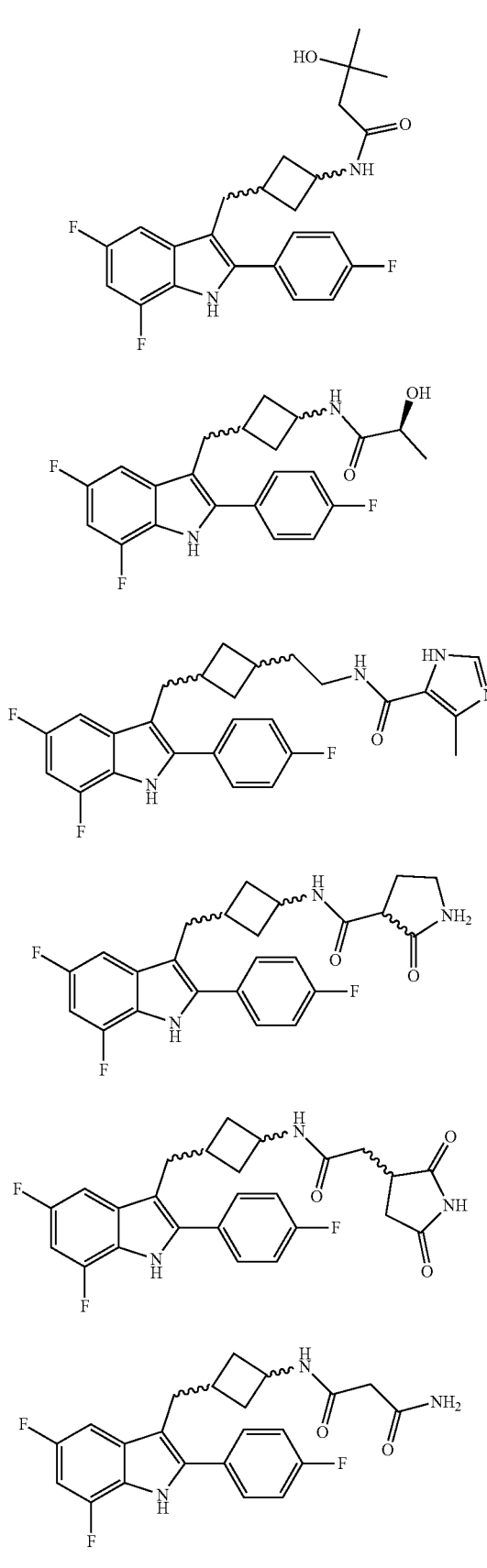
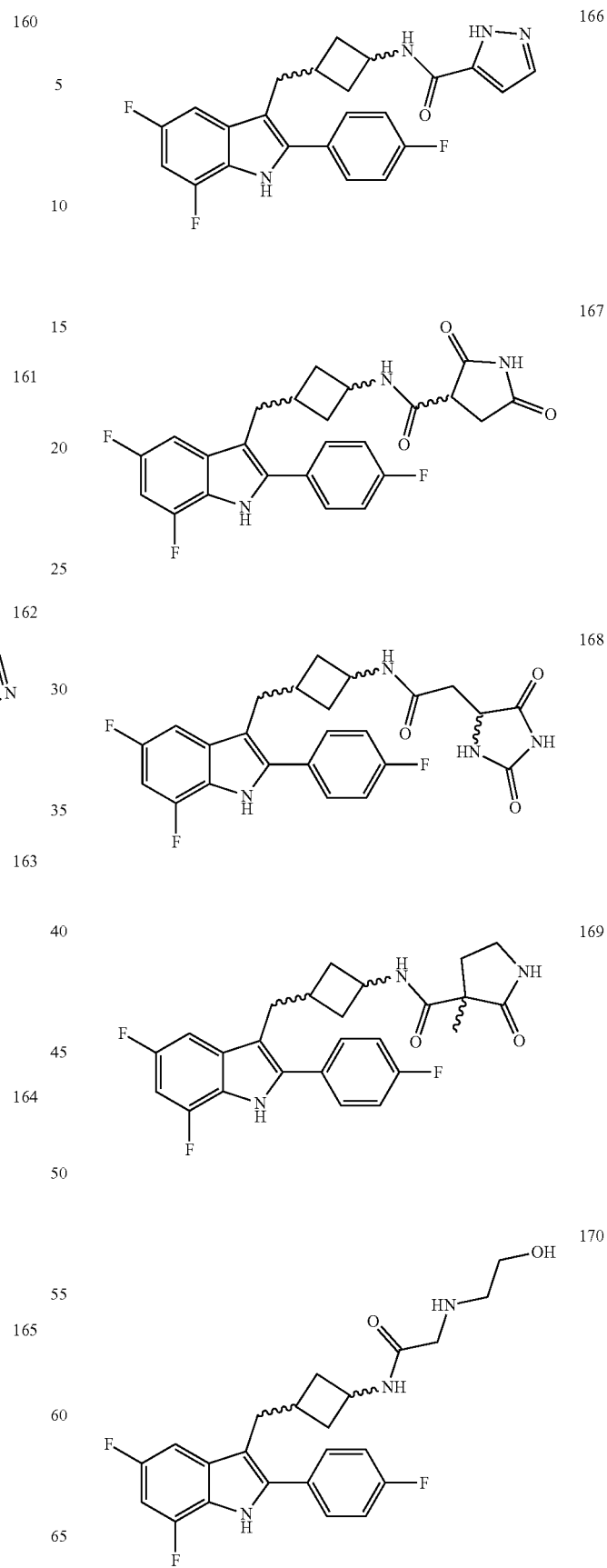

| 171 | 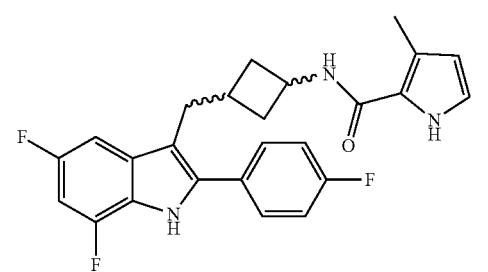 | 176 | 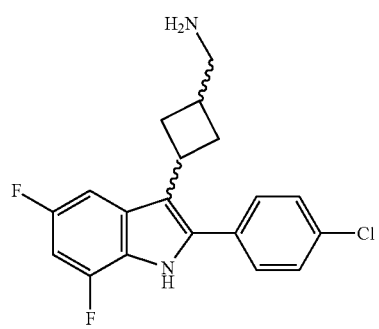 |
| 172 | 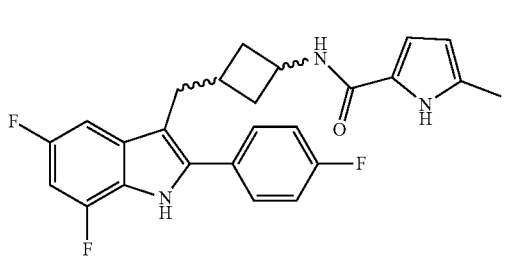 | 177 | 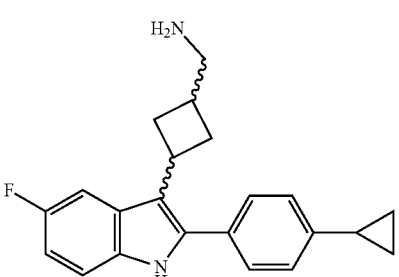 |
| 173 | 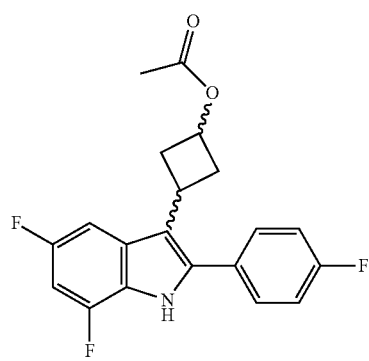 | 178 | 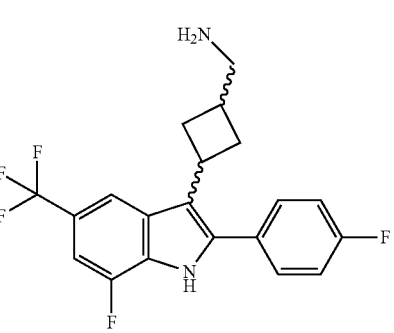 |
| 174 | 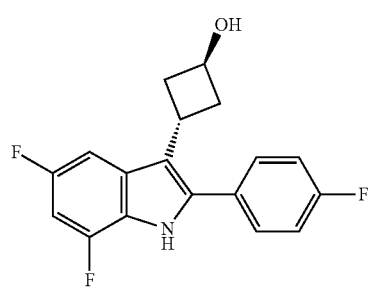 | 179 | 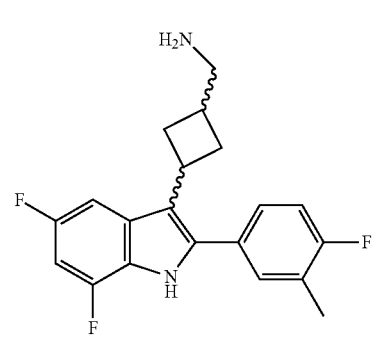 |
| 175 | 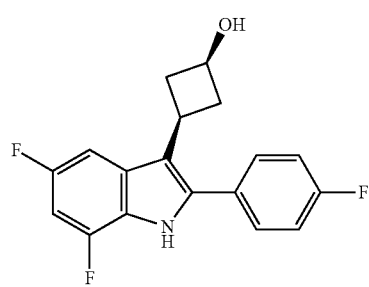 | 180 | 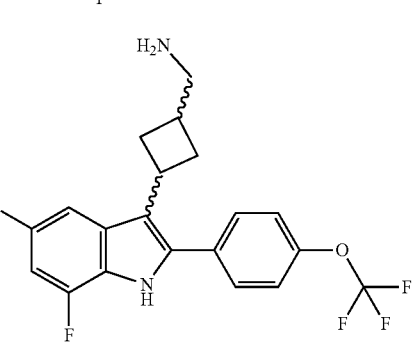 |

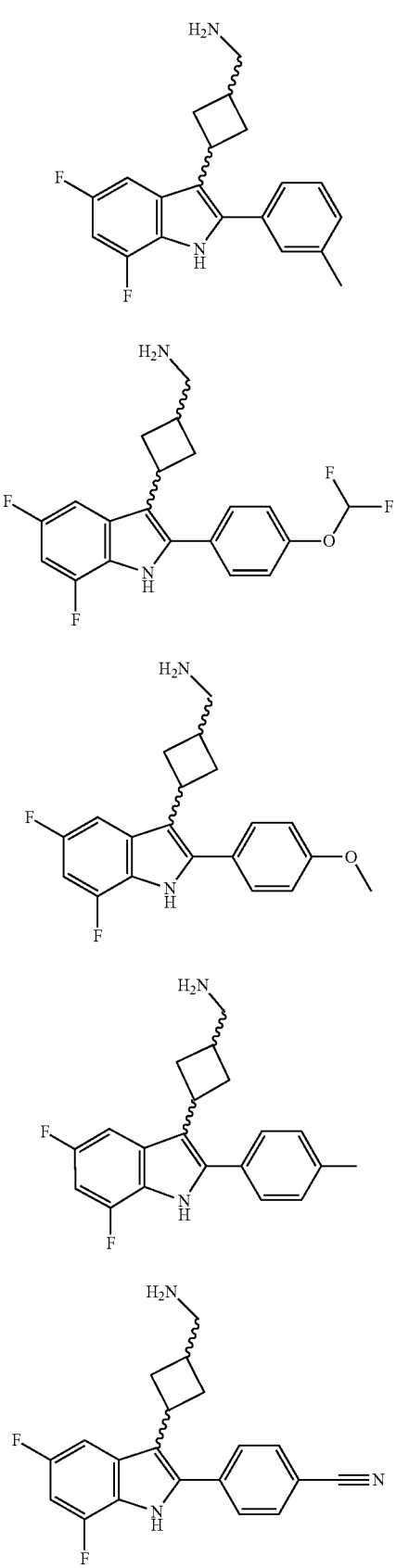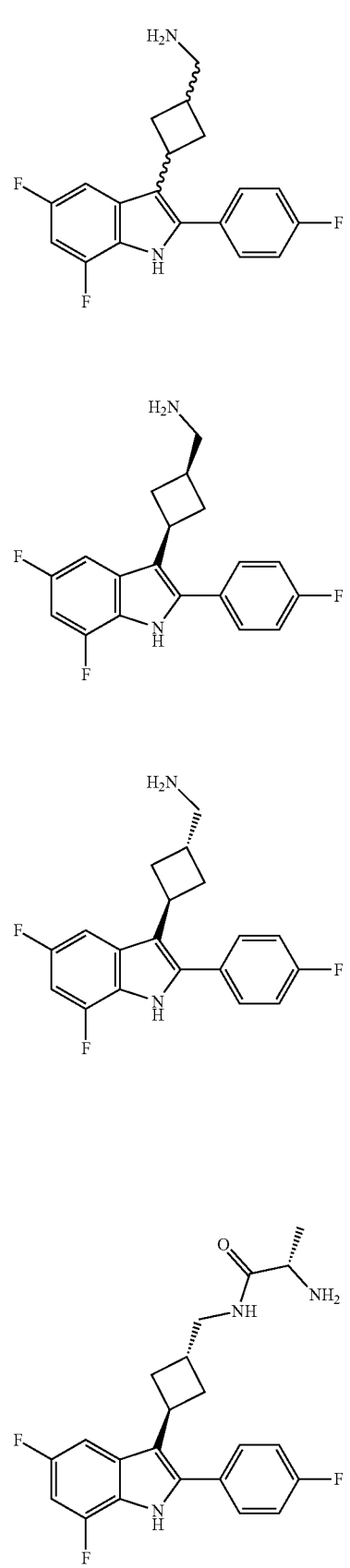

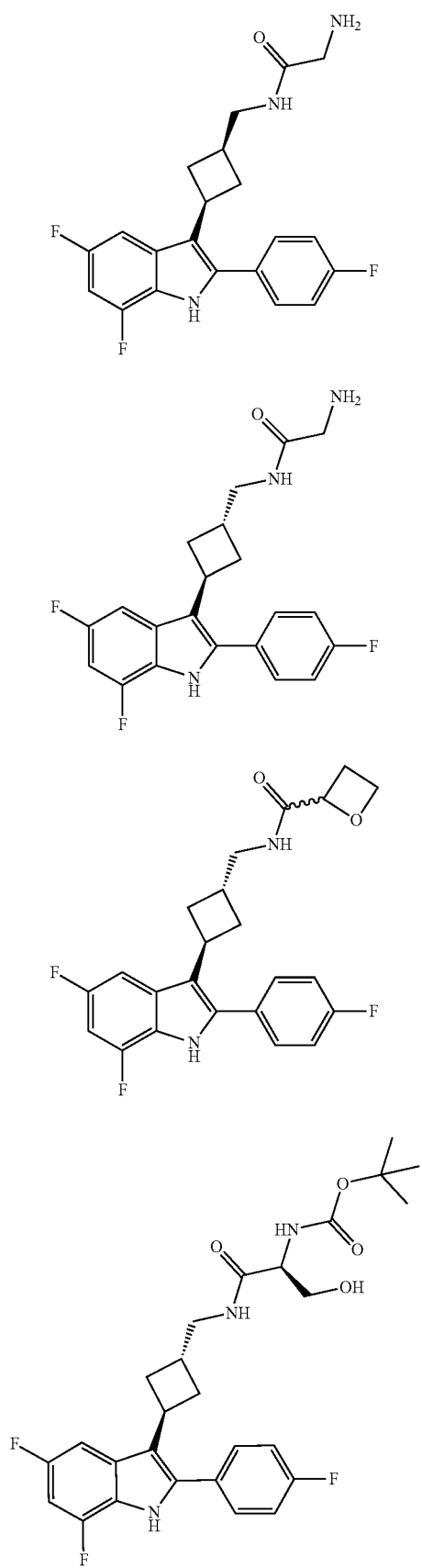
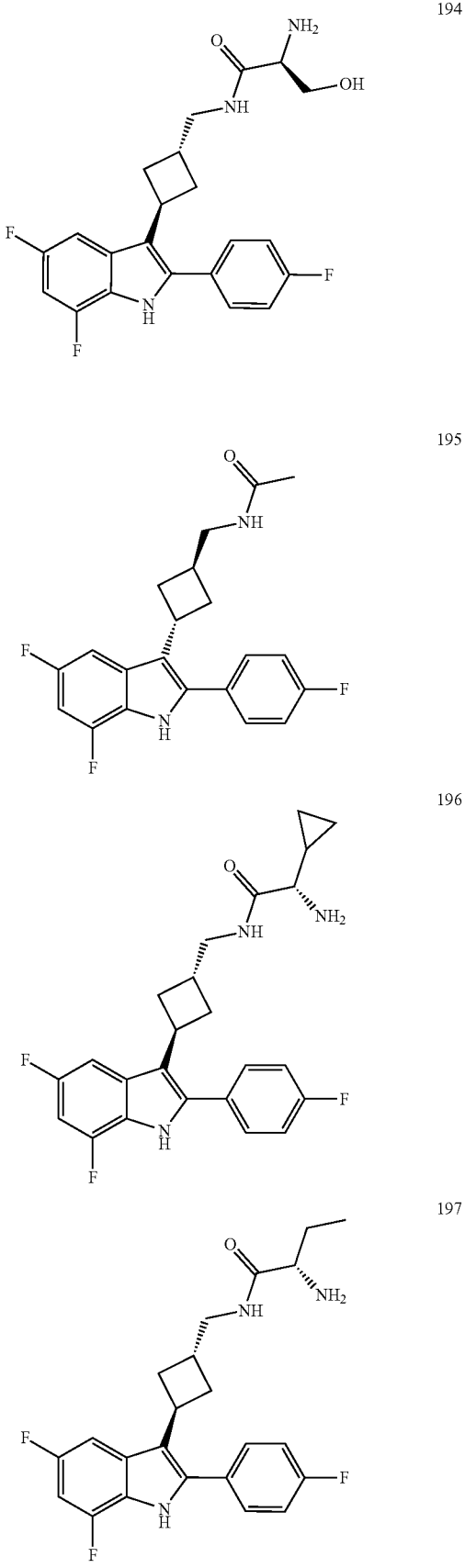

| 198 | 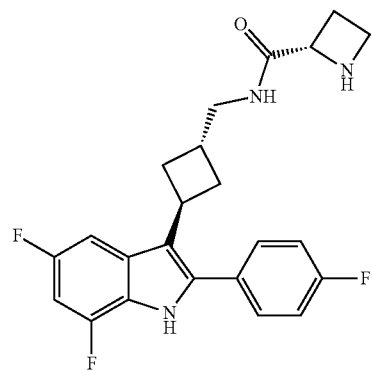 | 202 | 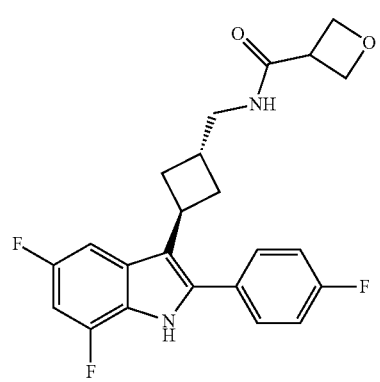 |
| --- | --- | --- | --- |
| 199 | 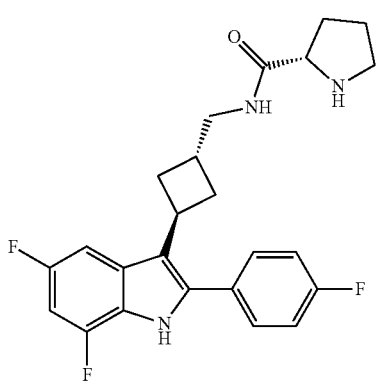 | 203 | 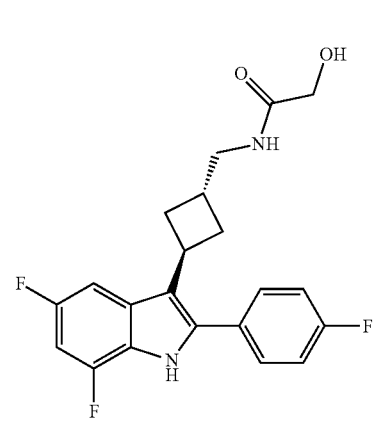 |
| 200 | 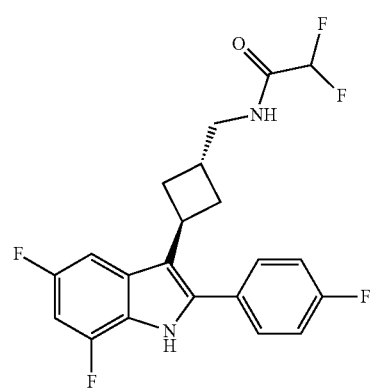 | 204 | 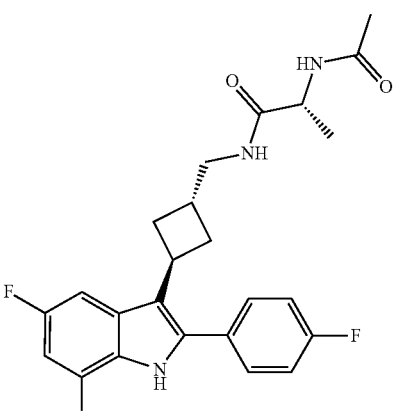 |
| 201 | 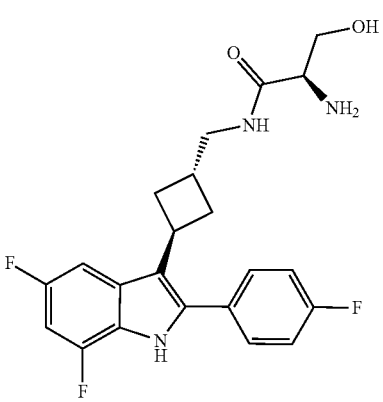 | 205 | 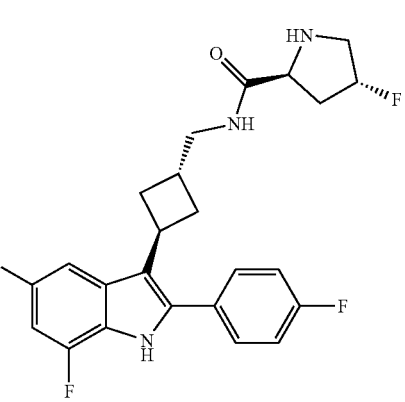 |

| 206 | 210 |
|---|---|
| 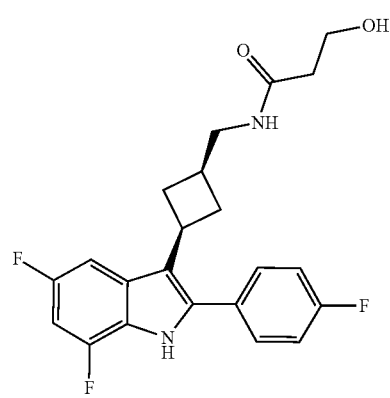 | 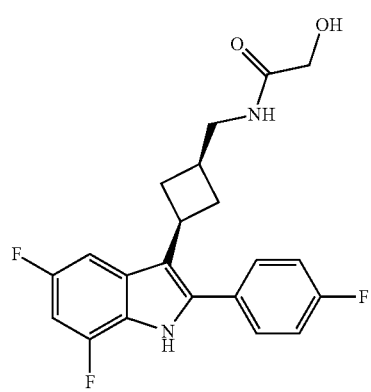 |
| 207 | 211 |
| 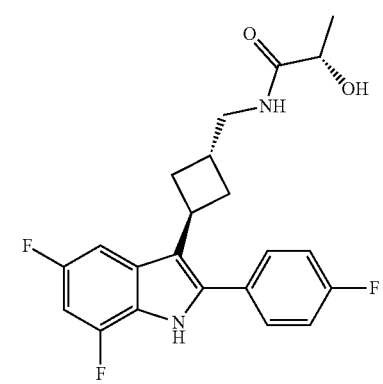 | 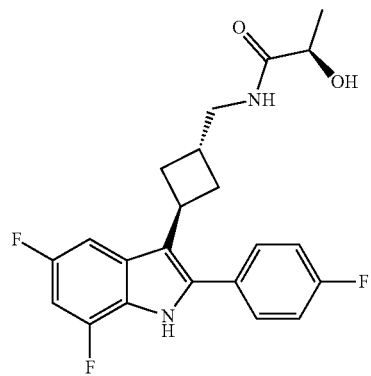 |
| 208 | 212 |
| 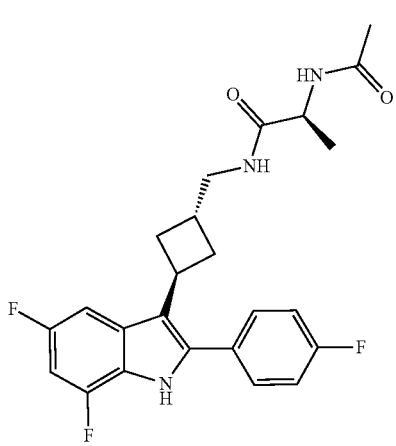 | 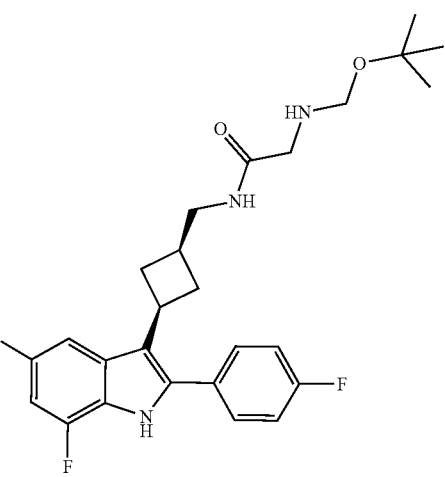 |
| 209 | 213 |
| 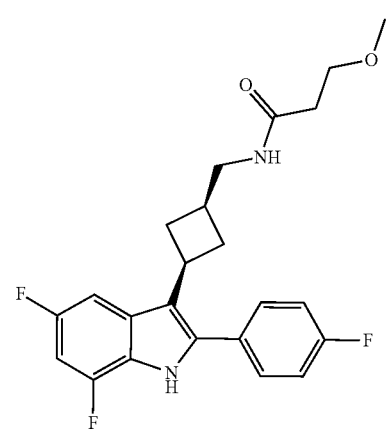 | 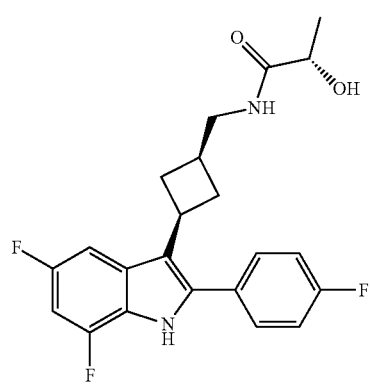 |

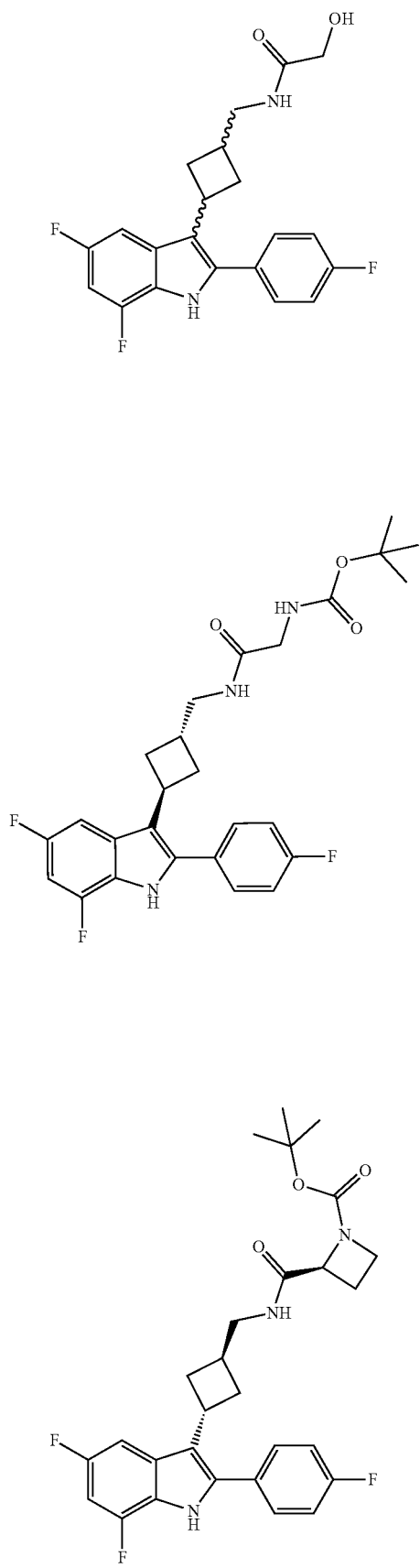
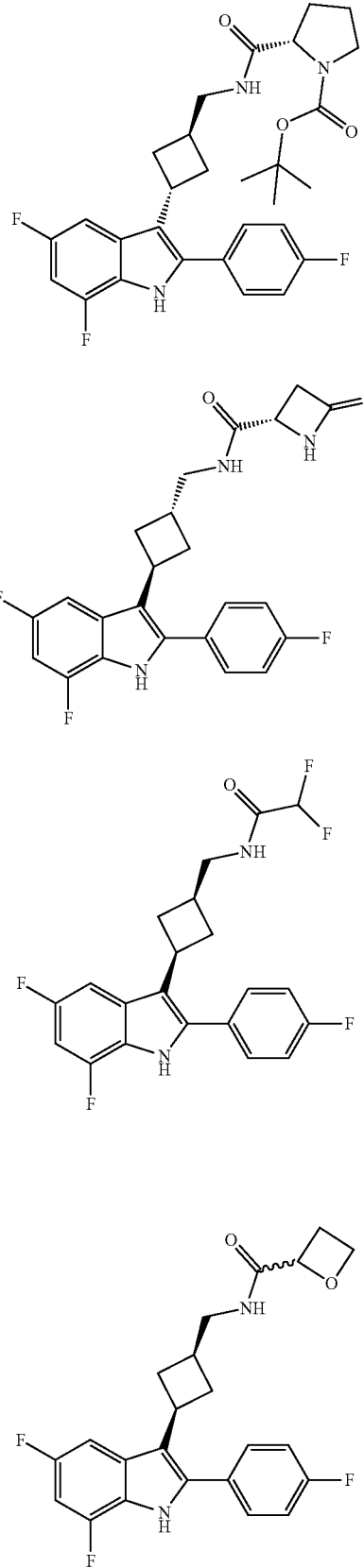

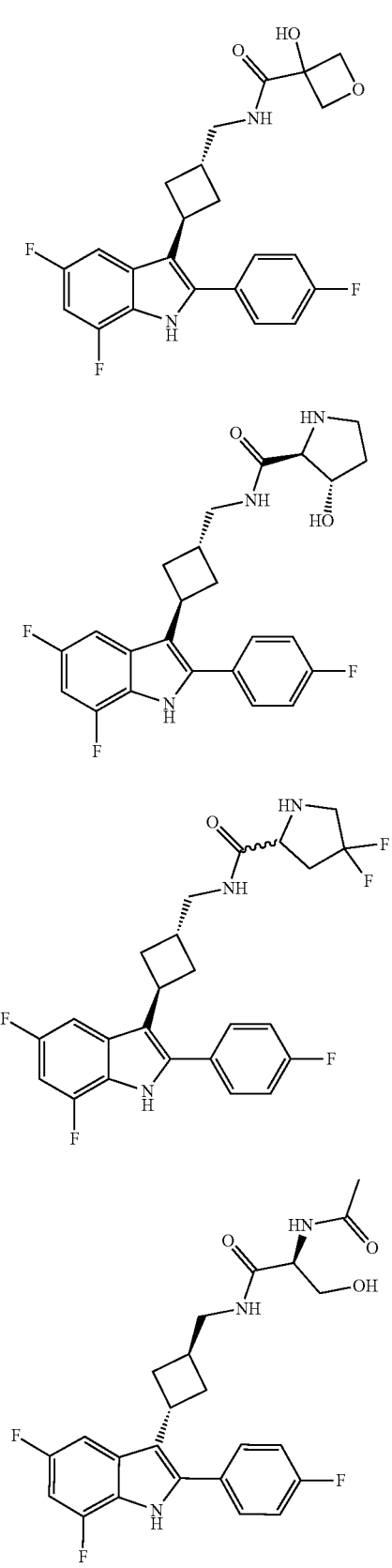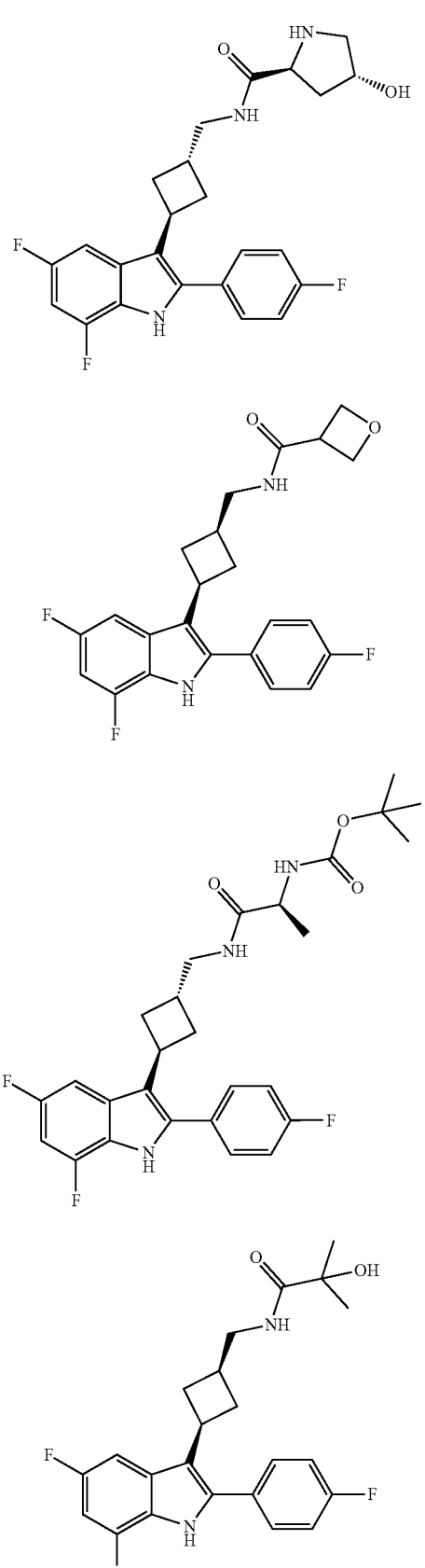

229 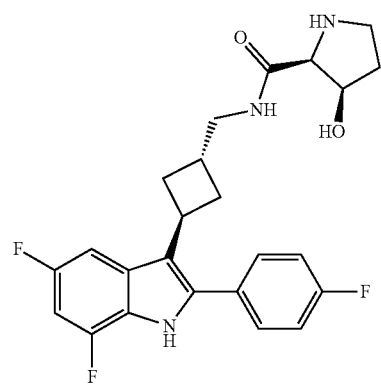
230 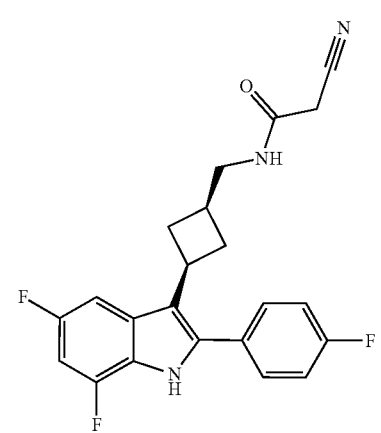
231 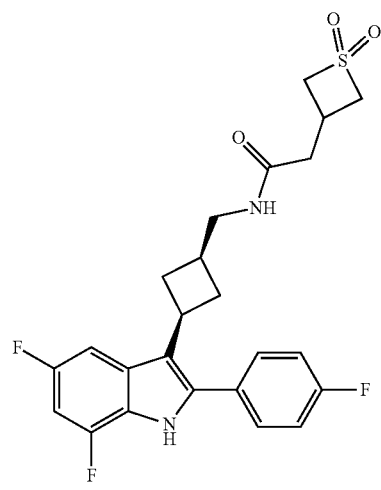
232 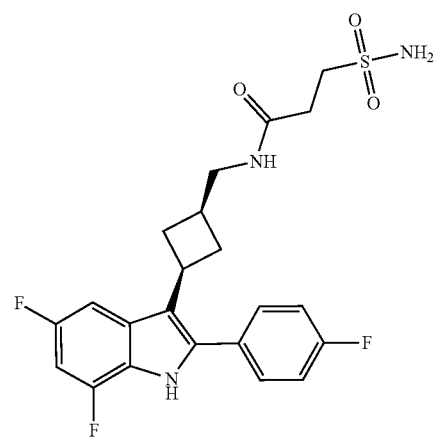
233 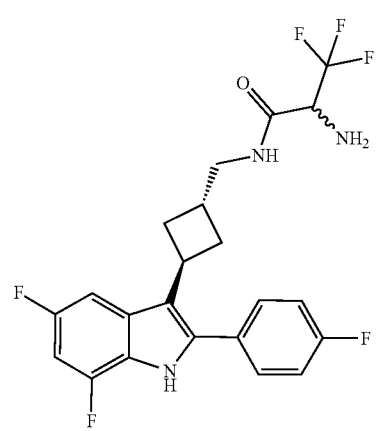
234 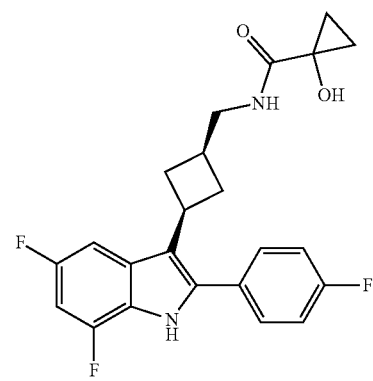
235 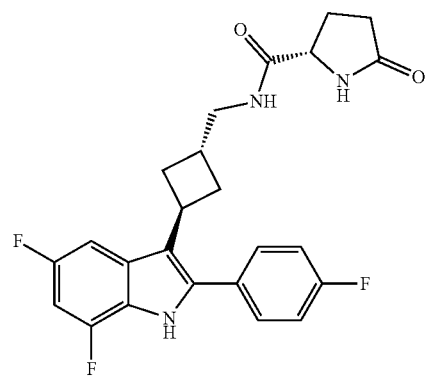

| 236 | 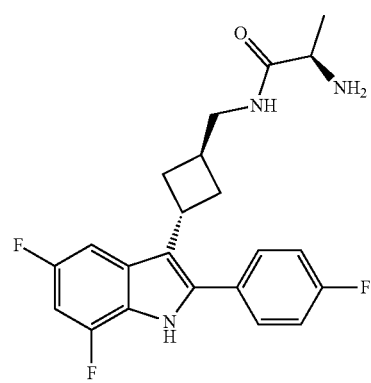 |
| 237 | 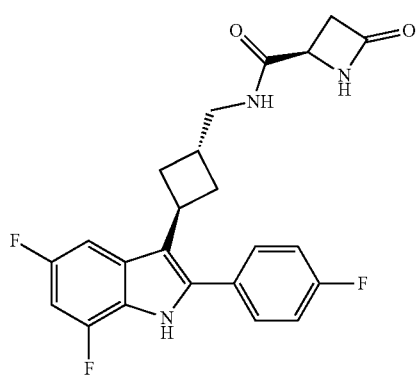 |
| 238 | 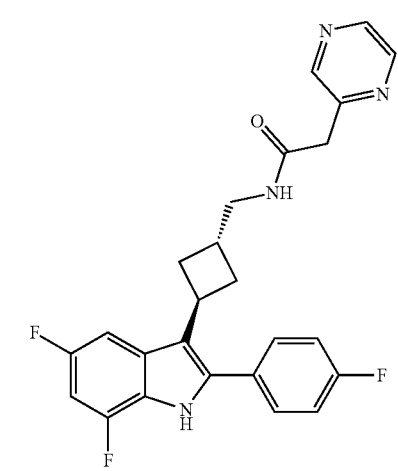 |
| 239 | 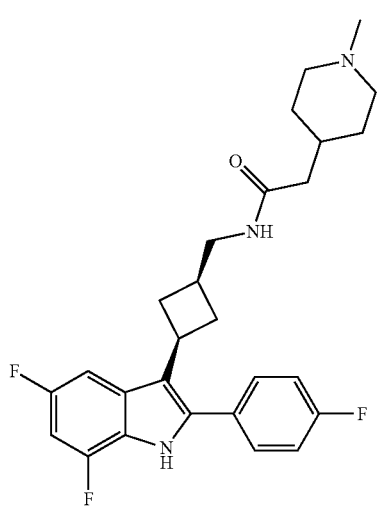 |
| 240 | |
| 241 | |

611
-continued
242
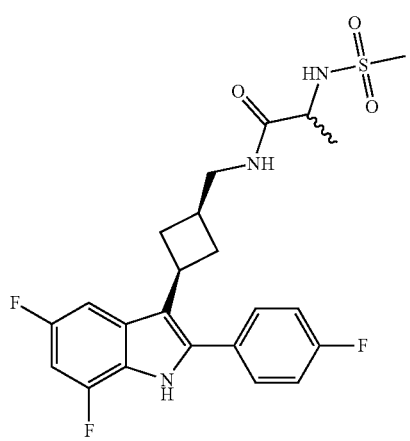
243
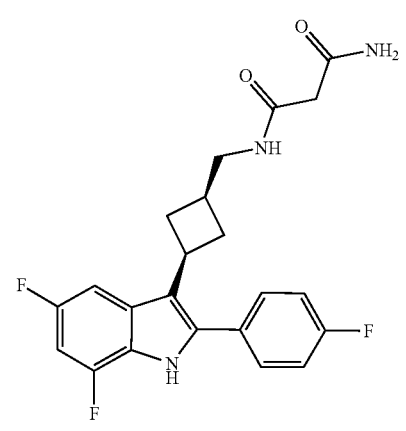
244
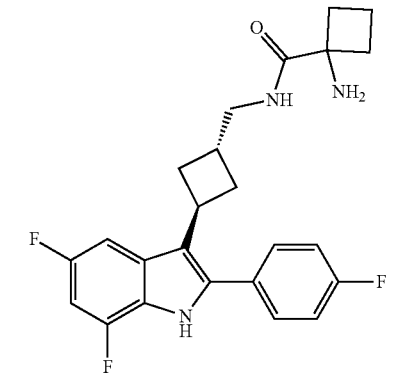
245
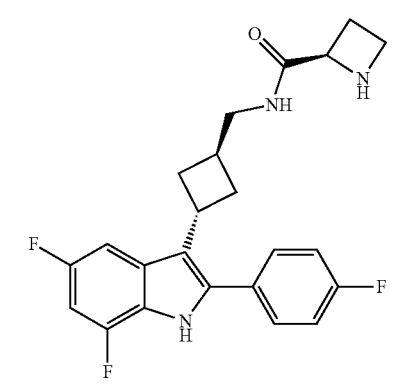
612
-continued
246
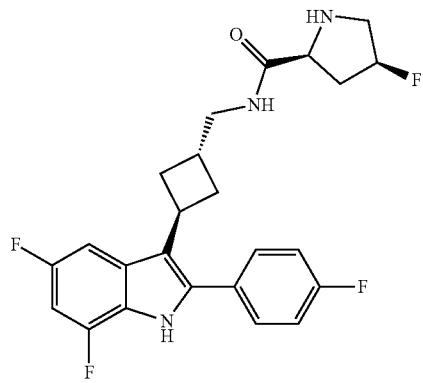
247
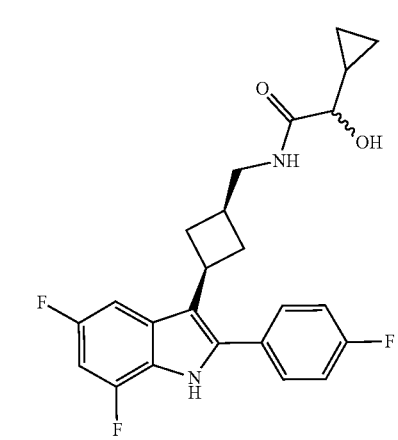
248
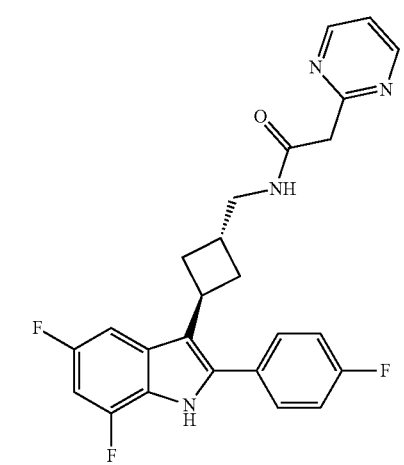
249
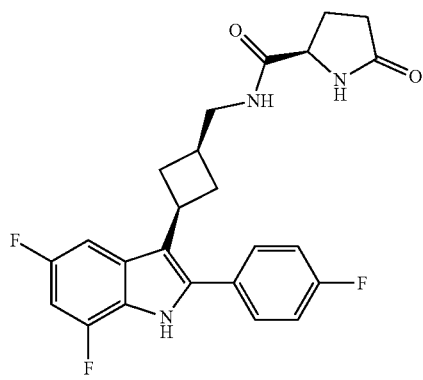

250
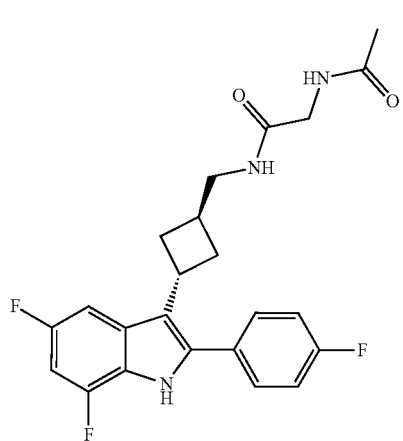
251
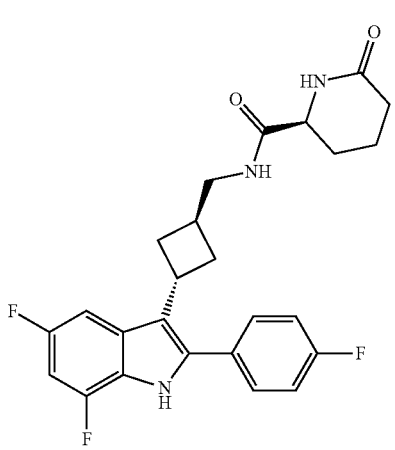
252
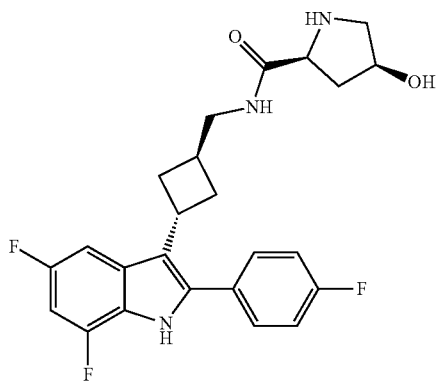
253
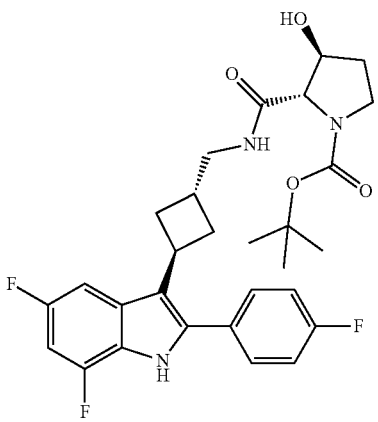
254
255
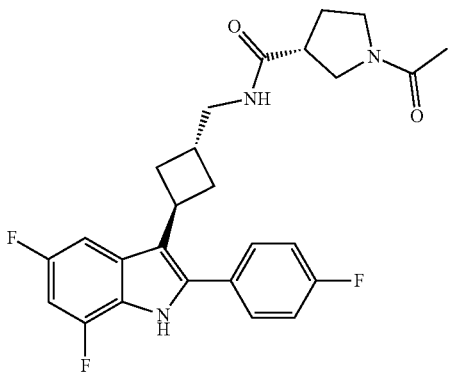
256

257
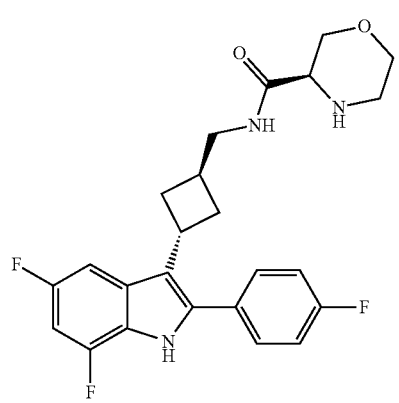
258
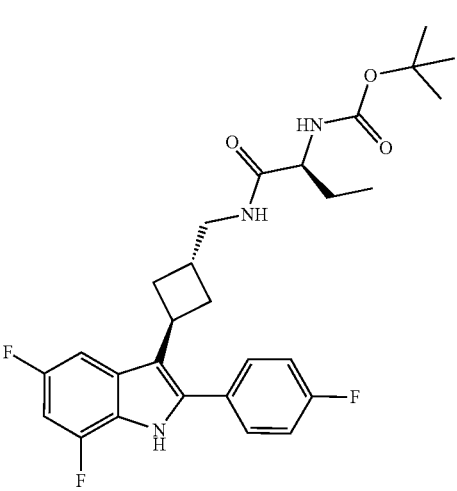
259
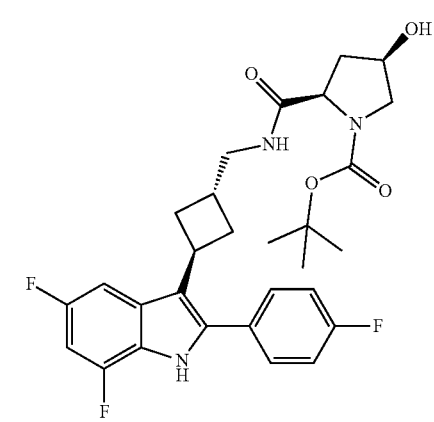
260
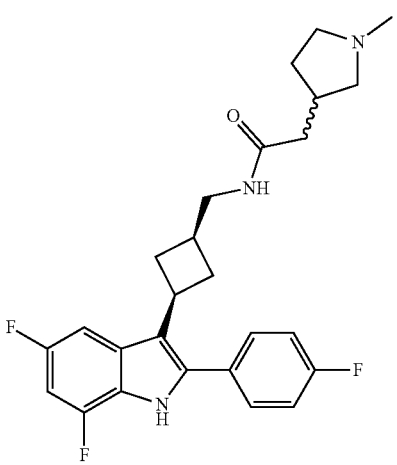
261
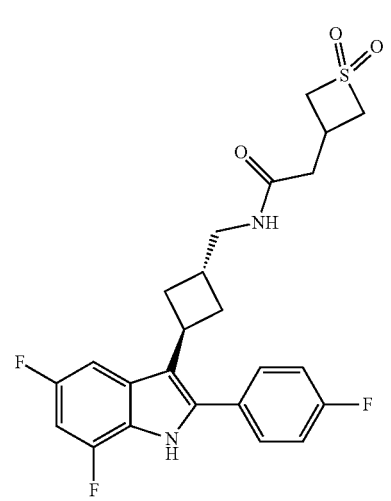
262
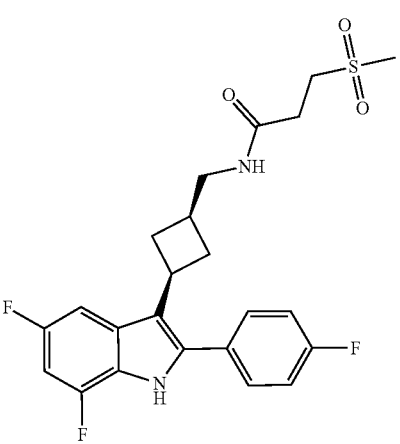

263
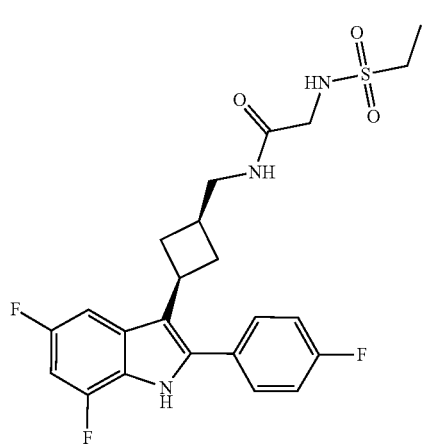
264
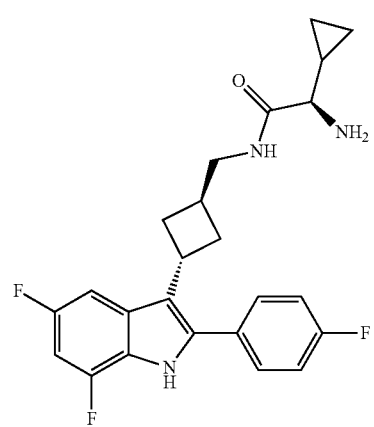
265
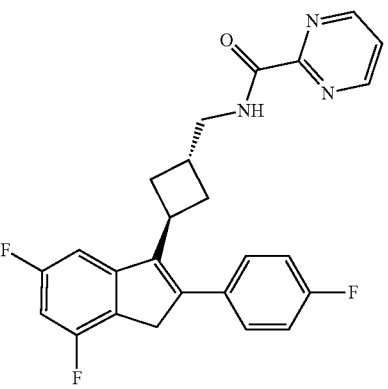
266
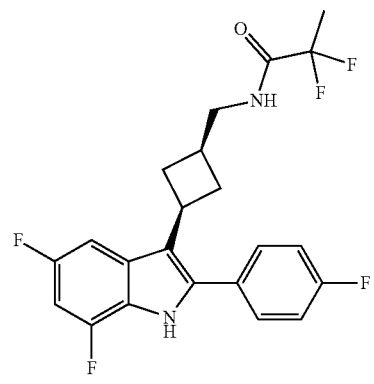
267
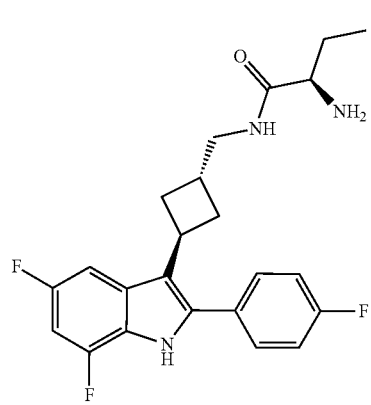
268
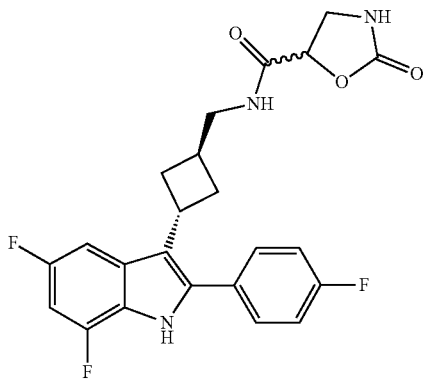
269
270
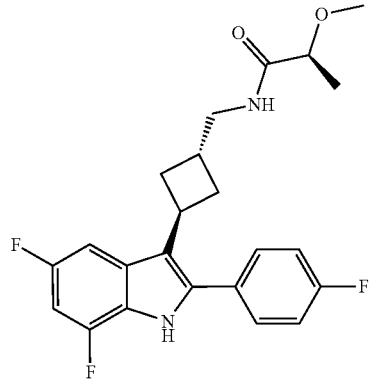

-continued
271
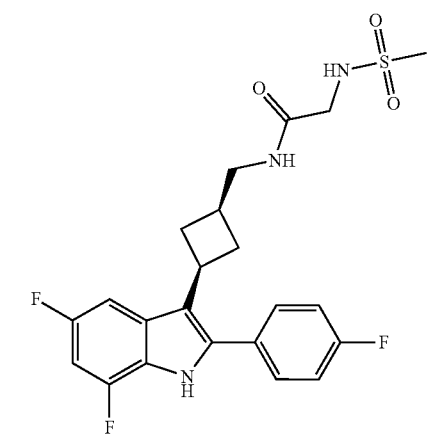
272
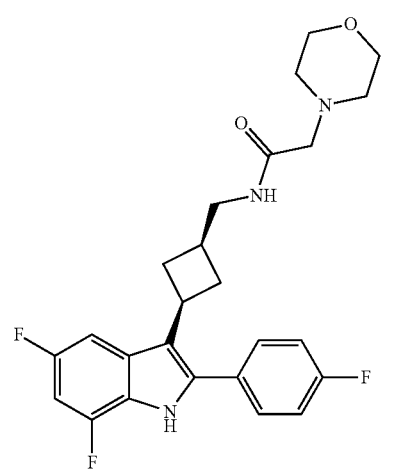
273
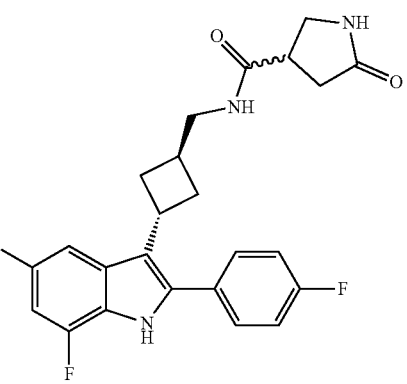
274
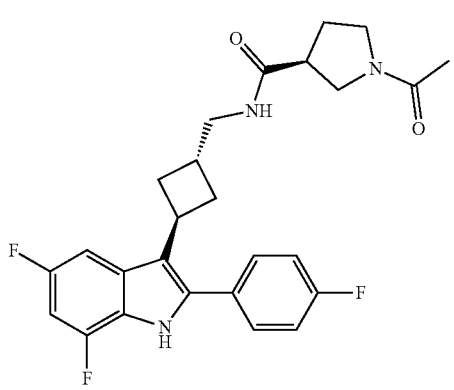
-continued
275
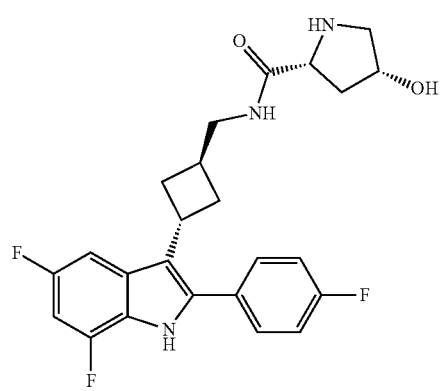
276
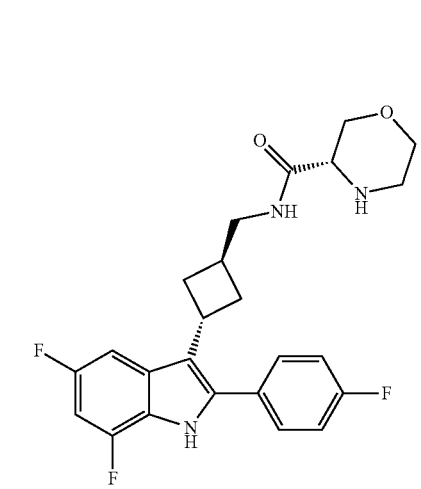
277
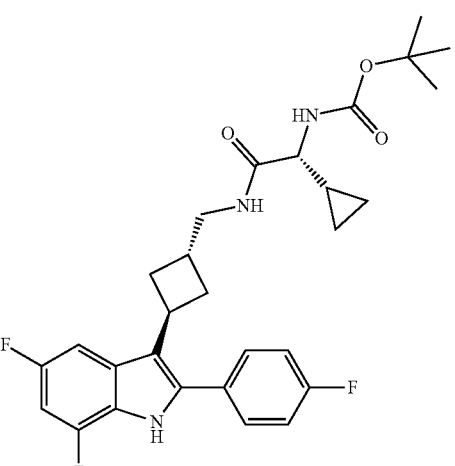

278
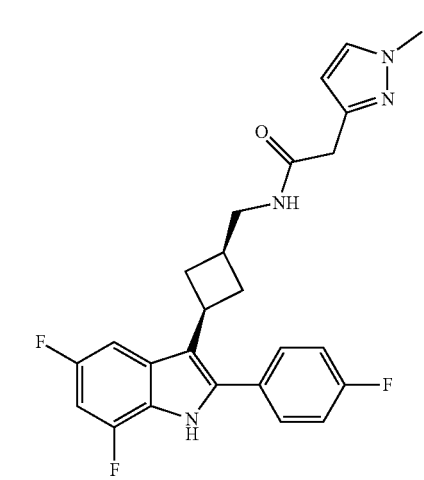
279
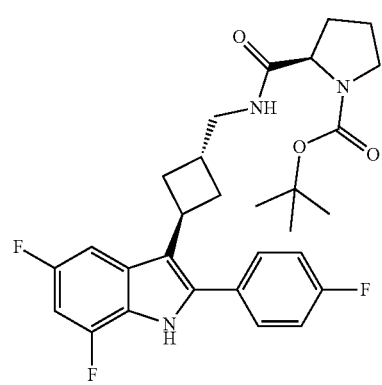
280
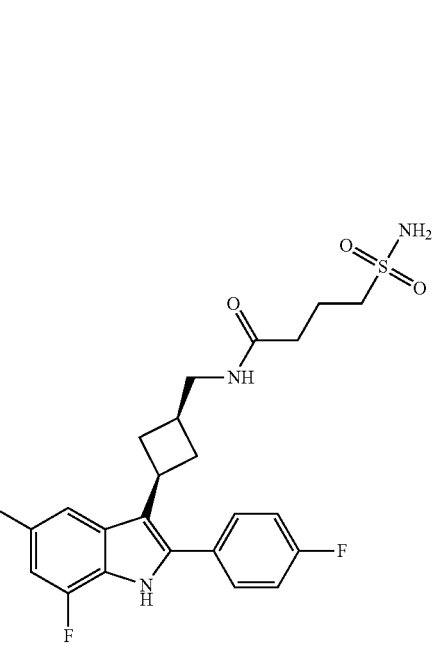
281
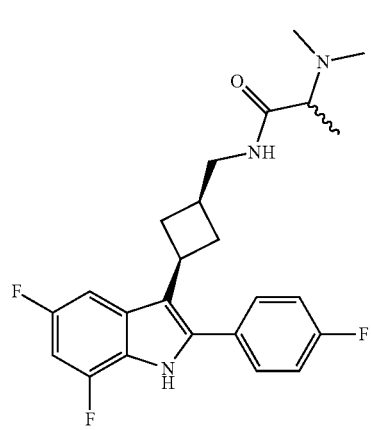
282
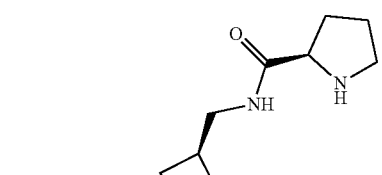
283
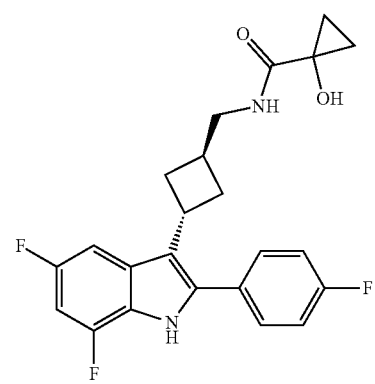
284
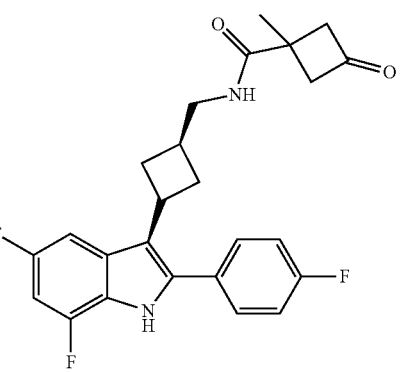

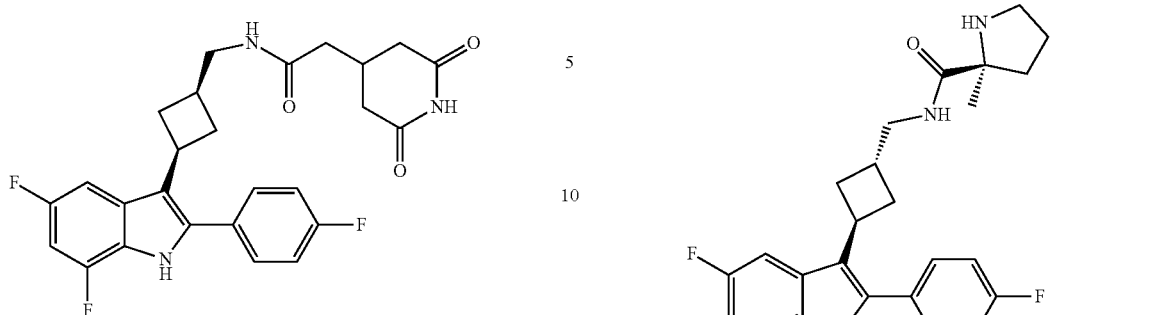

| 625 | 626 |
|---|---|
| -continued | -continued |
293
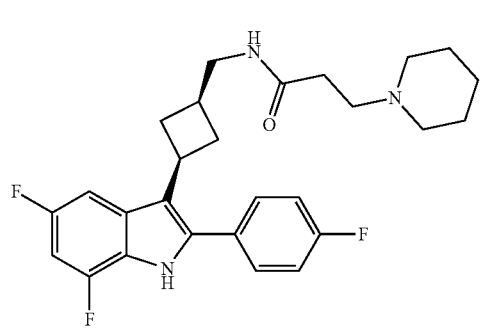
294
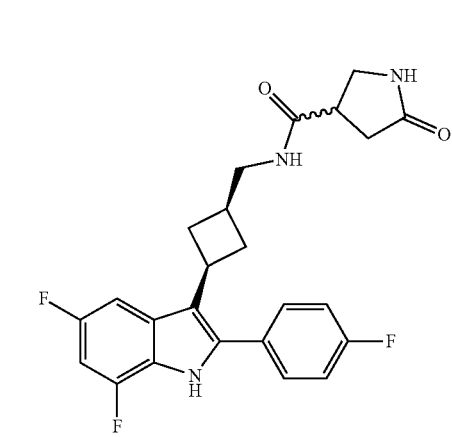
295
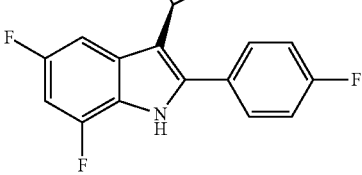
296
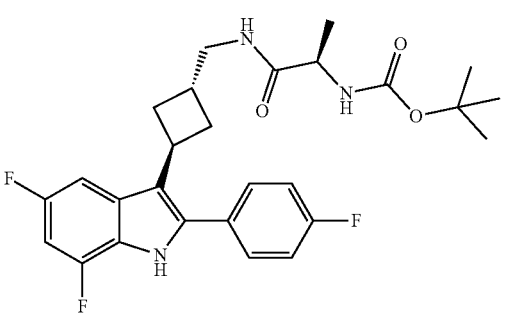
297
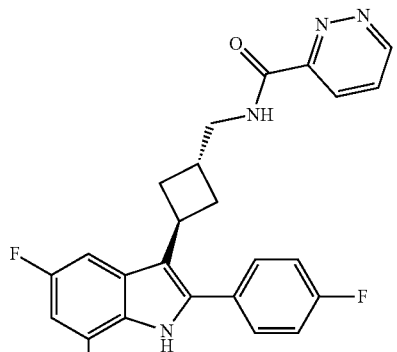
298
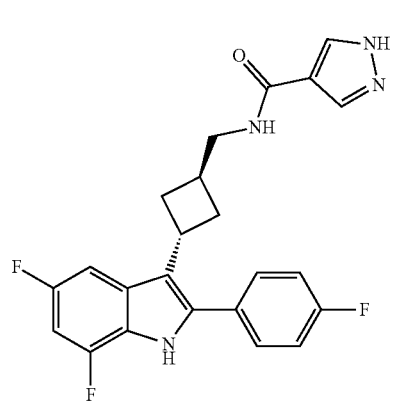
299
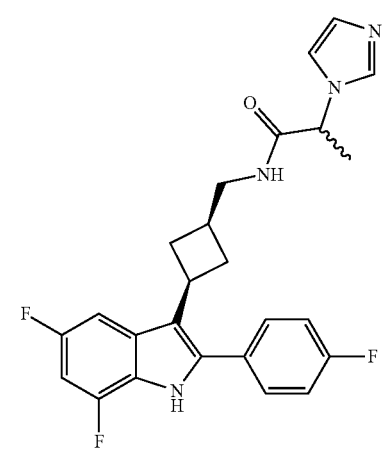
300
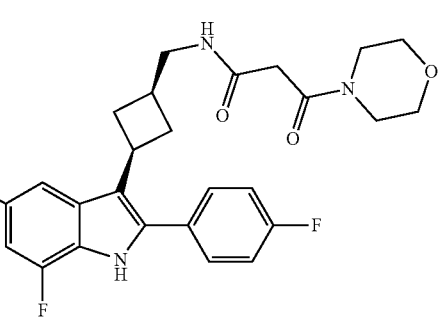

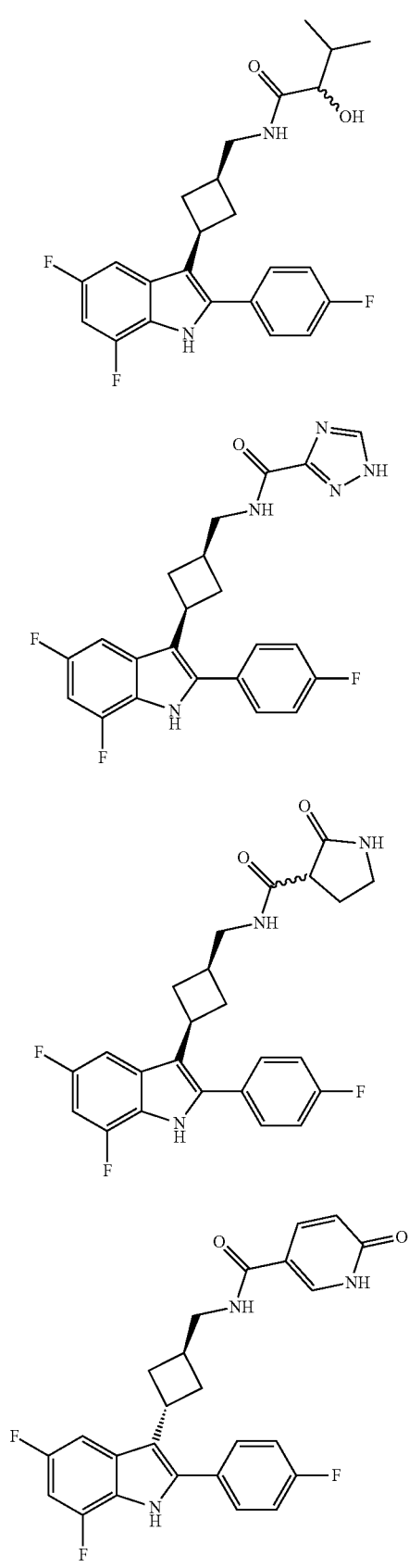
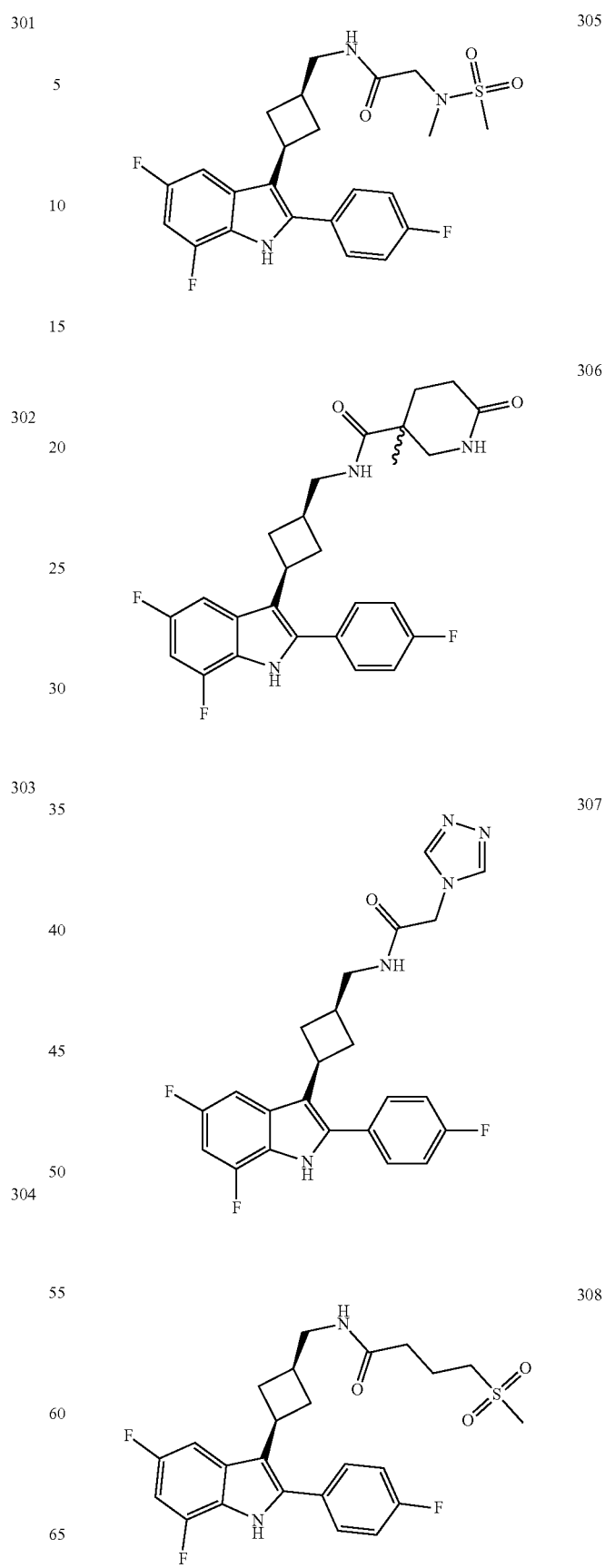

-continued
| | |
|---|---|
| 309 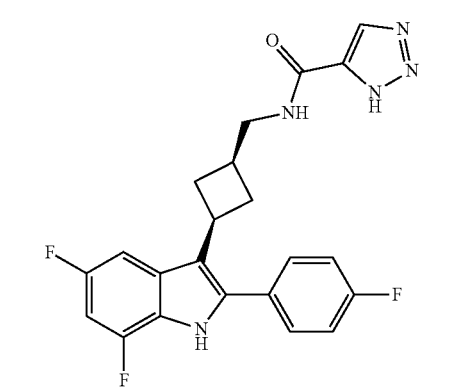 | 313 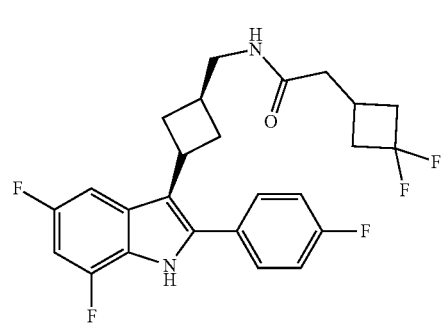 |
| 310 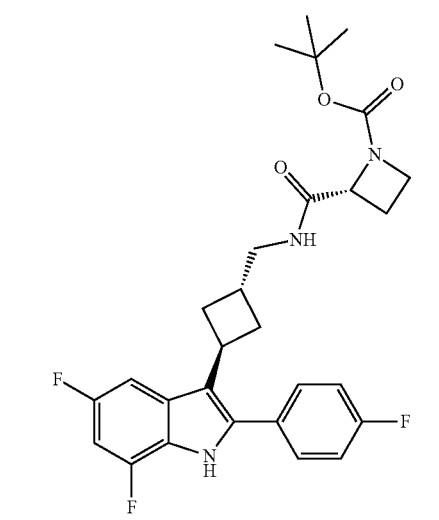 | 314 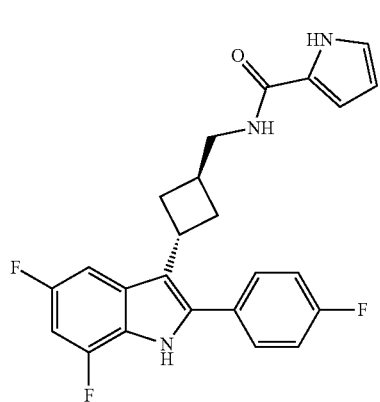 |
| 311 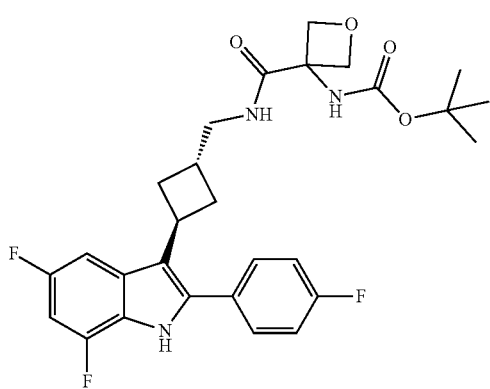 | 315 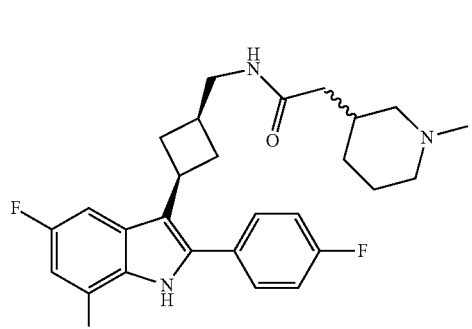 |
| 312 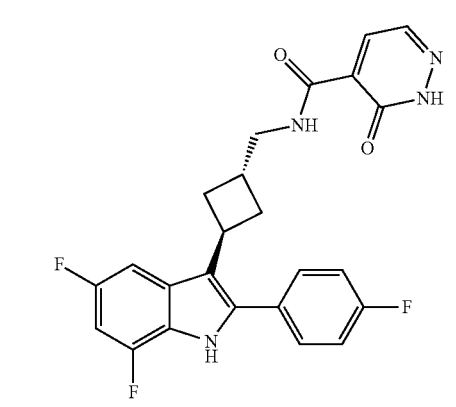 | 316 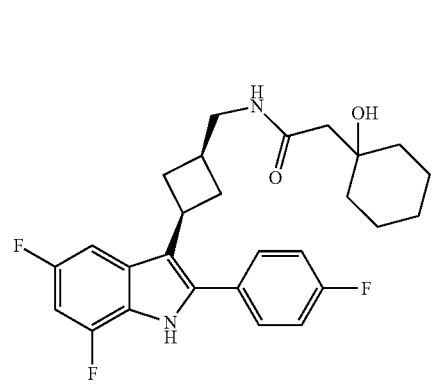 |

317 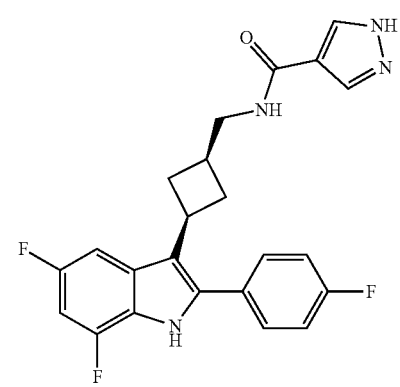
318 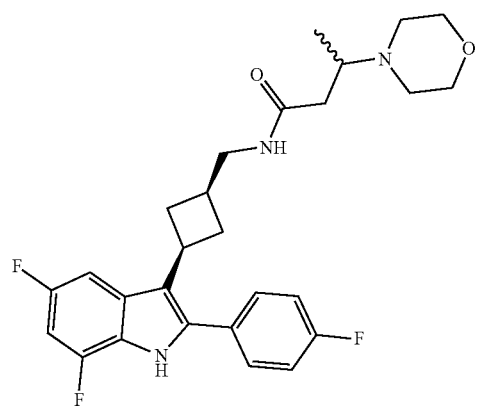
319 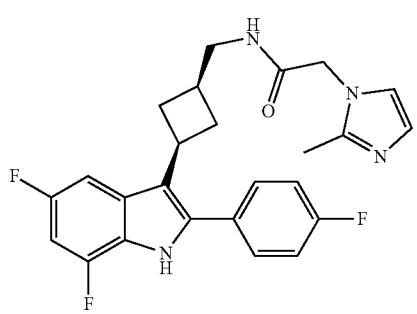
320 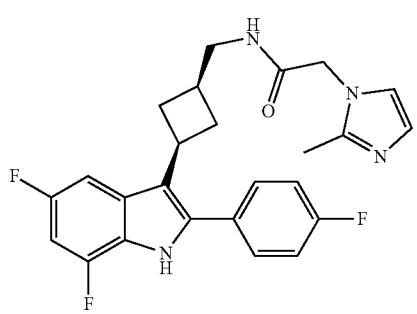
321 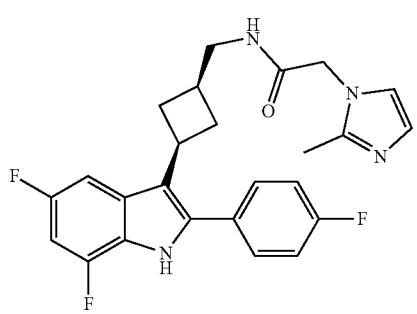
322 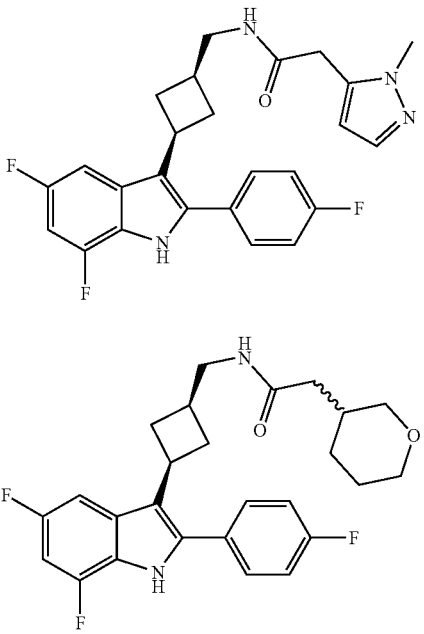
323 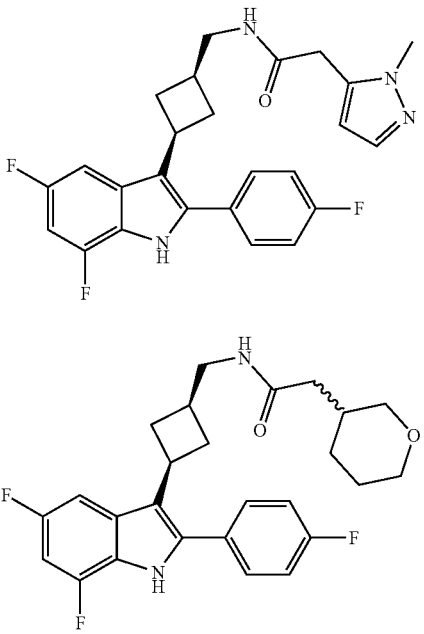
324 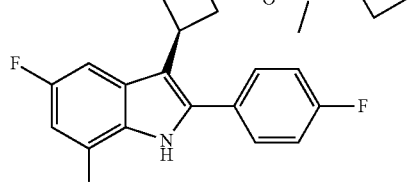
325 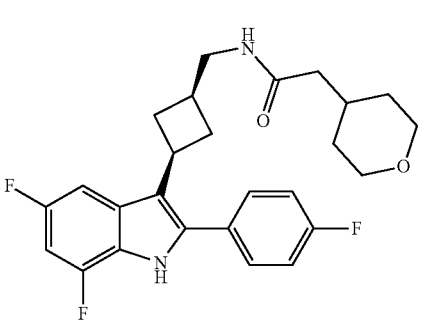

633
-continued
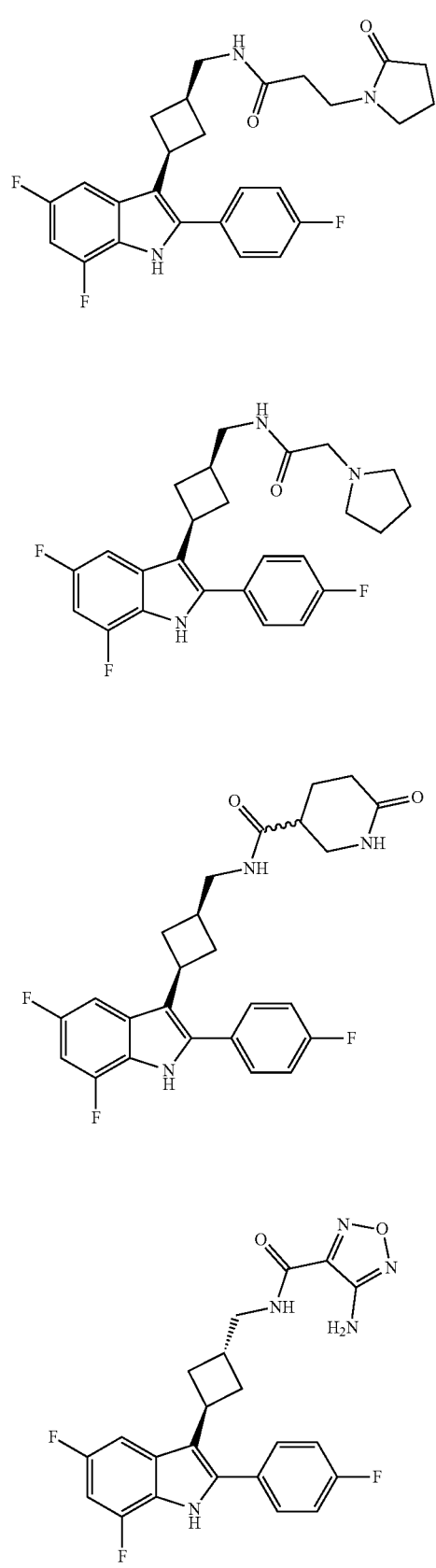
634
-continued
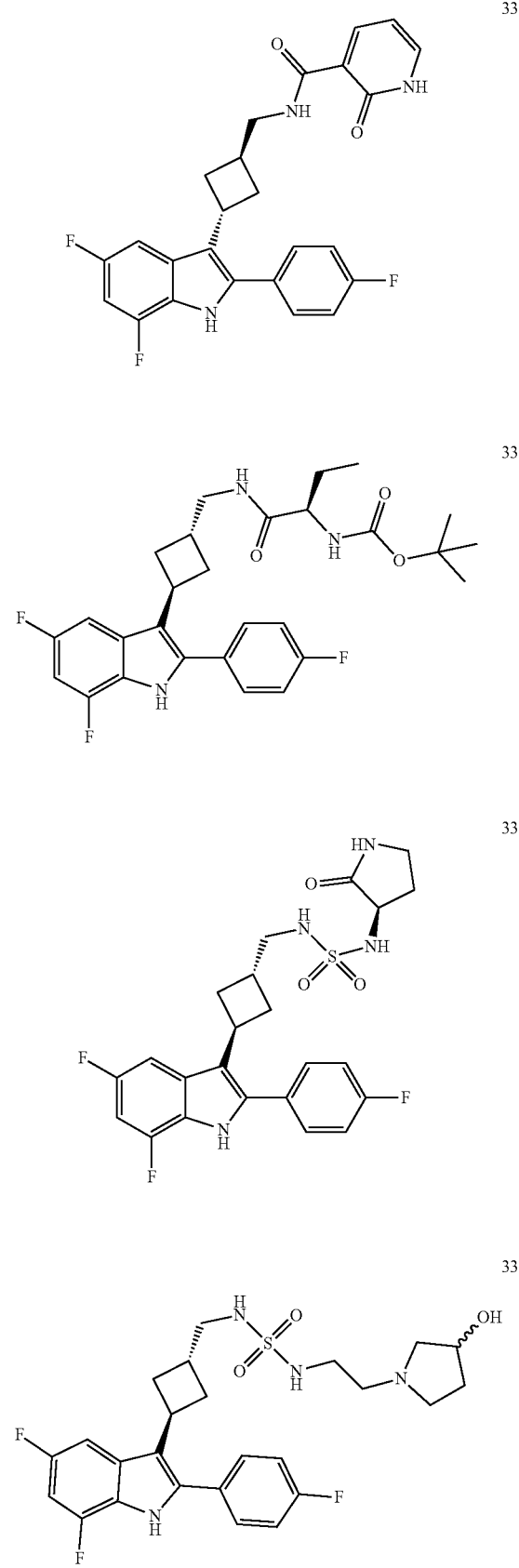

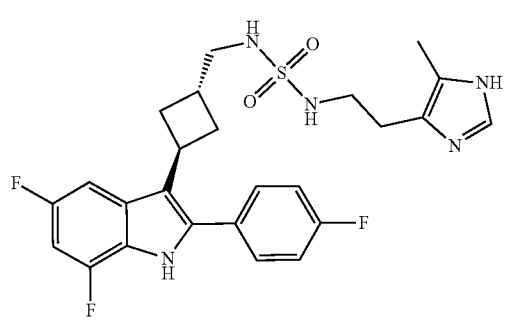
334
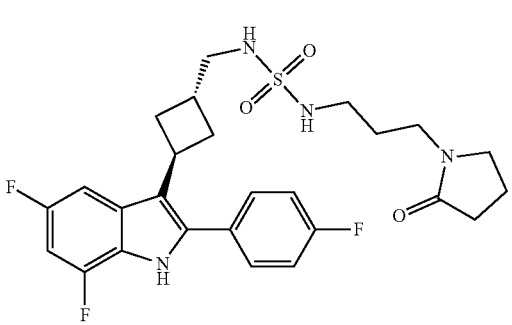
335
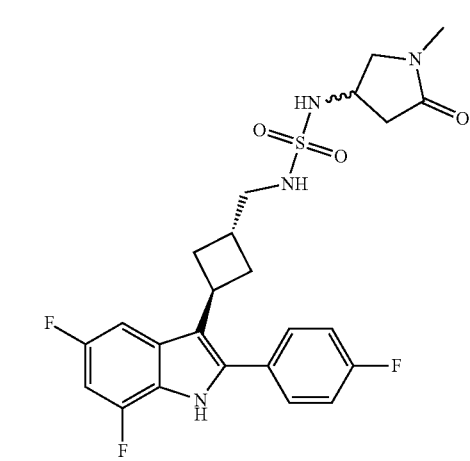
336
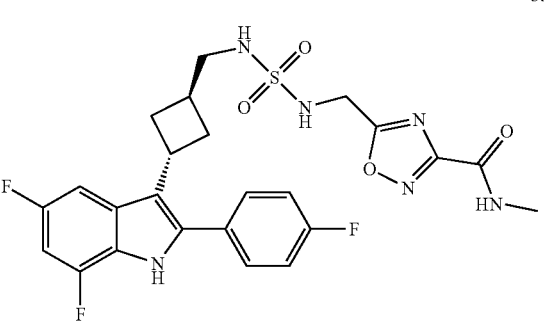
337
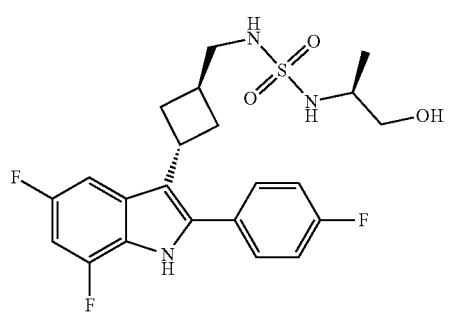
338
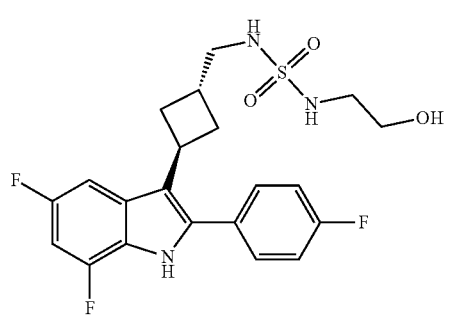
339
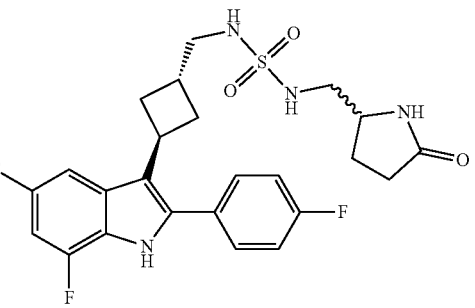
340
341
342

343
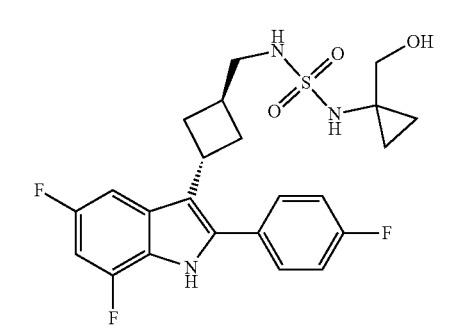
344
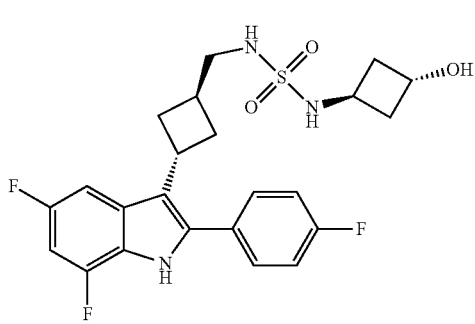
345
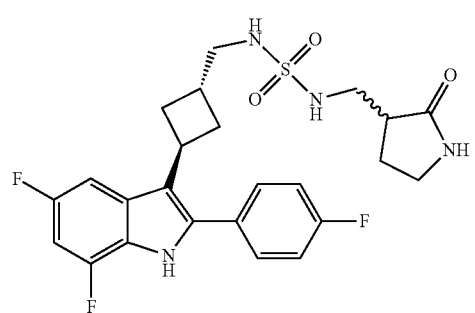
346
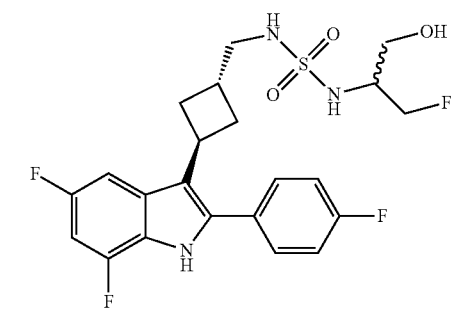
347
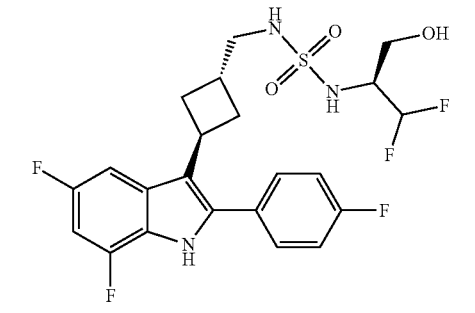
348
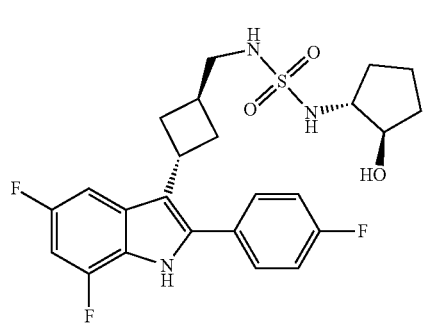
349
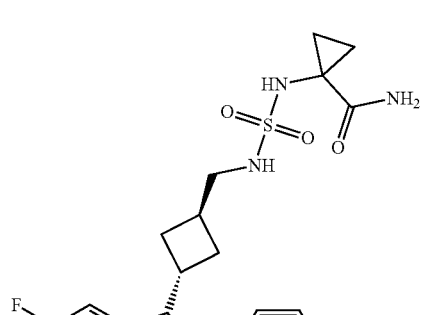
350
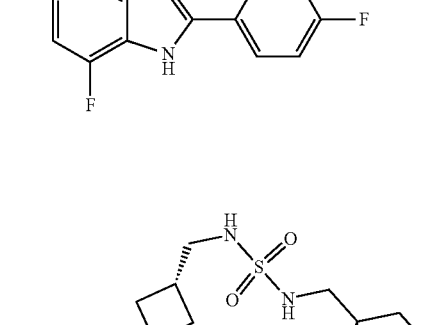
351
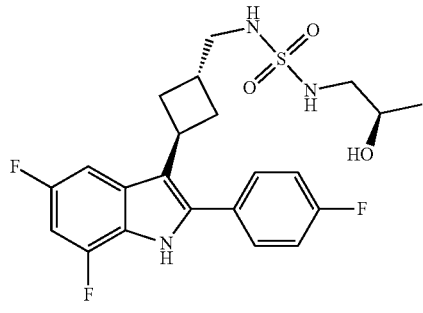

352 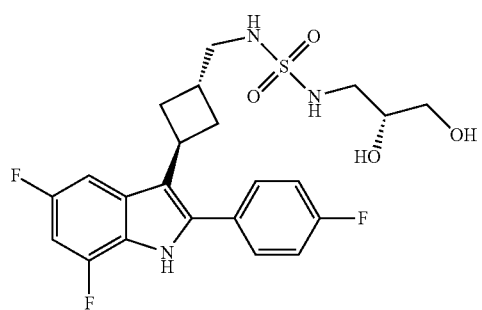
353 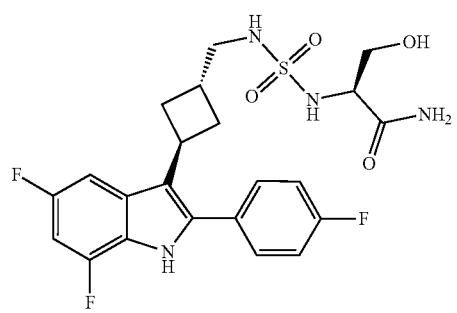
354 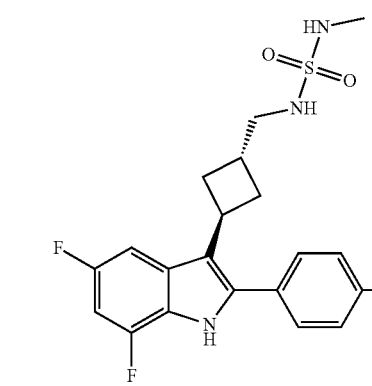
355 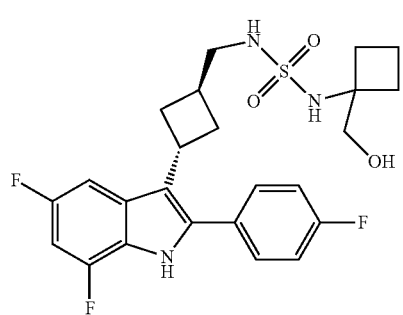
356 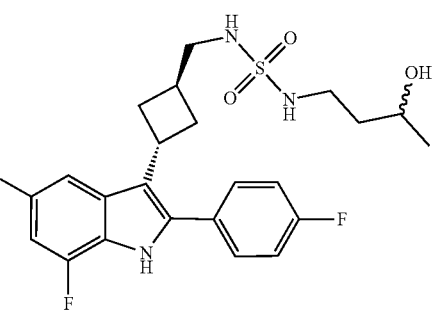
357 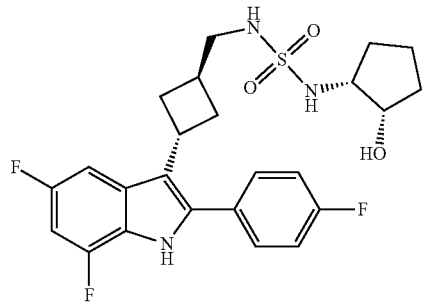
358 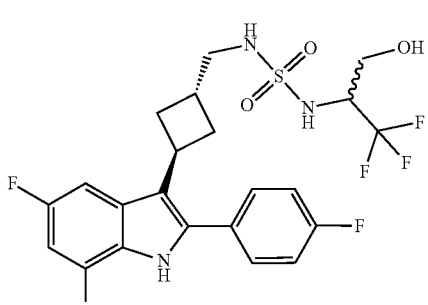
359 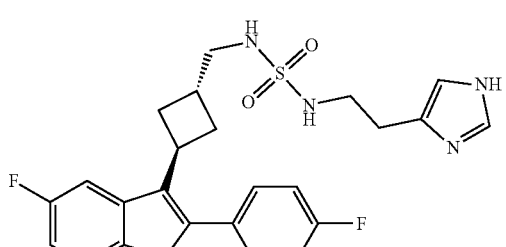
360 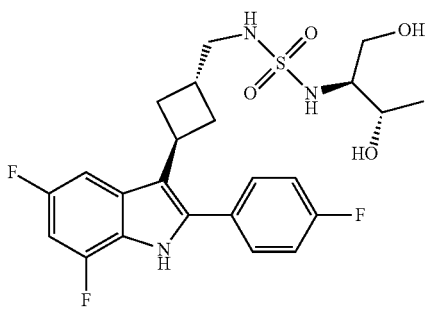

| 361 | 365 |
|---|---|
| 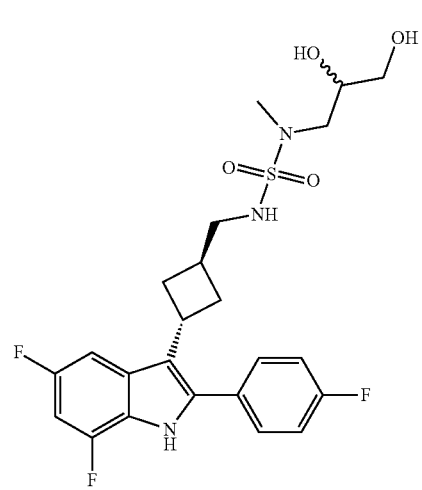 | 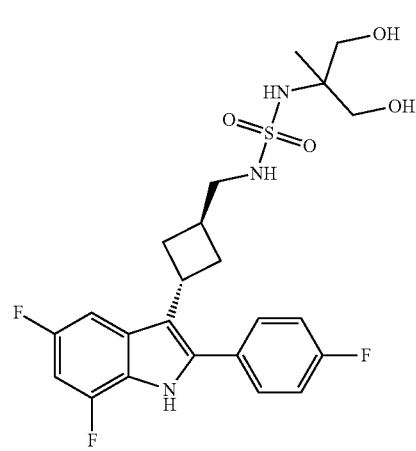 |
| | 366 |
|---|---|
| | 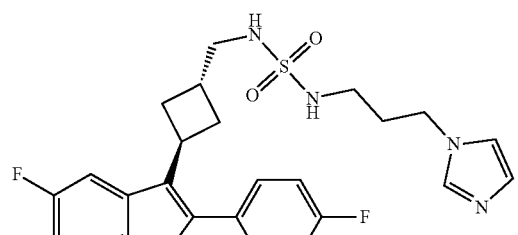 |
362
363
| | 367 |
|---|---|
| | 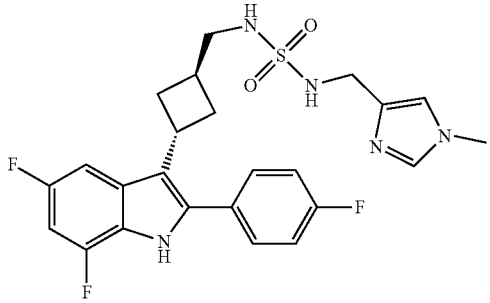 |
364
| | 368 |
|---|---|
| | 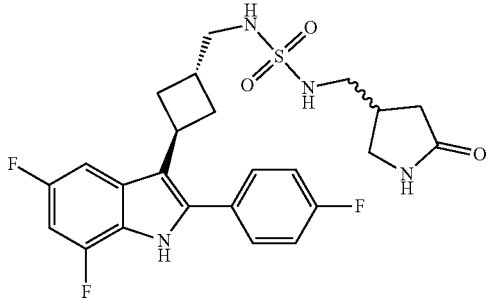 |

369 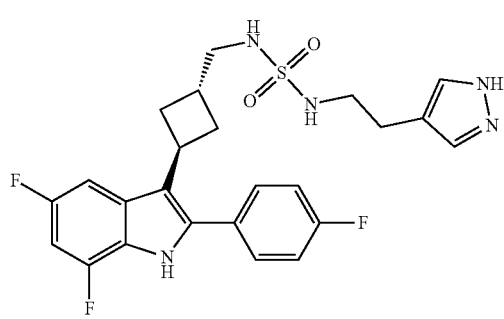
370 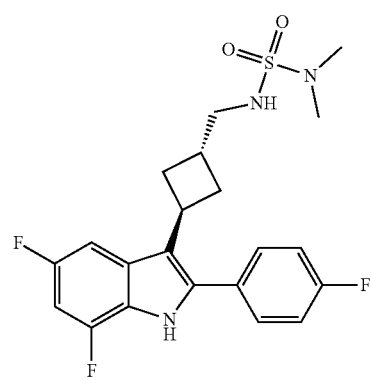
371 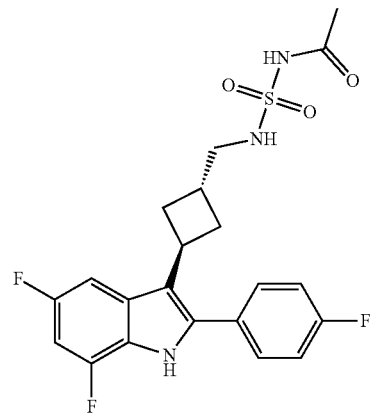
372 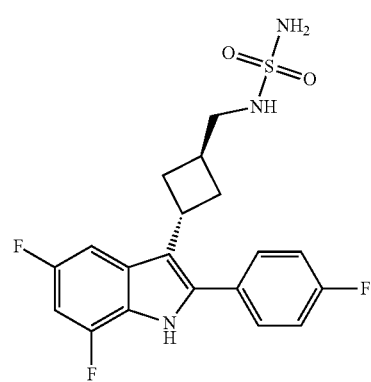
373 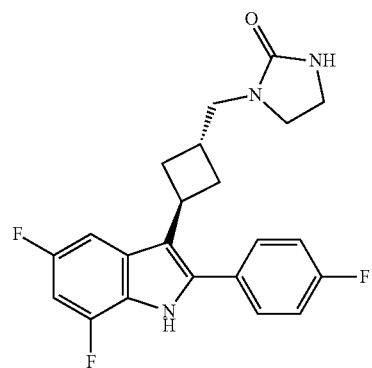
374 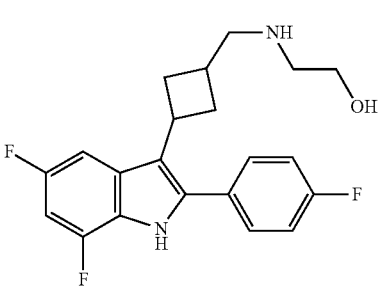
375 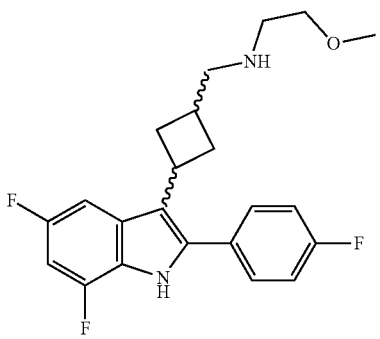
376 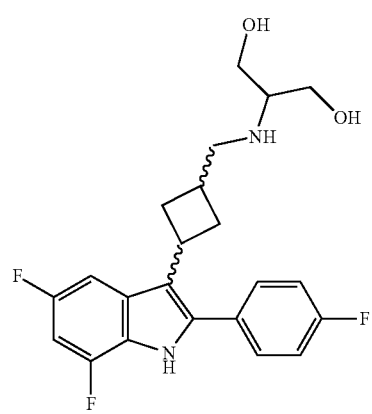

-continued
377
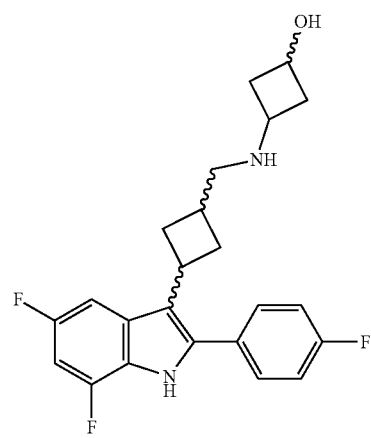
378
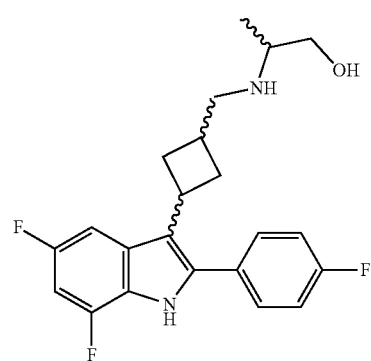
379
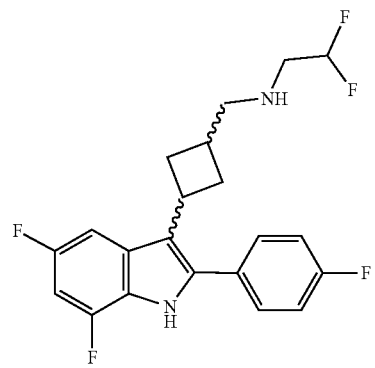
380
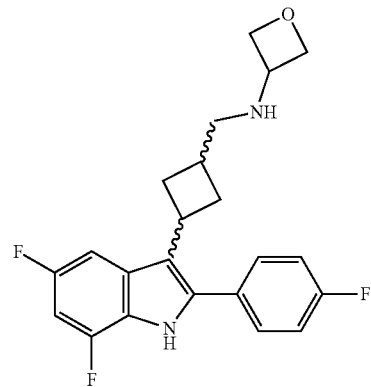
-continued
381
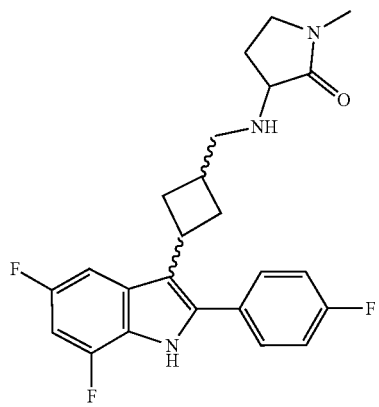
382
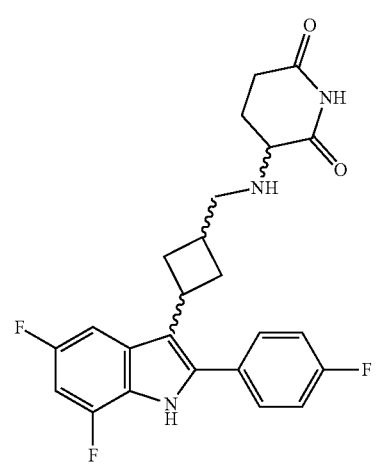
383
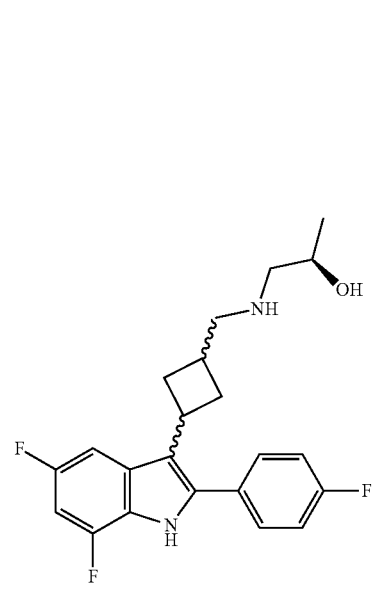

| 384 | 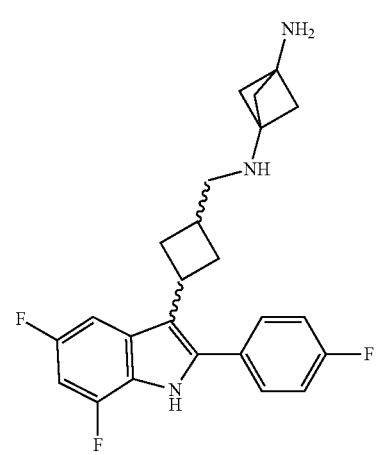 | 388 | 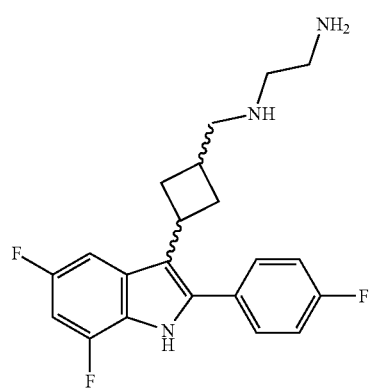 |
| --- | --- | --- | --- |
| 385 | 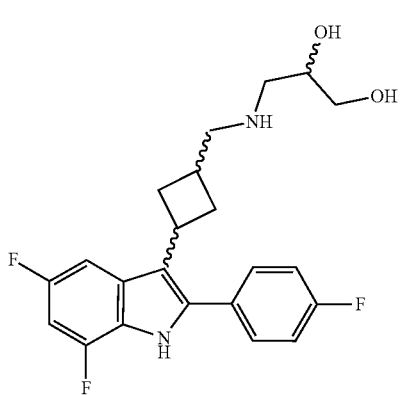 | 389 | 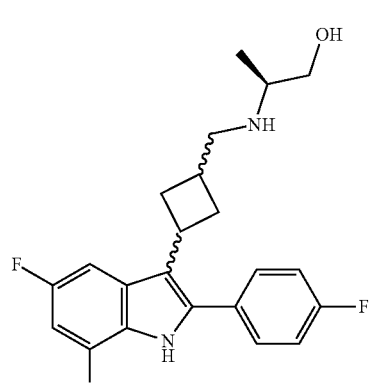 |
| 386 | 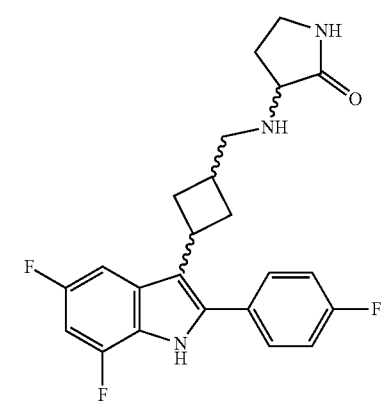 | 390 | 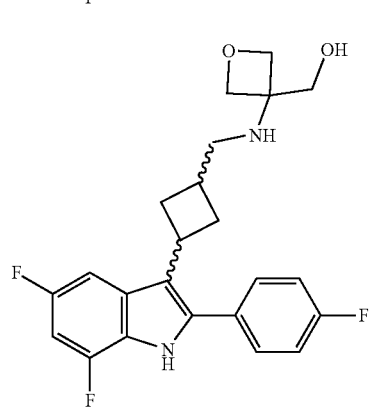 |
| 387 | 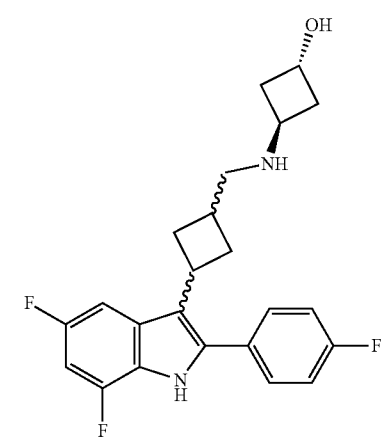 | 391 | 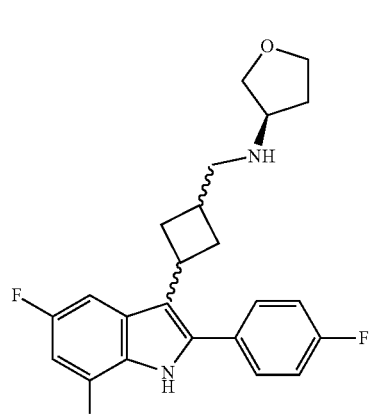 |

| | |
|---|---|
| 392 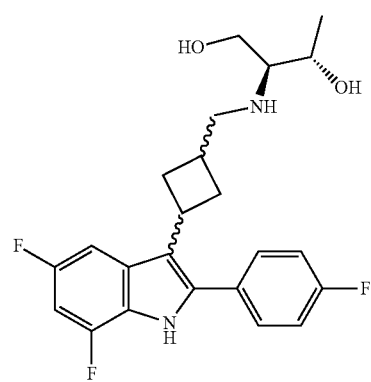 | 396 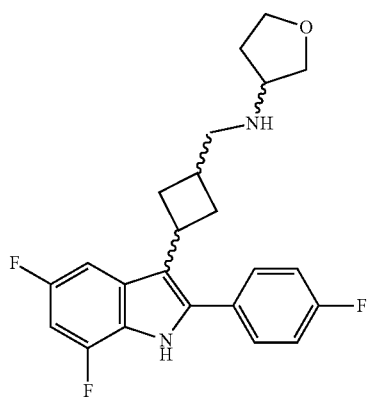 |
| 393 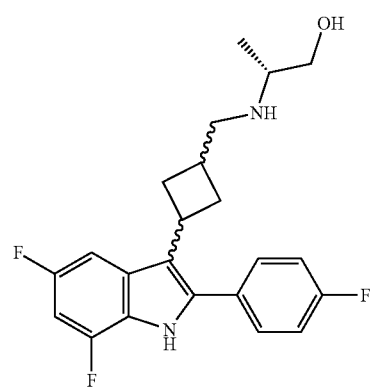 | |
| 394 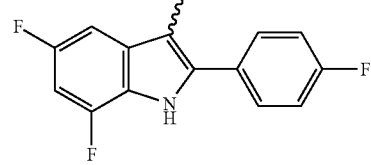 | 397 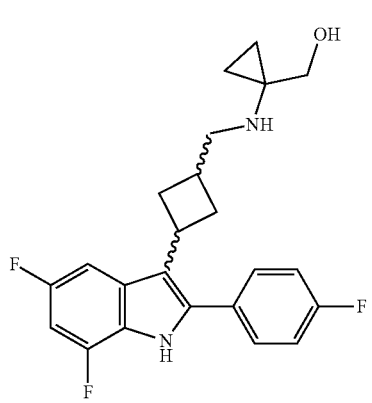 |
| 395 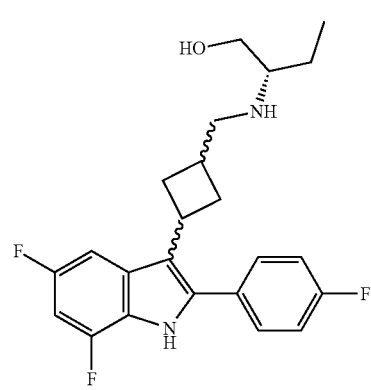 | 398 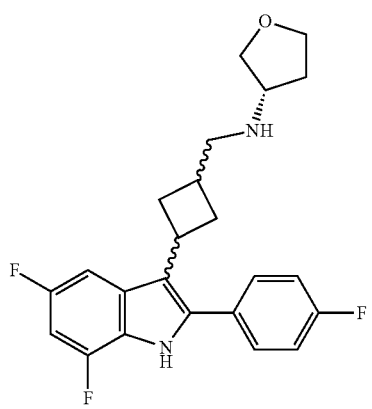 |

399
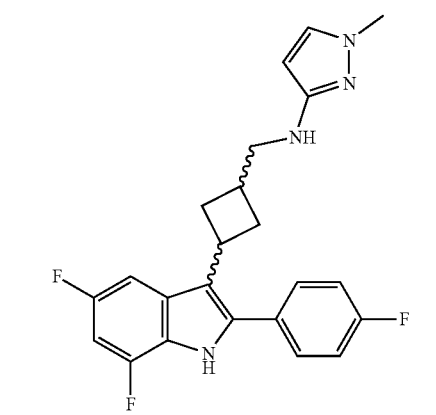
400
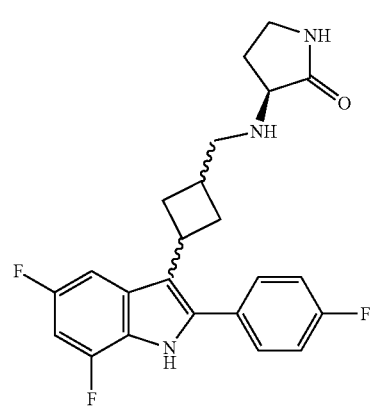
401
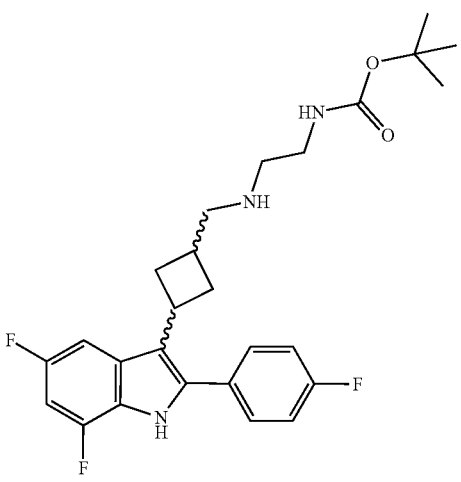
402
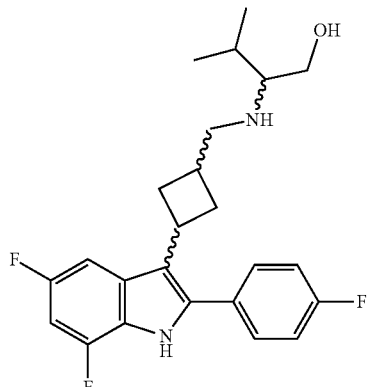
403
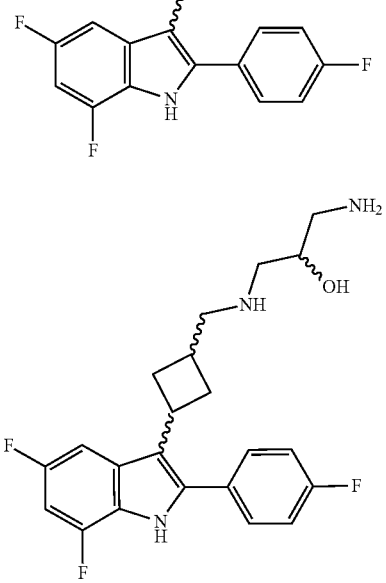
404
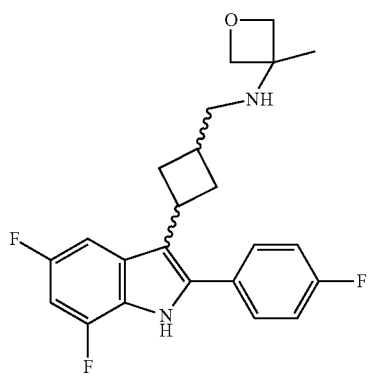
405
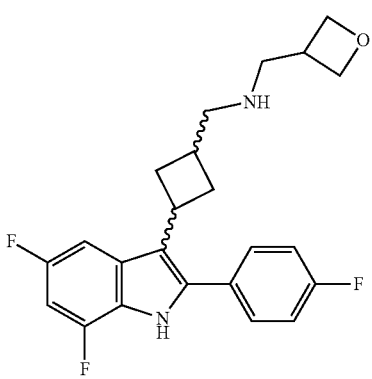

-continued
406
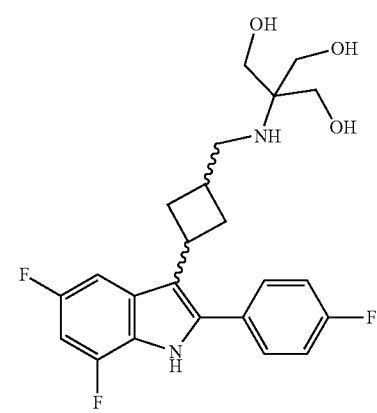
407
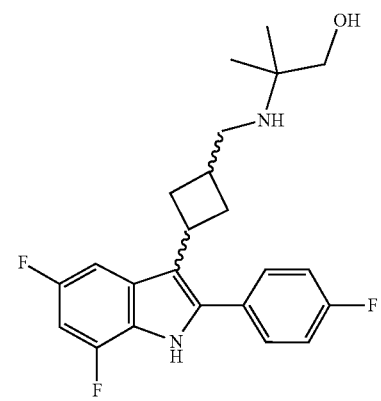
408
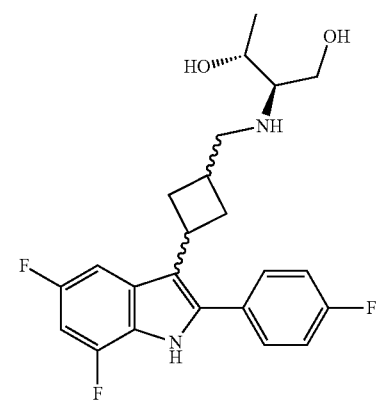
409
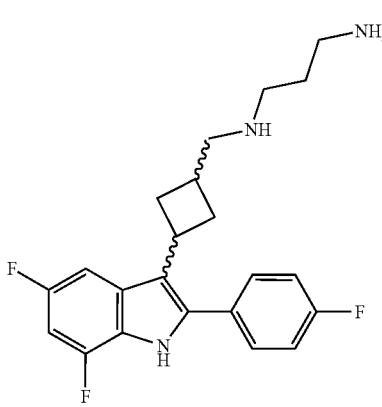
-continued
410
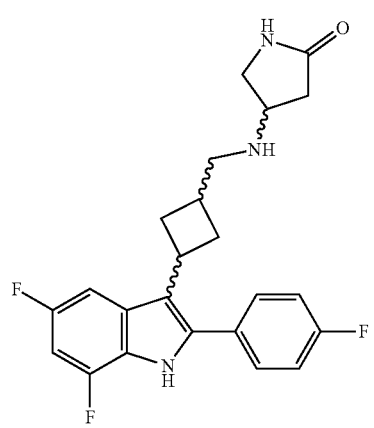
411
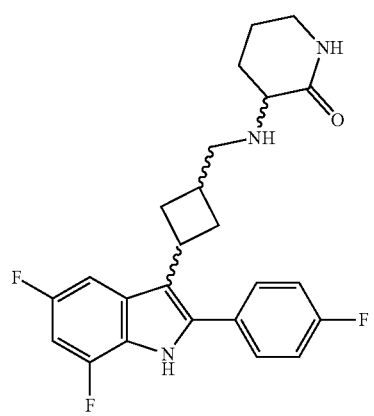
412
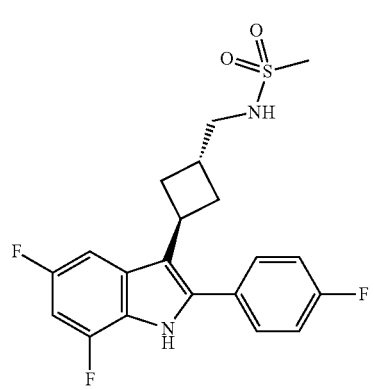
413
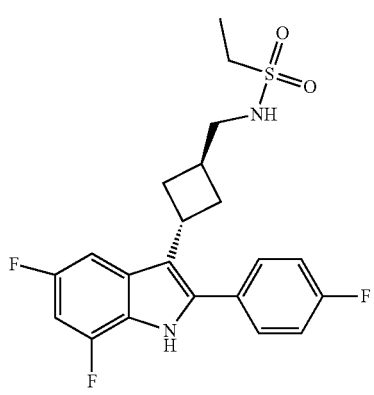

414 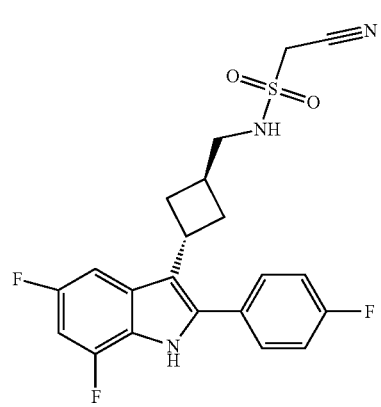
415 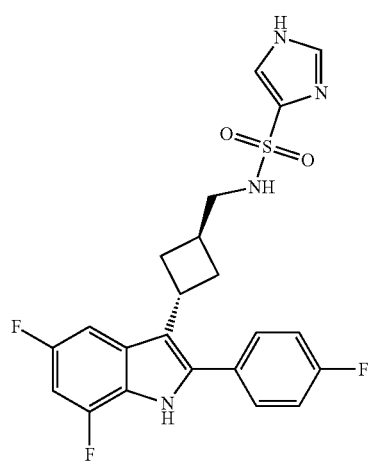 [SMILES: O=S(=O)(NC[C@H]1C[C@H](c2c(-c3ccc(F)cc3)[nH]c3c(F)cc(F)cc32)C1)c1c[nH]cn1]
416 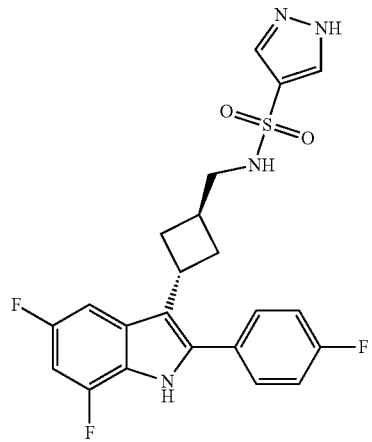 [SMILES: O=S(=O)(NC[C@H]1C[C@H](c2c(-c3ccc(F)cc3)[nH]c3c(F)cc(F)cc32)C1)c1cn[nH]c1]
417 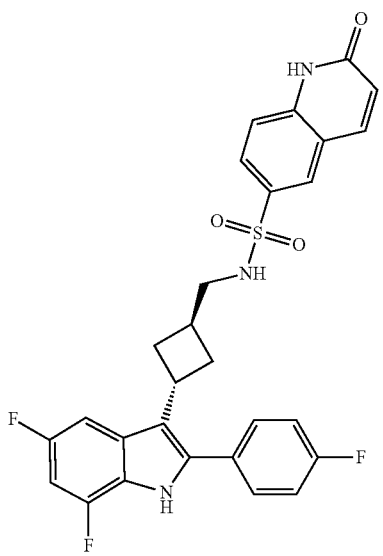
418 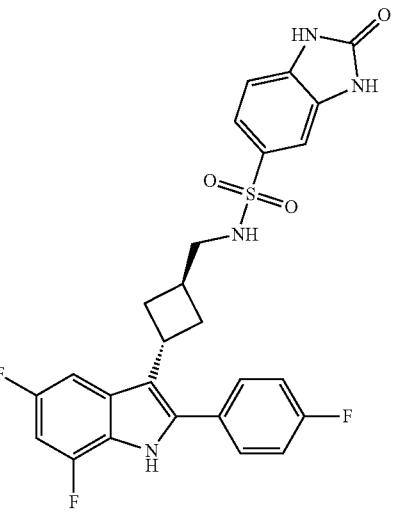
419 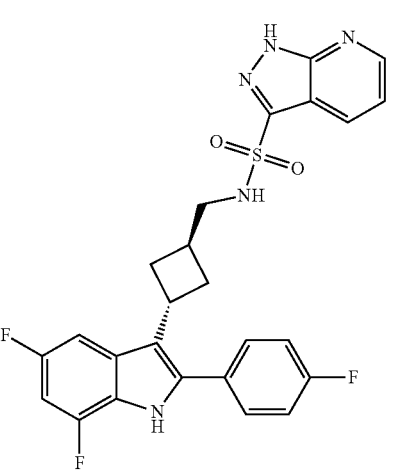

420 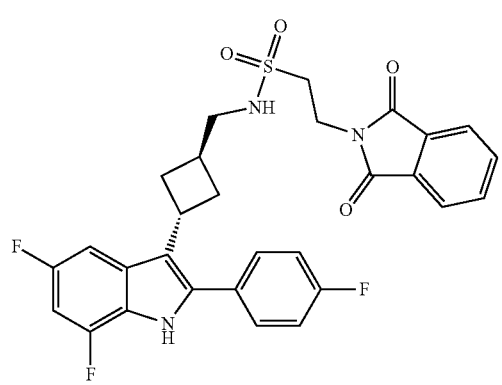
421 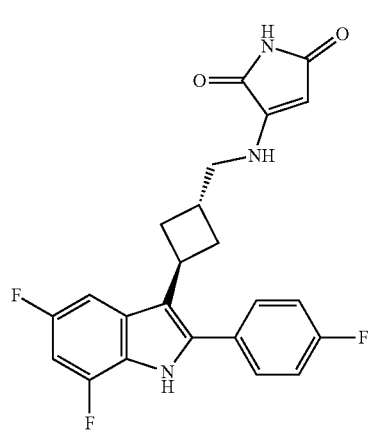
422 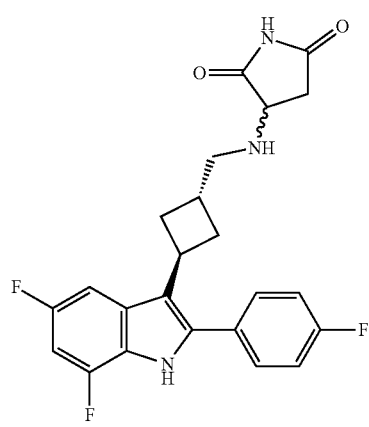
423 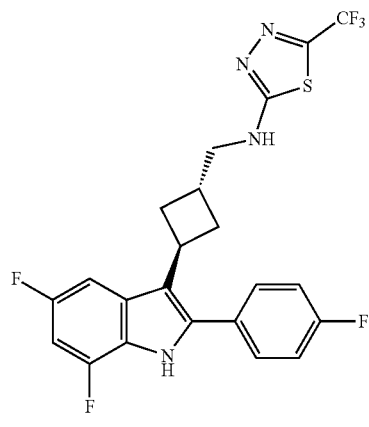
424 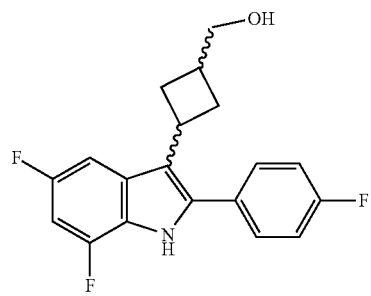
425 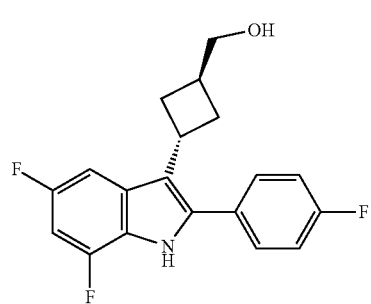
426 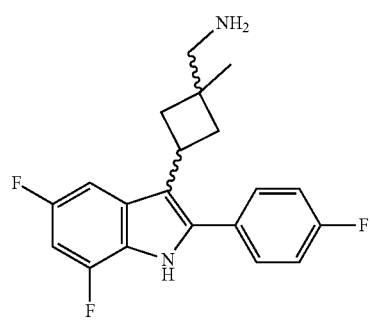
427 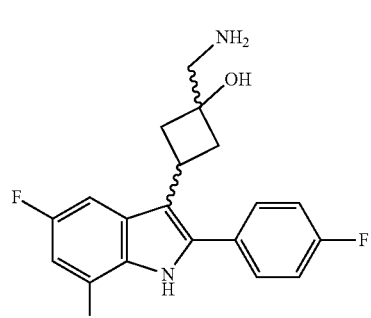
428 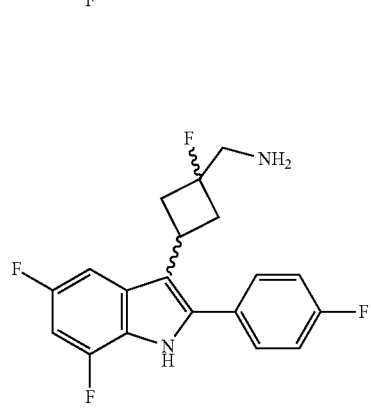

| 429 | 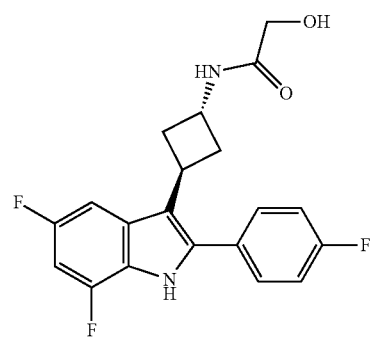 | 434 | 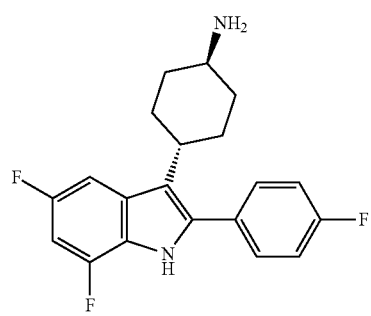 |
| 430 | 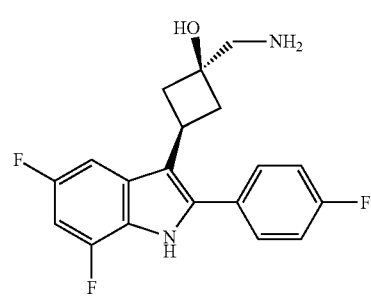 | 435 | 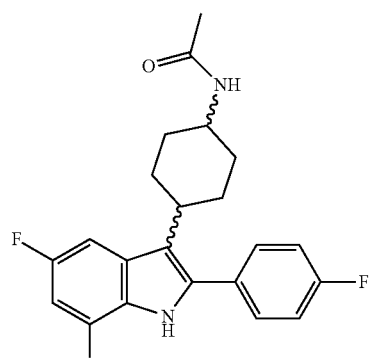 |
| 431 | 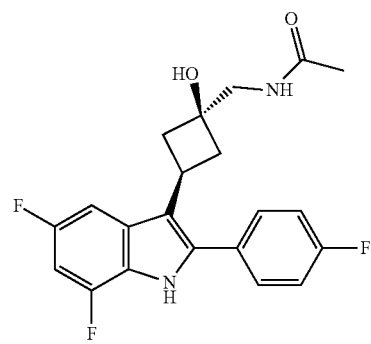 | 436 | 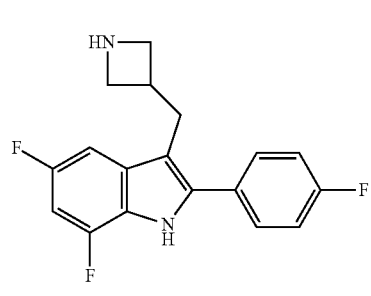 |
| 432 | 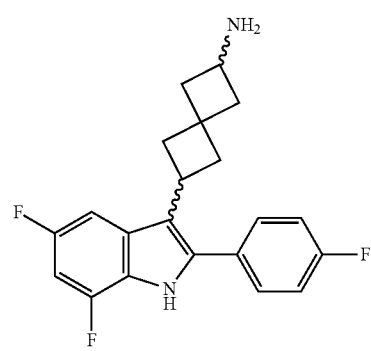 | 437 | 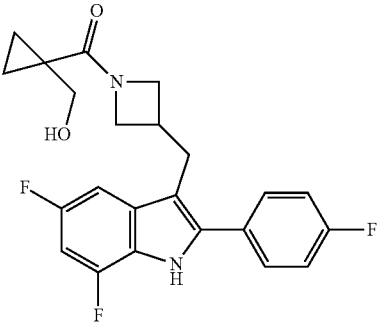 |
| 433 | 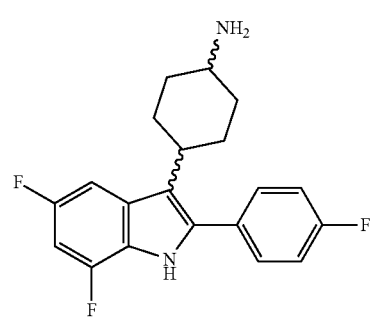 | 438 | 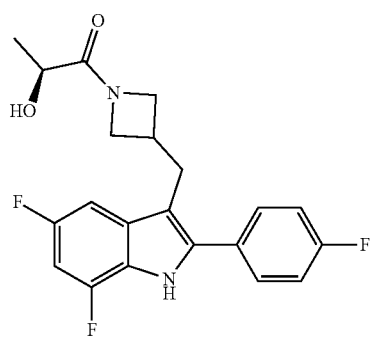 |

-continued
439
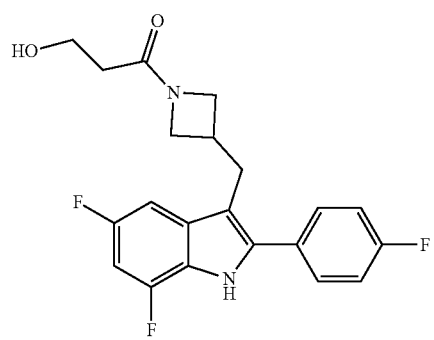
440
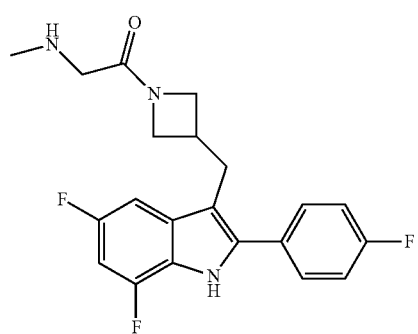 [SMILES: CNCC(=O)N1CC(Cc2c(-c3ccc(F)cc3)[nH]c3c(F)cc(F)cc23)C1]
441
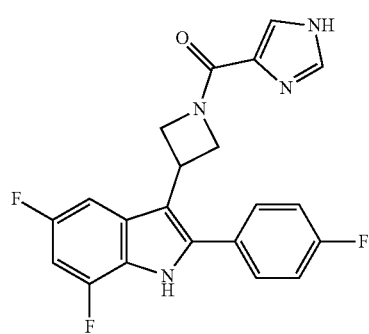
442
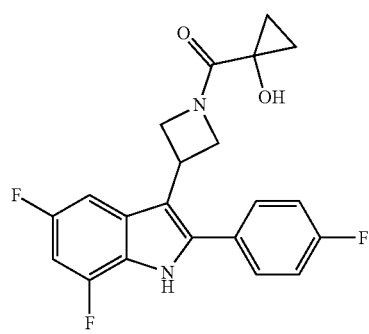
-continued
443
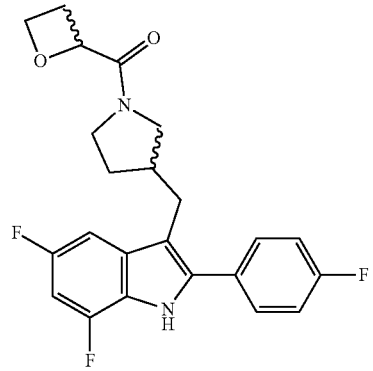
444
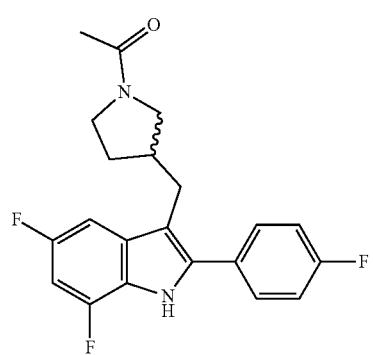
445
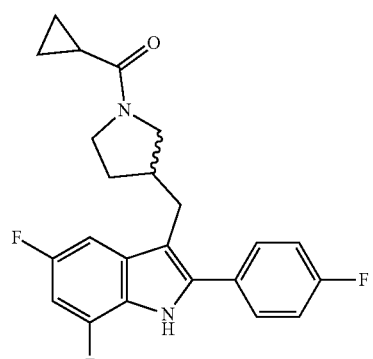
446
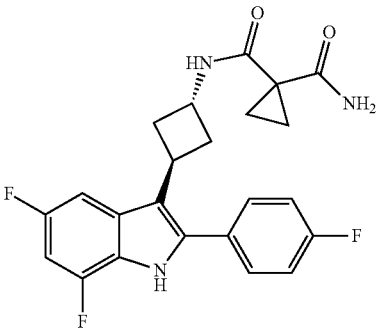

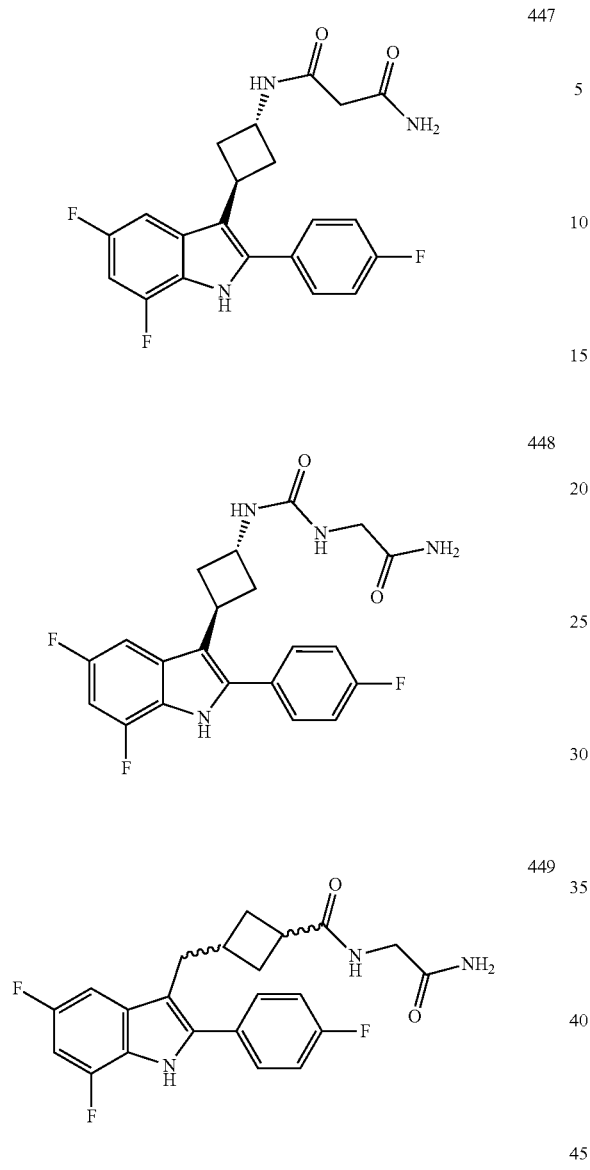
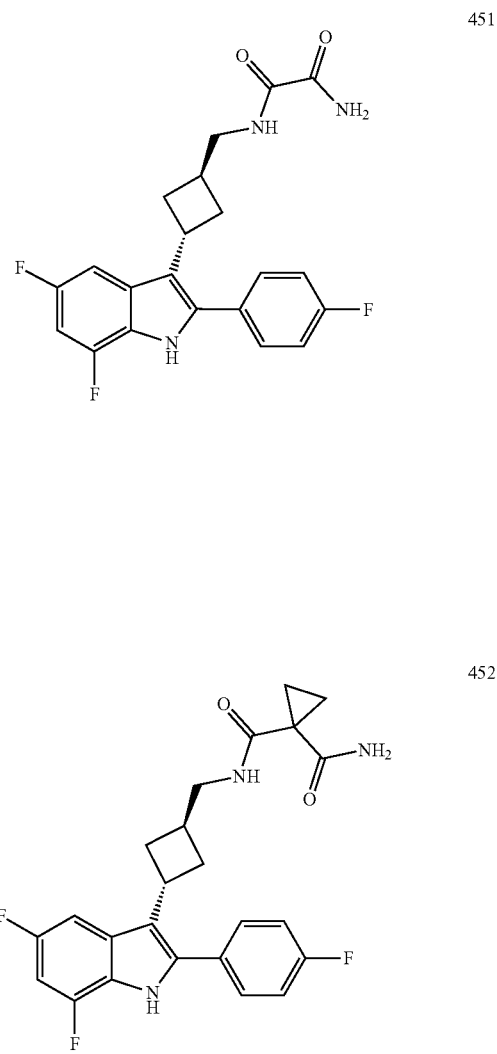

454

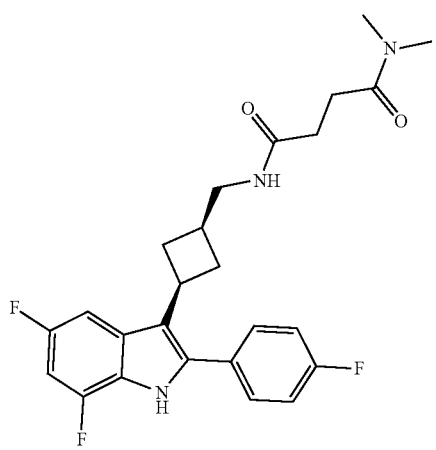

456

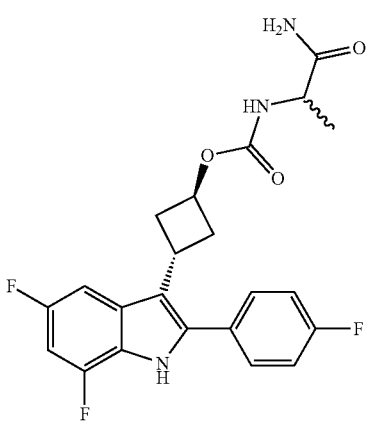

deuterated derivatives thereof, or pharmaceutically acceptable salts of any of the foregoing.

32. A pharmaceutical composition comprising the compound, deuterated derivative, or pharmaceutically acceptable salt according to claim 1 and a pharmaceutically acceptable carrier.

33. A method of treating APOL1 mediated kidney disease comprising administering to a patient in need thereof the compound, deuterated derivative, or pharmaceutically acceptable salt according to claim 1.

34. The method according to claim 33, wherein the APOL1 mediated kidney disease is selected from ESKD, NDKD, FSGS, HIV-associated nephropathy, sickle cell nephropathy, diabetic neuropathy, arterionephrosclerosis, lupus nephritis, microalbuminuria, and chronic kidney disease.

35. The method according to claim 33, wherein the APOL1 is associated with APOL1 genetic alleles chosen from homozygous G1: S342G:I384M and homozygous G2: N388del:Y389del.

36. A method of inhibiting APOL1 activity comprising contacting said APOL1 with the compound, deuterated derivative, or pharmaceutically acceptable salt according to claim 1.

37. The method according to claim 36, wherein the APOL1 is associated with APOL1 genetic alleles chosen from homozygous G1: S342G:I384M and homozygous G2: N388del:Y389del.

38. The method according to claim 36, wherein the APOL1 is associated with compound heterozygous G1: S342G:I1384M and G2: N388del:Y389del APOL1 genetic alleles.

455

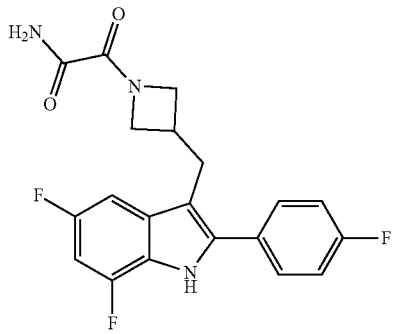

\* \* \* \* \*

UNITED STATES PATENT AND TRADEMARK OFFICE
CERTIFICATE OF CORRECTION

PATENT NO. : 12,281,102 B2
APPLICATION NO. : 17/345268
DATED : April 22, 2025
INVENTOR(S) : Leslie A. Dakin et al.

It is certified that error appears in the above-identified patent and that said Letters Patent is hereby corrected as shown below:

In the Claims

Claim 1, Column 540, Line 67, "—NRSC(O)R$^3$," should read as: -- —NR$^5$C(O)R$^3$,--.

Claim 1, Column 540, Line 67, "—NRSC(O)OR$^3$," should read as: -- —NR$^5$C(O)OR$^3$,--.

Claim 15, Column 547, Line 55, "—NRSC(O)R$^3$." should read as: -- —NR$^5$C(O)R$^3$.--.

Claim 18, Column 548, Line 48, "—NRSC(O)OR$^3$." should read as: -- —NR$^5$C(O)OR$^3$.--.

Claim 31, Column 591, Lines 35-45, Compound 163, " 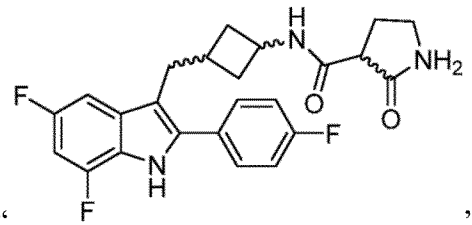 " should read as: -- 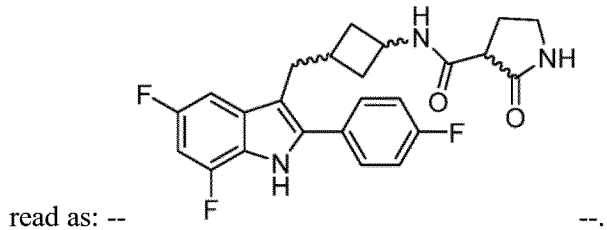 --.

Signed and Sealed this
Twenty-fourth Day of June, 2025

Coke Morgan Stewart
*Acting Director of the United States Patent and Trademark Office*